(12) United States Patent
Lampe et al.

(10) Patent No.: US 12,116,358 B2
(45) Date of Patent: Oct. 15, 2024

(54) SUBSTITUTED INDOLES AND METHODS OF USE THEREOF

(71) Applicant: EPIZYME, INC., Cambridge, MA (US)

(72) Inventors: John Lampe, Norfolk, MA (US); John Campbell, Cambridge, MA (US); Kenneth Duncan, Westwood, MA (US); Megan Alene Cloonan Foley, Somerville, MA (US); Darren Martin Harvey, Acton, MA (US); Michael John Munchhof, Salem, CT (US); Michael Thomenius, Arlington, MA (US); Lawrence Alan Reiter, Mystic, CT (US)

(73) Assignee: Epizyme, Inc., Cambridge, MA (US)

( * ) Notice: Subject to any disclaimer, the term of this patent is extended or adjusted under 35 U.S.C. 154(b) by 744 days.

(21) Appl. No.: 17/268,151

(22) PCT Filed: Aug. 14, 2019

(86) PCT No.: PCT/US2019/046569
§ 371 (c)(1),
(2) Date: Feb. 12, 2021

(87) PCT Pub. No.: WO2020/037079
PCT Pub. Date: Feb. 20, 2020

(65) Prior Publication Data
US 2023/0075198 A1 Mar. 9, 2023

Related U.S. Application Data

(60) Provisional application No. 62/857,120, filed on Jun. 4, 2019, provisional application No. 62/773,770, filed (Continued)

(51) Int. Cl.
*C07D 403/12* (2006.01)
*A61P 35/00* (2006.01)
(Continued)

(52) U.S. Cl.
CPC ............ *C07D 403/12* (2013.01); *A61P 35/00* (2018.01); *C07D 209/42* (2013.01); *C07D 209/96* (2013.01); *C07D 401/06* (2013.01); *C07D 401/12* (2013.01); *C07D 401/14* (2013.01); *C07D 403/14* (2013.01); *C07D 405/12* (2013.01); *C07D 405/14* (2013.01); *C07D 409/12* (2013.01); *C07D 413/12* (2013.01); *C07D 413/14* (2013.01); *C07D 417/12* (2013.01); *C07D 417/14* (2013.01); (Continued)

(58) Field of Classification Search
CPC ................ C07D 403/12; C07D 209/42; C07D 209/96; C07D 401/06; C07D 401/12; C07D 401/14; C07D 403/14; C07D 405/12; C07D 405/14; C07D 409/12; C07D 413/12; C07D 413/14; C07D 417/12; C07D 417/14; C07D 471/04; C07D 471/08; C07D 471/10; C07D 487/04; C07D 487/08; C07D 487/10; C07D 498/04; C07D 498/08; C07D 498/10; C07D 513/10; A61P 35/00
See application file for complete search history.

(56) References Cited

U.S. PATENT DOCUMENTS 4,582,788 A    4/1986   Erlich
4,595,766 A    6/1986   Roloff et al.
(Continued)

FOREIGN PATENT DOCUMENTS

CN    106317043 A    1/2016
EP    0050424 A1    4/1982
(Continued)

OTHER PUBLICATIONS

Chng et. al., (Sep. 2005), Genomics in multiple myeloma biology and clinical implications, Pharmacogenomics, 6, 563 -573. (Year: 2005).*
Vardiman et. al., (Apr. 8, 2009), The 2008 revision of the World Health Organization (WHO) classification of myleoid neoplasms [ . . . ], Blood, 114, 937-951 (Year: 2009).*
Zugazagoitia et. al., (Jul. 2016), Current Challenges in Cancer Treatment, Clinical Therapeutics, 38, 1551-1566 (Year: 2016).*
Altschul and Gish, "Local alignment statistics," Methods in Enzymology. 1996;266:460-480.
Altschul et al., "Gapped BLAST and PSI-BLAST: a new generation of protein database search programs," Nucleic Acids Res. 1997;25:3389-3402.
(Continued)

*Primary Examiner* — Kortney L. Klinkel
*Assistant Examiner* — Dawanna Shar-Day White
(74) *Attorney, Agent, or Firm* — Dechert LLP; Danielle M. Paglia; Erica M. D'Amato

(57) ABSTRACT

Compounds of Formula I: (I) and the pharmaceutically acceptable salts and solvates thereof, wherein $R^{1a}$, $R^{1e}$, G1, G2, $Q^1$, $Q^2$, $Q^3$, and (II) are defined as set forth in the specification, as are uses of compounds of Formula I to treat a disease, disorder, or condition such as cancer in a subject.

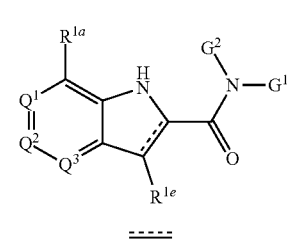

70 Claims, 5 Drawing Sheets

Related U.S. Application Data on Nov. 30, 2018, provisional application No. 62/718,746, filed on Aug. 14, 2018.

(51) Int. Cl.

| C07D 209/42 | (2006.01) |
|---|---|
| C07D 209/96 | (2006.01) |
| C07D 401/06 | (2006.01) |
| C07D 401/12 | (2006.01) |
| C07D 401/14 | (2006.01) |
| C07D 403/14 | (2006.01) |
| C07D 405/12 | (2006.01) |
| C07D 405/14 | (2006.01) |
| C07D 409/12 | (2006.01) |
| C07D 413/12 | (2006.01) |
| C07D 413/14 | (2006.01) |
| C07D 417/12 | (2006.01) |
| C07D 417/14 | (2006.01) |
| C07D 471/04 | (2006.01) |
| C07D 471/08 | (2006.01) |
| C07D 471/10 | (2006.01) |
| C07D 487/04 | (2006.01) |
| C07D 487/08 | (2006.01) |
| C07D 487/10 | (2006.01) |
| C07D 491/08 | (2006.01) |
| C07D 491/107 | (2006.01) |
| C07D 498/04 | (2006.01) |
| C07D 498/08 | (2006.01) |
| C07D 498/10 | (2006.01) |
| C07D 513/10 | (2006.01) |

(52) U.S. Cl.
CPC ......... *C07D 471/04* (2013.01); *C07D 471/08* (2013.01); *C07D 471/10* (2013.01); *C07D 487/04* (2013.01); *C07D 487/08* (2013.01); *C07D 487/10* (2013.01); *C07D 491/08* (2013.01); *C07D 491/107* (2013.01); *C07D 498/04* (2013.01); *C07D 498/08* (2013.01); *C07D 498/10* (2013.01); *C07D 513/10* (2013.01)

(56) References Cited

U.S. PATENT DOCUMENTS

| 4,683,194 | A | 7/1987 | Saiki et al. | |
|---|---|---|---|---|
| 4,683,202 | A | 7/1987 | Mullis | |
| 9,446,064 | B2 | 9/2016 | Klaus et al. | |
| 10,266,526 | B2 * | 4/2019 | Foley | A61P 43/00 |
| 2009/0082560 | A1 | 3/2009 | Kobayashi et al. | |
| 2011/0021362 | A1 | 1/2011 | Trojer et al. | |
| 2011/0136807 | A1 | 6/2011 | Hangauer, Jr. | |
| 2013/0137748 | A1 | 5/2013 | Hamamoto et al. | |
| 2014/0303106 | A1 | 10/2014 | Zheng et al. | |
| 2017/0044100 | A1 | 2/2017 | Bishai et al. | |
| 2017/0232030 | A1 | 8/2017 | Klaus et al. | |
| 2017/0281810 | A1 | 10/2017 | He | |
| 2017/0355695 | A1 | 12/2017 | Foley et al. | |
| 2021/0002645 | A1 | 1/2021 | Grassian et al. | |
| 2023/0049113 | A1 | 2/2023 | Thomenius et al. | |
| 2023/0133671 | A1 | 5/2023 | Raimondi et al. | |

FOREIGN PATENT DOCUMENTS

| EP | 0084796 | A2 | 8/1983 |
|---|---|---|---|
| EP | 00201184 | A2 | 11/1986 |
| EP | 00258017 | A2 | 3/1987 |
| EP | 00237362 | A1 | 9/1987 |
| EP | 1880994 | A1 | 1/2008 |
| EP | 1942105 | A1 | 7/2008 |
| JP | 2012-107001 | A | 6/2012 |
| WO | WO-2002080926 | A1 | 10/2002 |
| WO | WO-2004018428 | A1 | 3/2004 |
| WO | WO-2004018461 | A2 | 3/2004 |
| WO | WO-2009158375 | A1 | 12/2009 |
| WO | WO-2010028192 | A1 | 3/2010 |
| WO | WO-2011079102 | A1 | 6/2011 |
| WO | WO-2015143424 | A2 | 9/2015 |
| WO | WO-2015150097 | A1 | 10/2015 |
| WO | WO-2015164482 | A1 | 10/2015 |
| WO | WO-2016010950 | A1 | 1/2016 |
| WO | WO-2016040505 | A1 | 3/2016 |
| WO | WO-2016079321 | A1 | 5/2016 |
| WO | WO-2017106259 | A1 | 6/2017 |
| WO | WO-2019036466 | A1 | 2/2019 |
| WO | WO-2020112872 | A1 | 6/2020 |
| WO | WO-2021168313 | A1 | 8/2021 |
| WO | WO-2022261243 | A1 | 12/2022 |
| WO | WO-2023077117 | A1 | 5/2023 |

OTHER PUBLICATIONS

Bingham et al., "Over one hundred solvates of sulfathiazole," Chemical Communications. 2001;7(7):603-604.

Caira et al., "Preparation and crystal characterization of a polymorph, a monohydrate, and an ethyl acetate solvate of the antifungal fluconazole," 2003;93(3):601-11.

Chang et al., "Investigation of the inhibitors of histone-lysine N-methyltransferase SETD2 for acute lymphoblastic leukaemia from traditional Chinese medicine," SAR QSAR Environ Res. 2016;27(7):589-608.

Chavda et al., "A novel achiral seco-cyclopropylpyrido[e]indolone (CPyl) analog of CC-1065 and the duocarmycins: synthesis, DNA interactions, in vivo anticancer and anti-parasitic evaluation," Bioorg Med Chem. 2010;18(14):5016-24.

Chen et al., "CRISPR-Cas9: from Genome Editing to Cancer Research," Int. J Biol. Sci. 2016;12:1427-1436.

Chen et. al., "Histone methyltransferase SETD2: a potential tumor suppressor in solid cancers," J Cancer. 2020; 1(11):3349-3356.

Chesi et al., "The t(4;14) Translocation in Myeloma Dysregulates Both FGFR3and a Novel Gene, MMSET, Resulting in IgH/MMSET Hybrid Transcripts," Blood. 1998;92(9):3025-34.

"CID 108791761 Compound Summary: 7-Chloro-N-pyridin-2-yl-1H-indole-2-carboxamide," PubChem. Created Jan. 15, 2016: https://pubchem.ncbi.nlm.nih.gov/compound/108791761.

"CID 110853847 Compound Summary: ethyl 4-[(7-methyl-1H-indole-2-carbonyl)amino]piperidine-1-carboxylate," PubChem. Created Jan. 18, 2016: https://pubchem.ncbi.nlm.nih.gov/compound/110853847.

"CID 131900417 Compound Summary: (6-Methoxy-3,4-dihydro-1H-isoquinolin-2-yl)-(3,4,7-trimethyl-1H-indol-2-yl)methanone," PubChem. Created Dec. 12, 2017: https://pubchem.ncbi.nlm.nih.gov/compound/131900417.

Daigle et al., "Selective Killing of Mixed Lineage Leukemia Cells by a Potent Small-Molecule DOT1L Inhibitor" Cancer Cell. 2011;20:53-65.

Edmunds et al., "Dynamic histone H3 methylation during gene induction: HYPB/Setd2 mediates all H3K36 trimethylation," The EMBO Journal. 2008;27:406-420.

Engelhardt et al., "Detailed structure-activity relationship of indolecarboxamides as H4 receptor ligands," Eur J Med Chem. 2012;54:660-8.

Fahey and Davis, "SETting the Stage for Cancer Development: SETD2 and the Consequences of Lost Methylation," Cold Spring Harb Perspect Med. May 1, 2017;7(5):a026468.

Fonfara et al., "The CRISPR-associated DNA-cleaving enzyme Cpf1 also processes precursor CRISPR RNA," Nature. 2016;532:517-521.

Fontebasso et al., "Mutations in SETD2 and genes affecting histone H3K36 methylation target hemispheric high-grade gliomas," Acta Neuropathol. 2013;125(5):659-69.

Gaj et al., "ZFN, TALEN, and CRISPR/Cas-based methods for genome engineering," Trends Biotechnol. 2013;31:397-405.

Goossens et al., "Cancer biomarker discovery and validation," Transl Cancer Res. 2015;4(3):256-269.

(56) References Cited

OTHER PUBLICATIONS

Gupta and Zhang, "Angiogenesis: a curse or cure?," Postgrad Med J. 2005;81:236-242.
Hadjipavlou-Litina et al., "2D-QSAR and 3D-QSAR/CoMFA analyses of the N-terminal substituted anthranilic acid based CCK(1) receptor antagonists: 'Hic Rhodus, hic saltus'," Bioorg Med Chem. 2009;17(14):5198-206.
Herzog et al., "Trabectedin Followed by Irinotecan Can Stabilize Disease in Advanced Translocation-Positive Sarcomas with Acceptable Toxicity," 2016;2016:7461783.
Hudlebusch et al., "The Histone Methyltransferase and Putative Oncoprotein MMSET Is Overexpressed in a Large Variety of Human Tumors," Clin Cancer Res. 2011;17(9):2919-29.
Jin and Zhou, "Crucial role of the pentose phosphate pathway in malignant tumors," Oncology Letters. 2019;17(5):4213-4221.
Johnson et al., "End points and United States Food and Drug Administration approval of oncology drugs," J Clin. Oncol. 2003;21:1404-11.
Kalff and Spencer, "The t(4;14) translocation and FGFR3 overexpression in multiple myeloma: prognostic implications and current clinical strategies," Blood Cancer Journal. 2012;2:89.
Kamel et al., "Exploitation of Gene Expression and Cancer Biomarkers in Paving the Path to Era of Personalized Medicine," Genomics Proteomics Bioinformatics. 2017;15(4):220-235.
Karlin et al., "Applications and statistics for multiple high-scoring segments in molecular sequences" Proc. Natl. Acad Sci. 1993;90:5873-77.
Karlin et al., "Methods for assessing the statistical significance of molecular sequence features by using general scoring schemes," Proc. Natl. Acad Sci. 1990;87:2264-68.
Kassambara, et al., "MMSET is overexpressed in cancers: link with tumor aggressiveness," Biochemical and Biophysical Research Communications. 2009;379(4):840-845.
Konikova and Kusenda, "Altered expression of p53 and MDM2 proteins in hematological malignancies," Neoplasma. 2003;50(1):31-40.
Kuo et al., "NSD2 links dimethylation of histone H3 at lysine 36 to oncogenic programming," Molecular Cell. 2011;44:609-20.
Kwak et al. "Structure-activity relationship of indoline-2-carboxylic acid N-(substituted)phenylamide derivatives," Bioorg Med Chem Lett. Aug. 1, 2010;20(15):4620-3.
Larkin et al., "Epigenetic regulation in RCC: opportunities for therapeutic intervention?," Nat Rev Urol. 2012;9(3):147-55.
Li et al., "SETD2: an epigenetic modifier with tumor suppressor functionality," Oncotarget. 2016;7:50719-34.
Maeder and Gersbach, "Genome-editing Technologies for Gene and Cell Therapy," Mol. Ther. 2016;24:430-46.
Morera et. al., "Targeting histone methyltransferases and demethylases in clinical trials for cancer therapy," Clinical Epigenetics. 2016;8(57):1-16.
Mullis et al., "Specific enzymatic amplification of DNA in vitro: the polymerase chain reaction," Cold Spring Harb Symp Quant Biol. 1986;51 Pt 1:263-73.
Myers and Miller, "Optimal alignments in linear space," Cabios. 1988;4:11-17.
NCBI GenBank, "*Homo sapiens* SET domain containing 2, histone lysine methyltransferase (SETD2), transcript variant 1, mRNA," ncbi.nlm.nih.gov, Accession No. NM_014159.6, accessed at URL:[https://www.ncbi.nlm.nih.gov/nuccore/NM_014159.6] on Dec. 23, 2021, 12 pages.
NCBI Gene, "SETD2 SET domain containing 2, histone lysine methyltransferase [ *Homo sapiens* (human) ]," ncbi.nlm.nih.gov, Gene ID: 29072, HGNC: 18420, accessed at URL:[https://www.ncbi.nlm.nih.gov/gene?Db=gene&Cmd=DetailsSearch&Term=29072] on Dec. 23, 2021, 12 pages (Dec. 2021).
Needleman and Wunsch, "A General Method Applicable to the Search for Similarities in the Amino Acid Sequence of Two Proteins," J Mol. Biol. 1970;48:443-53.

Newbold, "Evidence for a tumour suppressor function of SETD2 in human breast cancer: a new hypothesis," Anticancer Res. 2010;30(9):3309-11.
Ohri et al., "Tumour necrosis factor-alpha expression in tumour islets confers a survival advantage in non-small cell lung cancer," BMC Cancer. 2010;10:323.
Park et al., "Metabolism of fluorine-containing drugs," Annu Rev Pharmacol Toxicol. 2001;41:443-70.
Park et al., "Methylation of Aurora kinase A by MMSET reduces p53 stability and regulates cell proliferation and apoptosis," Oncogne. 2018;37:6212-24.
Pawlyn and Morgan, "Evolutionary biology of high-risk multiple myeloma," Nature Reviews. Cancer. 2017;17(9):543-56.
PCT International Search Report and Written Opinion from PCT/US2018/046698, dated Oct. 19, 2018.
PCT International Search Report and Written Opinion from PCT/US2019/046569, dated Nov. 5, 2019.
PCT International Search Report and Written Opinion from PCT/US2019/063405, dated Apr. 21, 2021.
PCT International Search Report and Written Opinion from PCT/US2021/018863, dated Jul. 20, 2021.
PCT International Search Report and Written Opinion from PCT/US2022/032718, dated Sep. 12, 2022.
PCT International Search Report and Written Opinion from PCT/US2022/078962, dated Jan. 26, 2023.
Perez-Pinera et al., "Advances in targeted genome editing," Curr Opin Chem Biol. 2012;16:268-77.
Prideaux et al., "The genetic architecture of multiple myeloma," Advances in Hematology. 2014:1-16.
Sanchez-Rivera and Jacks, "Applications of the CRISPR-Cas9 System in Cancer Biology," Nat Rev Cancer. 2015;15:387-95.
Slagle et al., "Expression of ras, c-myc, and p53 proteins in cervical intraepithelial neoplasia," Cancer. 1998;83(7):1401-8.
Smith and Waterman, "Comparison of biosequences," Advances in Applied Mathematics. 1981;2:482-89.
Thomenius, et al., "Identification of a First-in-Class SETD2 Inhibitor That Shows Potent and Selective Anti-Proliferative Activity in t(4;14) Multiple Myeloma: T(4;14) Multiple Myeloma Cells Are Dependent on Both H3K36 Di and Tri-Methylation," Blood. 2018; 132(Supplement1):3207.
Tisi et al., "Structure of the Epigenetic Oncogene MMSET and Inhibition by N-Alkyl Sinefungin Derivatives," ACS Biol. 2016;11(11):3093-3105.
Van Tonder et al., "Preparation and physicochemical characterization of 5 niclosamide solvates and 1 hemisolvate," AAPS PharmSciTech. 2004;5(1):E12.
Xie et al., "MMSET regulates expression of IRF4 in t(4;14) myeloma and its silencing potentiates the effect of bortezomib," Leukemia. 2015;29:2347-54.
Zetsche et al., "Cpf1 Is a Single RNA-Guided Endonuclease of a Class 2 CRISPR-Cas System," Cell. 2015;163:759-71.
Zheng et al., "Sinefungin derivatives as inhibitors and structure probes of protein lysine methyltransferase SETD2," J Am Chem Soc. 2012;134(43):18004-14.
Zhu et al., "Identification of functional cooperative mutations of SETD2 in human acute leukemia," Nature Genetics. 2014;46:287-293.
Zips et al., "New Anticancer Agents: In Vitro and In Vivo Evaluation," in vivo. 2005;19:1-8.
Gura, "Systems for Identifying New Drugs are Often Faulty," Science. 1997;278, 1041-1042.
Johnson et al., "Relationships between drug activity in NCI preclinical in vitro and in vivo models and early clinical trials," British Journal of Cancer. 2001;84(10):1424-1431.
Maeda and Khatami, "Analyses of repeated failures in cancer therapy for solid tumors: poor tumor-selective drug delivery, low therapeutic efficacy and unsustainable costs," Clin Trans Med. 2018;7:11.
Richardson et al., "A Phase 1/1b Open-Label, Multicenter, Two-Part Study of SETD2 Inhibitor EZM0414 in Patients with Relapsed/Refractory Multiple Myeloma or Diffuse Large B-Cell Lymphoma," Blood. 2021;138(Supplement 1):1679.

(56) References Cited

OTHER PUBLICATIONS

Shi et al., "Discovery of cancer drug targets by CRISPR-Cas9 screening of protein domains," Nat Biotechnol. 2015;33(6):661-7.
U.S. Appl. No. 18/568,368, filed Dec. 8, 2023.
Alford et al., "Conformational-Design-Driven Discovery of EZM0414: A Selective, Potent SETD2 Inhibitor for Clinical Studies," ACS Med. Chem. Lett. 2022; 13:1137-1143.
Lampe et al., "Discovery of a First-in-Class Inhibitor of the Histone Methyltransferase SETD2 Suitable for Preclinical Studies," ACS Med Chem Lett. 2021;12(10): 539-1545.
Registry (STN) [online]; 2023; RN 2105115-46-4.

* cited by examiner

SUBSTITUTED INDOLES AND METHODS OF USE THEREOF

BACKGROUND OF THE INVENTION

Field of the Invention

The present disclosure provides substituted indoles and methods of use thereof. In some embodiments, the substituted indoles are SETD2 protein inhibitors. In some embodiments, the substituted indoles may be used in methods of treating diseases, disorders, or conditions in a subject.

Background

The selective addition of methyl groups to specific amino acid sites on histones is controlled by the action of a family of enzymes known as histone methyltransferases (HMTs). The level of expression of a particular gene is influenced by the presence or absence of one or more methyl groups at a relevant histone site. The specific effect of a methyl group at a particular histone site persists until the methyl group is removed by a histone demethylase, or until the modified histone is replaced through nucleosome turnover. In a like manner, other enzyme classes can decorate DNA and histones with other chemical species, and still other enzymes can remove these species to provide control of gene expression.

SETD2 is a human histone methyltransferase located at the cytogenic band p21.31 of chromosome 3 (3p21.31). The acronym "SETD2" stands for Suppressor of variegation, Enhancer of zeste, and Trithorax domain containing 2. The SETD2 protein comprises three conserved functional domains: (1) the triplicate AWS-SET-PostSET domain; (2) a WW domain; and (3) a Set2-Rbp1 interacting ("SRI") domain. These three functional domains define the biological function of SETD2. See, Li, J. et al., *Oncotarget* 7:50719-50734 (2016). SETD2 is believed to be the single human gene responsible for the trimethylation of lysine 36 (Lys-36) of histone H3 (H3K36me3) using dimethylated Lys-36 (H3K36me2) as substrate. Edmunds, J. W. et al., *The EMBO Journal* 27:406-420 (2008).

Human SETD2 has been shown to have tumor suppressor functionality. Li, J. et al., *Oncotarget* 7:50719-50734 (2016). For example, inactivation of human SETD2 has been reported in renal cell carcinoma (RCC). Larkin, J., et al., *Nature Reviews* 9:147-155 (2012). Also, expression levels of SETD2 in breast cancer samples have been reported as significantly lower than in adjacent non-cancerous tissue (ANCT) samples. Newbold, R. F. and Mokbel, K., *Anticancer Research* 30: 3309-3311 (2010). Additionally, biallelic mutations and loss-of-function point mutations in SETD2 were reported in patients with acute leukemia. Zhu, X. et al., *Nature Genetics* 46: 287-293 (2014). Mutations in SETD2 have also been reported in pediatric high-grade gliomas. Fontebasso, A. M. et al., *Acta Neuropathol.* 125: 659-669 (2013).

BRIEF SUMMARY OF THE INVENTION

The present disclosure relates to the surprising and unexpected discovery that inhibiting human SETD2 protein, despite its known functionality as a tumor suppressor, can be used to treat cancer. The present disclosure also provides novel substituted indoles. In some embodiments, the substituted indoles are inhibitors of SETD2. In some embodiments, the substituted indoles may be used in methods of treating diseases, e.g., cancer, disorders, or conditions in a subject. In some embodiments, the substituted indoles display selective anti-proliferative effects in t(4;14) multiple myeloma cell lines.

In one aspect, the present disclosure provides substituted indoles represented by any one of Formulae I, II, II-A, III, III-A, IV, IV-A, IV-B, IV-C, IV-D, V, V-A, V-B, VI, VII, VII-A, VII-B, VII-C, VII-D, VII-E, VII-F, VII-G, VII-H, VIII, VIII-A, and VIII-B, below, and the pharmaceutically acceptable salts and solvates thereof, collectively referred to herein as "Compounds of the Disclosure."

In another aspect, the present disclosure provides a pharmaceutical composition comprising a Compound of the Disclosure and one or more pharmaceutically acceptable carriers.

In another aspect, the present disclosure provides a method of inhibiting SETD2 protein in a subject, comprising administering to the mammal an effective amount of at least one Compound of the Disclosure.

In another aspect, the present disclosure provides methods for treating a disease, disorder, or condition, e.g., cancer, in a subject, comprising administering a therapeutically effective amount of a Compound of the Disclosure to a subject.

In another aspect, the present disclosure provides methods for treating a disease, disorder, or condition, e.g., cancer, responsive to inhibition of SETD2 protein comprising administering a therapeutically effective amount of a Compound of the Disclosure to a subject.

In another aspect, the present disclosure provides the use of Compounds of the Disclosure as inhibitors of SETD2 protein.

In another aspect, the present disclosure provides a pharmaceutical composition for treating a disease, disorder, or condition responsive to inhibition of SETD2 protein, wherein the pharmaceutical composition comprises a therapeutically effective amount of a Compound of the Disclosure in a mixture with one or more pharmaceutically acceptable carriers.

In another aspect, the present disclosure provides Compounds of the Disclosure for use in treating cancer, e.g., multiple myeloma, in a subject in need thereof.

In another aspect, the present disclosure provides a Compound of the Disclosure for use in the manufacture of a medicament for treating cancer in a mammal.

In another aspect, the present disclosure provides a kit comprising a Compound of the Disclosure.

In another aspect, the present disclosure provides a method of treating a subject having multiple myeloma, the method comprising: (a) determining whether a chromosomal translocation is present or absent in a biological sample taken from the subject; and (b) administering a therapeutically effective amount of a Compound of the Disclosure to the subject if a chromosomal translocation is present in the biological sample.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

Figure 1:
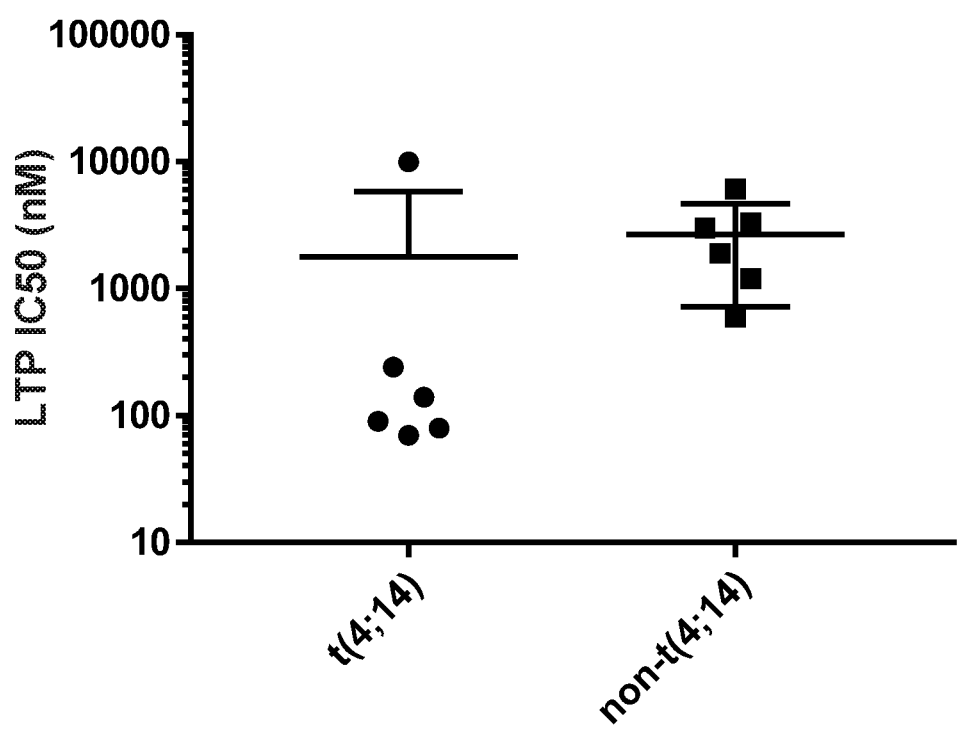
FIG. 1 is a scatter graph showing the selective antiproliferative effects of Cpd. No. 15 in t(4;14) and non-t(4;14) multiple myeloma cell lines.

Compounds of the Disclosure are useful for treating diseases, disorders, or conditions, e.g., cancer, in a subject. In one embodiment, the diseases, disorders, or conditions are responsive to SETD2 protein inhibition. In some embodiments, the Compounds of the Disclosure are SETD2 inhibitors.

I. Compounds of the Disclosure

In one embodiment, Compounds of the Disclosure are compounds having Formula I:

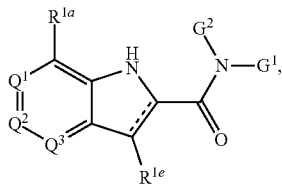

I wherein:
$R^{1a}$ is selected from the group consisting of halogen, alkyl, alkoxy, cycloalkyl, (hydroxy)alkyl, and (cycloalkyl)alkyl;
$Q^1$ is selected from the group consisting of —C($R^{1b}$)═ and —N═;
$Q^2$ is selected from the group consisting of —C($R^{1c}$)═ and —N═;
$Q^3$ is selected from the group consisting of —C($R^{1d}$)═ and —N═;
provided that at least one of $Q^1$, $Q^2$, or $Q^3$ is —C($R^{1b}$)═, —C($R^{1c}$)═, or —C($R^{1d}$)═, respectively;
$R^{1b}$, $R^{1c}$, and $R^{1d}$ are each independently selected from the group consisting of hydrogen, halogen, alkyl, alkenyl, (hydroxy)alkyl, and alkoxy;
$R^{1e}$ is selected from the group consisting of hydrogen, halogen, alkyl, cycloalkyl, (hydroxy)alkyl, and (cycloalkyl)alkyl;
═══ is a single or double bond;
$G^1$ is selected from the group consisting of optionally substituted aryl, optionally substituted heteroaryl, optionally substituted heterocyclo, optionally substituted cycloalkyl, (aryl)alkyl, (heteroaryl)alkyl, (heterocyclo)alkyl, (amino)(aryl)alkyl, (heteroaryl)(aryl)alkyl, (heteroaryl)(heterocyclo)alkyl, (heteroaryl)(carboxamido)alkyl, (heteroaryl)(cycloalkyl)alkyl, (aryl)(alkoxycarbonyl)alkyl, (cycloalkyl)alkyl, (heteroaryl)(amino)alkyl, (cycloalkyl)(alkoxycarbonyl)alkyl, (heteroaryl)(alkoxycarbonyl)alkyl, (heterocyclo)(cycloalkyl)alkyl, (aryl)(cycloalkyl)alkyl, (aryl)(hydroxy)alkyl, (cycloalkyl)(hydroxy)alkyl, (hydroxy)alkyl, optionally substituted alkyl, (aryl)(haloalkyl)alkyl, (cycloalkyl)(haloalkyl)alkyl, (hydroxy)(haloalkyl)alkyl, and (alkoxycarbonyl)(haloalkyl)alkyl; and
$G^2$ is selected from the group consisting of hydrogen and alkyl; or
$G^1$ and $G^2$ taken together with the nitrogen atom to which they are attached form an optionally substituted heterocyclo, or a pharmaceutically acceptable salt or solvate thereof.

In another embodiment, the compound having Formula I is not:

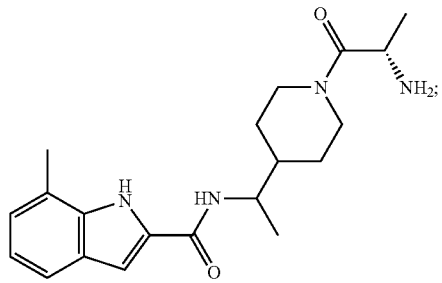

N-(1-(1-(L-alanyl)piperidin-4-yl)ethyl)-7-methyl-1H-indole-2-carboxamide

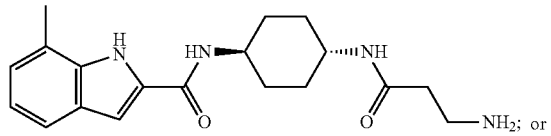

N-((1r,4r)-4-(3-aminopropanamido)cyclohexyl)-7-methyl-1H-indole-2-carboxamide

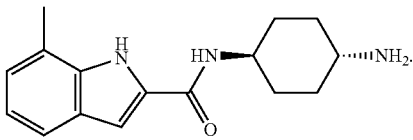

N-((1r,4r)-4-aminocyclohexyl)-7-methyl-1H-indole-2-carboxamide

In another embodiment, Compounds of the Disclosure are compounds having Formula I, wherein:
$R^{1a}$ is selected from the group consisting of halogen, $C_1$-$C_6$ alkyl, $C_1$-$C_6$ alkoxy, $C_3$-$C_8$ cycloalkyl, (hydroxy)$C_{1-6}$ alkyl, and ($C_3$-$C_6$ cycloalkyl)$C_{1-6}$ alkyl;
$R^{1b}$, $R^{1c}$, and $R^{1d}$ are each independently selected from the group consisting of hydrogen, halogen, $C_1$-$C_6$ alkyl, $C_2$-$C_6$ alkenyl, (hydroxy)$C_1$-$C_6$ alkyl, and $C_1$-$C_6$ alkoxy;
$R^{1e}$ is selected from the group consisting of hydrogen and $C_1$-$C_6$ alkyl;
$G^1$ is selected from the group consisting of optionally substituted $C_6$-$C_{10}$ aryl, optionally substituted 5- to 10-membered heteroaryl, optionally substituted 3- to 10-membered heterocyclo, optionally substituted $C_3$-$C_8$ cycloalkyl, ($C_6$-$C_{10}$ aryl)$C_1$-$C_6$ alkyl, (5- to 10-membered heteroaryl)$C_1$-$C_6$ alkyl, (3- to 10-membered heterocyclo)$C_1$-$C_6$ alkyl, (amino)($C_6$-$C_{10}$ aryl)$C_1$-$C_6$ alkyl, (5- to 14-membered heteroaryl)($C_6$-$C_{10}$ aryl)$C_1$-$C_6$ alkyl, (5- to 10-membered heteroaryl)(3- to 10-membered heterocyclo)$C_1$-$C_6$ alkyl, (5- to 10-membered heteroaryl)(carboxamido)$C_1$-$C_6$ alkyl, (5- to 10-membered heteroaryl)($C_3$-$C_6$ cycloalkyl)$C_1$-$C_6$ alkyl, ($C_6$-$C_{10}$ aryl)(alkoxycarbonyl)$C_1$-$C_6$ alkyl, ($C_3$-$C_6$ cycloalkyl)$C_1$-$C_6$ alkyl, (5- to 10-membered heteroaryl)(amino)$C_1$-$C_6$ alkyl, ($C_3$-$C_6$ cycloalkyl)(alkoxycarbonyl)$C_1$-$C_6$ alkyl, (5- to 14-membered heteroaryl)(alkoxycarbonyl)$C_1$-$C_6$ alkyl, (3- to 14-membered heterocyclo)($C_3$-$C_8$ cycloalkyl)$C_1$-$C_6$ alkyl, ($C_{6-10}$ aryl)($C_3$-$C_8$ cycloalkyl)$C_1$-$C_6$ alkyl, ($C_6$-$C_{10}$ aryl)(hydroxy)$C_1$-$C_6$ alkyl, ($C_3$-$C_6$ cycloalkyl)(hydroxy)$C_1$-$C_6$ alkyl, (hydroxy)$C_1$-$C_6$ alkyl, optionally substituted $C_1$-$C_6$ alkyl, ($C_6$-$C_{10}$ aryl)($C_1$-$C_6$ haloalkyl)$C_1$-$C_6$ alkyl, ($C_3$-$C_6$ cycloalkyl)($C_1$-$C_6$ haloalkyl)$C_1$-$C_6$ alkyl, (hydroxy)($C_1$-$C_6$ haloalkyl)$C_1$-$C_6$ alkyl; and (alkoxycarbonyl)($C_1$-$C_6$ haloalkyl)$C_1$-$C_6$ alkyl; and $G^2$ is selected from the group consisting of hydrogen and $C_1$-$C_6$ alkyl; or $G^1$ and $G^2$ taken together with the nitrogen atom to which they are attached form a 5- to 10-membered optionally substituted heterocyclo, or a pharmaceutically acceptable salt or solvate thereof.

In another embodiment, Compounds of the Disclosure are compounds having Formula I, wherein:

$R^{1a}$ is selected from the group consisting of halogen, $C_1$-$C_3$ alkyl, $C_1$-$C_3$ alkoxy, $C_3$-$C_6$ cycloalkyl, (hydroxy)$C_{1-4}$ alkyl, and ($C_3$-$C_6$ cycloalkyl)$C_{1-4}$ alkyl;

$R^{1b}$, $R^{1c}$, and $R^{1d}$ are each independently selected from the group consisting of hydrogen, halogen, $C_1$-$C_3$ alkyl, $C_2$-$C_4$ alkenyl, (hydroxy)$C_1$-$C_4$ alkyl, and $C_1$-$C_3$ alkoxy;

$R^{1e}$ is selected from the group consisting of hydrogen and $C_1$-$C_3$ alkyl;

$G^1$ is selected from the group consisting of optionally substituted $C_6$-$C_{10}$ aryl, optionally substituted 5- to 10-membered heteroaryl, optionally substituted 3- to 10-membered heterocyclo, optionally substituted $C_3$-$C_8$ cycloalkyl, ($C_6$-$C_{10}$ aryl)$C_1$-$C_4$ alkyl, (5- to 10-membered heteroaryl)$C_1$-$C_6$ alkyl, (3- to 10-membered heterocyclo)$C_1$-$C_4$ alkyl, (amino)($C_6$-$C_{10}$ aryl)$C_1$-$C_6$ alkyl, (5- to 14-membered heteroaryl)($C_6$-$C_{10}$ aryl)$C_1$-$C_4$ alkyl, (5- to 10-membered heteroaryl)(3- to 10-membered heterocyclo)$C_1$-$C_4$ alkyl, (5- to 10-membered heteroaryl)(carboxamido)$C_1$-$C_4$ alkyl, (5- to 10-membered heteroaryl)($C_3$-$C_6$ cycloalkyl)$C_1$-$C_4$ alkyl, ($C_6$-$C_{10}$ aryl)(alkoxycarbonyl)$C_1$-$C_4$ alkyl, ($C_3$-$C_6$ cycloalkyl)$C_1$-$C_4$ alkyl, (5- to 10-membered heteroaryl)(amino)$C_1$-$C_4$ alkyl, ($C_3$-$C_6$ cycloalkyl)(alkoxycarbonyl)$C_1$-$C_4$ alkyl, (5- to 14-membered heteroaryl)(alkoxycarbonyl)$C_1$-$C_4$ alkyl, (3- to 14-membered heterocyclo)($C_3$-$C_6$ cycloalkyl)$C_1$-$C_4$ alkyl, ($C_{6-10}$ aryl)($C_3$-$C_6$ cycloalkyl)$C_1$-$C_4$ alkyl, ($C_6$-$C_{10}$ aryl)(hydroxy)$C_1$-$C_4$ alkyl, ($C_3$-$C_6$ cycloalkyl)(hydroxy)$C_1$-$C_4$ alkyl, (hydroxy)$C_1$-$C_4$ alkyl, optionally substituted $C_1$-$C_4$ alkyl, ($C_6$-$C_{10}$ aryl)($C_1$-$C_4$ haloalkyl)$C_1$-$C_4$ alkyl, ($C_3$-$C_6$ cycloalkyl)($C_1$-$C_4$ haloalkyl)$C_1$-$C_4$ alkyl, (hydroxy)($C_1$-$C_4$ haloalkyl)$C_1$-$C_4$ alkyl, and (alkoxycarbonyl)($C_1$-$C_4$ haloalkyl)$C_1$-$C_4$ alkyl; and $G^2$ is selected from the group consisting of hydrogen and $C_1$-$C_4$ alkyl; or $G^1$ and $G^2$ taken together with the nitrogen atom to which they are attached form a 5- to 10-membered optionally substituted heterocyclo, or a pharmaceutically acceptable salt or solvate thereof.

In another embodiment, Compounds of the Disclosure are compounds having Formula I, wherein === is a double bond, or a pharmaceutically acceptable salt or solvate thereof.

In another embodiment, Compounds of the Disclosure are compounds having Formula I, wherein $Q^1$ and $Q^2$ are —C(H)=, or a pharmaceutically acceptable salt or solvate thereof.

In another embodiment, Compounds of the Disclosure are compounds having Formula I, wherein $Q^3$ is —C($R^{1d}$)=; and $R^{1d}$ is selected from the group consisting of hydrogen and halo, or a pharmaceutically acceptable salt or solvate thereof.

In another embodiment, Compounds of the Disclosure are compounds having Formula I, wherein $R^{1e}$ is hydrogen, or a pharmaceutically acceptable salt or solvate thereof.

In another embodiment, Compounds of the Disclosure are compounds having Formula I, wherein $R^{1a}$ is $C_1$-$C_3$ alkyl, or a pharmaceutically acceptable salt or solvate thereof.

In another embodiment, Compounds of the Disclosure are compounds having Formula I, wherein $G^2$ is hydrogen, or a pharmaceutically acceptable salt or solvate thereof.

In another embodiment, Compounds of the Disclosure are compounds having Formula II:

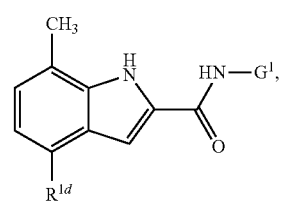

II or a pharmaceutically acceptable salt or solvate thereof, wherein $R^{1d}$ and $G^1$ are as defined in connection with Formula I.

In another embodiment, Compounds of the Disclosure are compounds having Formulae I or II, wherein $R^{1d}$ is selected from the group consisting of hydrogen and fluoro, or a pharmaceutically acceptable salt or solvate thereof.

In another embodiment, Compounds of the Disclosure are compounds having Formula II-A:

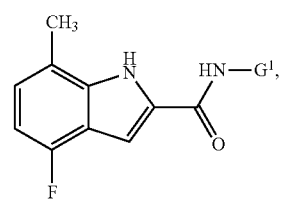

II-A or a pharmaceutically acceptable salt or solvate thereof, wherein $G^1$ is as defined in connection with Formula II.

In another embodiment, Compounds of the Disclosure are compounds having Formulae I, II, or II-A, wherein $G^1$ is selected from the group consisting of optionally substituted $C_6$-$C_{10}$ aryl, optionally substituted 5- to 9-membered heteroaryl, optionally substituted 3- to 10-membered heterocyclo, optionally substituted $C_6$-$C_8$ cycloalkyl, (5- to 9-membered heteroaryl)$C_1$-$C_6$ alkyl, (5- to 9-membered heteroaryl)($C_{6-10}$ aryl)$C_1$-$C_4$ alkyl, (5- to 9-membered heteroaryl heteroaryl)($C_3$-$C_6$ cycloalkyl)$C_1$-$C_4$ alkyl, and ($C_3$-$C_6$ cycloalkyl)$C_1$-$C_4$ alkyl, or a pharmaceutically acceptable salt or solvate thereof.

In another embodiment, Compounds of the Disclosure are compounds having Formula III:

III wherein:
$A^1$ is selected from the group consisting of —N= and —C($R^{2a}$)=;
$R^{2a}$ is selected from the group consisting of hydrogen, alkyl, halogen, and haloalkyl;
$R^{2b}$ is selected from the group consisting of optionally substituted alkyl, optionally substituted heterocyclo, optionally substituted cycloalkyl, optionally substituted heteroaryl, optionally substituted aryl, (carboxamido)alkyl, —$OR^{10c}$, amino, (heterocyclo)alkyl, (amino)alkyl, (hydroxy)alkyl, carboxamido, (heteroaryl)alkyl, —S(=O)$R^{9b}$, —S(=O)$_2R^{9b}$, and —C(=O)$R^{9c}$;
$A^2$ is selected from the group consisting of —N= and —C($R^{2c}$)=;
$R^{2c}$ is selected from the group consisting of hydrogen, alkyl, halogen, and haloalkyl;
$R^{2d}$ is selected from the group consisting of hydrogen, alkyl, halogen, cyano, and haloalkyl;
$R^{2e}$ is selected from the group consisting of hydrogen, alkyl, halogen, and haloalkyl;
$R^{9b}$ is selected from the group consisting of amino, alkyl, optionally substituted cycloalkyl, optionally substituted aryl, optionally substituted heterocyclo, and optionally substituted heteroaryl;
$R^{9c}$ is selected from the group consisting of amino, alkyl, optionally substituted cycloalkyl, optionally substituted aryl, optionally substituted heterocyclo, and optionally substituted heteroaryl; and
$R^{10c}$ is selected from the group consisting of alkyl, (hydroxy)alkyl, and (amino)alkyl; and
$R^{1d}$ is as defined in connection with Formula I, or a pharmaceutically acceptable salt or solvate thereof.

In another embodiment, Compounds of the Disclosure are compounds having Formula III-A:

III-A wherein $R^{1d}$, $R^{2a}$, $R^{2b}$, $R^{2c}$, $R^{2d}$, and $R^{2e}$ are as defined in connection with Formula III, or a pharmaceutically acceptable salt or solvate thereof.

In another embodiment, Compounds of the Disclosure are compounds having Formula III or Formula III-A, wherein:
$R^{2a}$ is selected from the group consisting of hydrogen, $C_1$-$C_4$ alkyl, halogen, and $C_1$-$C_4$ haloalkyl;
$R^{2b}$ is selected from the group consisting of:
(A) unsubstituted 4- to 10-membered heterocyclo;
(B) substituted 4- to 10-membered heterocyclo having one, two, three, or four substituents independently selected from the group consisting of (i) —N($R^{3a}$)C(=O)$R^{4a}$; (ii) —$NR^{5a}R^{5b}$; (iii) unsubstituted 4- to 10-membered heterocyclo; (iv) substituted 4- to 10-membered heterocyclo having one, two, or three substituents independently selected from the group consisting of hydroxy, —$NR^{5c}R^{5d}$, $C_1$-$C_4$ alkyl, $C_1$-$C_6$ alkoxy, —C($R^{6a}$)($R^{6b}$)C(=O)$NR^{5e}R^{5f}$, —C(=O)$R^{4b}$, (hydroxy)$C_1$-$C_4$ alkyl, and halo; (v) unsubstituted $C_3$-$C_6$ cycloalkyl; (vi) (hydroxy)$C_1$-$C_4$ alkyl; (vii) $C_1$-$C_6$ alkyl; (viii) —C(=O)$NR^{5g}R^{5h}$; (ix) halo; (x) —C(=O)$R^{4c}$; (xi) $C_1$-$C_6$ haloalkyl; (xii) hydroxy; (xiii) (amino)$C_1$-$C_4$ alkyl; (xiv) ($C_1$-$C_4$ alkoxy)$C_1$-$C_4$ alkyl; (xv) —S(=O)$_2R^{9a}$; (xvi) (3- to 8-membered heterocyclo)$C_1$-$C_4$ alkyl; (xvii) $C_1$-$C_6$ alkoxy; (xviii) ($C_3$-$C_6$ cycloalkyl)$C_{1-4}$ alkyl; (xix) ($C_{6-10}$ aryl)$C_1$-$C_4$ alkyl; and (xxii) —$OR^{10b}$;
(C) unsubstituted $C_3$-$C_8$ cycloalkyl;
(D) substituted $C_3$-$C_8$ cycloalkyl having one, two, three, or four substituents independently selected from the group consisting of (i) unsubstituted 4- to 10-membered heterocyclo; (ii) substituted 4- to 10-membered heterocyclo having one or two substituents, independently selected from the group consisting of amino and $C_1$-$C_4$ alkyl; (iii) unsubstituted 5- or 6-membered heteroaryl; (iv) substituted 5- or 6-membered heteroaryl having one, two, or three substituents independently selected from the group consisting of halo, $C_1$-$C_4$ alkyl, (3- to 8-membered heterocyclo)alkyl, hydroxy, and amino; (v) —$NR^{5i}R^{5j}$; (vi) cyano; (vii) —N($R^{3d}$)C(=O)$R^{4f}$; (viii) hydroxy; and (ix) $C_1$-$C_4$ alkyl;
(E) unsubstituted 5- to 10-membered heteroaryl;
(F) substituted 5- to 10-membered heteroaryl having one, two, three, or four substituents independently selected from the group consisting of (i) halo; (ii) $C_1$-$C_4$ alkyl; ($C_1$-$C_4$ alkoxy)$C_1$-$C_4$ alkyl; (hydroxy)$C_1$-$C_4$ alkyl; $C_3$-$C_6$ cycloalkyl; (amino)$C_1$-$C_4$ alkyl; unsubstituted $C_3$-$C_6$ cycloalkyl; substituted $C_3$-$C_6$ cycloalkyl having one, two, three, or four substituents independently selected from the group consisting of —$NR^{5g}R^{5h}$; unsubstituted 4- to 14-membered heterocyclo; substituted 4- to 14-membered heterocyclo having one or two substituents independently selected from the group consisting of hydroxy, amino, and $C_1$-$C_4$ alkyl; —$NR^{5q}R^{5r}$; and (ix) (3- to 8-membered heterocyclo) $C_1$-$C_4$ alkyl;
(G) unsubstituted $C_6$-$C_{10}$ aryl;
(H) substituted $C_6$-$C_{10}$ aryl, having one, two, three, or four substituents independently selected from the group consisting of (i) halo; (ii) $C_1$-$C_4$ alkyl; (iii) —$CH_2$N(H)S(=O)$_2R^8$; (iv) (5- to 9-membered heteroaryl)$C_1$-$C_4$ alkyl; (v) —$OR^{10a}$; (vi) —N($R^{3b}$)C(=O)$R^{4b}$; (vii) (amino)$C_1$-$C_4$ alkyl; and (viii) (hydroxy)$C_1$-$C_4$ alkyl;
(I) (carboxamido)$C_1$-$C_4$ alkyl;
(J) —$OR^{10c}$;
(K) —$NR^{5o}R^{5p}$;
(L) (3- to 8-membered heterocyclo)$C_1$-$C_4$ alkyl;
(M) (amino)$C_1$-$C_4$ alkyl;
(N) (hydroxy)$C_1$-$C_4$ alkyl;
(O) —C(=O)$NR^{5s}R^{5t}$;

(P) (5- to 9-membered heteroaryl)$C_1$-$C_4$ alkyl; and
(Q) —S(=O)$_2$$R^{9b}$;

$R^{2c}$ is selected from the group consisting of hydrogen, $C_1$-$C_4$ alkyl, halogen, and $C_1$-$C_4$ haloalkyl;

$R^{2d}$ is selected from the group consisting of hydrogen, $C_1$-$C_4$ alkyl, halogen, cyano, and $C_1$-$C_4$ haloalkyl;

$R^{2e}$ is selected from the group consisting of hydrogen, $C_1$-$C_4$ alkyl, halogen, and $C_1$-$C_4$ haloalkyl;

$R^{3a}$, $R^{3b}$, $R^{3c}$, and $R^{3d}$ are each independently selected from the group consisting of hydrogen, $C_1$-$C_4$ alkyl, optionally substituted $C_3$-$C_6$ cycloalkyl, and optionally substituted 4- to 14-membered heterocyclo;

$R^{4a}$, $R^{4b}$, $R^{4c}$, $R^{4d}$, $R^{4e}$, and $R^{4f}$ are each independently selected from the group consisting of $C_1$-$C_6$ alkyl; $C_1$-$C_6$ haloalkyl; $C_3$-$C_6$ cycloalkyl; $C_1$-$C_6$ alkoxy; ($C_1$-$C_4$ alkoxy)$C_1$-$C_4$ alkyl; ($C_{6-10}$ aryl)$C_1$-$C_4$ alkyl; (5- to 9-membered heteroaryl)$C_1$-$C_4$ alkyl; (amino)$C_1$-$C_4$ alkyl; (hydroxy)$C_1$-$C_4$ alkyl; (cyano)$C_1$-$C_4$ alkyl; unsubstituted 4- to 14-membered heterocyclo; substituted 4- to 14-membered heterocyclo having one or two substituents independently selected from the group consisting of halo and $C_1$-$C_4$ alkyl; unsubstituted $C_6$-$C_{10}$ aryl; substituted $C_6$-$C_{10}$ aryl, having one, two, three, or four substituents independently selected from the group consisting of halo and $C_1$-$C_4$ alkyl; unsubstituted 5- or 6-membered heteroaryl; and substituted 5- or 6-membered heteroaryl having one, two, three, or four substituents independently selected from the group consisting of halo and $C_1$-$C_4$ alkyl;

$R^{5a}$ and $R^{5b}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl;

$R^{5c}$ and $R^{5d}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5c}$ and $R^{5d}$ taken together with the nitrogen atom to which they are attached form an optionally substituted 4- to 14-membered heterocyclo;

$R^{5e}$ and $R^{5f}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5e}$ and $R^{5f}$ taken together with the nitrogen atom to which they are attached form an optionally substituted 4- to 14-membered heterocyclo;

$R^{5g}$ and $R^{5h}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5g}$ and $R^{5h}$ taken together with the nitrogen atom to which they are attached form an optionally substituted 4- to 14-membered heterocyclo;

$R^{5i}$ and $R^{5j}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5i}$ and $R^{5j}$ taken together with the nitrogen atom to which they are attached form an optionally substituted 4- to 14-membered heterocyclo;

$R^{5k}$ and $R^{5l}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5k}$ and $R^{5l}$ taken together with the nitrogen atom to which they are attached form an optionally substituted 4- to 14-membered heterocyclo;

$R^{5m}$ and $R^{5n}$ are independently selected from the group consisting of hydrogen; $C_1$-$C_4$ alkyl; $C_1$-$C_4$ haloalkyl; (hydroxy)$C_1$-$C_4$ alkyl; (amino)$C_1$-$C_4$ alkyl; ($C_1$-$C_4$ alkoxy)$C_1$-$C_4$ alkyl; (5- to 9-membered heteroaryl)$C_1$-$C_4$ alkyl; unsubstituted 5- or 6-membered heteroaryl; substituted 5- or 6-membered heteroaryl having one or two substituents independently selected from the group consisting of halo and $C_1$-$C_4$ alkyl; unsubstituted 4- to 14-membered heterocyclo; and substituted 4- to 14-membered heterocyclo having one or two substituents independently selected from the group consisting of hydroxy, amino, and $C_1$-$C_4$ alkyl; or $R^{5m}$ and $R^{5n}$ taken together with the nitrogen atom to which they are attached form an optionally substituted 4- to 14-membered heterocyclo;

$R^{5o}$ and $R^{5p}$ are independently selected from the group consisting of hydrogen; $C_1$-$C_4$ alkyl; $C_1$-$C_4$ haloalkyl;

(hydroxy)C$_1$-C$_4$ alkyl; (amino)C$_1$-C$_4$ alkyl; (C$_1$-C$_4$ alkoxy)C$_1$-C$_4$ alkyl; (5- to 9-membered heteroaryl)C$_1$-C$_4$ alkyl; unsubstituted 5- or 6-membered heteroaryl; substituted 5- or 6-membered heteroaryl having one or two substituents independently selected from the group consisting of halo and C$_1$-C$_4$ alkyl; unsubstituted 4- to 14-membered heterocyclo; and substituted 4- to 14-membered heterocyclo having one or two substituents independently selected from the group consisting of hydroxy, amino, and C$_1$-C$_4$ alkyl; or R$^{5o}$ and R$^{5p}$ taken together with the nitrogen atom to which they are attached form an optionally substituted 4- to 14-membered heterocyclo;

R$^{5q}$ and R$^{5r}$ are independently selected from the group consisting of hydrogen; C$_1$-C$_4$ alkyl; C$_1$-C$_4$ haloalkyl; (hydroxy)C$_1$-C$_4$ alkyl; (amino)C$_1$-C$_4$ alkyl; (C$_1$-C$_4$ alkoxy)C$_1$-C$_4$ alkyl; (5- to 9-membered heteroaryl)C$_1$-C$_4$ alkyl; unsubstituted 5- or 6-membered heteroaryl; substituted 5- or 6-membered heteroaryl having one or two substituents independently selected from the group consisting of halo and C$_1$-C$_4$ alkyl; unsubstituted 4- to 14-membered heterocyclo; and substituted 4- to 14-membered heterocyclo having one or two substituents independently selected from the group consisting of hydroxy, amino, and C$_1$-C$_4$ alkyl;

R$^{5s}$ and R$^{5t}$ are independently selected from the group consisting of hydrogen; C$_1$-C$_4$ alkyl; C$_1$-C$_4$ haloalkyl; (hydroxy)C$_1$-C$_4$ alkyl; (amino)C$_1$-C$_4$ alkyl; (C$_1$-C$_4$ alkoxy)C$_1$-C$_4$ alkyl; (5- to 9-membered heteroaryl)C$_1$-C$_4$ alkyl; unsubstituted 5- or 6-membered heteroaryl; substituted 5- or 6-membered heteroaryl having one or two substituents independently selected from the group consisting of halo and C$_1$-C$_4$ alkyl; unsubstituted 4- to 14-membered heterocyclo; and substituted 4- to 14-membered heterocyclo having one or two substituents independently selected from the group consisting of hydroxy, amino, and C$_1$-C$_4$ alkyl;

R$^{6a}$, R$^{6b}$, R$^{6c}$, and R$^{6d}$ are each independently selected from the group consisting of hydrogen and C$_1$-C$_4$ alkyl;

R$^8$ is C$_1$-C$_6$ alkyl;

R$^{9a}$ is selected from the group consisting of C$_1$-C$_6$ alkyl; unsubstituted C$_3$-C$_8$ cycloalkyl; and substituted C$_3$-C$_8$ cycloalkyl having one or two substituents independently selected from the group consisting of halo, C$_1$-C$_4$ alkyl, amino, and (amino)C$_1$-C$_4$ alkyl;

R$^{9b}$ is selected from the group consisting of C$_1$-C$_6$ alkyl and amino;

R$^{10a}$ is selected from the group consisting of alkyl, (hydroxy)C$_1$-C$_4$ alkyl, and (amino)C$_1$-C$_4$ alkyl;

R$^{10b}$ is (amino)C$_1$-C$_4$ alkyl; and

R$^{10c}$ is (amino)C$_1$-C$_4$ alkyl, or a pharmaceutically acceptable salt or solvate thereof.

In another embodiment, Compounds of the Disclosure are compounds having Formula III or Formula III-A, wherein R$^{2b}$ is an optionally substituted 3- to 10-membered heterocycle linked to the rest of the molecule through a nitrogen atom, e.g., R$^{2b}$ is:

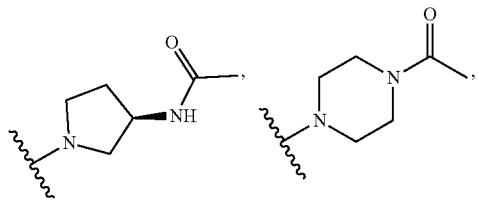

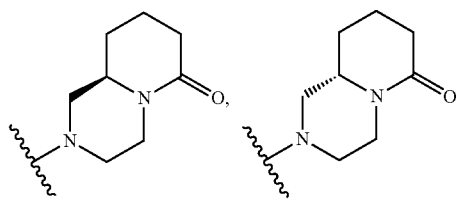

and the like.

In another embodiment, Compounds of the Disclosure are compounds having Formula III or Formula III-A, wherein:

R$^{2b}$ is selected from the group consisting of:

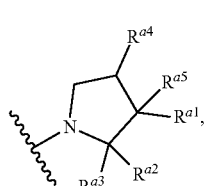

R$^{2b}$-1

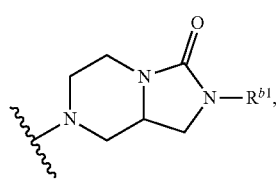

R$^{2b}$-2

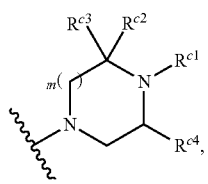

R$^{2b}$-3

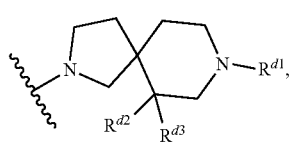

R$^{2b}$-4

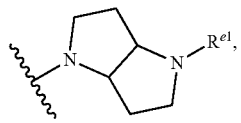

R$^{2b}$-5

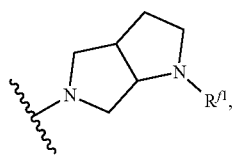

R$^{2b}$-6

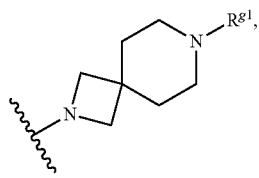

R$^{2b}$-7

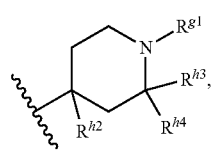
R2b-8
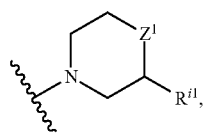
R2b-9
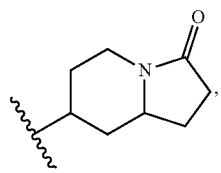
R2b-10
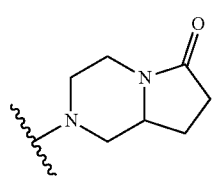
R2b-11
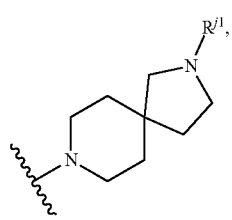
R2b-12
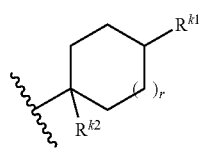
R2b-13
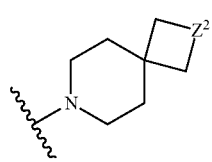
R2b-14
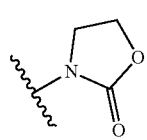
R2b-15
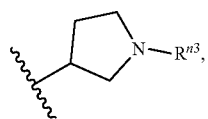
R2b-16
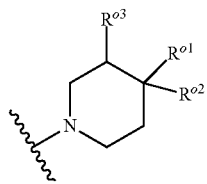
R2b-17
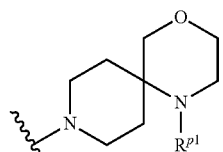
R2b-18
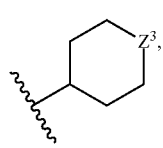
R2b-19
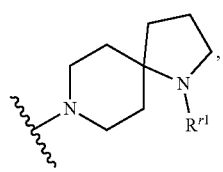
R2b-20
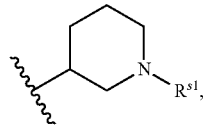
R2b-21
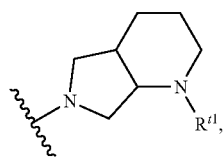
R2b-22
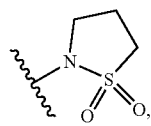
R2b-23
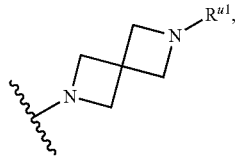
R2b-24
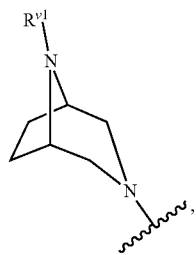
R2b-25

-continued

R$^{2b}$-26

[structure]

R$^{2b}$-27

[structure]

R$^{2b}$-28

[structure]

R$^{2b}$-29

[structure] and

R$^{2b}$-30

[structure]

R$^{a1}$ is selected from the group consisting of —N(R$^{3a}$)C(=O)R$^{4a}$; —NR$^{5a}$R$^{5b}$; unsubstituted 4- to 10-membered heterocyclo; substituted 4- to 10-membered heterocyclo having one, two, or three substituents independently selected from the group consisting of hydroxy, —NR$^{5c}$R$^{5d}$, C$_1$-C$_4$ alkyl, C$_1$-C$_6$ alkoxy, —C(R$^{6a}$)(R$^{6b}$)C(=O)NR$^{5e}$R$^{5f}$, —C(=O)R$^{4b}$, (hydroxy)C$_1$-C$_4$ alkyl, and halo;

R$^{a2}$ and R$^{a3}$ are each hydrogen; or

R$^{a2}$ and R$^{a3}$ taken together with the carbon atom to which they are attached form a C(=O) group;

R$^{a4}$ is selected from the group consisting of hydrogen, halo, and hydroxy;

R$^{a5}$ is selected from the group consisting of hydrogen, C$_1$-C$_4$ alkyl, and C$_3$-C$_6$ cycloalkyl;

R$^{b1}$ is selected from the group consisting of hydrogen, C$_1$-C$_4$ alkyl, and C$_3$-C$_6$ cycloalkyl;

R$^{c1}$ is selected from the group consisting of hydrogen, C$_1$-C$_4$ alkyl, C$_3$-C$_6$ cycloalkyl, and —C(=O)R$^{4c}$;

R$^{c2}$ and R$^{c3}$ are each independently selected from the group consisting of hydrogen, C$_1$-C$_4$ alkyl, and C$_1$-C$_4$ haloalkyl; or R$^{c2}$ and R$^{c3}$ taken together with the carbon atom to which they are attached form a C(=O) group;

R$^{c4}$ is selected from the group consisting of hydrogen and C$_1$-C$_4$ alkyl;

m is 1 or 2;

R$^{d1}$ is selected from the group consisting of hydrogen, C$_1$-C$_4$ alkyl, and —C(=O)R$^{4c}$;

R$^{d2}$ and R$^{d3}$ are each independently selected from the group consisting of hydrogen and fluoro;

R$^{e1}$ is selected from the group consisting of hydrogen, C$_1$-C$_4$ alkyl, C$_3$-C$_6$ cycloalkyl, and —C(=O)R$^{4c}$;

R$^{f1}$ is selected from the group consisting of hydrogen, C$_1$-C$_4$ alkyl, C$_3$-C$_6$ cycloalkyl, and —C(=O)R$^{4c}$;

R$^{g1}$ is selected from the group consisting of hydrogen, C$_1$-C$_4$ alkyl, —C(=O)R$^{4c}$, C$_1$-C$_4$ haloalkyl, (C$_1$-C$_4$ alkoxy)C$_1$-C$_4$ alkyl R$^{h1}$ is selected from the group consisting of hydrogen, C$_1$-C$_4$ alkyl, C$_3$-C$_6$ cycloalkyl, and —C(=O)R$^{4c}$;

R$^{h2}$ is selected from the group consisting of hydrogen and C$_1$-C$_4$ alkyl;

R$^{h3}$ and R$^{h4}$ are each independently selected from the group consisting of hydrogen and C$_1$-C$_4$ alkyl; or R$^{h3}$ and R$^{h4}$ taken together with the carbon atom to which they are attached form a C(=O) group;

R$^{i1}$ is selected from the group consisting of hydrogen, C$_1$-C$_4$ alkyl, C$_3$-C$_6$ cycloalkyl, (hydroxy)C$_1$-C$_4$ alkyl, —N(R$^{3a}$)C(=O)R$^{4a}$, and (amino)C$_1$-C$_4$ alkyl;

Z$^1$ is selected from the group consisting of —CH$_2$— and —O—;

R$^{j1}$ is selected from the group consisting of hydrogen, C$_1$-C$_4$ alkyl, C$_3$-C$_6$ cycloalkyl, and —C(=O)R$^{4c}$;

R$^{k1}$ is selected from the group consisting of C$_1$-C$_4$ alkyl, unsubstituted 4- to 14-membered heterocyclo and —NR$^{5a}$R$^{5b}$;

R$^{k2}$ is selected from the group consisting of hydrogen, hydroxy, and C$_1$-C$_4$ alkyl;

r is 0, 1, or 2;

Z$^2$ is selected from the group consisting of —O— and —N(R$^{m3}$)—;

R$^{m3}$ is selected from the group consisting of hydrogen, C$_1$-C$_4$ alkyl, and C$_1$-C$_4$ haloalkyl;

R$^{n3}$ is selected from the group consisting of hydrogen, C$_1$-C$_4$ alkyl, and —C(=O)R$^{4c}$;

R$^{o1}$ is selected from the group consisting of hydroxy, (hydroxy)C$_1$-C$_4$ alkyl, (amino)C$_1$-C$_4$ alkyl, (C$_1$-C$_4$ alkoxy)C$_1$-C$_4$ alkyl, C$_1$-C$_4$ alkoxy, —NR$^{5a}$R$^{5b}$, unsubstituted 4- to 14-membered heterocyclo, substituted 4- to 14-membered heterocyclo having one, two, or three substituents independently selected from the group consisting of halo, C$_1$-C$_4$ alkyl and C$_1$-C$_4$ alkoxy;

R$^{o2}$ is selected from the group consisting of hydrogen, C$_1$-C$_4$ alkyl, and (C$_1$-C$_4$ alkoxy)C$_1$-C$_4$ alkyl R$^{o3}$ is selected from the group consisting of hydrogen, fluoro, and C$_1$-C$_4$ alkyl;

R$^{p1}$ is selected from the group consisting of hydrogen, C$_1$-C$_4$ alkyl, and —C(=O)R$^{4c}$;

Z$^3$ is selected from the group consisting of —O— and —N(R$^{q1}$)—;

R$^{q1}$ is selected from the group consisting of hydrogen and C$_1$-C$_4$ alkyl;

R$^{r1}$ is selected from the group consisting of hydrogen, C$_1$-C$_4$ alkyl, and —C(=O)R$^{4c}$;

R$^{s1}$ is selected from the group consisting of hydrogen, C$_1$-C$_4$ alkyl, and —C(=O)R$^{4c}$;

R$^{t1}$ is selected from the group consisting of hydrogen, C$_1$-C$_4$ alkyl, and —C(=O)R$^{4c}$;

R$^{u1}$ is selected from the group consisting of hydrogen, C$_1$-C$_4$ alkyl, and —C(=O)R$^{4c}$;

R$^{v1}$ is selected from the group consisting of hydrogen, C$_1$-C$_4$ alkyl, and —C(=O)R$^{4c}$;

R$^{x1}$ is selected from the group consisting of hydrogen, C$_1$-C$_4$ alkyl, and —C(=O)R$^{4c}$;

R$^{y1}$ is selected from the group consisting of hydrogen, C$_1$-C$_4$ alkyl, and —C(=O)R$^{4c}$;

$R^{z1}$ is selected from the group consisting of hydrogen and $C_1$-$C_4$ alkyl; and $R^{z1}$ is selected from the group consisting of hydrogen and $C_1$-$C_4$ alkyl, or a pharmaceutically acceptable salt or solvate thereof.

In another embodiment, Compounds of the Disclosure are compounds having Formula III or Formula III-A, wherein:

$R^{2b}$ is selected from the group consisting of:

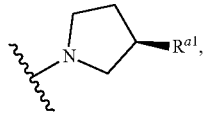
$R^{2b}$-1A

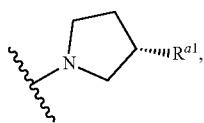
$R^{2b}$-1B

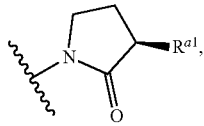
$R^{2b}$-1C

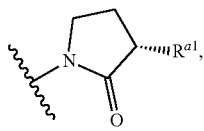
$R^{2b}$-1D

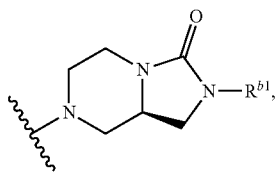
$R^{2b}$-2A

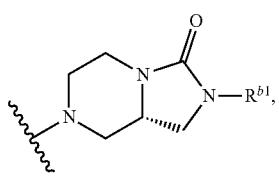
$R^{2b}$-2B

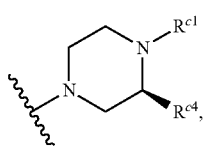
$R^{2b}$-3A

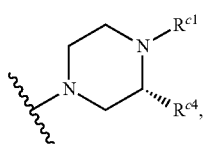
$R^{2b}$-3B

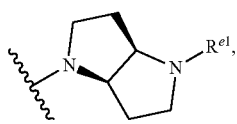
$R^{2b}$-5A

-continued

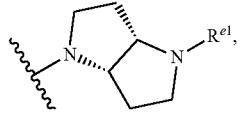
$R^{2b}$-5B

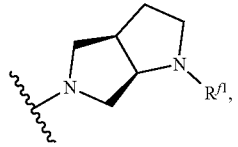
$R^{2b}$-6A

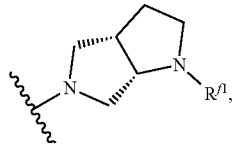
$R^{2b}$-6B

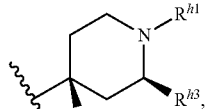
$R^{2b}$-8A

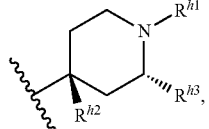
$R^{2b}$-8B

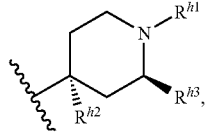
$R^{2b}$-8C

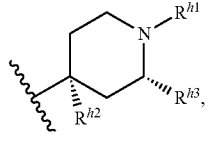
$R^{2b}$-8D

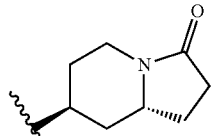
$R^{2b}$-10A $R^{2b}$-10B

-continued
R²ᵇ-10C
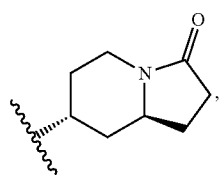
R²ᵇ-10D
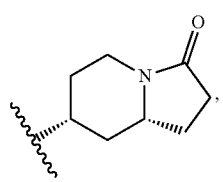
R²ᵇ-11A
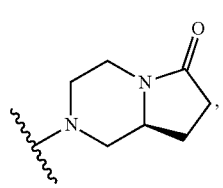
R²ᵇ-11B
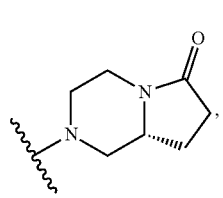
R²ᵇ-13A
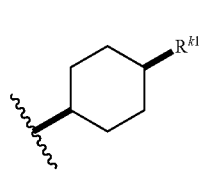
R²ᵇ-13B
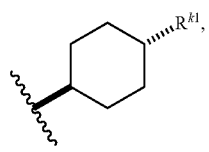
R²ᵇ-13C
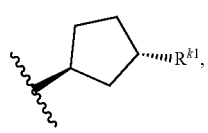
R²ᵇ-13D
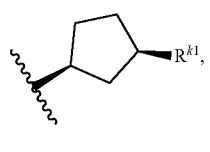
R²ᵇ-13E
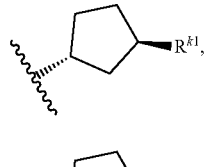
R²ᵇ-13F
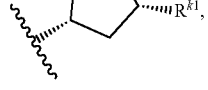
-continued
R²ᵇ-16A
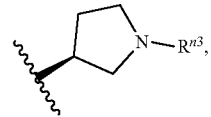
R²ᵇ-16B
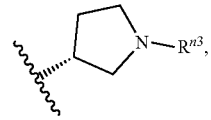
R²ᵇ-21A
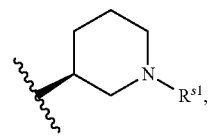
R²ᵇ-21B
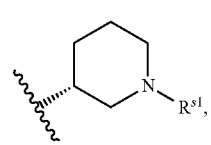
R²ᵇ-22A
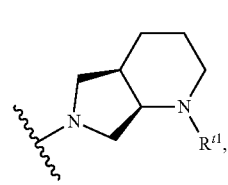
R²ᵇ-22B
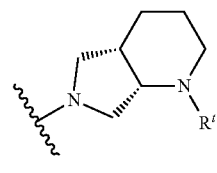
R²ᵇ-26A
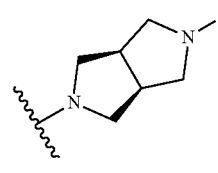
R²ᵇ-26B
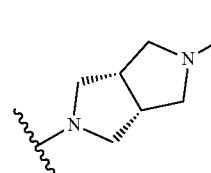
R²ᵇ-27A
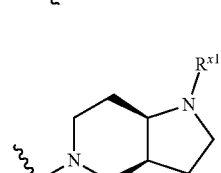
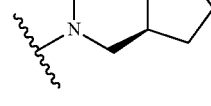

21

-continued

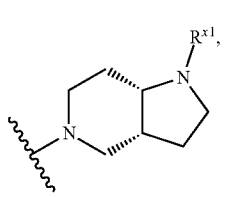 R$^{2b}$-27B

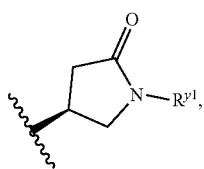 R$^{2b}$-28A

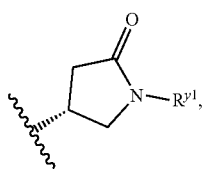 R$^{2b}$-28B

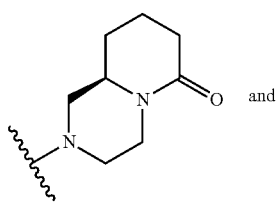 R$^{2b}$-30A and

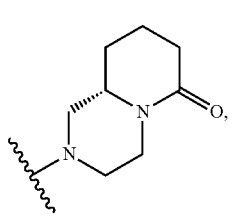 R$^{2b}$-30B or a pharmaceutically acceptable salt or solvate thereof.

In another embodiment, Compounds of the Disclosure are compounds having Formula III or Formula III-A, wherein R$^{2b}$ is R$^{2b}$-1, R$^{2b}$-1A, R$^{2b}$-1B, R$^{2b}$-1C, or R$^{2b}$-1D, or a pharmaceutically acceptable salt or solvate thereof. In another embodiment, R$^{a1}$ is —N(R$^{3a}$)C(=O)R$^{4a}$. In another embodiment, R$^{a1}$ is —NR$^{5a}$R$^{5b}$ In another embodiment, R$_{a1}$ is —NR$^{5a}$R$^{5b}$ and R$^{5a}$ and R$^{5b}$ are independently selected from the group consisting of hydrogen and C$_1$-C$_4$ alkyl. In another embodiment, R$^{a1}$ is optionally substituted 4- to 10-membered heterocyclo.

In another embodiment, Compounds of the Disclosure are compounds having Formula III or Formula III-A, wherein R$^{2b}$ is R$^{2b}$-2, R$^{2b}$-2A, or R$^{2b}$-2b, or a pharmaceutically acceptable salt or solvate thereof. In another embodiment, R$^{b1}$ is C$_1$-C$_4$ alkyl.

In another embodiment, Compounds of the Disclosure are compounds having Formula III or Formula III-A, wherein R$^{2b}$ is R$^{2b}$-3, R$^{2b}$-3A, or R$^{2b}$-3B, or a pharmaceutically acceptable salt or solvate thereof. In another embodiment, R$^{c1}$ is selected from the group consisting of C$_1$-C$_4$ alkyl, C$_3$-C$_6$ cycloalkyl, and —C(=O)R$^{4c}$. In another embodiment, R$^{c2}$ and R$^{c3}$ are each hydrogen. In another embodiment, R$^{c2}$ and R$^{c3}$ taken together with the carbon atom to which they are attached form a C(=O) group. In another embodiment, R$^{c4}$ is hydrogen. In another embodiment, m is 1.

22

In another embodiment, Compounds of the Disclosure are compounds having Formula III or Formula III-A, wherein R$^{2b}$ is R$^{2b}$-4, or a pharmaceutically acceptable salt or solvate thereof. In another embodiment, R$^{d1}$ is C(=O)R$^{4c}$. In another embodiment, R$^{d2}$ and R$^{d3}$ are each hydrogen or fluoro.

In another embodiment, Compounds of the Disclosure are compounds having Formula III or Formula III-A, wherein R$^{2b}$ is R$^{2b}$-5, R$^{2b}$-5A, or R$^{2b}$-5B, or a pharmaceutically acceptable salt or solvate thereof. In another embodiment, R$^{c1}$ is —C(=O)R$^{4c}$.

In another embodiment, Compounds of the Disclosure are compounds having Formula III or Formula III-A, wherein R$^{2b}$ is R$^{2b}$-6, R$^{2b}$-6A, or R$^{2b}$-6B, or a pharmaceutically acceptable salt or solvate thereof. In another embodiment, R$^1$ is C(=O)R$^{4c}$.

In another embodiment, Compounds of the Disclosure are compounds having Formula III or Formula III-A, wherein R$^{2b}$ is R$^{2b}$-7, or a pharmaceutically acceptable salt or solvate thereof. In another embodiment, R$^{g1}$ is C(=O)R$^{4c}$.

In another embodiment, Compounds of the Disclosure are compounds having Formula III or Formula III-A, wherein R$^{2b}$ is R$^{2b}$-8, R$^{2b}$-8A, R$^{2b}$-8B, R$^{2b}$-8C, or R$^{2b}$-8D, or a pharmaceutically acceptable salt or solvate thereof. In another embodiment, R$^{h1}$ is —C(=O)R$^{4c}$. In another embodiment, R$^{h2}$ is selected from the group consisting of hydrogen and C$_1$-C$_3$ alkyl. In another embodiment, R$^{h3}$ is hydrogen.

In another embodiment, Compounds of the Disclosure are compounds having Formula III or Formula III-A, wherein R$^{2b}$ is R$^{2b}$-9, or a pharmaceutically acceptable salt or solvate thereof.

In another embodiment, Compounds of the Disclosure are compounds having Formula III or Formula III-A, wherein R$^{2b}$ is selected from the group consisting of R$^{2b}$-10, R$^{2b}$-10A, R$^{2b}$-10B, R$^{2b}$-10C, and R$^{2b}$-10d, or a pharmaceutically acceptable salt or solvate thereof.

In another embodiment, Compounds of the Disclosure are compounds having Formula III or Formula III-A, wherein R$^{2b}$ is selected from the group consisting of R$^{2b}$-11, R$^{2b}$-11A and R$^{2b}$-11B, or a pharmaceutically acceptable salt or solvate thereof.

In another embodiment, Compounds of the Disclosure are compounds having Formula III or Formula III-A, wherein R$^{2b}$ is R$^{2b}$-12, or a pharmaceutically acceptable salt or solvate thereof. In another embodiment, R$^{i1}$ is —C(=O)R$^{4c}$.

In another embodiment, Compounds of the Disclosure are compounds having Formula III or Formula III-A, wherein R$^{2b}$ is selected from the group consisting of R$^{2b}$-13, R$^{2b}$-13A, R$^{2b}$-13B, R$^{2b}$-13C, R$^{2b}$-13D, R$^{2b}$-13E, and R$^{2b}$-13F, or a pharmaceutically acceptable salt or solvate thereof.

In another embodiment, Compounds of the Disclosure are compounds having Formula III or Formula III-A, wherein R$^{2b}$ is R$^{2b}$-14, or a pharmaceutically acceptable salt or solvate thereof.

In another embodiment, Compounds of the Disclosure are compounds having Formula III or Formula III-A, wherein R$^{2b}$ is R$^{2b}$-15, or a pharmaceutically acceptable salt or solvate thereof.

In another embodiment, Compounds of the Disclosure are compounds having Formula III or Formula III-A, wherein R$^{2b}$ is selected from the group consisting of R$^{2b}$-16, R$^{2b}$-16A and R$^{2b}$-16B, or a pharmaceutically acceptable salt or solvate thereof. In another embodiment, R$^{n3}$ is —C(=O)R$^{4c}$.

In another embodiment, Compounds of the Disclosure are compounds having Formula III or Formula III-A, wherein $R^{2b}$ is $R^{2b}$-17, or a pharmaceutically acceptable salt or solvate thereof.

In another embodiment, Compounds of the Disclosure are compounds having Formula III or Formula III-A, wherein $R^{2b}$ is $R^{2b}$-18, or a pharmaceutically acceptable salt or solvate thereof.

In another embodiment, Compounds of the Disclosure are compounds having Formula III or Formula III-A, wherein $R^{2b}$ is $R^{2b}$-19, or a pharmaceutically acceptable salt or solvate thereof.

In another embodiment, Compounds of the Disclosure are compounds having Formula III or Formula III-A, wherein $R^{2b}$ is $R^{2b}$-20, or a pharmaceutically acceptable salt or solvate thereof.

In another embodiment, Compounds of the Disclosure are compounds having Formula III or Formula III-A, wherein $R^{2b}$ is selected from the group consisting of $R^{2b}$-21, $R^{2b}$-21A and $R^{2b}$-21B, or a pharmaceutically acceptable salt or solvate thereof.

In another embodiment, Compounds of the Disclosure are compounds having Formula III, wherein $R^{2b}$ is selected from the group consisting of $R^{2b}$-22, $R^{2b}$-22A and $R^{2b}$-22B, or a pharmaceutically acceptable salt or solvate thereof.

In another embodiment, Compounds of the Disclosure are compounds having Formula III or Formula III-A, wherein $R^{2b}$ is $R^{2b}$-23, or a pharmaceutically acceptable salt or solvate thereof.

In another embodiment, Compounds of the Disclosure are compounds having Formula III or Formula III-A, wherein $R^{2b}$ is $R^{2b}$-24, or a pharmaceutically acceptable salt or solvate thereof.

In another embodiment, Compounds of the Disclosure are compounds having Formula III or Formula III-A, wherein $R^{2b}$ is $R^{2b}$-25, or a pharmaceutically acceptable salt or solvate thereof.

In another embodiment, Compounds of the Disclosure are compounds having Formula III or Formula III-A, wherein $R^{2b}$ is selected from the group consisting of $R^{2b}$-26, $R^{2b}$-26A and $R^{2b}$-26B, or a pharmaceutically acceptable salt or solvate thereof.

In another embodiment, Compounds of the Disclosure are compounds having Formula III or Formula III-A, wherein $R^{2b}$ is selected from the group consisting of $R^{2b}$-27, $R^{2b}$-27A and $R^{2b}$-27B, or a pharmaceutically acceptable salt or solvate thereof.

In another embodiment, Compounds of the Disclosure are compounds having Formula III or Formula III-A, wherein $R^{2b}$ is selected from the group consisting of $R^{2b}$-28, $R^{2b}$-28A and $R^{2b}$-28B, or a pharmaceutically acceptable salt or solvate thereof.

In another embodiment, Compounds of the Disclosure are compounds having Formula III or Formula III-A, wherein $R^{2b}$ is $R^{2b}$-29, or a pharmaceutically acceptable salt or solvate thereof.

In another embodiment, Compounds of the Disclosure are compounds having Formula III or Formula III-A, wherein $R^{2b}$ is $R^{2b}$-30, $R^{2b}$-30A, or $R^{2b}$-30B, or a pharmaceutically acceptable salt or solvate thereof.

In another embodiment, Compounds of the Disclosure are compounds having Formula III or Formula III-A, wherein $R^{2b}$ is any one or more of the $R^{11a}$ groups provided in connection with Formula IV, see below, or a pharmaceutically acceptable salt or solvate thereof.

In another embodiment, Compounds of the Disclosure are compounds having Formula III or Formula III-A, wherein $R^{4c}$; is $C_1$-$C_4$ alkyl, or a pharmaceutically acceptable salt or solvate thereof.

In another embodiment, Compounds of the Disclosure are compounds having Formula III or Formula III-A, wherein $R^{2d}$ is selected from the group consisting of hydrogen, fluoro, and chloro, or a pharmaceutically acceptable salt or solvate thereof.

In another embodiment, Compounds of the Disclosure are compounds having Formula III or Formula III-A, wherein $R^{2d}$ is hydrogen, or a pharmaceutically acceptable salt or solvate thereof.

In another embodiment, Compounds of the Disclosure are compounds having Formula III in any of the above described embodiments, wherein $A^1$ and $A^2$ are —C(H)=; $R^{2e}$ is hydrogen; and $R^{2d}$ is selected from the group consisting of hydrogen and halogen, or a pharmaceutically acceptable salt or solvate thereof.

In another embodiment, Compounds of the Disclosure are compounds having Formula III or Formula III-A, wherein $R^{2d}$ is fluoro, or a pharmaceutically acceptable salt or solvate thereof.

In another embodiment, Compounds of the Disclosure are compounds having Formula IV:

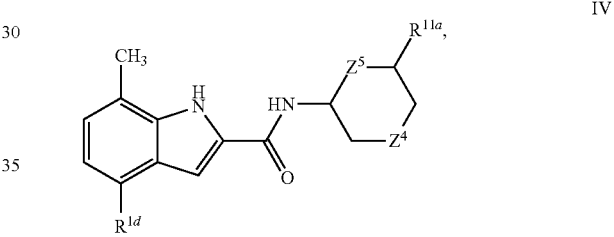

IV wherein:
$Z^4$ is selected from the group consisting of —O—, —C($R^{28a}$)($R^{28b}$)—, and —N($R^{23}$)—; or $Z^4$ is absent;
$Z^5$ is selected from the group consisting of —CH$_2$— and —CH$_2$CH$_2$—;
$R^{11a}$ is selected from the group consisting of optionally substituted alkyl, optionally substituted heterocyclo, optionally substituted heteroaryl, and —N($R^{12b}$)C(=O)$R^{13c}$;
$R^{12b}$ is selected from the group consisting of hydrogen, alkyl, cycloalkyl, and heterocyclo;
$R^{13c}$ is selected from the group consisting of alkyl, haloalkyl, alkoxy, (alkoxy)alkyl, (hydroxy)alkyl, (cyano)alkyl, optionally substituted aryl, optionally substituted heteroaryl, optionally substituted cycloalkyl, and optionally substituted heterocycle, amino, (amino)alkyl, ($C_3$-$C_6$ cycloalkyl)oxy, and (4- to 8-membered heterocyclo)oxy;
$R^{23}$ is selected from the group consisting of hydrogen and $C_1$-$C_4$ alkyl;
$R^{28a}$ and $R^{28b}$ are independently selected from the group consisting of hydrogen, alkyl, and halo; and
$R^{1d}$ is as defined in connection with Formula I, or a pharmaceutically acceptable salt or solvate thereof.

In another embodiment, Compounds of the Disclosure are compounds having Formula IV, wherein $Z^4$ is selected from the group consisting of —O— and —CH$_2$—; or $Z^4$ is absent, or a pharmaceutically acceptable salt or solvate thereof.

In another embodiment, Compounds of the Disclosure are compounds having Formula IV, wherein:
- $Z^4$ is selected from the group consisting of —O— and —CH$_2$—; or $Z^4$ is absent;
- $Z^5$ is selected from the group consisting of —CH$_2$— and —CH$_2$CH$_2$—;
- $R^{13}$, is selected from the group consisting of alkyl, haloalkyl, alkoxy, (alkoxy)alkyl, (hydroxy)alkyl, (cyano)alkyl, optionally substituted aryl, optionally substituted heteroaryl, optionally substituted cycloalkyl, and optionally substituted heterocycle, and
- $R^{1d}$ is as defined in connection with Formula I, or a pharmaceutically acceptable salt or solvate thereof.

In another embodiment, Compounds of the Disclosure are compounds having Formula IV-A:

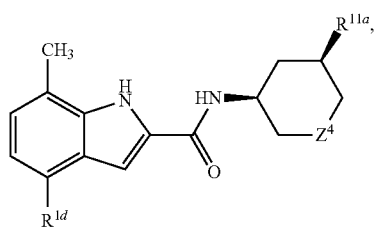

IV-A or a pharmaceutically acceptable salt or solvate thereof, wherein $R^{1d}$, $R^{11a}$, and $Z^4$ are as defined in connection with Formula IV.

In another embodiment, Compounds of the Disclosure are compounds having Formula IV-B:

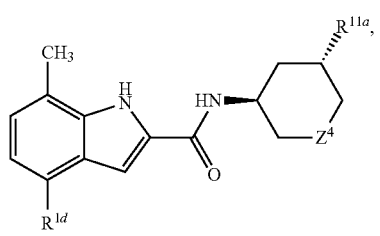

IV-B or a pharmaceutically acceptable salt or solvate thereof, wherein $R^{1d}$, $R^{11a}$, and $Z^4$ are as defined in connection with Formula IV.

In another embodiment, Compounds of the Disclosure are compounds having Formula IV-C:

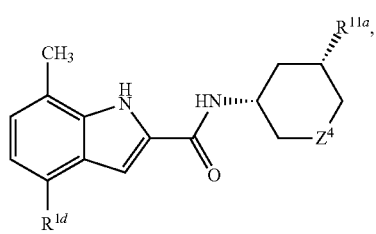

IV-C or a pharmaceutically acceptable salt or solvate thereof, wherein $R^{1d}$, $R^{11a}$ and $Z^4$ are as defined in connection with Formula IV.

In another embodiment, Compounds of the Disclosure are compounds having Formula IV-D:

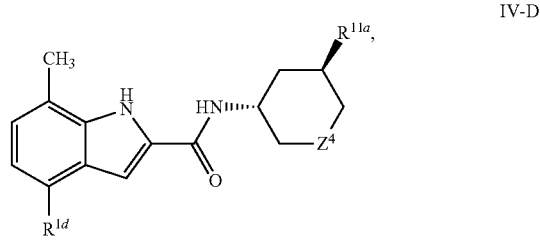

IV-D or a pharmaceutically acceptable salt or solvate thereof, wherein $R^{1d}$, $R^{11a}$, and $Z^4$ are as defined in connection with Formula IV.

In another embodiment, Compounds of the Disclosure are compounds having any one of Formulae IV, IV-A, IV-B, IV-C, or IV-D, wherein:
- $R^{11a}$ is selected from the group consisting of: (A) unsubstituted 4- to 14-membered heterocyclo; (B) substituted 4- to 14-membered heterocyclo having one, two or three substituents independently selected from the group consisting of —N(R$^{12a}$)C(=O)R$^{13a}$; —C(=O)R$^{13b}$; C$_1$-C$_4$ alkyl; (C$_1$-C$_4$ alkoxy)C$_1$-C$_4$ alkyl; (hydroxy)C$_1$-C$_4$ alkyl; C$_1$-C$_4$ haloalkyl; amino; hydroxy; —N(R$^{12a}$)S(=O)$_2$R$^{24}$; —S(=O)$_2$R$^{24}$; unsubstituted C$_3$-C$_6$ cycloalkyl; substituted C$_3$-C$_6$ cycloalkyl having one or two substituents independently selected from the group consisting of halo, hydroxy, C$_1$-C$_4$ alkyl, amino, and (amino)C$_1$-C$_4$ alkyl; unsubstituted 4- to 14-membered heterocyclo; and substituted 4- to 14-membered heterocyclo having one or two substituents independently selected from the group consisting of amino, hydroxy, and C$_1$-C$_4$ alkyl; (C) unsubstituted 5- to 10-membered heteroaryl; (D) substituted 5- or 6-membered heteroaryl having one, two, three, or four substituents independently selected from the group consisting of halo, C$_1$-C$_4$ alkyl, and (amino)alkyl; (E) C$_1$-C$_6$ alkyl; and (F) —N(R$^{12b}$)C(=O)R$^{13c}$;
- $R^{12a}$ and $R^{12b}$ are each independently selected from the group consisting of hydrogen, C$_1$-C$_4$ alkyl, (C$_1$-C$_4$ alkoxy)C$_1$-C$_4$ alkyl, and (hydroxy)C$_1$-C$_4$ alkyl;
- $R^{13a}$, $R^{13b}$, and $R^{13c}$ are each independently selected from the group consisting of C$_1$-C$_6$ alkyl; C$_1$-C$_6$ haloalkyl; unsubstituted C$_3$-C$_6$ cycloalkyl; C$_1$-C$_6$ alkoxy; (C$_1$-C$_4$ alkoxy)C$_1$-C$_4$ alkyl; (hydroxy)C$_1$-C$_4$ alkyl; (cyano)alkyl; unsubstituted C$_6$-C$_{10}$ aryl; substituted C$_6$-C$_{10}$ aryl, having one, two, three, or four substituents independently selected from the group consisting of halo, amino, hydroxy, and C$_1$-C$_4$ alkyl; unsubstituted 5- or 6-membered heteroaryl; substituted 5- or 6-membered heteroaryl having one, two, three, or four substituents independently selected from the group consisting of halo, amino, hydroxy, and C$_1$-C$_4$ alkyl; unsubstituted 4- to 14-membered heterocyclo; substituted 4- to 14-membered heterocyclo having one or two substituents independently selected from the group consisting of amino, hydroxy, and C$_1$-C$_4$ alkyl; amino; (amino)alkyl; (C$_3$-C$_6$ cycloalkyl)oxy; and (4- to 8-membered heterocyclo)oxy; and
- $R^{24}$ is selected from the group consisting of C$_1$-C$_4$ alkyl and (hydroxy)C$_1$-C$_4$ alkyl.

In another embodiment, Compounds of the Disclosure are compounds having Formula IV, IV-A, IV-B, IV-C, or IV-D, wherein $Z^4$ is —C(R$^{21a}$)(R$^{28b}$)—; and R$^{28a}$ and R$^{28b}$ are independently selected from the group consisting of hydrogen, $C_1$-$C_4$ alkyl, and fluoro, or a pharmaceutically acceptable salt or solvate thereof.

In another embodiment, Compounds of the Disclosure are compounds having Formula IV, IV-A, IV-B, IV-C, or IV-D, wherein $Z^4$ is —$C(R^{28a})(R^{28b})$—; $R^{28a}$ is hydrogen; and $R^{28b}$ is selected from the group consisting of $C_1$-$C_4$ alkyl and fluoro, or a pharmaceutically acceptable salt or solvate thereof.

In another embodiment, Compounds of the Disclosure are compounds having Formula IV, IV-A, IV-B, IV-C, or IV-D, wherein $Z^4$ is —$C(R^{28a})(R^{28b})$—; and $R^{28a}$ and $R^{28b}$ are independently $C_1$-$C_4$ alkyl, or a pharmaceutically acceptable salt or solvate thereof.

In another embodiment, Compounds of the Disclosure are compounds having Formula IV, IV-A, IV-B, IV-C, or IV-D, wherein $Z^4$ is selected from the group consisting of —O—, —$CH_2$—, and —$N(R^{23})$, or $Z^4$ is absent, or a pharmaceutically acceptable salt or solvate thereof.

In another embodiment, Compounds of the Disclosure are compounds having any one of Formulae IV, IV-A, IV-B, IV-C, or IV-D, wherein $Z^4$ is —$CH_2$—, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is an optionally substituted 3- to 10-membered heterocycle linked to the rest of the molecule through a nitrogen atom, e.g., $R^{11a}$ is

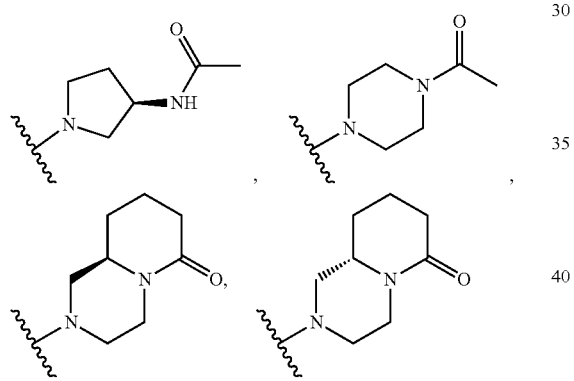

and the like.

In another embodiment, Compounds of the Disclosure are compounds having any one of Formulae IV, IV-A, IV-B, IV-C, or IV-D, wherein $R^{11a}$ is a substituted 4- to 14-membered heterocyclo selected from the group consisting of:

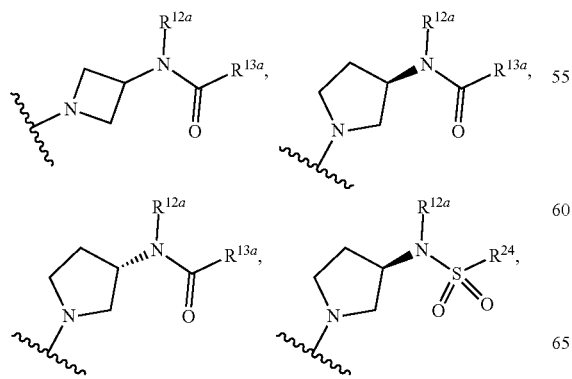

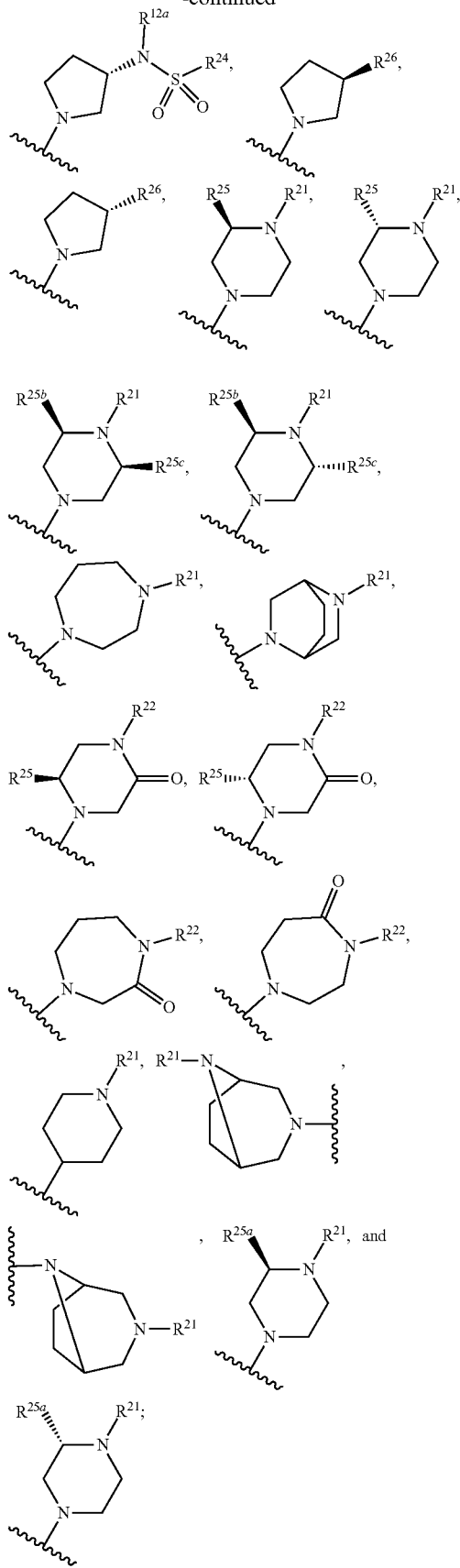

R$^{12a}$ is selected from the group consisting of hydrogen, C$_1$-C$_3$ alkyl, (C$_1$-C$_4$ alkoxy)C$_1$-C$_4$ alkyl; and (hydroxy)C$_1$-C$_4$ alkyl;

R$^{13a}$ is selected from the group consisting of C$_1$-C$_4$ alkyl; amino; unsubstituted C$_3$-C$_6$ cycloalkyl; substituted C$_3$-C$_6$ cycloalkyl having one or two substituents independently selected from the group consisting of halo, hydroxy, C$_1$-C$_4$ alkyl, amino, and (amino)C$_1$-C$_4$ alkyl; (C$_1$-C$_4$ alkoxy)C$_1$-C$_4$ alkyl; (hydroxy)C$_1$-C$_4$ alkyl; unsubstituted 4- to 14-membered heterocyclo; and substituted 4- to 14-membered heterocyclo having one or two substituents independently selected from the group consisting of amino, hydroxy, and C$_1$-C$_4$ alkyl;

R$^{13b}$ is selected from the group consisting of C$_1$-C$_4$ alkyl; amino; C$_1$-C$_4$ haloalkyl; C$_1$-C$_4$ alkoxy; (hydroxy)C$_1$-C$_4$ alkyl; (C$_1$-C$_4$ alkoxy)C$_1$-C$_4$ alkyl; (amino)alkyl; unsubstituted C$_3$-C$_6$ cycloalkyl; substituted C$_3$-C$_6$ cycloalkyl having one or two substituents independently selected from the group consisting of halo, hydroxy, C$_1$-C$_4$ alkyl, amino, and (amino)C$_1$-C$_4$ alkyl; unsubstituted 4- to 14-membered heterocyclo; and substituted 4- to 14-membered heterocyclo having one or two substituents independently selected from the group consisting of amino, hydroxy, and C$_1$-C$_4$ alkyl; (C$_3$-C$_6$ cycloalkyl)oxy; and (4- to 8-membered heterocyclo)oxy;

R$^{21}$ is selected from the group consisting of hydrogen, —C(=O)R$^{13b}$, C$_1$-C$_4$ alkyl, C$_1$-C$_4$ haloalkyl, unsubstituted 4- to 14-membered heterocyclo, and —S(=O)$_2$R$^{24}$;

R$^{22}$ is C$_1$-C$_4$ alkyl; unsubstituted C$_3$-C$_6$ cycloalkyl; substituted C$_3$-C$_6$ cycloalkyl having one or two substituents independently selected from the group consisting of halo, hydroxy, C$_1$-C$_4$ alkyl, amino, and (amino)C$_1$-C$_4$ alkyl; unsubstituted 4- to 14-membered heterocyclo; and substituted 4- to 14-membered heterocyclo having one or two substituents independently selected from the group consisting of amino, hydroxy, and C$_1$-C$_4$ alkyl;

R$^{24}$ is selected from the group consisting of C$_1$-C$_4$ alkyl and (hydroxy)C$_1$-C$_4$ alkyl;

R$^{25}$ is selected from the group consisting of hydrogen, C$_1$-C$_4$ alkyl, and C$_1$-C$_4$ haloalkyl;

R$^{25b}$ and R$^{25c}$ are independently selected from the group consisting of C$_1$-C$_4$ alkyl and C$_1$-C$_4$ haloalkyl;

R$^{26}$ is selected from the group consisting of unsubstituted 4- to 14-membered heterocyclo; and substituted 4- to 14-membered heterocyclo having one or two substituents independently selected from the group consisting of amino, hydroxy, and C$_1$-C$_4$ alkyl; and R$^{21a}$ and R$^{25a}$ taken together with the atoms to which they are attached form an optionally substituted 4- to 8-membered heterocyclo, or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is selected from the group consisting of:

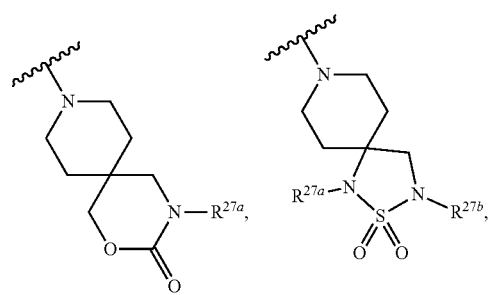

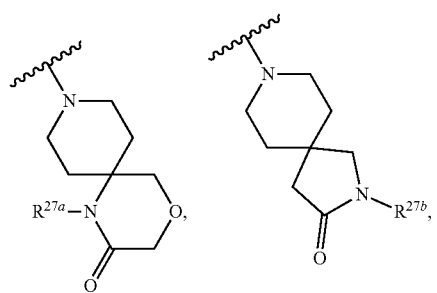

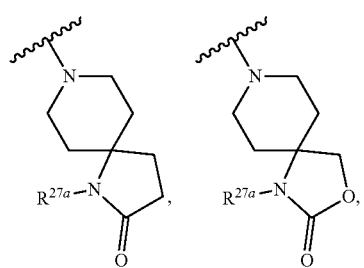

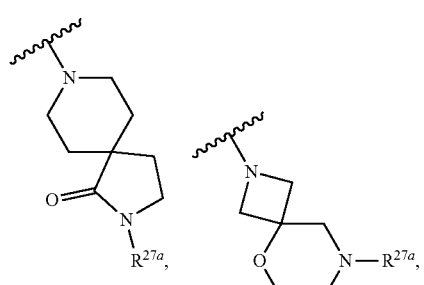

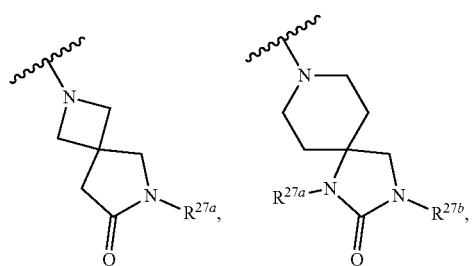

-continued

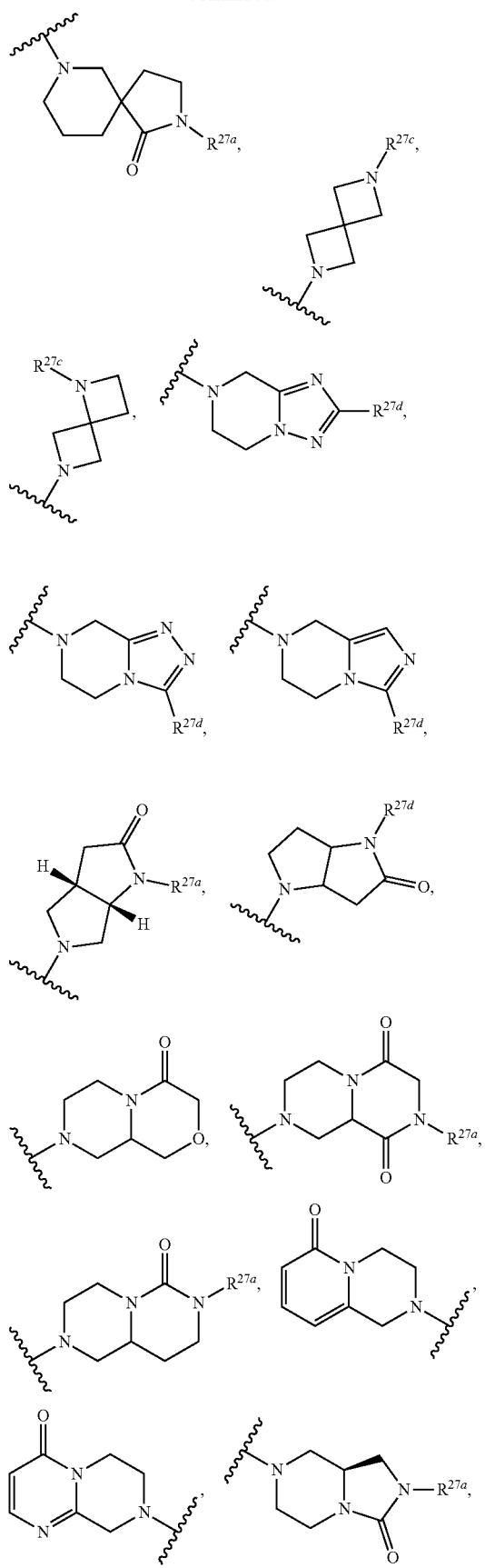

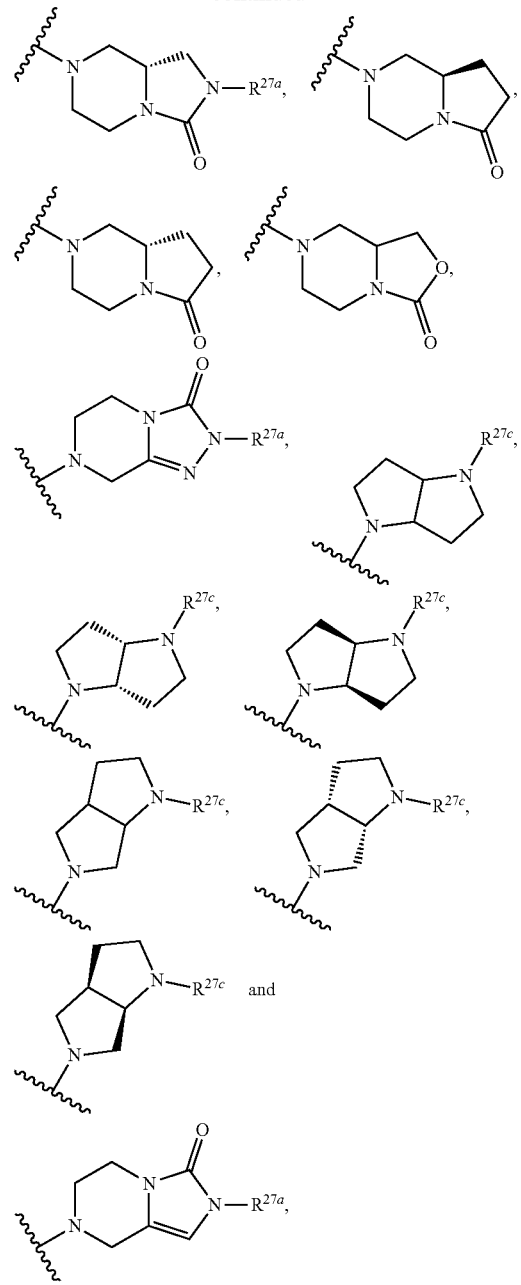

wherein:

$R^{27a}$ and $R^{27b}$ are each independently selected from the group consisting of hydrogen, $C_1$-$C_4$ alkyl, $C_1$-$C_4$ haloalkyl, ($C_1$-$C_4$ alkoxy)$C_1$-$C_4$ alkyl; and (hydroxy) $C_1$-$C_4$ alkyl;

$R^{27c}$ is selected from the group consisting of hydrogen; —C(=O)$R^{13b}$; $C_1$-$C_4$ alkyl; $C_1$-$C_4$ haloalkyl; unsubstituted 4- to 14-membered heterocyclo; and substituted 4- to 14-membered heterocyclo having one or two substituents independently selected from the group consisting of amino, hydroxy, and $C_1$-$C_4$ alkyl; and —S(=O)$_2$$R^{24}$;

$R^{27d}$ is selected from the group consisting of hydrogen; $C_1$-$C_4$ alkyl; and $C_1$-$C_4$ haloalkyl;

$R^{13b}$ is selected from the group consisting of $C_1$-$C_4$ alkyl; amino$C_1$-$C_4$ haloalky; $C_1$-$C_4$ alkoxy; (hydroxy)$C_1$-$C_4$ alkyl; ($C_1$-$C_4$ alkoxy)$C_1$-$C_4$ alkyl; (amino)alkyl; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; unsubstituted 4- to 14-membered heterocyclo; substituted 4- to 14-membered heterocyclo having one or two substituents independently selected from the group consisting of amino, hydroxy, and $C_1$-$C_4$ alkyl; ($C_3$-$C_6$ cycloalkyl)oxy; and (4- to 8-membered heterocyclo)oxy; and $R^{24}$ is selected from the group consisting of $C_1$-$C_4$ alkyl and (hydroxy)$C_1$-$C_4$ alkyl, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of

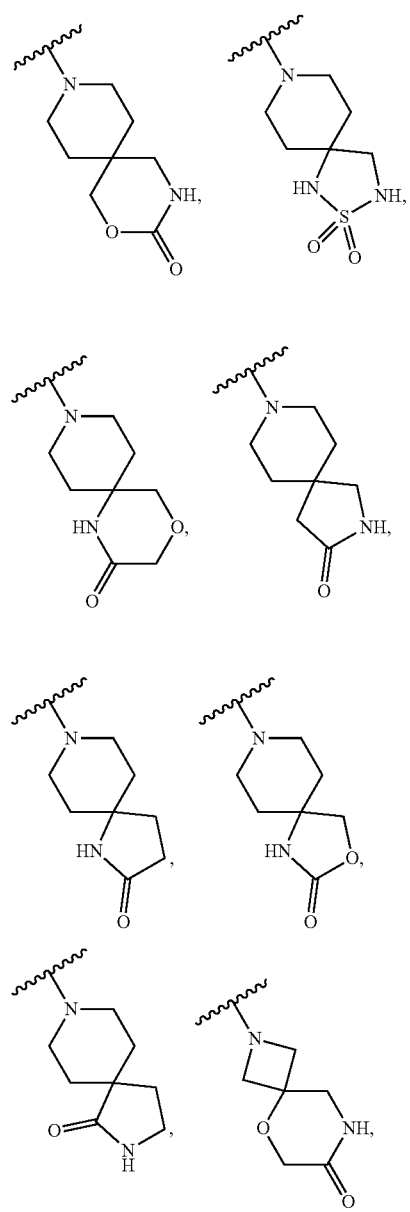

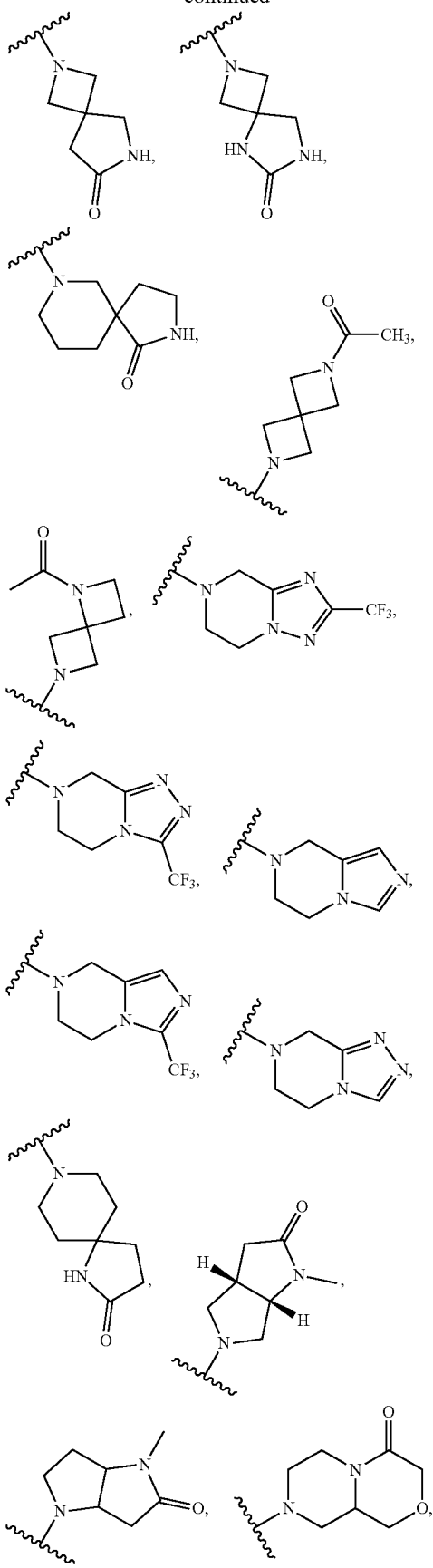

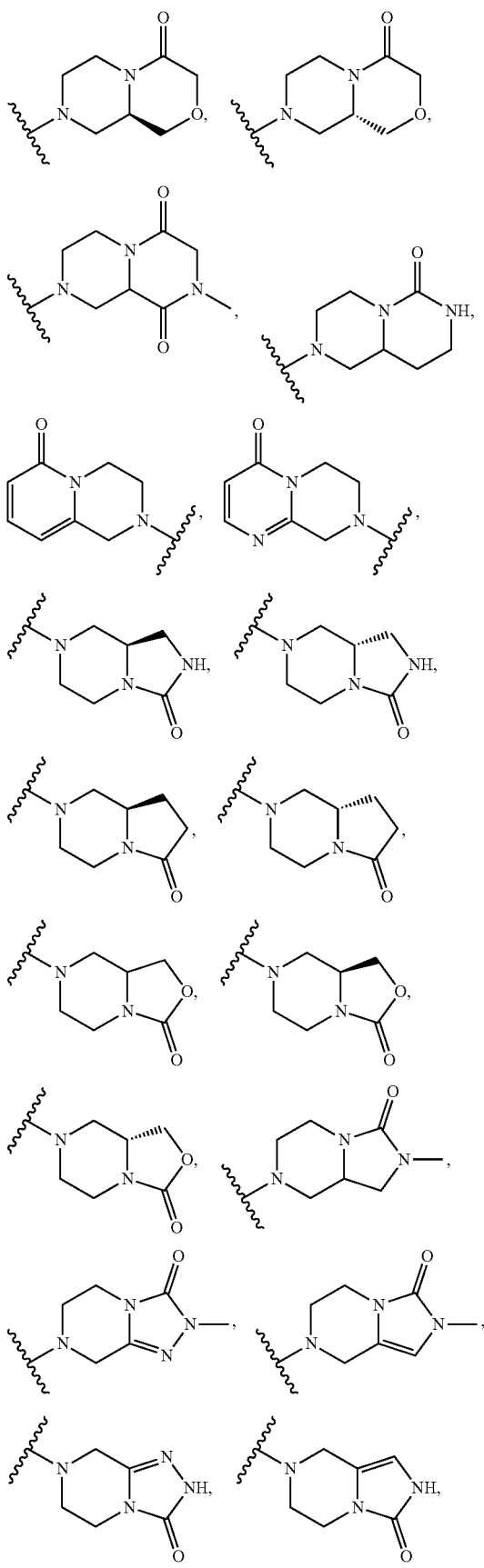
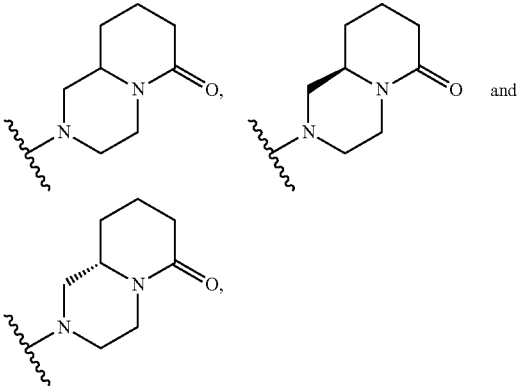

or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of unsubstituted 4- to 14-membered heterocyclo; substituted 4- to 14-membered heterocyclo having one or two substituents independently selected from the group consisting of $-N(R^{12a})C(=O)R^{13a}$, $-C(=O)R^{13b}$, and $C_1$-$C_4$ alkyl; unsubstituted 5- to 10-membered heteroaryl; and substituted 5- or 6-membered heteroaryl having one or two substituents independently selected from the group consisting of halo and $C_1$-$C_4$ alkyl, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is a substituted 4- to 14-membered heterocyclo is selected from the group consisting of:

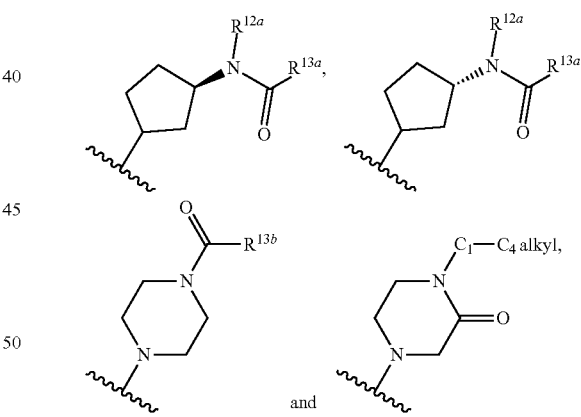

or a pharmaceutically acceptable salt or solvate thereof. In another embodiment, $R^{12a}$ is selected from the group consisting of hydrogen and $C_1$-$C_3$ alkyl; $R^{13a}$ is $C_1$-$C_4$ alkyl; and $R^{13b}$ is $C_1$-$C_4$ alkyl, or a pharmaceutically acceptable salt or solvate thereof. In another embodiment, $R^{12a}$ is selected from the group consisting of hydrogen and methyl; $R^{13a}$ is methyl; and $R^{13b}$ is methyl, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is any one or more of the $R^{2b}$ groups provided in connection with Formula III, see above, or a pharmaceutically acceptable salt or solvate thereof.

In another embodiment, Compounds of the Disclosure are compounds having any one of Formulae IV, TV-A, TV-B, TV-C, or TV-D, wherein:
$R^{11a}$ is selected from the group consisting of:
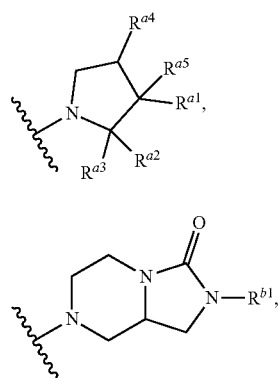
$R^{11a}$-1
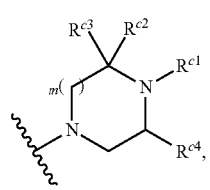
$R^{11a}$-2
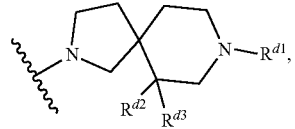
$R^{11a}$-3
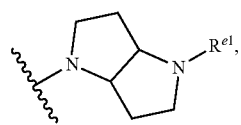
$R^{11a}$-4
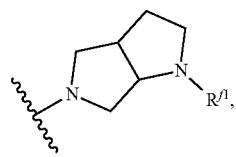
$R^{11a}$-5
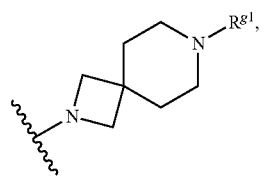
$R^{11a}$-6
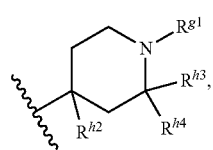
$R^{11a}$-7
-continued
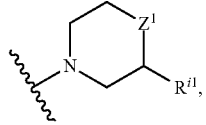
$R^{11a}$-8
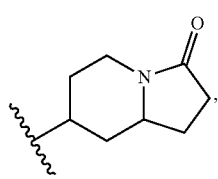
$R^{11a}$-9
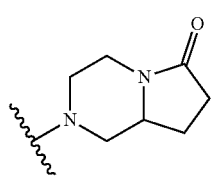
$R^{11a}$-10
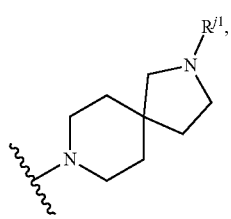
$R^{11a}$-11
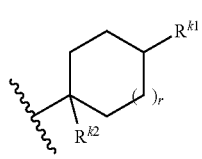
$R^{11a}$-12
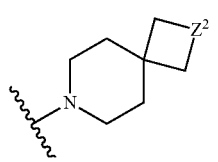
$R^{11a}$-13
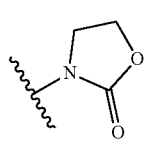
$R^{11a}$-14
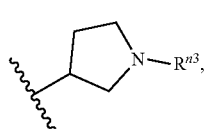
$R^{11a}$-15
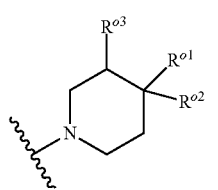
$R^{11a}$-16
$R^{11a}$-17

-continued

R^{11a}-18
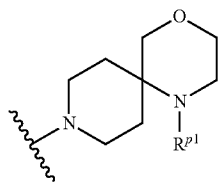

R^{11a}-19
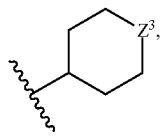

R^{11a}-20
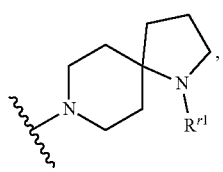

R^{11a}-21
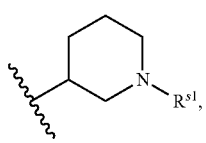

R^{11a}-22
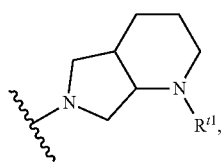

R^{11a}-23
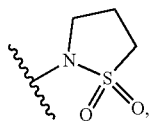

R^{11a}-24
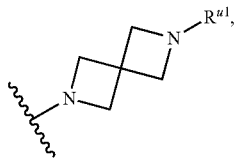

R^{11a}-25
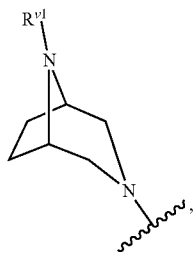

R^{11a}-26
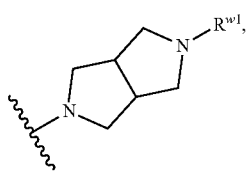

-continued

R^{11a}-27
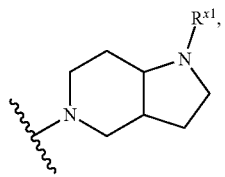

R^{11a}-28
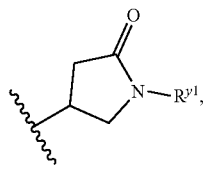

R^{11a}-29 and
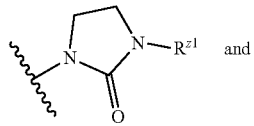

R^{11a}-30
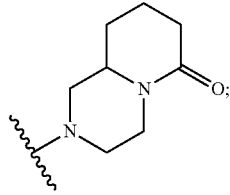

and $R^{a1}$, $R^{a2}$, $R^{a3}$, $R^{a4}$, $R^{a5}$, $R^{b1}$, $R^{c1}$, $R^{c2}$, $R^{c3}$, $R^{c4}$, m, $R^{d1}$, $R^{d2}$, $R^{d3}$, $R^{e1}$, $R^{f1}$, $R^{g1}$, $R^{h1}$, $R^{h2}$, $R^{h3}$, $R^{h4}$, $R^{i1}$, $Z^1$, $R^{j1}$, $R^{k1}$, $R^{k2}$, r, $Z^2$, $R^{n3}$, $R^{o1}$, $R^{o2}$, $R^{o3}$, $R^{p1}$, $Z^3$, $R^{r1}$, $R^{s1}$, $R^{t1}$, $R^{u1}$, $R^{v1}$, $R^{w1}$, $R^{x1}$, $R^{y1}$, and $R^{z1}$ are as defined in connection with Formula III; or a pharmaceutically acceptable salt or solvate thereof.

In another embodiment, Compounds of the Disclosure are compounds having any one of Formulae IV, IV-A, IV-B, IV-C, or IV-D, wherein:

$R^{11a}$ is selected from the group consisting of:

R^{11a}-1A
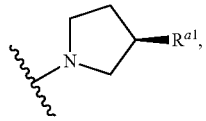

R^{11a}-1B
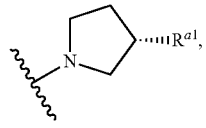

R^{11a}-1C
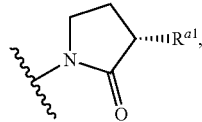

R^{11a}-1D

-continued
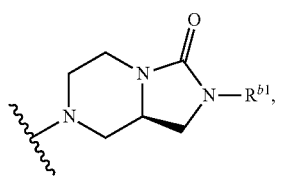 R$^{11a}$-2A
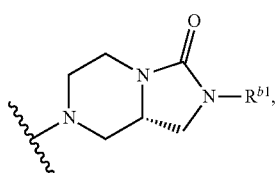 R$^{11a}$-2B
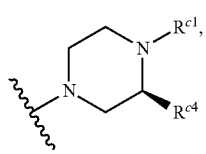 R$^{11a}$-3A
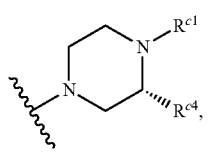 R$^{11a}$-3B
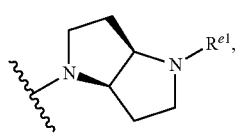 R$^{11a}$-5A
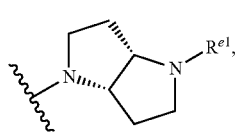 R$^{11a}$-5B
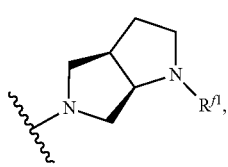 R$^{11a}$-6A
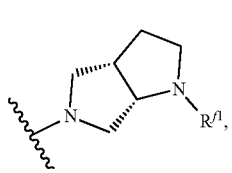 R$^{11a}$-6B
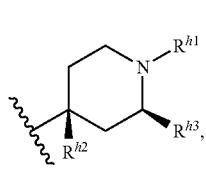 R$^{11a}$-6A
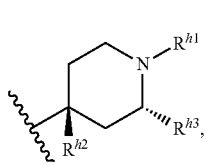 R$^{11a}$-8B
-continued
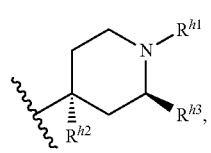 R$^{11a}$-8C
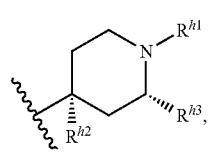 R$^{11a}$-8D
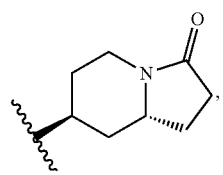 R$^{11a}$-10A
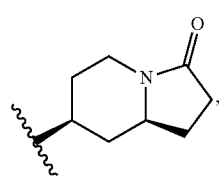 R$^{11a}$-10B
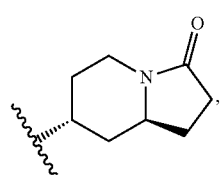 R$^{11a}$-10C
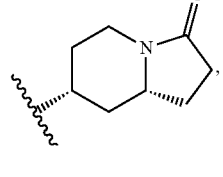 R$^{11a}$-10D
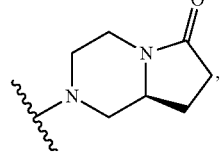 R$^{11a}$-11A
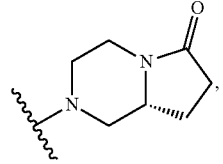 R$^{11a}$-11B
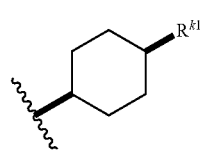 R$^{11a}$-13A

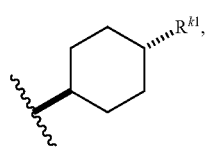 R$^{11a}$-13B
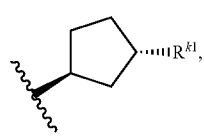 R$^{11a}$-13C
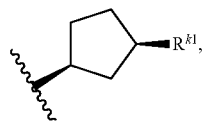 R$^{11a}$-13D
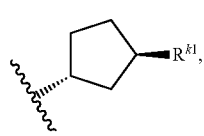 R$^{11a}$-13E
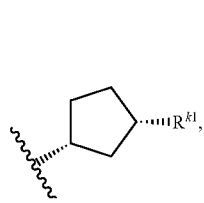 R$^{11a}$-13F
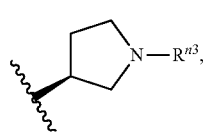 R$^{11a}$-16A
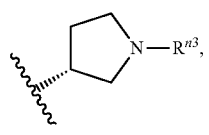 R$^{11a}$-16B
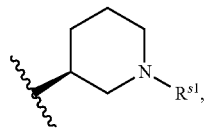 R$^{11a}$-21A
 R$^{11a}$-21B
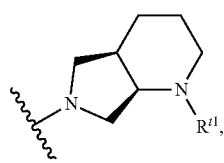 R$^{11a}$-22A
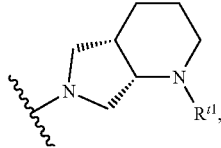 R$^{11a}$-22B
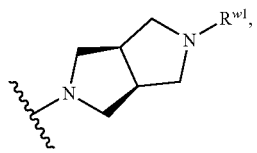 R$^{11a}$-26A
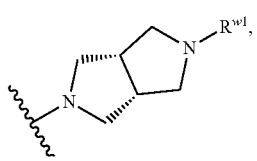 R$^{11a}$-26B
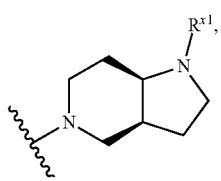 R$^{11a}$-27A
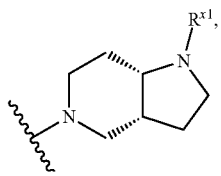 R$^{11a}$-27B
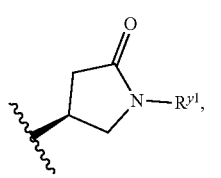 R$^{11a}$-28A
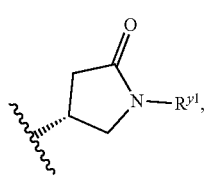 R$^{11a}$-28B
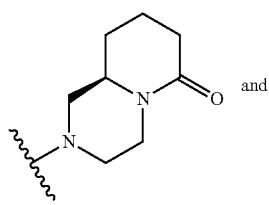 R$^{11a}$-30A
and -continued

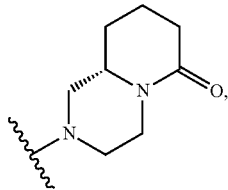
R$^{11a}$-30 and R$^{a1}$, R$^{a5}$, R$^{b1}$, R$^{e1}$, R$^{f1}$, R$^{h1}$, R$^{h2}$, R$^{h3}$, R$^{k1}$, R$^{n3}$, R$^{s1}$, R$^{t1}$, R$^{w1}$, R$^{x1}$, and R$^{y1}$ are as defined in connection with Formula III; or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is R$^{11a}$-1, R$^{11a}$-1A, R$^{11a}$-1B, R$^{11a}$-1C, or R$^{11a}$-1D, or a pharmaceutically acceptable salt or solvate thereof. In another embodiment, R$^{a1}$ is —N(R$^{3a}$)C(=O)R$^{4a}$. In another embodiment, R$^{a1}$ is —NR$^{5a}$R$^{5b}$. In another embodiment, R$^{a1}$ is —NR$^{5a}$R$^{5b}$ and R$^{5a}$ and R$^{5b}$ are independently selected from the group consisting of hydrogen and C$_1$-C$_4$ alkyl. In another embodiment, R$^{a1}$ is optionally substituted 4- to 10-membered heterocyclo.

In another embodiment, Compounds of the Disclosure are compounds having any one of Formulae IV, IV-A, IV-B, IV-C, or IV-D, wherein R$^{11a}$ is R$^{11a}$-2, R$^{11a}$-2A, or R$^{11a}$-2b, or a pharmaceutically acceptable salt or solvate thereof. In another embodiment, R$^{b1}$ is C$_1$-C$_4$ alkyl.

In another embodiment, Compounds of the Disclosure are compounds having any one of Formulae IV, IV-A, IV-B, IV-C, or IV-D, wherein R$^{11a}$ is R$^{11a}$-3, R$^{11a}$-3A, or R$^{11a}$-3B, or a pharmaceutically acceptable salt or solvate thereof. In another embodiment, R$^{c1}$ is selected from the group consisting of C$_1$-C$_4$ alkyl, C$_3$-C$_6$ cycloalkyl, and —C(=O)R$^{4c}$. In another embodiment, R$^{c2}$ and R$^{c3}$ are each hydrogen. In another embodiment, R$^{c2}$ and R$^{c3}$ taken together with the carbon atom to which they are attached form a C(=O) group. In another embodiment, R$^{c4}$ is hydrogen. In another embodiment, m is 1.

In another embodiment, Compounds of the Disclosure are compounds having any one of Formulae IV, IV-A, IV-B, IV-C, or IV-D, wherein R$^{11a}$ is R$^{11a}$-4, or a pharmaceutically acceptable salt or solvate thereof. In another embodiment, R$^{d1}$ is C(=O)R$^{4c}$. In another embodiment, R$^{d2}$ and R$^{d3}$ are each hydrogen or fluoro.

In another embodiment, Compounds of the Disclosure are compounds having any one of Formulae IV, IV-A, IV-B, IV-C, or IV-D, wherein R$^{11a}$ is R$^{11a}$-5, R$^{11a}$-5A, or R$^{11a}$-5B, or a pharmaceutically acceptable salt or solvate thereof. In another embodiment, R$^{e1}$ is —C(=O)R$^{4c}$.

In another embodiment, Compounds of the Disclosure are compounds having any one of Formulae IV, IV-A, IV-B, IV-C, or IV-D, wherein R$^{11a}$ is R$^{11a}$-6, R$^{11a}$-6A, or R$^{11a}$-6B, or a pharmaceutically acceptable salt or solvate thereof. In another embodiment, R$^{f1}$ is C(=O)R$^{4c}$.

In another embodiment, Compounds of the Disclosure are compounds having any one of Formulae IV, IV-A, IV-B, IV-C, or IV-D, wherein R$^{11a}$ is R$^{11a}$-7, or a pharmaceutically acceptable salt or solvate thereof. In another embodiment, R$^{g1}$ is C(=O)R$^{4c}$.

In another embodiment, Compounds of the Disclosure are compounds having any one of Formulae IV, IV-A, IV-B, IV-C, or IV-D, wherein R$^{11a}$ is R$^{11a}$-8, R$^{11a}$-8A, R$^{11a}$-8B, R$^{11a}$-8C, or R$^{11a}$-8D, or a pharmaceutically acceptable salt or solvate thereof. In another embodiment, R$^{h1}$ is —C(=O)R$^{4c}$. In another embodiment, R$^{h2}$ is selected from the group consisting of hydrogen and C$_1$-C$_3$ alkyl. In another embodiment, R$^{h3}$ is hydrogen.

In another embodiment, Compounds of the Disclosure are compounds any one of Formulae IV, IV-A, IV-B, IV-C, or IV-D, wherein R$^{11a}$ is R$^{11a}$-9, or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is selected from the group consisting of R$^{11a}$-10, R$^{11a}$-10A, R$^{11a}$-10B, R$^{11a}$-10C, and R$^{11a}$-10d, or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is selected from the group consisting of R$^{11a}$-11, R$^{11a}$-11A and R$^{11a}$-11B, or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is R$^{11a}$-12, or a pharmaceutically acceptable salt or solvate thereof. In another embodiment, R$^{j1}$ is —C(=O)R$^{4c}$.

In another embodiment, Compounds of the Disclosure are compounds having any one of Formulae IV, IV-A, IV-B, IV-C, or IV-D, wherein R$^{11a}$ is selected from the group consisting of R$^{11a}$-13, R$^{11a}$-13A, R$^{11a}$-13B, R$^{11a}$-13C, R$^{11a}$-13D, R$^{11a}$-13E, and R$^{11a}$-13F, or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is R$^{11a}$-14, or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is R$^{11a}$-15, or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is selected from the group consisting of R$^{11a}$-16, R$^{11a}$-16A and R$^{11a}$-16B, or a pharmaceutically acceptable salt or solvate thereof. In another embodiment, R$^{n3}$ is —C(=O)R$^{4c}$.

In another embodiment, Compounds of the Disclosure are compounds having any one of Formulae IV, IV-A, IV-B, IV-C, or IV-D, wherein R$^{11a}$ is R$^{11a}$-17, or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is R$^{11a}$-18, or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is R$^{11a}$-19, or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is R$^{11a}$-20, or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is selected from the group consisting of R$^{11a}$-21, R$^{11a}$-21A and R$^{11a}$-21B, or a pharmaceutically acceptable salt or solvate thereof.

In another embodiment, Compounds of the Disclosure are compounds having any one of Formulae IV, IV-A, IV-B, IV-C, or IV-D, wherein R$^{11a}$ is selected from the group consisting of $R^{11a}$-22, $R^{11a}$-22A and $R^{11a}$-22B, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-23, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-24, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-25, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of $R^{11a}$-26, $R^{11a}$-26A and $R^{11a}$-26B, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of $R^{11a}$-27, $R^{11a}$-27A and $R^{11a}$-27B, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is selected from the group consisting of $R^{11a}$-28, $R^{11a}$-28A and $R^{11a}$-28B, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-29, or a pharmaceutically acceptable salt or solvate thereof.

In another embodiment, Compounds of the Disclosure are compounds having any one of Formulae IV, IV-A, IV-B, IV-C, or IV-D, wherein $R^{11a}$ is $R^{11a}$-30, $R^{11a}$-30A, or $R^{11a}$-30B, or a pharmaceutically acceptable salt or solvate thereof.

In another embodiment, Compounds of the Disclosure are compounds having any one of Formulae IV-A, IV-B, IV-C, or IV-D, wherein:

$Z^4$ is —$CH_2$—;

$R^{11a}$ is selected from the group consisting of:

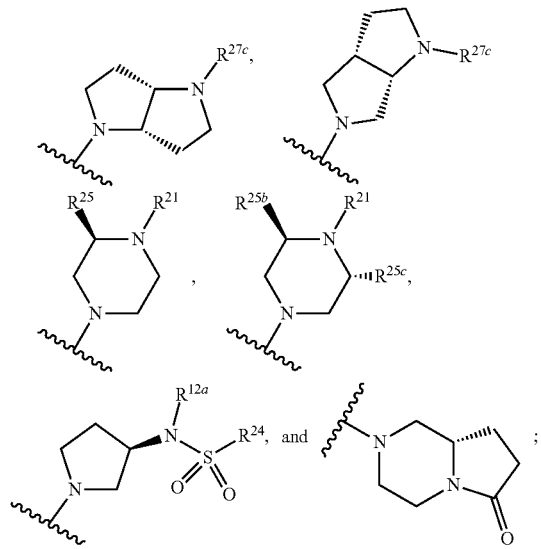

$R^{12a}$ is selected from the group consisting of hydrogen and $C_1$-$C_3$ alkyl;

$R^{21}$ is —C(=O)$R^{13b}$;

$R^{27c}$ is —C(=O)$R^{13b}$;

$R^{13b}$ is selected from the group consisting of $C_1$-$C_4$ alkyl and (hydroxy)$C_1$-$C_4$ alkyl;

$R^{24}$ is $C_1$-$C_4$ alkyl;

$R^{25}$ is selected from the group consisting of hydrogen, $C_1$-$C_4$ alkyl, and $C_1$-$C_4$ haloalkyl; and $R^{25b}$ and $R^{25c}$ are independently selected from the group consisting of $C_1$-$C_4$ alkyl and $C_1$-$C_4$ haloalkyl, or a pharmaceutically acceptable salt or solvate thereof.

In another embodiment, Compounds of the Disclosure are compounds having any one of Formulae IV-A, IV-B, IV-C, or IV-D, wherein:

$Z^4$ is —$CH_2$—;

$R^{11a}$ is selected from the group consisting of:

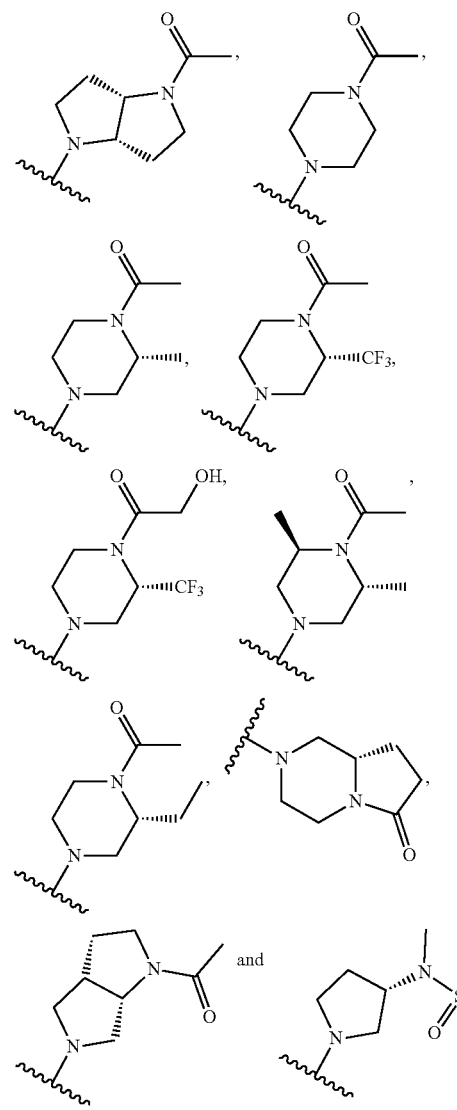

or a pharmaceutically acceptable salt or solvate thereof.

In another embodiment, Compounds of the Disclosure are compounds Formula V:

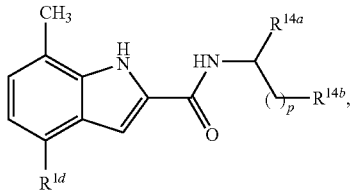

wherein:
$R^{14a}$ is selected from the group consisting of optionally substituted alkyl and optionally substituted heteroaryl;
$R^{14b}$ is selected from the group consisting of optionally substituted alkyl, optionally substituted heteroaryl, optionally substituted aryl, optionally substituted heterocyclo, optionally substituted cycloalkyl, and carboxamido; and
p is 0, 1, 2, or 3; or a pharmaceutically acceptable salt or solvate thereof.

In another embodiment, Compounds of the Disclosure are compounds having Formula V-A:

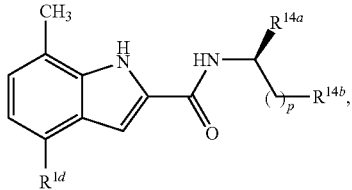

wherein $R^{1d}$, $R^{14a}$, $R^{14d}$, and p are as defined in connection with Formula V, or a pharmaceutically acceptable salt or solvate thereof.

In another embodiment, Compounds of the Disclosure are compounds having Formula V-B:

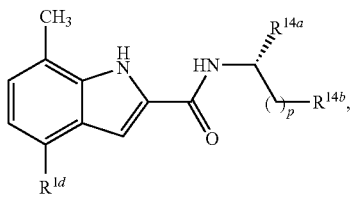

wherein $R^{1d}$, $R^{14a}$, $R^{14d}$, and p are as defined in connection with Formula V, or a pharmaceutically acceptable salt or solvate thereof.

In another embodiment, Compounds of the Disclosure are compounds having any one of Formulae V, V-A, or V-B, wherein:
$R^{14a}$ is selected from the group consisting of (A) unsubstituted 5- to 10-membered heteroaryl; (B) substituted 5- or 10-membered heteroaryl having one, two, three, or four substituents independently selected from the group consisting of (i) halo; (ii) $C_1$-$C_4$ alkyl; (iii) $C_1$-$C_4$ alkoxy; (iv) (3- to 8-membered heterocyclo)$C_1$-$C_4$ alkyl; (v) (5- to 9-membered heteroaryl)$C_1$-$C_4$ alkyl; (vi) —C(=O)$NR^{15a}R^{15b}$; (vii) unsubstituted 5- to 10-membered heteroaryl; (viii) substituted 5- or 10-membered heteroaryl having one, two, or three substituents independently selected from the group consisting of halo, $C_1$-$C_4$ alkyl, (3- to 8-membered heterocyclo)$C_1$-$C_4$ alkyl, 5- to 9-membered heteroaryl, and —$NR^{15e}R^{15f}$; (ix) —$OR^{16}$ (x) unsubstituted $C_3$-$C_6$ cycloalkyl; (xi) substituted $C_3$-$C_6$ cycloalkyl having one, two, three, or four substituents independently selected from the group consisting of $C_1$-$C_4$ alkyl and —N($R^{17a}$)C(=O)$R^{18a}$; (xii) cyano; (xiii) unsubstituted 4- to 14-membered heterocyclo; (xiv) substituted 4- to 14-membered heterocyclo having one or two substituents independently selected from the group consisting of $C_1$-$C_4$ alkyl, (5- to 9-membered heteroaryl)$C_1$-$C_4$ alkyl; (xv) (carboxy)$C_1$-$C_4$ alkyl; (xvi) (carboxamido) $C_1$-$C_4$ alkyl; and (xvii) carboxy; and (C) $C_1$-$C_6$ alkyl;
$R^{14b}$ is selected from the group consisting of: (A) unsubstituted 5- to 10-membered heteroaryl; (B) substituted 5- or 10-membered heteroaryl having one, two, three, or four substituents independently selected from the group consisting of halo, $C_1$-$C_4$ alkyl, and ($C_3$-$C_6$ cycloalkyl)$C_1$-$C_4$ alkyl; (C) unsubstituted $C_6$-$C_{10}$ aryl; (D) substituted $C_6$-$C_{10}$ aryl, having one, two, three, or four substituents independently selected from the group consisting of halo, $C_1$-$C_4$ alkyl, and (3- to 8-membered heterocyclo)$C_1$-$C_4$ alkyl; (E) unsubstituted 4- to 14-membered heterocyclo; (F) substituted 4- to 14-membered heterocyclo having one, two, three, or four substituents independently selected from the group consisting of hydroxy, amino, and $C_1$-$C_4$ alkyl; (G) —C(=O)$NR^{15c}R^{15d}$; (H) unsubstituted $C_3$-$C_6$ cycloalkyl; and (I) $C_1$-$C_6$ alkyl;
p is 0, 1, 2, or 3;
$R^{15a}$ and $R^{15b}$ are independently selected from the group consisting of: (A) hydrogen; (B) $C_1$-$C_6$ alkyl; (C) $C_1$-$C_6$ haloalkyl; (D) ($C_1$-$C_4$ alkoxy)$C_1$-$C_4$ alkyl; (E) (hydroxy)$C_1$-$C_4$ alkyl; (F) (cyano)alkyl; (G) unsubstituted $C_6$-$C_{10}$ aryl; (H) substituted $C_6$-$C_{10}$ aryl, having one, two, three, or four substituents independently selected from the group consisting of halo, amino, hydroxy, and $C_1$-$C_4$ alkyl; (I) unsubstituted 5- or 6-membered heteroaryl; (J) substituted 5- or 6-membered heteroaryl having one, two, three, or four substituents independently selected from the group consisting of halo, amino, hydroxy, and $C_1$-$C_4$ alkyl; (K) unsubstituted 4- to 14-membered heterocyclo; (L) substituted 4- to 14-membered heterocyclo having one or two substituents independently selected from the group consisting of amino, hydroxy, and $C_1$-$C_4$ alkyl; (M) unsubstituted $C_3$-$C_8$ cycloalkyl; and (N) substituted $C_3$-$C_8$ cycloalkyl having one, two, three, or four substituents independently selected from the group consisting of $C_1$-$C_6$ alkyl and —$NR^{15g}R^{15h}$; or
$R^{15a}$ and $R^{15b}$ taken together with the nitrogen atom to which they are attached form an optionally substituted 4- to 14-membered heterocyclo;
$R^{15c}$ and $R^{15d}$ are independently selected from the group consisting of: (A) hydrogen; (B) $C_1$-$C_6$ alkyl; (C) $C_1$-$C_6$ haloalkyl; (D) ($C_1$-$C_4$ alkoxy)$C_1$-$C_4$ alkyl; (E) (hydroxy)$C_1$-$C_4$ alkyl; (F) (cyano)alkyl; (G) unsubstituted $C_6$-$C_{10}$ aryl; (H) substituted $C_6$-$C_{10}$ aryl, having one, two, three, or four substituents independently selected from the group consisting of halo, amino, hydroxy, and $C_1$-$C_4$ alkyl; (I) unsubstituted 5- or 6-membered heteroaryl; (J) substituted 5- or 6-membered heteroaryl having one, two, three, or four substituents independently selected from the group consisting of halo, amino, hydroxy, and $C_1$-$C_4$ alkyl; (K) unsubstituted 4- to 14-membered heterocyclo; (L) substituted 4- to 14-membered heterocyclo having one or two substituents independently selected from the group consisting of amino, hydroxy, and $C_1$-$C_4$ alkyl; (M) unsubstituted $C_3$-$C_8$ cycloalkyl; and (N) substituted $C_3$-$C_8$ cycloalkyl having one, two, three, or four substituents independently selected from the group consisting of $C_1$-$C_6$ alkyl and —$NR^{15g}R^{15h}$; or $R^{15c}$ and $R^{15d}$ taken together with the nitrogen atom to which they are attached form an optionally substituted 4- to 14-membered heterocyclo;

$R^{15e}$ and $R^{15f}$ are independently selected from the group consisting of: (A) hydrogen; (B) $C_1$-$C_6$ alkyl; (C) $C_1$-$C_6$ haloalkyl; (D) ($C_1$-$C_4$ alkoxy)$C_1$-$C_4$ alkyl; (E) (hydroxy)$C_1$-$C_4$ alkyl; (F) (cyano)alkyl; (G) unsubstituted $C_6$-$C_{10}$ aryl; (H) substituted $C_6$-$C_{10}$ aryl, having one, two, three, or four substituents independently selected from the group consisting of halo, amino, hydroxy, and $C_1$-$C_4$ alkyl; (I) unsubstituted 5- or 6-membered heteroaryl; (J) substituted 5- or 6-membered heteroaryl having one, two, three, or four substituents independently selected from the group consisting of halo, amino, hydroxy, and $C_1$-$C_4$ alkyl; (K) unsubstituted 4- to 14-membered heterocyclo; (L) substituted 4- to 14-membered heterocyclo having one or two substituents independently selected from the group consisting of amino, hydroxy, and $C_1$-$C_4$ alkyl; (M) unsubstituted $C_3$-$C_8$ cycloalkyl; and (N) substituted $C_3$-$C_8$ cycloalkyl having one, two, three, or four substituents independently selected from the group consisting of $C_1$-$C_6$ alkyl and —$NR^{15g}R^{15h}$; or $R^{15e}$ and $R^{15f}$ taken together with the nitrogen atom to which they are attached form an optionally substituted 4- to 14-membered heterocyclo;

$R^{15g}$ and $R^{15h}$ are independently selected from the group consisting of: (A) hydrogen; (B) $C_1$-$C_6$ alkyl; (C) $C_1$-$C_6$ haloalkyl; (D) CHA, alkoxy; (E) ($C_1$-$C_4$ alkoxy)$C_1$-$C_4$ alkyl; (F) (hydroxy)$C_1$-$C_4$ alkyl; (G) (cyano)alkyl; (H) unsubstituted $C_6$-$C_{10}$ aryl; (I) substituted $C_6$-$C_{10}$ aryl, having one, two, three, or four substituents independently selected from the group consisting of halo, amino, hydroxy, and $C_1$-$C_4$ alkyl; (J) unsubstituted 5- or 6-membered heteroaryl; (K) substituted 5- or 6-membered heteroaryl having one, two, three, or four substituents independently selected from the group consisting of halo, amino, hydroxy, and $C_1$-$C_4$ alkyl; (L) unsubstituted 4- to 14-membered heterocyclo; (M) substituted 4- to 14-membered heterocyclo having one or two substituents independently selected from the group consisting of amino, hydroxy, and $C_1$-$C_4$ alkyl; (N) unsubstituted $C_3$-$C_8$ cycloalkyl; and (O) substituted $C_3$-$C_8$ cycloalkyl having one, two, three, or four substituents independently selected from the group consisting of $C_1$-$C_6$ alkyl and —$NR^{15g}R^{15h}$; or $R^{15g}$ and $R^{15g}$ taken together with the nitrogen atom to which they are attached form an optionally substituted 4- to 14-membered heterocyclo;

$R^{16}$ is (amino)(hydroxy)$C_1$-$C_4$ alkyl;

$R^{17a}$ is selected from the group consisting of hydrogen and $C_1$-$C_4$ alkyl;

$R^{18a}$ is selected from the group consisting of: (A) $C_1$-$C_6$ alkyl; (B) $C_1$-$C_6$ haloalkyl; (C) $C_1$-$C_6$ alkoxy; (D) ($C_1$-$C_4$ alkoxy)$C_1$-$C_4$ alkyl; (E) (hydroxy)$C_1$-$C_4$ alkyl; (F) (cyano)alkyl; (G) unsubstituted $C_6$-$C_{10}$ aryl; (H) substituted $C_6$-$C_{10}$ aryl, having one, two, three, or four substituents independently selected from the group consisting of halo, amino, hydroxy, and $C_1$-$C_4$ alkyl; (I) unsubstituted 5- or 6-membered heteroaryl; (J) substituted 5- or 6-membered heteroaryl having one, two, three, or four substituents independently selected from the group consisting of halo, amino, hydroxy, and $C_1$-$C_4$ alkyl; (K) unsubstituted 4- to 14-membered heterocyclo; (L) substituted 4- to 14-membered heterocyclo having one or two substituents independently selected from the group consisting of amino, hydroxy, and $C_1$-$C_4$ alkyl; (M) unsubstituted $C_3$-$C_8$ cycloalkyl; and (N) substituted $C_3$-$C_8$ cycloalkyl having one, two, three, or four substituents independently selected from the group consisting of amino, hydroxy, and $C_1$-$C_4$ alkyl, or a pharmaceutically acceptable salt or solvate thereof.

In another embodiment, Compounds of the Disclosure are compounds having any one of Formulae V, V-A, or V-B, wherein $R^{14a}$ is selected from the group consisting of unsubstituted 5- to 10-membered heteroaryl; and substituted 5- or 10-membered heteroaryl having one, two, or three substituents independently selected from the group consisting of $C_1$-$C_4$ alkyl; $C_1$-$C_4$ alkoxy; (3- to 8-membered heterocyclo)$C_1$-$C_4$ alkyl; (5- to 9-membered heteroaryl)$C_1$-$C_4$ alkyl; —C(=O)$NR^{15a}R^{15b}$; unsubstituted 5- to 10-membered heteroaryl; substituted 5- or 10-membered heteroaryl having one, two, or three substituents independently selected from the group consisting of halo, $C_1$-$C_4$ alkyl, (3- to 8-membered heterocyclo)$C_1$-$C_4$ alkyl, 5- to 9-membered heteroaryl, and —$NR^{15e}R^{15f}$; unsubstituted $C_3$-$C_6$ cycloalkyl; and substituted $C_3$-$C_6$ cycloalkyl having one, two, or three substituents independently selected from the group consisting of $C_1$-$C_4$ alkyl and —N($R^{17a}$)C(=O)$R^{18a}$, or a pharmaceutically acceptable salt or solvate thereof.

In another embodiment, Compounds of the Disclosure are compounds having any one of Formulae V, V-A, or V-B, wherein $R^{14a}$ is a substituted pyridyl having one, two, or three substituents independently selected from the group consisting of $C_1$-$C_4$ alkyl; $C_1$-$C_4$ alkoxy; (3- to 8-membered heterocyclo)$C_1$-$C_4$ alkyl; (5- to 9-membered heteroaryl)$C_1$-$C_4$ alkyl; —C(=O)$NR^{15a}R^{15b}$; unsubstituted 5- to 10-membered heteroaryl; substituted 5- to 10-membered heteroaryl having one, two, or three substituents independently selected from the group consisting of halo, $C_1$-$C_4$ alkyl, (3- to 8-membered heterocyclo)$C_1$-$C_4$ alkyl, 5- to 9-membered heteroaryl, and —$NR^{15e}R^{15f}$; unsubstituted $C_3$-$C_6$ cycloalkyl; and substituted $C_3$-$C_6$ cycloalkyl having one, two, or three substituents independently selected from the group consisting of $C_1$-$C_4$ alkyl and —N($R^{17a}$)C(=O)$R^{18a}$, or a pharmaceutically acceptable salt or solvate thereof.

In another embodiment, Compounds of the Disclosure are compounds having any one of Formulae V, V-A, or V-B, wherein $R^{14b}$ is selected from the group consisting of unsubstituted 5- to 10-membered heteroaryl; substituted 5- to 10-membered heteroaryl having one or two substituents independently selected from the group consisting of $C_1$-$C_4$ alkyl and ($C_3$-$C_6$ cycloalkyl)$C_1$-$C_4$ alkyl; unsubstituted $C_6$-$C_{10}$ aryl; substituted $C_6$-$C_{10}$ aryl, having one or two substituents independently selected from the group consisting of $C_1$-$C_4$ alkyl and (3- to 8-membered heterocyclo)$C_1$-$C_4$ alkyl; unsubstituted 4- to 14-membered heterocyclo; substituted 4- to 14-membered heterocyclo having one or two substituents independently selected from the group consisting of hydroxy, amino, and $C_1$-$C_4$ alkyl; and unsubstituted $C_3$-$C_6$ cycloalkyl, or a pharmaceutically acceptable salt or solvate thereof.

In another embodiment, Compounds of the Disclosure are compounds having any one of Formulae V, V-A, or V-B, wherein $R^{14b}$ is selected from the group consisting of unsubstituted 5- or 6-membered heteroaryl; substituted 5- or 6-membered heteroaryl having one or two substituents independently selected from the group consisting of $C_1$-$C_4$ alkyl and ($C_3$-$C_6$ cycloalkyl)$C_1$-$C_4$ alkyl; unsubstituted phenyl; substituted phenyl, having one or two substituents independently selected from the group consisting of $C_1$-$C_4$ alkyl and (3- to 8-membered heterocyclo)$C_1$-$C_4$ alkyl; and unsubstituted $C_3$-$C_6$ cycloalkyl, or a pharmaceutically acceptable salt or solvate thereof.

In another embodiment, Compounds of the Disclosure are compounds having any one of Formulae V, V-A, or V-B, wherein p is 0, or a pharmaceutically acceptable salt or solvate thereof.

In another embodiment, Compounds of the Disclosure are compounds having any one of Formulae V, V-A, or V-B, wherein p is 1, or a pharmaceutically acceptable salt or solvate thereof.

In another embodiment, Compounds of the Disclosure are compounds having Formula VI:

VI wherein:
$R^{19}$ is selected from the group consisting of unsubstituted 4- to 14-membered heterocyclo; and substituted 4- to 14-membered heterocyclo having one or two substituents independently selected from the group consisting of amino, hydroxy, and $C_1$-$C_4$ alkyl;
$R^{20}$ is selected from the group consisting of hydrogen, halo, and $C_1$-$C_4$ alkyl; and
q is 1, 2, or 3, or a pharmaceutically acceptable salt or solvate thereof.

In another embodiment, Compounds of the Disclosure are compounds having Formula VI, wherein q is 1.

In another embodiment, Compounds of the Disclosure are compounds having Formula VII:

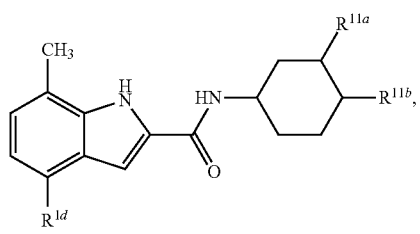

VII wherein:
$R^{11b}$ is selected from the group consisting of $C_1$-$C_4$ alkyl, halo, and $C_1$-$C_4$ haloalkyl; and
$R^{1d}$ and $R^{11a}$ are as defined in connection with Formula IV, or a pharmaceutically acceptable salt or solvate thereof.

In another embodiment, Compounds of the Disclosure are compounds having Formula VII-A:

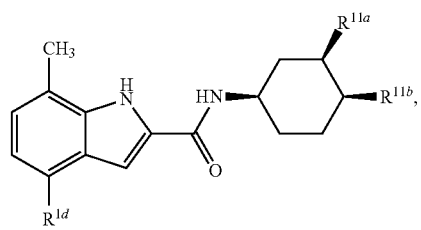

VII-A wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-B:

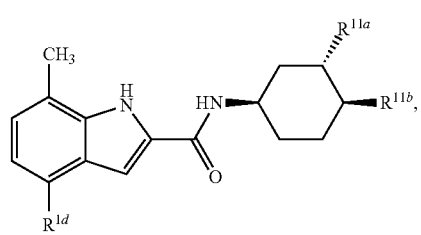

VII-B wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-C:

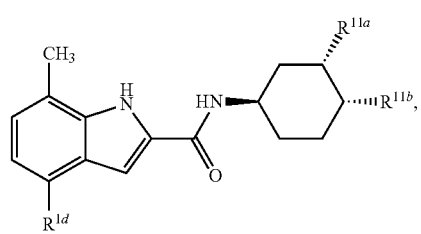

VII-C wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-D:

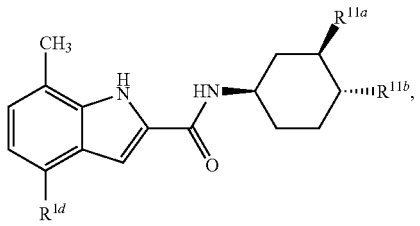

VII-D wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-E:

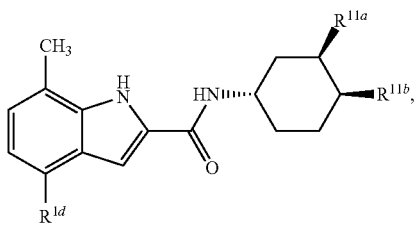

VII-E wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-F:

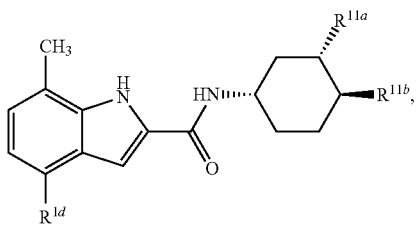

VII-F wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-G:

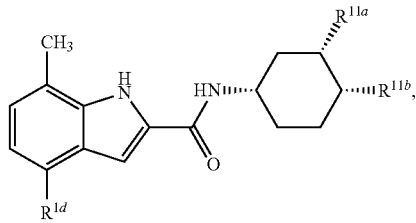

VII-G wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VII-H:

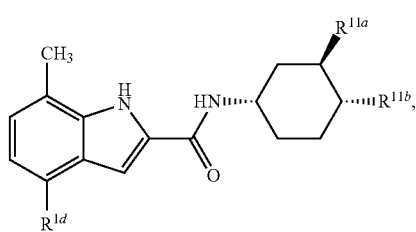

VII-H wherein $R^{1d}$, $R^{11a}$, and $R^{11b}$ are as defined in connection with Formula VII, or a pharmaceutically acceptable salt or solvate thereof.

In another embodiment, Compounds of the Disclosure are compounds having Formula VIII:

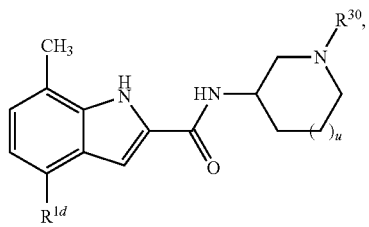

VIII wherein:

$R^{30}$ is selected from the group consisting of hydrogen; $C_1$-$C_6$ alkyl; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; unsubstituted 4- to 14-membered heterocyclo; and substituted 4- to 14-membered heterocyclo having one or two substituents independently selected from the group consisting of amino, hydroxy, and $C_1$-$C_4$ alkyl; —C(=O)$R^{13b}$, and —S(=O)$_2R^{24}$;

$R^{13b}$ is selected from the group consisting of $C_1$-$C_4$ alkyl; amino; $C_1$-$C_4$ haloalkyl; $C_1$-$C_4$ alkoxy; (hydroxy)$C_1$-$C_4$ alkyl; ($C_1$-$C_4$ alkoxy)$C_1$-$C_4$ alkyl; (amino)alkyl; unsubstituted $C_3$-$C_6$ cycloalkyl; substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; unsubstituted 4- to 14-membered heterocyclo; substituted 4- to 14-membered heterocyclo having one or two substituents independently selected from the group consisting of amino, hydroxy, and $C_1$-$C_4$ alkyl; ($C_3$-$C_6$ cycloalkyl)oxy; and (4- to 8-membered heterocyclo)oxy;

$R^{24}$ is selected from the group consisting of $C_1$-$C_4$ alkyl and (hydroxy)$C_1$-$C_4$ alkyl;

u is 0, 1, 2, or 3; and $R^{1d}$ is as defined in connection with Formula I, or a pharmaceutically acceptable salt or solvate thereof.

In another embodiment, Compounds of the Disclosure are compounds having Formula VIII-A:

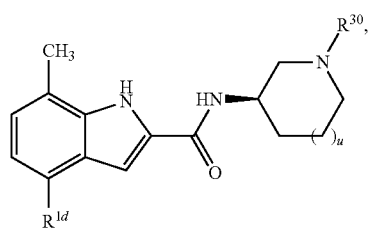

VIII-A wherein $R^{1d}$, $R^{30}$, and u are as defined in connection with Formula VIII, or a pharmaceutically acceptable salt or solvate thereof.

In another embodiment, Compounds of the Disclosure are compounds having Formula VIII-B:

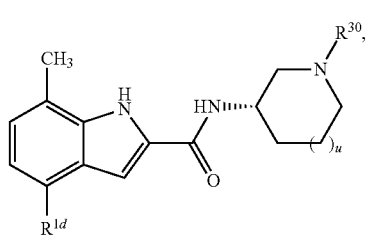

VIII-B wherein $R^{1d}$, $R^{30}$, and u are as defined in connection with Formula VIII, or a pharmaceutically acceptable salt or solvate thereof.

In another embodiment, Compounds of the Disclosure are compounds of Table 1, and the pharmaceutically acceptable salts or solvates thereof. Mass spectroscopy and representative biological data of Compounds of the Disclosure are provided in Table 1B. The "SMYD2" and "SYMD3" assays of Table 1B are described in WO 2016/040515.

In another embodiment, Compounds of the Disclosure are selected from the group consisting of Cpd. Nos. 1, 2, 3, 4, 5, 6, 7, 8, 9, 10, 11, 12, 13, 14, 15, 16, 17, 18, 824, 828, 839, 870, 922, 930, 942, 995, 1007, 1025, 1043, 1044, 1045, 1048, 1051, 1055, 1070, 1078, 1083, 1097, 1117, 1138, 1180, 1184, and 1192, and the pharmaceutically acceptable salts or solvates thereof. In another embodiment, Compounds of the Disclosure are selected from the group consisting of Cpd. Nos. 15, 922, 930, 942, 1055, 1070, 1117, 1180, 1184, and 1192, and the pharmaceutically acceptable salts or solvates thereof.

TABLE 1

| Cpd. No. | Chemical Structure |
|---|---|
| 1 | 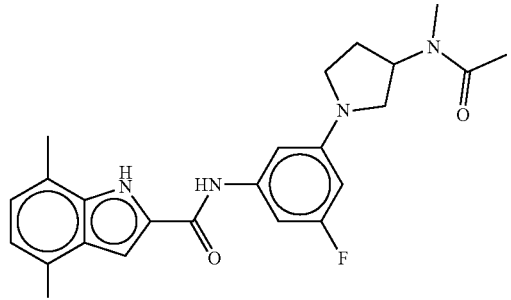 |
| 2 | 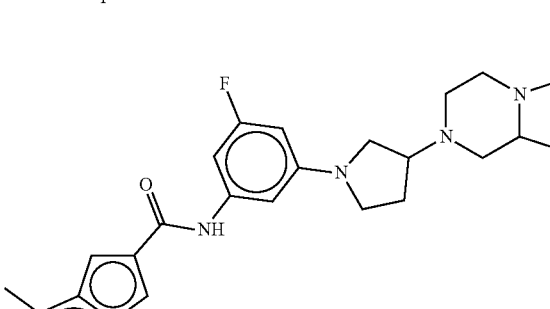 |

TABLE 1-continued
| Cpd. No. | Chemical Structure |
|---|---|
| 3 | 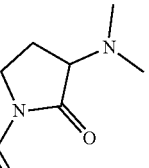 |
| 4 | 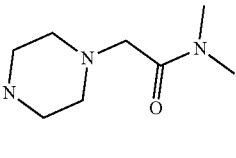 |
| 5 | 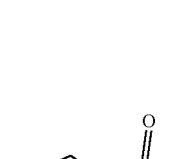 |
| 6 | 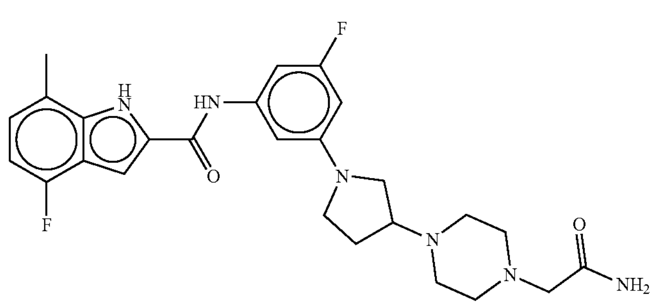 |

TABLE 1-continued
| Cpd. No. | Chemical Structure |
|---|---|
| 7 | 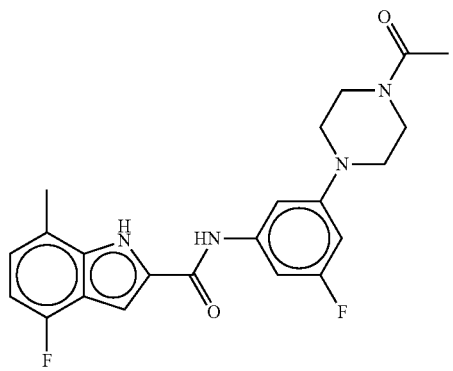 |
| 8 | 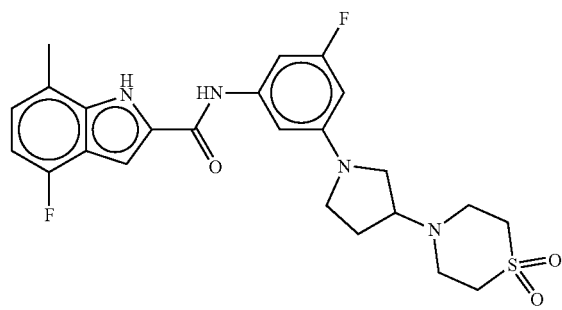 |
| 9 | 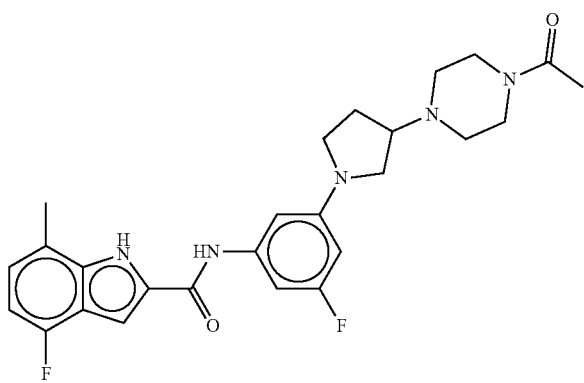 |
| 10 | 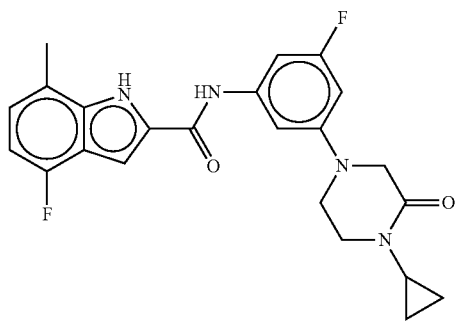 |

TABLE 1-continued
| Cpd. No. | Chemical Structure |
|---|---|
| 11 | 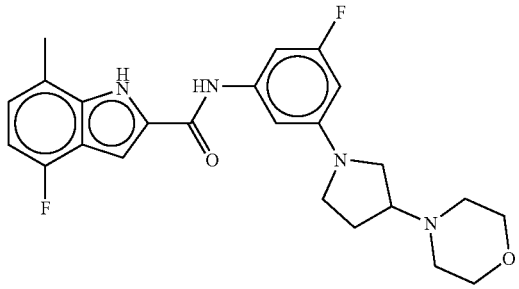 |
| 12 | 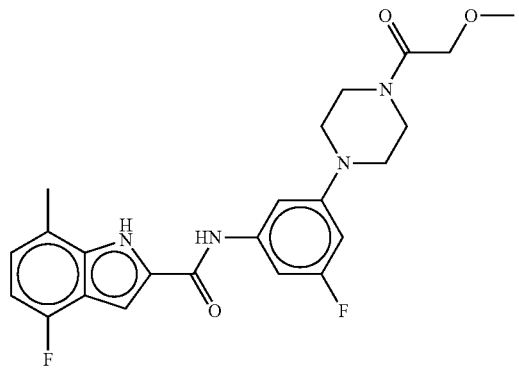 |
| 13 | 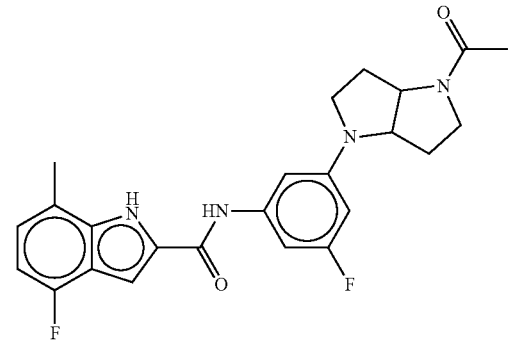 |
| 14 | 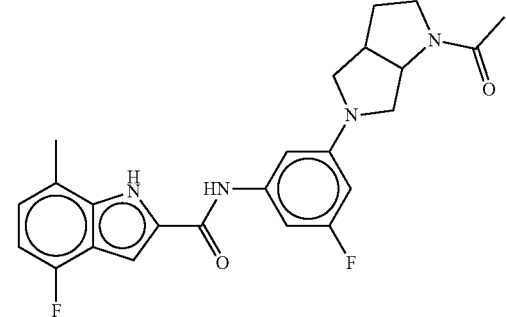 |

TABLE 1-continued

| Cpd. No. | Chemical Structure |
|---|---|
| 15 | 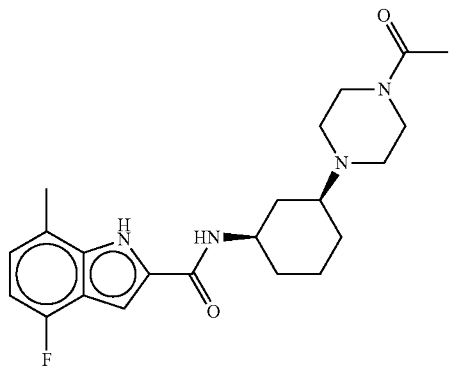 |
| 16 | 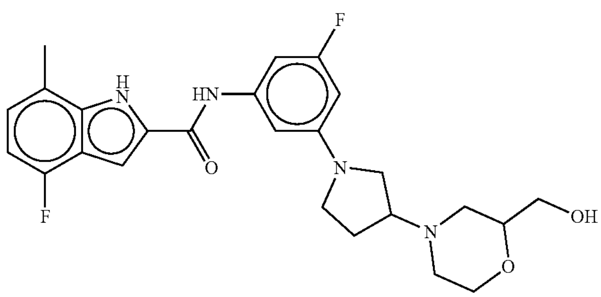 |
| 17 | 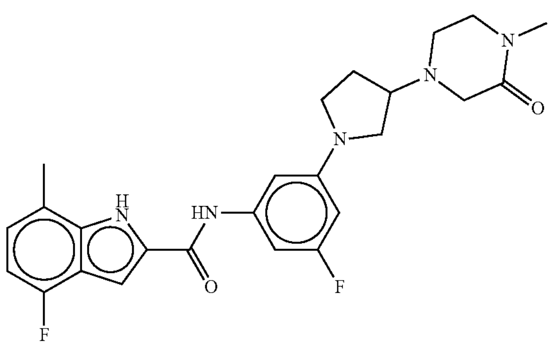 |
| 18 | 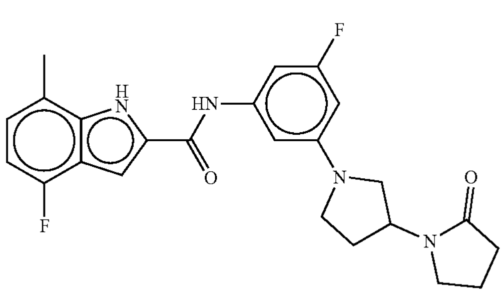 |

TABLE 1-continued
| Cpd. No. | Chemical Structure |
|---|---|
| 19 | 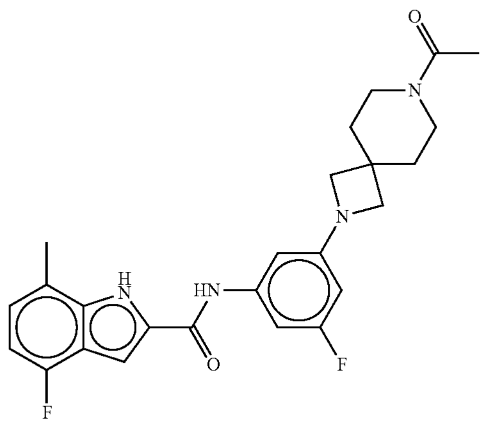 |
| 20 | 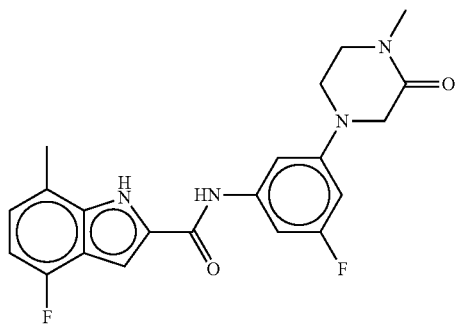 |
| 21 | 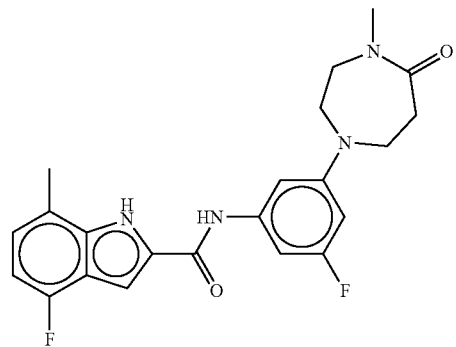 |
| 22 | 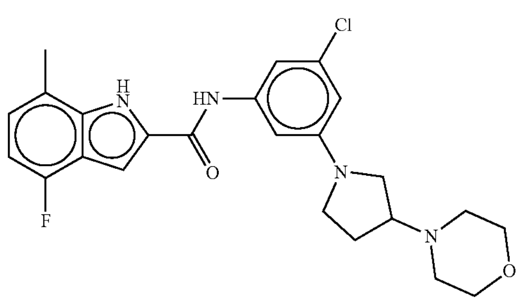 |

TABLE 1-continued
| Cpd. No. | Chemical Structure |
|---|---|
| 23 | 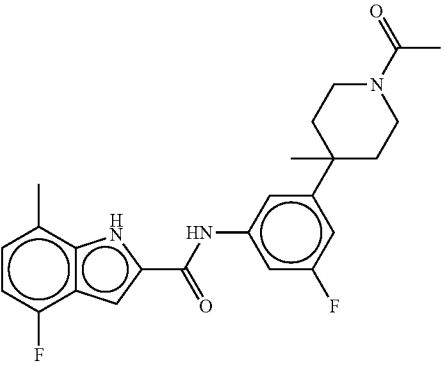 |
| 24 | 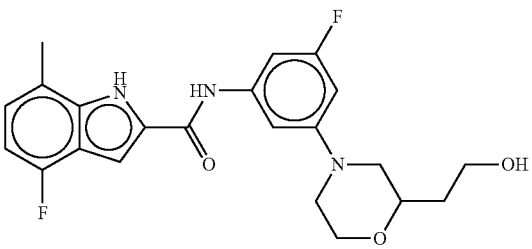 |
| 25 | 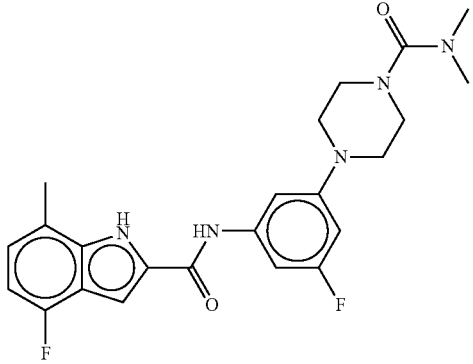 |
| 26 | 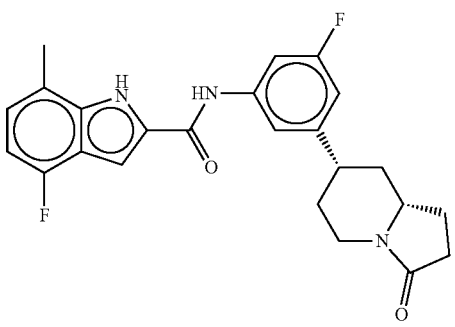 |
| 27 | 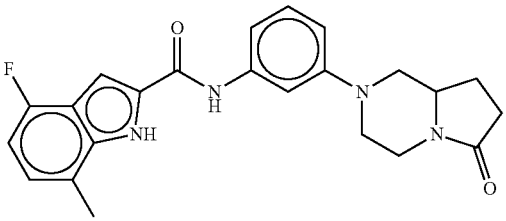 |

TABLE 1-continued
| Cpd. No. | Chemical Structure |
|---|---|
| 28 | 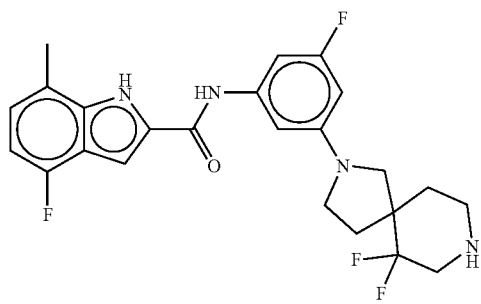 |
| 29 | 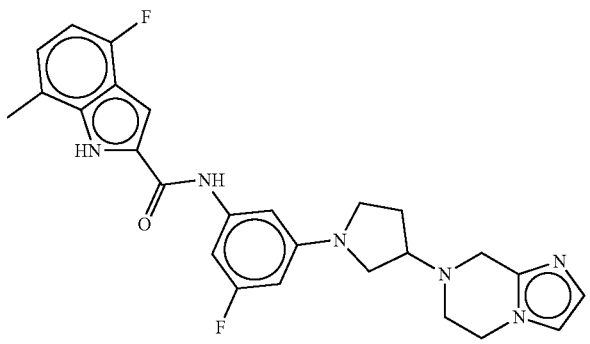 |
| 30 | 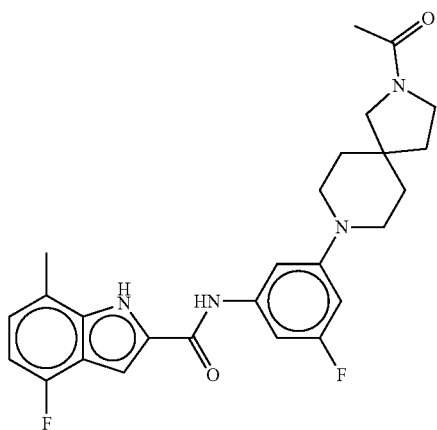 |
| 31 | 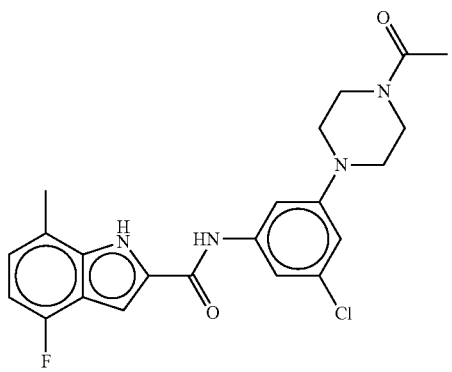 |

TABLE 1-continued
| Cpd. No. | Chemical Structure |
|---|---|
| 32 | 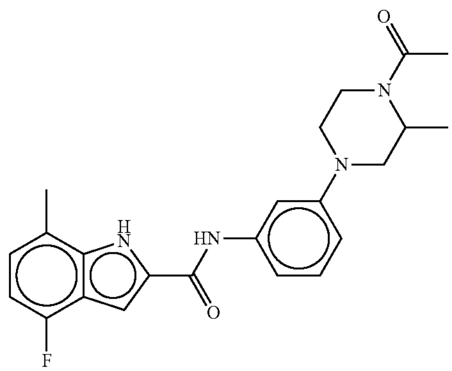 |
| 34 | 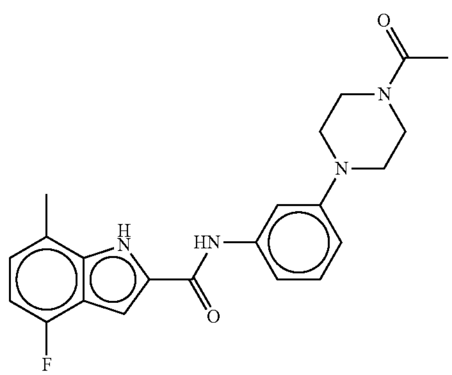 |
| 35 | 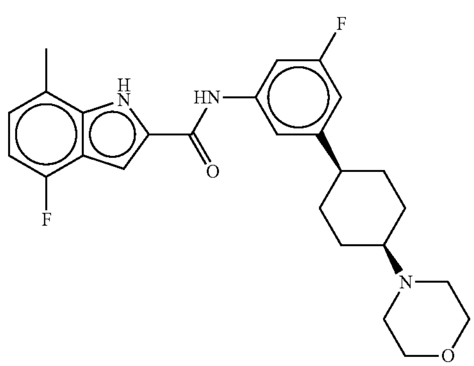 |
| 36 | 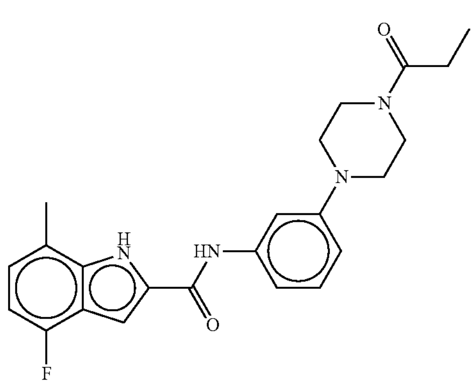 |

TABLE 1-continued
| Cpd. No. | Chemical Structure |
|---|---|
| 37 | 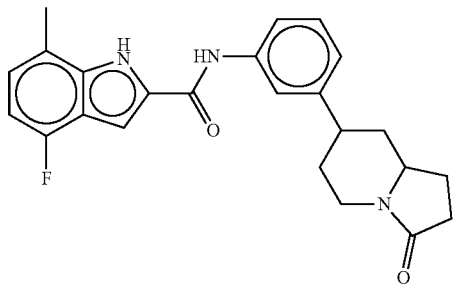 |
| 38 | 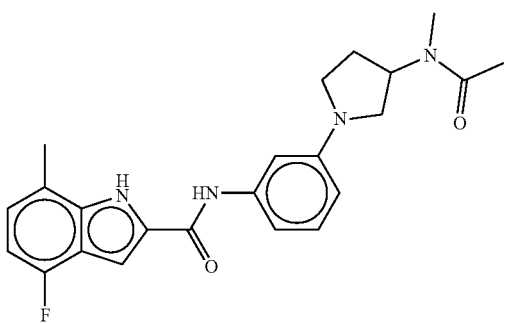 |
| 39 | 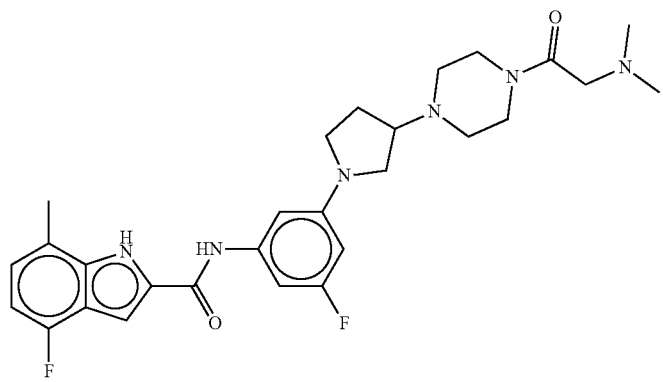 |
| 40 | 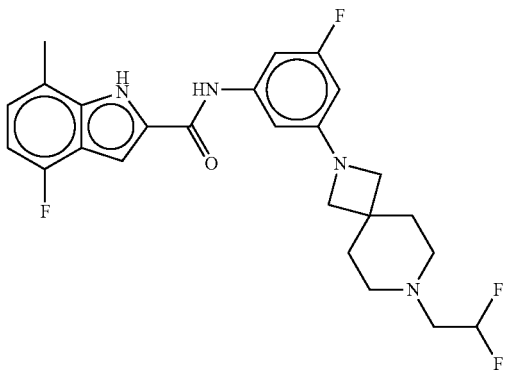 |

TABLE 1-continued
| Cpd. No. | Chemical Structure |
|---|---|
| 41 | 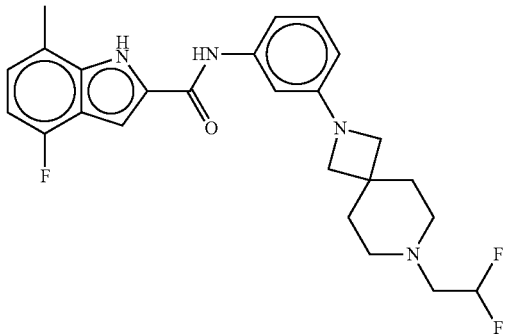 |
| 42 | 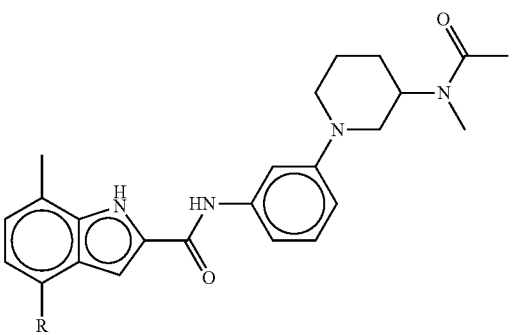 |
| 43 | 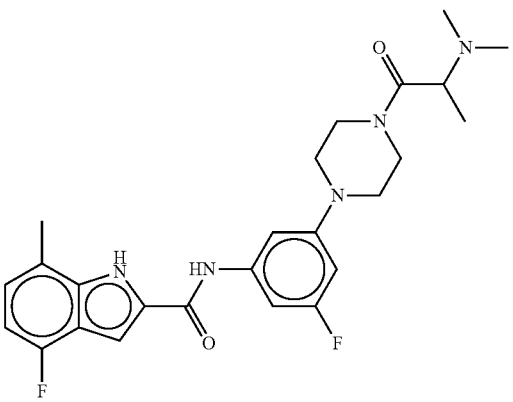 |
| 44 | 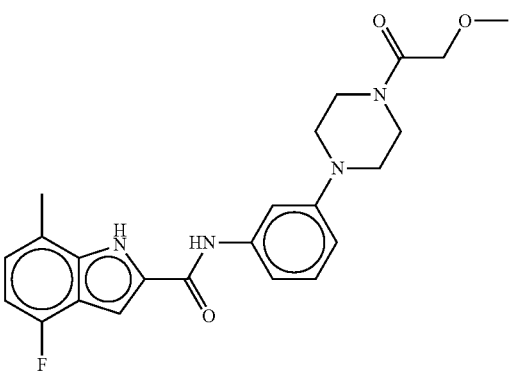 |

TABLE 1-continued

| Cpd. No. | Chemical Structure |
|---|---|
| 45 | 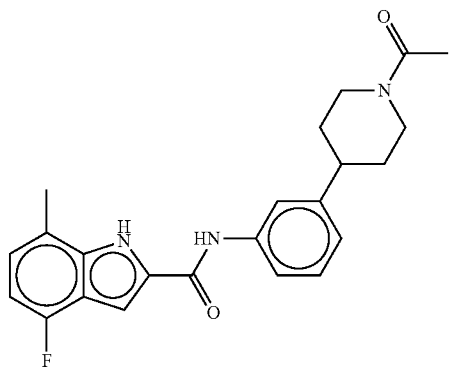 |
| 46 | 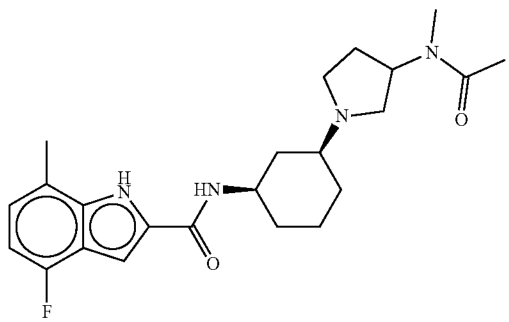 |
| 47 | 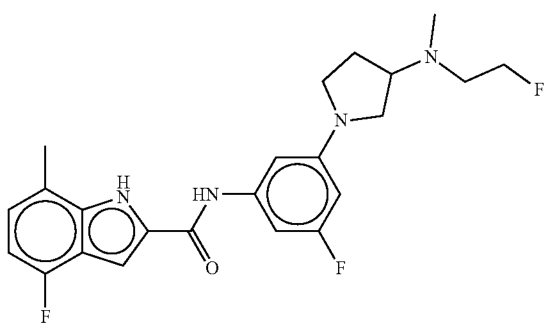 |
| 48 | 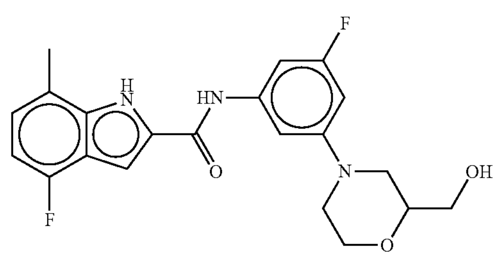 |
| 49 | 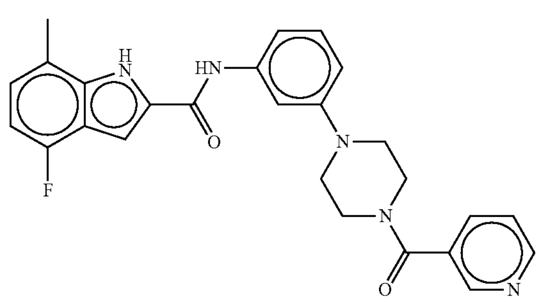 |

TABLE 1-continued
| Cpd. No. | Chemical Structure |
|---|---|
| 50 | 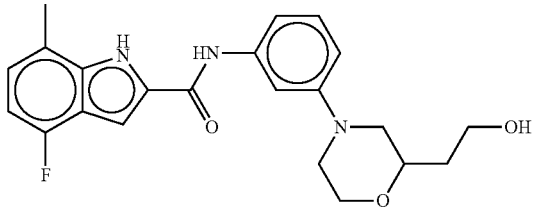 |
| 51 | 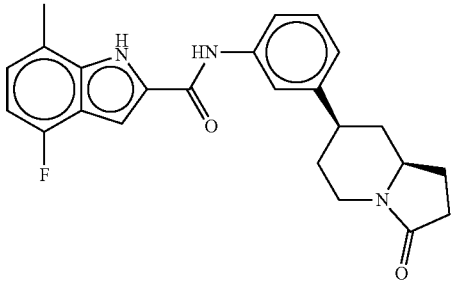 |
| 52 | 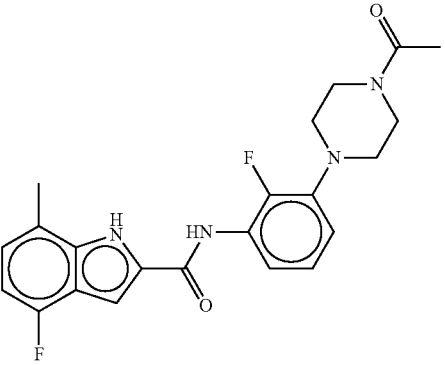 |
| 53 | 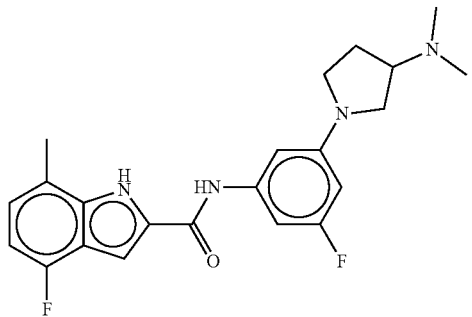 |
| 54 | 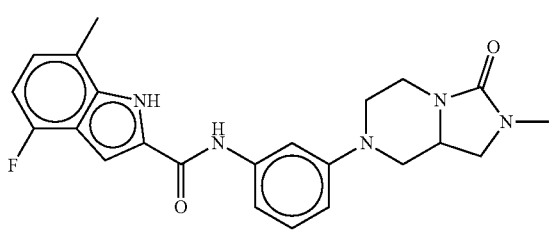 |

TABLE 1-continued
| Cpd. No. | Chemical Structure |
|---|---|
| 55 | 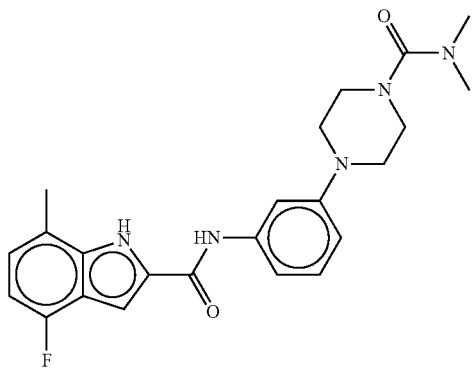 |
| 56 | 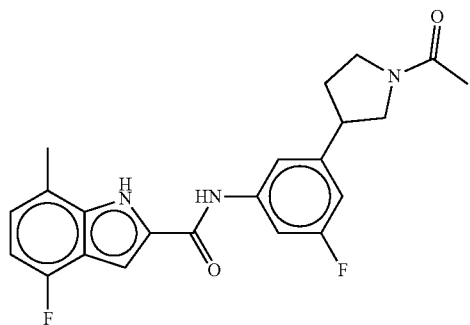 |
| 57 | 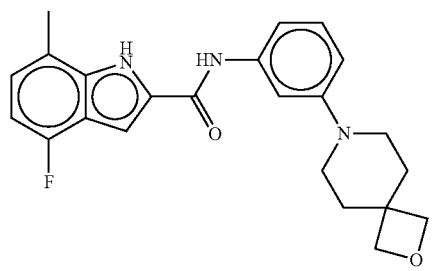 |
| 58 | 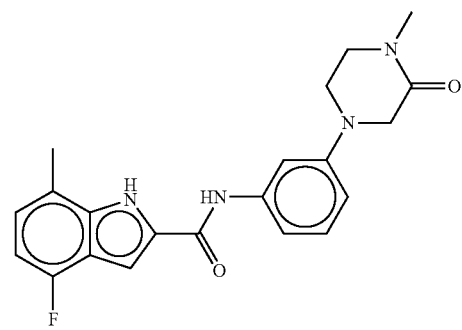 |

TABLE 1-continued
| Cpd. No. | Chemical Structure |
|---|---|
| 59 | 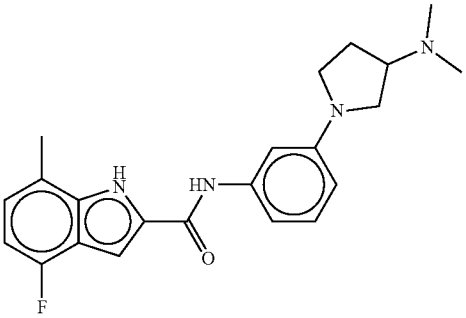 |
| 60 | 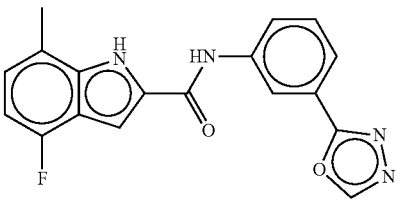 |
| 61 | 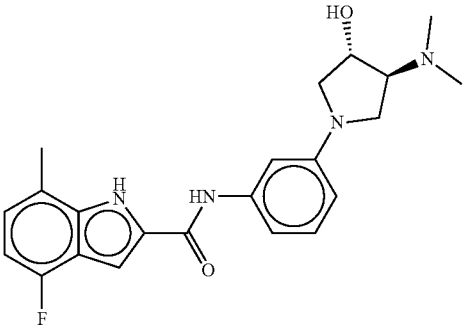 |
| 62 | 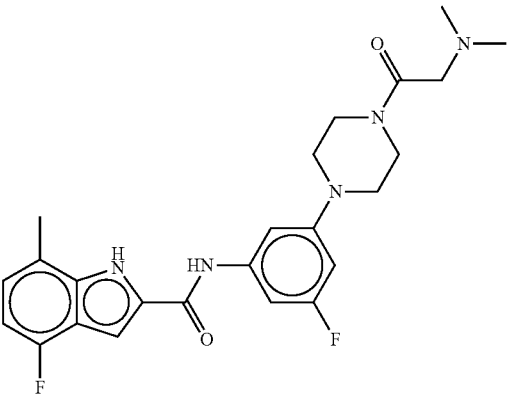 |

TABLE 1-continued

| Cpd. No. | Chemical Structure |
|---|---|
| 63 | 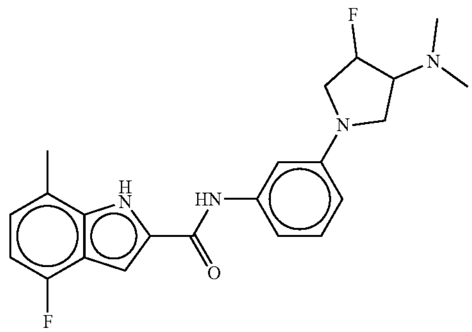 |
| 64 | 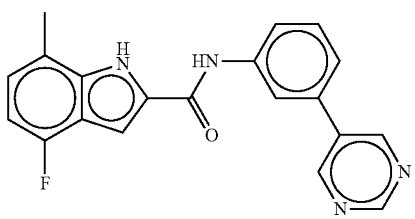 |
| 65 | 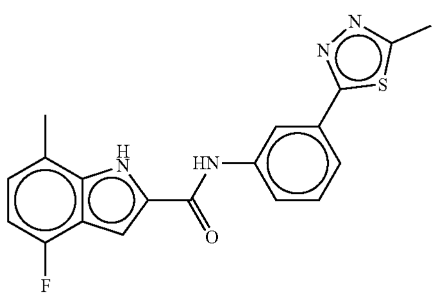 |
| 66 | 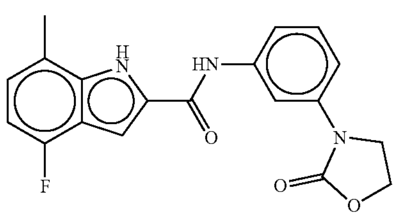 |
| 68 | 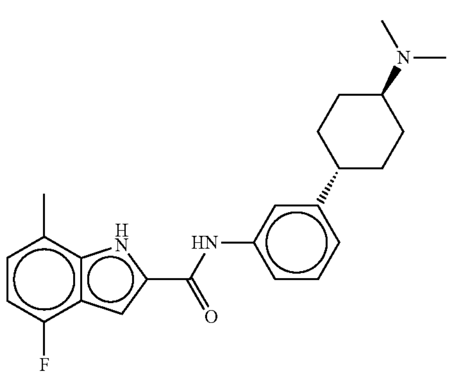 |

TABLE 1-continued
| Cpd. No. | Chemical Structure |
|---|---|
| 69 | 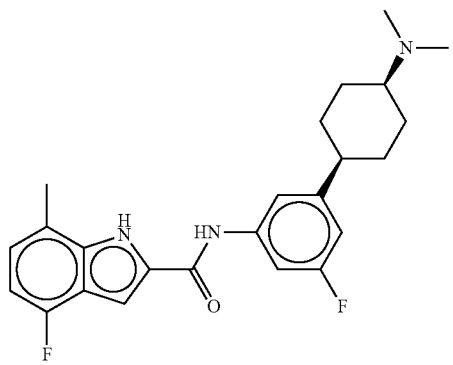 |
| 70 | 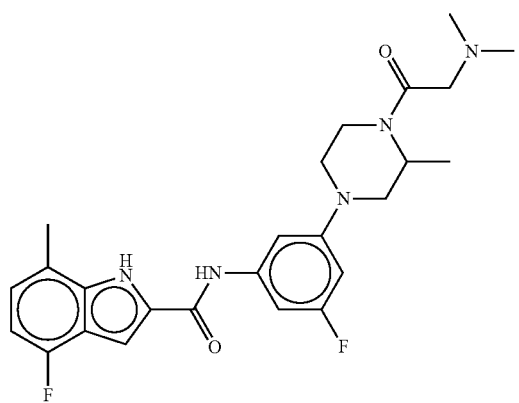 |
| 71 | 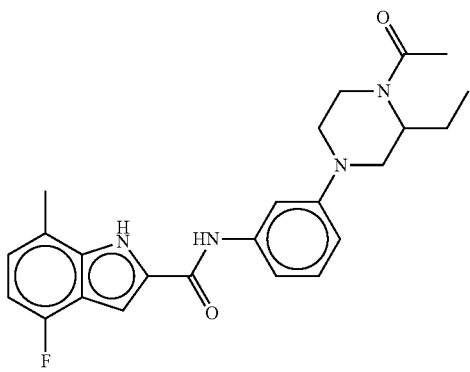 |
| 72 | 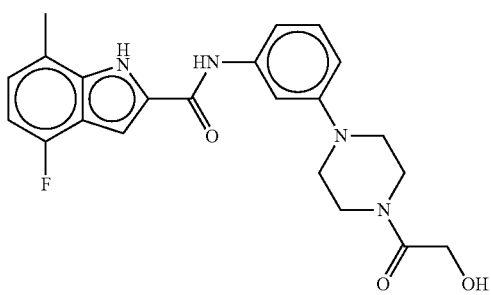 |

TABLE 1-continued
| Cpd. No. | Chemical Structure |
|---|---|
| 73 | 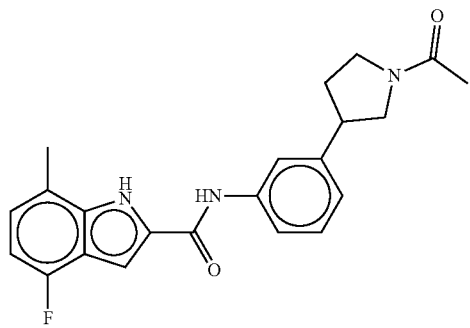 |
| 74 | 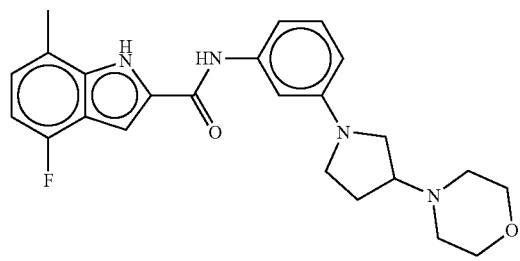 |
| 75 | 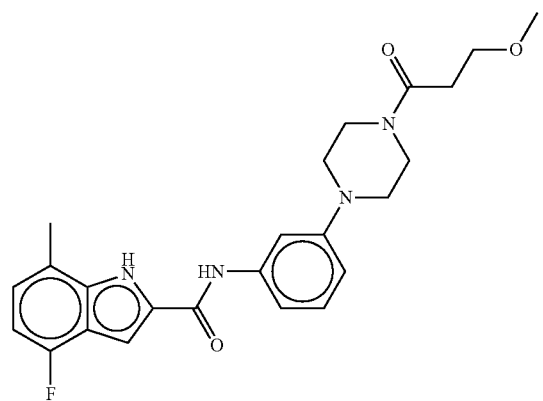 |
| 76 | 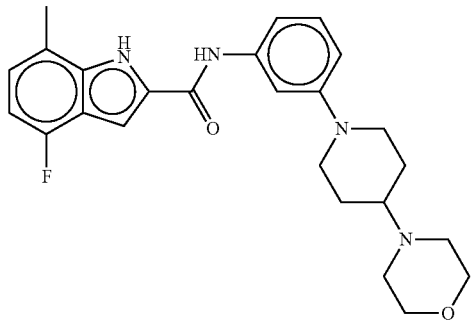 |

TABLE 1-continued
| Cpd. No. | Chemical Structure |
|---|---|
| 77 | 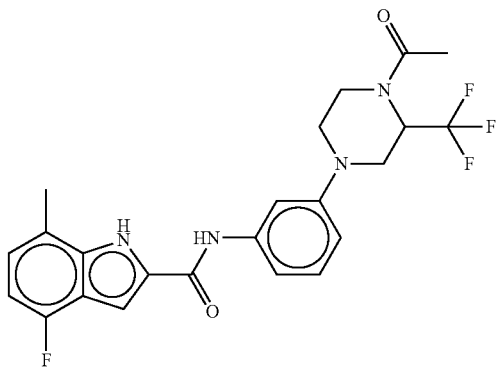 |
| 78 | 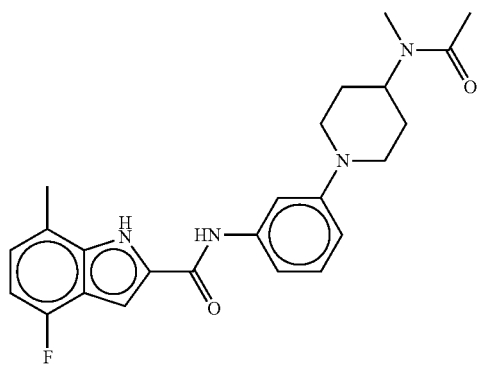 |
| 79 | 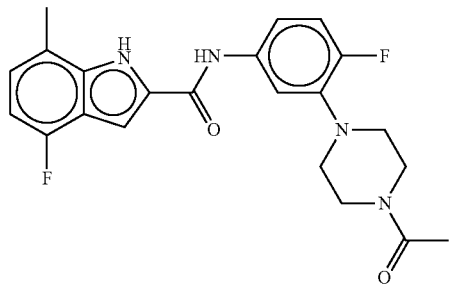 |
| 80 | 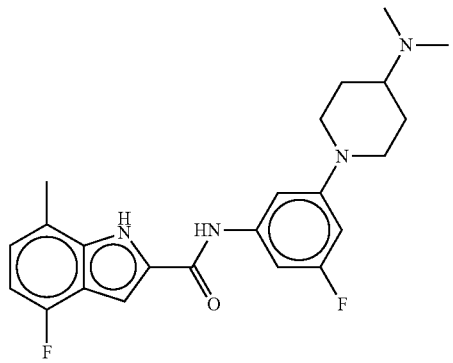 |

TABLE 1-continued
| Cpd. No. | Chemical Structure |
|---|---|
| 81 | 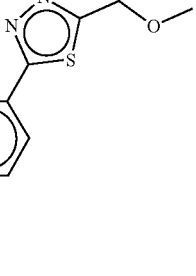 |
| 82 | 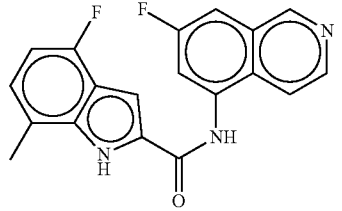 |
| 83 | 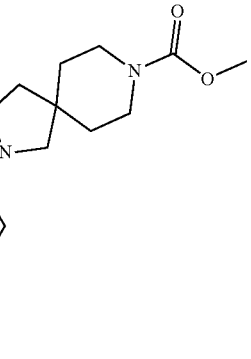 |
| 84 | 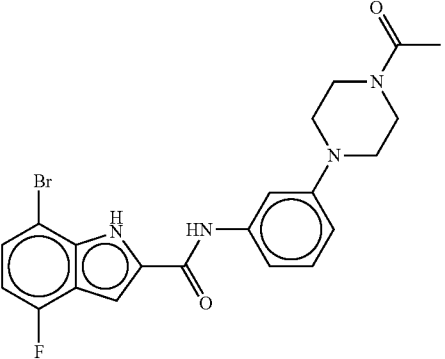 |
| 85 | 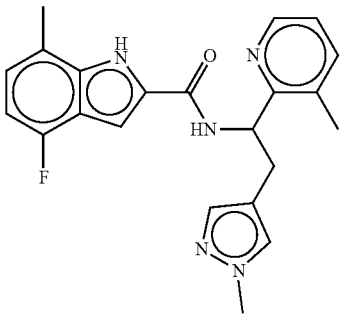 |

TABLE 1-continued
| Cpd. No. | Chemical Structure |
|---|---|
| 86 | 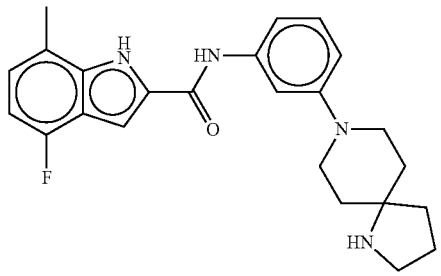 |
| 87 | 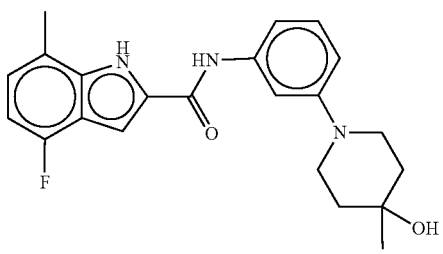 |
| 88 | 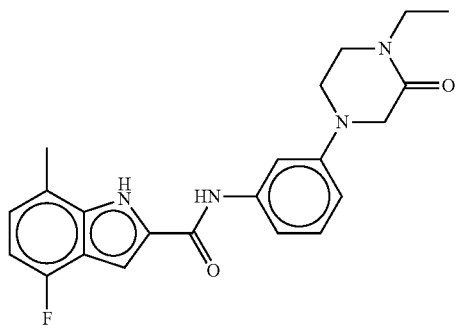 |
| 89 | 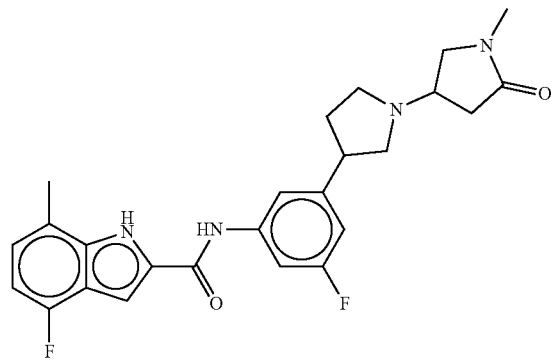 |
| 90 | 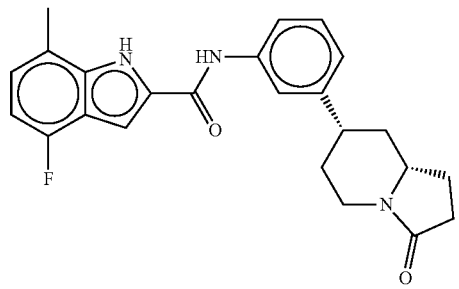 |

TABLE 1-continued

| Cpd. No. | Chemical Structure |
|---|---|
| 91 | 4-fluoro-7-methyl-N-(3-(4-methylpiperazin-1-yl)-5-chlorophenyl)-1H-indole-2-carboxamide |
| 92 | 4-fluoro-7-methyl-N-(3-(4-(2-fluoroacetyl)piperazin-1-yl)phenyl)-1H-indole-2-carboxamide |
| 93 | 4-fluoro-7-methyl-N-(3-(4-(cyclopropanecarbonyl)piperazin-1-yl)phenyl)-1H-indole-2-carboxamide |
| 94 | 4-fluoro-7-methyl-N-(3-((3-(dimethylamino)pyrrolidin-1-yl)phenyl)-1H-indole-2-carboxamide |
| 95 | 4-fluoro-7-methyl-N-(3-(1-oxa-4,9-diazaspiro[5.5]undecan-9-yl)phenyl)-1H-indole-2-carboxamide |

TABLE 1-continued
| Cpd. No. | Chemical Structure |
|---|---|
| 96 | 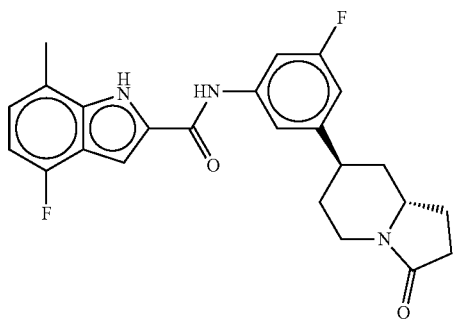 |
| 97 | 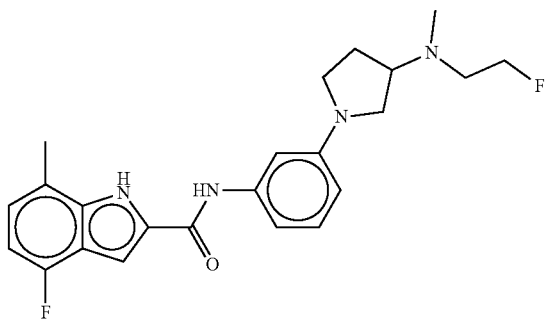 |
| 98 | 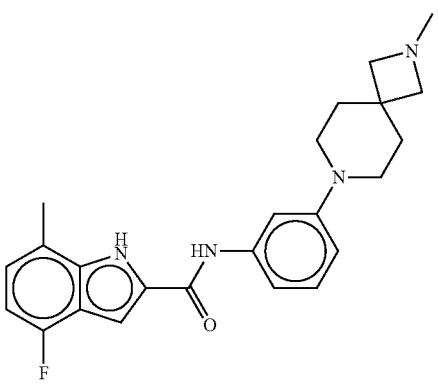 |
| 99 | 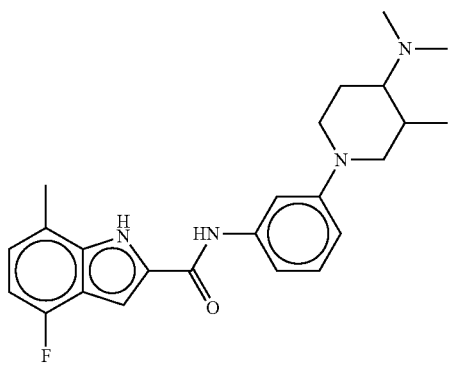 |

TABLE 1-continued
| Cpd. No. | Chemical Structure |
|---|---|
| 100 | 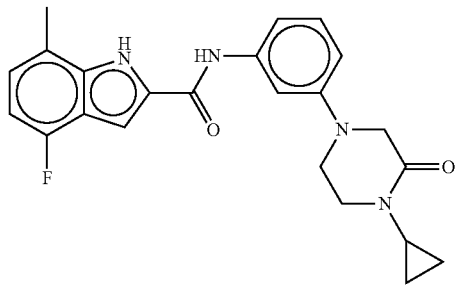 |
| 101 | 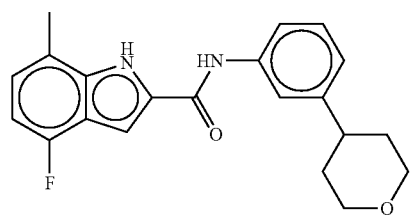 |
| 102 | 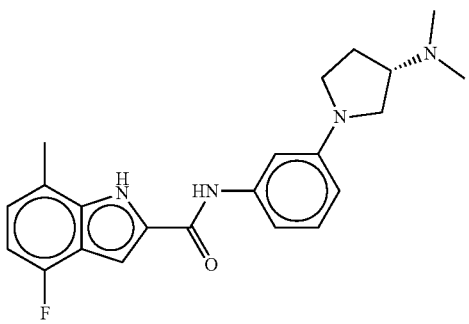 |
| 103 | 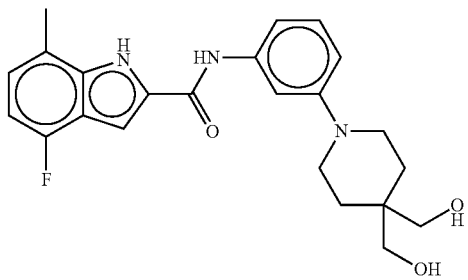 |
| 104 | 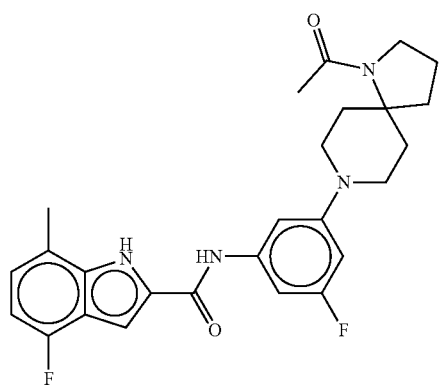 |

TABLE 1-continued

| Cpd. No. | Chemical Structure |
|---|---|
| 105 | 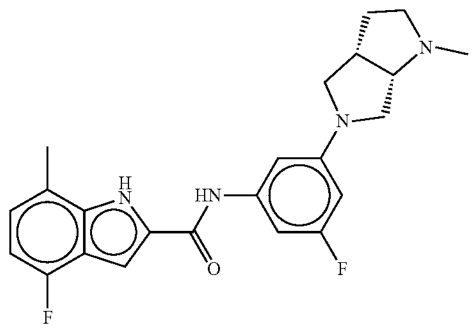 |
| 106 | 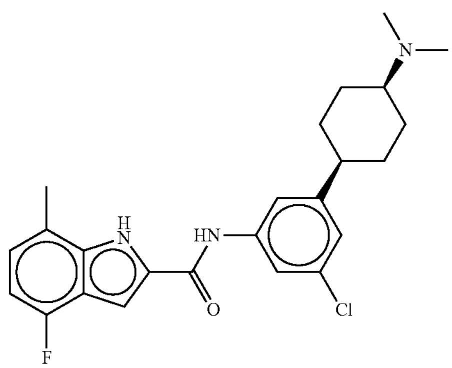 |
| 107 | 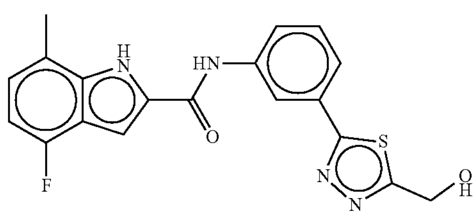 |
| 108 | 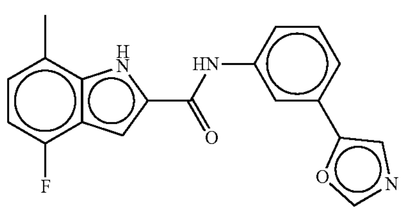 |
| 109 | 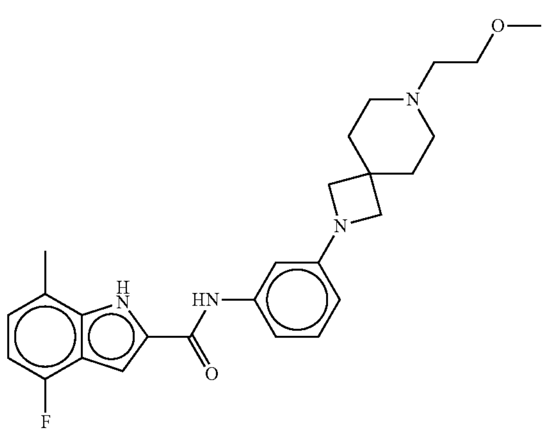 |

TABLE 1-continued
| Cpd. No. | Chemical Structure |
|---|---|
| 110 | 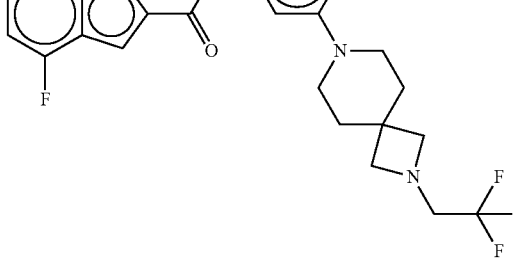 |
| 111 | 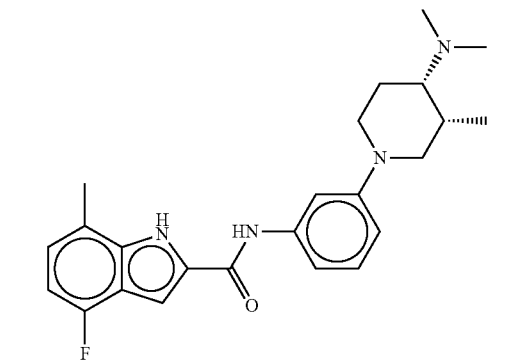 |
| 112 | 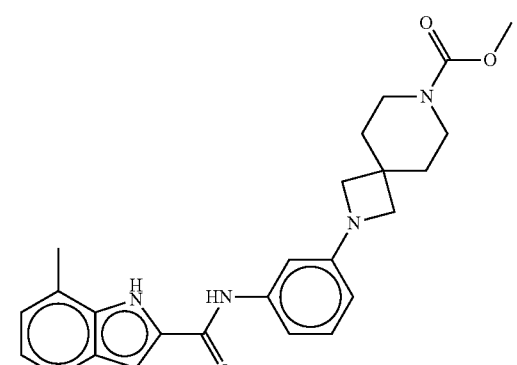 |
| 113 | 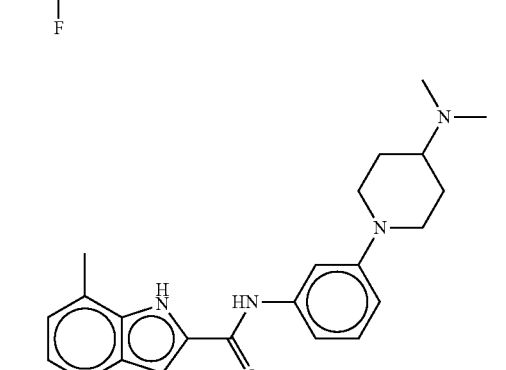 |

TABLE 1-continued

| Cpd. No. | Chemical Structure |
|---|---|
| 114 | 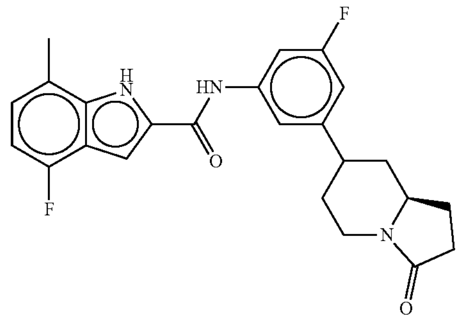 |
| 115 | 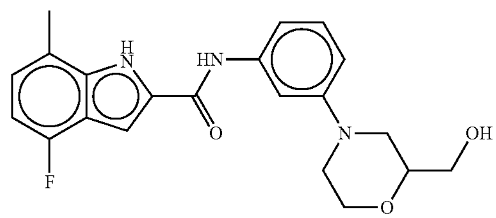 |
| 116 | 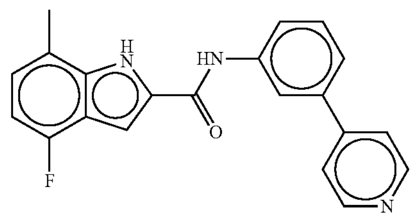 |
| 117 | 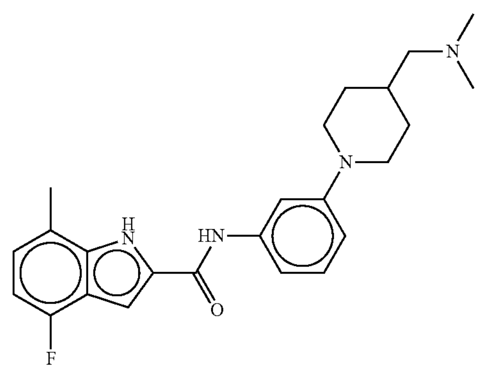 |
| 118 | 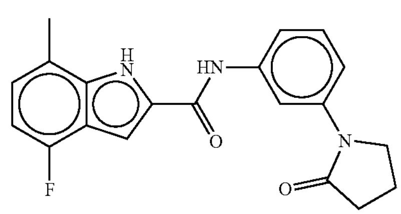 |
| 119 | 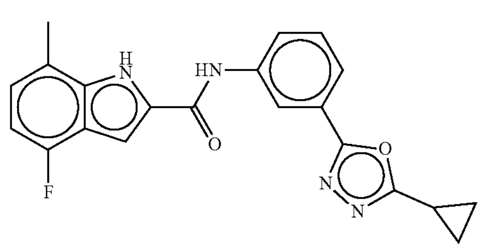 |

TABLE 1-continued
| Cpd. No. | Chemical Structure |
|---|---|
| 120 | 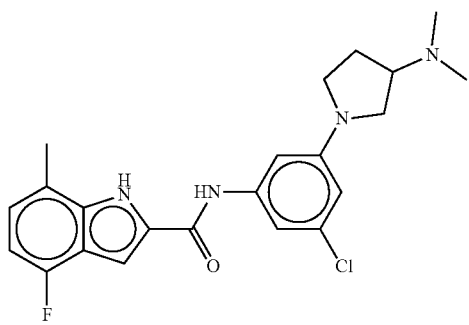 |
| 121 | 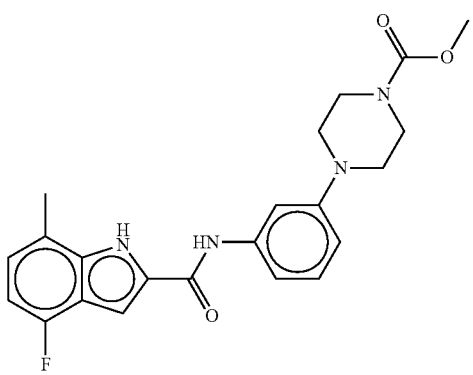 |
| 122 | 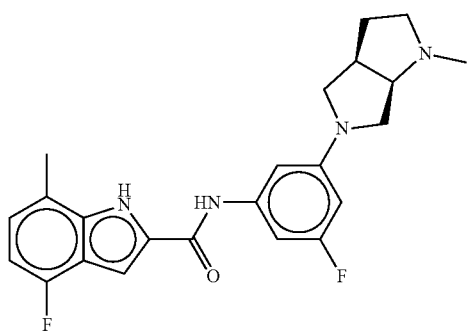 |
| 123 | 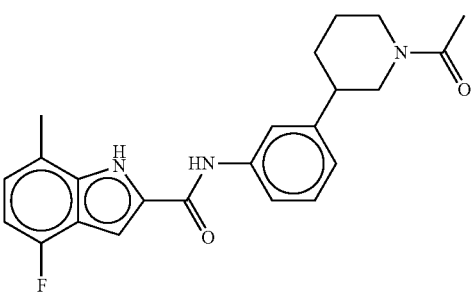 |

TABLE 1-continued
| Cpd. No. | Chemical Structure |
|---|---|
| 124 | 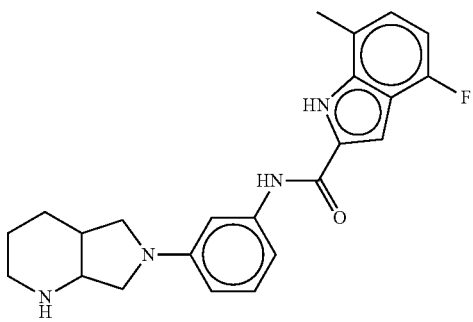 |
| 125 | 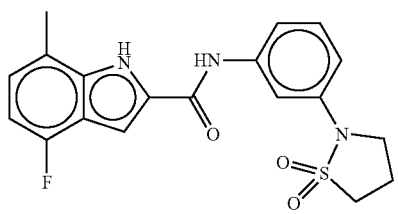 |
| 126 | 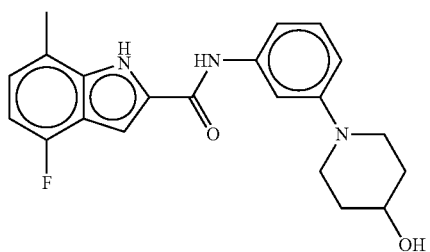 |
| 127 | 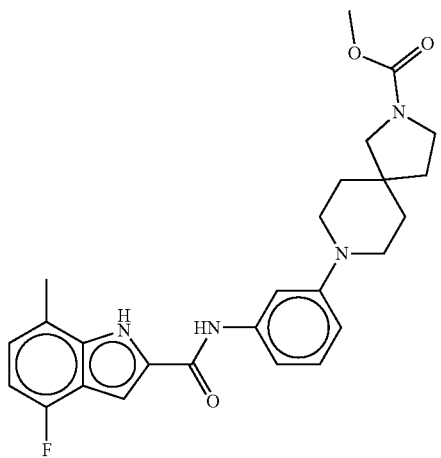 |
| 128 | 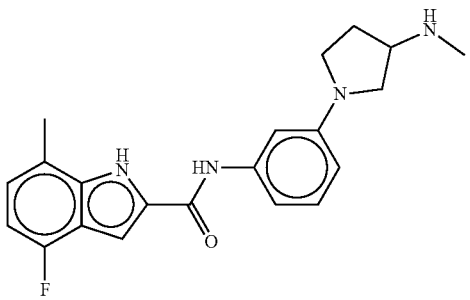 |

TABLE 1-continued
| Cpd. No. | Chemical Structure |
|---|---|
| 129 | 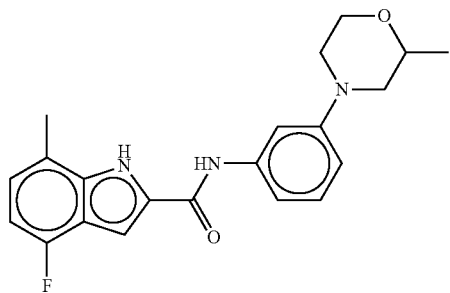 |
| 130 | 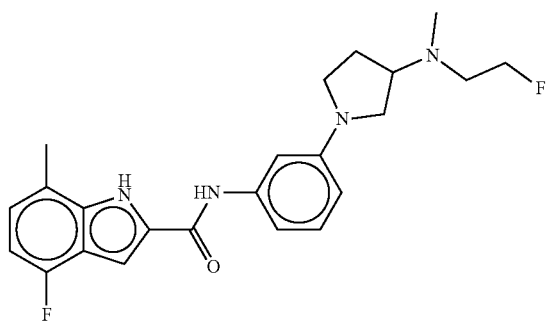 |
| 131 | 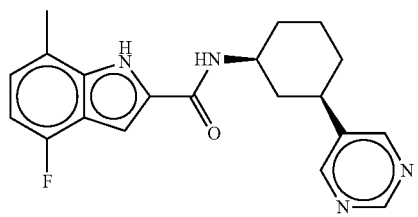 |
| 132 | 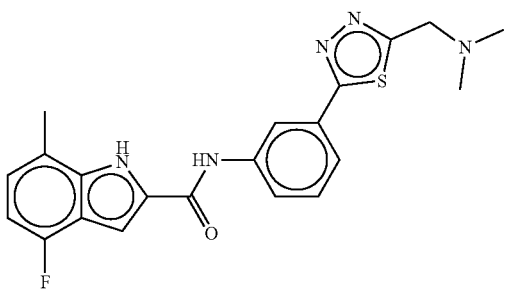 |
| 133 | 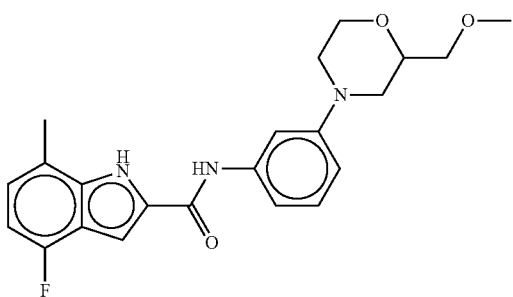 |

TABLE 1-continued

| Cpd. No. | Chemical Structure |
|---|---|
| 134 | 4-fluoro-7-methyl-N-(isoquinolin-5-yl)-1H-indole-2-carboxamide |
| 135 | 4-fluoro-7-methyl-N-(3-(6-methyl-2,6-diazaspiro[3.3]heptan-2-yl)phenyl)-1H-indole-2-carboxamide |
| 136 | 4-fluoro-7-methyl-N-(4'-((methylsulfonamido)methyl)-[1,1'-biphenyl]-3-yl)-1H-indole-2-carboxamide |
| 137 | 4-fluoro-7-methyl-N-(3-(pyridin-3-yl)phenyl)-1H-indole-2-carboxamide |
| 138 | 4-fluoro-7-methyl-N-(3-(4-(1-methylpiperidine-3-carbonyl)piperazin-1-yl)phenyl)-1H-indole-2-carboxamide |

TABLE 1-continued
| Cpd. No. | Chemical Structure |
|---|---|
| 139 | 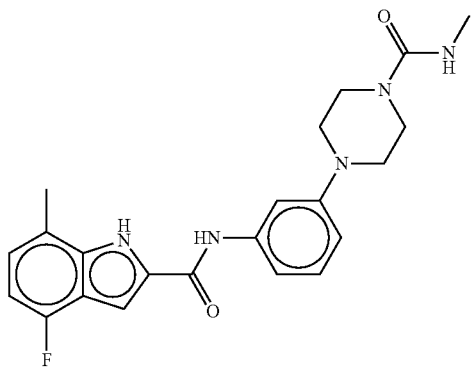 |
| 140 | 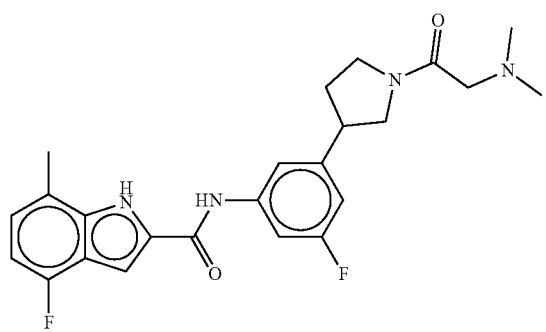 |
| 141 | 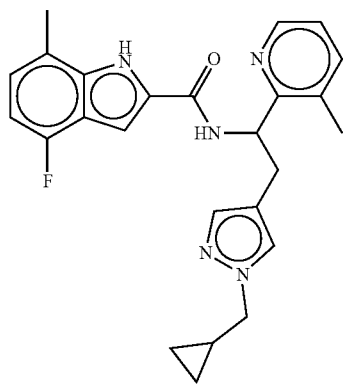 |
| 142 | 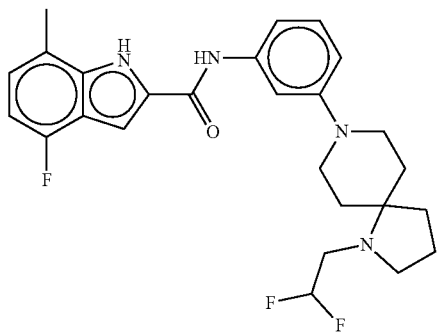 |

TABLE 1-continued
| Cpd. No. | Chemical Structure |
|---|---|
| 143 | 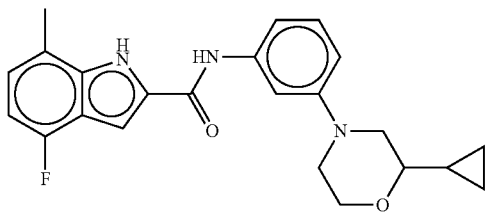 |
| 144 | 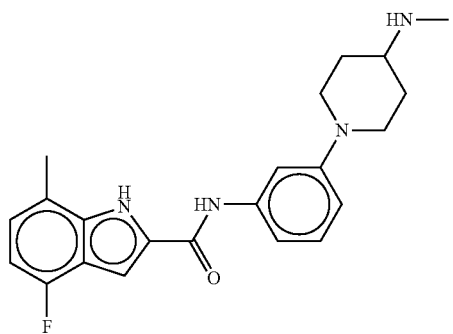 |
| 145 | 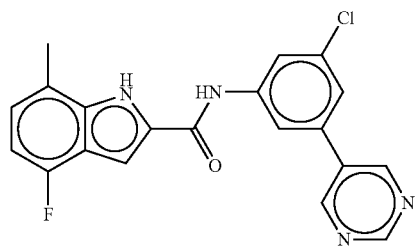 |
| 146 | 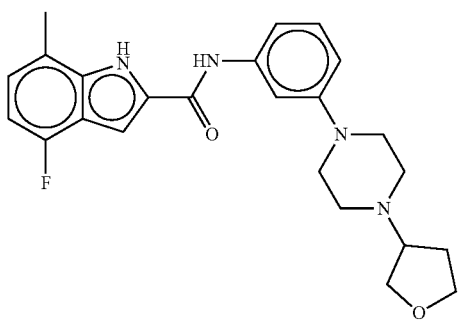 |
| 147 | 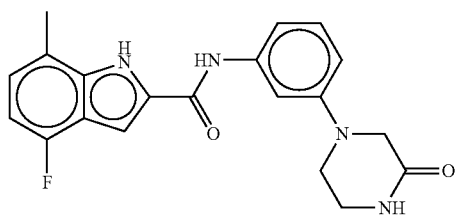 |

TABLE 1-continued

| Cpd. No. | Chemical Structure |
|---|---|
| 148 | 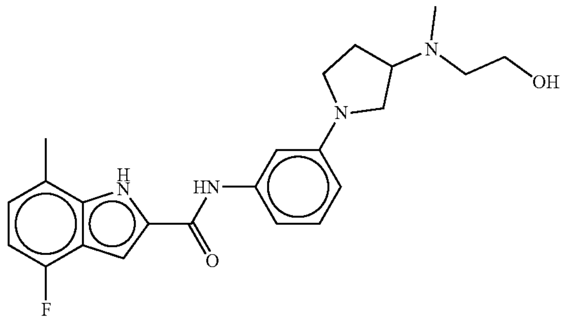 |
| 149 | 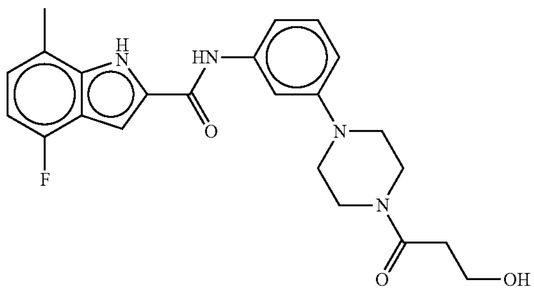 |
| 150 | 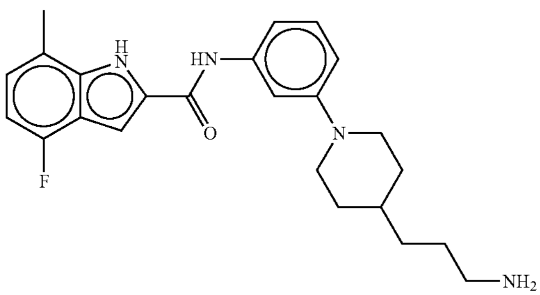 |
| 151 | 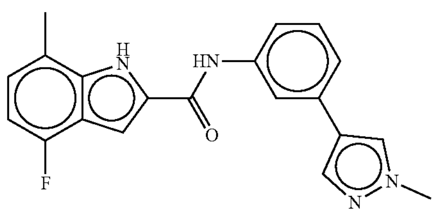 |
| 152 | 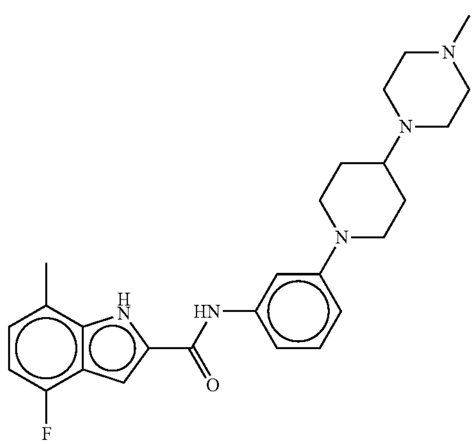 |

TABLE 1-continued
| Cpd. No. | Chemical Structure |
|---|---|
| 153 | 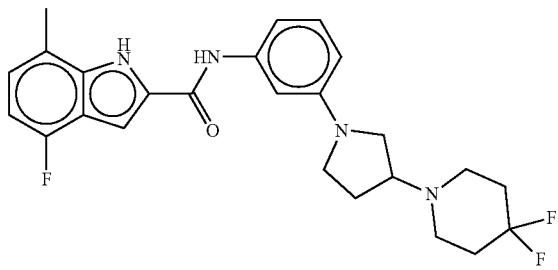 |
| 154 | 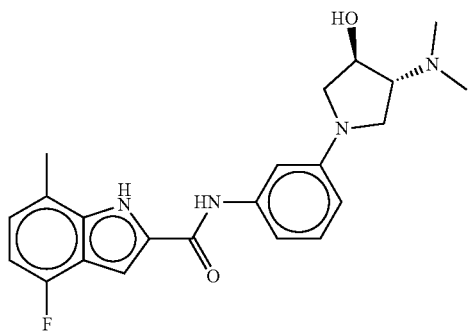 |
| 155 | 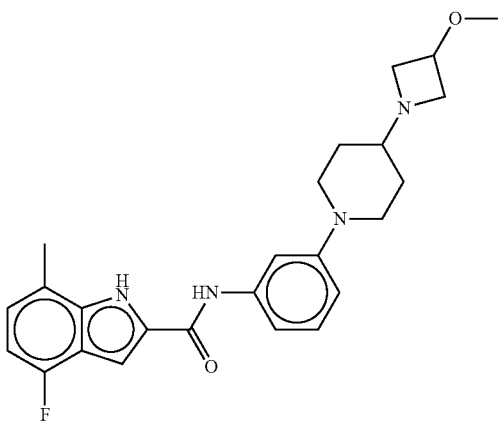 |
| 156 | 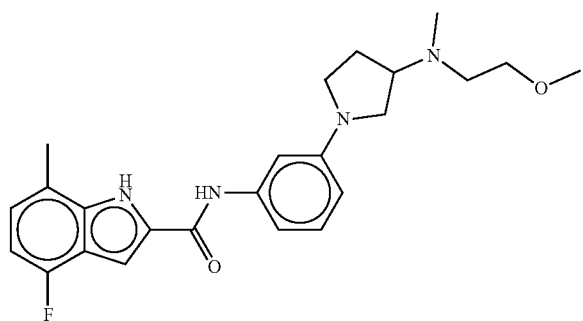 |

TABLE 1-continued
| Cpd. No. | Chemical Structure |
|---|---|
| 157 | 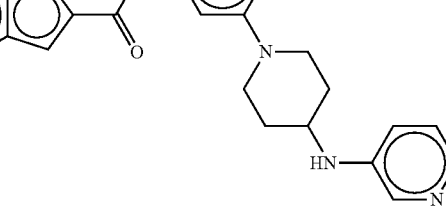 |
| 159 | 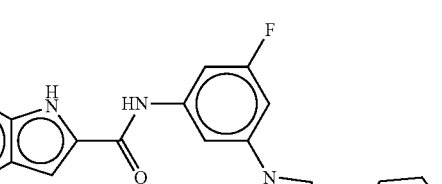 |
| 160 | 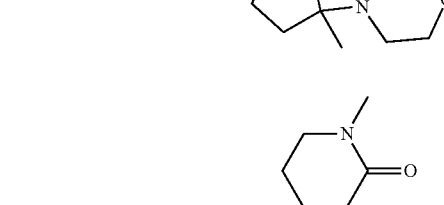 |
| 161 | 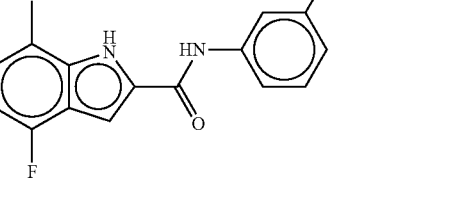 |
| 162 | 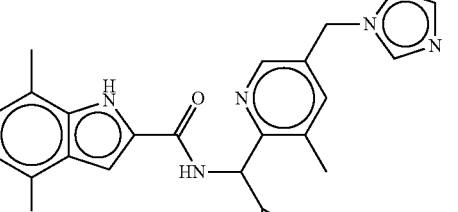 |

TABLE 1-continued

| Cpd. No. | Chemical Structure |
|---|---|
| 163 | 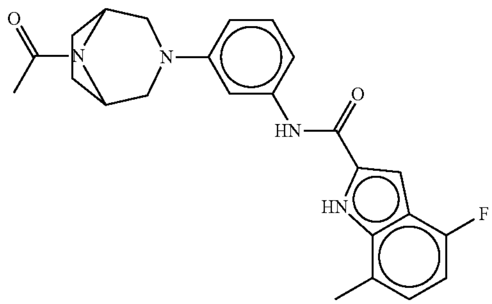 |
| 164 | 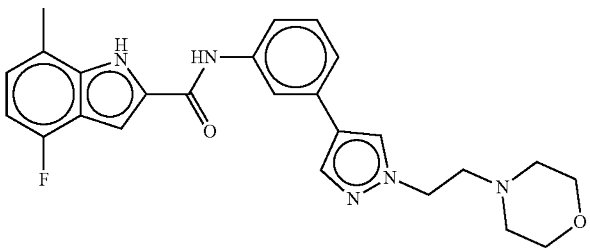 |
| 165 | 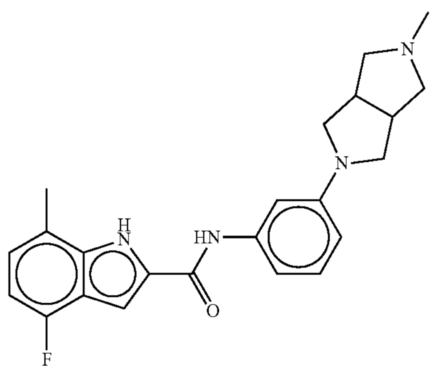 |
| 166 | 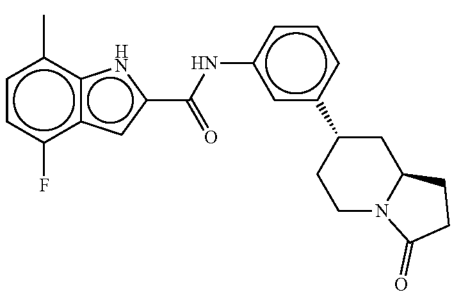 |
| 167 | 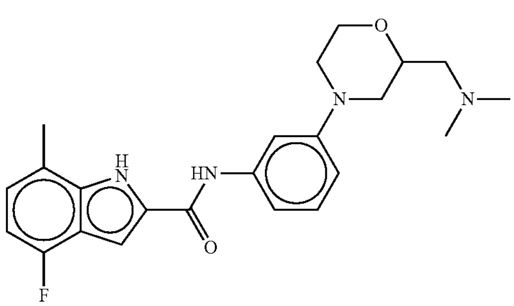 |

TABLE 1-continued
| Cpd. No. | Chemical Structure |
|---|---|
| 168 | 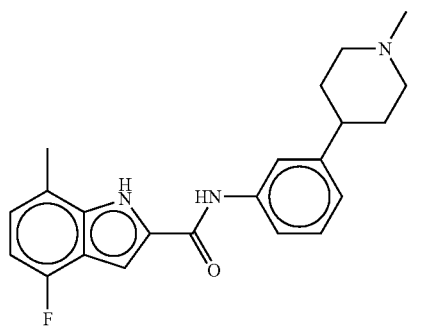 |
| 169 | 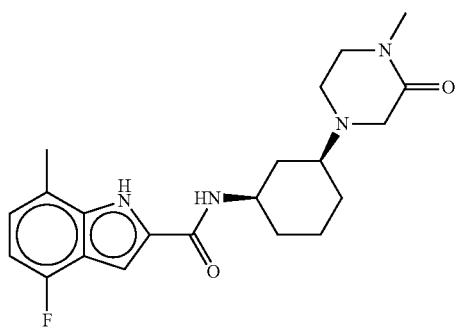 |
| 170 | 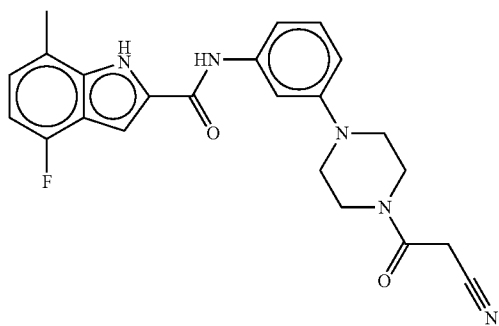 |
| 171 | 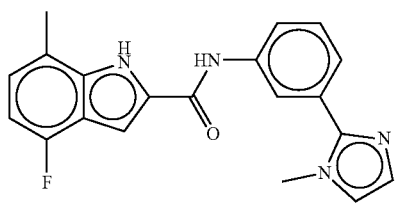 |
| 172 | 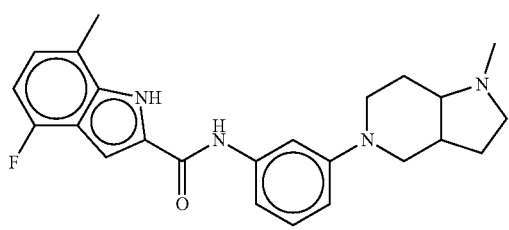 |

TABLE 1-continued
| Cpd. No. | Chemical Structure |
|---|---|
| 173 | 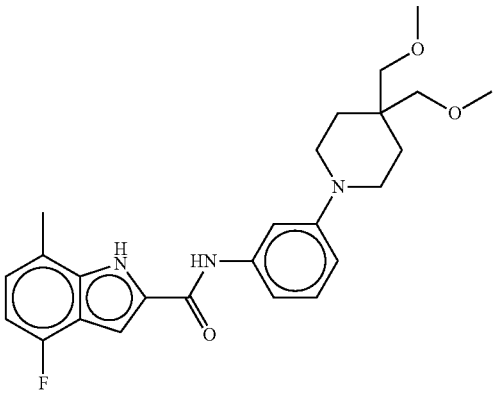 |
| 174 | 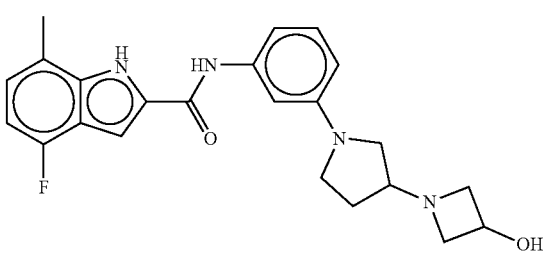 |
| 175 | 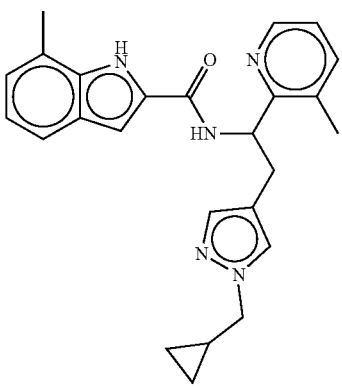 |
| 176 | 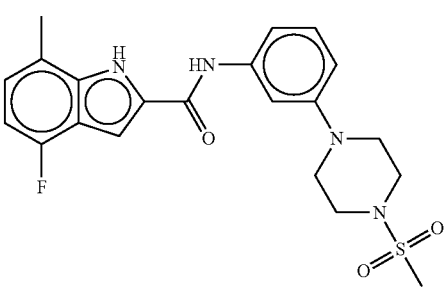 |
| 177 | 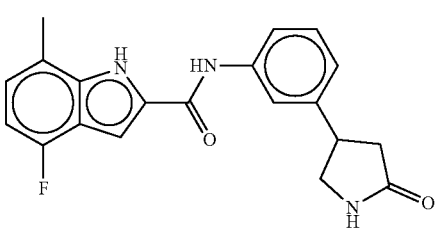 |

TABLE 1-continued
| Cpd. No. | Chemical Structure |
|---|---|
| 178 | 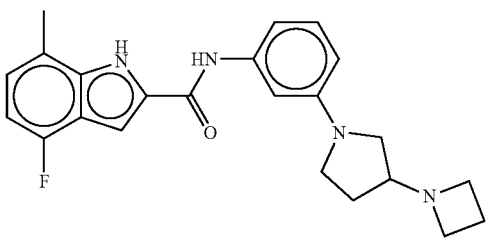 |
| 179 | 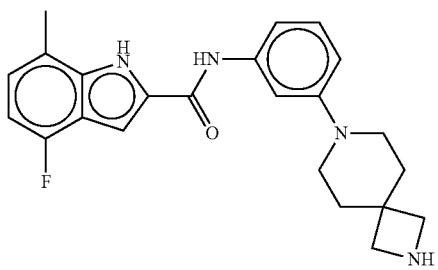 |
| 180 | 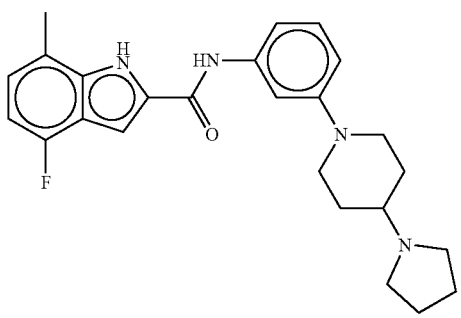 |
| 181 | 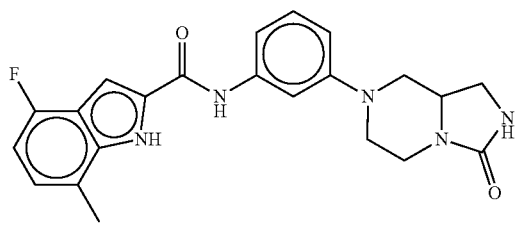 |
| 182 | 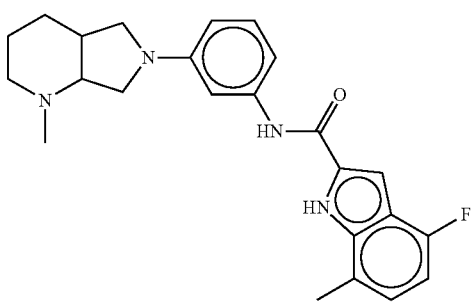 |

TABLE 1-continued
| Cpd. No. | Chemical Structure |
|---|---|
| 183 | 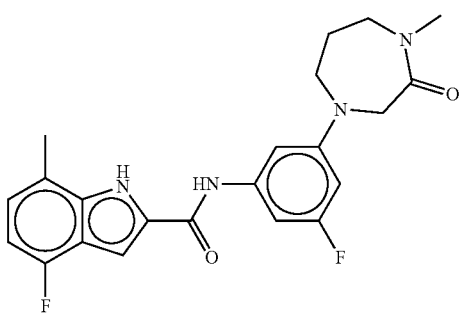 |
| 184 | 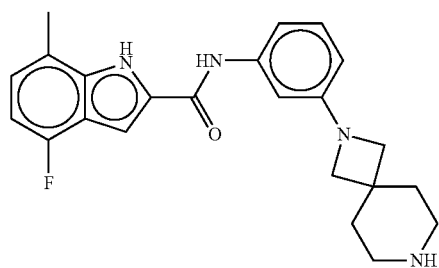 |
| 185 | 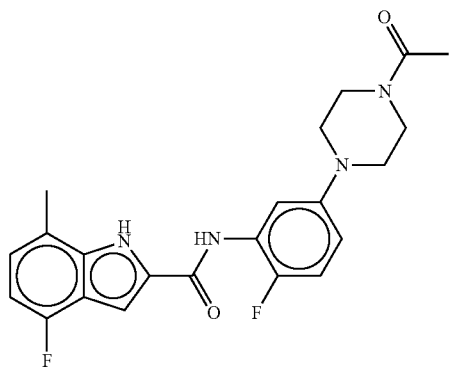 |
| 186 | 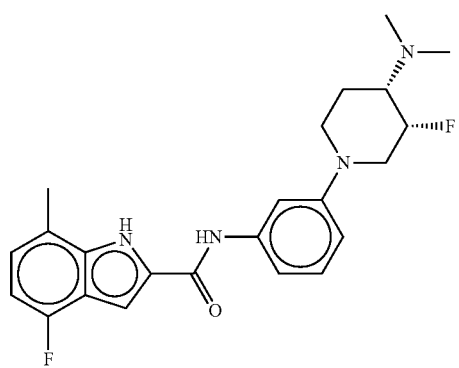 |

TABLE 1-continued
| Cpd. No. | Chemical Structure |
|---|---|
| 187 | 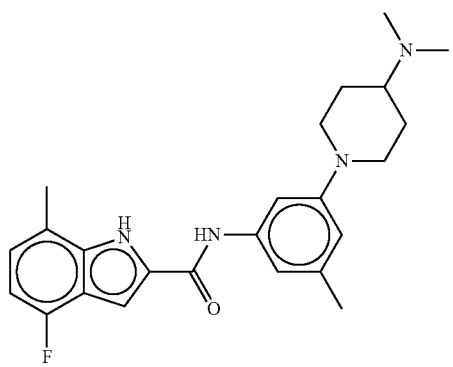 |
| 188 | 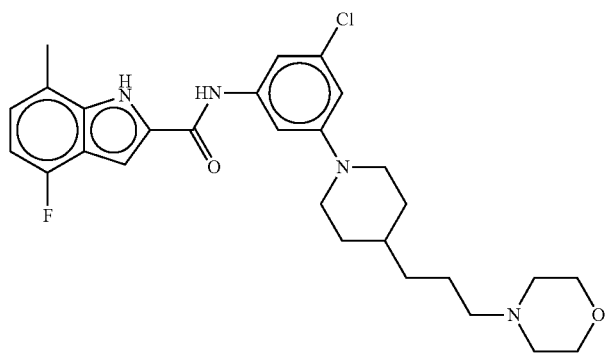 |
| 189 | 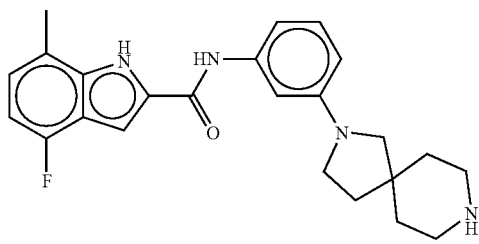 |
| 190 | 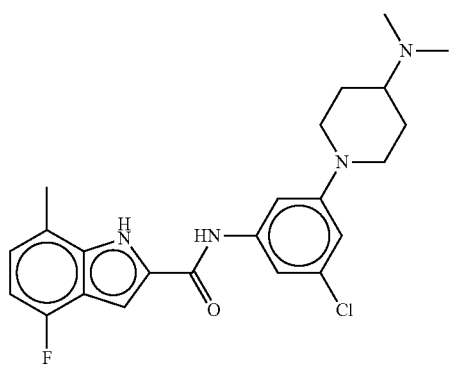 |

TABLE 1-continued
| Cpd. No. | Chemical Structure |
|---|---|
| 191 | 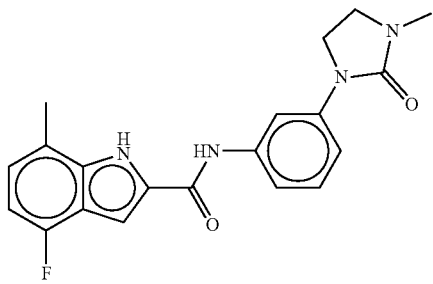 |
| 192 | 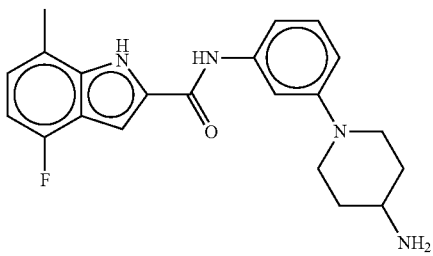 |
| 193 | 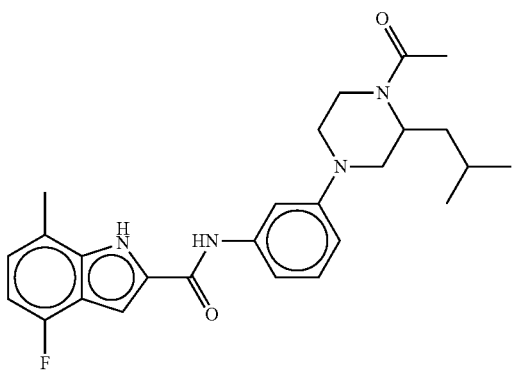 |
| 194 | 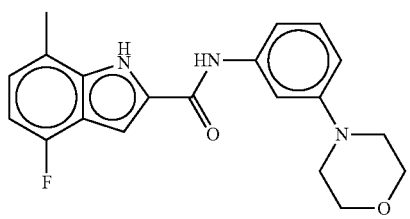 |
| 195 | 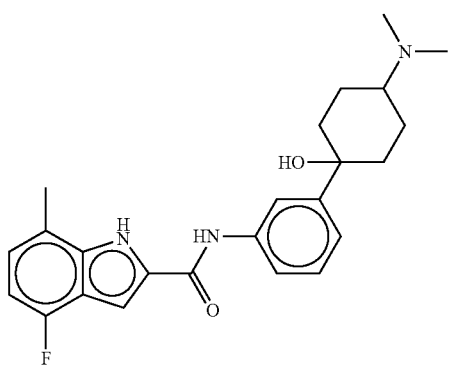 |

TABLE 1-continued
| Cpd. No. | Chemical Structure |
|---|---|
| 196 | 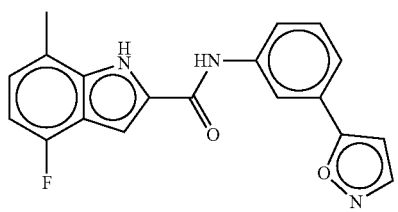 |
| 197 | 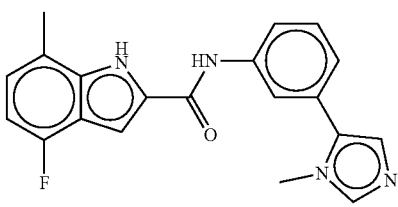 |
| 198 | 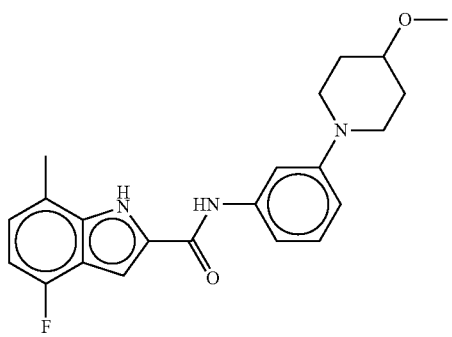 |
| 199 | 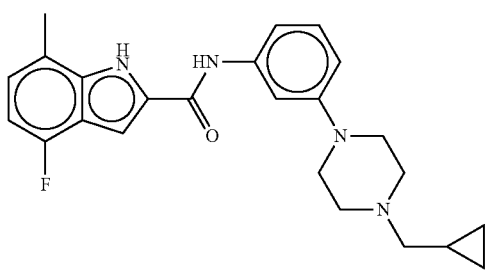 |
| 200 | 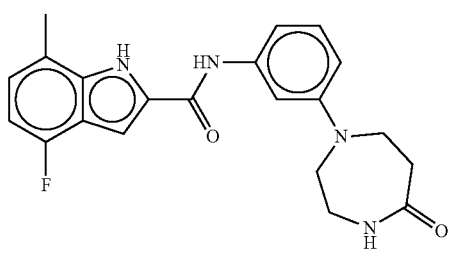 |

TABLE 1-continued
| Cpd. No. | Chemical Structure |
|---|---|
| 201 | 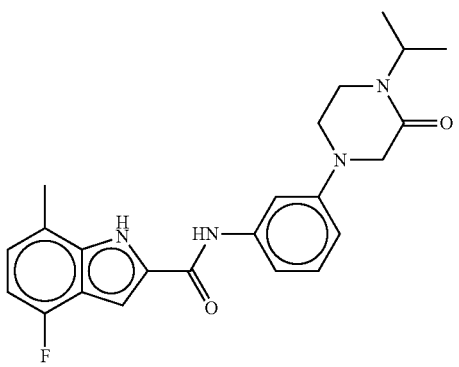 |
| 202 | 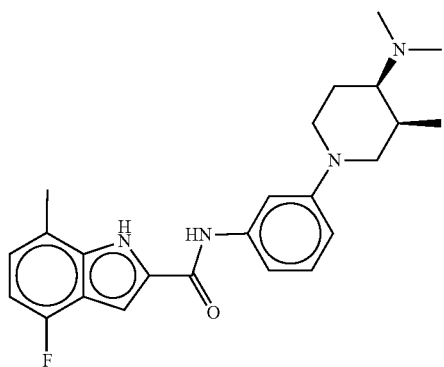 |
| 203 | 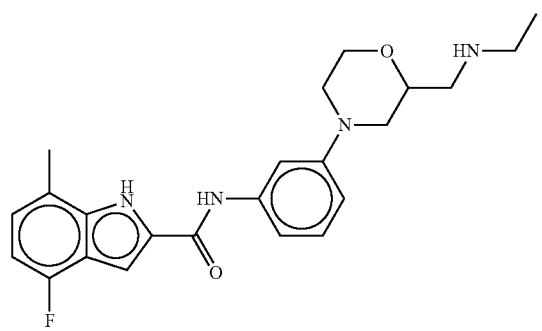 |
| 204 | 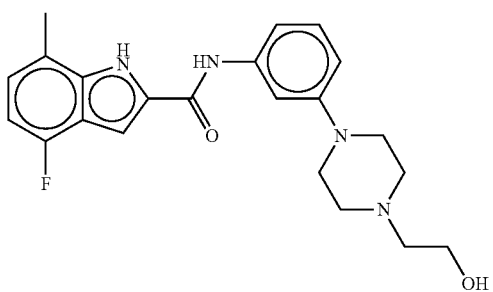 |

TABLE 1-continued

| Cpd. No. | Chemical Structure |
|---|---|
| 205 | 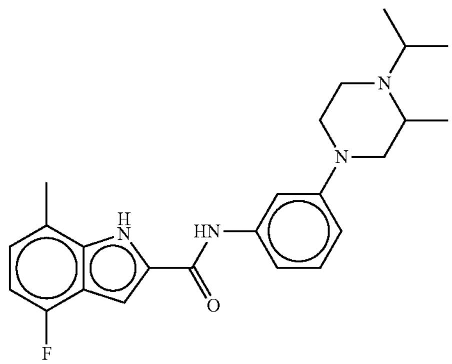 |
| 206 | 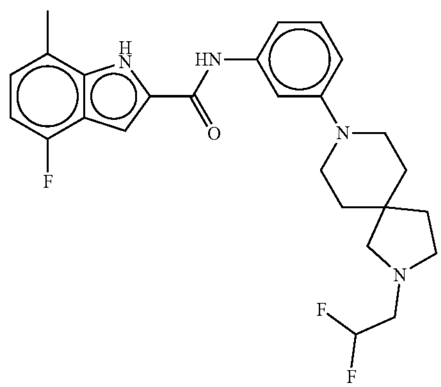 |
| 207 | 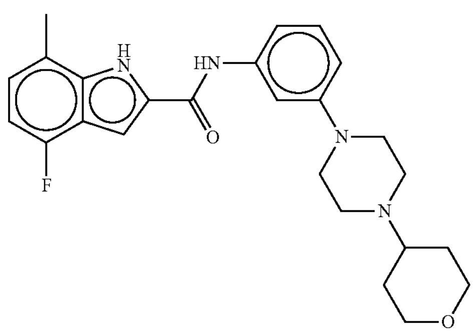 |
| 208 | 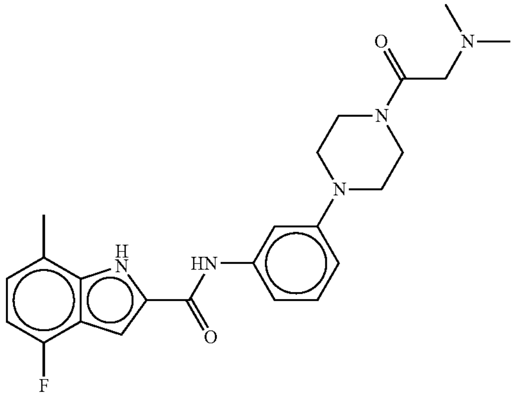 |

TABLE 1-continued
| Cpd. No. | Chemical Structure |
|---|---|
| 209 | 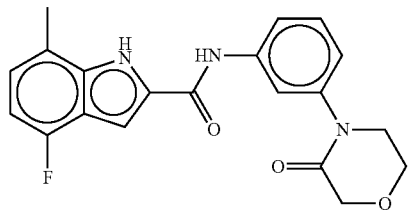 |
| 210 | 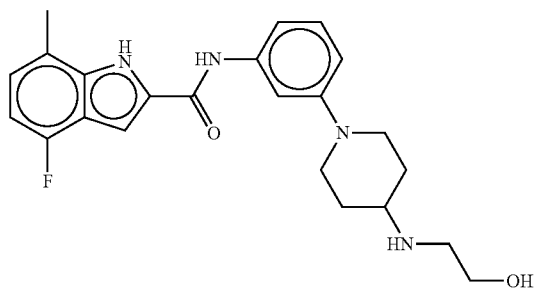 |
| 211 | 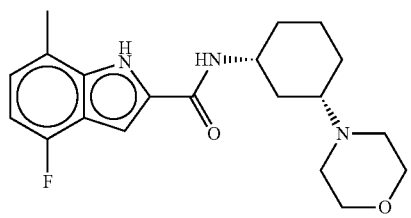 |
| 212 | 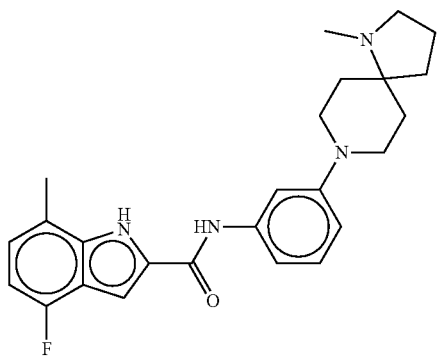 |
| 213 | 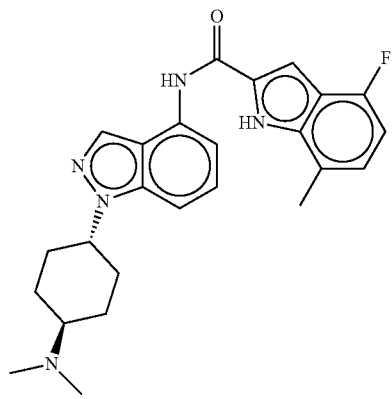 |

151
TABLE 1-continued
| Cpd. No. | Chemical Structure |
|---|---|
| 214 | 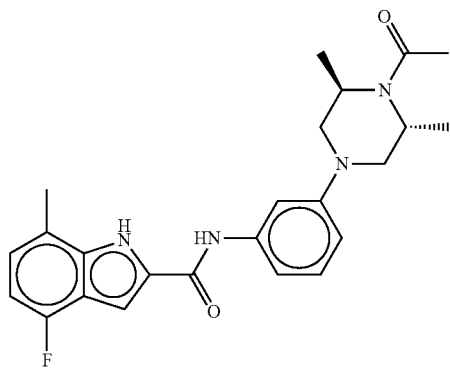 |
| 215 | 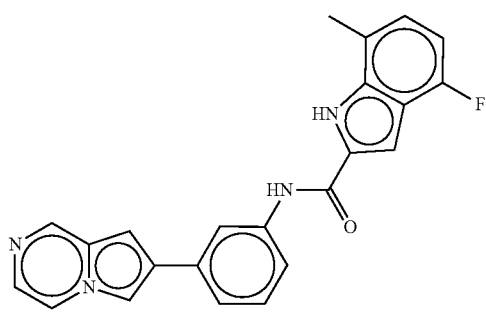 |
| 216 | 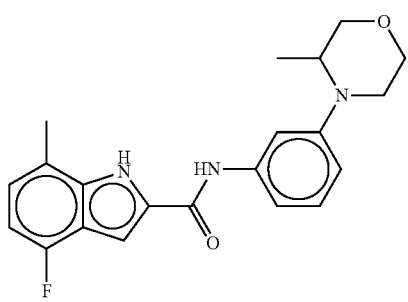 |
| 217 | 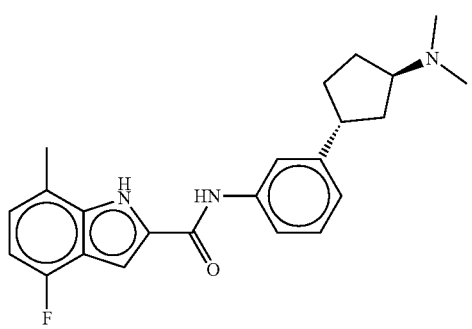 |
| 218 | 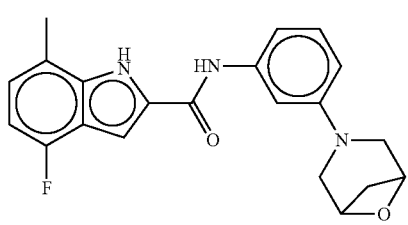 |

TABLE 1-continued
| Cpd. No. | Chemical Structure |
|---|---|
| 219 | 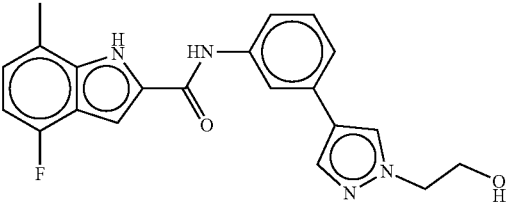 |
| 220 | 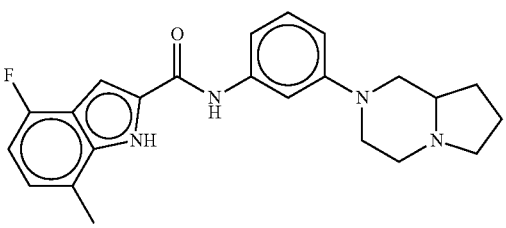 |
| 221 | 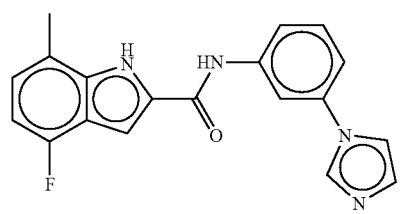 |
| 222 | 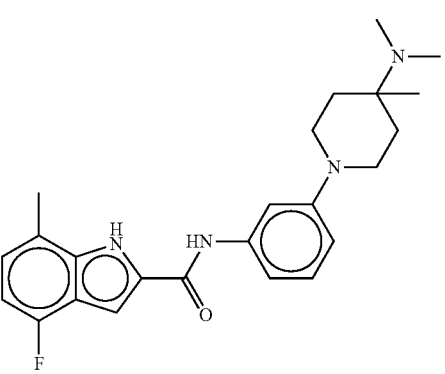 |
| 223 | 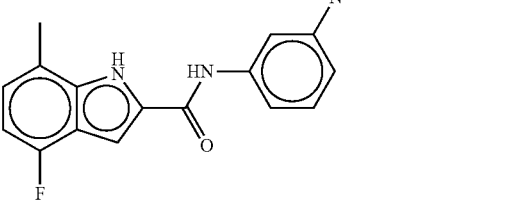 |

TABLE 1-continued
| Cpd. No. | Chemical Structure |
|---|---|
| 224 | 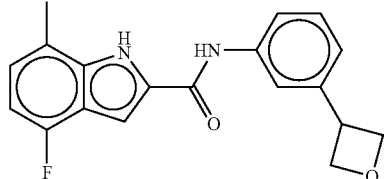 |
| 225 | 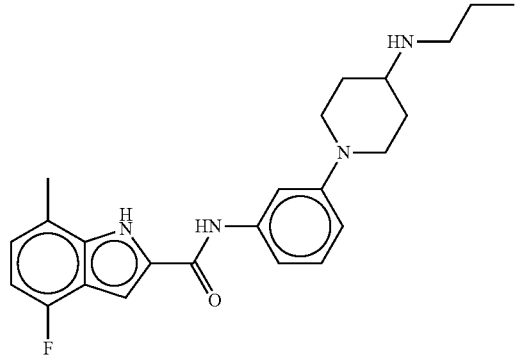 |
| 226 | 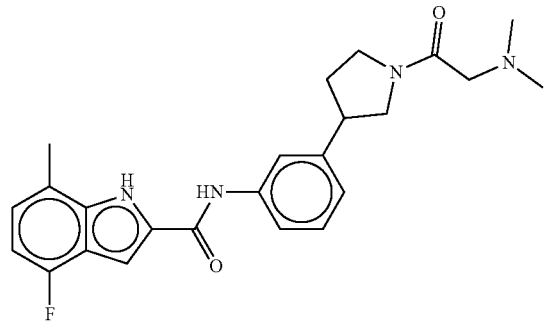 |
| 227 | 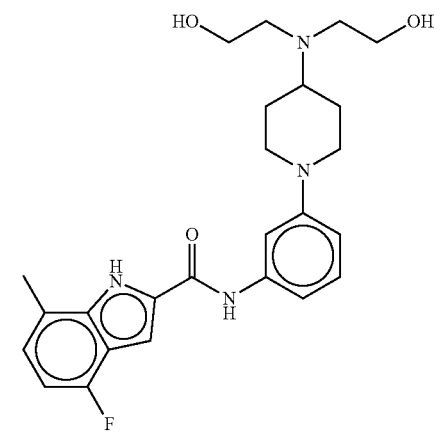 |

TABLE 1-continued
| Cpd. No. | Chemical Structure |
|---|---|
| 228 | 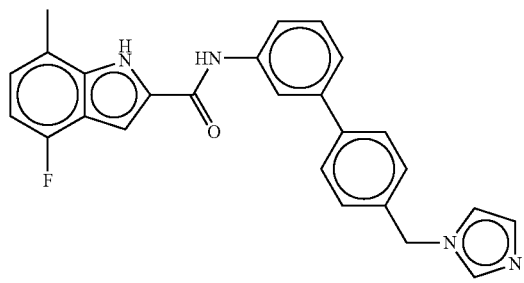 |
| 229 | 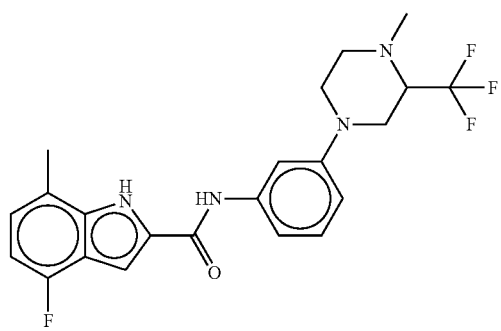 |
| 230 | 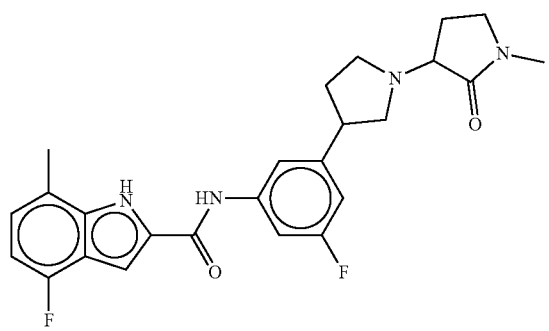 |
| 231 | 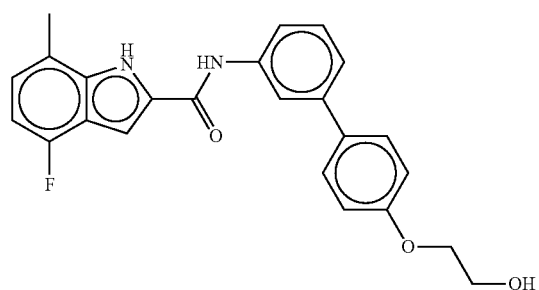 |

TABLE 1-continued

| Cpd. No. | Chemical Structure |
|---|---|
| 232 | 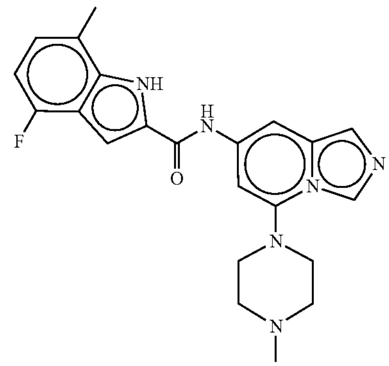 |
| 233 | 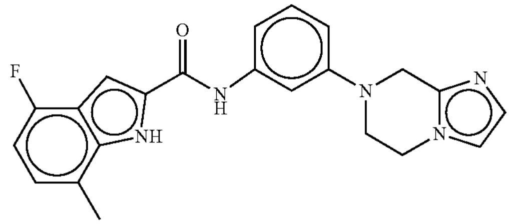 |
| 234 | 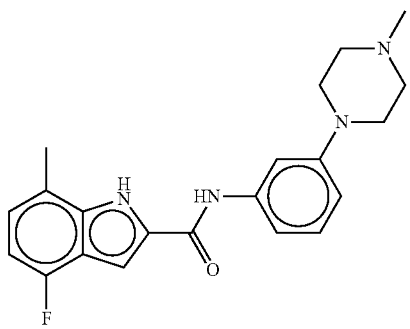 |
| 235 | 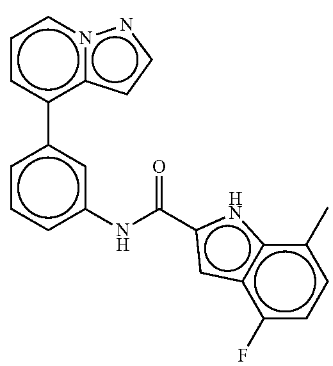 |
| 236 | 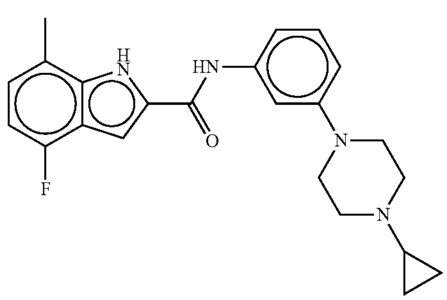 |

TABLE 1-continued
| Cpd. No. | Chemical Structure |
|---|---|
| 237 | 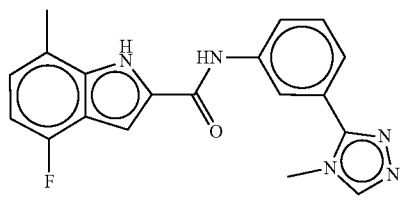 |
| 238 | 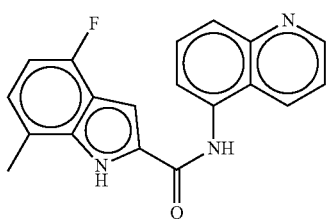 |
| 239 | 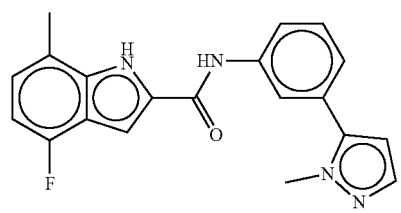 |
| 240 | 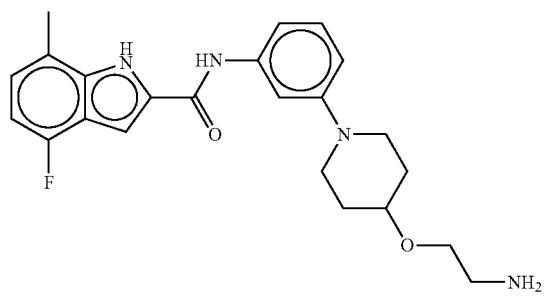 |
| 241 | 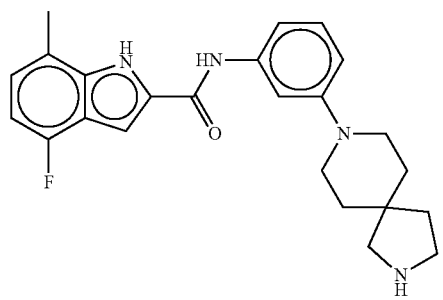 |

TABLE 1-continued
| Cpd. No. | Chemical Structure |
|---|---|
| 242 | 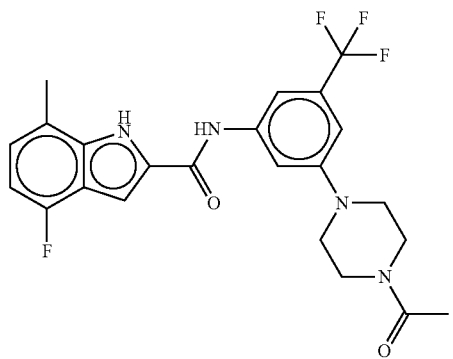 |
| 243 | 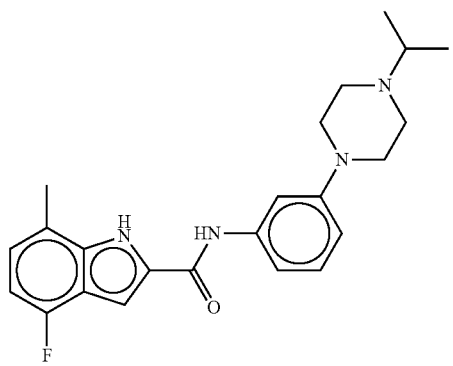 |
| 244 | 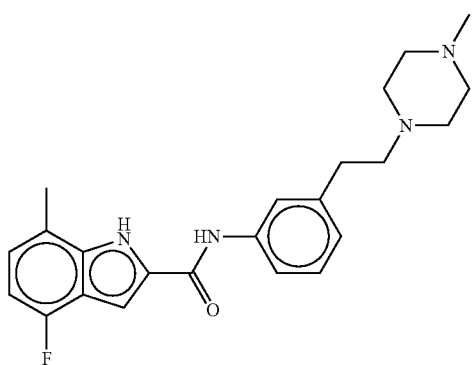 |
| 245 | 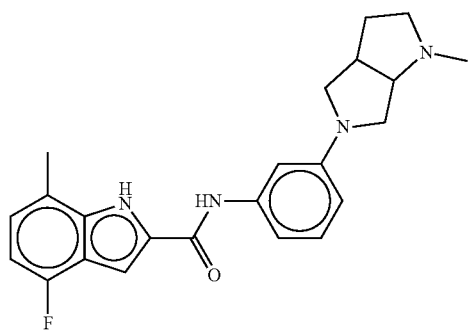 |

TABLE 1-continued
| Cpd. No. | Chemical Structure |
|---|---|
| 246 | 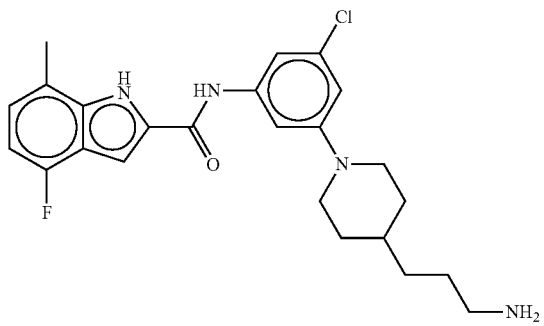 |
| 247 | 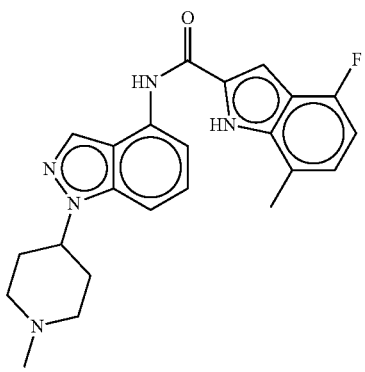 |
| 248 | 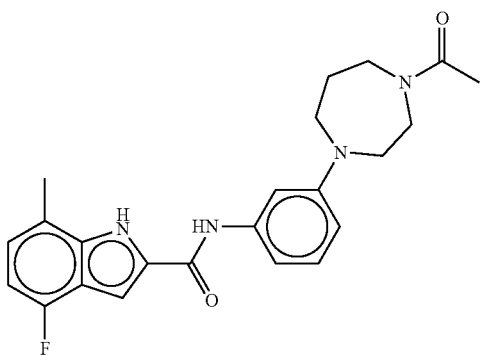 |
| 249 | 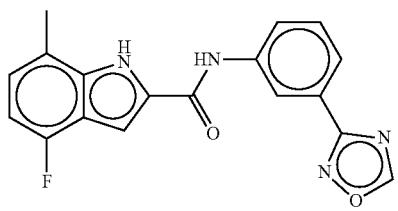 |
| 250 | 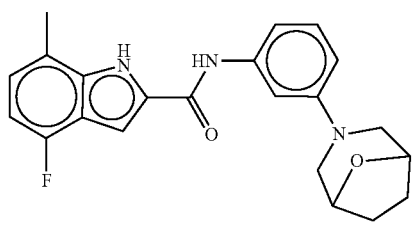 |

TABLE 1-continued

| Cpd. No. | Chemical Structure |
|---|---|
| 251 | 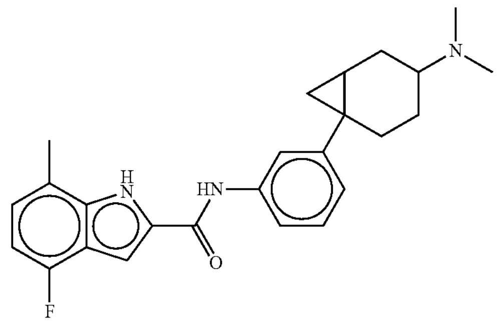 |
| 252 | 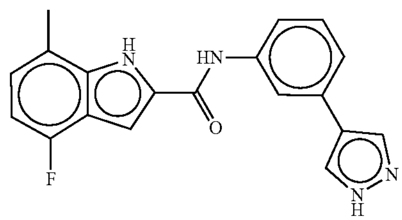 |
| 253 | 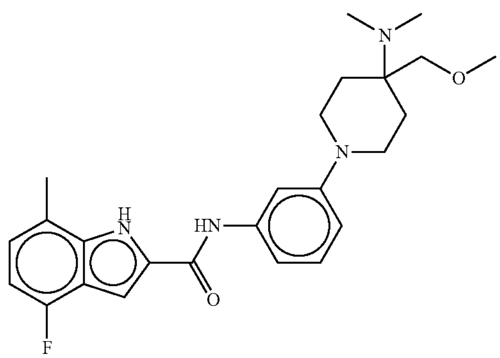 |
| 254 | 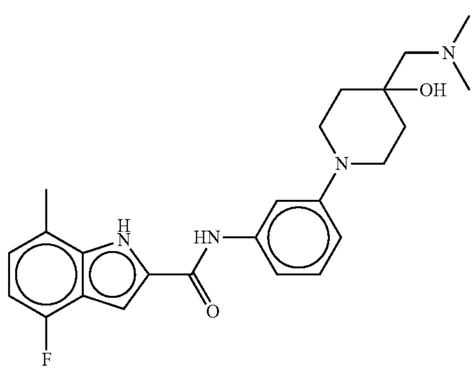 |
| 255 | 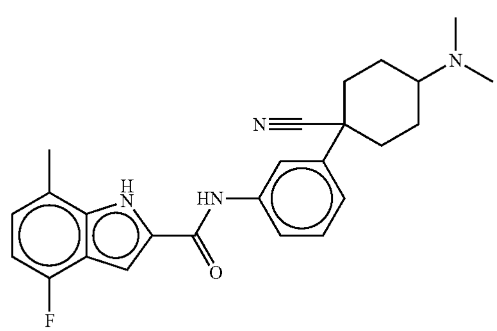 |

TABLE 1-continued
| Cpd. No. | Chemical Structure |
|---|---|
| 256 | 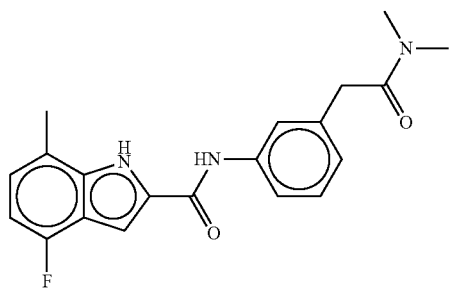 |
| 257 | 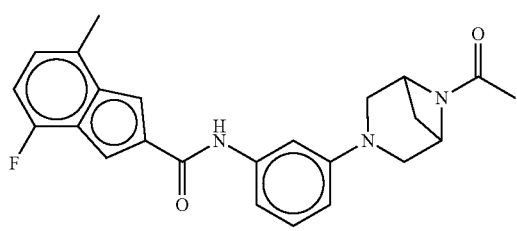 |
| 258 | 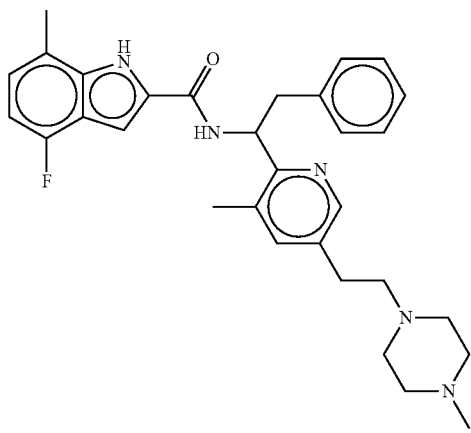 |
| 259 | 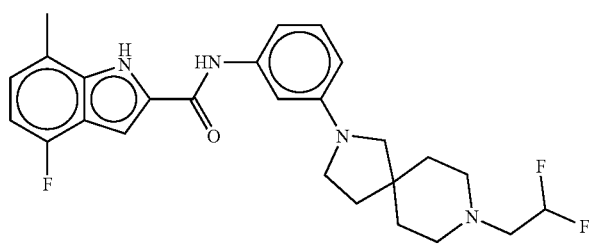 |
| 260 | 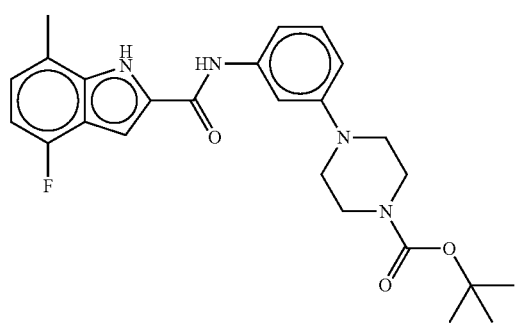 |

TABLE 1-continued
| Cpd. No. | Chemical Structure |
|---|---|
| 261 | 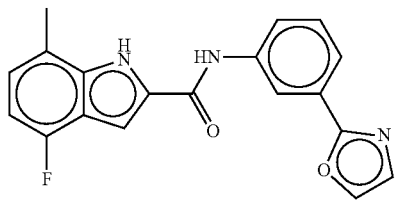 |
| 262 | 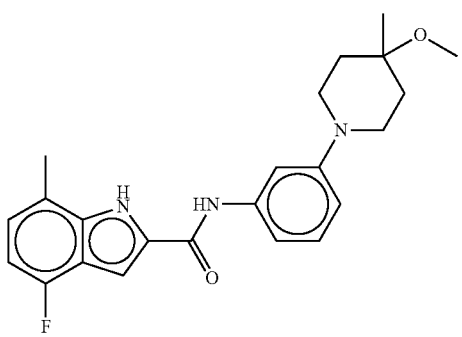 |
| 263 | 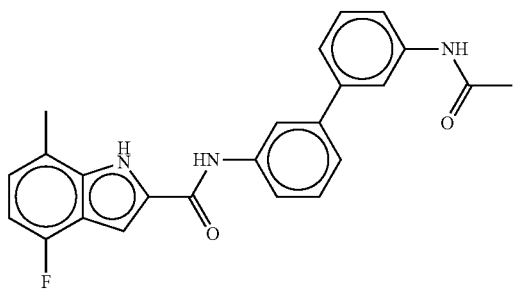 |
| 264 | 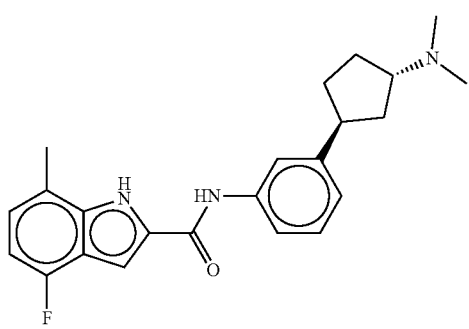 |
| 265 | 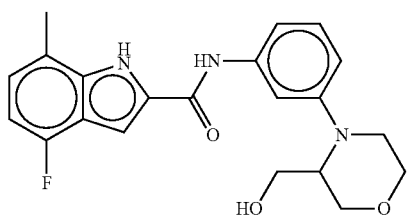 |

TABLE 1-continued
| Cpd. No. | Chemical Structure |
|---|---|
| 266 | 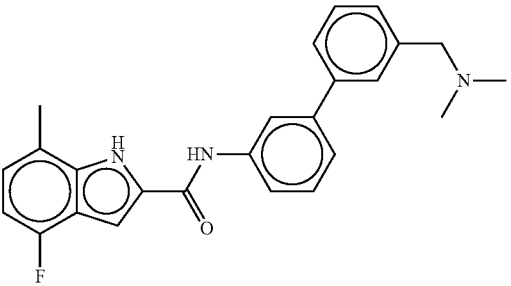 |
| 267 | 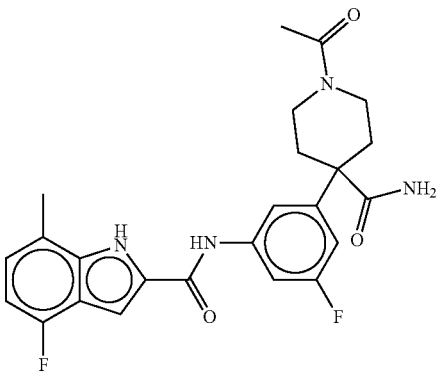 |
| 268 | 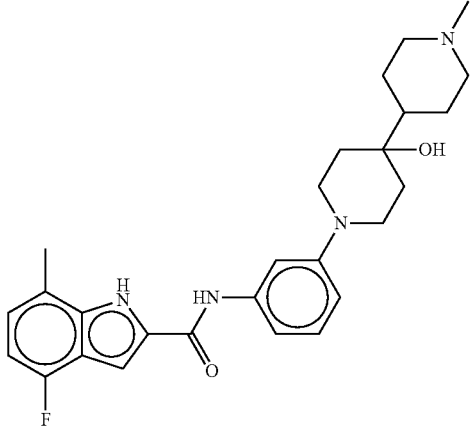 |
| 269 | 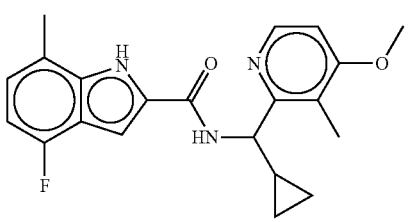 |
| 270 | 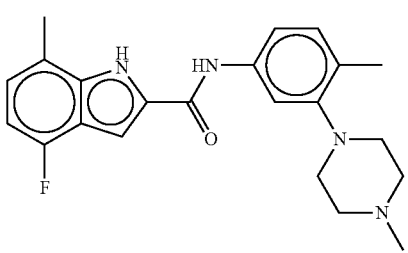 |

TABLE 1-continued
| Cpd. No. | Chemical Structure |
|---|---|
| 271 | 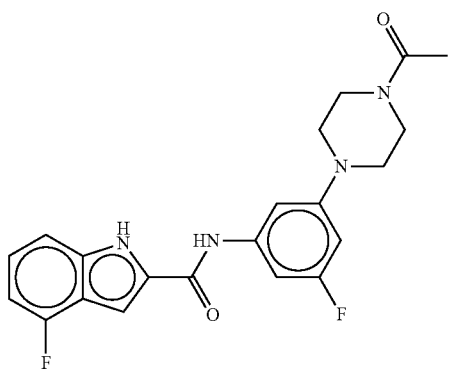 |
| 272 | 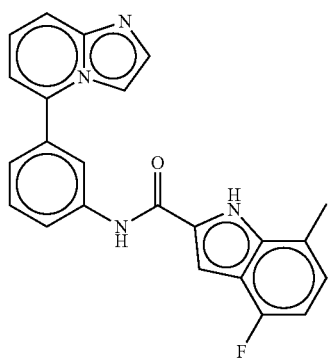 |
| 273 | 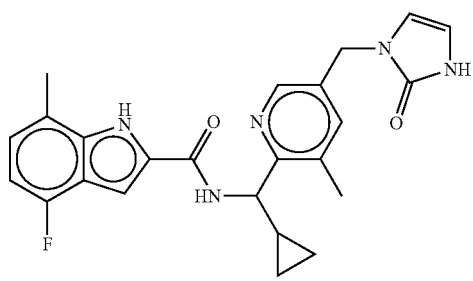 |
| 274 | 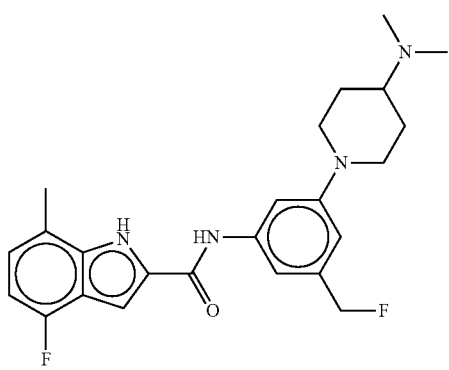 |

TABLE 1-continued

| Cpd. No. | Chemical Structure |
|---|---|
| 276 | 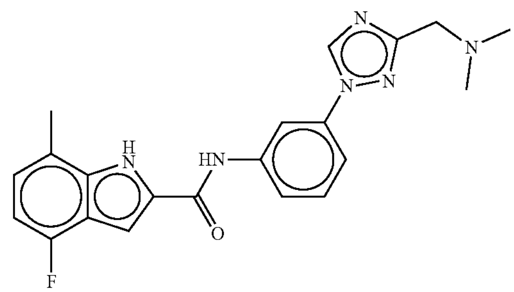 |
| 277 | 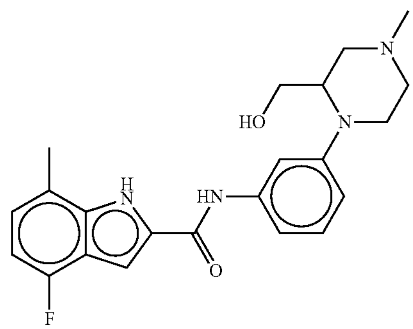 |
| 278 | 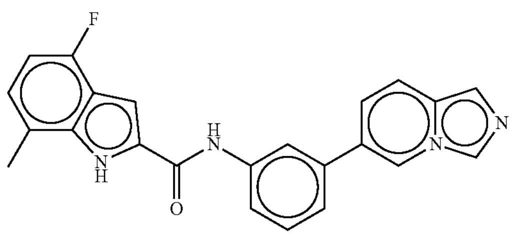 |
| 279 | 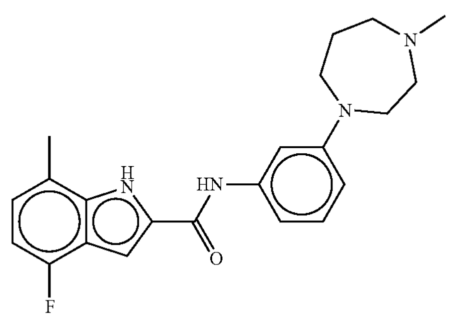 |
| 280 | 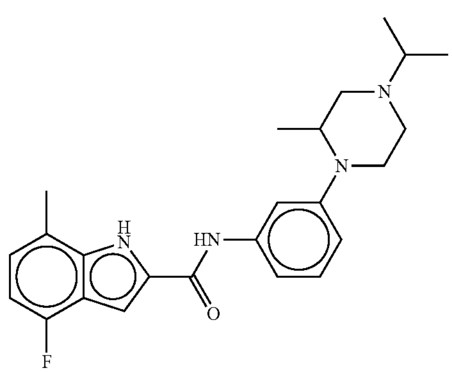 |

TABLE 1-continued
| Cpd. No. | Chemical Structure |
|---|---|
| 281 | 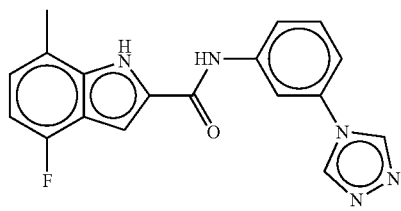 |
| 282 | 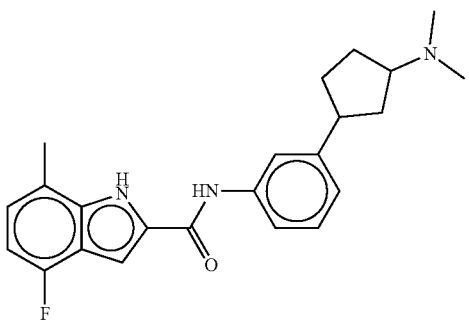 |
| 283 | 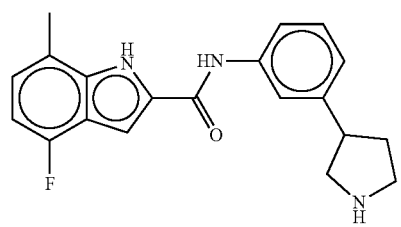 |
| 284 | 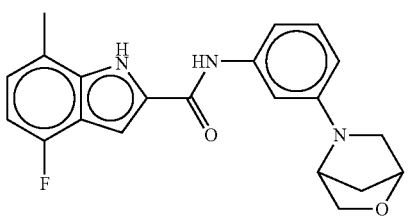 |
| 285 | 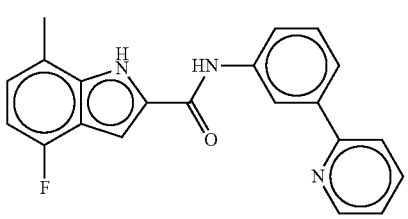 |
| 286 | 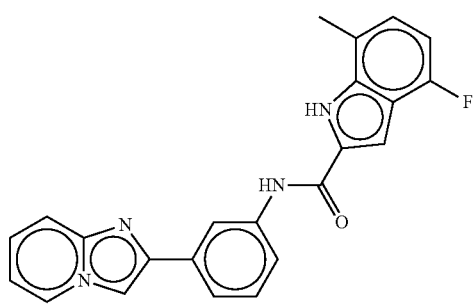 |

TABLE 1-continued
| Cpd. No. | Chemical Structure |
|---|---|
| 287 | 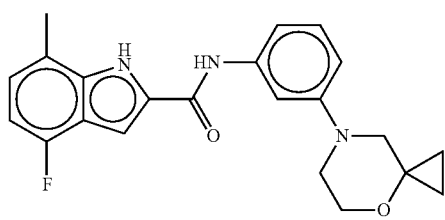 |
| 288 | 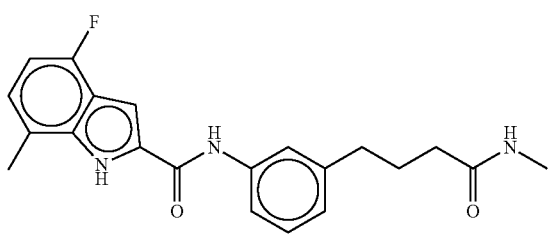 |
| 289 | 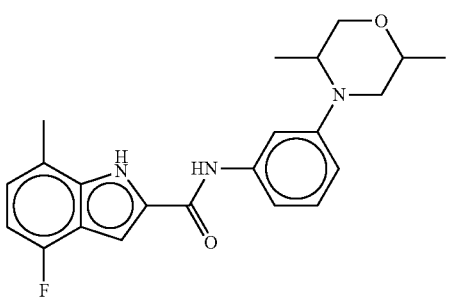 |
| 290 | 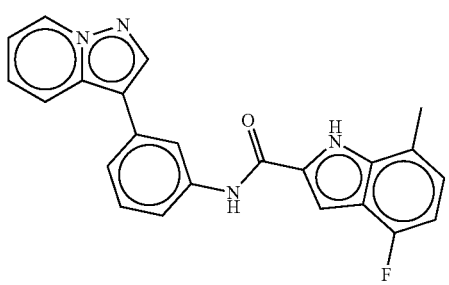 |
| 291 | 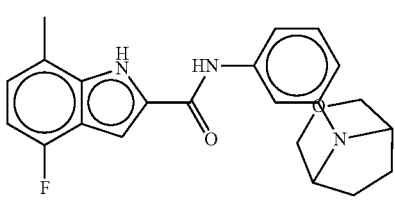 |
| 292 | 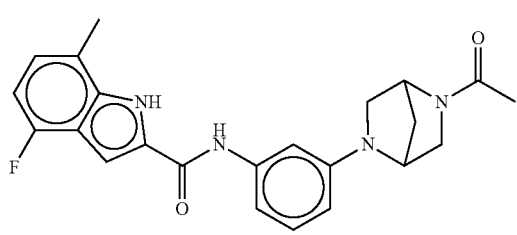 |

TABLE 1-continued

| Cpd. No. | Chemical Structure |
|---|---|
| 293 | 4-fluoro-7-methyl-1H-indole-2-carboxamide with N-[3-(2-(methylamino)-2-oxoethyl)phenyl] (N-methyl propanamide on phenyl) |
| 294 | 4-fluoro-7-methyl-1H-indole-2-carboxamide with N-[3-(1-methyloctahydro-1H-indol-5-yl)phenyl] |
| 295 | 4-fluoro-7-methyl-1H-indole-2-carboxamide with N-[2-(4-acetylpiperazin-1-yl)pyrimidin-4-yl] |
| 296 | 4-fluoro-7-methyl-1H-indole-2-carboxamide with N-[3-(1,2,4-oxadiazol-5-yl)phenyl] |
| 297 | 4-fluoro-7-methyl-1H-indole-2-carboxamide with N-[3-(piperidin-1-yl)phenyl] |

TABLE 1-continued
| Cpd. No. | Chemical Structure |
|---|---|
| 298 | 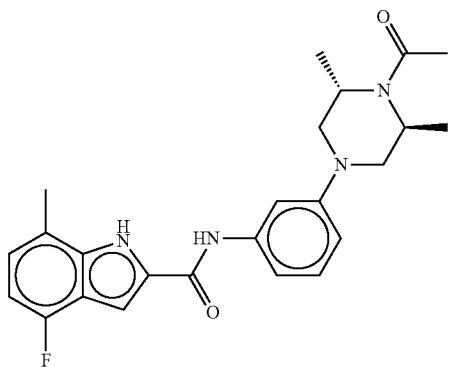 |
| 299 | 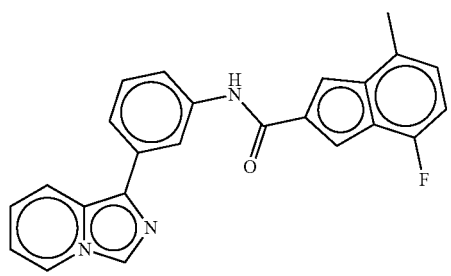 |
| 300 | 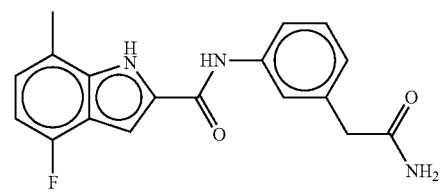 |
| 301 | 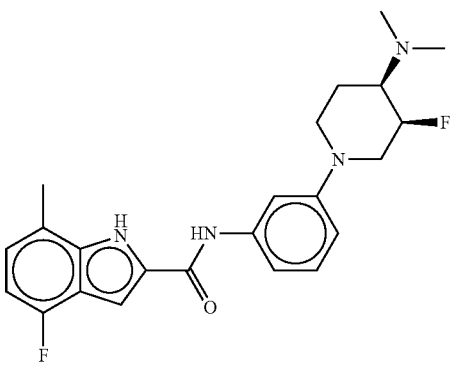 |
| 302 | 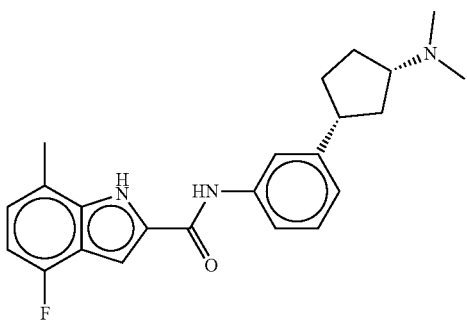 |

TABLE 1-continued
| Cpd. No. | Chemical Structure |
|---|---|
| 303 | 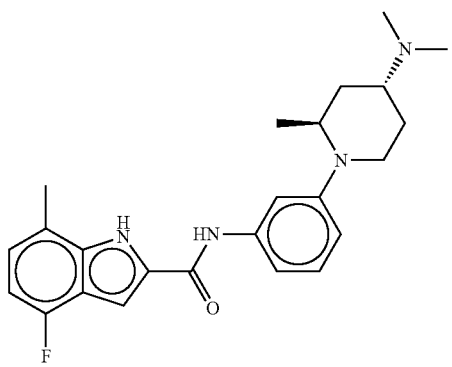 |
| 304 | 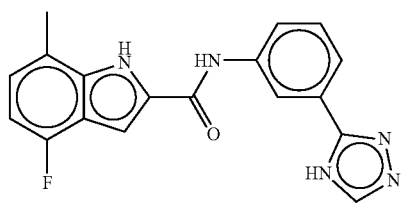 |
| 305 | 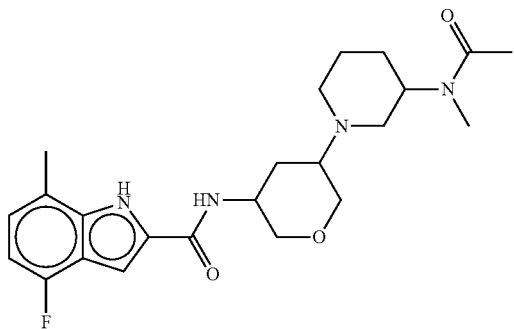 |
| 306 | 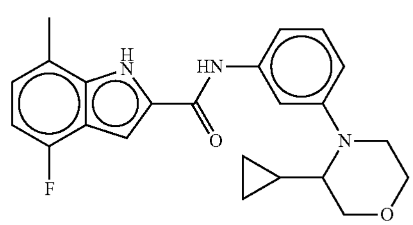 |
| 307 | 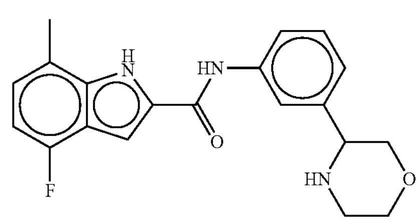 |

TABLE 1-continued

| Cpd. No. | Chemical Structure |
|---|---|
| 308 | 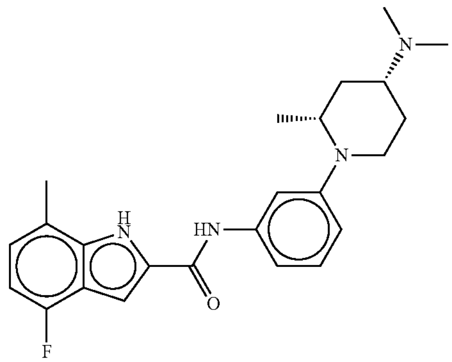 |
| 309 | 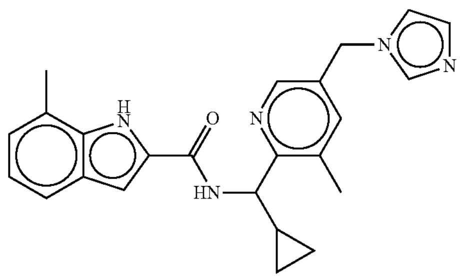 |
| 310 | 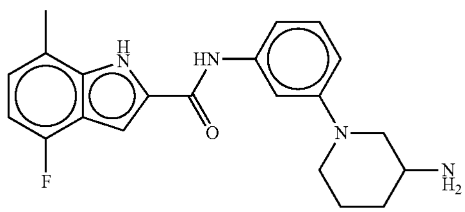 |
| 311 | 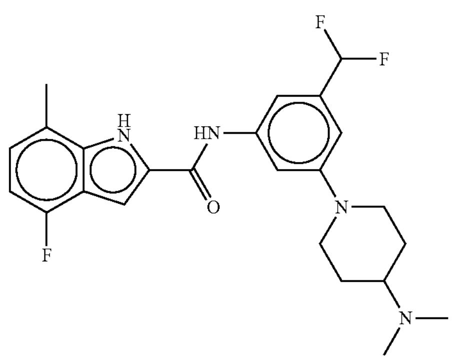 |
| 312 | 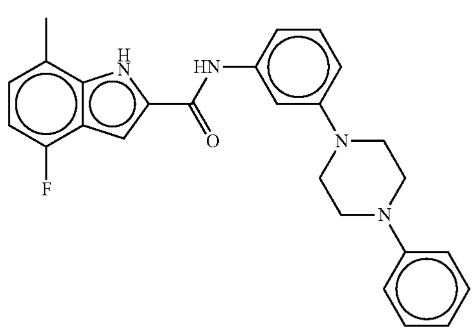 |

TABLE 1-continued
| Cpd. No. | Chemical Structure |
|---|---|
| 313 | 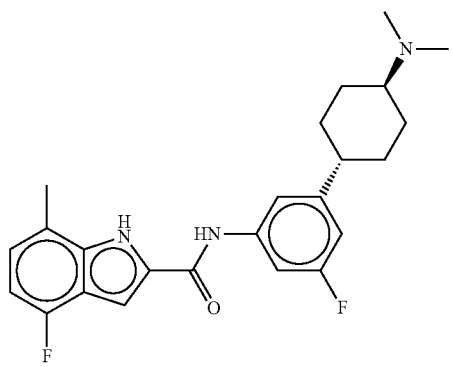 |
| 314 | 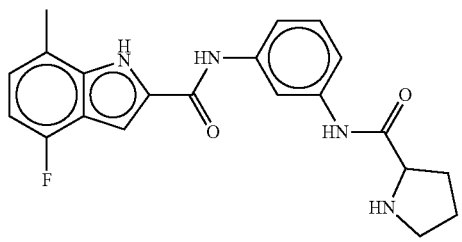 |
| 315 | 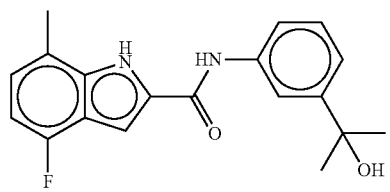 |
| 316 | 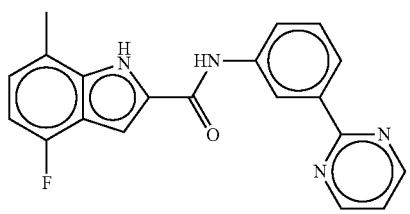 |
| 317 | 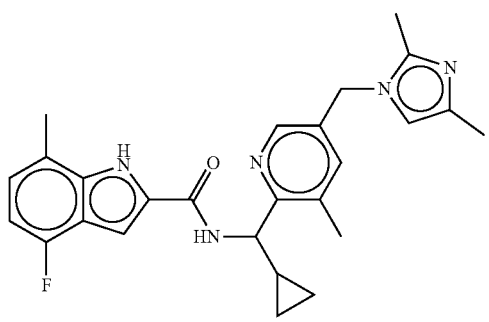 |

TABLE 1-continued

| Cpd. No. | Chemical Structure |
|---|---|
| 318 | 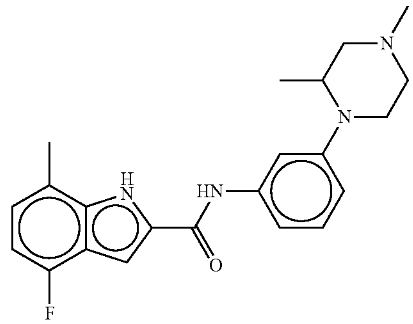 |
| 319 | 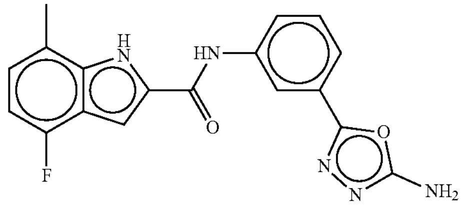 |
| 320 | 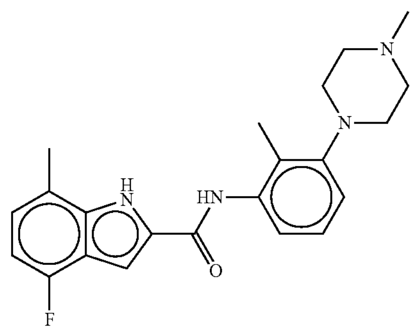 |
| 321 | 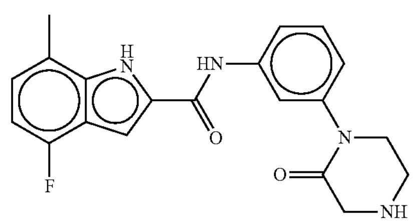 |
| 322 | 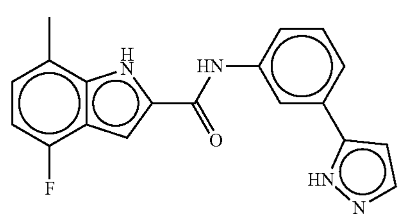 |
| 323 | 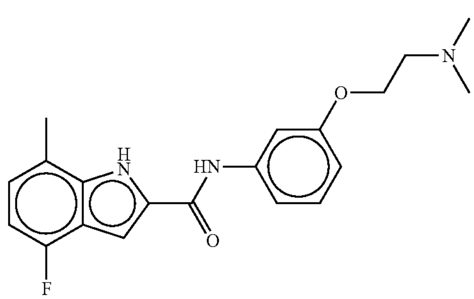 |

195 196
TABLE 1-continued
| Cpd. No. | Chemical Structure |
|---|---|
| 324 | 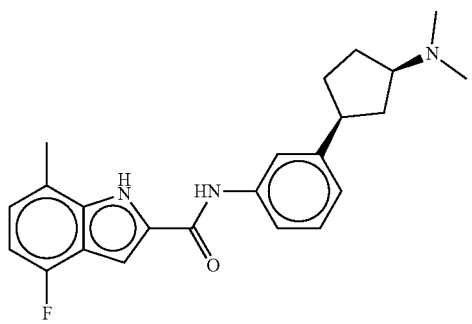 |
| 325 | 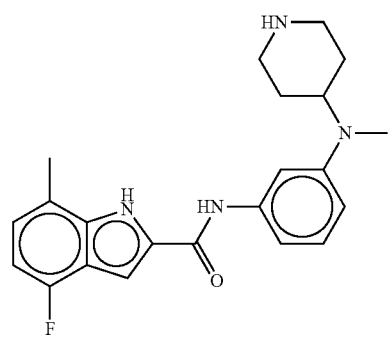 |
| 326 | 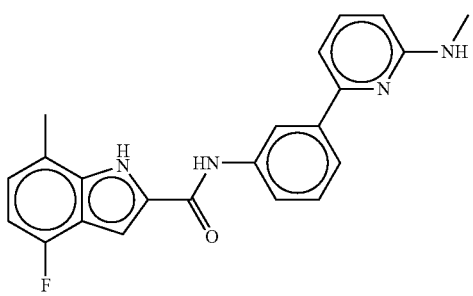 |
| 327 | 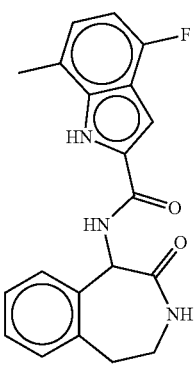 |
| 328 | 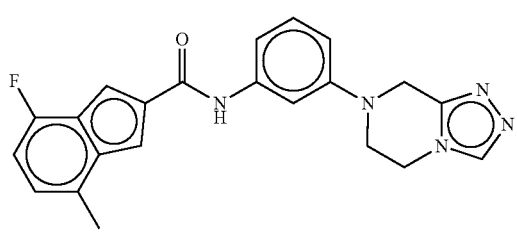 |

TABLE 1-continued
| Cpd. No. | Chemical Structure |
|---|---|
| 329 | 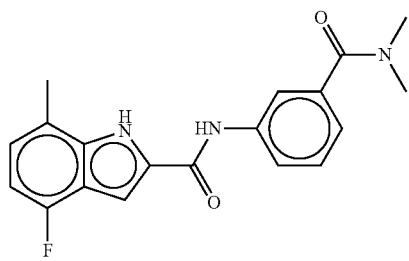 |
| 330 | 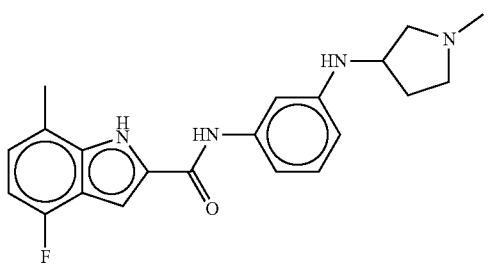 |
| 331 | 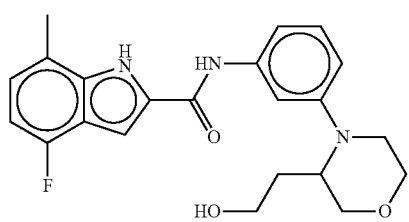 |
| 332 | 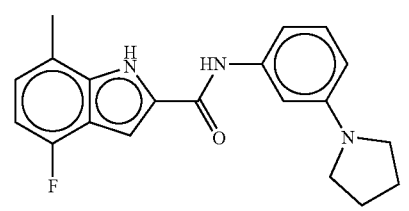 |
| 333 | 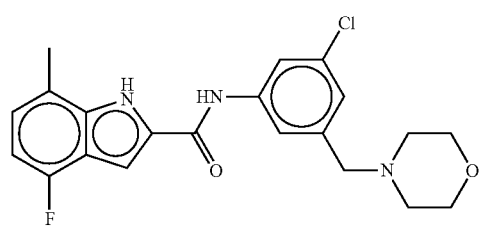 |
| 334 | 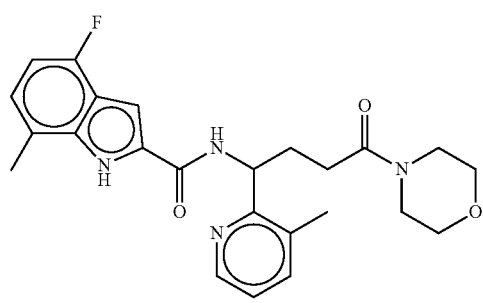 |

TABLE 1-continued
| Cpd. No. | Chemical Structure |
|---|---|
| 335 | 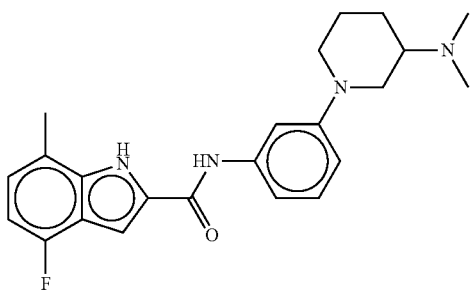 |
| 336 | 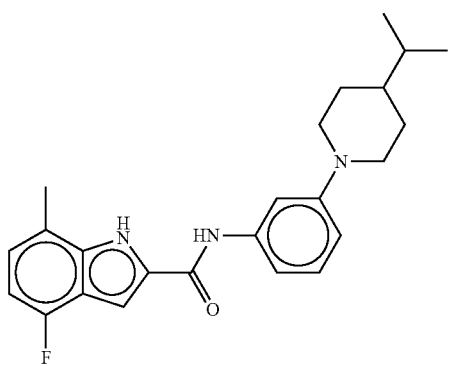 |
| 337 | 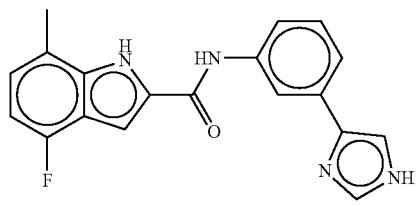 |
| 338 | 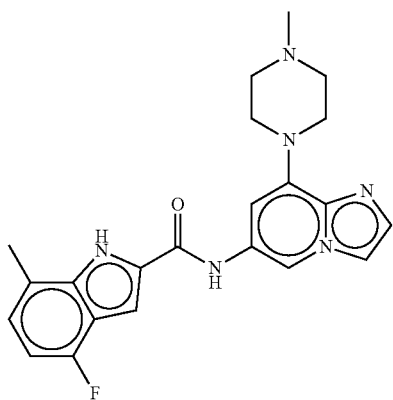 |

TABLE 1-continued
| Cpd. No. | Chemical Structure |
|---|---|
| 339 | 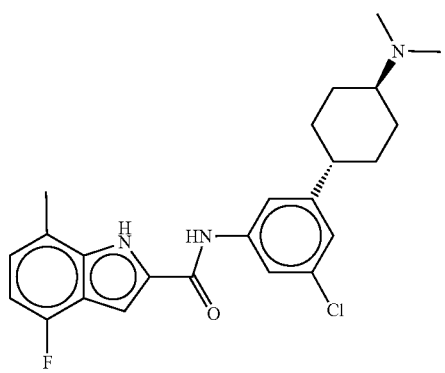 |
| 340 | 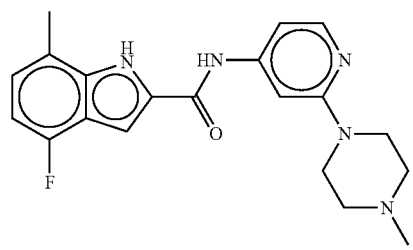 |
| 341 | 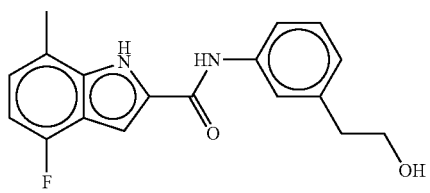 |
| 342 | 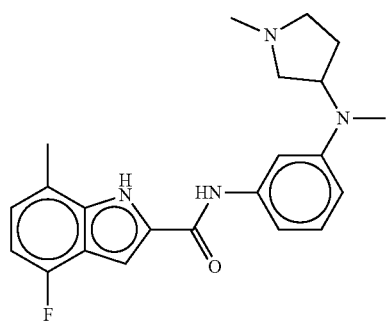 |
| 343 | 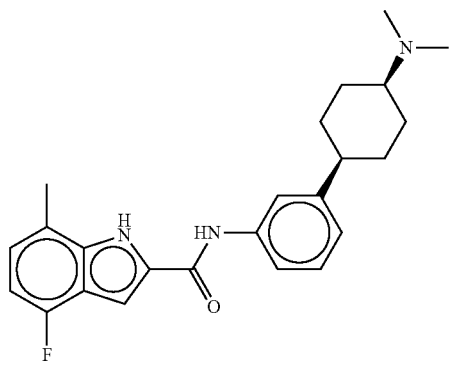 |

TABLE 1-continued
| Cpd. No. | Chemical Structure |
|---|---|
| 344 | 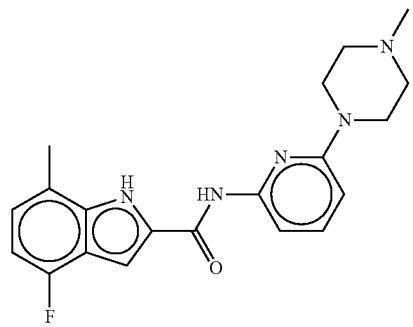 |
| 345 | 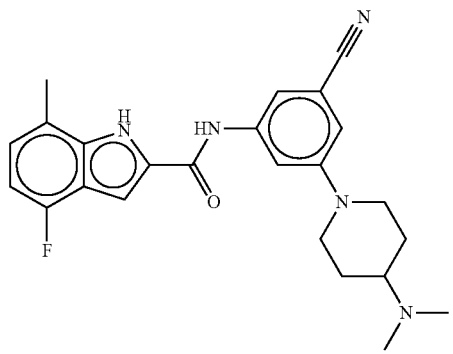 |
| 346 | 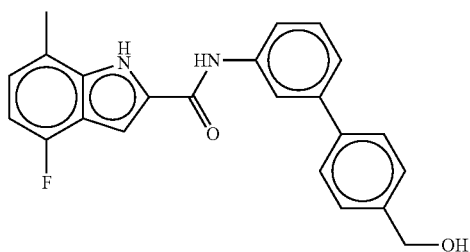 |
| 347 | 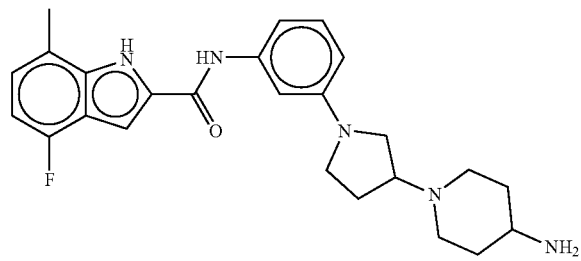 |
| 348 | 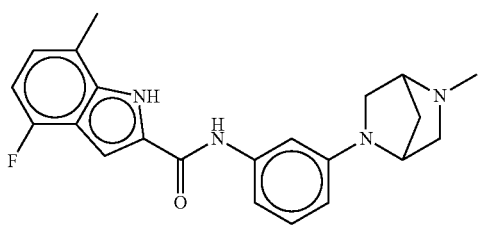 |

TABLE 1-continued
| Cpd. No. | Chemical Structure |
|---|---|
| 349 | 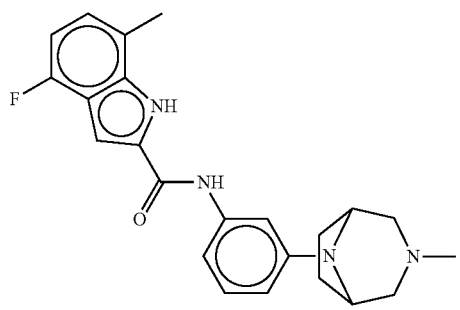 |
| 350 | 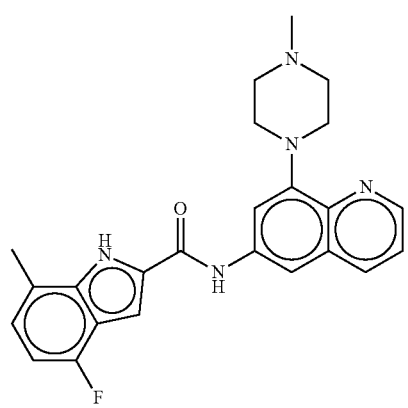 |
| 351 | 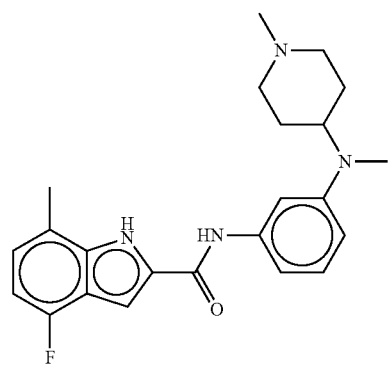 |
| 352 | 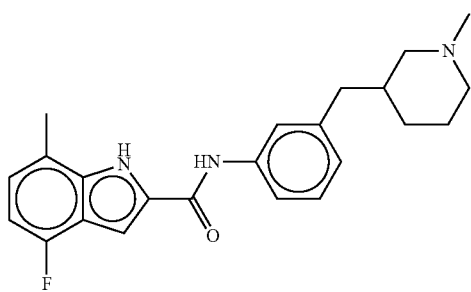 |

TABLE 1-continued
| Cpd. No. | Chemical Structure |
|---|---|
| 353 | 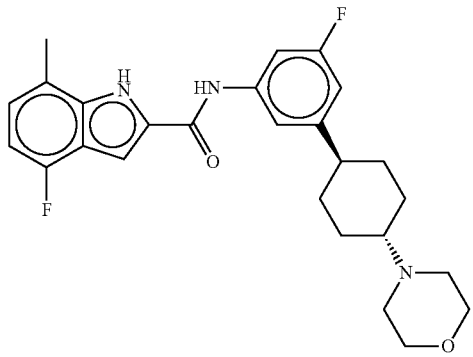 |
| 354 | 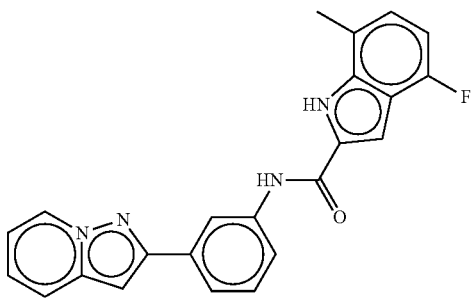 |
| 355 | 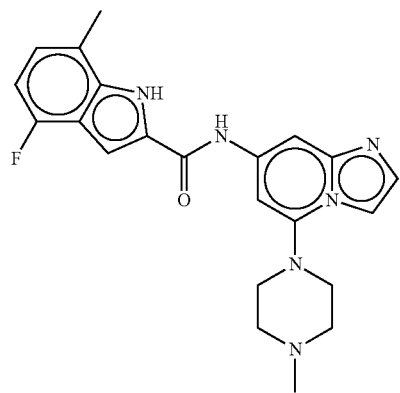 |
| 356 | 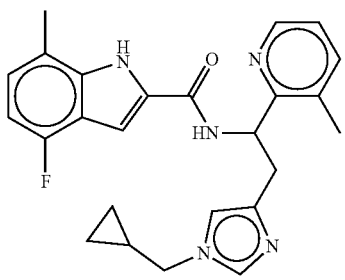 |
| 357 | 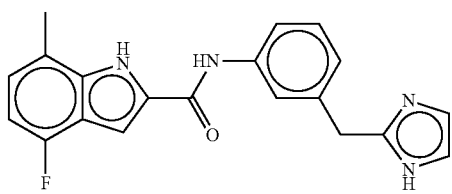 |

TABLE 1-continued
| Cpd. No. | Chemical Structure |
|---|---|
| 358 | 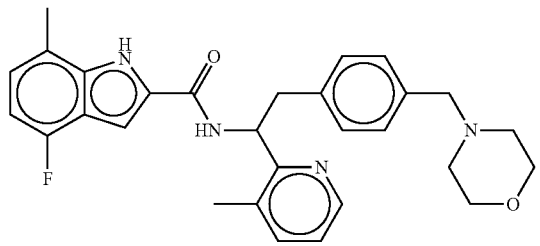 |
| 359 | 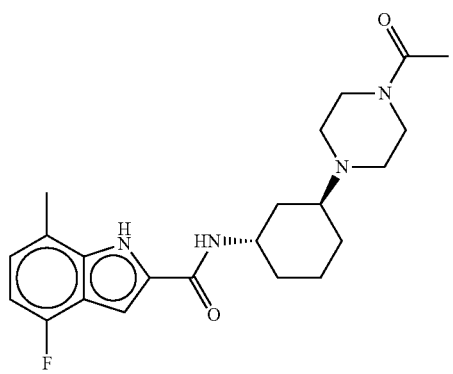 |
| 360 | 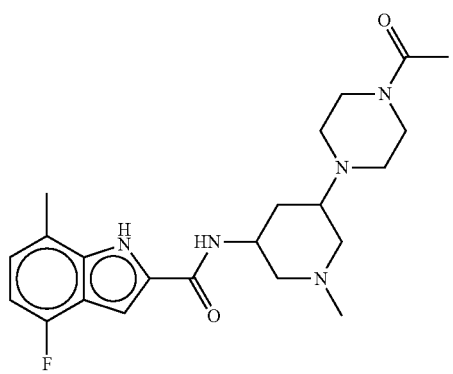 |
| 361 | 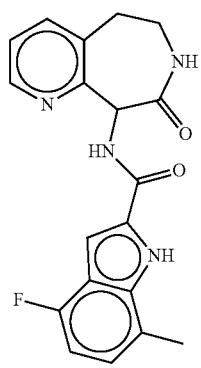 |

TABLE 1-continued

| Cpd. No. | Chemical Structure |
|---|---|
| 362 | 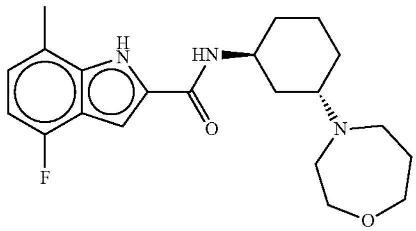 |
| 363 | 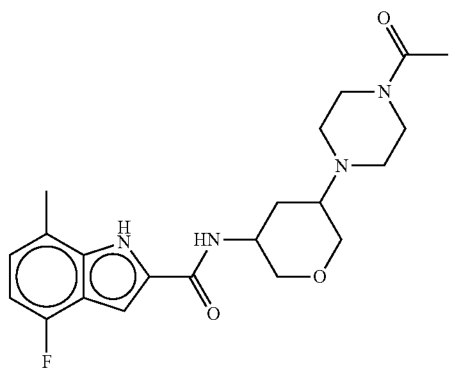 |
| 364 | 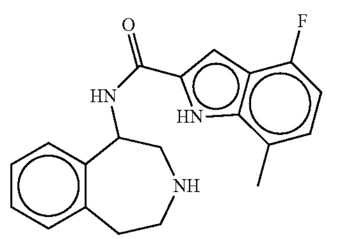 |
| 365 | 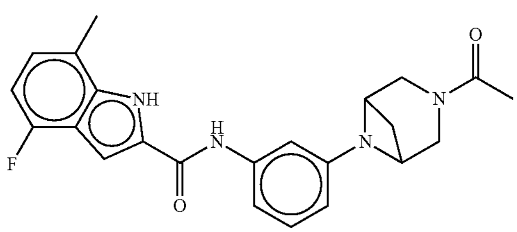 |
| 366 | 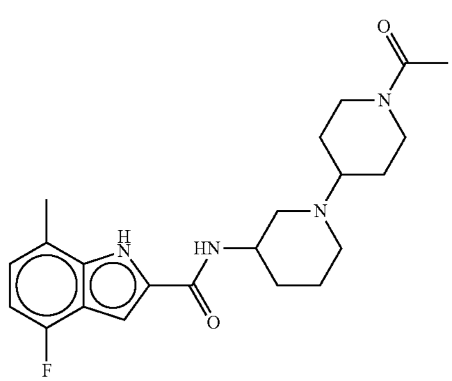 |

TABLE 1-continued
| Cpd. No. | Chemical Structure |
|---|---|
| 367 | 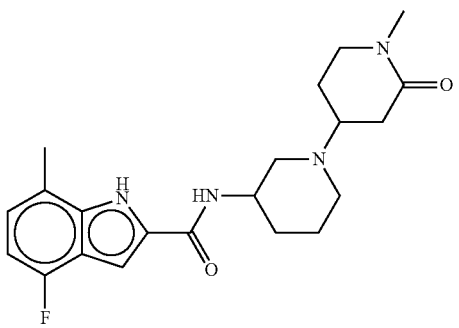 |
| 368 | 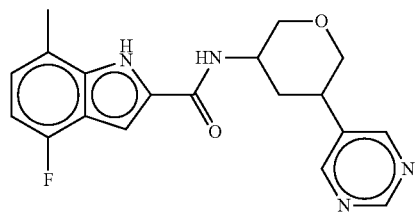 |
| 369 | 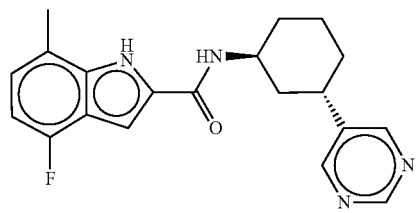 |
| 370 | 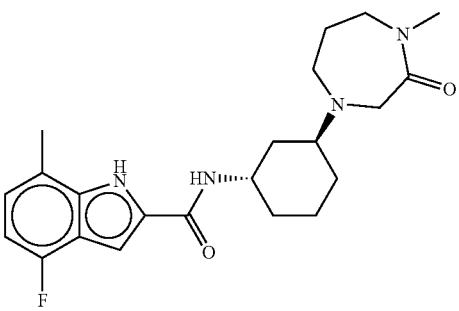 |
| 371 | 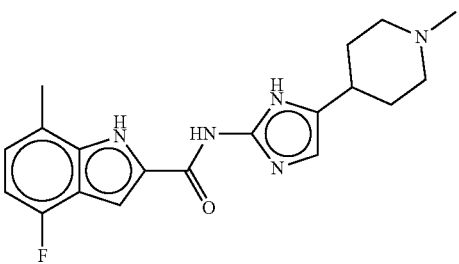 |

TABLE 1-continued
| Cpd. No. | Chemical Structure |
|---|---|
| 372 | 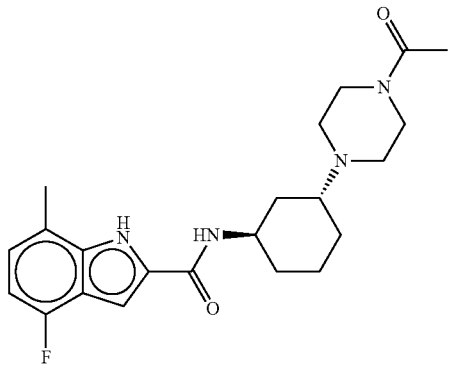 |
| 373 | 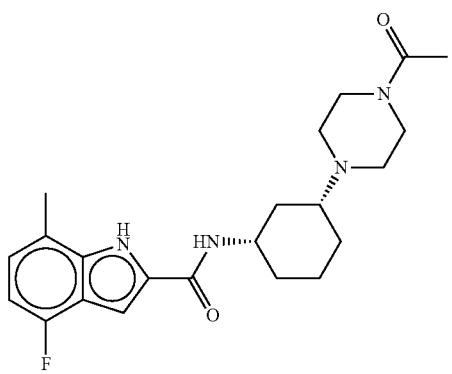 |
| 374 | 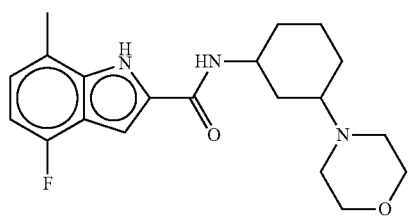 |
| 375 | 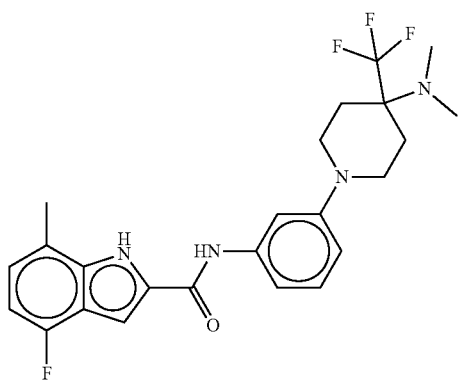 |

TABLE 1-continued

| Cpd. No. | Chemical Structure |
|---|---|
| 376 | 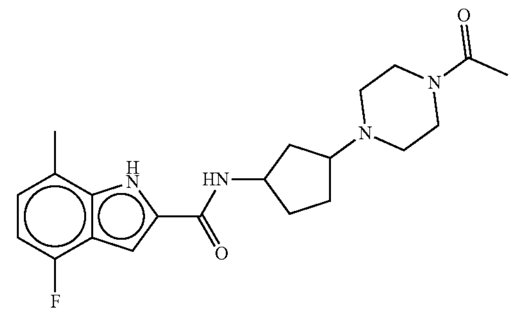 |
| 377 | 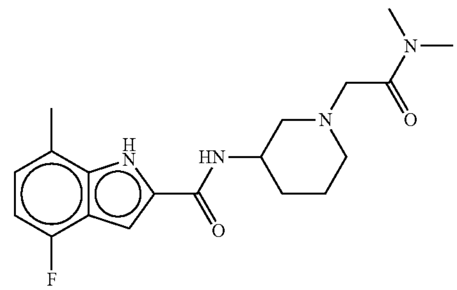 |
| 378 | 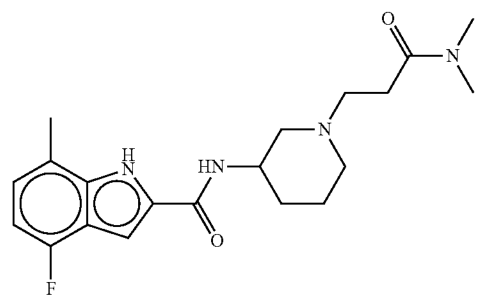 |
| 379 | 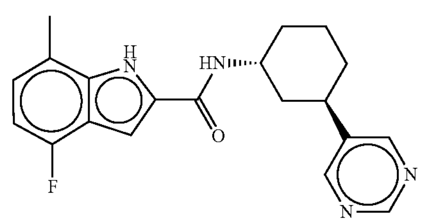 |
| 380 | 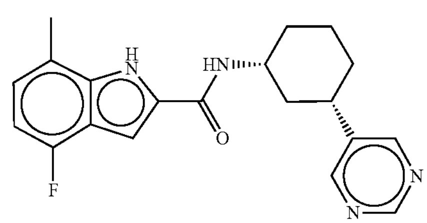 |
| 381 | 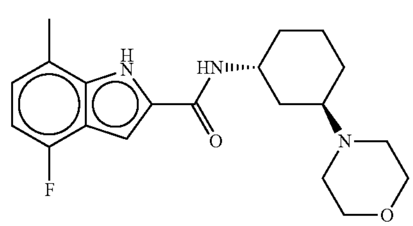 |

TABLE 1-continued
| Cpd. No. | Chemical Structure |
|---|---|
| 382 | 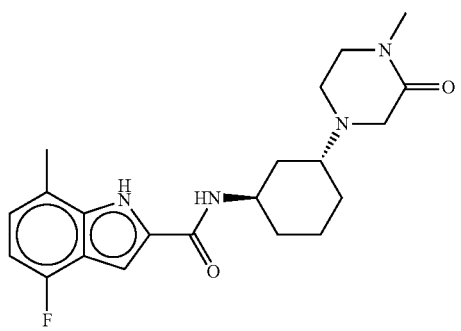 |
| 383 | 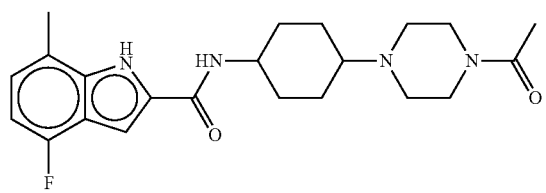 |
| 384 | 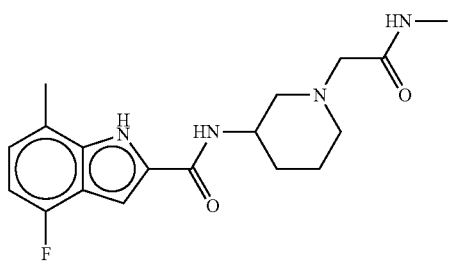 |
| 385 | 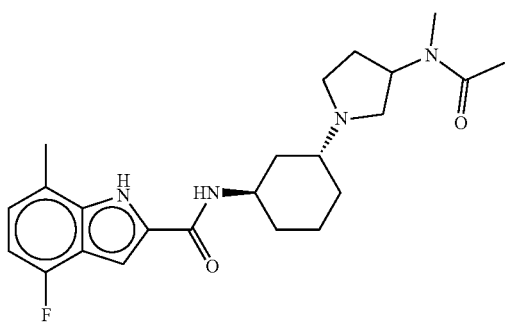 |
| 386 | 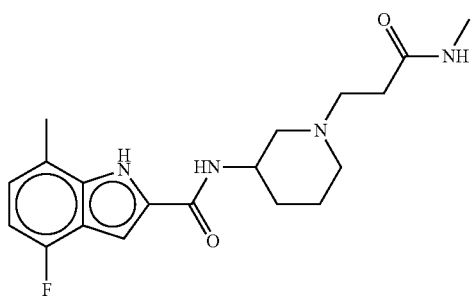 |

TABLE 1-continued
| Cpd. No. | Chemical Structure |
|---|---|
| 387 | 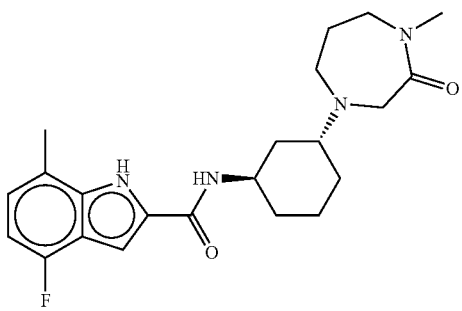 |
| 388 | 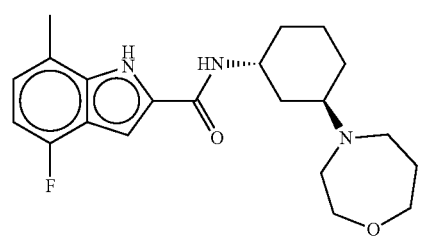 |
| 389 | 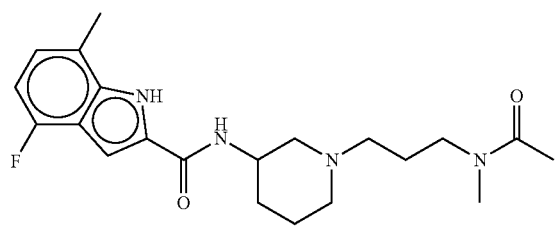 |
| 390 | 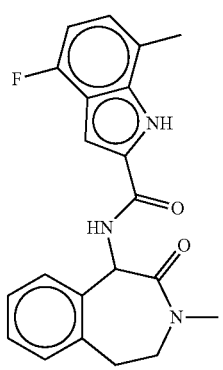 |
| 391 | 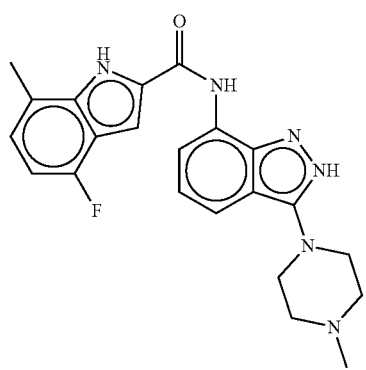 |

TABLE 1-continued
| Cpd. No. | Chemical Structure |
|---|---|
| 392 | 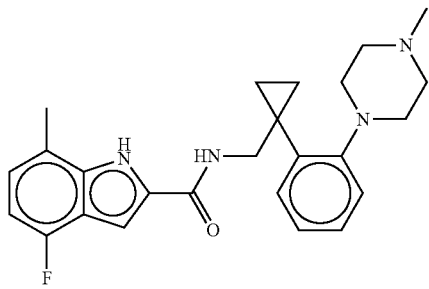 |
| 393 | 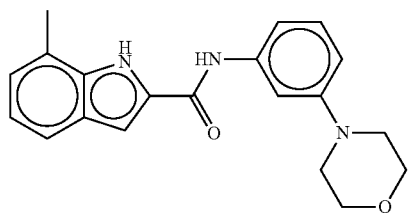 |
| 394 | 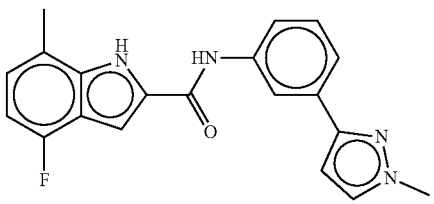 |
| 395 | 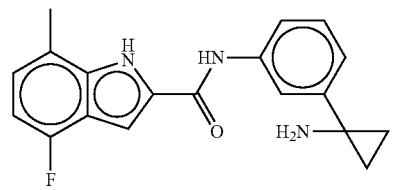 |
| 396 | 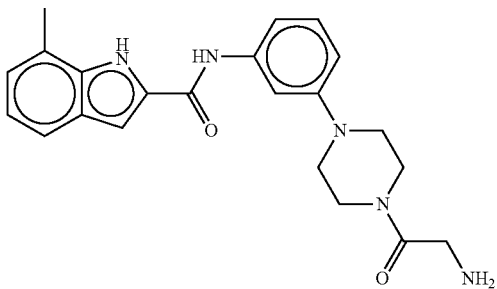 |
| 397 | 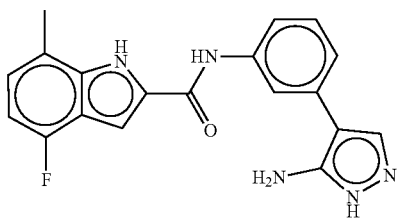 |

TABLE 1-continued
| Cpd. No. | Chemical Structure |
|---|---|
| 398 | 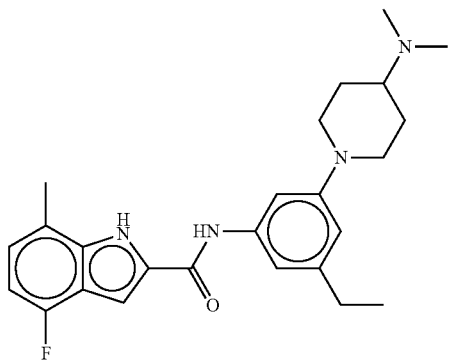 |
| 399 | 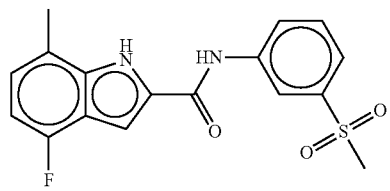 |
| 400 | 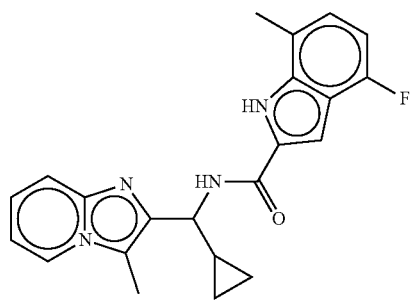 |
| 401 | 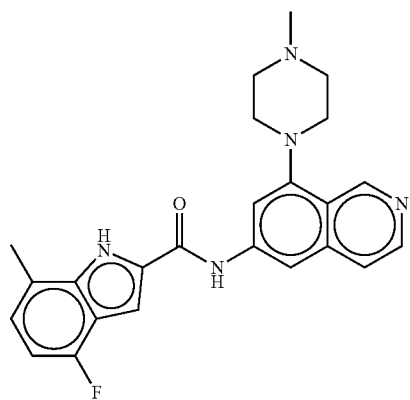 |

TABLE 1-continued
| Cpd. No. | Chemical Structure |
|---|---|
| 402 | 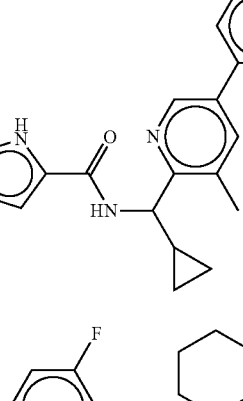 |
| 403 | 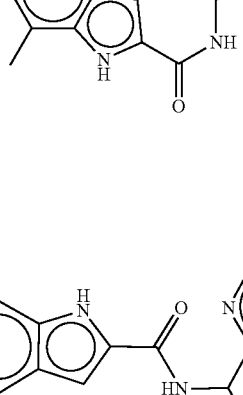 |
| 404 | 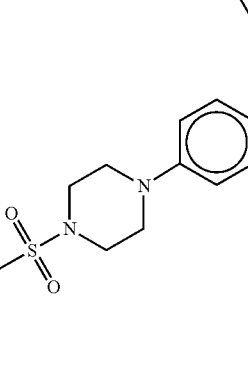 |
| 405 | 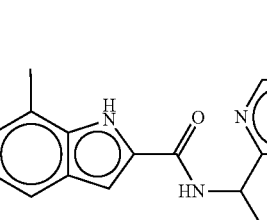 |
| 406 | 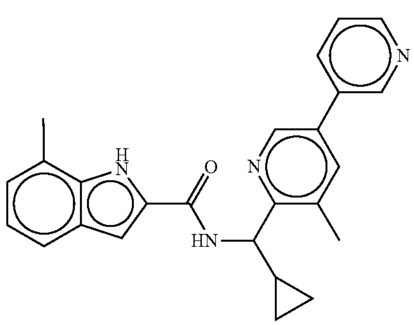 |

US 12,116,358 B2
229                                                                                  230
TABLE 1-continued
| Cpd. No. | Chemical Structure |
|---|---|
| 407 | 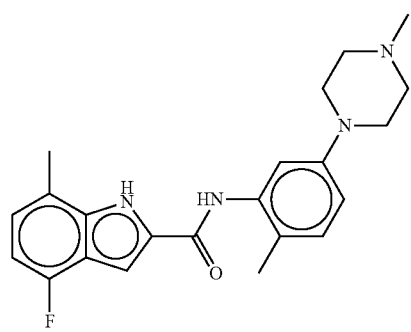 |
| 408 | 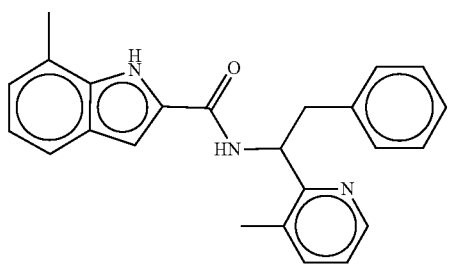 |
| 409 | 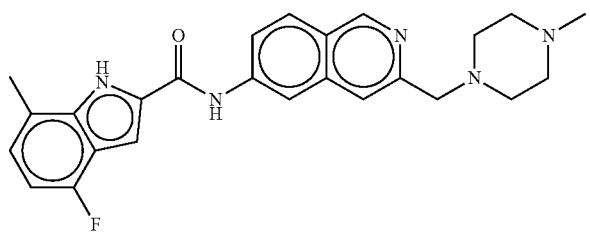 |
| 410 | 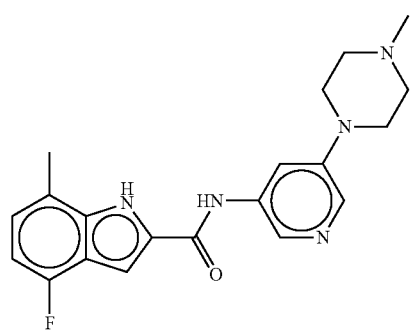 |
| 411 | 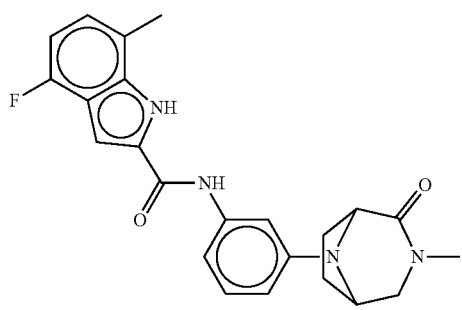 |

TABLE 1-continued

| Cpd. No. | Chemical Structure |
|---|---|
| 412 | 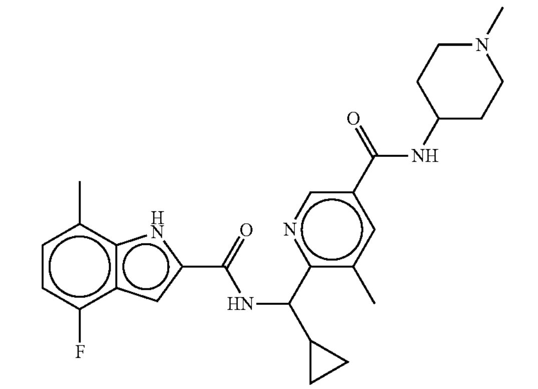 |
| 413 | 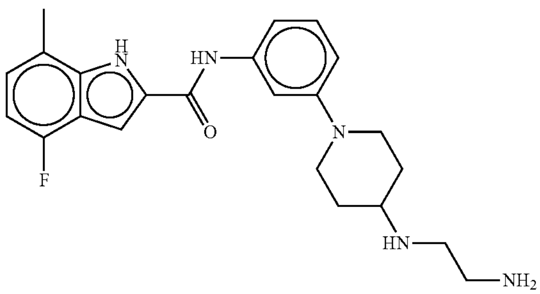 |
| 414 | 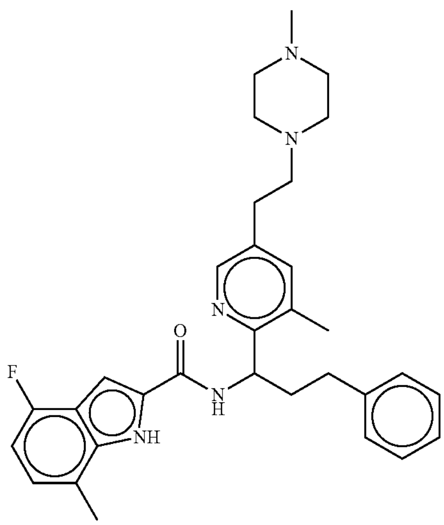 |
| 415 | 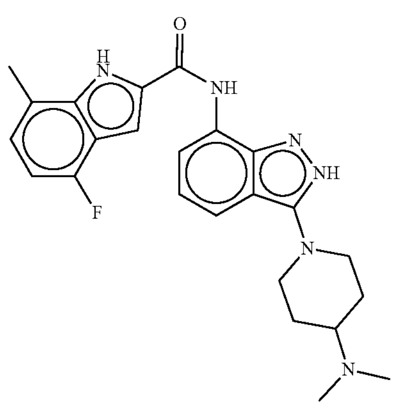 |

TABLE 1-continued
| Cpd. No. | Chemical Structure |
|---|---|
| 416 | 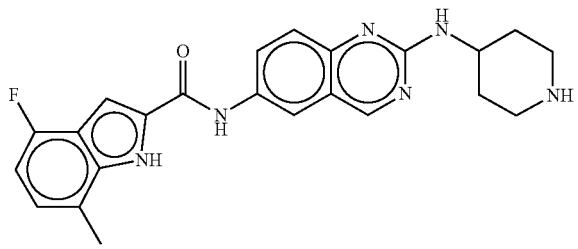 |
| 417 | 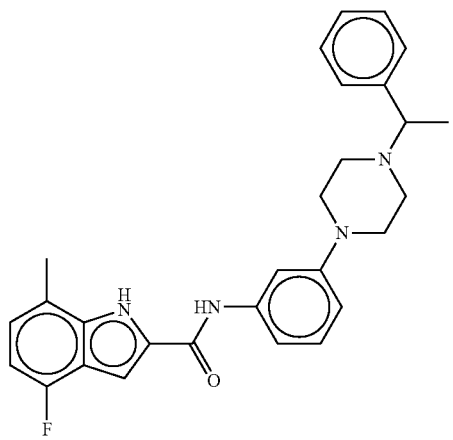 |
| 418 | 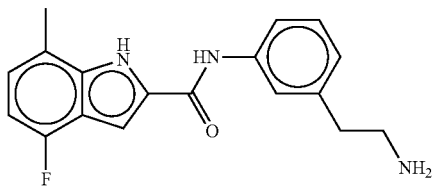 |
| 419 | 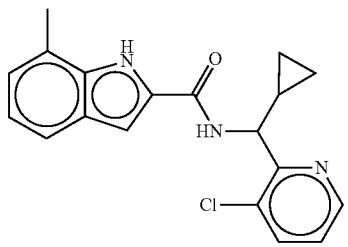 |
| 420 | 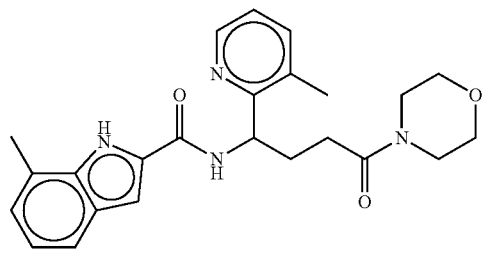 |

TABLE 1-continued
| Cpd. No. | Chemical Structure |
|---|---|
| 421 | 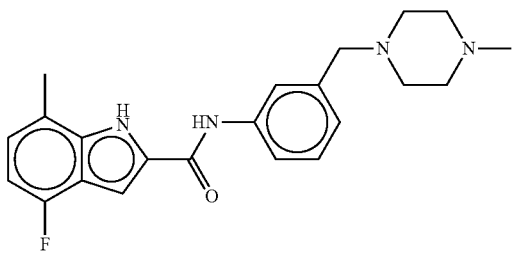 |
| 422 | 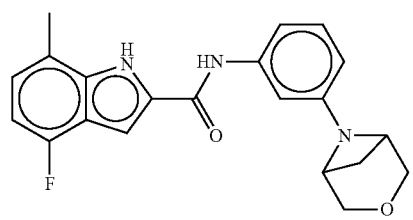 |
| 423 | 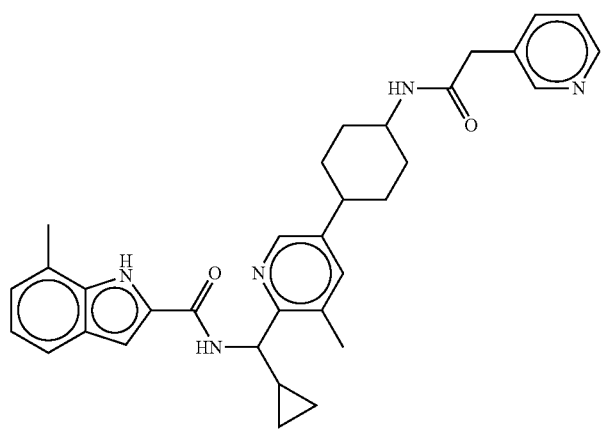 |
| 424 | 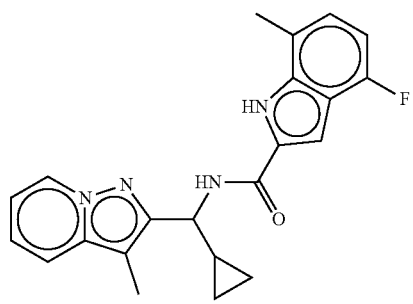 |
| 425 | 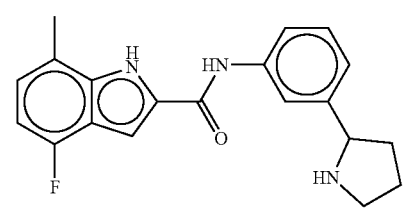 |

TABLE 1-continued
| Cpd. No. | Chemical Structure |
|---|---|
| 426 | 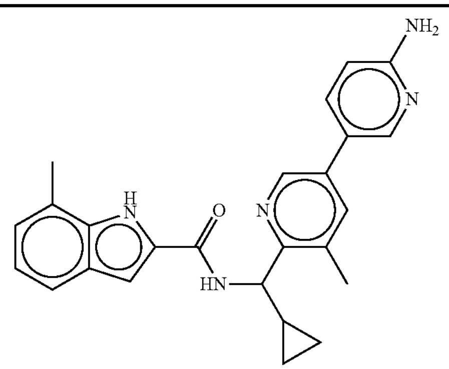 |
| 427 | 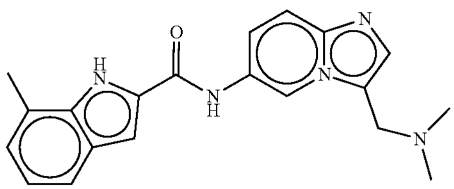 |
| 428 | 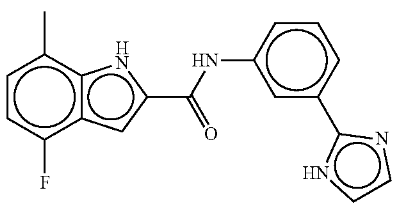 |
| 429 | 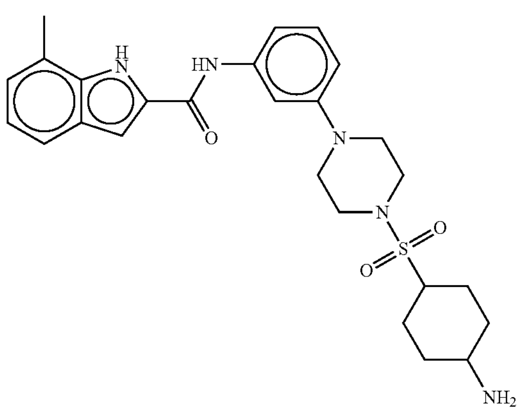 |
| 430 | 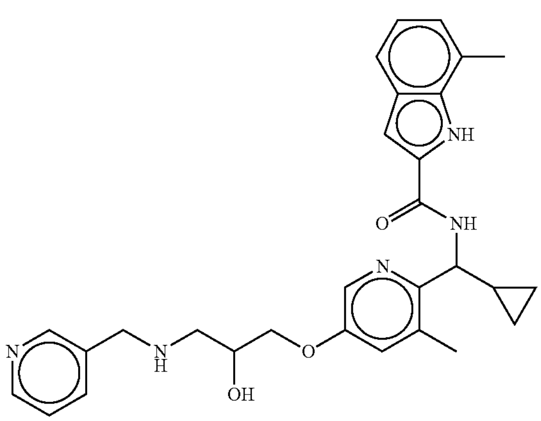 |

TABLE 1-continued
| Cpd. No. | Chemical Structure |
|---|---|
| 431 | 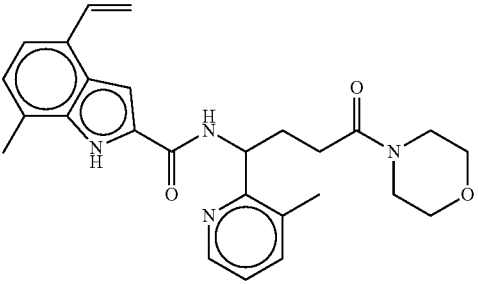 |
| 432 | 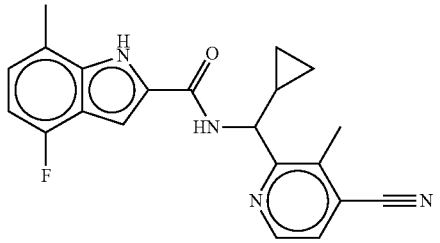 |
| 433 | 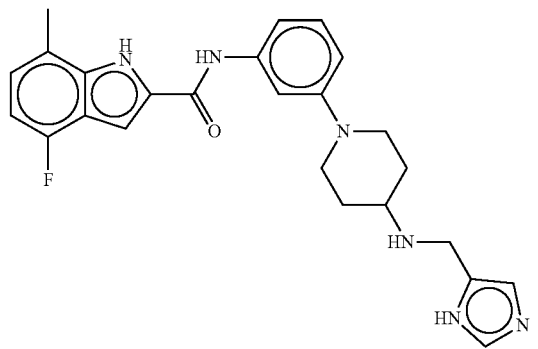 |
| 434 | 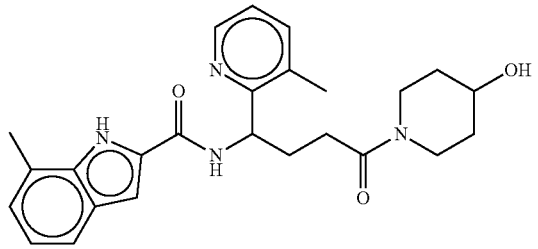 |
| 435 | 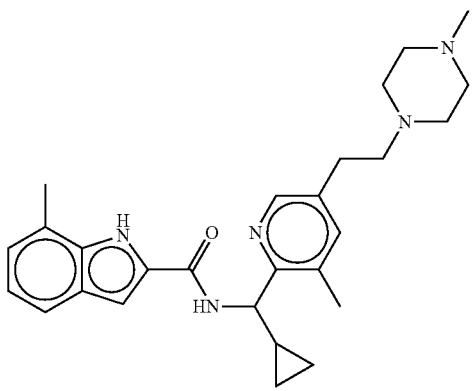 |

TABLE 1-continued

| Cpd. No. | Chemical Structure |
|---|---|
| 436 | 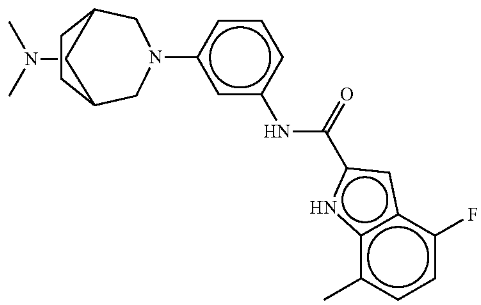 |
| 437 | 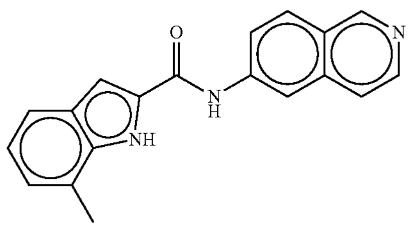 |
| 438 | 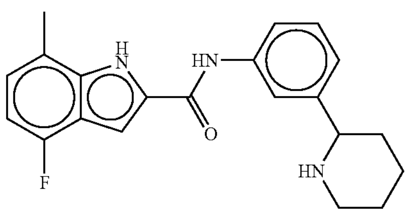 |
| 439 | 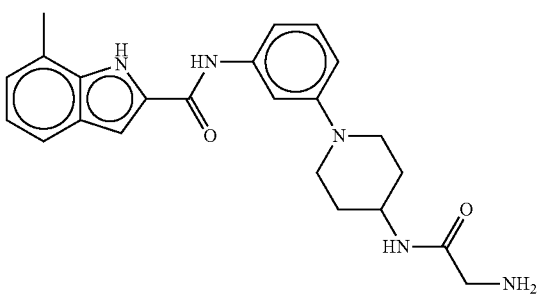 |
| 440 | 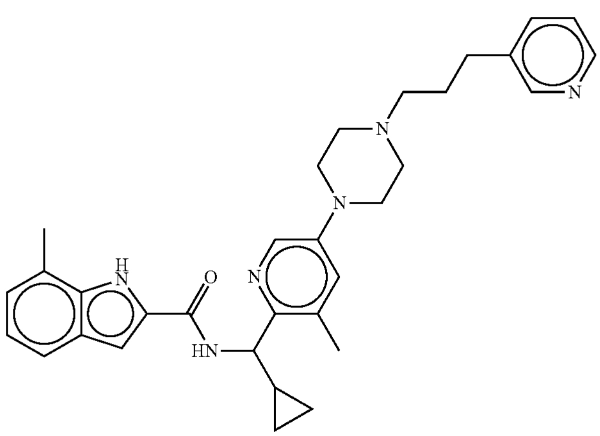 |

TABLE 1-continued
| Cpd. No. | Chemical Structure |
|---|---|
| 441 | 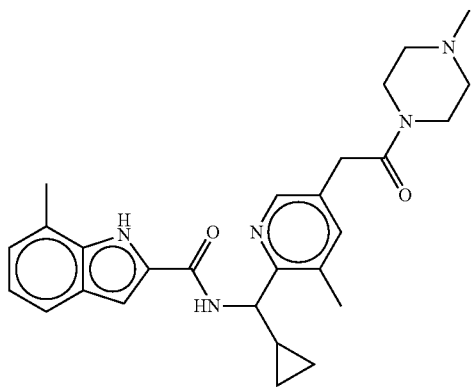 |
| 442 | 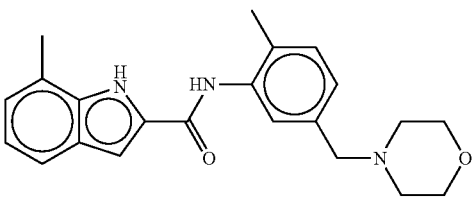 |
| 443 | 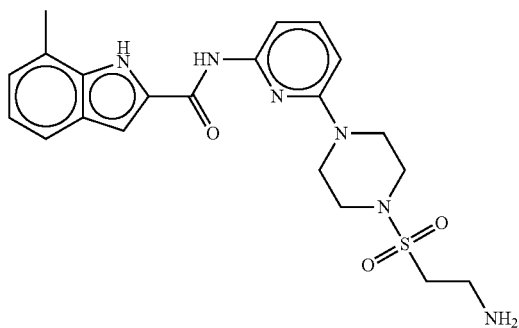 |
| 444 | 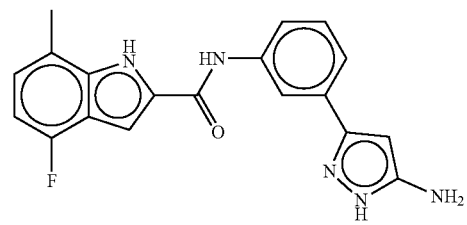 |
| 445 | 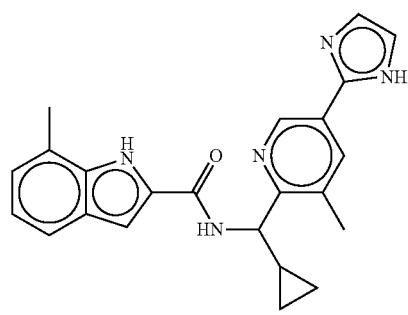 |

TABLE 1-continued
| Cpd. No. | Chemical Structure |
|---|---|
| 446 | 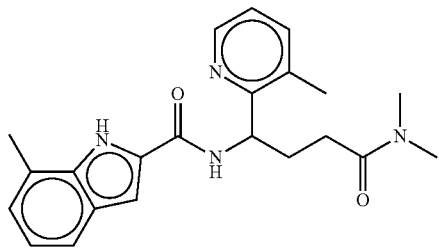 |
| 447 | 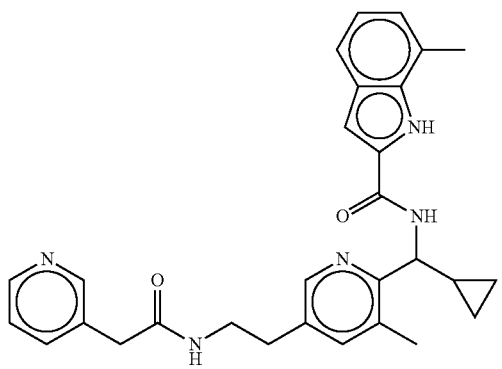 |
| 448 | 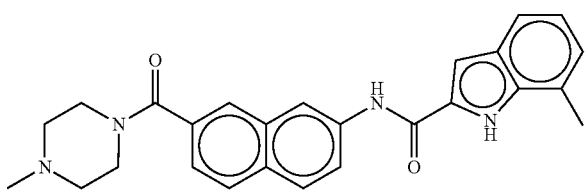 |
| 449 | 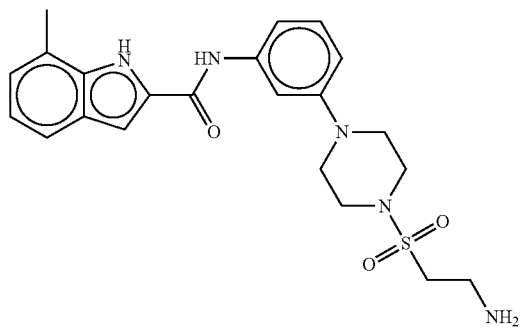 |
| 450 | 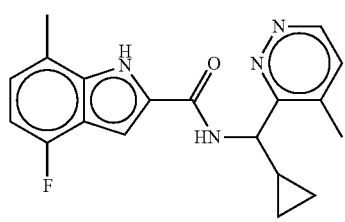 |

TABLE 1-continued
| Cpd. No. | Chemical Structure |
|---|---|
| 451 | 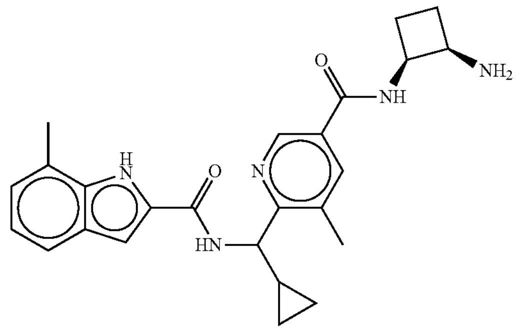 |
| 452 | 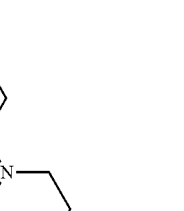 |
| 453 | 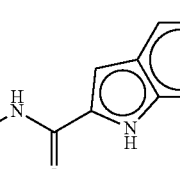 |
| 454 | 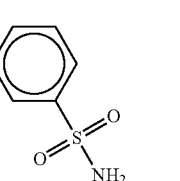 |
| 455 | 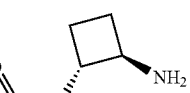 |
| 456 | 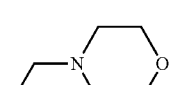 |

TABLE 1-continued
| Cpd. No. | Chemical Structure |
|---|---|
| 457 | 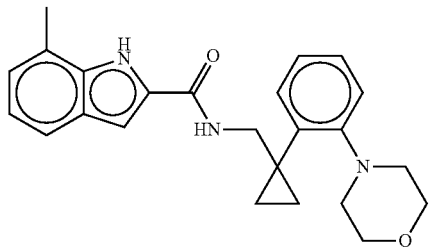 |
| 458 | 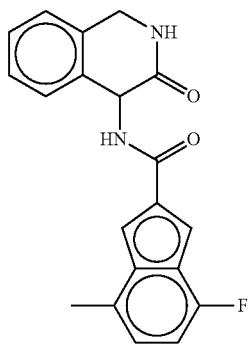 |
| 459 | 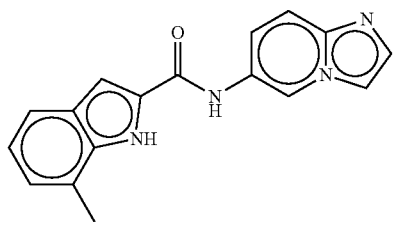 |
| 460 | 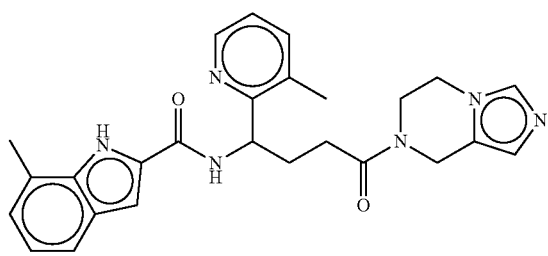 |
| 461 | 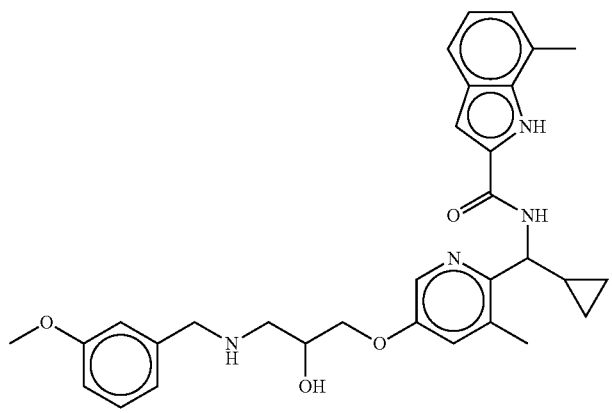 |

TABLE 1-continued
| Cpd. No. | Chemical Structure |
|---|---|
| 462 | 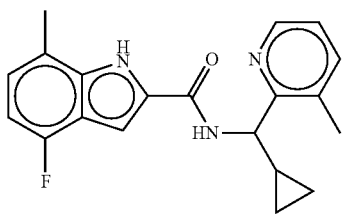 |
| 463 | 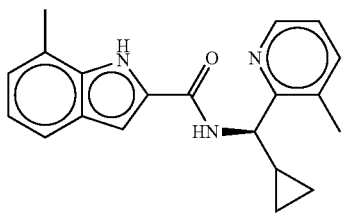 |
| 464 | 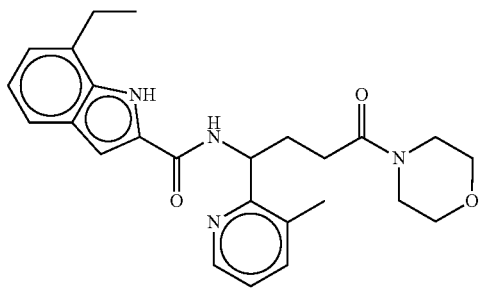 |
| 465 | 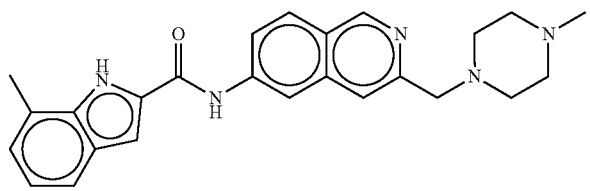 |
| 466 | 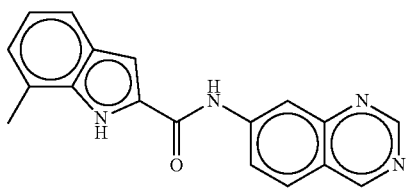 |
| 467 | 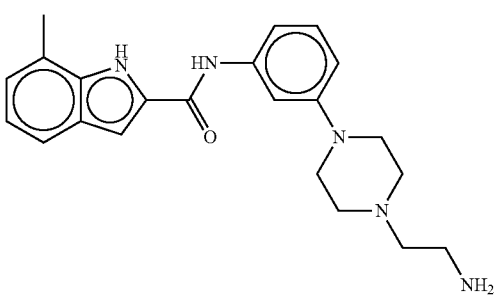 |

TABLE 1-continued
| Cpd. No. | Chemical Structure |
|---|---|
| 468 | 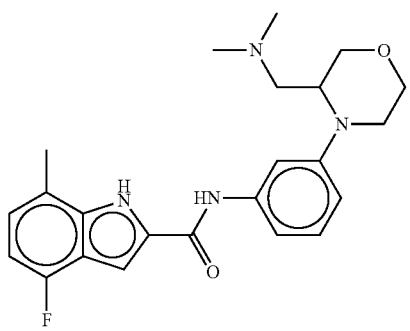 |
| 469 | 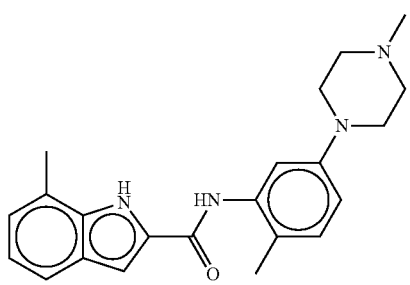 |
| 470 | 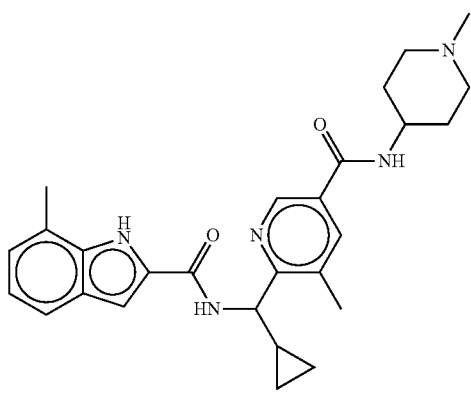 |
| 471 | 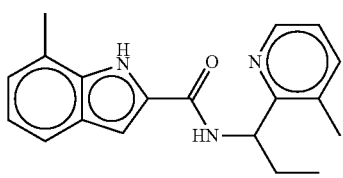 |
| 472 | 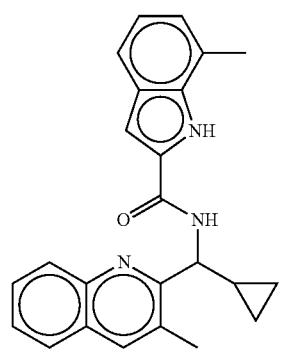 |

TABLE 1-continued
| Cpd. No. | Chemical Structure |
|---|---|
| 473 | 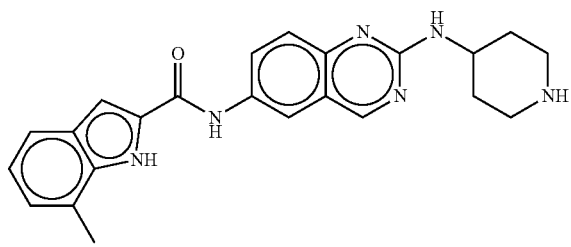 |
| 474 | 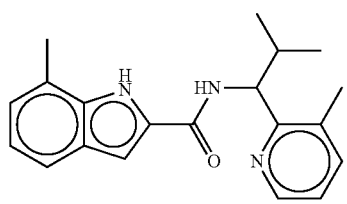 |
| 475 | 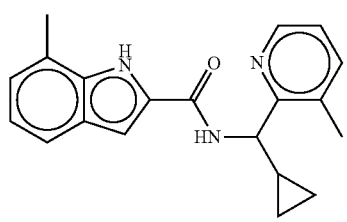 |
| 476 | 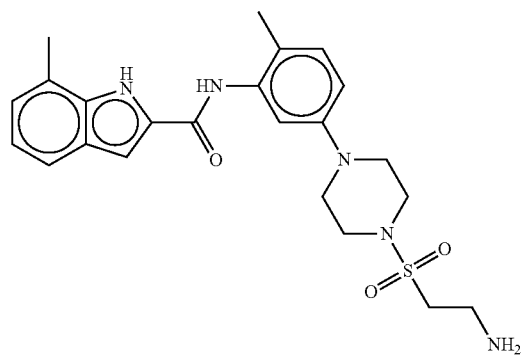 |
| 477 | 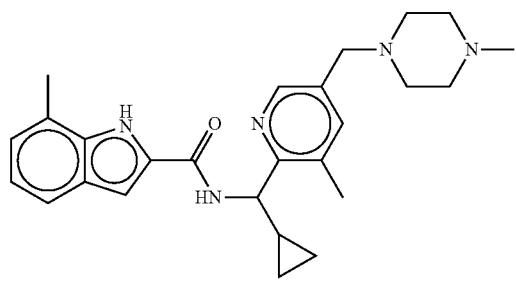 |
| 478 | 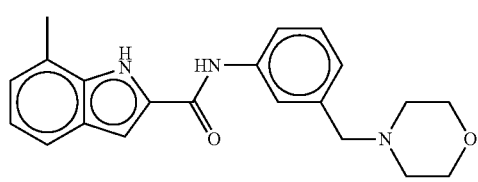 |

TABLE 1-continued
| Cpd. No. | Chemical Structure |
|---|---|
| 479 | 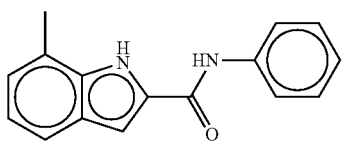 |
| 480 | 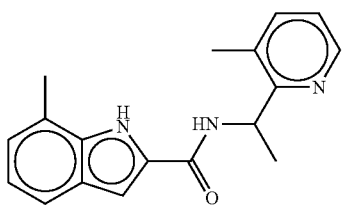 |
| 481 | 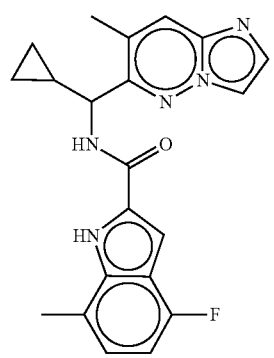 |
| 482 | 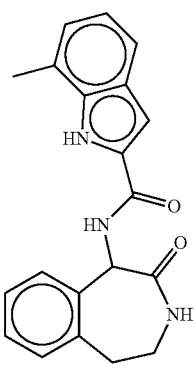 |
| 483 | 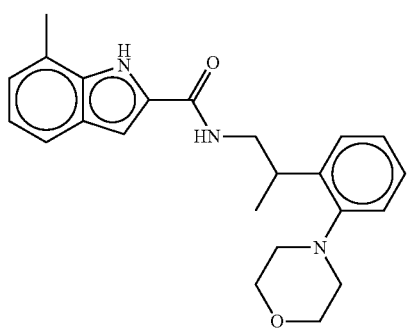 |

TABLE 1-continued
| Cpd. No. | Chemical Structure |
|---|---|
| 484 | 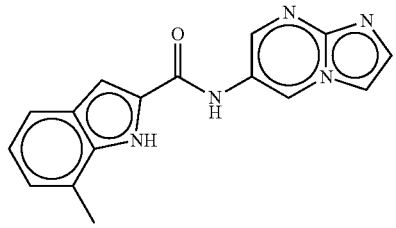 |
| 485 | 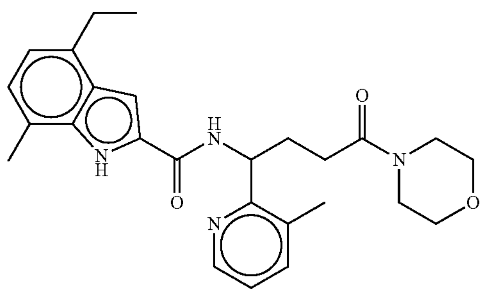 |
| 486 | 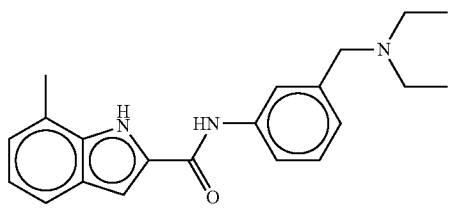 |
| 487 | 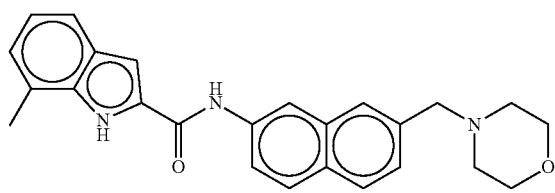 |
| 488 | 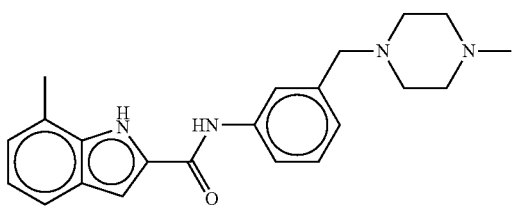 |
| 489 | 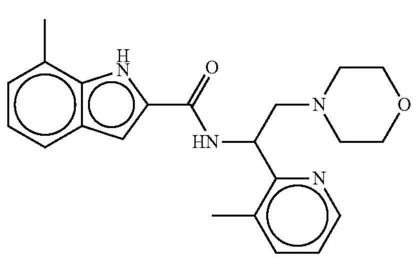 |

TABLE 1-continued
| Cpd. No. | Chemical Structure |
|---|---|
| 490 | 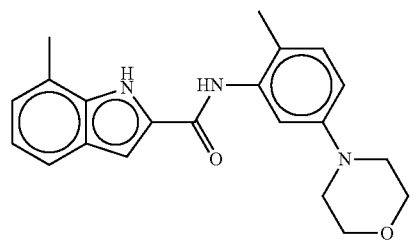 |
| 491 | 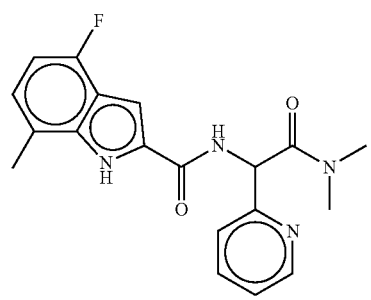 |
| 492 | 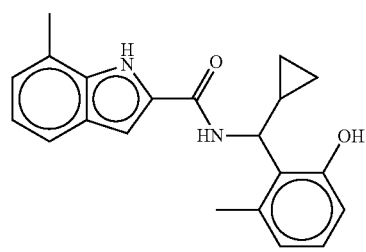 |
| 493 | 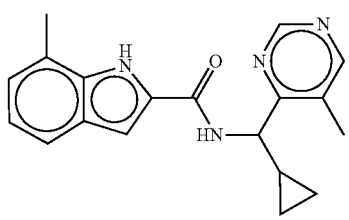 |
| 494 | 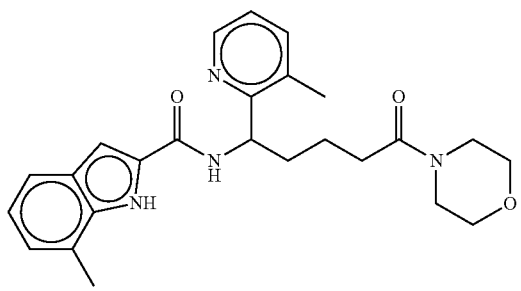 |
| 495 | 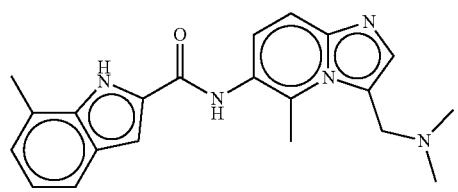 |

TABLE 1-continued
| Cpd. No. | Chemical Structure |
|---|---|
| 496 | 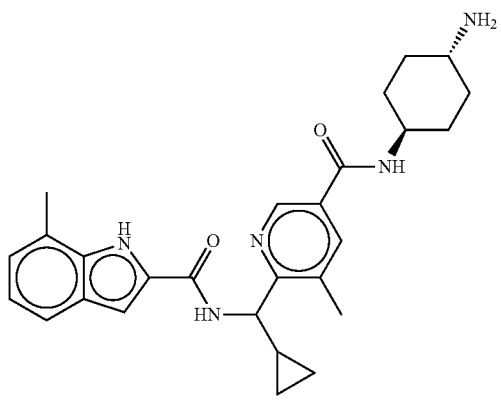 |
| 497 | 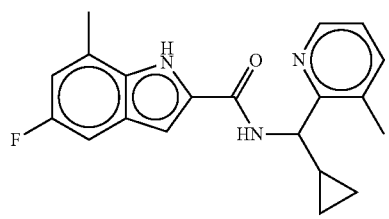 |
| 498 | 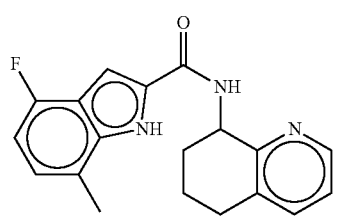 |
| 499 | 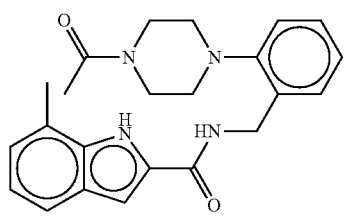 |
| 500 | 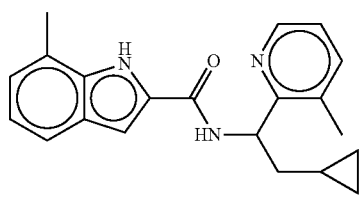 |
| 501 | 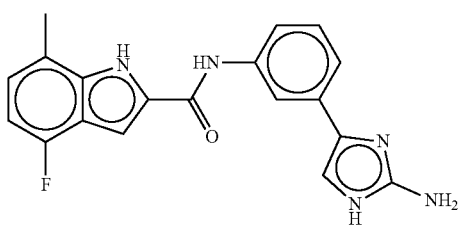 |

TABLE 1-continued
| Cpd. No. | Chemical Structure |
|---|---|
| 502 | 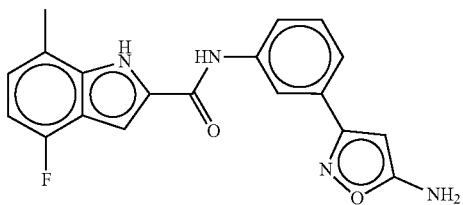 |
| 503 | 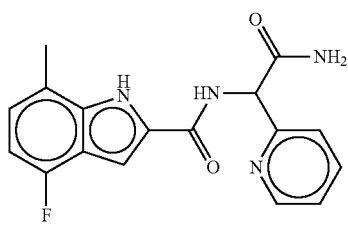 |
| 504 | 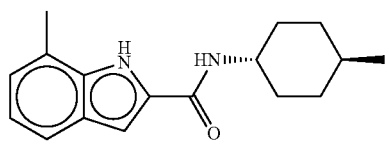 |
| 505 | 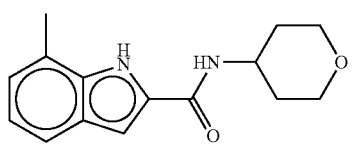 |
| 506 | 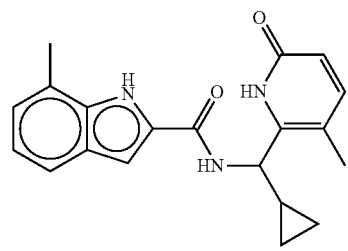 |
| 507 | 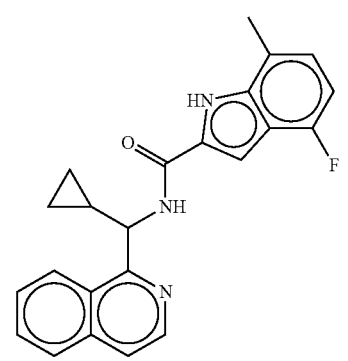 |

TABLE 1-continued
| Cpd. No. | Chemical Structure |
|---|---|
| 508 | 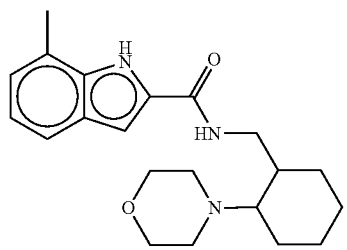 |
| 509 | 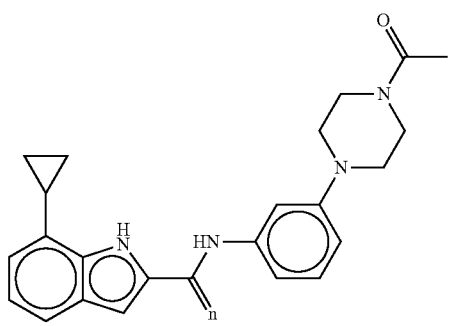 |
| 510 | 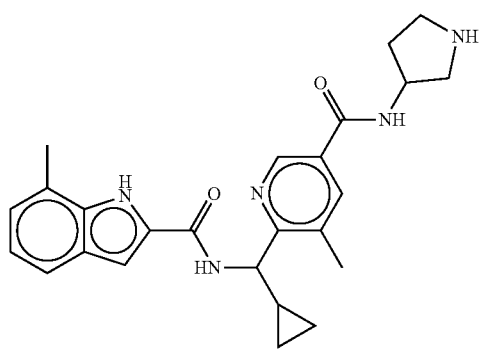 |
| 511 | 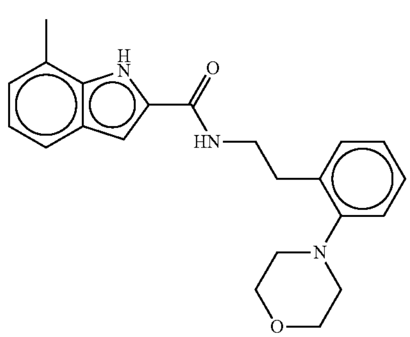 |
| 512 | 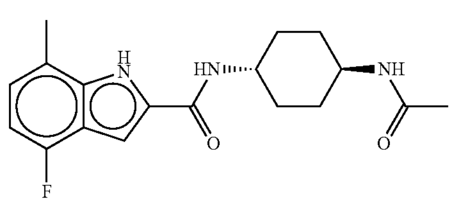 |

TABLE 1-continued
| Cpd. No. | Chemical Structure |
|---|---|
| 513 | 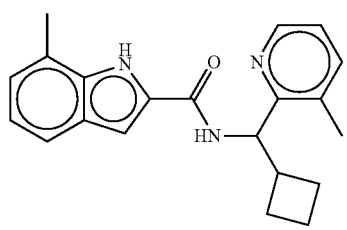 |
| 514 | 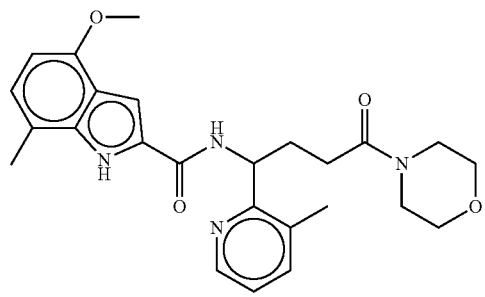 |
| 515 | 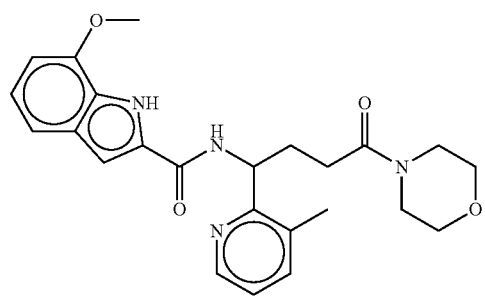 |
| 516 | 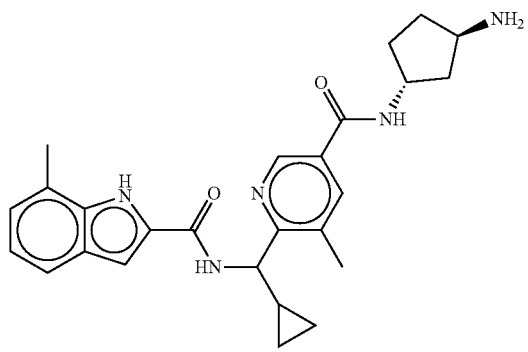 |
| 517 | 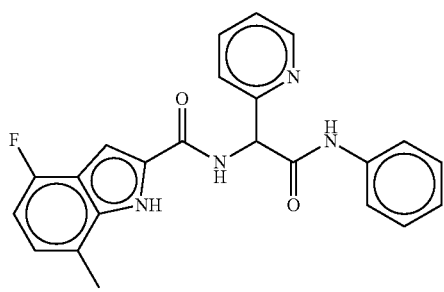 |

TABLE 1-continued
| Cpd. No. | Chemical Structure |
|---|---|
| 518 | 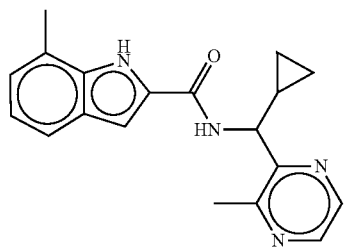 |
| 519 | 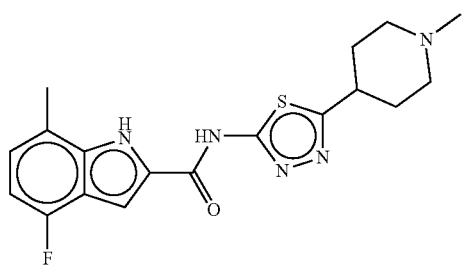 |
| 520 | 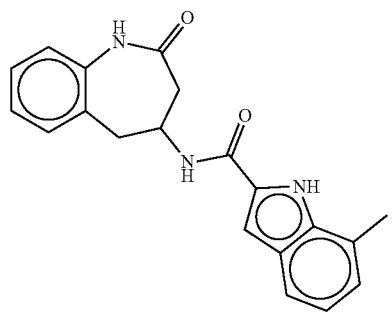 |
| 521 | 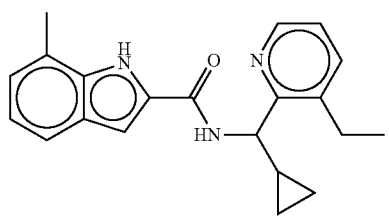 |
| 522 | 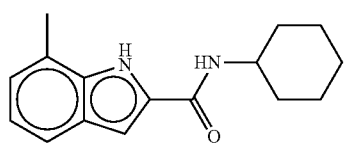 |
| 523 | 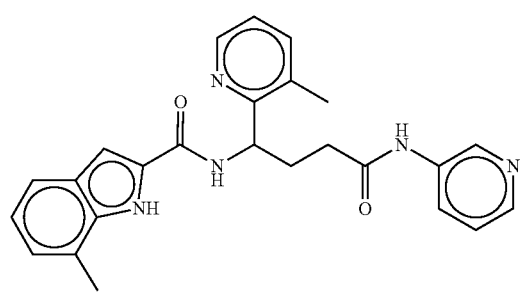 |

TABLE 1-continued
| Cpd. No. | Chemical Structure |
|---|---|
| 524 | 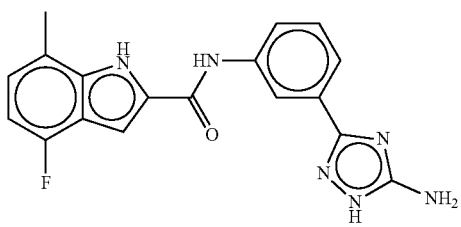 |
| 525 | 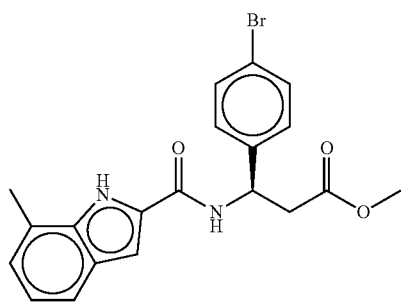 |
| 526 | 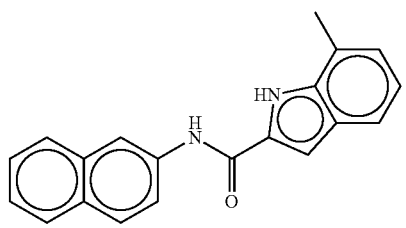 |
| 527 | 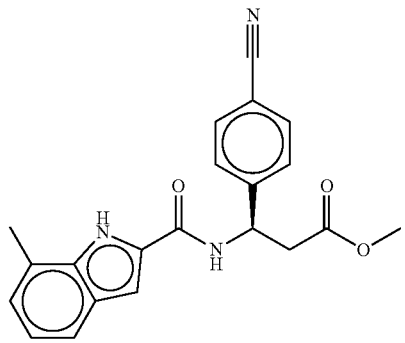 |
| 528 | 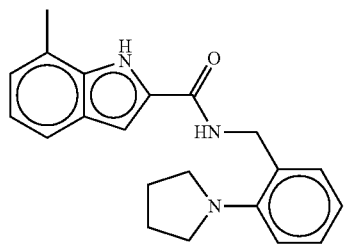 |

TABLE 1-continued
| Cpd. No. | Chemical Structure |
|---|---|
| 529 | 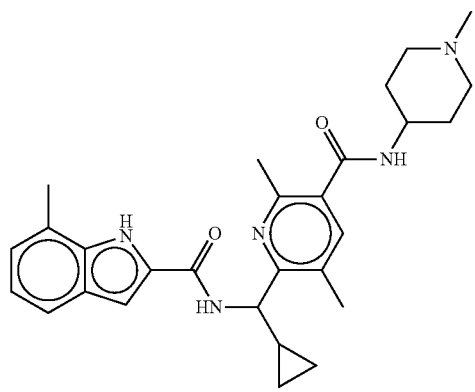 |
| 530 | 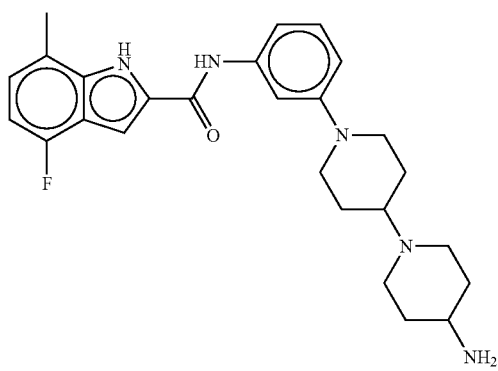 |
| 531 | 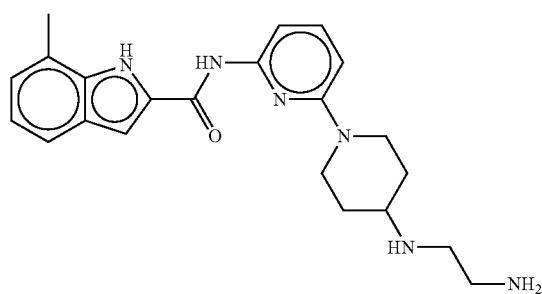 |
| 532 | 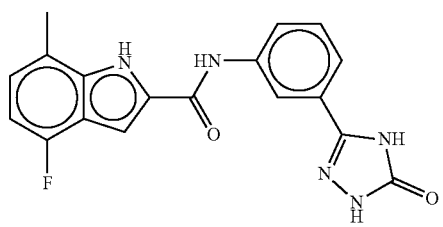 |
| 533 | 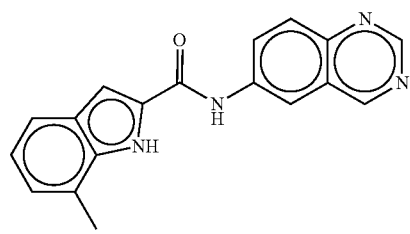 |

TABLE 1-continued

| Cpd. No. | Chemical Structure |
|---|---|
| 534 | 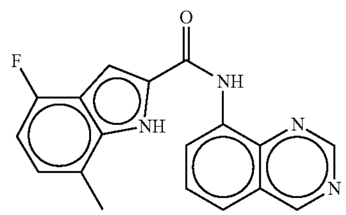 |
| 535 | 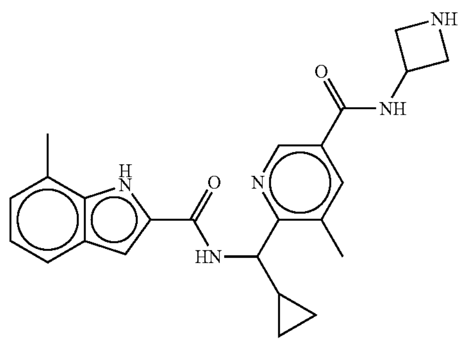 |
| 536 | 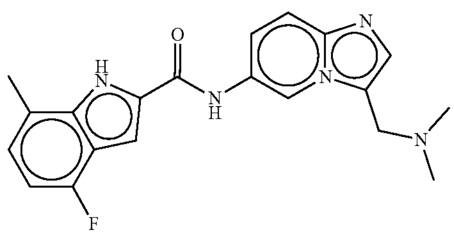 |
| 537 | 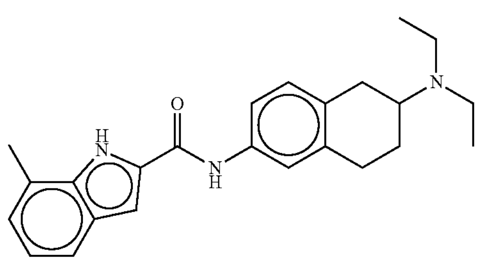 |
| 538 | 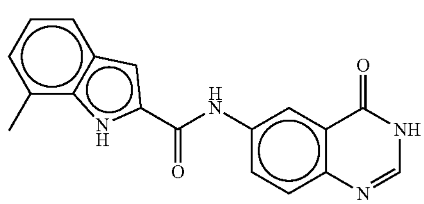 |
| 539 | 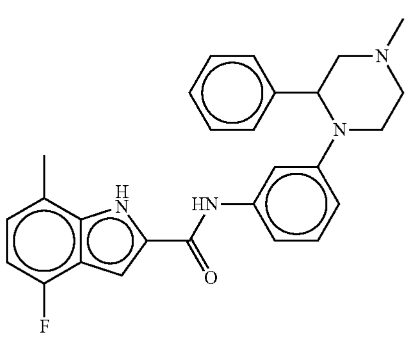 |

TABLE 1-continued
| Cpd. No. | Chemical Structure |
|---|---|
| 540 | 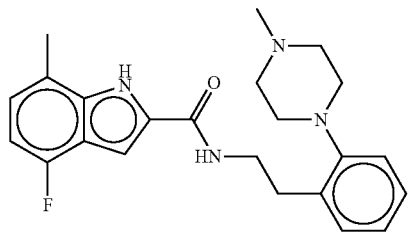 |
| 541 | 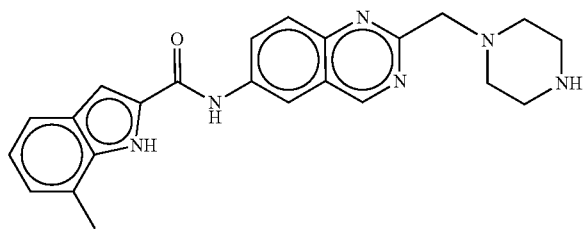 |
| 542 | 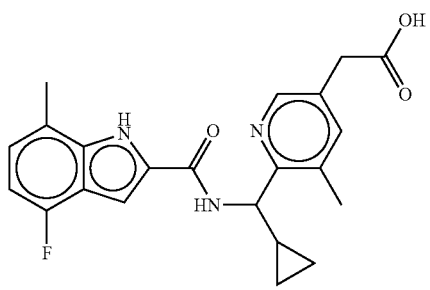 |
| 543 | 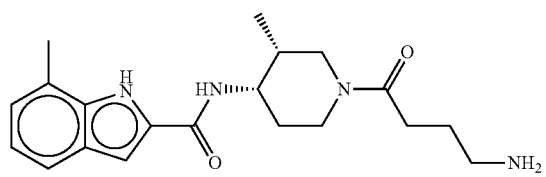 |
| 544 | 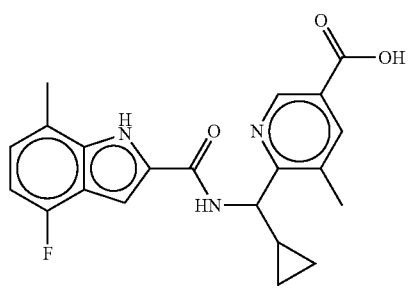 |
| 545 | 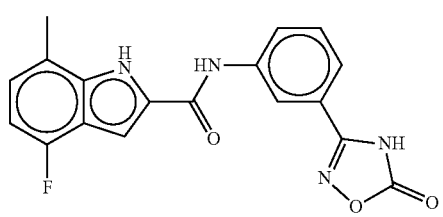 |

TABLE 1-continued
| Cpd. No. | Chemical Structure |
|---|---|
| 546 | 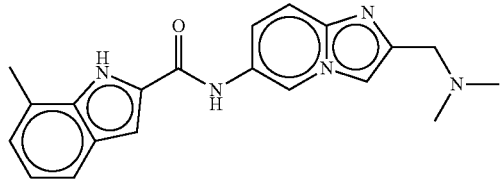 |
| 547 | 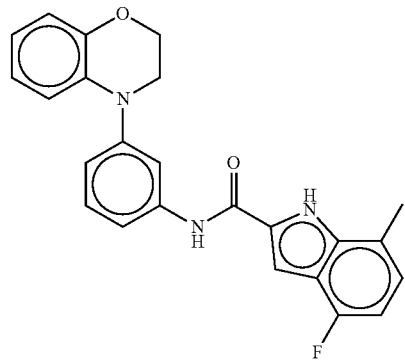 |
| 548 | 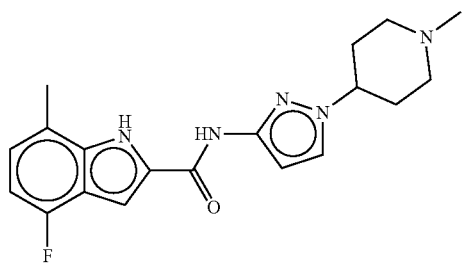 |
| 549 | 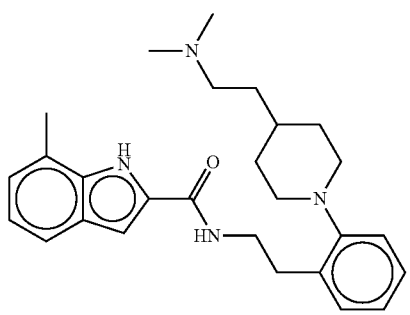 |
| 550 | 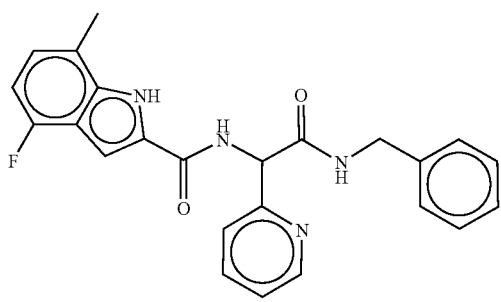 |

TABLE 1-continued
| Cpd. No. | Chemical Structure |
|---|---|
| 551 | 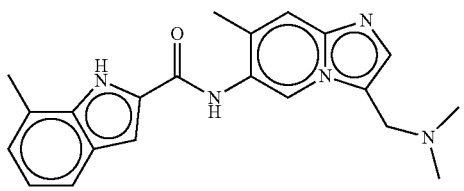 |
| 552 | 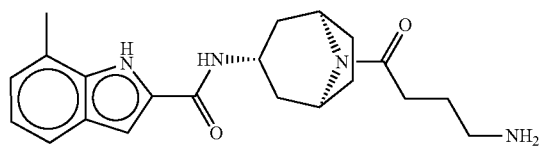 |
| 553 | 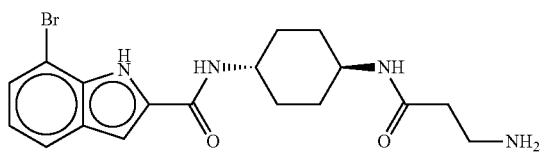 |
| 554 | 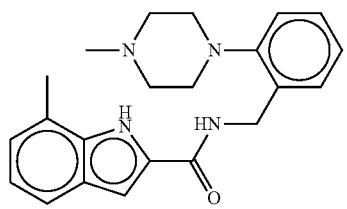 |
| 555 | 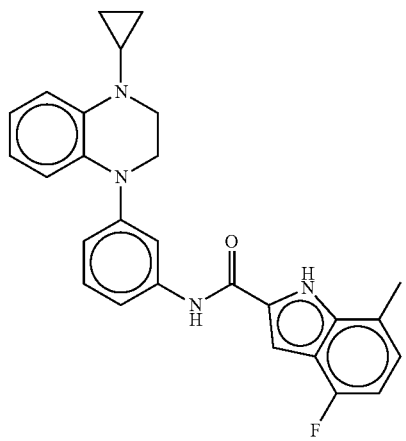 |
| 556 | 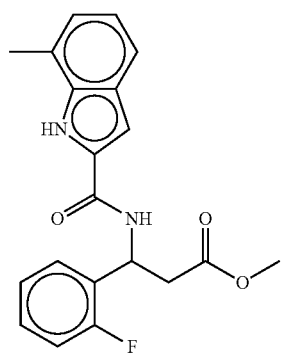 |

TABLE 1-continued
| Cpd. No. | Chemical Structure |
|---|---|
| 557 | 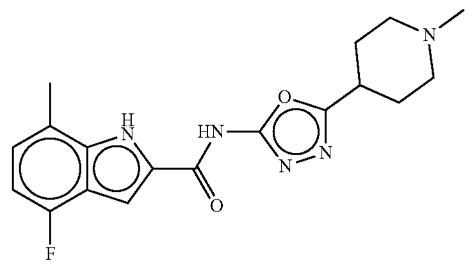 |
| 558 | 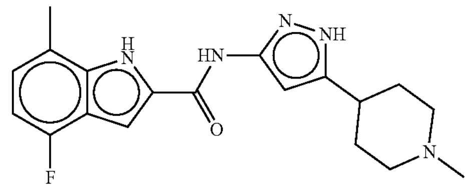 |
| 559 | 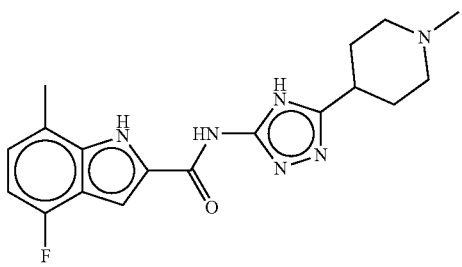 |
| 560 | 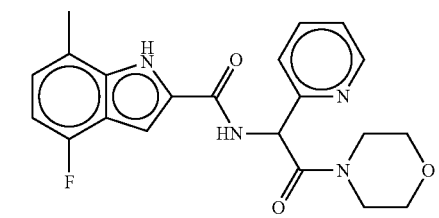 |
| 561 | 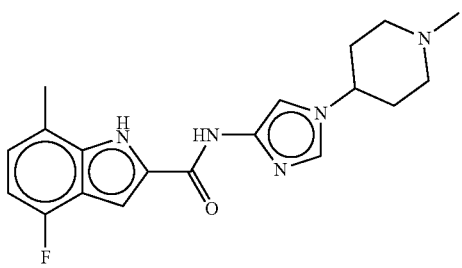 |
| 562 | 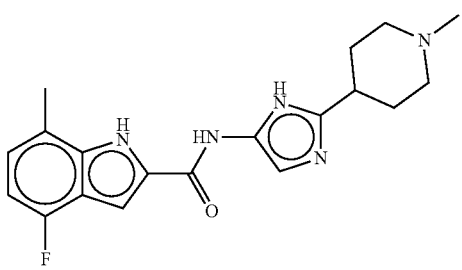 |

TABLE 1-continued
| Cpd. No. | Chemical Structure |
|---|---|
| 563 | 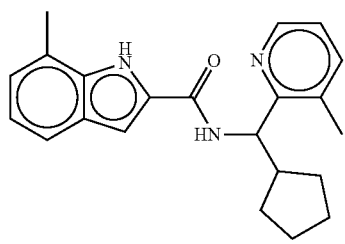 |
| 564 | 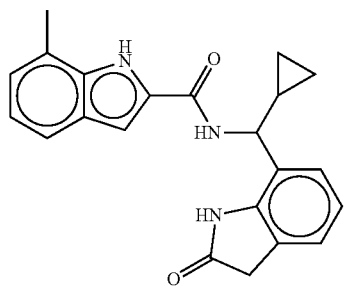 |
| 565 | 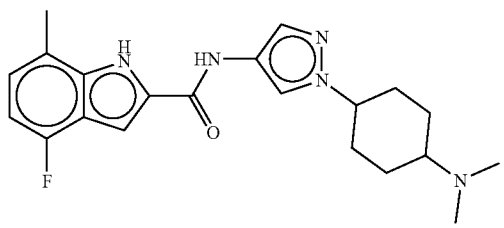 |
| 566 | 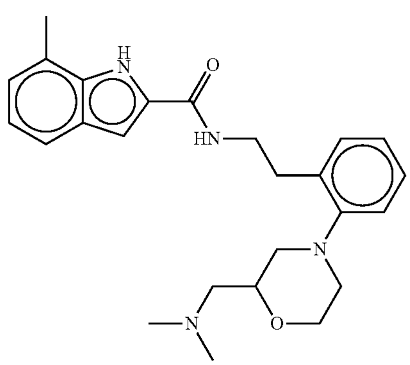 |
| 567 | 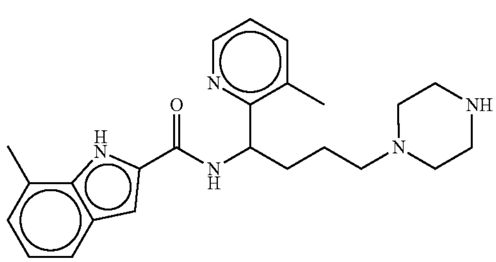 |

TABLE 1-continued
| Cpd. No. | Chemical Structure |
|---|---|
| 568 | 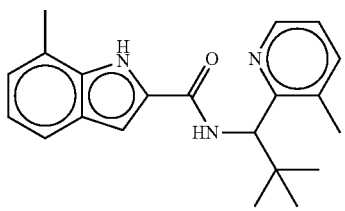 |
| 569 | 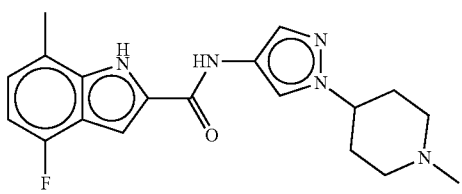 |
| 570 | 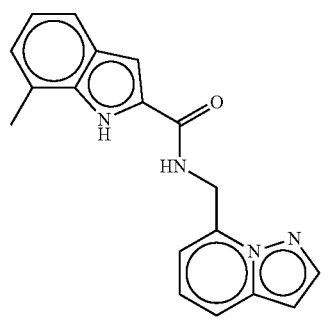 |
| 571 | 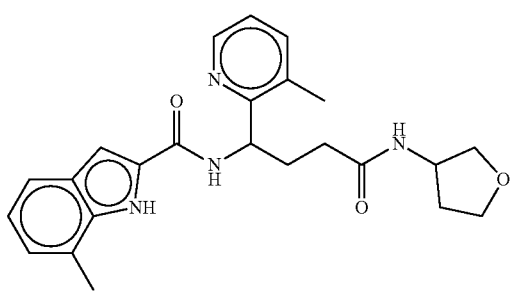 |
| 572 | 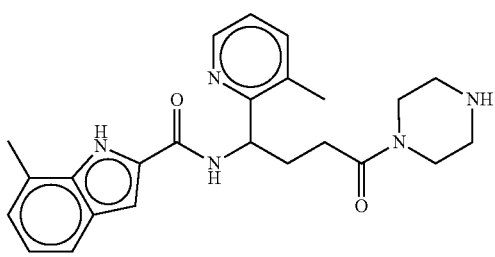 |

TABLE 1-continued
| Cpd. No. | Chemical Structure |
|---|---|
| 573 | 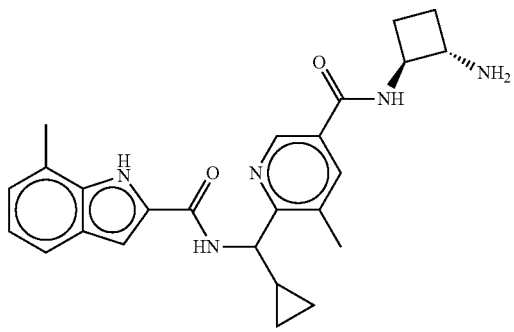 |
| 574 | 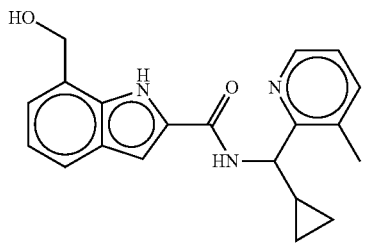 |
| 575 | 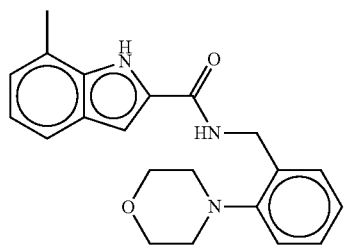 |
| 576 | 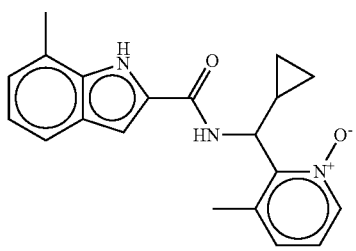 |
| 577 | 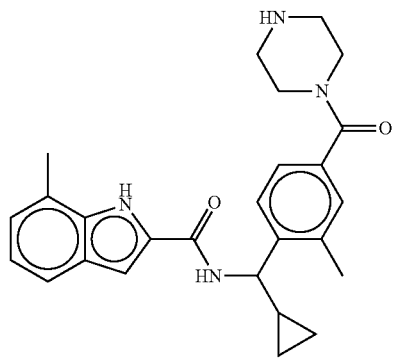 |

TABLE 1-continued

| Cpd. No. | Chemical Structure |
|---|---|
| 578 | 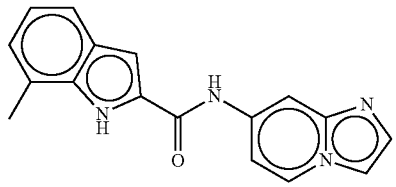 |
| 579 | 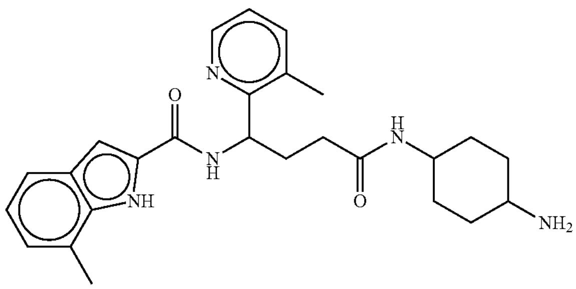 |
| 580 | 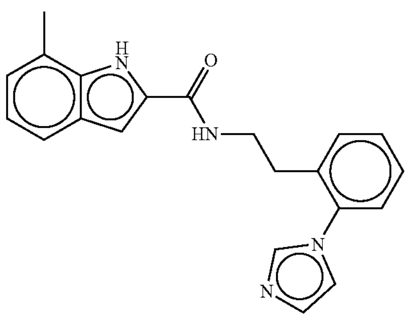 |
| 581 | 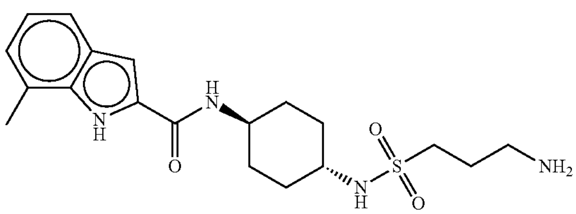 |
| 582 | 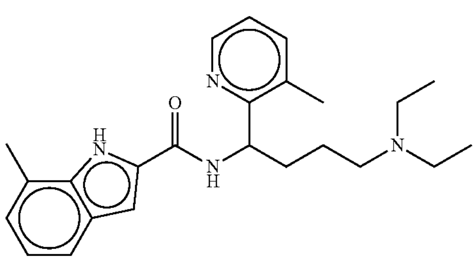 |
| 583 | 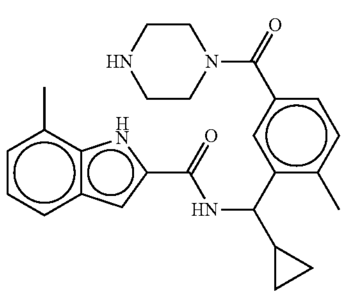 |

TABLE 1-continued

| Cpd. No. | Chemical Structure |
|---|---|
| 584 | 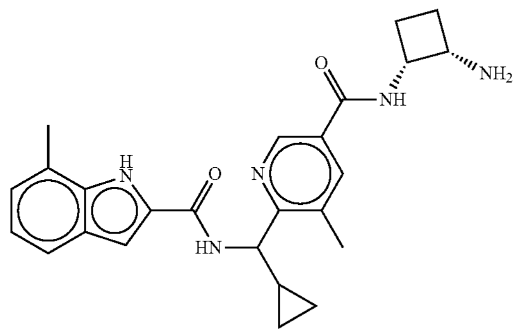 |
| 585 | 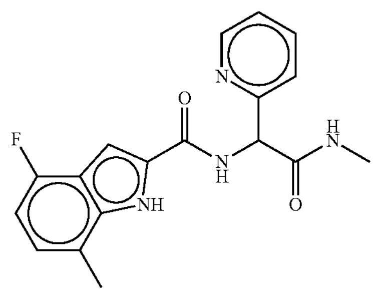 |
| 586 | 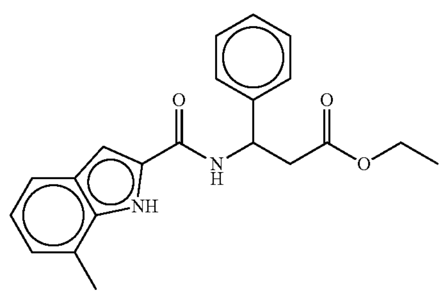 |
| 587 | 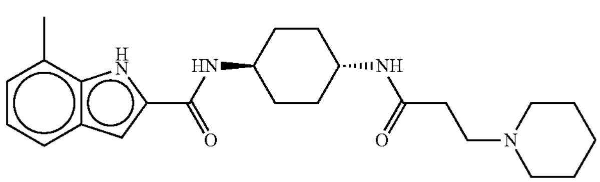 |
| 588 | 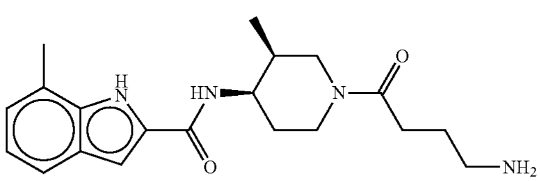 |
| 589 | 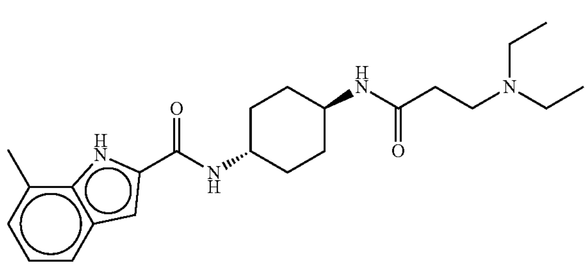 |

TABLE 1-continued
| Cpd. No. | Chemical Structure |
|---|---|
| 590 | 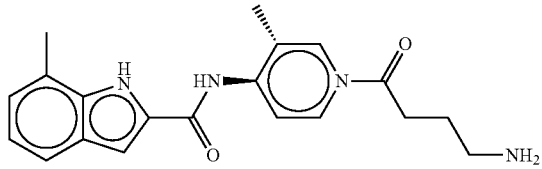 |
| 591 | 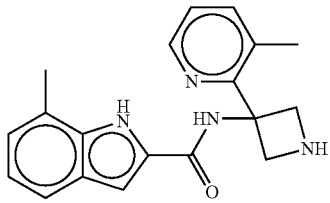 |
| 592 | 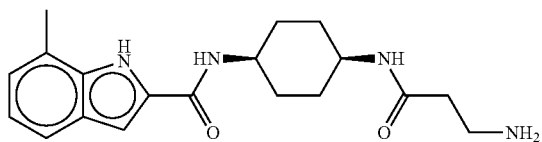 |
| 593 | 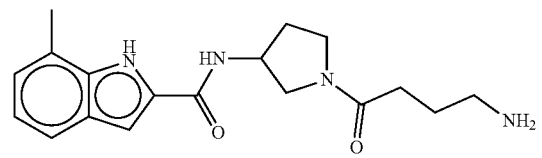 |
| 594 | 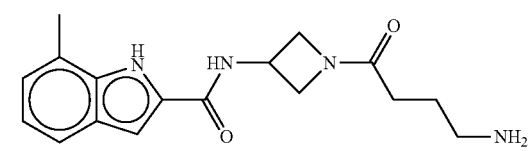 |
| 595 | 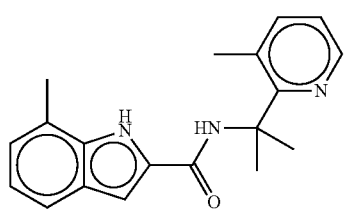 |
| 596 | 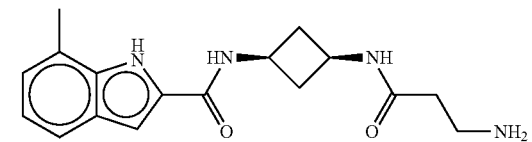 |
| 597 | 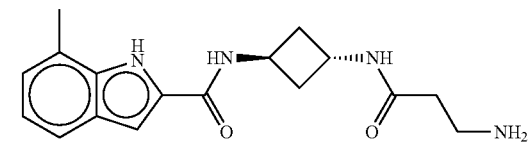 |

TABLE 1-continued
| Cpd. No. | Chemical Structure |
|---|---|
| 598 | 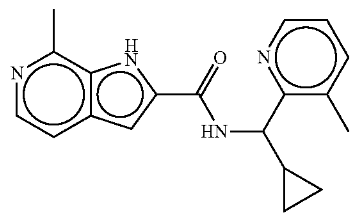 |
| 599 | 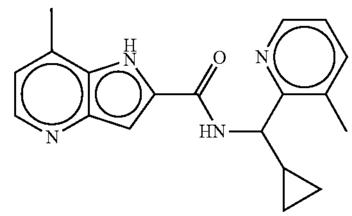 |
| 600 | 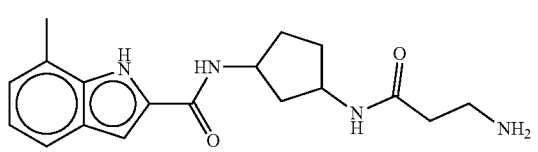 |
| 601 | 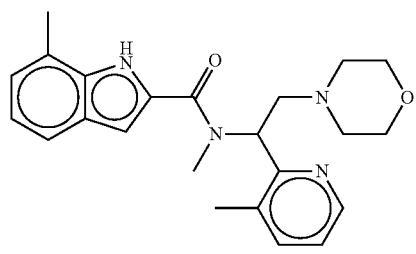 |
| 602 | 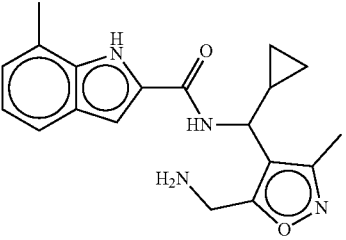 |
| 603 | 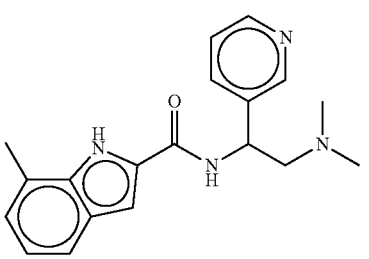 |
| 604 | 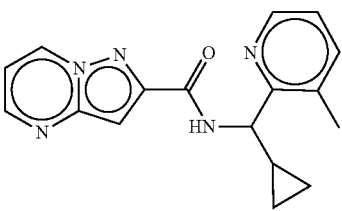 |

TABLE 1-continued
| Cpd. No. | Chemical Structure |
|---|---|
| 605 | 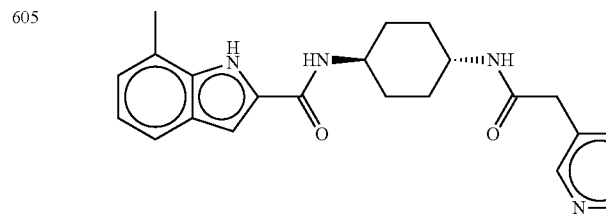 |
| 606 | 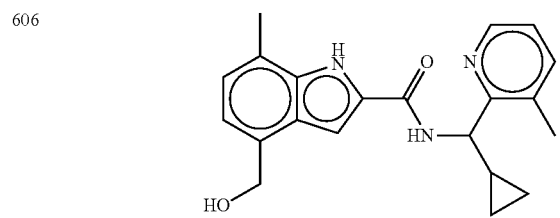 |
| 607 | 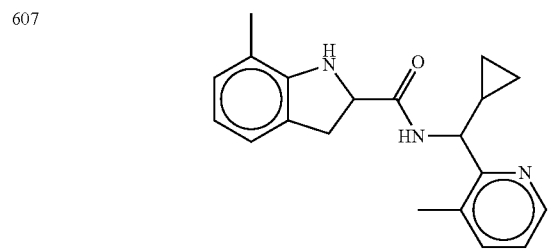 |
| 608 | 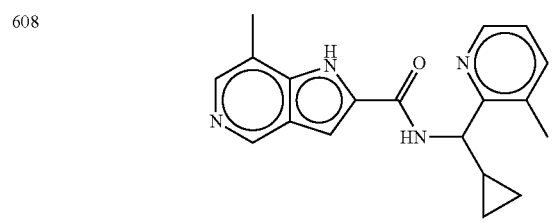 |
| 609 | 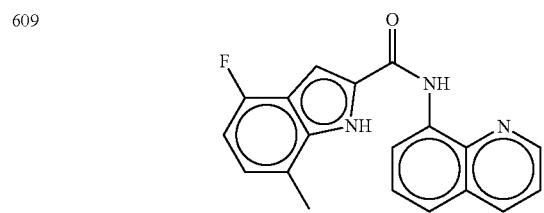 |
| 612 | 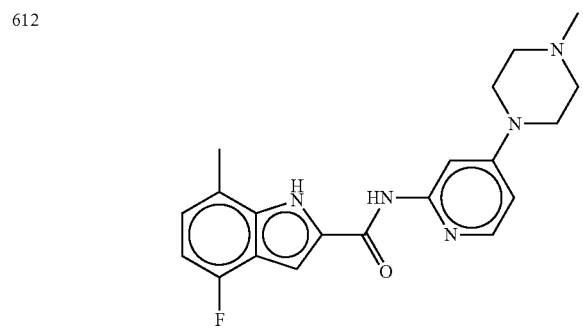 |

TABLE 1-continued
| Cpd. No. | Chemical Structure |
|---|---|
| 613 | 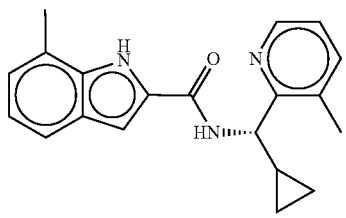 |
| 614 | 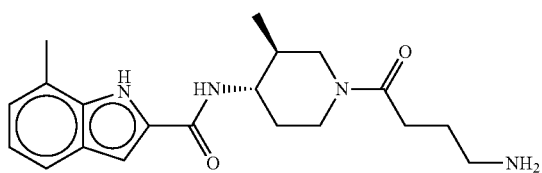 |
| 615 | 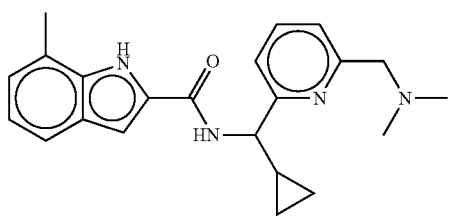 |
| 616 | 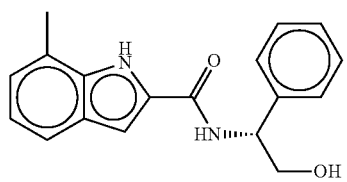 |
| 617 | 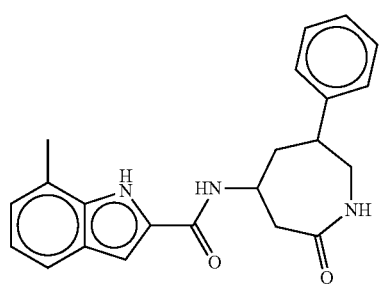 |
| 618 | 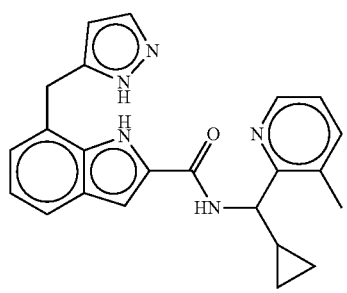 |

TABLE 1-continued
| Cpd. No. | Chemical Structure |
|---|---|
| 619 | 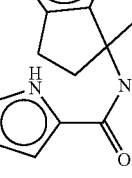 |
| 620 | 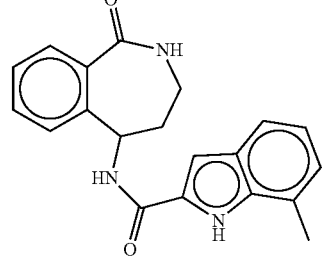 |
| 622 | 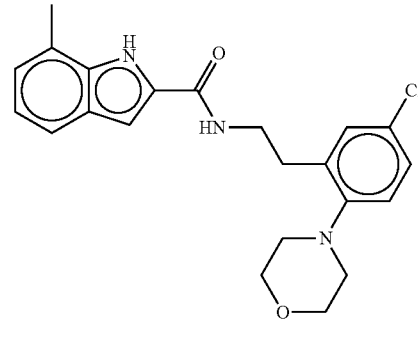 |
| 623 | 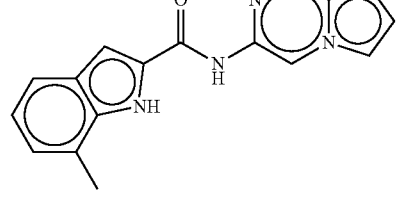 |
| 624 | 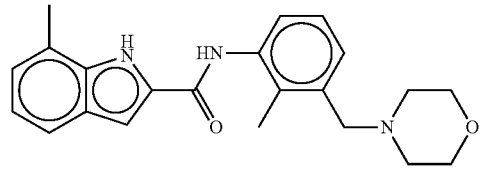 |
| 625 | 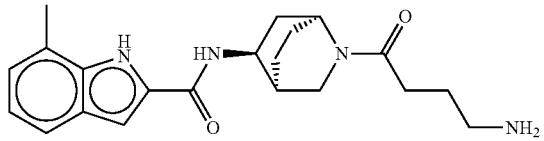 |

TABLE 1-continued

| Cpd. No. | Chemical Structure |
|---|---|
| 626 | 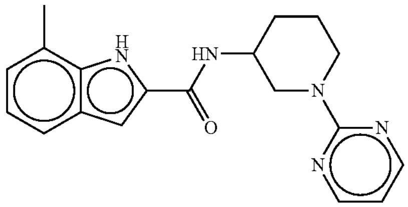 |
| 627 | 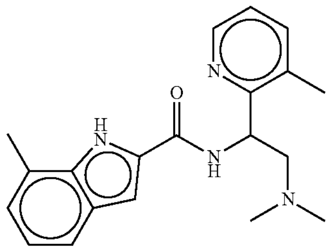 |
| 628 | 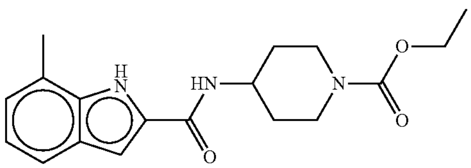 |
| 629 | 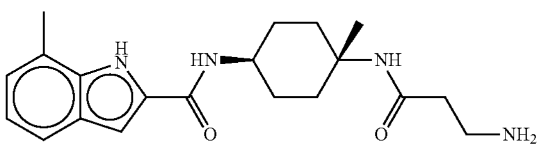 |
| 630 | 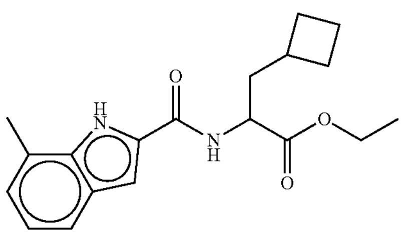 |
| 631 | 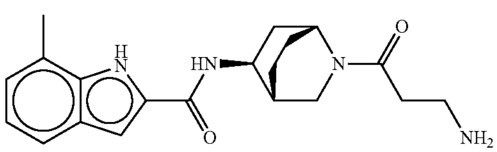 |
| 632 | 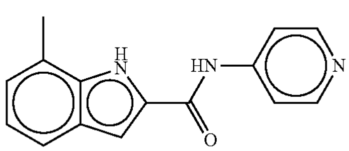 |
| 633 | 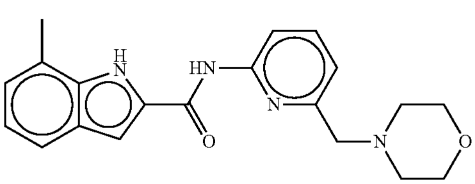 |

TABLE 1-continued

| Cpd. No. | Chemical Structure |
|---|---|
| 634 | 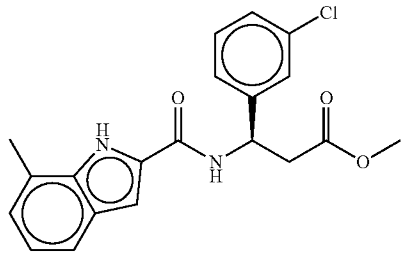 |
| 635 | 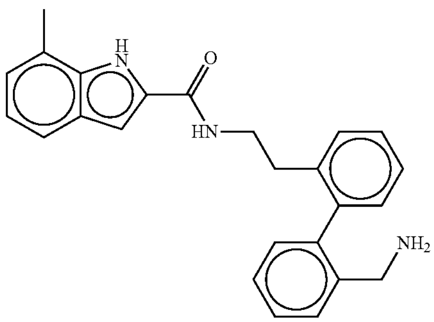 |
| 636 | 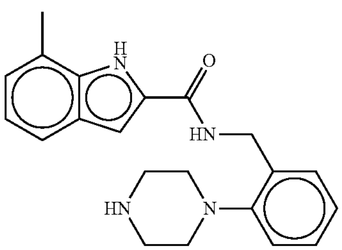 |
| 637 | 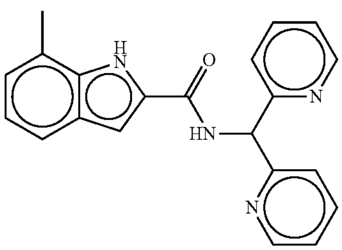 |
| 638 | 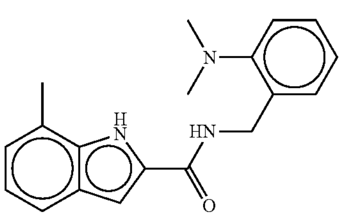 |
| 639 | 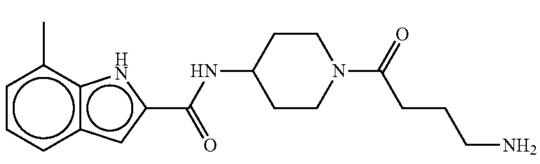 |

TABLE 1-continued

| Cpd. No. | Chemical Structure |
|---|---|
| 640 | 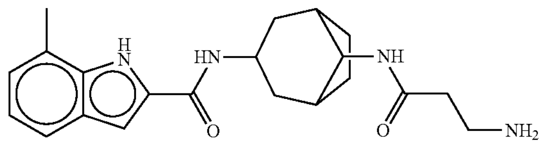 |
| 641 | 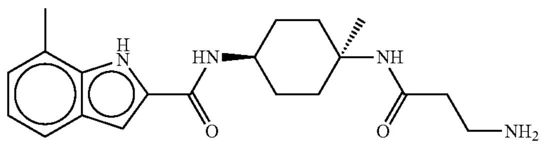 |
| 642 | 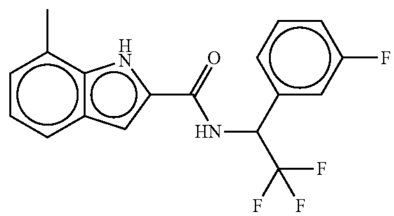 |
| 643 | 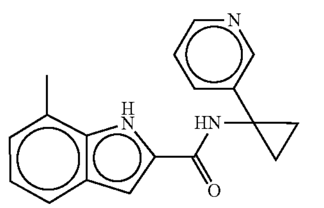 |
| 644 | 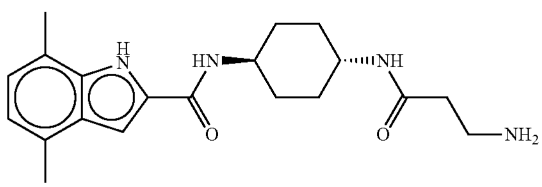 |
| 645 | 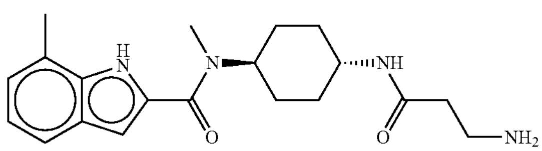 |
| 646 | 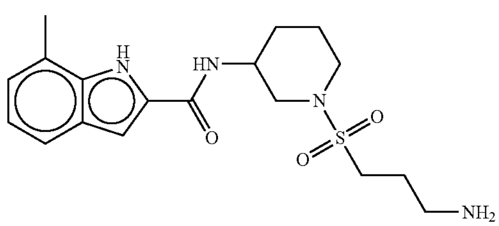 |
| 648 | 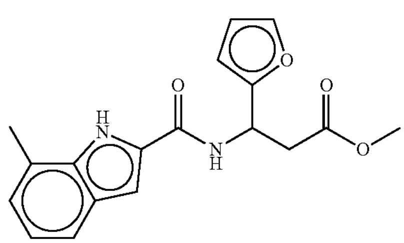 |

TABLE 1-continued
| Cpd. No. | Chemical Structure |
|---|---|
| 649 | 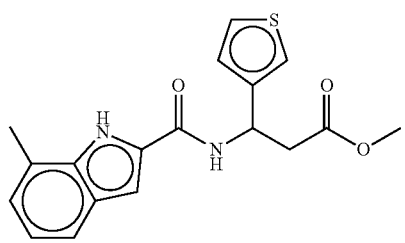 |
| 650 | 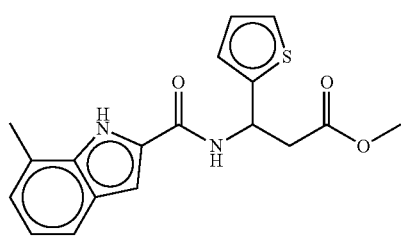 |
| 652 | 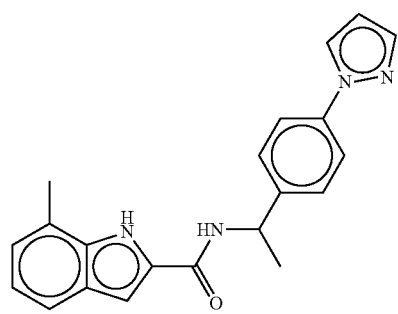 |
| 653 | 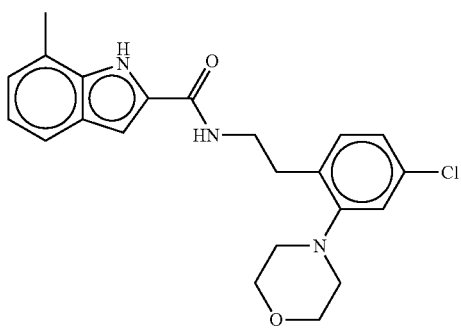 |
| 654 | 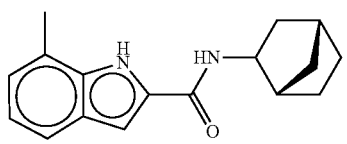 |
| 655 | 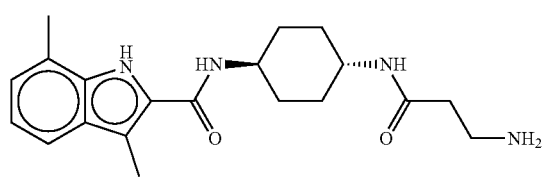 |

TABLE 1-continued
| Cpd. No. | Chemical Structure |
|---|---|
| 656 | 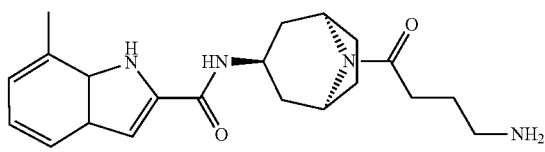 [SMILES: CC1=CC=CC2C=C(C(=O)N[C@H]3C[C@H]4CC[C@@H](C3)N4C(=O)CCCN)NC12] |
| 657 | 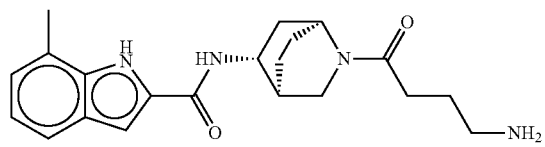 |
| 658 | 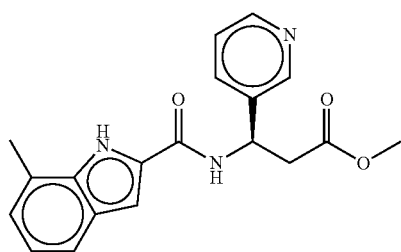 |
| 659 | 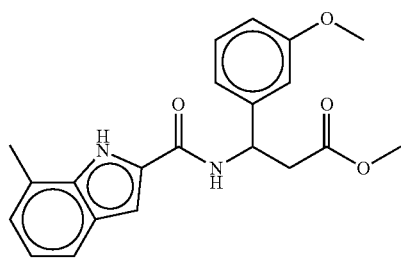 |
| 660 | 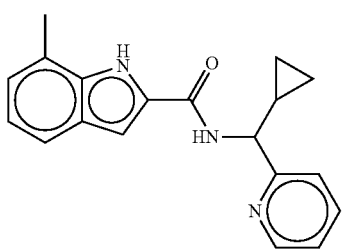 |
| 661 | 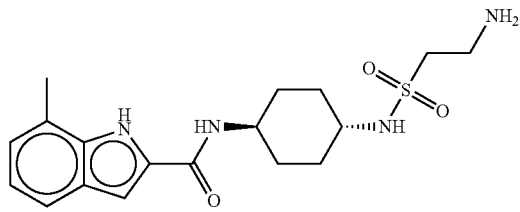 |
| 662 | 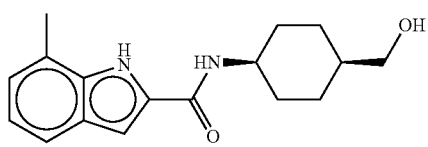 |

TABLE 1-continued

| Cpd. No. | Chemical Structure |
|---|---|
| 663 | 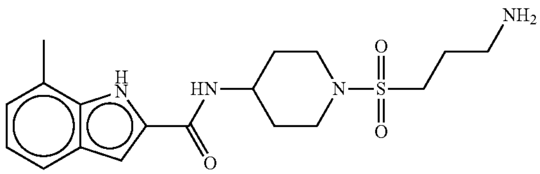 |
| 664 | 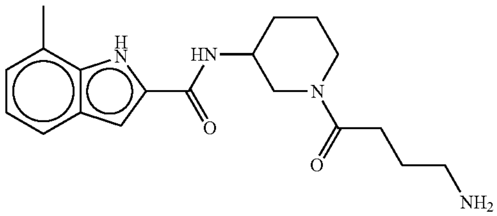 |
| 665 | 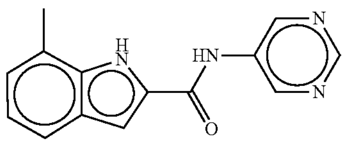 |
| 666 | 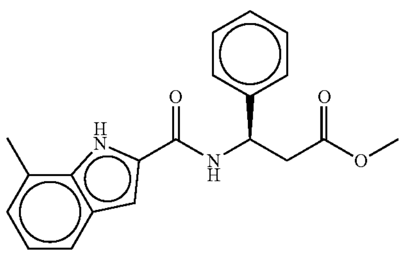 |
| 667 | 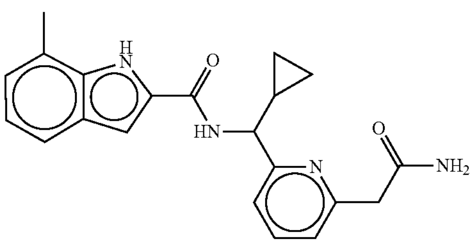 |
| 668 | 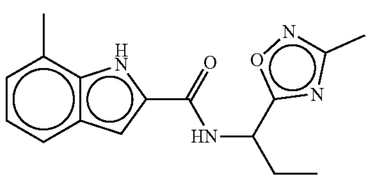 |
| 669 | 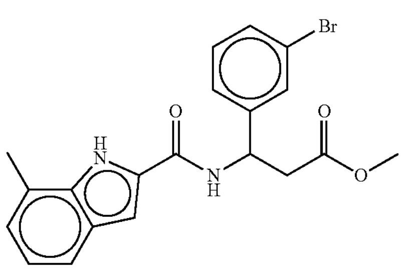 |

TABLE 1-continued

| Cpd. No. | Chemical Structure |
|---|---|
| 670 | 7-methyl-1H-indole-2-carboxamide linked to 1-acetylpiperidin-4-ylamine |
| 671 | 7-methyl-1H-indole-2-carboxamide linked to methyl 3-(pyridin-3-yl)-3-aminopropanoate |
| 672 | 7-methyl-1H-indole-2-carboxamide linked to 8-(3-aminopropanoyl)-8-azabicyclo[3.2.1]octan-3-ylamine |
| 673 | 7-methyl-1H-indole-2-carboxamide linked to 2-aminopyridine |
| 674 | 7-methyl-1H-indole-2-carboxamide linked to 3-(pyrrolidin-1-ylmethyl)benzylamine |
| 675 | 7-methyl-1H-indole-2-carboxamide linked to ethyl 2-amino-3,3,3-trifluoropropanoate |
| 676 | 7-methyl-1H-indole-2-carboxamide linked to methyl (3S)-3-(pyridin-3-yl)-3-aminopropanoate |

TABLE 1-continued

| Cpd. No. | Chemical Structure |
|---|---|
| 677 | 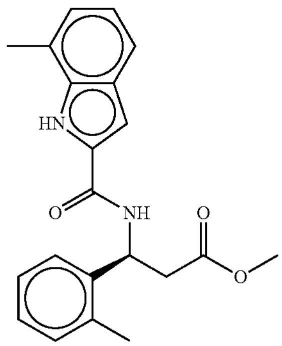 |
| 678 | 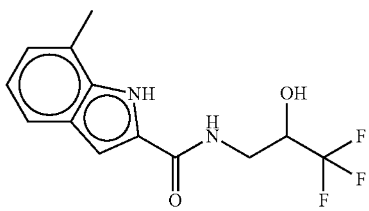 |
| 679 | 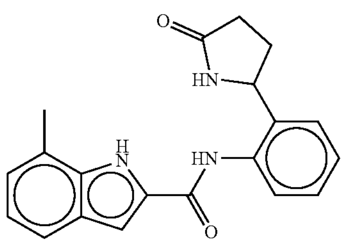 |
| 680 | 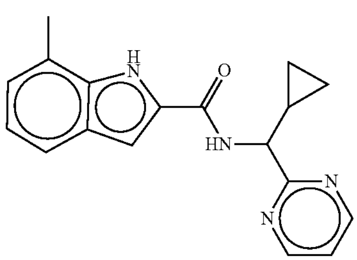 |
| 681 | 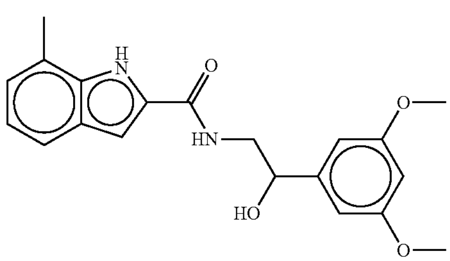 |

323 324
TABLE 1-continued
| Cpd. No. | Chemical Structure |
|---|---|
| 682 | 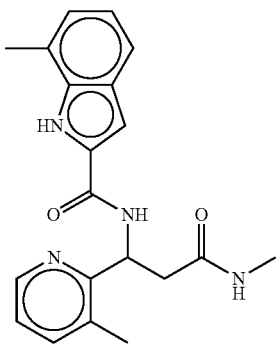 |
| 683 | 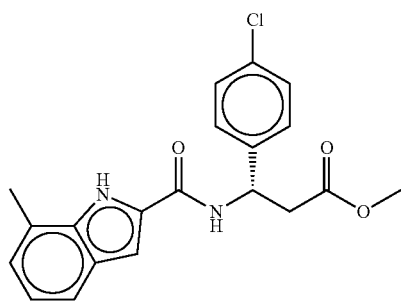 |
| 684 | 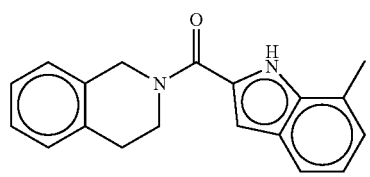 |
| 685 | 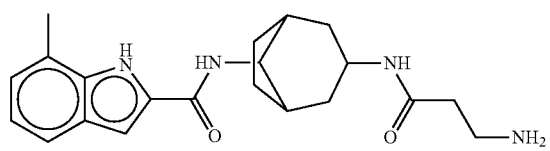 |
| 686 | 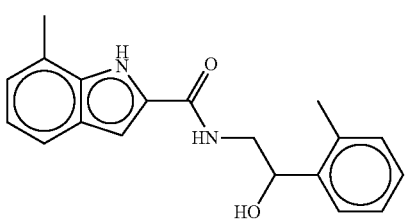 |
| 687 | 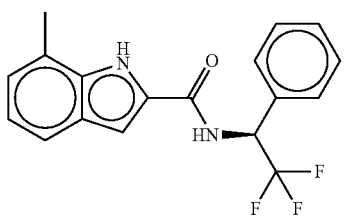 |

TABLE 1-continued

| Cpd. No. | Chemical Structure |
|---|---|
| 688 | 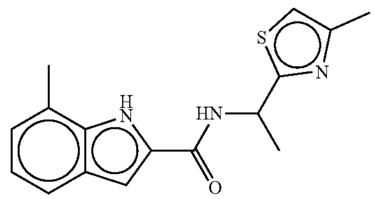 |
| 689 | 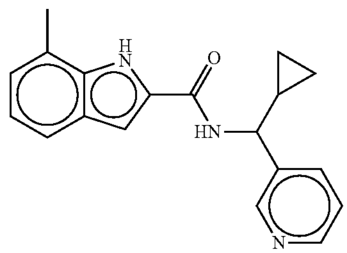 |
| 690 | 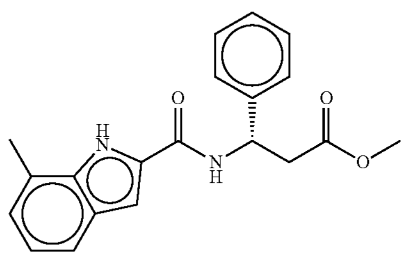 |
| 691 | 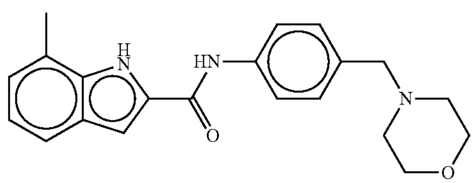 |
| 692 | 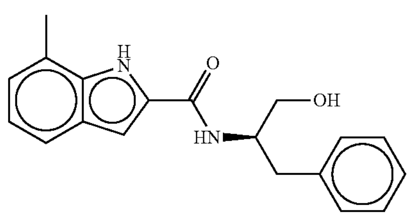 |
| 693 | 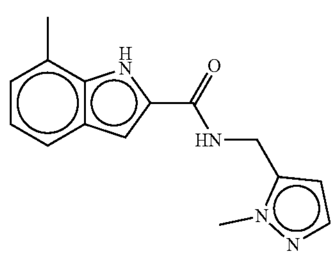 |

327
TABLE 1-continued
| Cpd. No. | Chemical Structure |
|---|---|
| 694 | 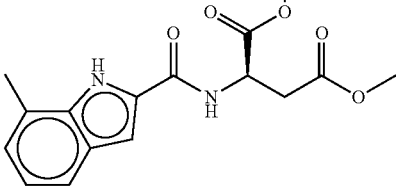 |
| 695 | 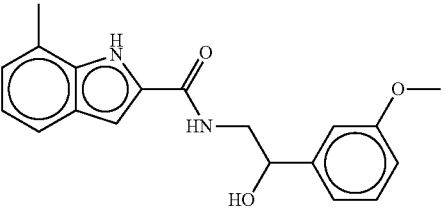 |
| 697 | 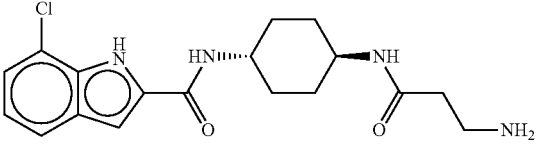 |
| 698 | 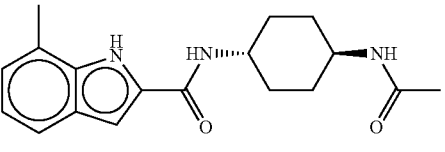 |
| 699 | 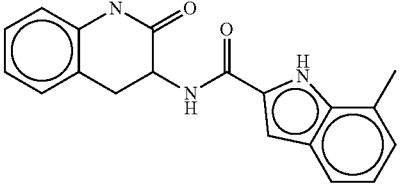 |
| 700 | 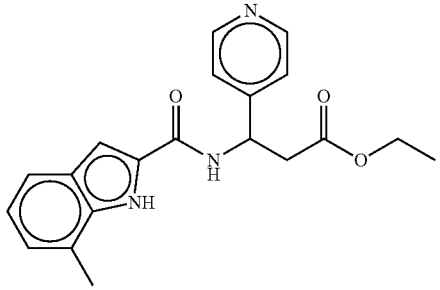 |
| 701 | 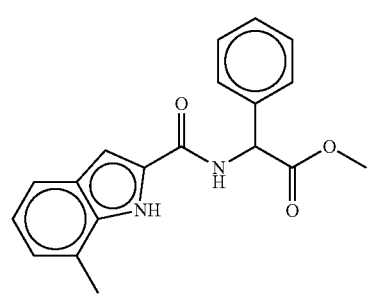 |

TABLE 1-continued

| Cpd. No. | Chemical Structure |
|---|---|
| 702 | 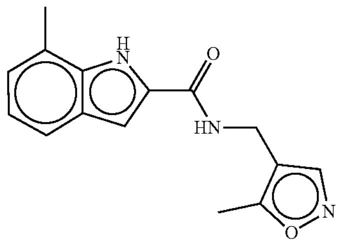 |
| 703 | 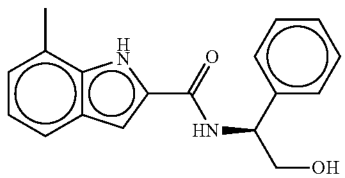 |
| 704 | 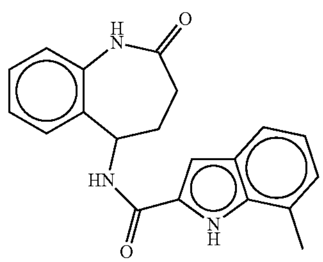 |
| 705 | 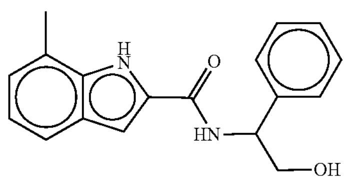 |
| 706 | 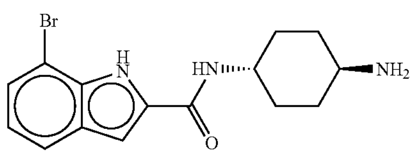 |
| 707 | 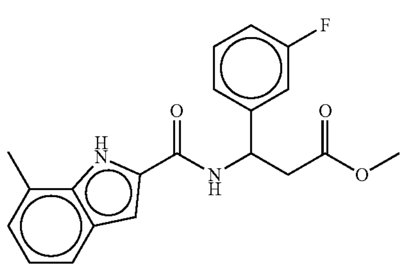 |
| 708 | 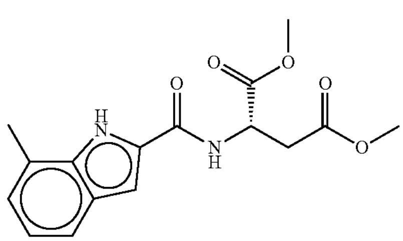 |

TABLE 1-continued

| Cpd. No. | Chemical Structure |
|---|---|
| 709 | 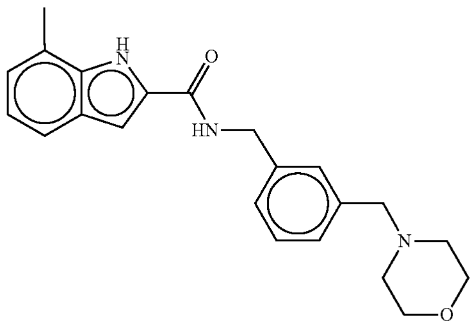 |
| 710 | 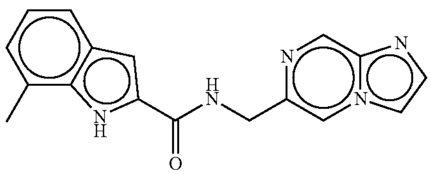 |
| 711 | 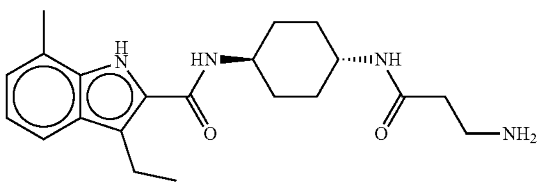 |
| 712 | 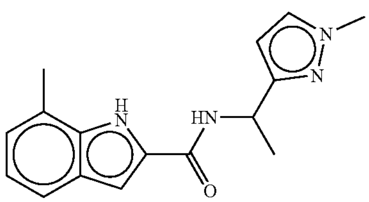 |
| 713 | 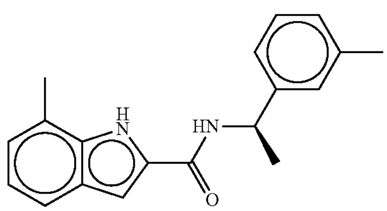 |
| 714 | 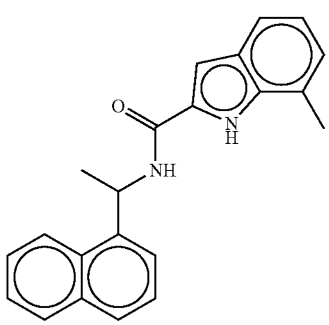 |
| 715 | 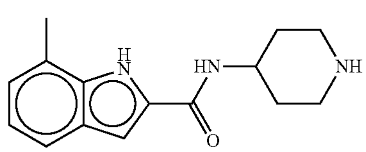 |

TABLE 1-continued
| Cpd. No. | Chemical Structure |
|---|---|
| 716 | 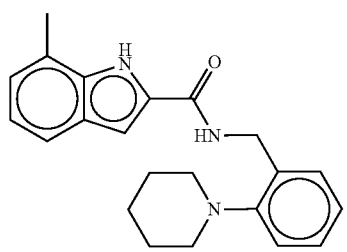 |
| 717 | 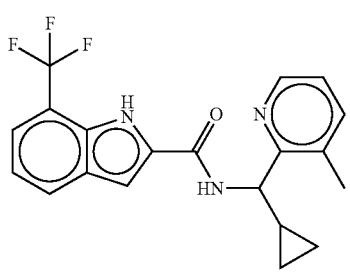 |
| 718 | 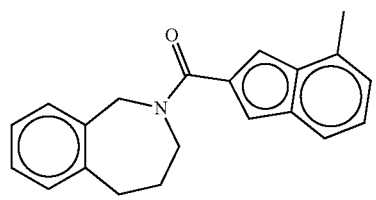 |
| 719 | 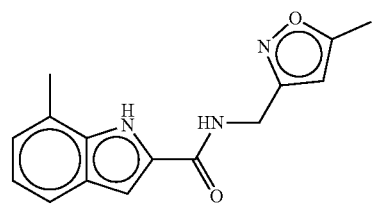 |
| 720 | 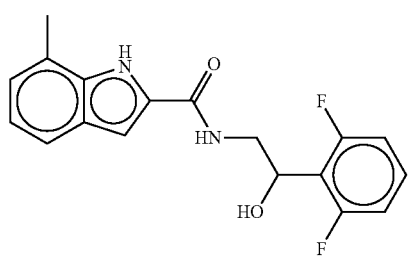 |
| 721 | 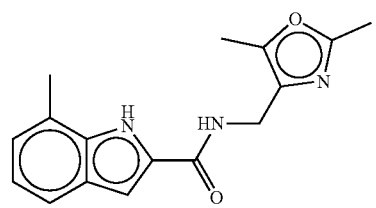 |

TABLE 1-continued
| Cpd. No. | Chemical Structure |
|---|---|
| 722 | 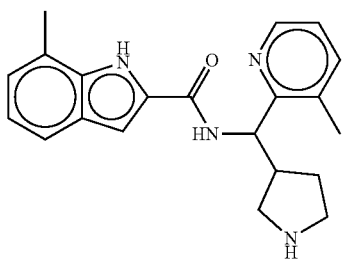 |
| 723 | 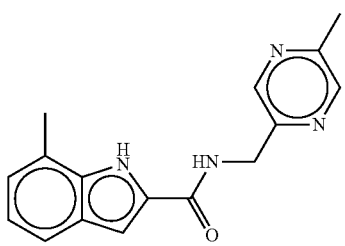 |
| 724 | 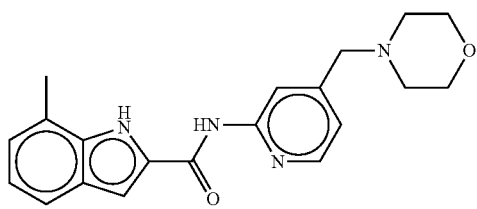 |
| 725 | 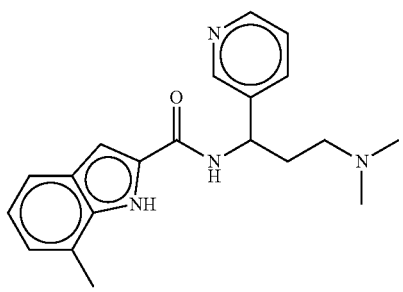 |
| 726 | 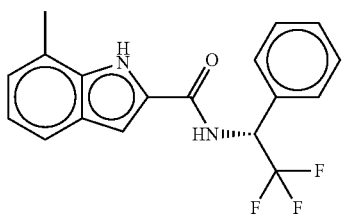 |
| 727 | 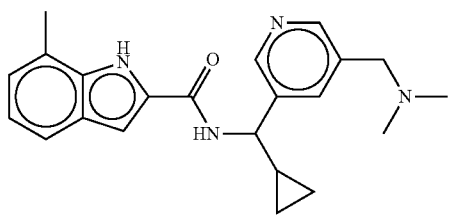 |

TABLE 1-continued

| Cpd. No. | Chemical Structure |
|---|---|
| 728 | 7-methyl-N-(1-(3-methylpyridin-2-yl)-3-(dimethylamino)propyl)-1H-indole-2-carboxamide |
| 729 | 7-methyl-N-((1H-imidazol-4-yl)methyl)-1H-indole-2-carboxamide |
| 730 | 4,7-dimethyl-N-(trans-4-aminocyclohexyl)-1H-indole-2-carboxamide |
| 731 | 7-methyl-N-(2-cyclopropyl-2-hydroxyethyl)-1H-indole-2-carboxamide |
| 732 | 7-methyl-N-((4-methyl-1,2,5-oxadiazol-3-yl)methyl)-1H-indole-2-carboxamide |
| 733 | 7-methyl-N-(oxazol-4-ylmethyl)-1H-indole-2-carboxamide |

TABLE 1-continued

| Cpd. No. | Chemical Structure |
|---|---|
| 735 | 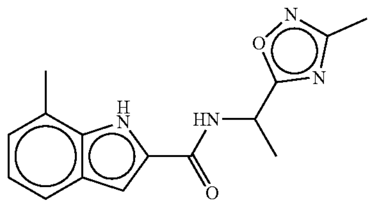 |
| 736 | 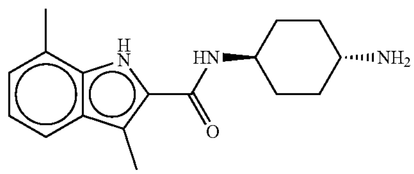 |
| 738 | 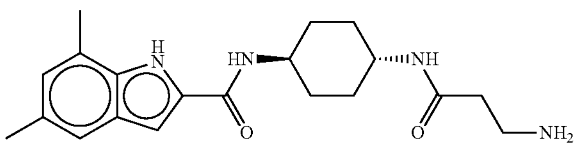 |
| 746 | 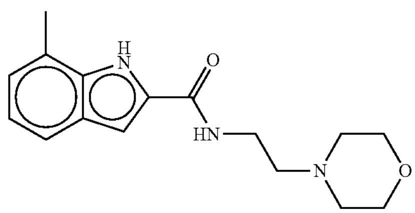 |
| 747 | 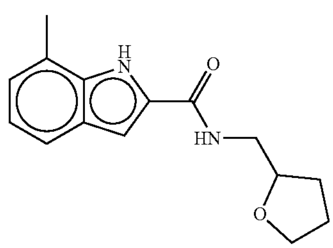 |
| 748 | 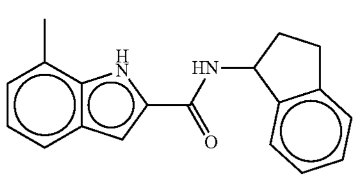 |
| 749 | 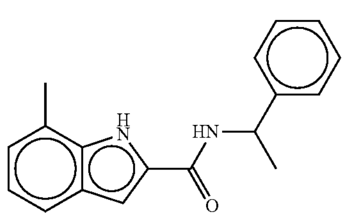 |

TABLE 1-continued

| Cpd. No. | Chemical Structure |
|---|---|
| 750 | 7-methyl-N-(3-(piperidin-1-yl)benzyl)-1H-indole-2-carboxamide |
| 751 | 7-methyl-N-(3-(piperidin-1-ylsulfonyl)benzyl)-1H-indole-2-carboxamide |
| 752 | N-(1-benzylpiperidin-4-yl)-7-methyl-1H-indole-2-carboxamide |
| 753 | 7-methyl-N-(1,2,3,4-tetrahydronaphthalen-1-yl)-1H-indole-2-carboxamide |
| 754 | N-(2-hydroxy-2-(4-methoxyphenyl)ethyl)-7-methyl-1H-indole-2-carboxamide |
| 755 | 7-methyl-N-(4-(morpholinomethyl)benzyl)-1H-indole-2-carboxamide |

TABLE 1-continued

| Cpd. No. | Chemical Structure |
|---|---|
| 756 | 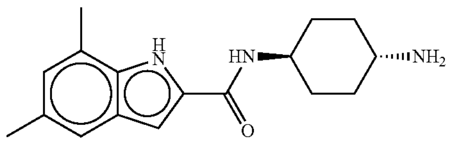 |
| 757 | 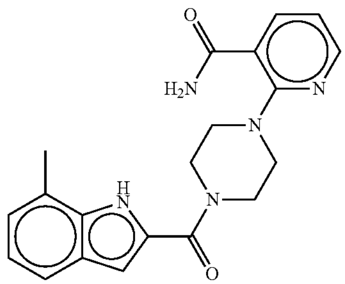 |
| 758 | 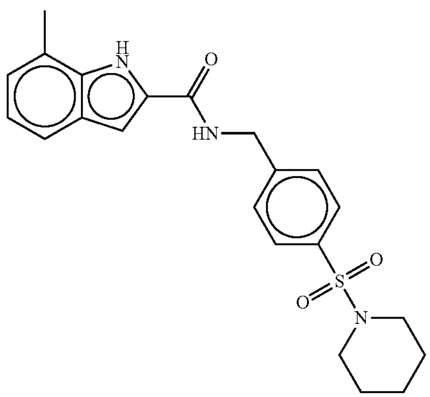 |
| 759 | 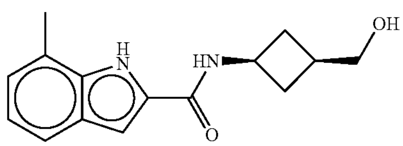 |
| 761 | 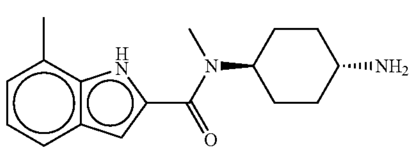 |
| 763 | 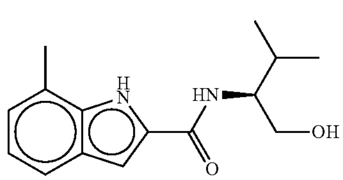 |

TABLE 1-continued
| Cpd. No. | Chemical Structure |
|---|---|
| 764 | 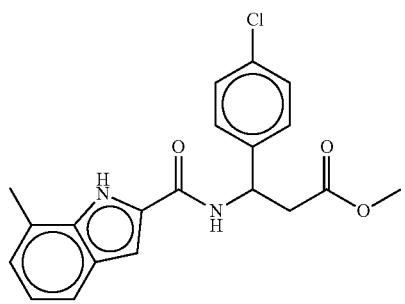 |
| 765 | 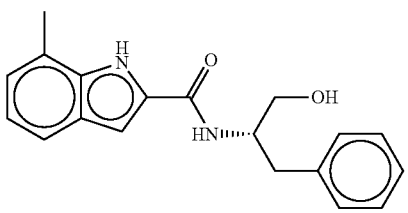 |
| 766 | 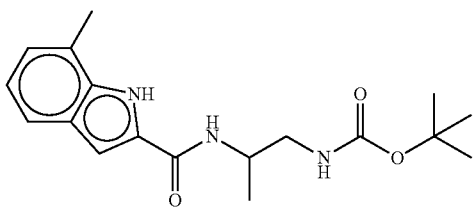 |
| 767 | 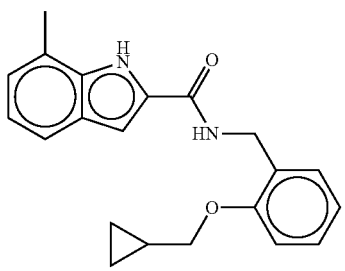 |
| 768 | 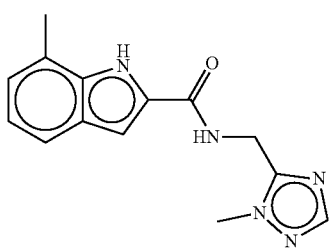 |
| 769 | 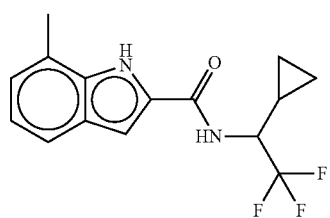 |

TABLE 1-continued
| Cpd. No. | Chemical Structure |
|---|---|
| 771 | 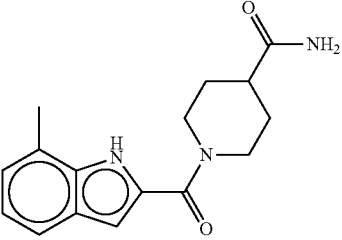 |
| 773 | 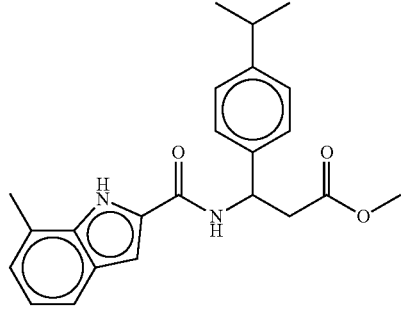 |
| 774 | 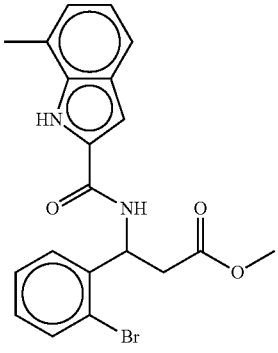 |
| 775 | 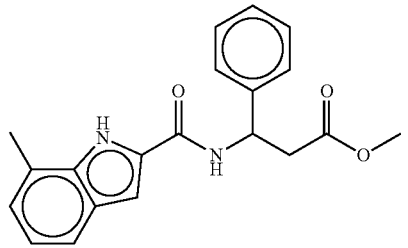 |
| 776 | 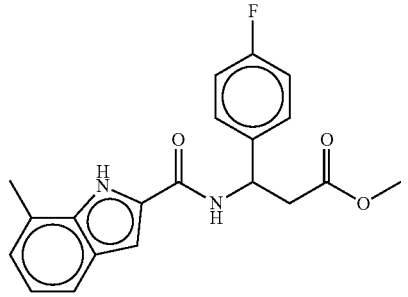 |

TABLE 1-continued

| Cpd. No. | Chemical Structure |
|---|---|
| 777 | 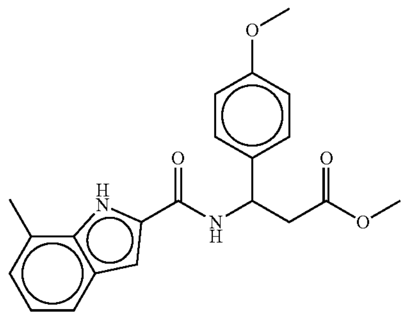 |
| 778 | 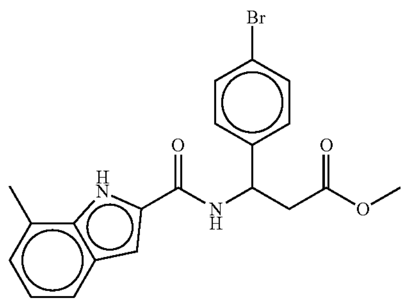 |
| 779 | 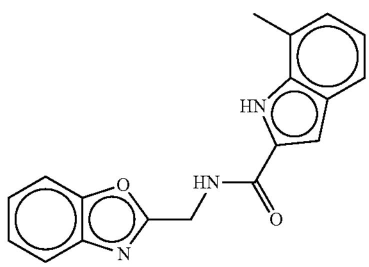 |
| 780 | 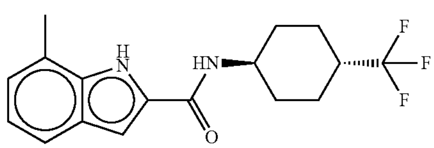 |
| 781 | 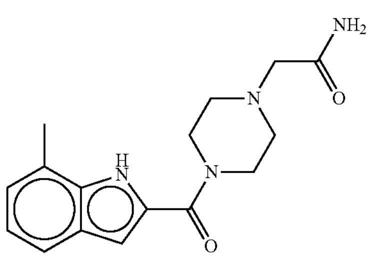 |
| 782 | 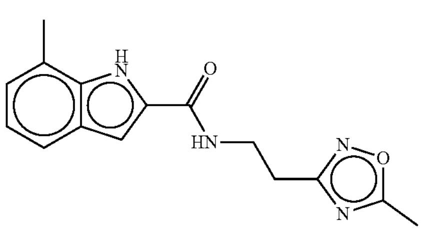 |

TABLE 1-continued

| Cpd. No. | Chemical Structure |
|---|---|
| 783 | 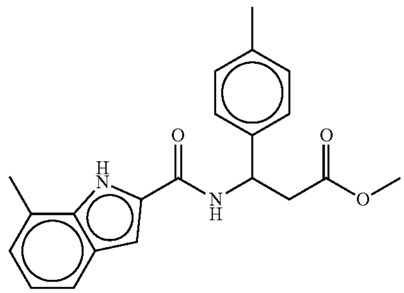 |
| 784 | 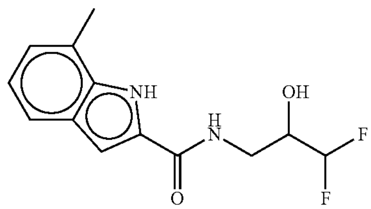 |
| 785 | 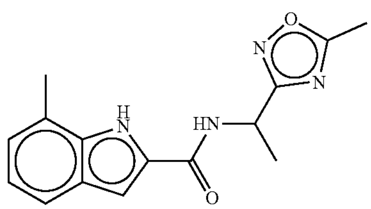 |
| 786 | 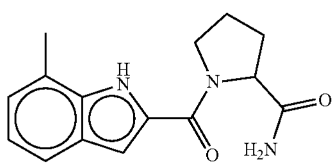 |
| 787 | 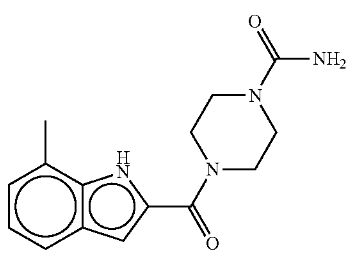 |
| 788 | 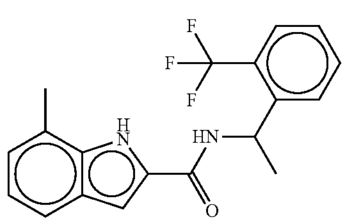 |
| 790 | 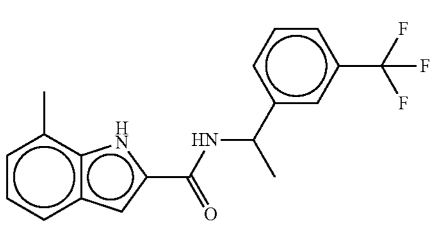 |

TABLE 1-continued
| Cpd. No. | Chemical Structure |
|---|---|
| 791 | 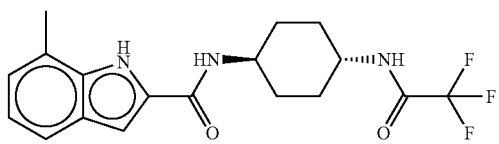 |
| 793 | 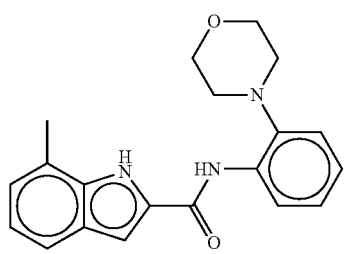 |
| 794 | 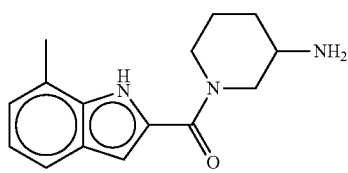 |
| 795 | 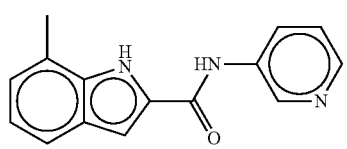 |
| 796 | 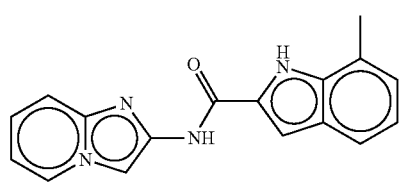 |
| 797 | 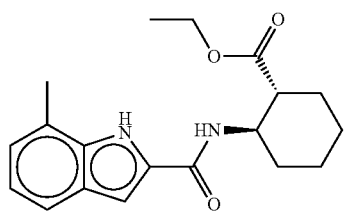 |
| 798 | 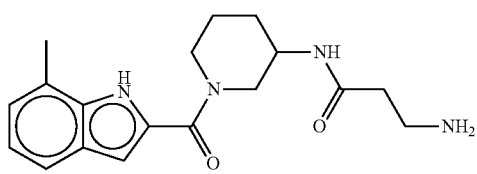 |
| 799 | 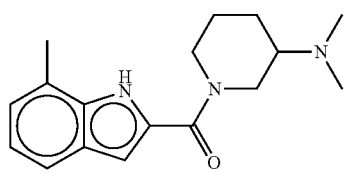 |

TABLE 1-continued
| Cpd. No. | Chemical Structure |
|---|---|
| 800 | 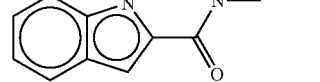 |
| 801 | 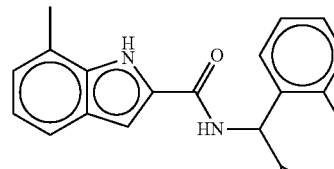 |
| 802 | 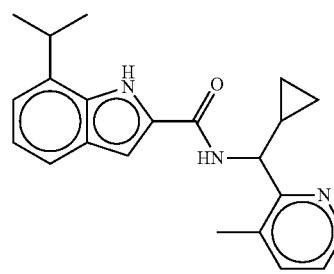 |
| 803 | 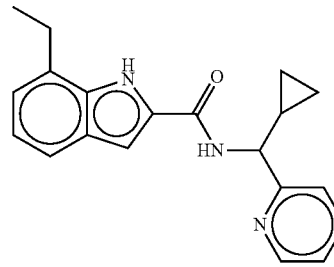 |
| 804 | 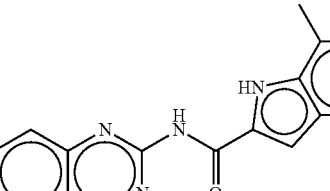 |
| 805 | 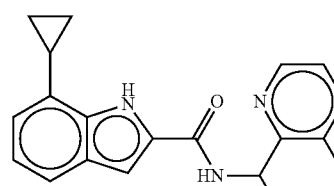 |

TABLE 1-continued
| Cpd. No. | Chemical Structure |
|---|---|
| 808 | 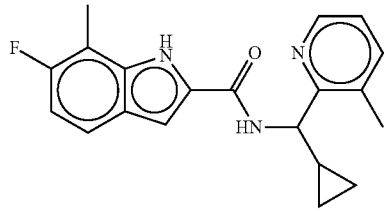 |
| 809 | 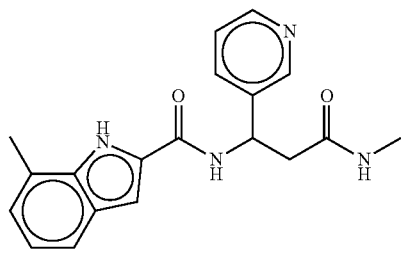 |
| 810 | 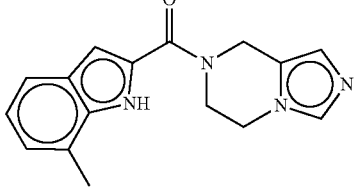 |
| 811 | 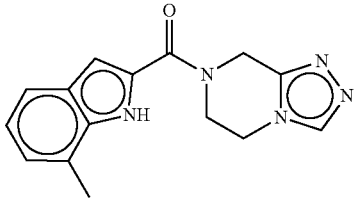 |
| 812 | 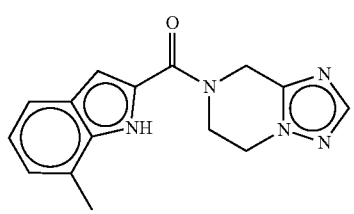 |
| 814 | 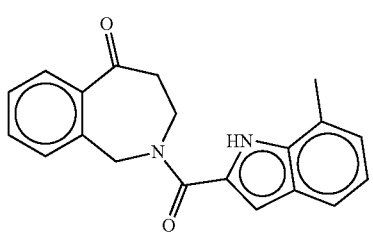 |
| 815 | 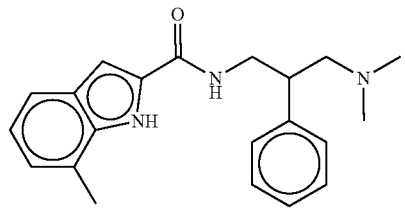 |

TABLE 1-continued

| Cpd. No. | Chemical Structure |
|---|---|
| 816 | 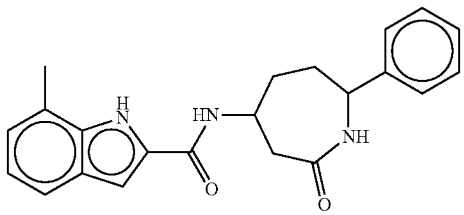 |
| 817 | 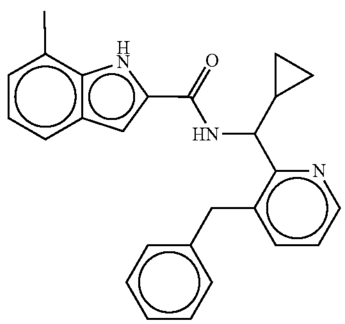 |
| 818 | 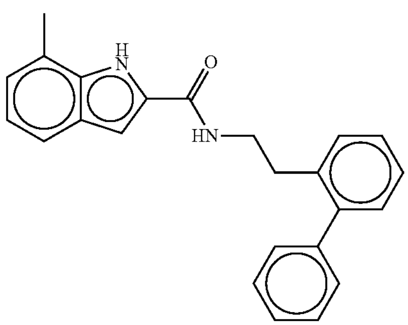 |
| 819 | 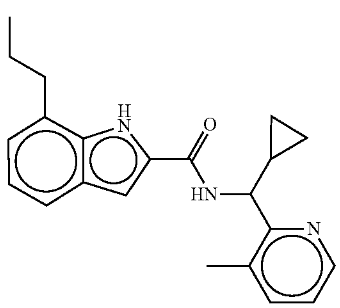 |
| 820 | 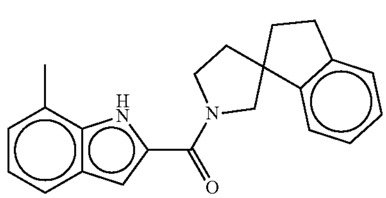 |

TABLE 1-continued
| Cpd. No. | Chemical Structure |
|---|---|
| 821 | 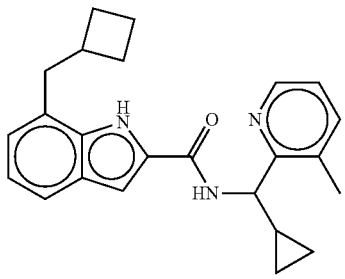 |
| 822 | 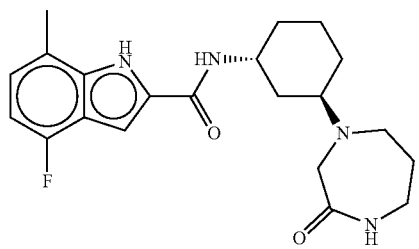 |
| 823 | 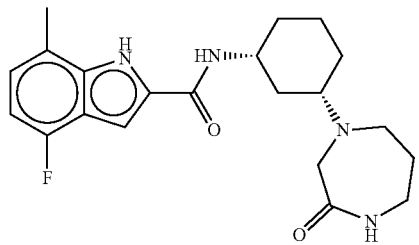 |
| 824 | 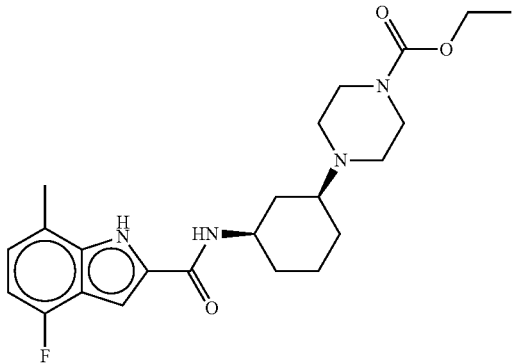 |
| 825 | 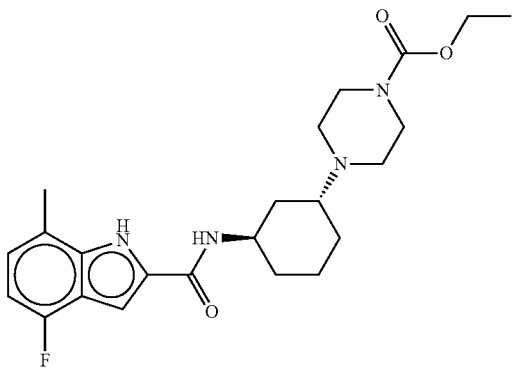 |

TABLE 1-continued
| Cpd. No. | Chemical Structure |
|---|---|
| 826 | 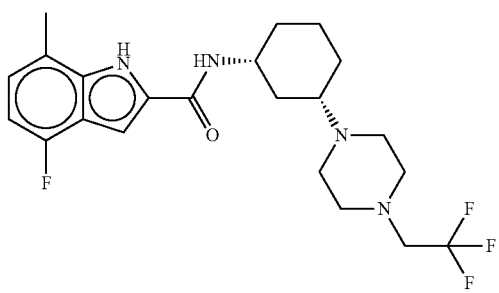 |
| 827 | 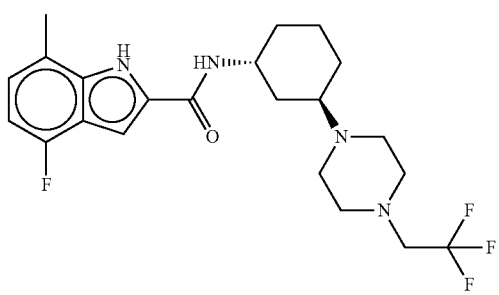 |
| 828 | 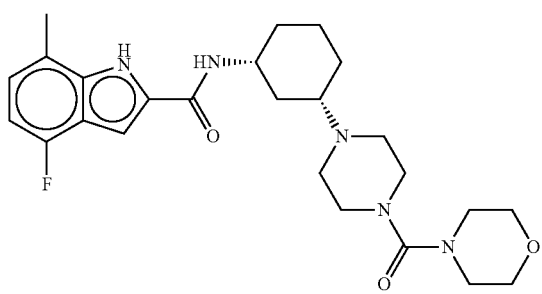 |
| 829 | 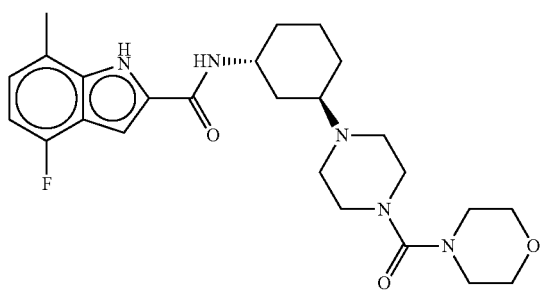 |
| 830 | 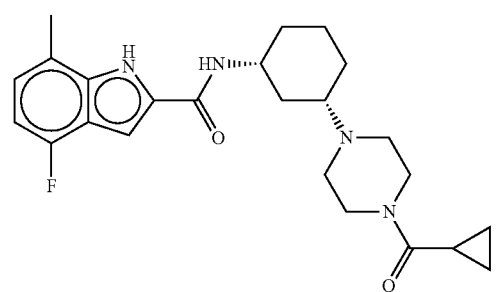 |

TABLE 1-continued

| Cpd. No. | Chemical Structure |
|---|---|
| 831 | 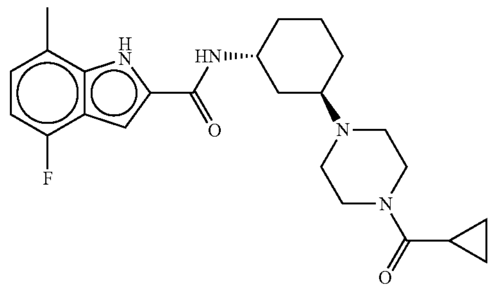 |
| 832 | 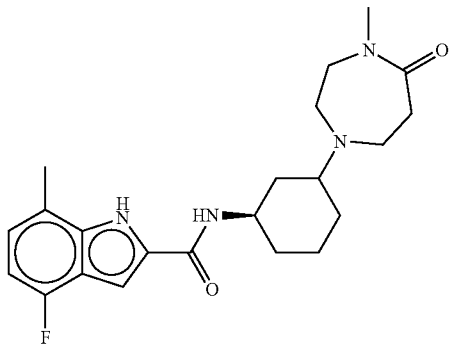 |
| 833 | 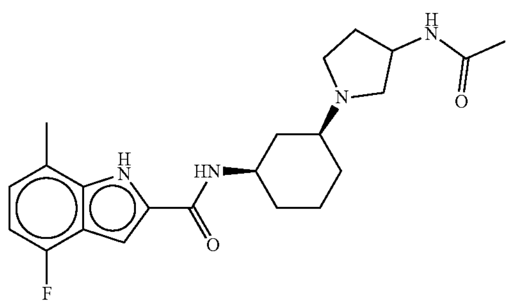 |
| 834 | 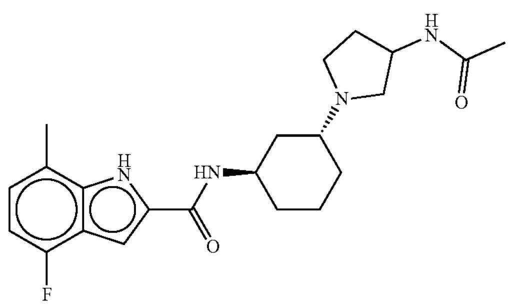 |
| 835 | 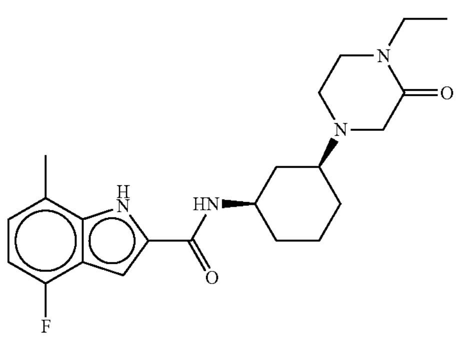 |

TABLE 1-continued
| Cpd. No. | Chemical Structure |
|---|---|
| 836 | 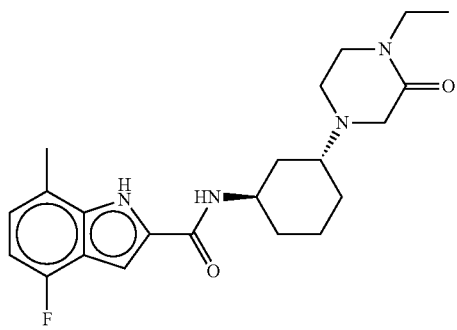 |
| 837 | 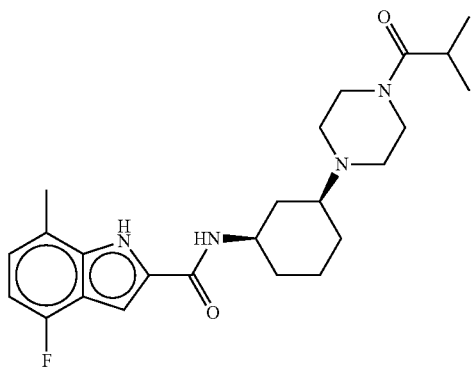 |
| 838 | 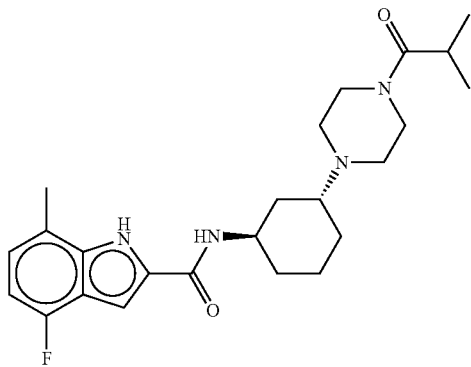 |
| 839 | 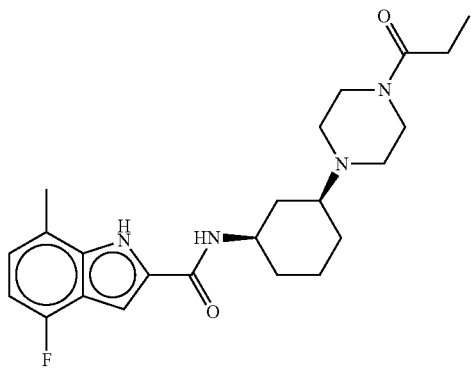 |

TABLE 1-continued
| Cpd. No. | Chemical Structure |
|---|---|
| 840 | 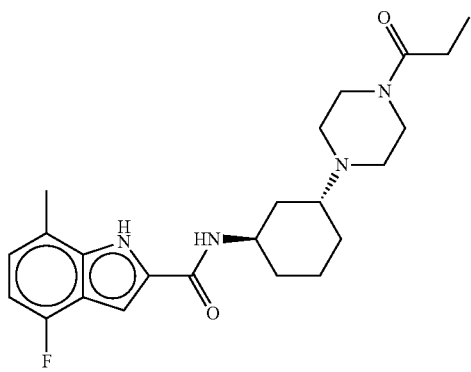 |
| 841 | 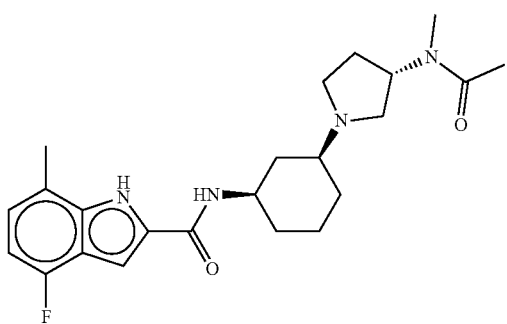 |
| 842 | 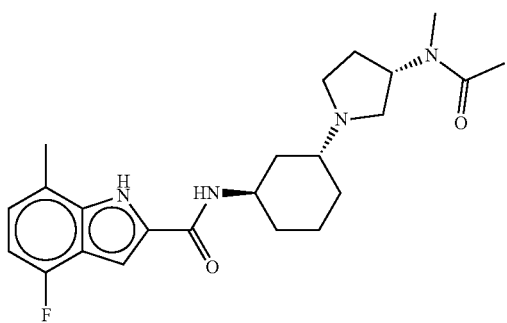 |
| 843 | 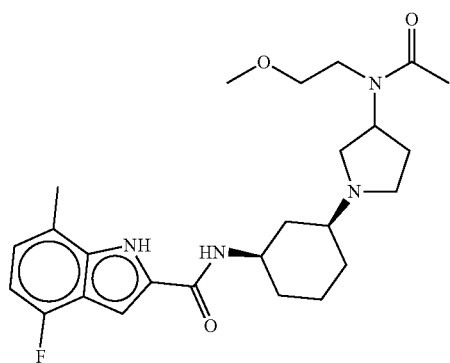 |

TABLE 1-continued
| Cpd. No. | Chemical Structure |
|---|---|
| 844 | 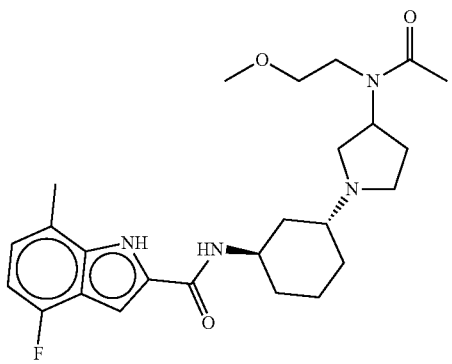 |
| 845 | 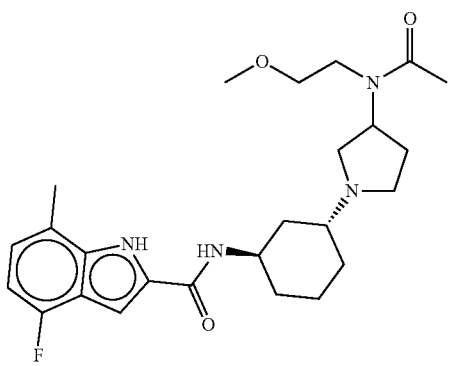 |
| 846 | 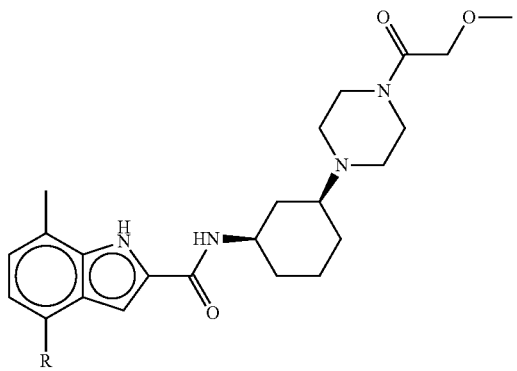 |
| 847 | 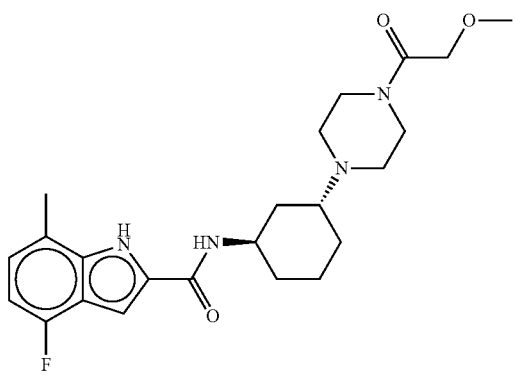 |

TABLE 1-continued
| Cpd. No. | Chemical Structure |
|---|---|
| 848 | 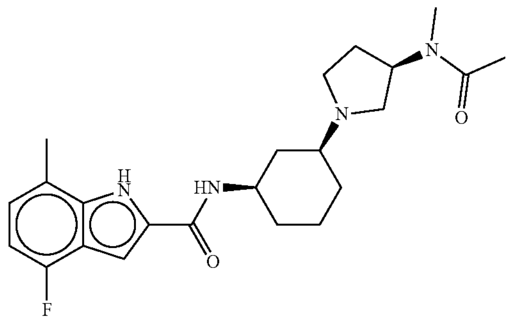 |
| 849 | 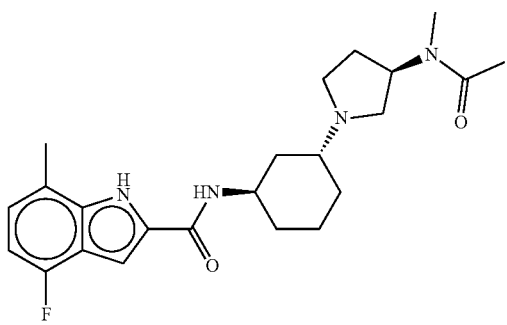 |
| 850 | 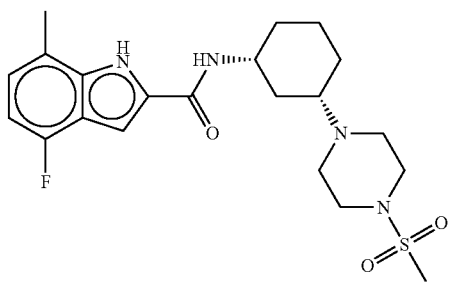 |
| 851 | 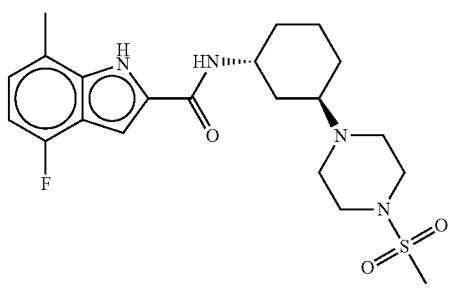 |
| 852 | 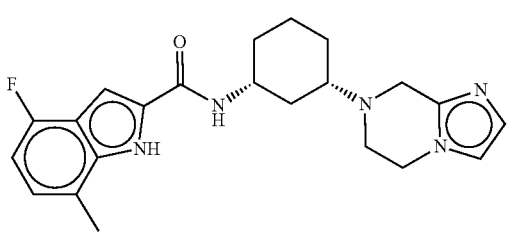 |

TABLE 1-continued
| Cpd. No. | Chemical Structure |
|---|---|
| 853 | 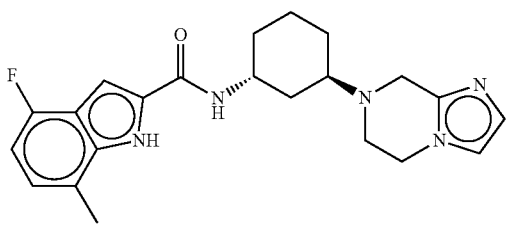 |
| 854 | 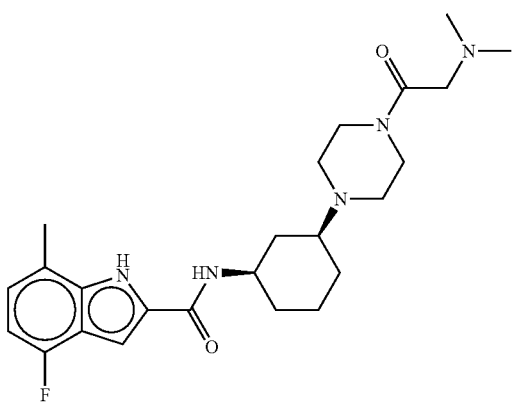 |
| 855 | 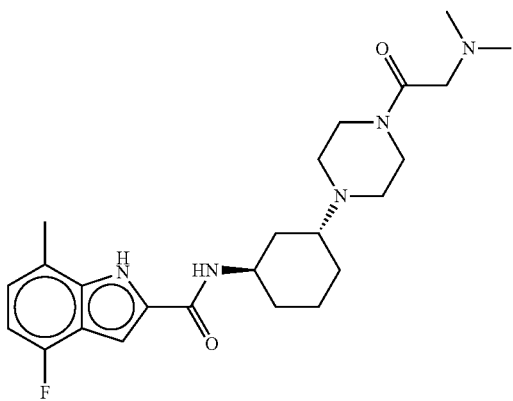 |
| 856 | 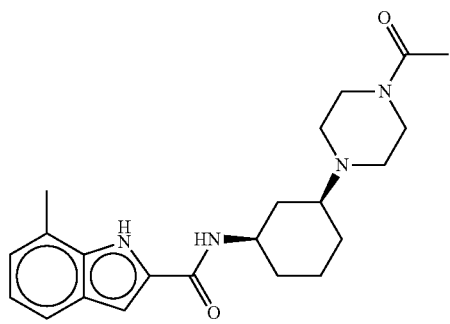 |

TABLE 1-continued
| Cpd. No. | Chemical Structure |
|---|---|
| 857 | 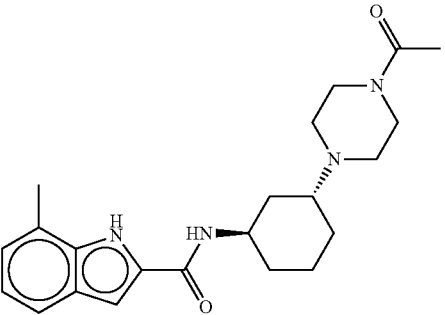 |
| 858 | 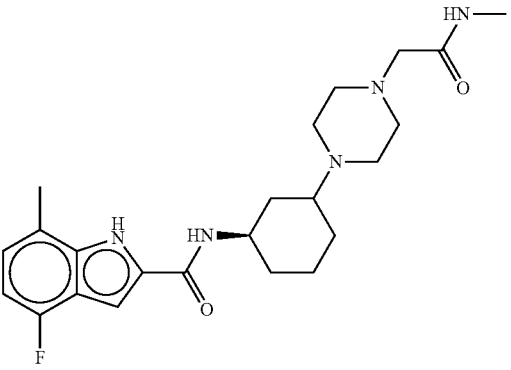 |
| 859 | 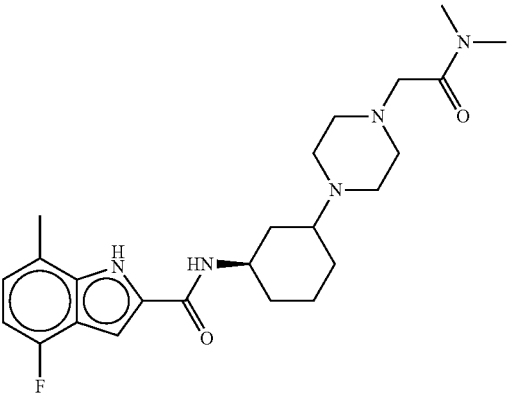 |
| 860 | 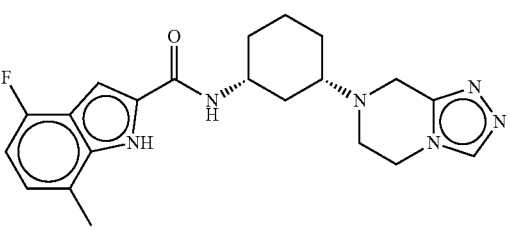 |
| 861 | 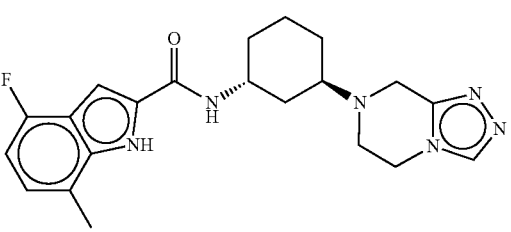 |

TABLE 1-continued
| Cpd. No. | Chemical Structure |
|---|---|
| 862 | 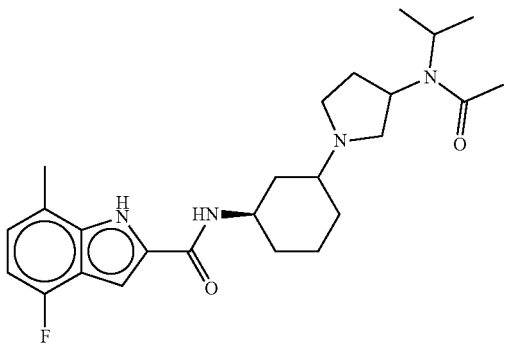 |
| 863 | 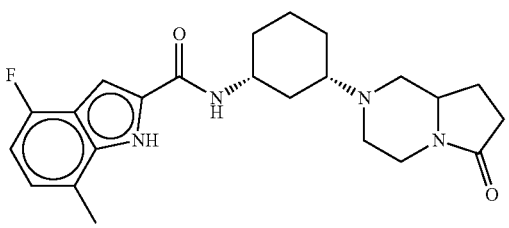 |
| 864 | 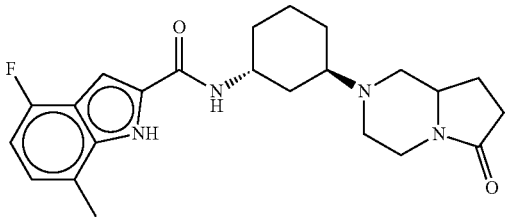 |
| 865 | 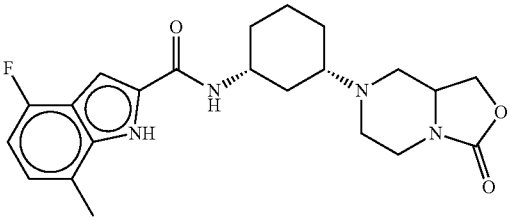 |
| 866 | 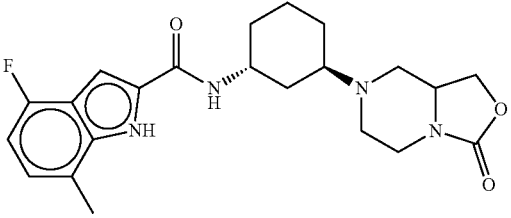 |

TABLE 1-continued
| Cpd. No. | Chemical Structure |
|---|---|
| 867 | 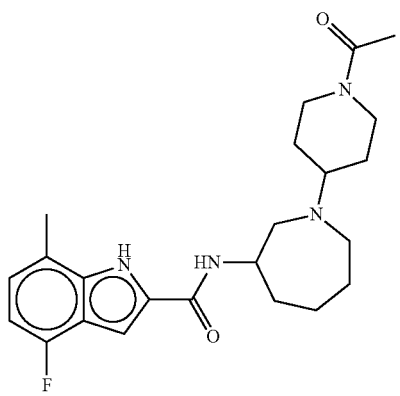 |
| 868 | 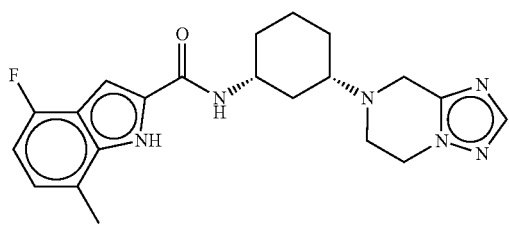 |
| 869 | 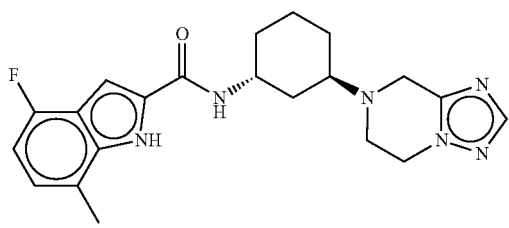 |
| 870 | 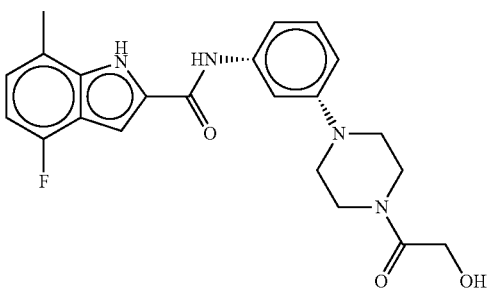 |
| 871 | 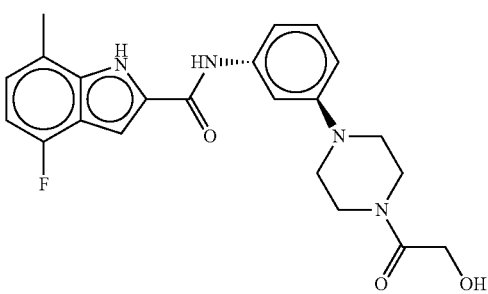 |

TABLE 1-continued
| Cpd. No. | Chemical Structure |
|---|---|
| 872 | 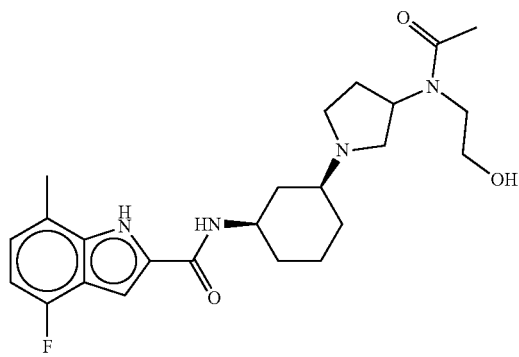 |
| 873 | 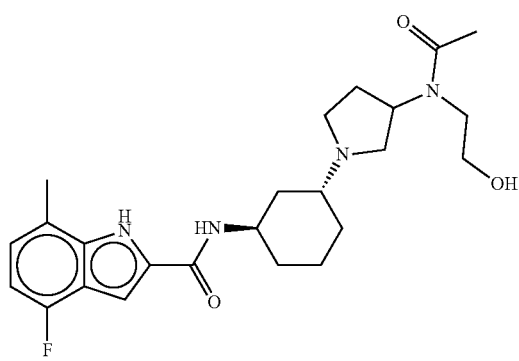 |
| 874 | 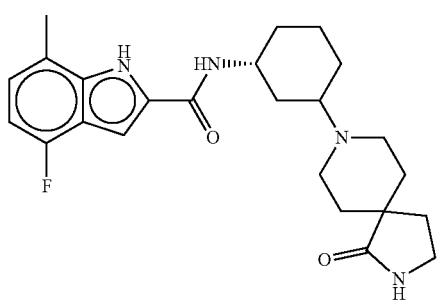 |
| 875 | 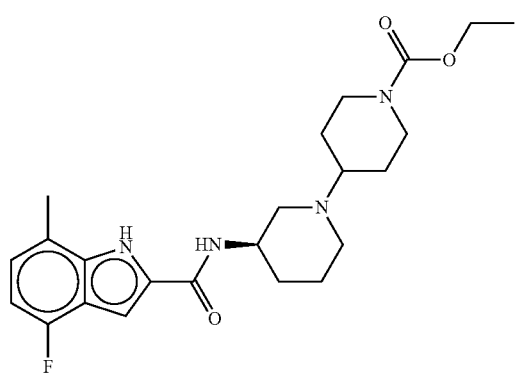 |

TABLE 1-continued

| Cpd. No. | Chemical Structure |
|---|---|
| 876 | 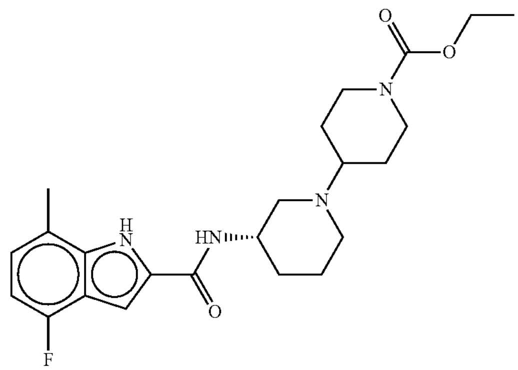 |
| 877 | 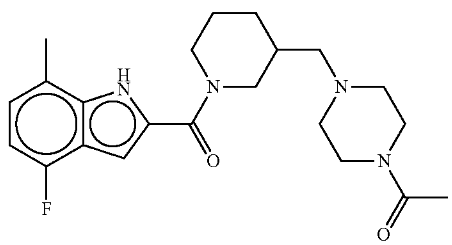 |
| 878 | 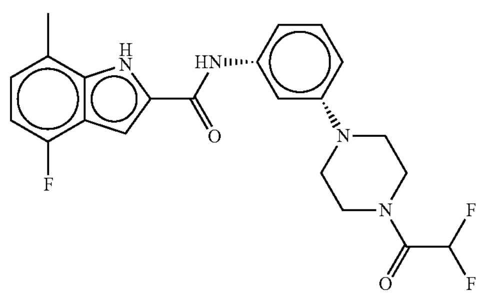 |
| 879 | 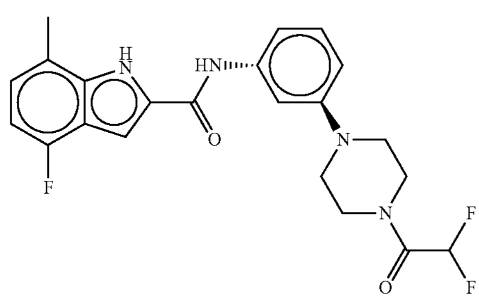 |
| 880 | 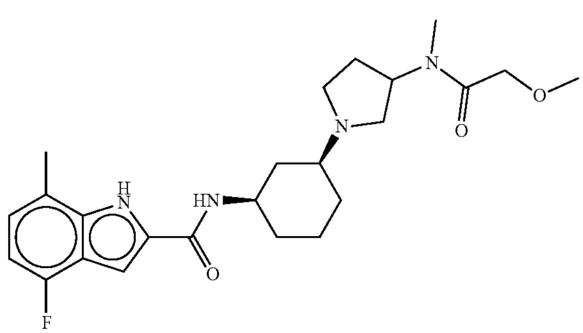 |

TABLE 1-continued
| Cpd. No. | Chemical Structure |
|---|---|
| 881 | 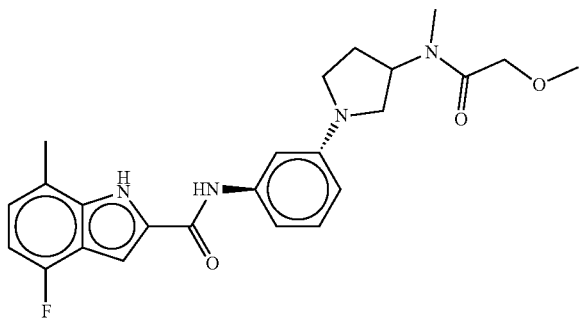 |
| 882 | 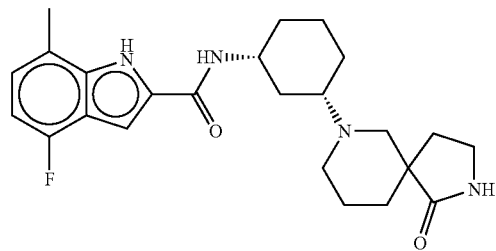 |
| 883 | 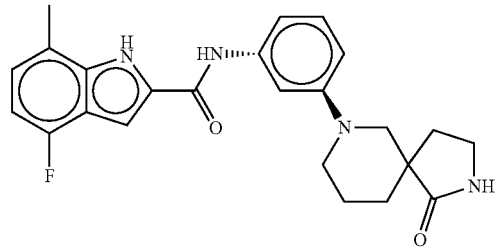 |
| 884 | 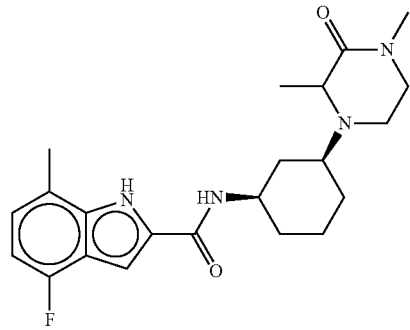 |
| 885 | 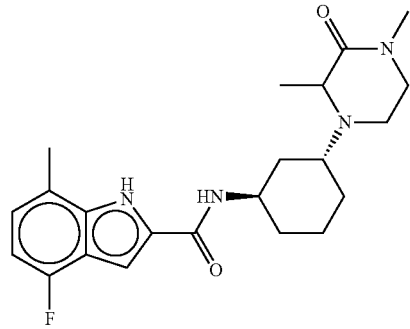 |

TABLE 1-continued
| Cpd. No. | Chemical Structure |
|---|---|
| 886 | 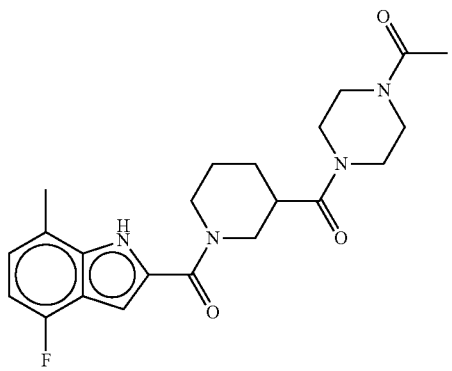 |
| 887 | 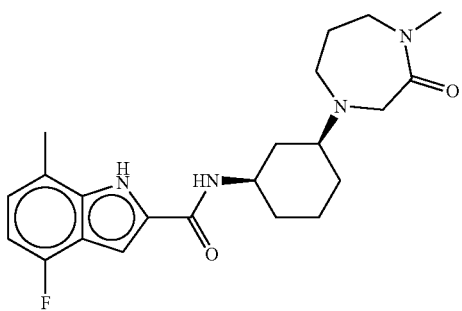 |
| 888 | 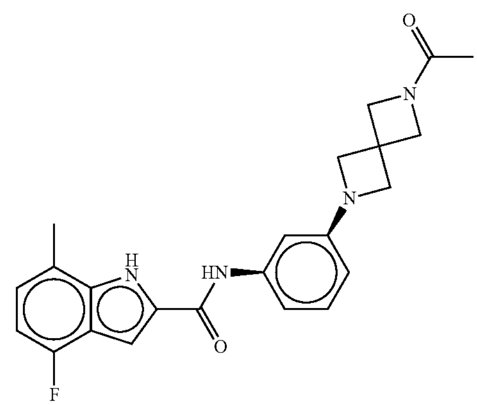 |
| 889 | 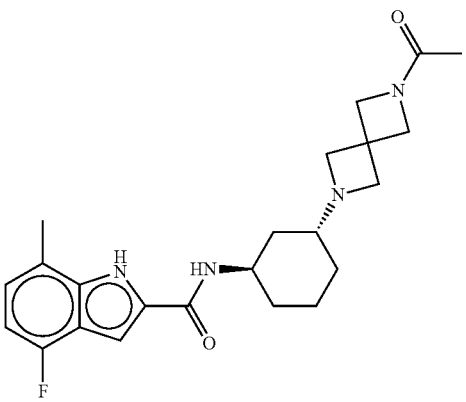 |

TABLE 1-continued
| Cpd. No. | Chemical Structure |
|---|---|
| 890 | 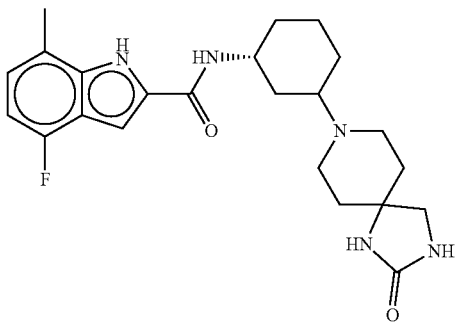 |
| 891 | 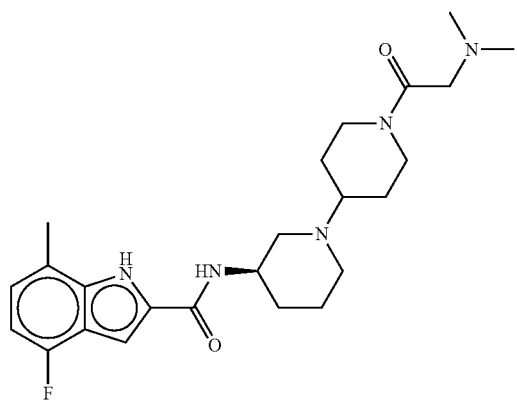 |
| 892 | 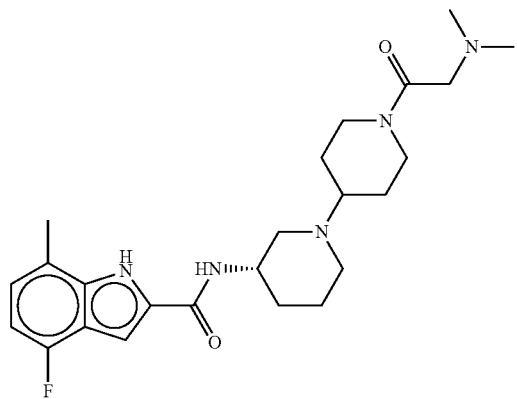 |
| 893 | 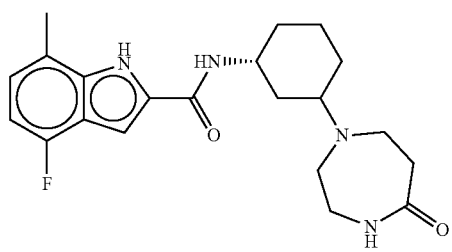 |

TABLE 1-continued
| Cpd. No. | Chemical Structure |
|---|---|
| 894 | 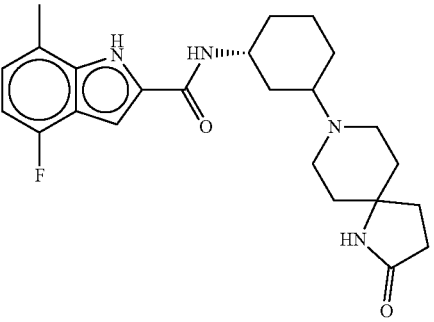 |
| 895 | 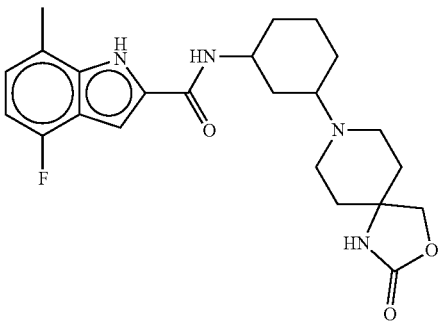 |
| 896 | 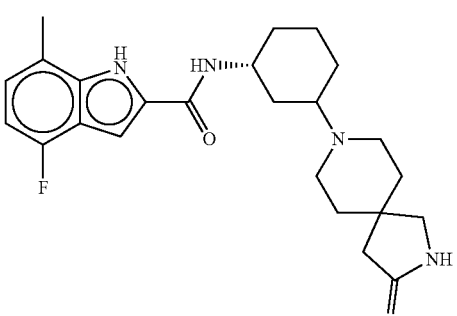 |
| 897 | 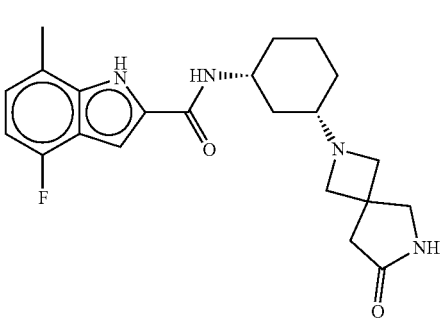 |
| 898 | 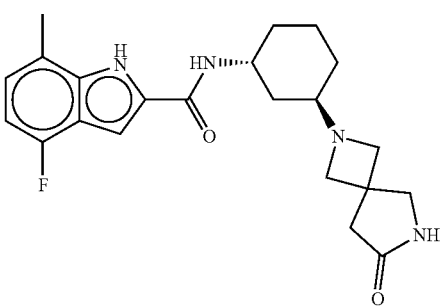 |

TABLE 1-continued
| Cpd. No. | Chemical Structure |
|---|---|
| 899 | 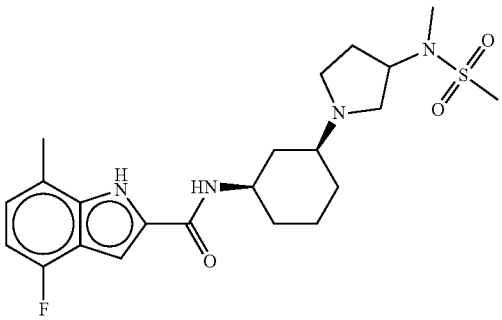 |
| 900 | 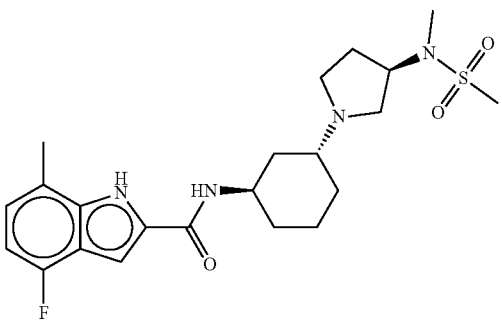 |
| 901 | 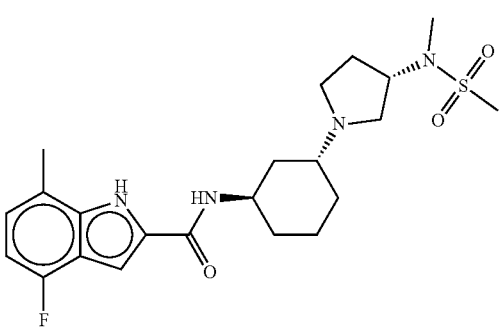 |
| 902 | 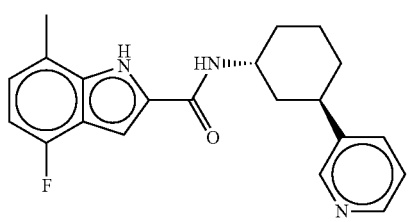 |
| 903 | 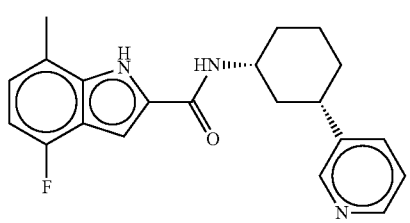 |

TABLE 1-continued
| Cpd. No. | Chemical Structure |
|---|---|
| 904 | 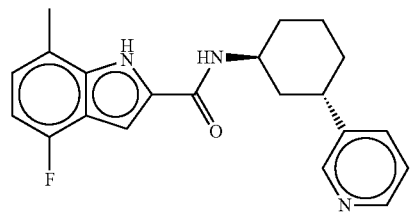 |
| 905 | 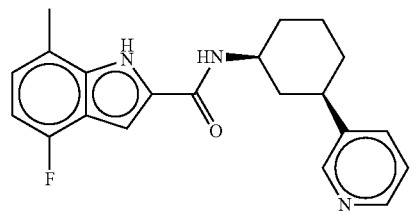 |
| 906 | 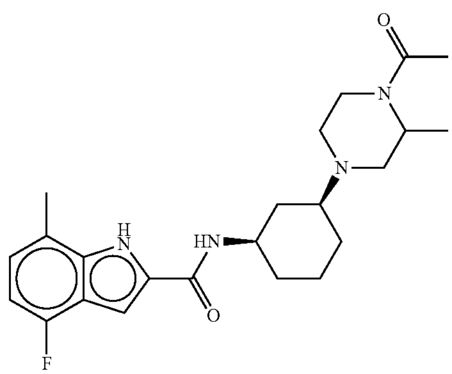 |
| 907 | 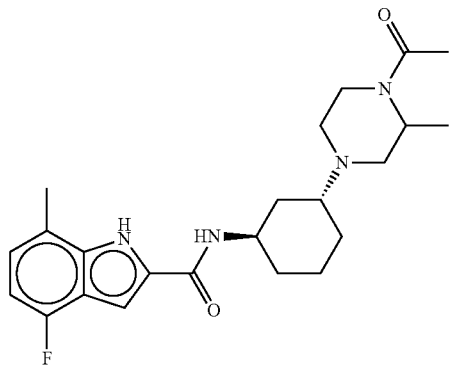 |
| 908 | 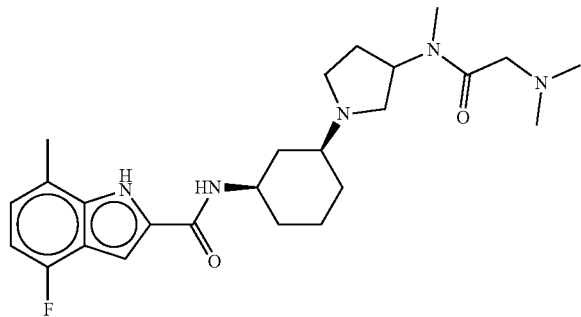 |

TABLE 1-continued
| Cpd. No. | Chemical Structure |
|---|---|
| 909 | 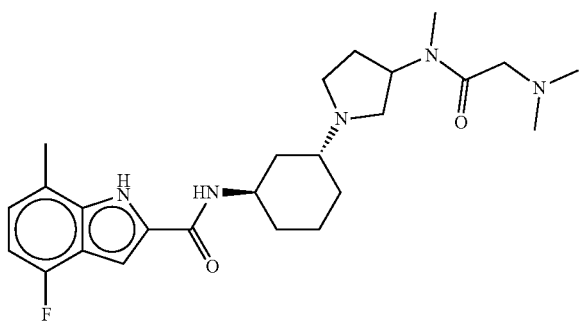 |
| 910 | 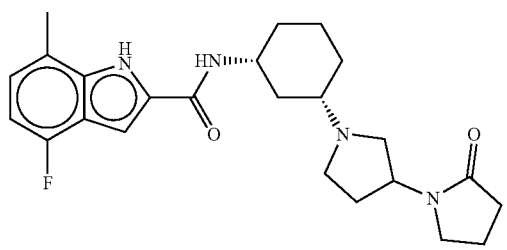 |
| 911 | 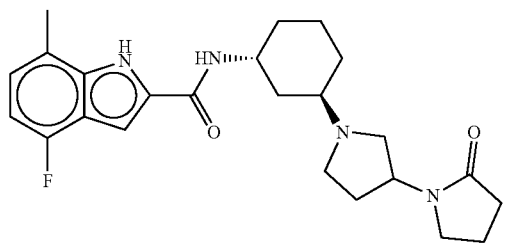 |
| 912 | 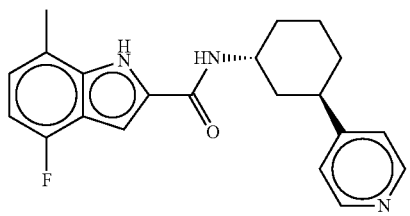 |
| 913 | 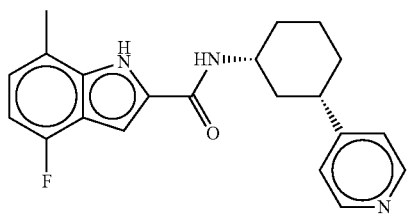 |
| 914 | 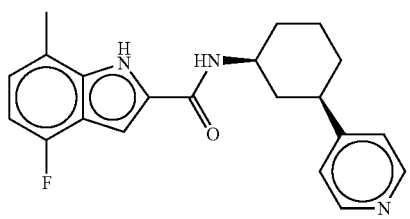 |

TABLE 1-continued
| Cpd. No. | Chemical Structure |
|---|---|
| 915 | 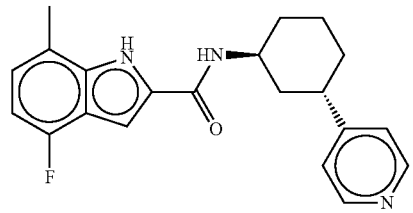 |
| 916 | 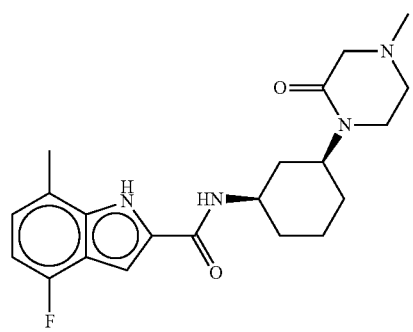 |
| 917 | 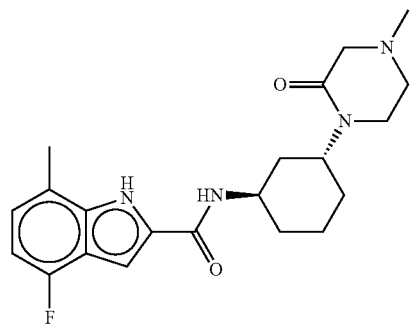 |
| 918 | 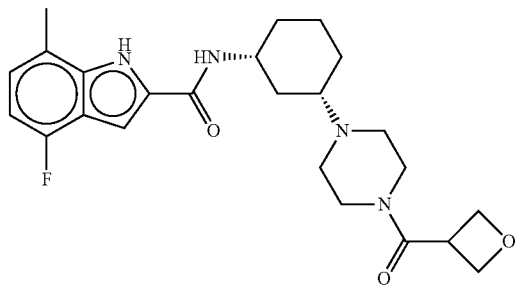 |
| 919 | 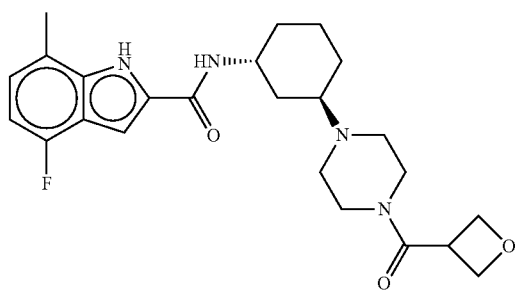 |

TABLE 1-continued

| Cpd. No. | Chemical Structure |
|---|---|
| 920 | 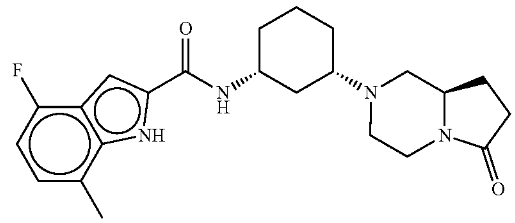 |
| 921 | 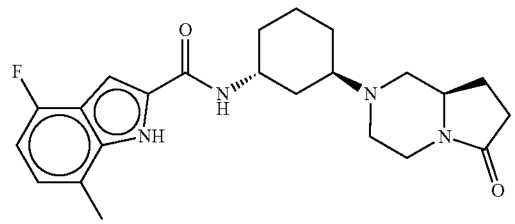 |
| 922 | 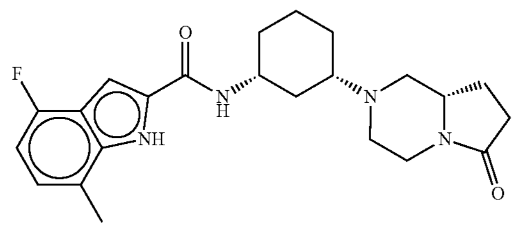 |
| 923 | 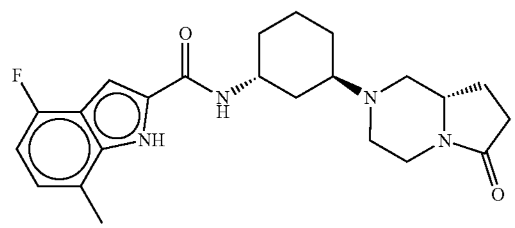 |
| 924 | 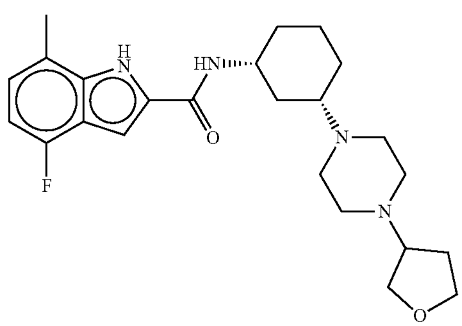 |
| 925 | 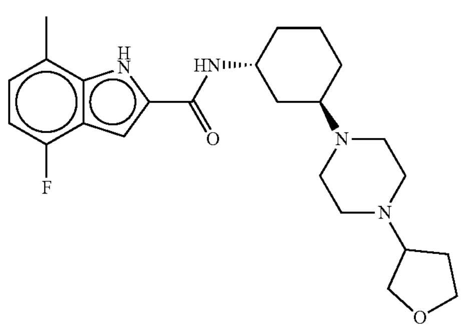 |

TABLE 1-continued
| Cpd. No. | Chemical Structure |
|---|---|
| 926 | 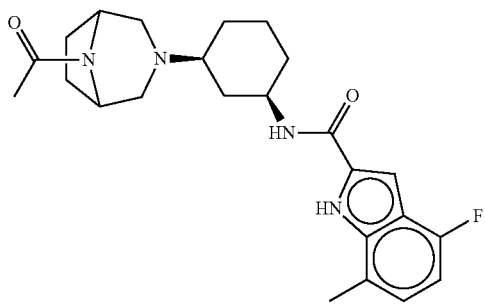 |
| 927 | 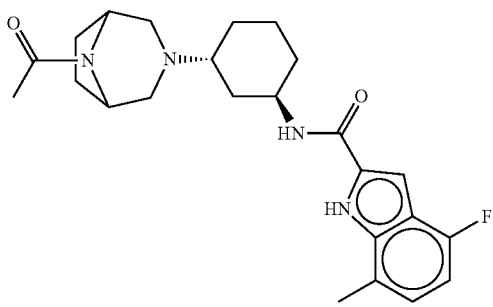 |
| 928 | 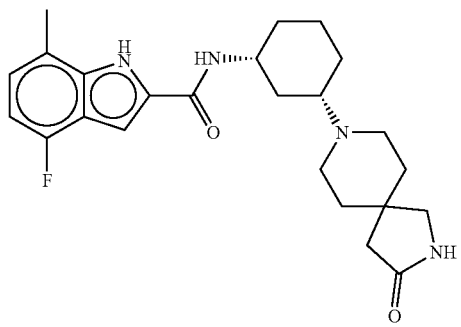 |
| 929 | 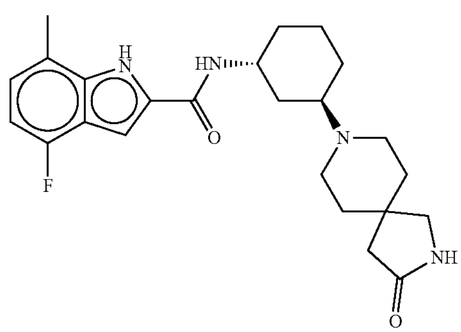 |

TABLE 1-continued

| Cpd. No. | Chemical Structure |
|---|---|
| 930 | 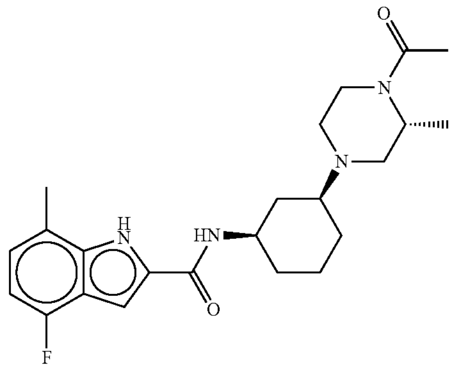 |
| 931 | 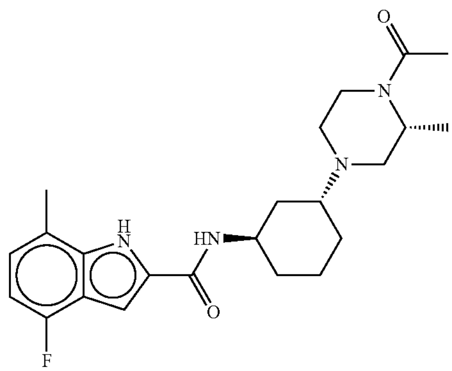 |
| 932 | 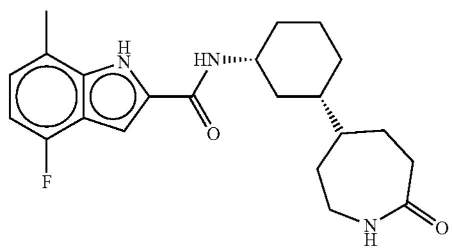 |
| 933 | 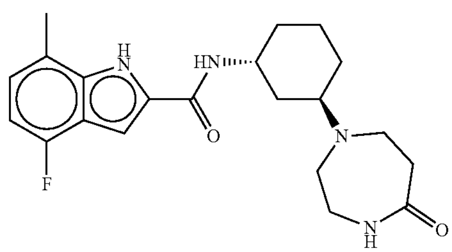 |
| 934 | 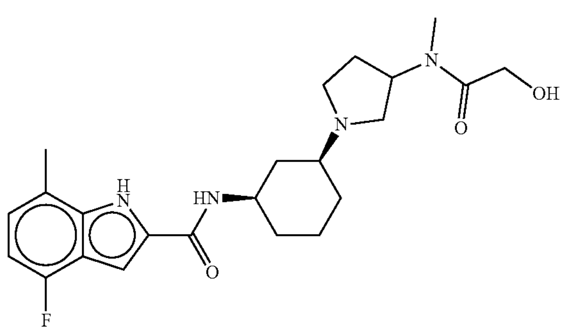 |

US 12,116,358 B2
409
410
TABLE 1-continued
| Cpd. No. | Chemical Structure |
|---|---|
| 935 | 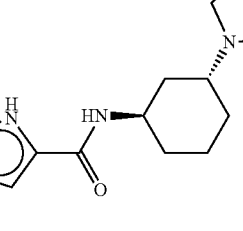 |
| 936 | 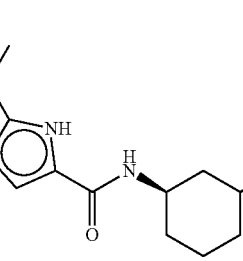 |
| 937 | 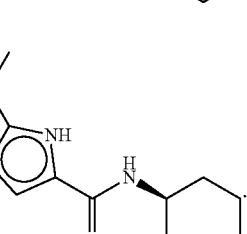 |
| 938 | 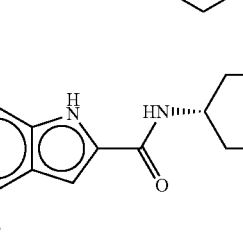 |
| 939 | 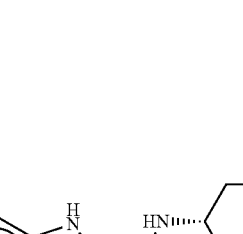 |

TABLE 1-continued
| Cpd. No. | Chemical Structure |
|---|---|
| 940 | 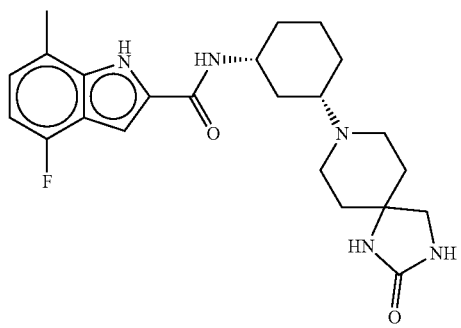 |
| 941 | 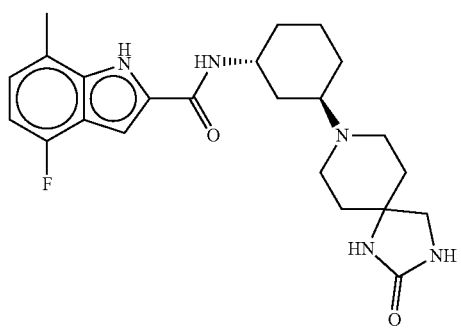 |
| 942 | 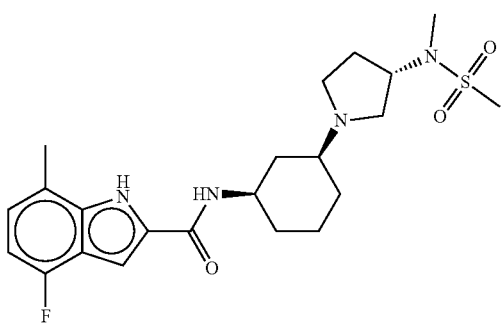 |
| 943 | 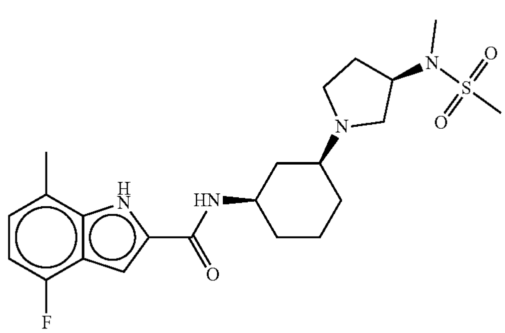 |

TABLE 1-continued
| Cpd. No. | Chemical Structure |
|---|---|
| 944 | 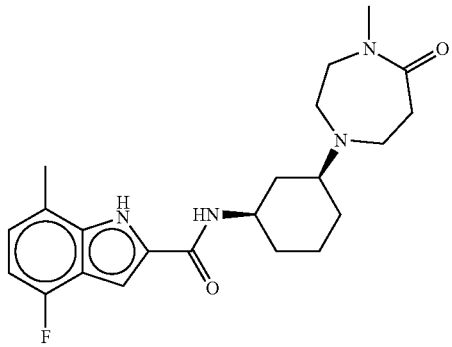 |
| 945 | 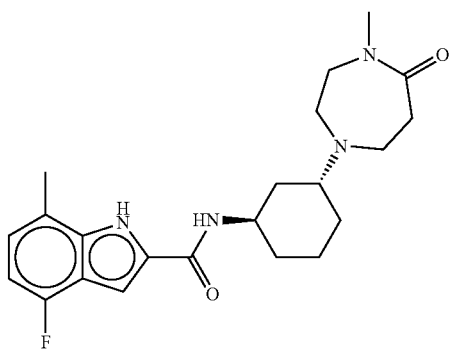 |
| 946 | 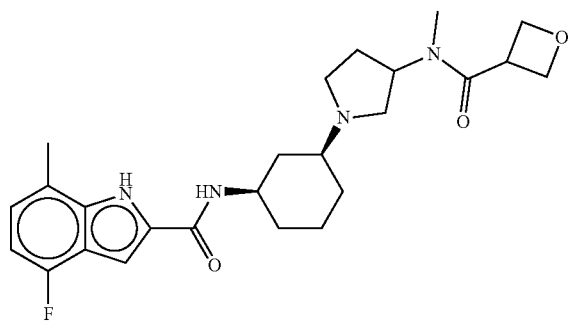 |
| 947 | 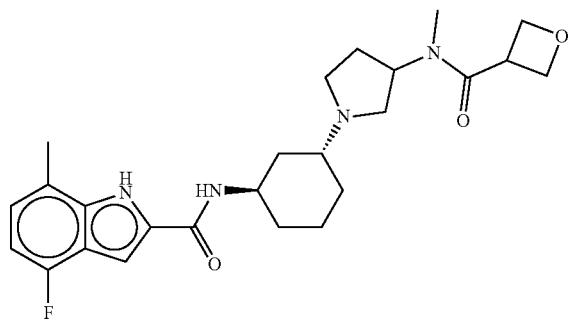 |

TABLE 1-continued
| Cpd. No. | Chemical Structure |
|---|---|
| 948 | 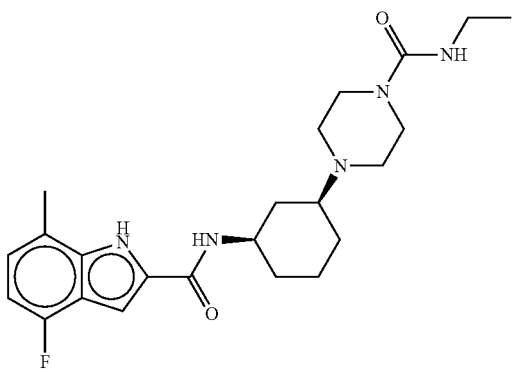 |
| 949 | 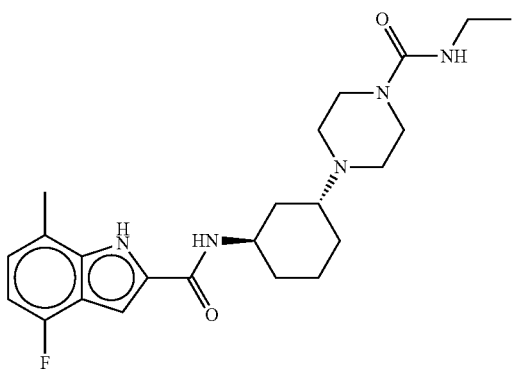 |
| 950 | 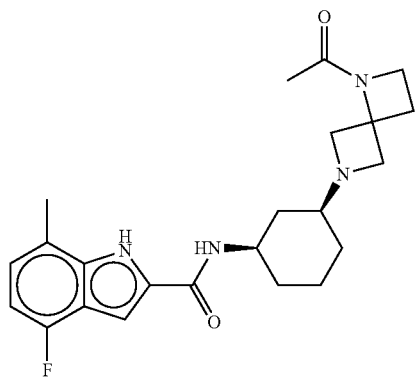 |
| 951 | 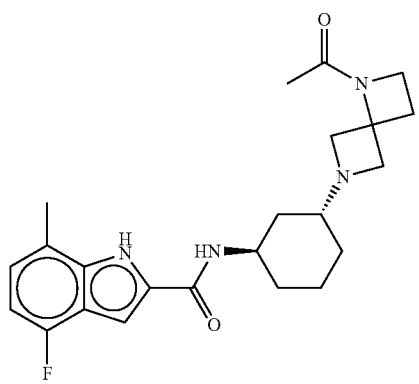 |

417
TABLE 1-continued
| Cpd. No. | Chemical Structure |
|---|---|
| 952 | 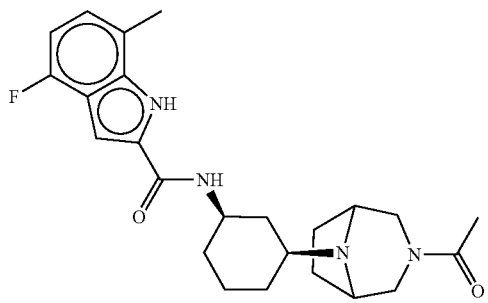 |
| 953 | 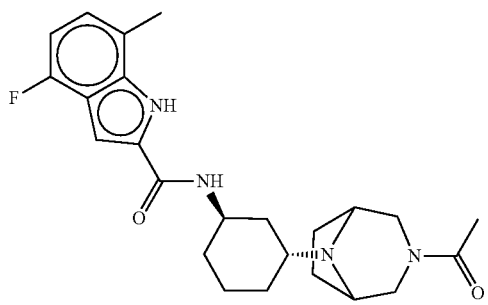 |
| 954 | 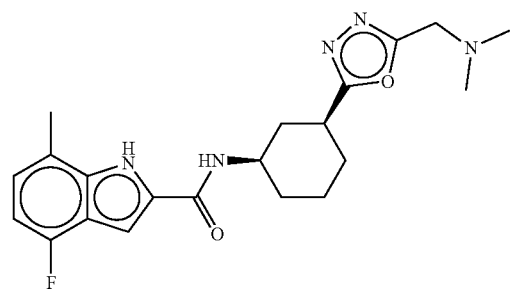 |
| 955 | 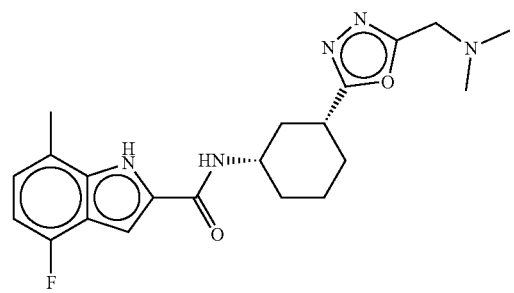 |
| 956 | 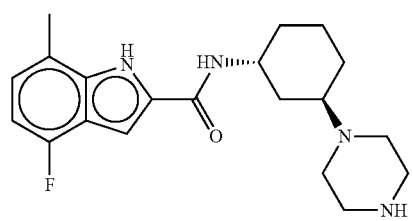 |

TABLE 1-continued
| Cpd. No. | Chemical Structure |
|---|---|
| 957 | 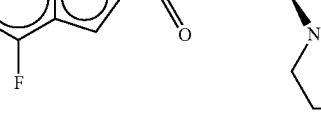 |
| 958 | 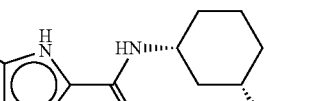 |
| 959 | 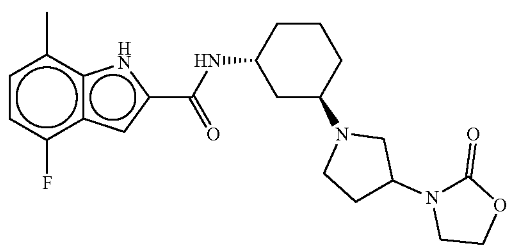 |
| 960 | 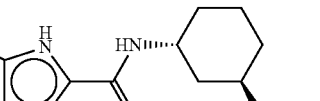 |
| 961 | 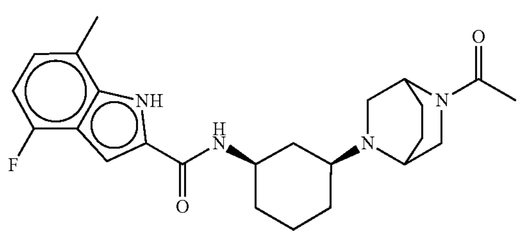 |
| 962 | 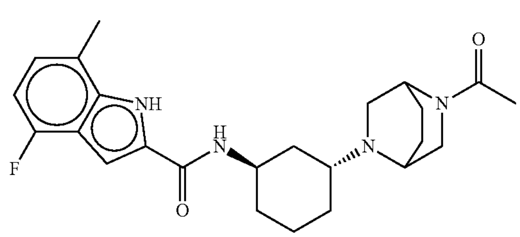 |

| Cpd. No. | Chemical Structure |
|---|---|
| 963 | 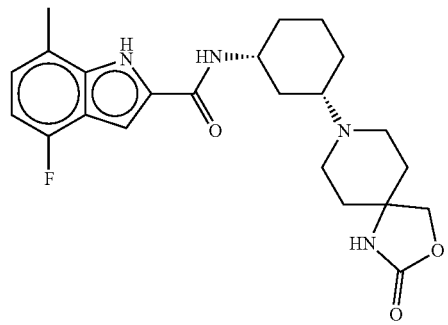 |
| 964 | 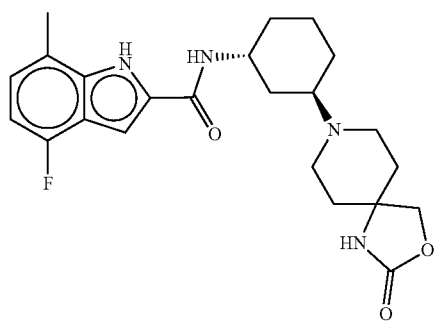 |
| 965 | 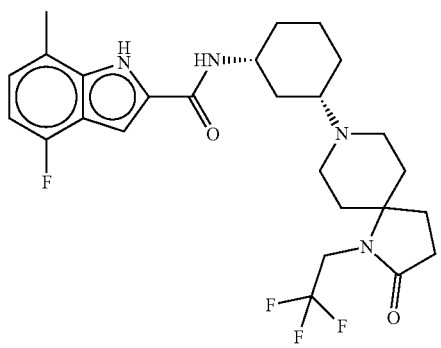 |
| 966 | 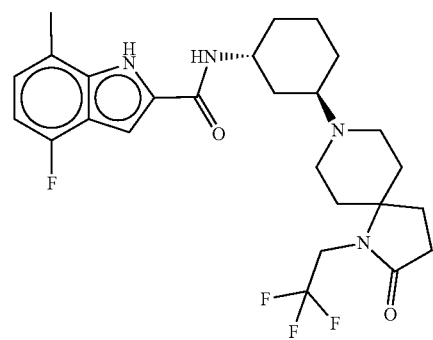 |

TABLE 1-continued
| Cpd. No. | Chemical Structure |
|---|---|
| 967 | 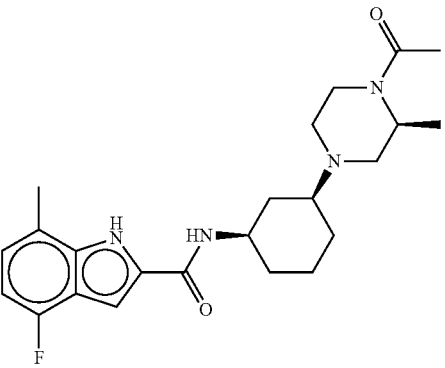 |
| 968 | 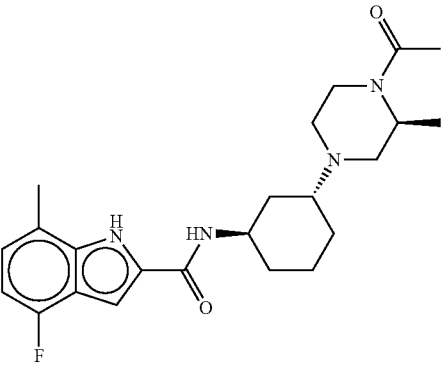 |
| 969 | 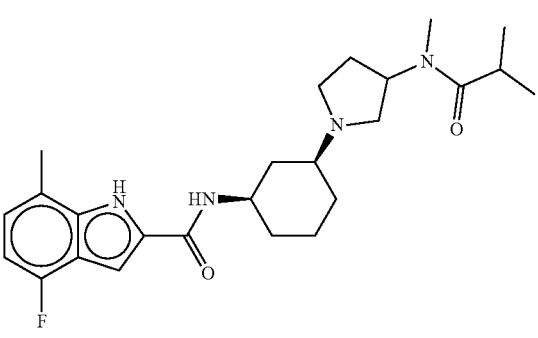 |
| 970 | 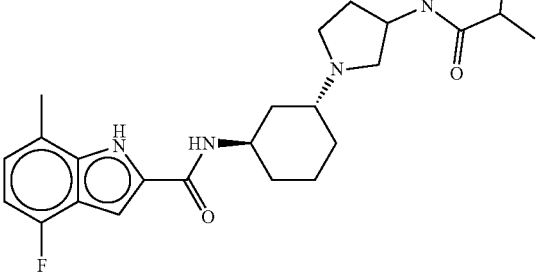 |

TABLE 1-continued
| Cpd. No. | Chemical Structure |
|---|---|
| 971 | 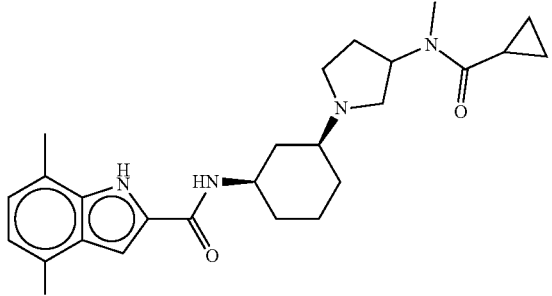 |
| 972 | 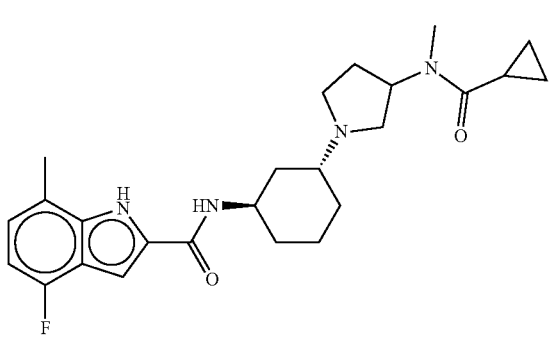 |
| 973 | 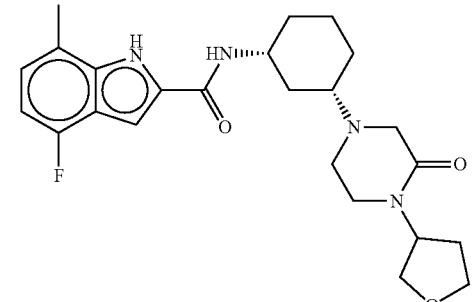 |
| 974 | 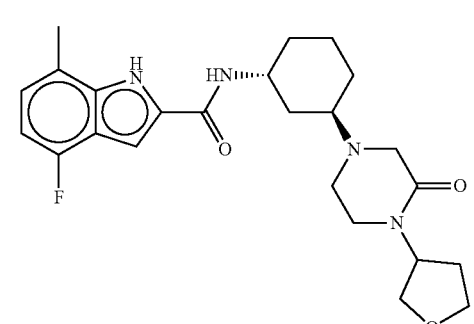 |
| 975 | 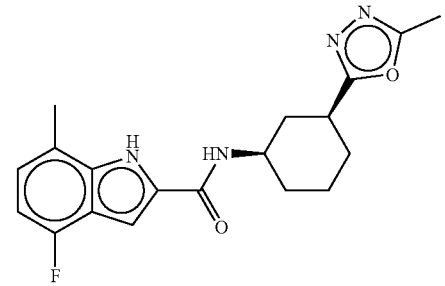 |

TABLE 1-continued
| Cpd. No. | Chemical Structure |
|---|---|
| 976 | 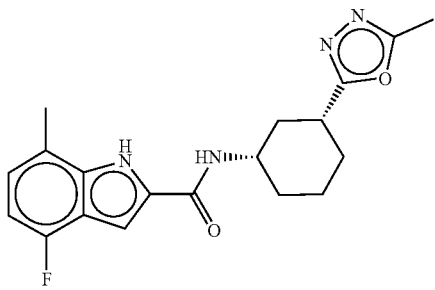 |
| 977 | 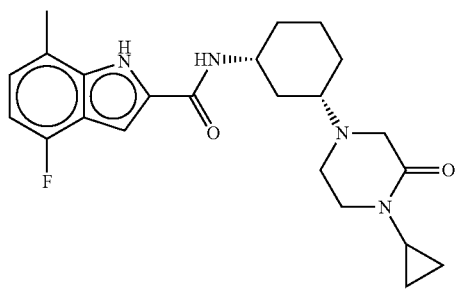 |
| 978 | 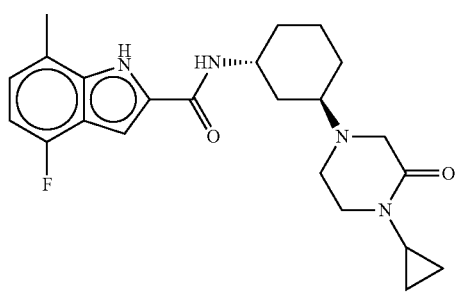 |
| 979 | 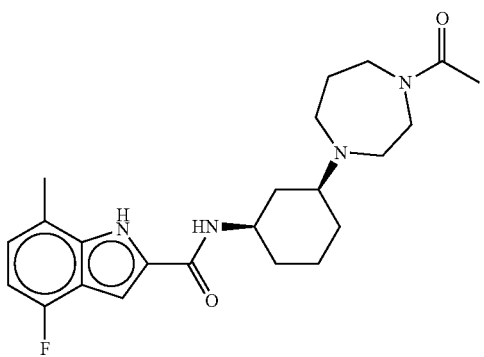 |

TABLE 1-continued

| Cpd. No. | Chemical Structure |
|---|---|
| 980 | 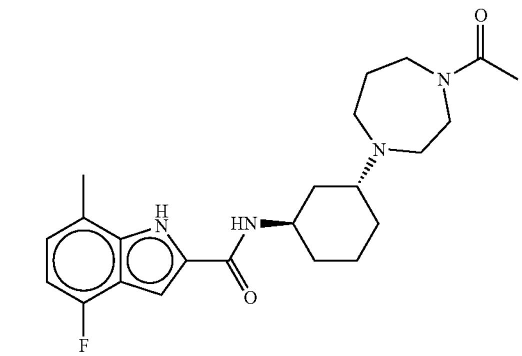 |
| 981 | 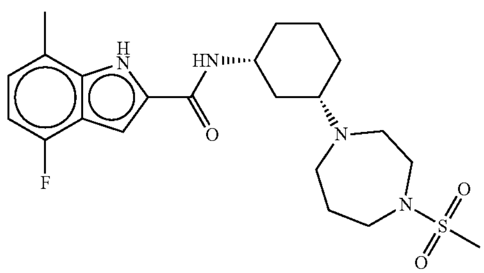 |
| 982 | 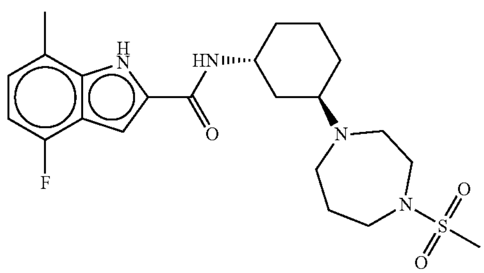 |
| 983 | 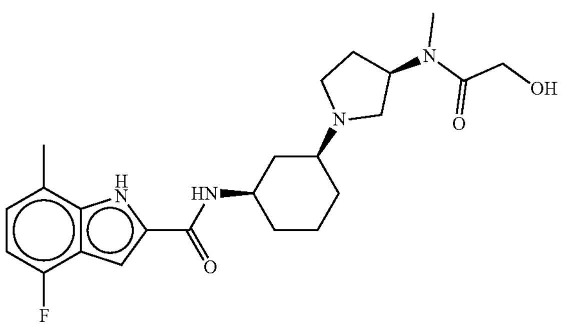 |
| 984 | 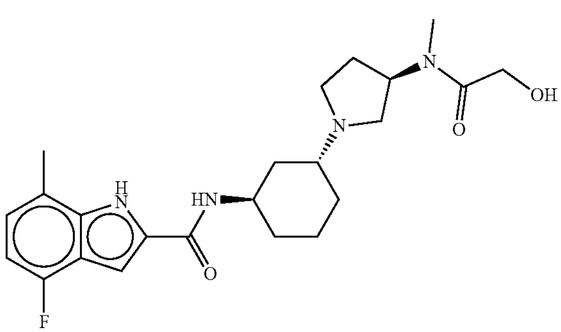 |

TABLE 1-continued

| Cpd. No. | Chemical Structure |
|---|---|
| 985 | 4-fluoro-7-methyl-1H-indole-2-carboxamide linked via NH to tetrahydropyran bearing 4-acetylpiperazinyl substituent |
| 986 | 4-fluoro-7-methyl-1H-indole-2-carboxamide linked via NH to tetrahydropyran bearing 4-acetylpiperazinyl substituent (stereoisomer) |
| 987 | 4-fluoro-7-methyl-1H-indole-2-carboxamide linked via NH to tetrahydropyran bearing 4-acetylpiperazinyl substituent (stereoisomer) |
| 988 | 4-fluoro-7-methyl-1H-indole-2-carboxamide linked via NH to tetrahydropyran bearing 4-acetylpiperazinyl substituent (stereoisomer) |

TABLE 1-continued
| Cpd. No. | Chemical Structure |
|---|---|
| 989 | 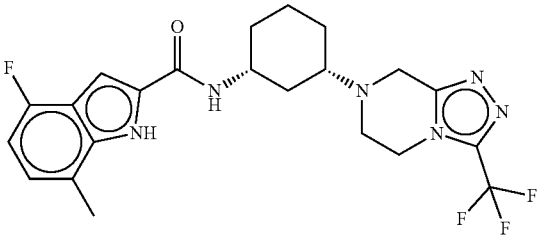 |
| 990 | 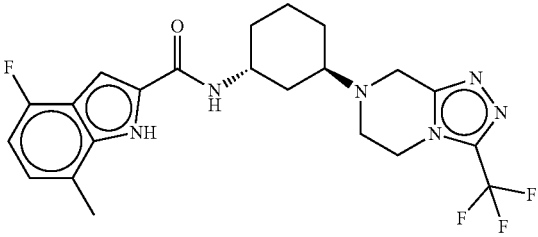 |
| 991 | 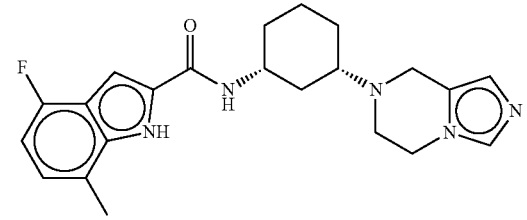 |
| 992 | 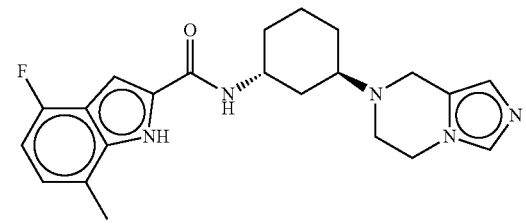 |
| 993 | 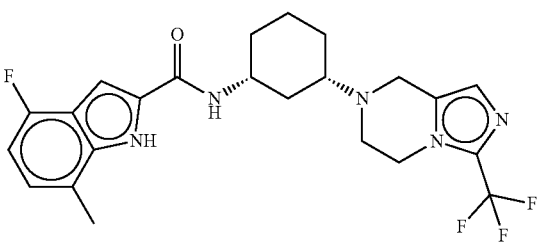 |
| 994 | 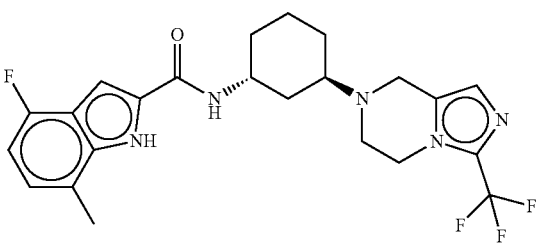 |

TABLE 1-continued
| Cpd. No. | Chemical Structure |
|---|---|
| 995 | 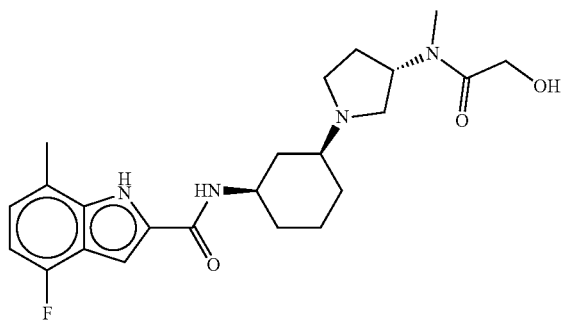 |
| 996 | 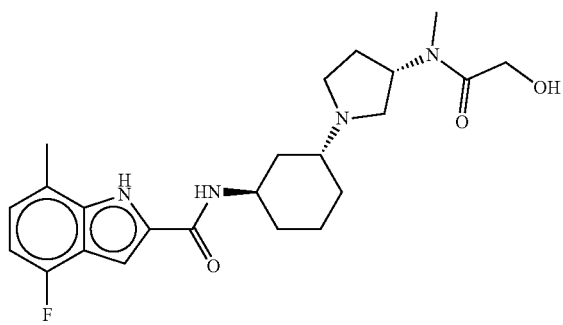 |
| 997 | 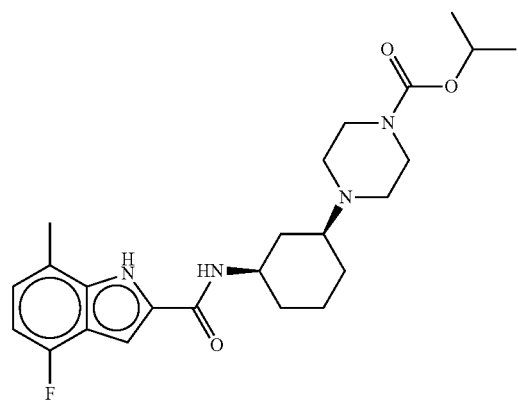 |
| 998 | 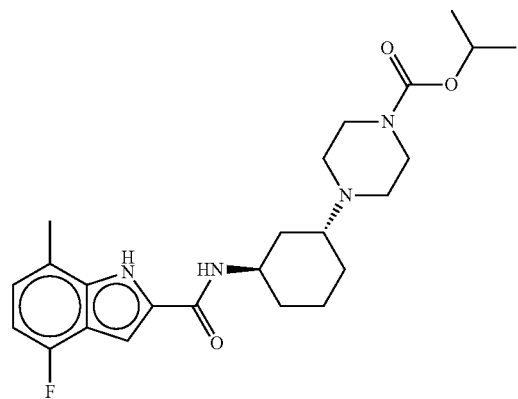 |

TABLE 1-continued
| Cpd. No. | Chemical Structure |
|---|---|
| 999 | 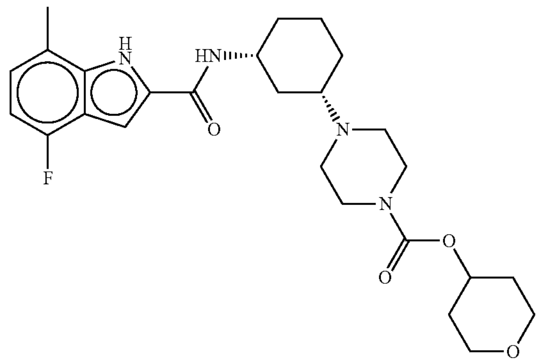 |
| 1000 | 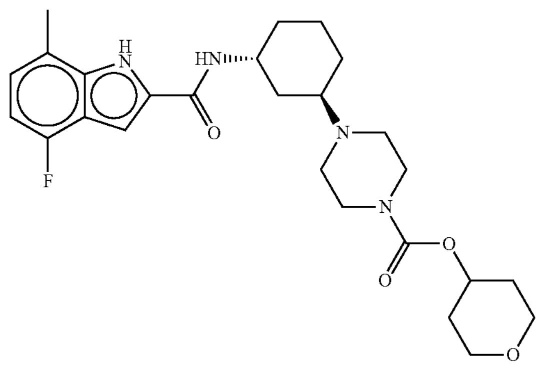 |
| 1002 | 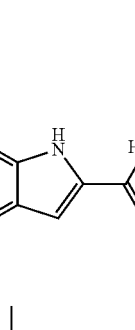 |
| 1003 | 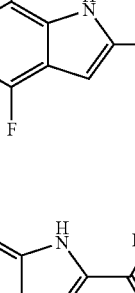 |
| 1004 | 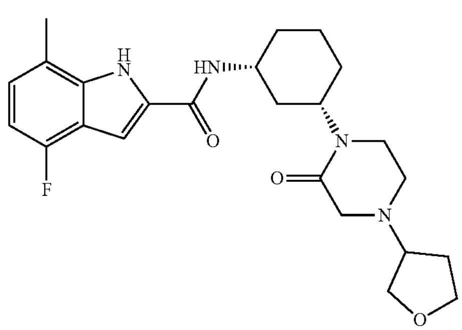 [SMILES: Cc1ccc(F)c2cc(C(=O)N[C@@H]3CCC[C@H](N4CCN(C5CCOC5)CC4=O)C3)[nH]c12] |

TABLE 1-continued
| Cpd. No. | Chemical Structure |
|---|---|
| 1005 | 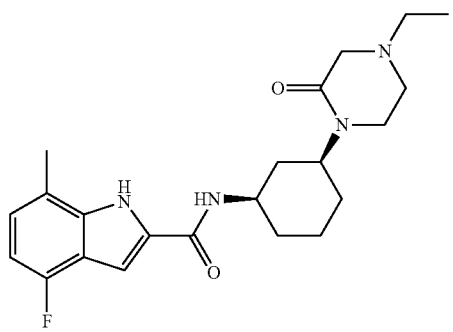 [SMILES: CCN1CCN([C@H]2CCC[C@@H](NC(=O)c3cc4c(F)ccc(C)c4[nH]3)C2)C(=O)C1] |
| 1006 | 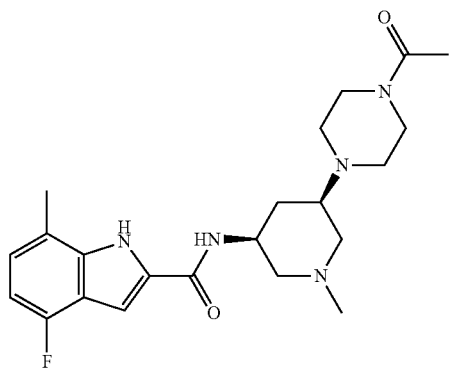 [SMILES: CC(=O)N1CCN([C@@H]2C[C@H](NC(=O)c3cc4c(F)ccc(C)c4[nH]3)CN(C)C2)CC1] |
| 1007 | 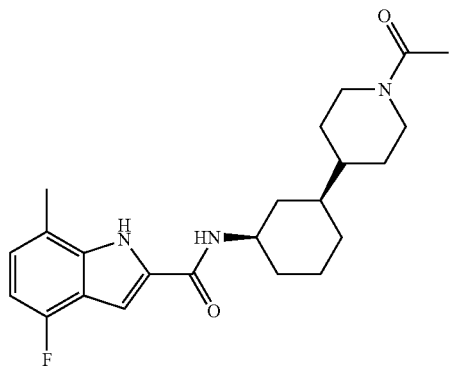 [SMILES: CC(=O)N1CCC([C@H]2CCC[C@@H](NC(=O)c3cc4c(F)ccc(C)c4[nH]3)C2)CC1] |
| 1008 | 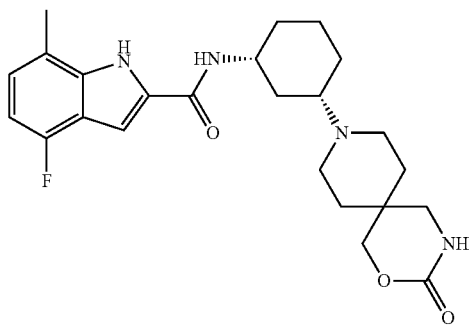 [SMILES: Cc1ccc(F)c2cc(C(=O)N[C@@H]3CCC[C@H](N4CCC5(CC4)CNC(=O)OC5)C3)[nH]c12] |

TABLE 1-continued

| Cpd. No. | Chemical Structure |
|---|---|
| 1009 | 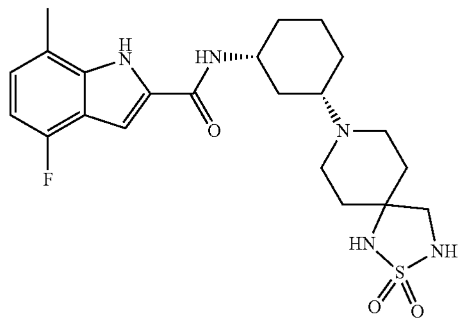 [SMILES: Cc1ccc(F)c2cc(C(=O)N[C@@H]3CCC[C@H](N4CCC5(CC4)CNS(=O)(=O)N5)C3)[nH]c12] |
| 1010 | 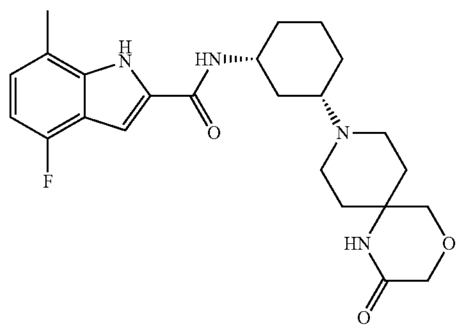 [SMILES: Cc1ccc(F)c2cc(C(=O)N[C@@H]3CCC[C@H](N4CCC5(CC4)COCC(=O)N5)C3)[nH]c12] |
| 1011 | 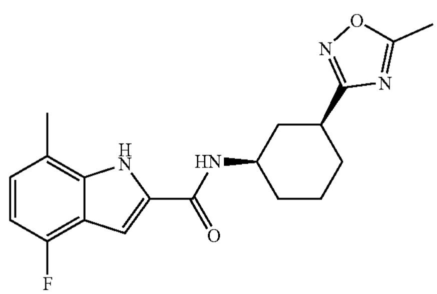 [SMILES: Cc1nc([C@H]2CCC[C@@H](NC(=O)c3cc4c(F)ccc(C)c4[nH]3)C2)no1] |
| 1012 | 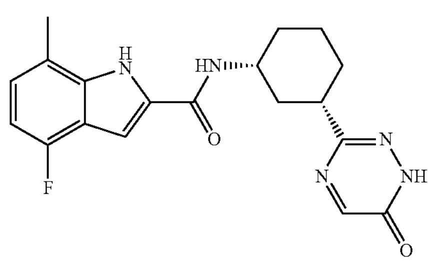 [SMILES: Cc1ccc(F)c2cc(C(=O)N[C@@H]3CCC[C@H](c4ncc(=O)[nH]n4)C3)[nH]c12] |
| 1013 | 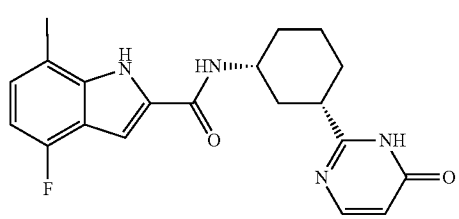 [SMILES: Cc1ccc(F)c2cc(C(=O)N[C@@H]3CCC[C@H](c4nccc(=O)[nH]4)C3)[nH]c12] |

TABLE 1-continued
| Cpd. No. | Chemical Structure |
|---|---|
| 1014 | 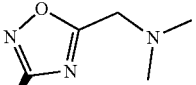 |
| 1015 | 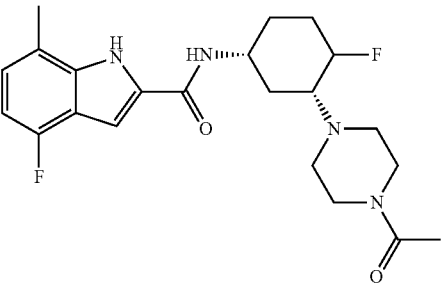 [SMILES: CC(=O)N1CCN([C@@H]2C[C@H](NC(=O)c3cc4c(F)ccc(C)c4[nH]3)CCC2F)CC1] |
| 1016 | 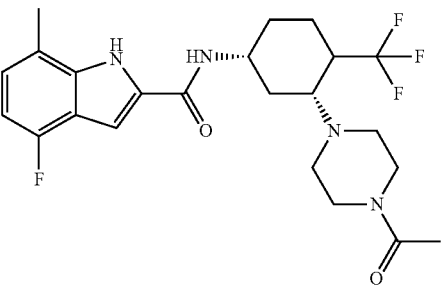 [SMILES: CC(=O)N1CCN([C@@H]2C[C@H](NC(=O)c3cc4c(F)ccc(C)c4[nH]3)CCC2C(F)(F)F)CC1] |
| 1017 | 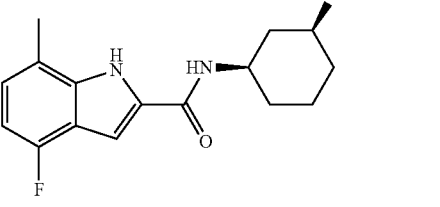 |

TABLE 1-continued

| Cpd. No. | Chemical Structure |
|---|---|
| 1018 | 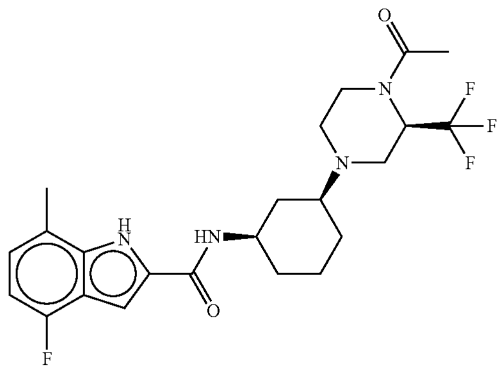 |
| 1020 | 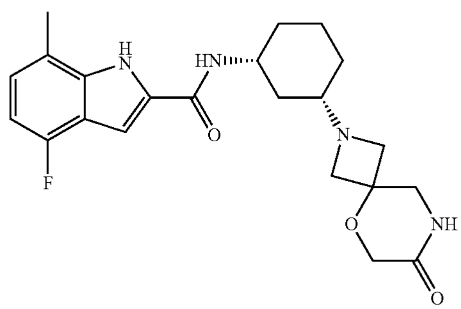 [SMILES: Cc1ccc(F)c2cc(C(=O)N[C@@H]3CCC[C@H](N4CC5(CNC(=O)CO5)C4)C3)[nH]c12] |
| 1021 | 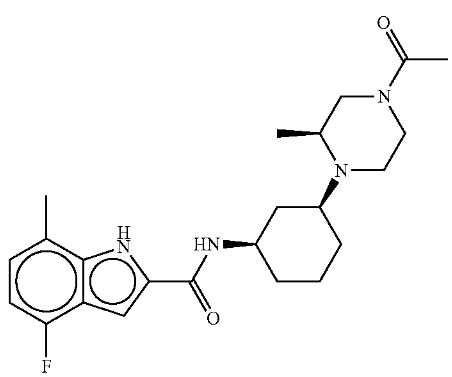 |
| 1022 | 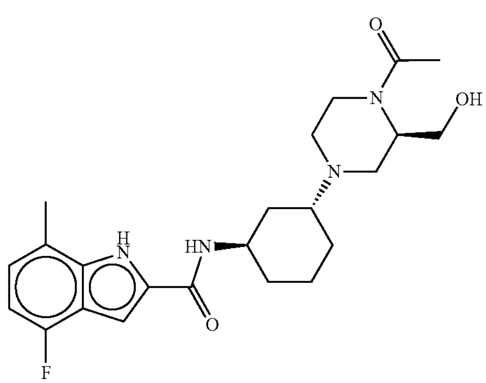 |

TABLE 1-continued
| Cpd. No. | Chemical Structure |
|---|---|
| 1023 | 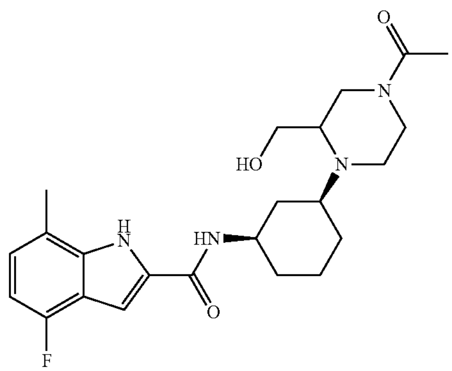 [SMILES: CC(=O)N1CCN([C@H]2CCC[C@@H](NC(=O)c3cc4c(F)ccc(C)c4[nH]3)C2)C(CO)C1] |
| 1024 | 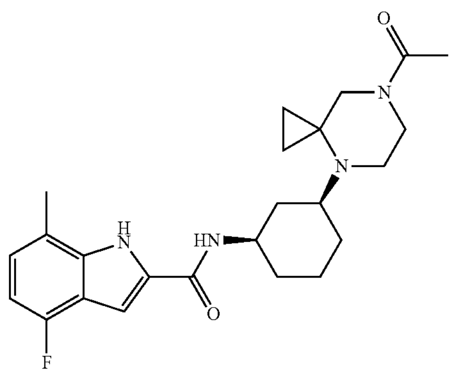 [SMILES: CC(=O)N1CCN([C@H]2CCC[C@@H](NC(=O)c3cc4c(F)ccc(C)c4[nH]3)C2)C2(CC2)C1] |
| 1025 | 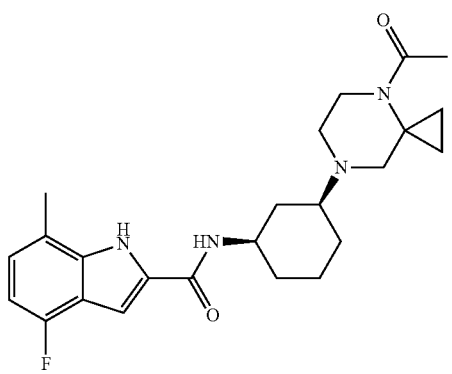 [SMILES: CC(=O)N1CCN([C@H]2CCC[C@@H](NC(=O)c3cc4c(F)ccc(C)c4[nH]3)C2)CC12CC2] |
| 1026 | 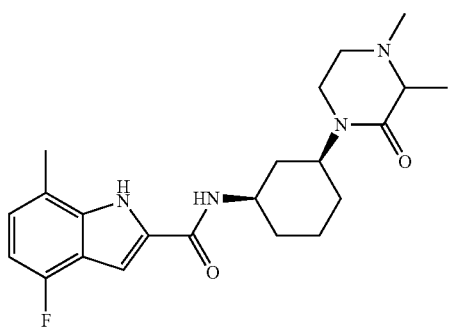 [SMILES: Cc1ccc(F)c2cc(C(=O)N[C@@H]3CCC[C@H](N4CCN(C)C(C)C4=O)C3)[nH]c12] |

TABLE 1-continued

| Cpd. No. | Chemical Structure |
|---|---|
| 1027 | 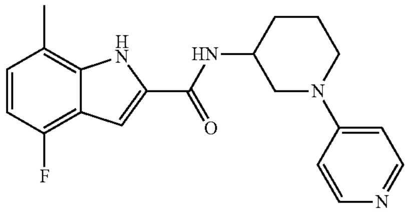 [SMILES: Cc1ccc(F)c2cc(C(=O)NC3CCCN(c4ccncc4)C3)[nH]c12] |
| 1031 | 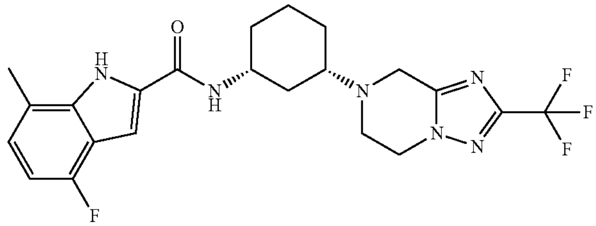 [SMILES: Cc1ccc(F)c2cc(C(=O)N[C@@H]3CCC[C@H](N4CCn5nc(C(F)(F)F)nc5C4)C3)[nH]c12] |
| 1032 | 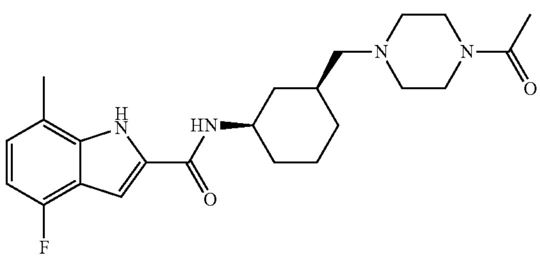 [SMILES: CC(=O)N1CCN(C[C@H]2CCC[C@@H](NC(=O)c3cc4c(F)ccc(C)c4[nH]3)C2)CC1] |
| 1035 | 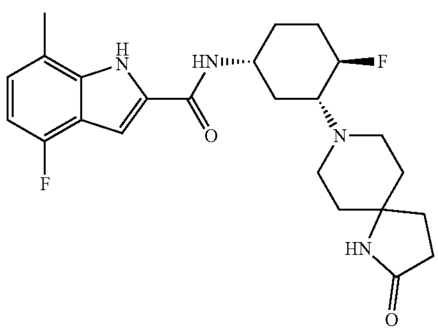 [SMILES: Cc1ccc(F)c2cc(C(=O)N[C@@H]3CC[C@@H](F)[C@H](N4CCC5(CCC(=O)N5)CC4)C3)[nH]c12] |
| 1036 | 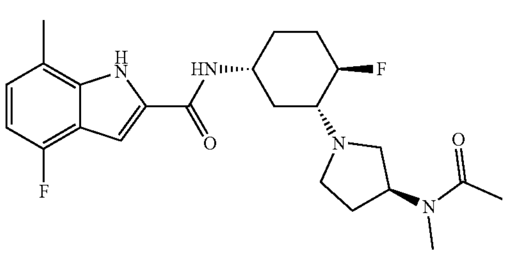 [SMILES: CC(=O)N(C)[C@H]1CCN([C@@H]2C[C@H](NC(=O)c3cc4c(F)ccc(C)c4[nH]3)CC[C@H]2F)C1] |

TABLE 1-continued
| Cpd. No. | Chemical Structure |
|---|---|
| 1037 | 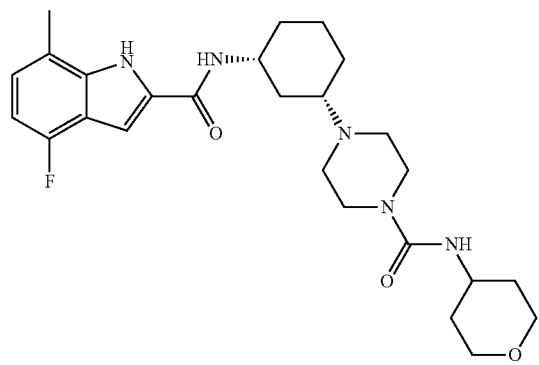 [SMILES: Cc1ccc(F)c2cc(C(=O)N[C@@H]3CCC[C@H](N4CCN(C(=O)NC5CCOCC5)CC4)C3)[nH]c12] |
| 1038 | 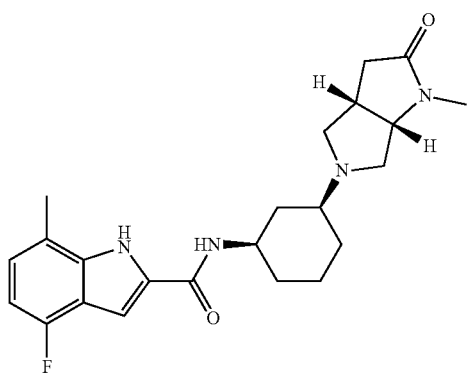 [SMILES: Cc1ccc(F)c2cc(C(=O)N[C@@H]3CCC[C@H](N4C[C@@H]5CC(=O)N(C)[C@@H]5C4)C3)[nH]c12] |
| 1039 | 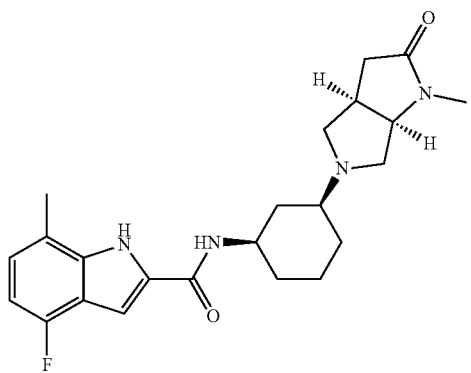 [SMILES: Cc1ccc(F)c2cc(C(=O)N[C@@H]3CCC[C@H](N4C[C@H]5CC(=O)N(C)[C@H]5C4)C3)[nH]c12] |
| 1040 | 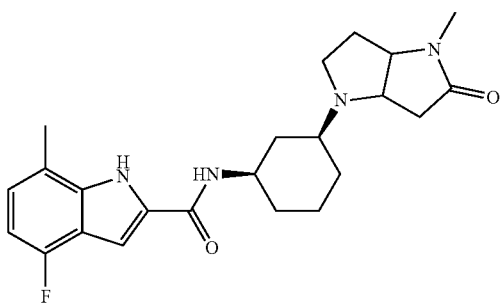 [SMILES: Cc1ccc(F)c2cc(C(=O)N[C@@H]3CCC[C@H](N4CCC5C4CC(=O)N5C)C3)[nH]c12] |

TABLE 1-continued
| Cpd. No. | Chemical Structure |
|---|---|
| 1042 | 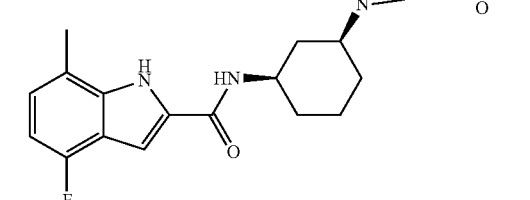 |
| 1043 | 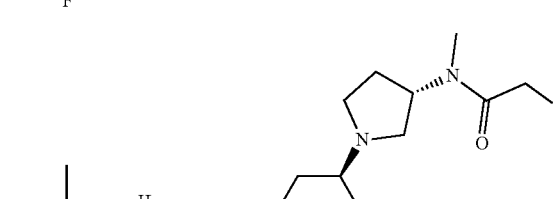 |
| 1044 | 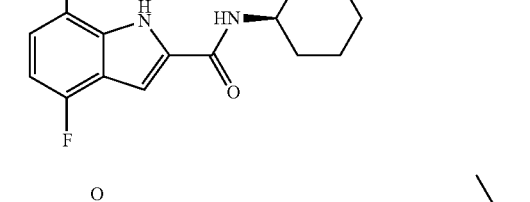 |
| 1045 | 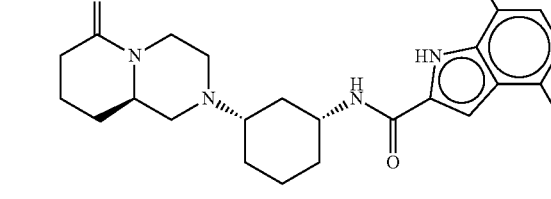 |
| 1046 | 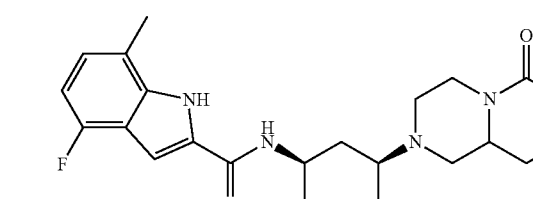 |
| 1047 | 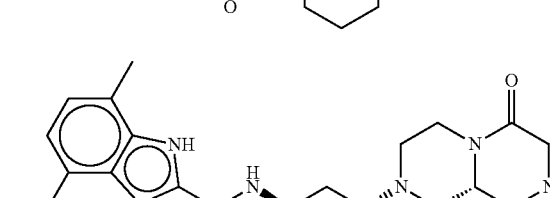 |

TABLE 1-continued
| Cpd. No. | Chemical Structure |
|---|---|
| 1048 | 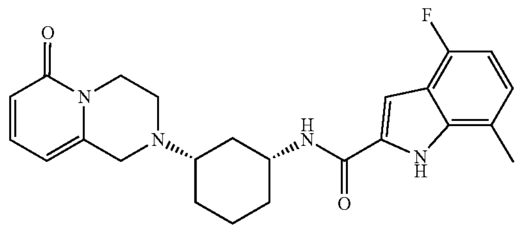 [SMILES: Cc1ccc(F)c2cc(C(=O)N[C@@H]3CCC[C@H](N4CCn5c(cccc5=O)C4)C3)[nH]c12] |
| 1049 | 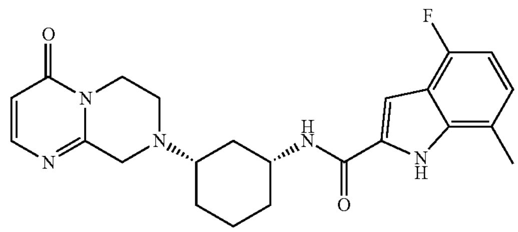 [SMILES: Cc1ccc(F)c2cc(C(=O)N[C@@H]3CCC[C@H](N4CCn5c(nccc5=O)C4)C3)[nH]c12] |
| 1050 | 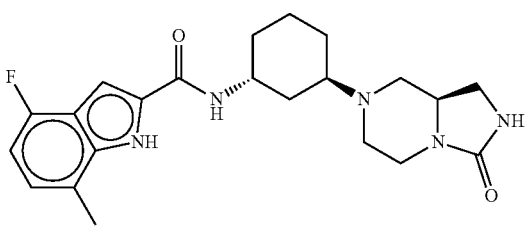 |
| 1051 | 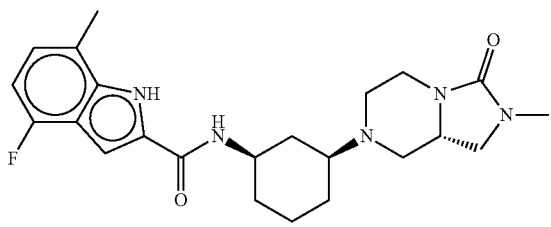 |
| 1052 | 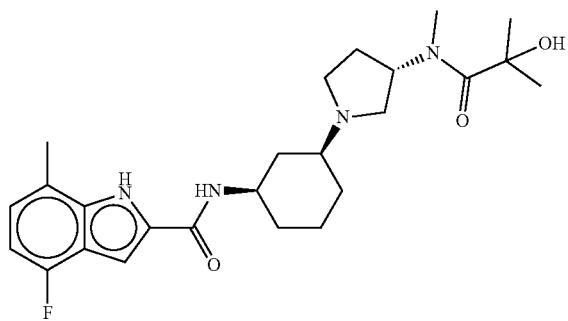 |

TABLE 1-continued

| Cpd. No. | Chemical Structure |
|---|---|
| 1053 | 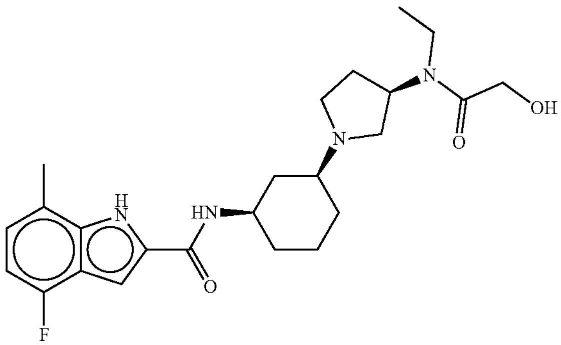 |
| 1054 | 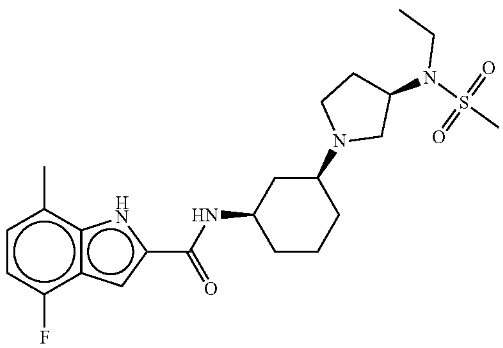 |
| 1055 | 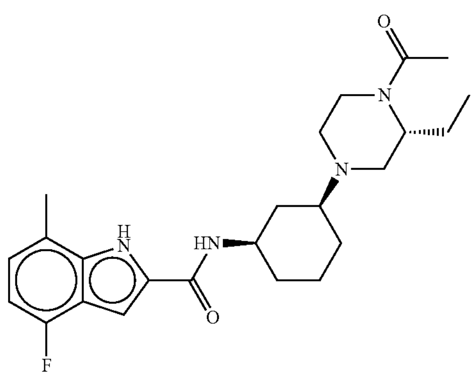 |
| 1056 | 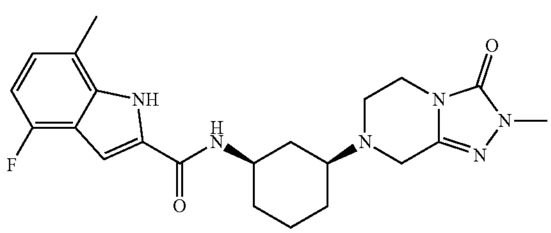 [SMILES: Cc1ccc(F)c2cc(C(=O)N[C@@H]3CCC[C@H](N4CCn5c(nn(C)c5=O)C4)C3)[nH]c12] |
| 1057 | 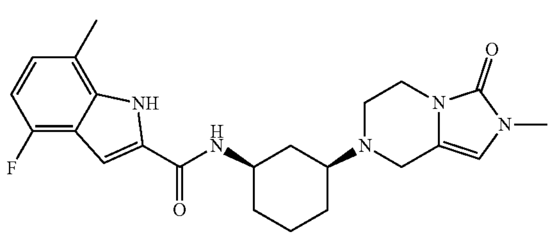 [SMILES: Cc1ccc(F)c2cc(C(=O)N[C@@H]3CCC[C@H](N4CCn5c(cn(C)c5=O)C4)C3)[nH]c12] |

TABLE 1-continued

| Cpd. No. | Chemical Structure |
|---|---|
| 1058 | 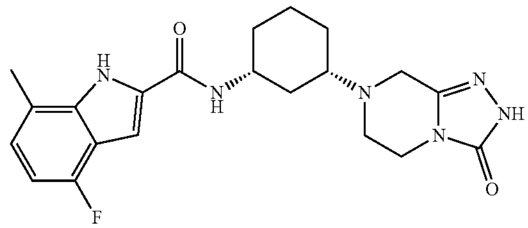 |
| 1059 | 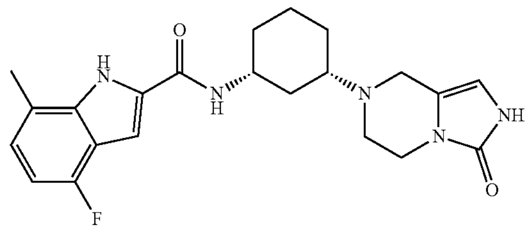 [SMILES: Cc1ccc(F)c2cc(C(=O)N[C@@H]3CCC[C@H](N4CCn5c(c[nH]c5=O)C4)C3)[nH]c12] |
| 1060 | 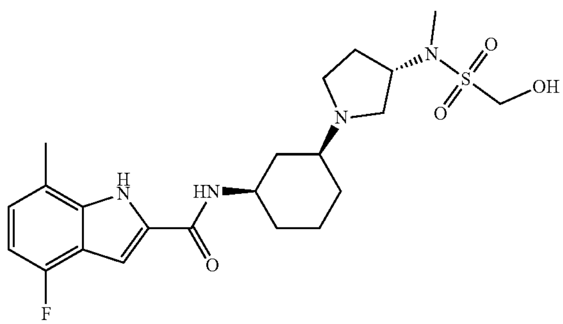 [SMILES: Cc1ccc(F)c2cc(C(=O)N[C@@H]3CCC[C@H](N4CC[C@H](N(C)S(=O)(=O)CO)C4)C3)[nH]c12] |
| 1061 | 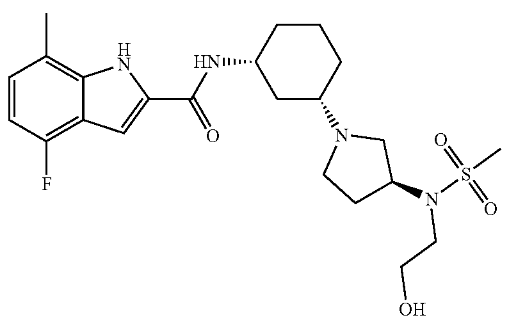 [SMILES: Cc1ccc(F)c2cc(C(=O)N[C@@H]3CCC[C@H](N4CC[C@H](N(CCO)S(C)(=O)=O)C4)C3)[nH]c12] |
| 1062 | 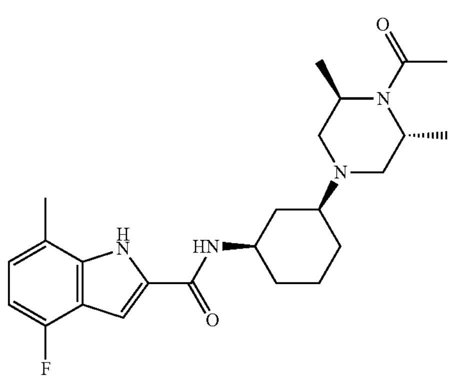 [SMILES: CC(=O)N1[C@H](C)CN([C@H]2CCC[C@@H](NC(=O)c3cc4c(F)ccc(C)c4[nH]3)C2)C[C@H]1C] |

TABLE 1-continued

| Cpd. No. | Chemical Structure |
|---|---|
| 1063 | 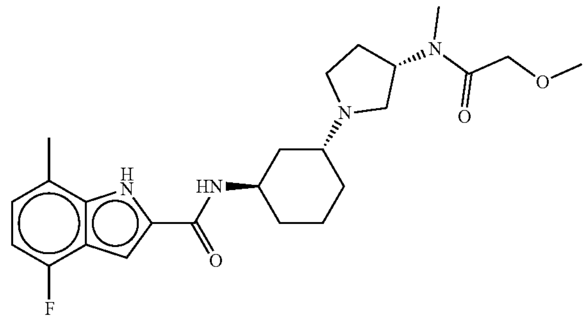 |
| 1064 | 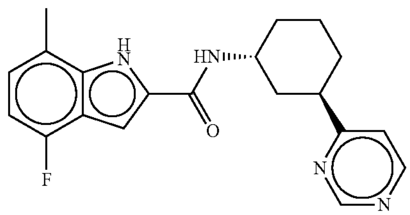 |
| 1065 | 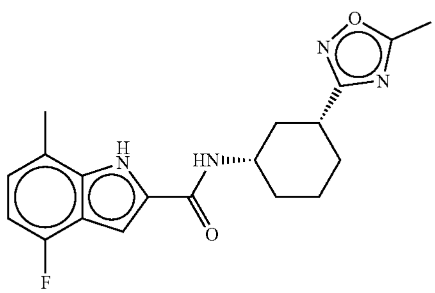 |
| 1066 | 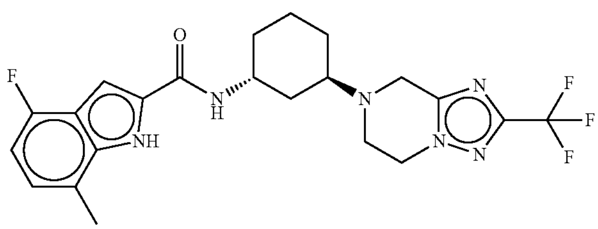 |
| 1067 | 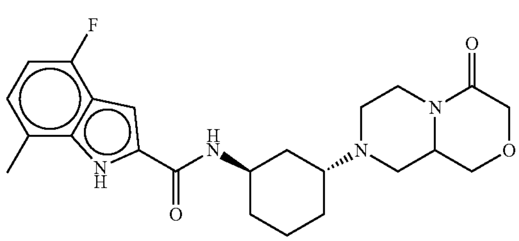 |
| 1068 | 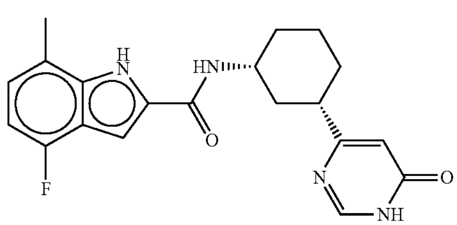 |

TABLE 1-continued
| Cpd. No. | Chemical Structure |
|---|---|
| 1070 | 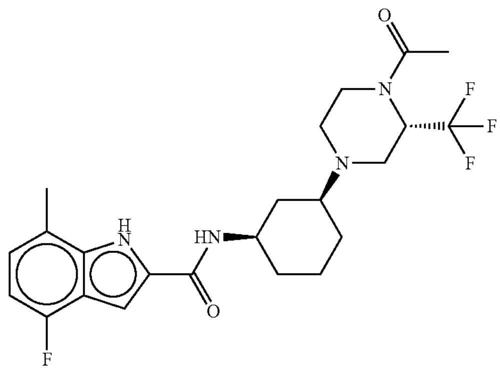 |
| 1071 | 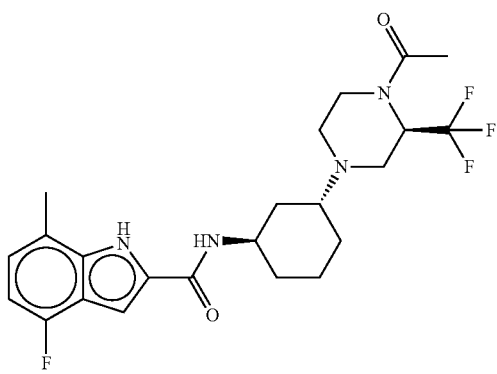 |
| 1072 | 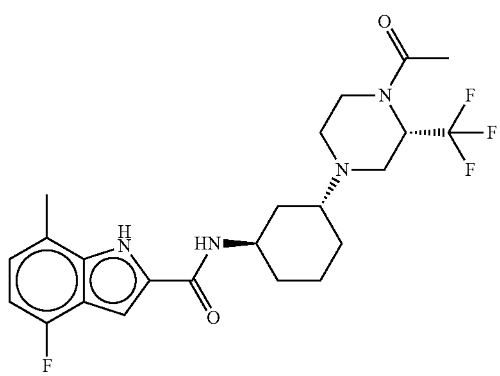 |
| 1074 | 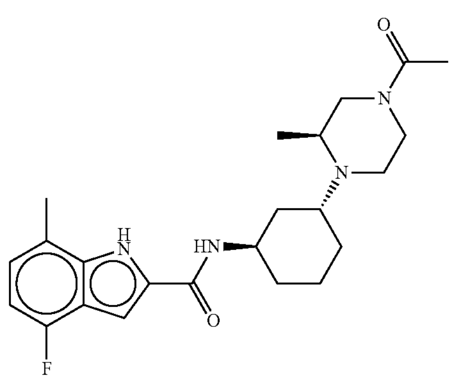 |

TABLE 1-continued
| Cpd. No. | Chemical Structure |
|---|---|
| 1076 | 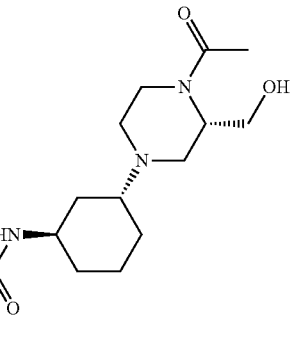 |
| 1077 | 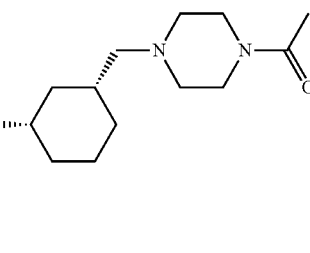 |
| 1078 | 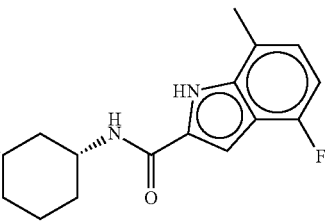 |
| 1079 | 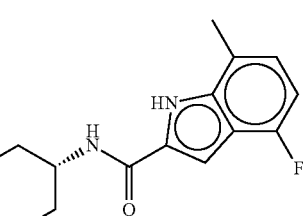 |
| 1080 | 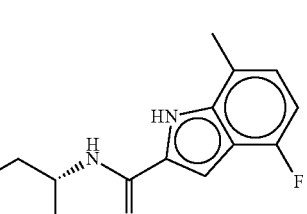 |
| 1082 | 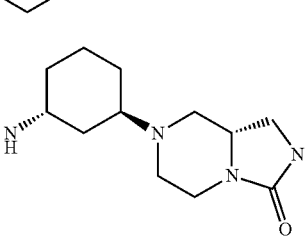 |

TABLE 1-continued

| Cpd. No. | Chemical Structure |
|---|---|
| 1083 | 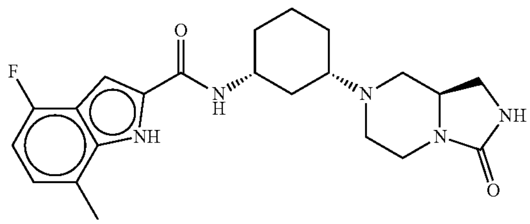 |
| 1084 | 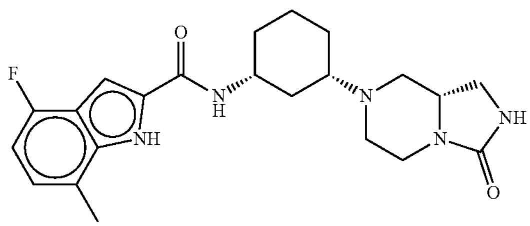 |
| 1085 | 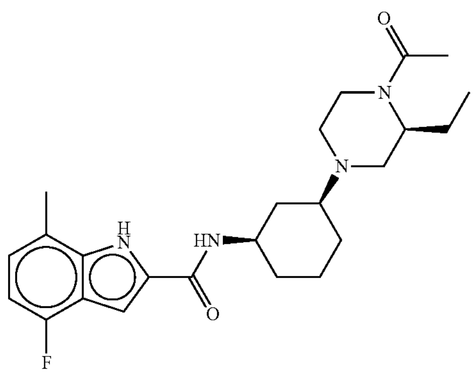 |
| 1086 | 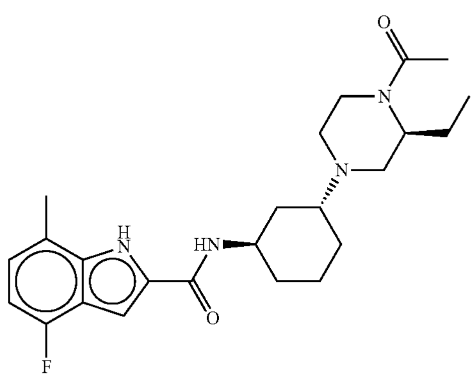 |
| 1087 | 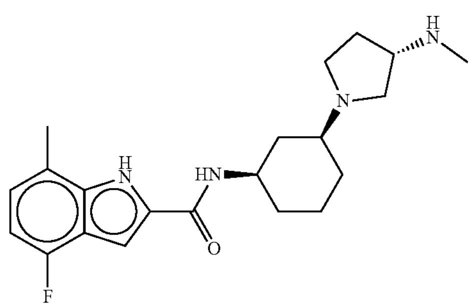 |

TABLE 1-continued
| Cpd. No. | Chemical Structure |
|---|---|
| 1088 | 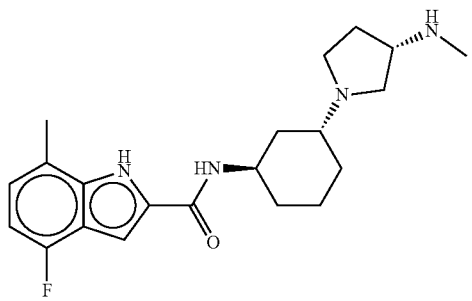 |
| 1090 | 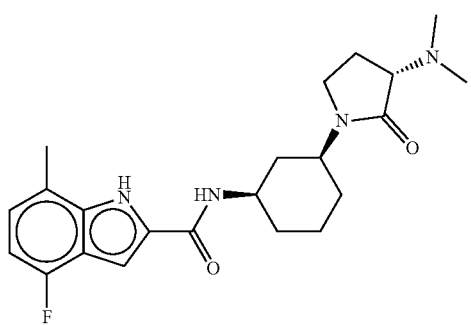 |
| 1091 | 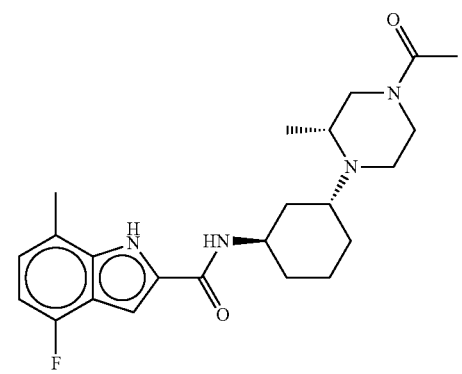 |
| 1092 | 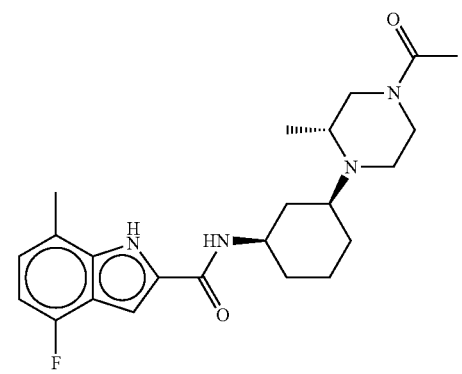 |

TABLE 1-continued
| Cpd. No. | Chemical Structure |
|---|---|
| 1095 | 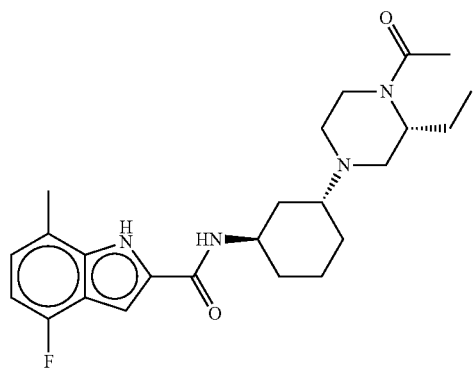 |
| 1096 | 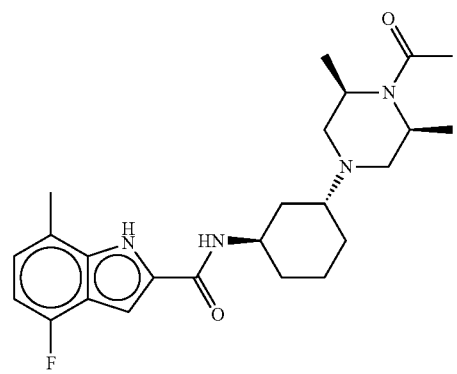 |
| 1097 | 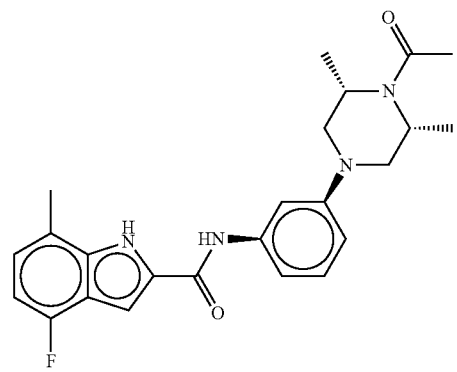 |
| 1098 | 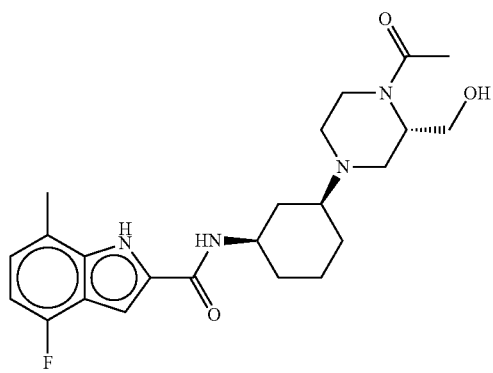 |

473
TABLE 1-continued
| Cpd. No. | Chemical Structure |
|---|---|
| 1099 | 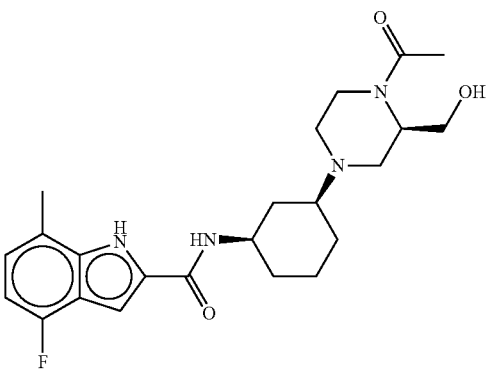 |
| 1100 | 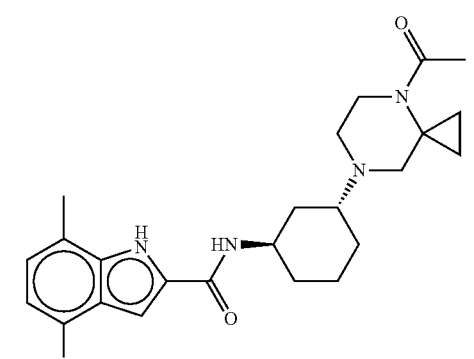 |
| 1102 | 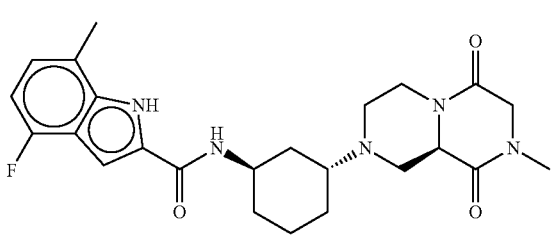 |
| 1103 | 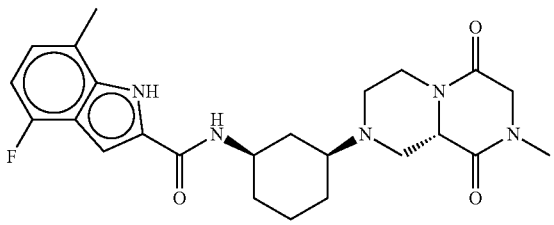 |
| 1104 | 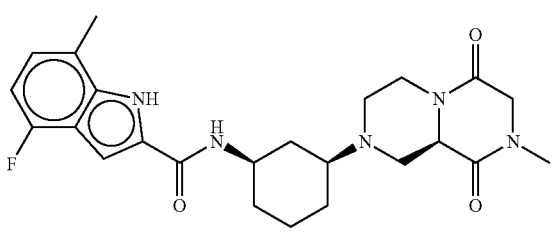 |
474

TABLE 1-continued

| Cpd. No. | Chemical Structure |
|---|---|
| 1106 | 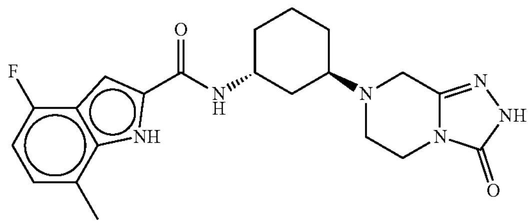 |
| 1107 | 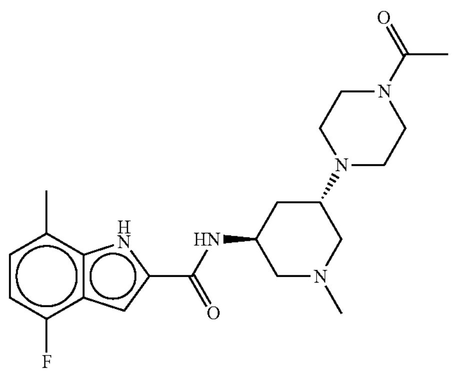 |
| 1108 | 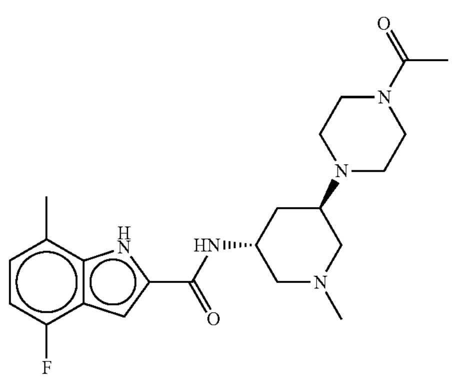 |
| 1109 | 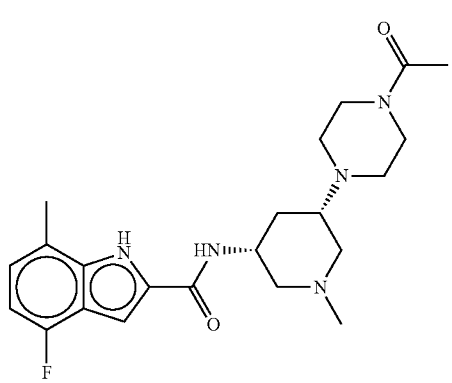 |

TABLE 1-continued
| Cpd. No. | Chemical Structure |
|---|---|
| 1110 | 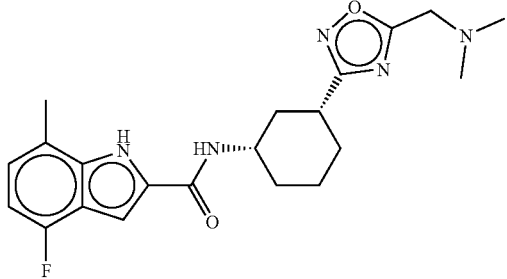 |
| 1111 | 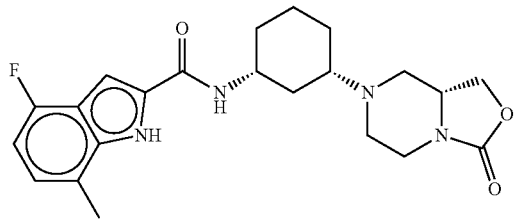 |
| 1112 | 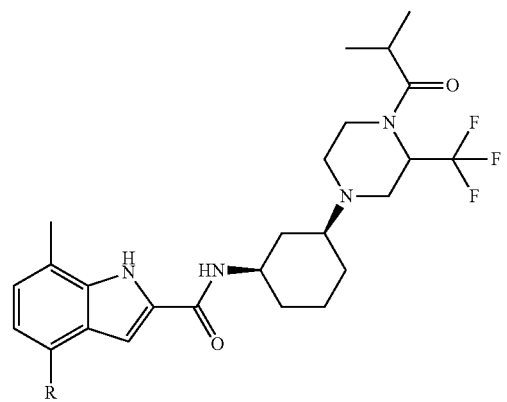 |
| 1113 | 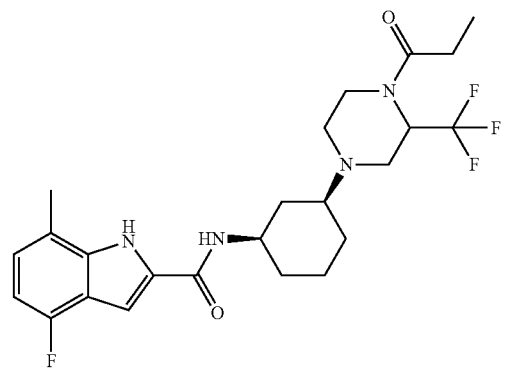 [SMILES: CCC(=O)N1CCN([C@H]2CCC[C@@H](NC(=O)c3cc4c(F)ccc(C)c4[nH]3)C2)CC1C(F)(F)F] |

TABLE 1-continued
| Cpd. No. | Chemical Structure |
|---|---|
| 1114 | 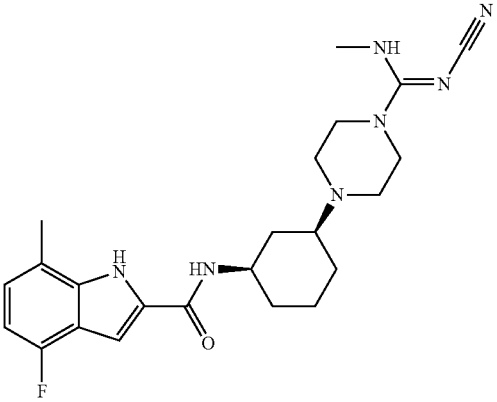 [SMILES: CN/C(=N\C#N)N1CCN([C@H]2CCC[C@@H](NC(=O)c3cc4c(F)ccc(C)c4[nH]3)C2)CC1] |
| 1115 | 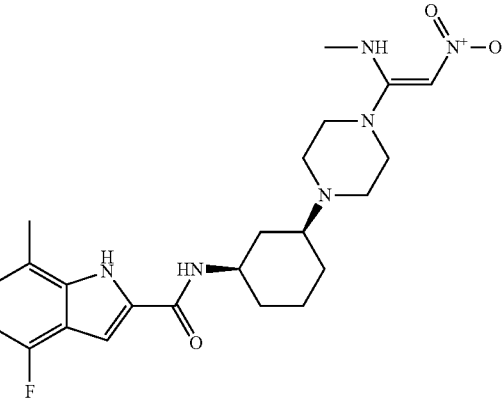 |
| 1116 | 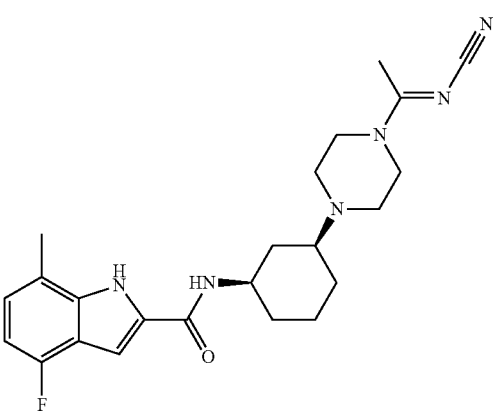 [SMILES: C/C(=N\C#N)N1CCN([C@H]2CCC[C@@H](NC(=O)c3cc4c(F)ccc(C)c4[nH]3)C2)CC1] |
| 1117 | 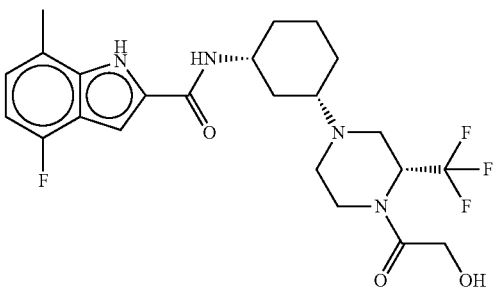 |

TABLE 1-continued
| Cpd. No. | Chemical Structure |
|---|---|
| 1118 | 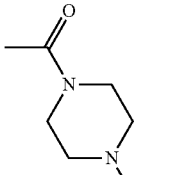 |
| 1120 | 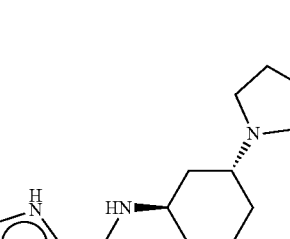 |
| 1122 | 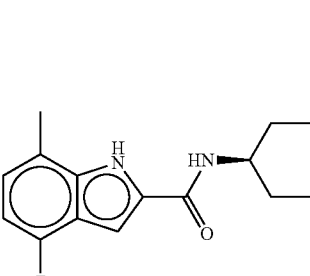 |
| 1123 | 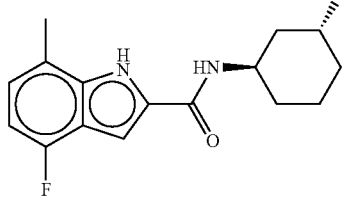 |

TABLE 1-continued
| Cpd. No. | Chemical Structure |
|---|---|
| 1124 | 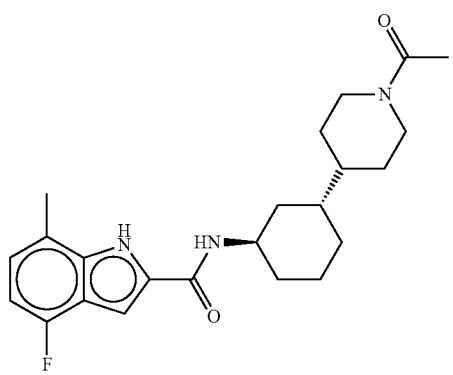 |
| 1126 | 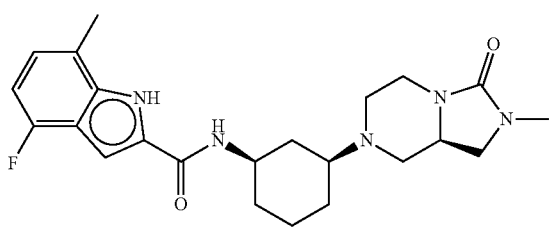 |
| 1127 | 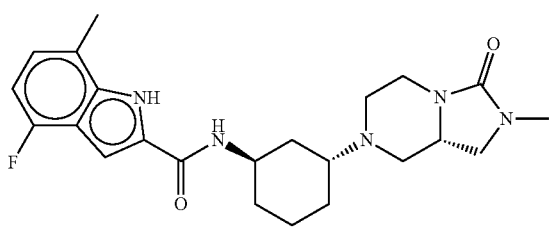 |
| 1128 | 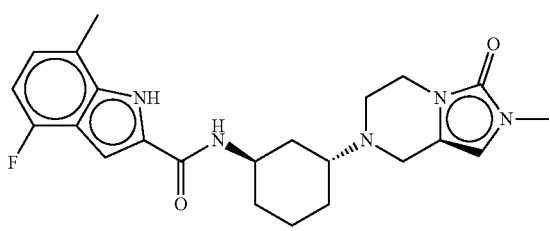 |
| 1129 | 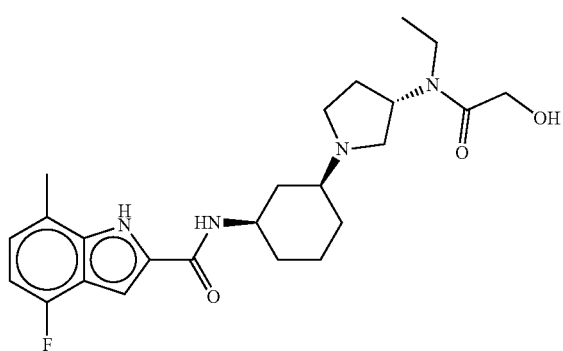 |

TABLE 1-continued
| Cpd. No. | Chemical Structure |
|---|---|
| 1130 | 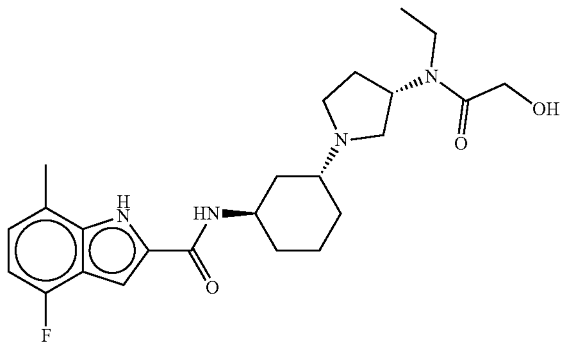 |
| 1131 | 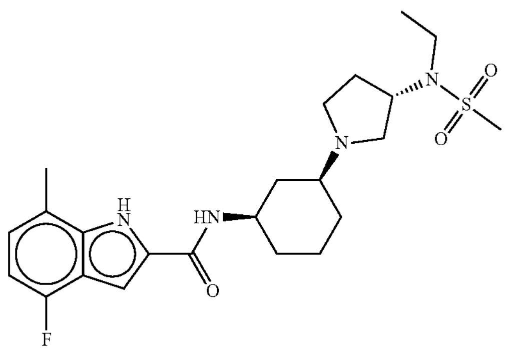 |
| 1132 | 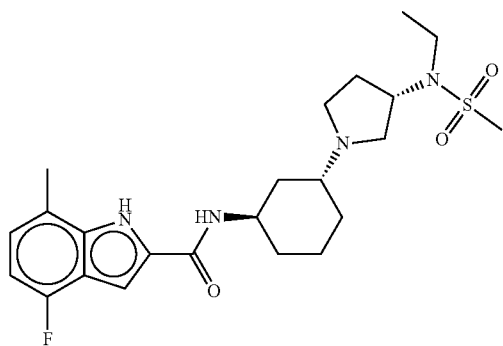 |
| 1134 | 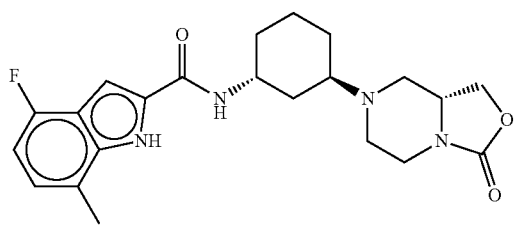 |
| 1135 | 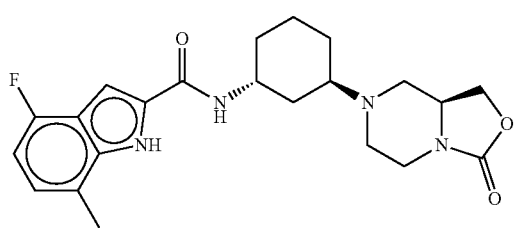 |

TABLE 1-continued

| Cpd. No. | Chemical Structure |
|---|---|
| 1136 | 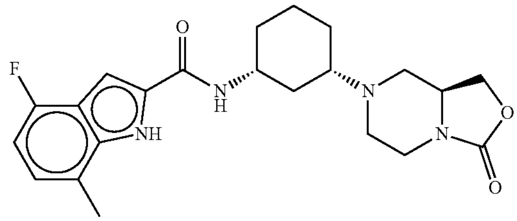 |
| 1137 | 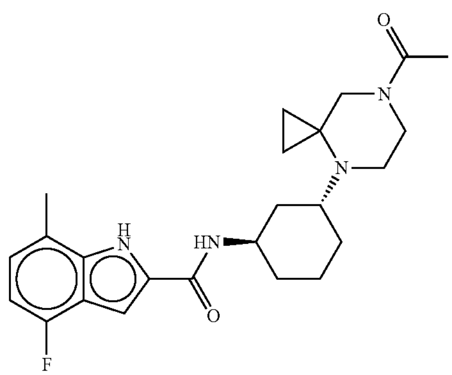 |
| 1138 | 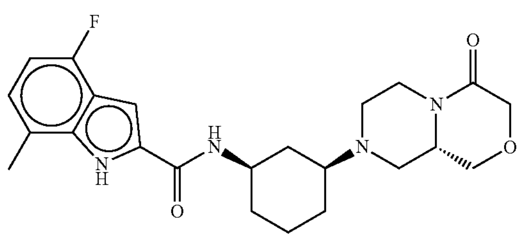 |
| 1139 | 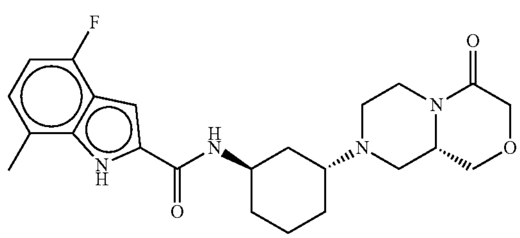 |
| 1140 | 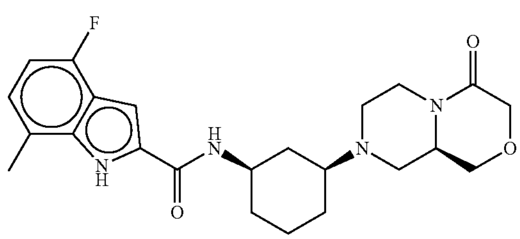 |
| 1141 | 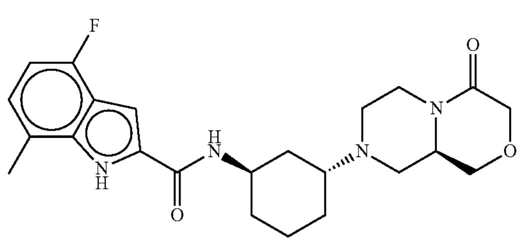 |

TABLE 1-continued
| Cpd. No. | Chemical Structure |
|---|---|
| 1142 | 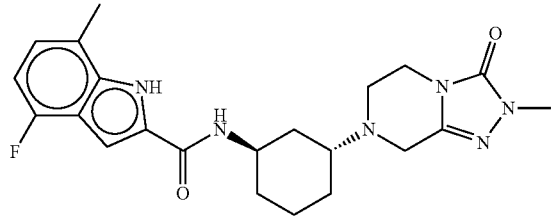 |
| 1143 | 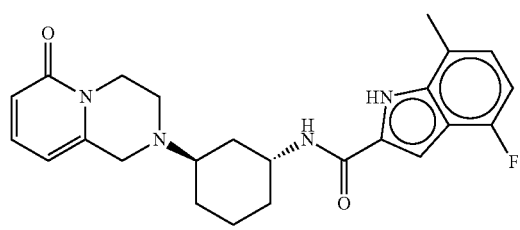 |
| 1145 | 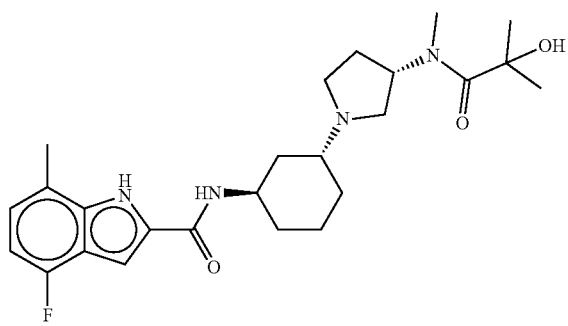 |
| 1146 | 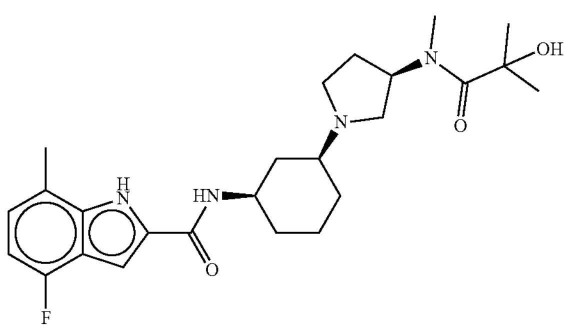 |
| 1147 | 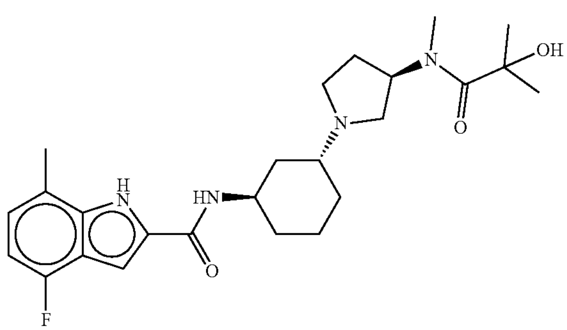 |

491
TABLE 1-continued
| Cpd. No. | Chemical Structure |
|---|---|
| 1148 | 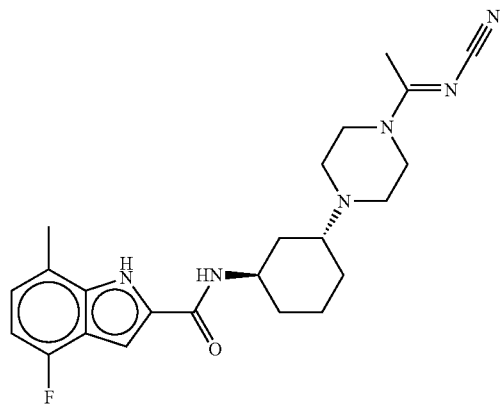 |
| 1150 | 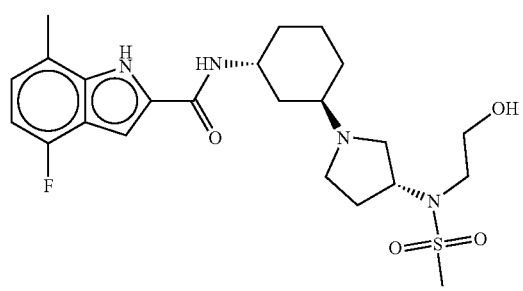 |
| 1151 | 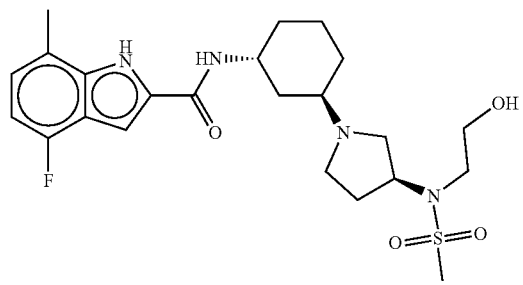 |
| 1152 | 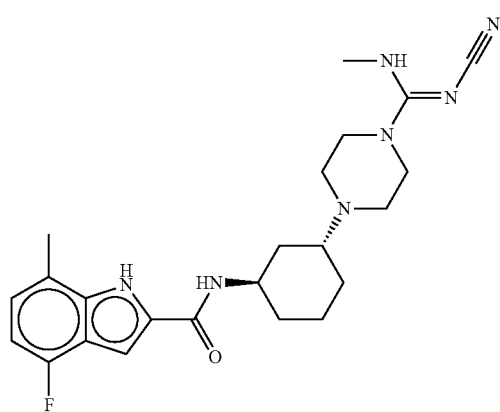 |

TABLE 1-continued
| Cpd. No. | Chemical Structure |
|---|---|
| 1153 | 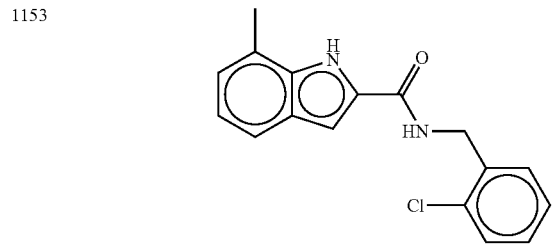 |
| 1154 | 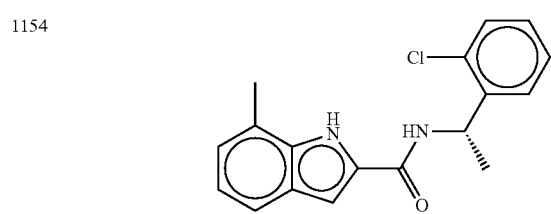 |
| 1155 | 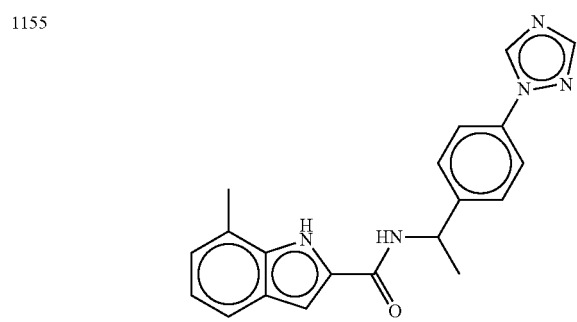 |
| 1156 | 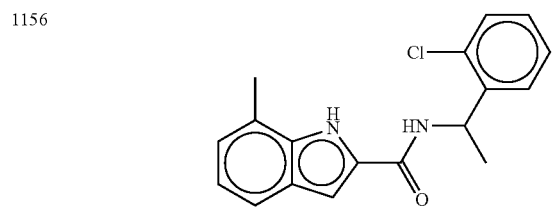 |
| 1157 | 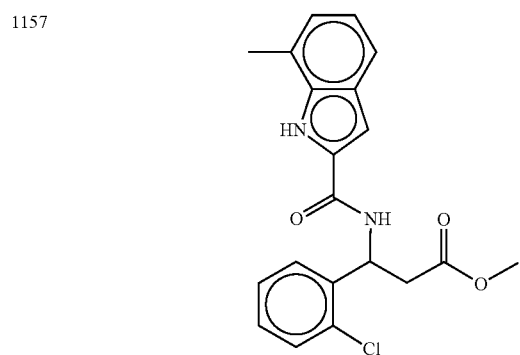 |

TABLE 1-continued
| Cpd. No. | Chemical Structure |
|---|---|
| 1158 | 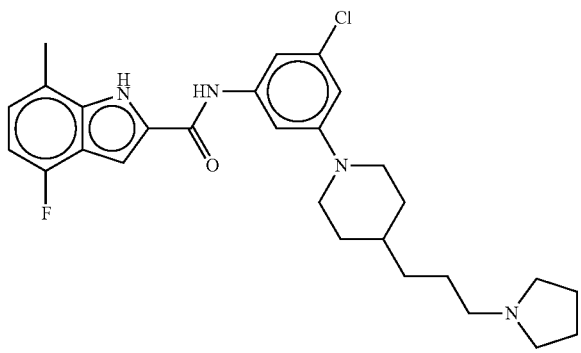 |
| 1159 | 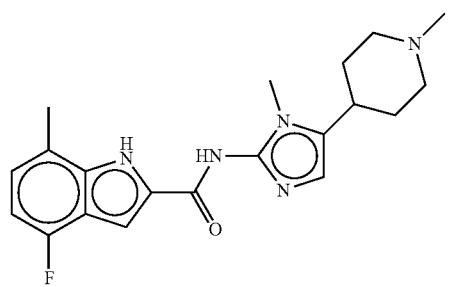 |
| 1160 | 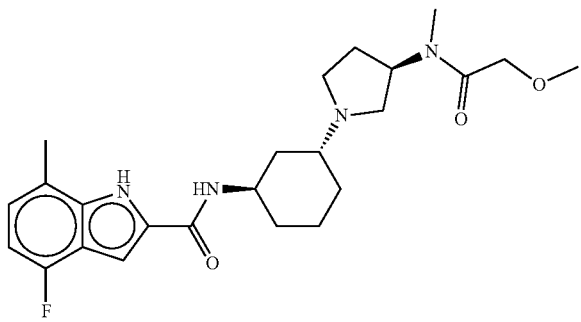 |
| 1161 | 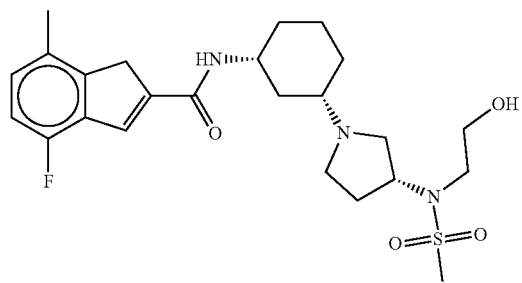 |

TABLE 1-continued
| Cpd. No. | Chemical Structure |
|---|---|
| 1162 | 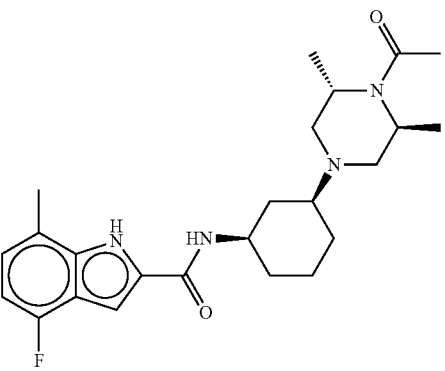 |
| 1163 | 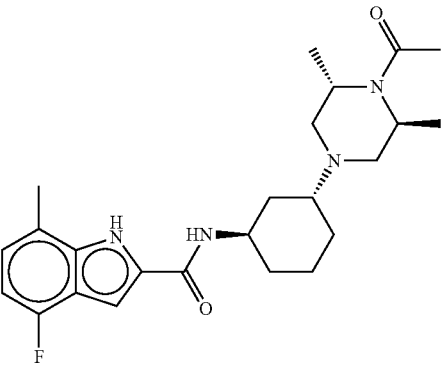 |
| 1164 | 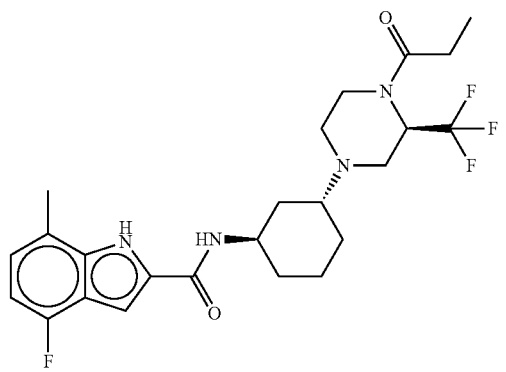 |
| 1165 | 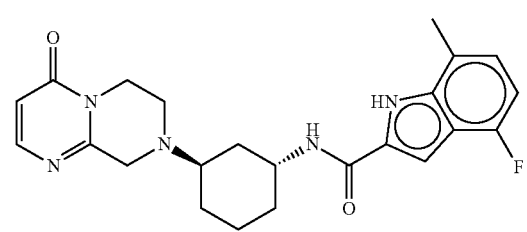 |
| 1166 | 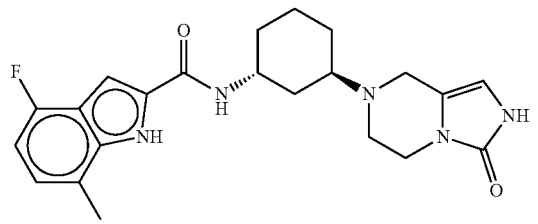 |

TABLE 1-continued
| Cpd. No. | Chemical Structure |
|---|---|
| 1167 | 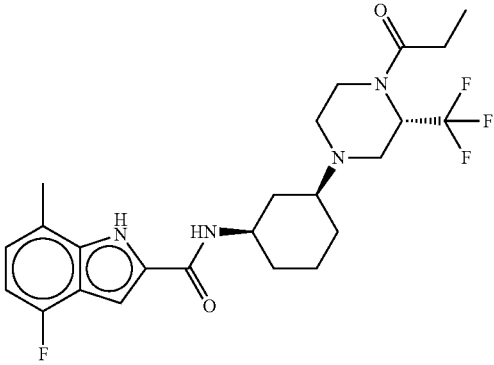 |
| 1168 | 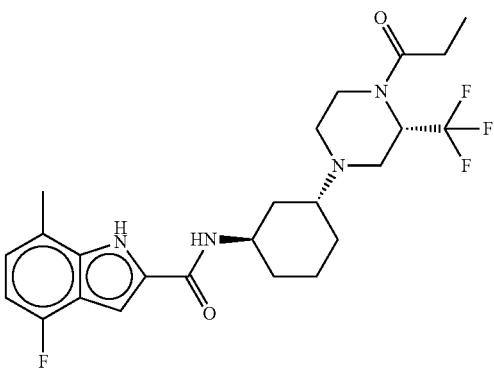 |
| 1169 | 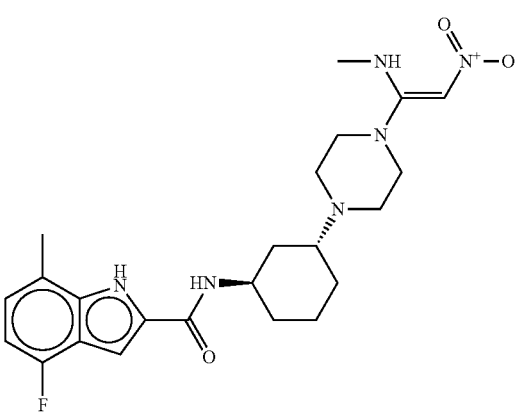 |
| 1170 | 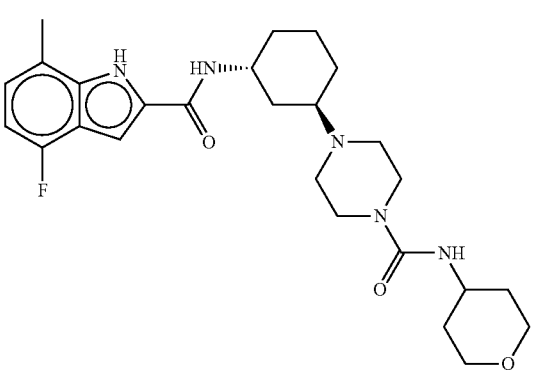 |

TABLE 1-continued
| Cpd. No. | Chemical Structure |
|---|---|
| 1171 | 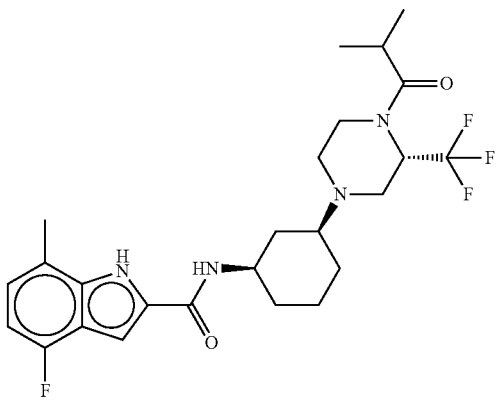 |
| 1172 | 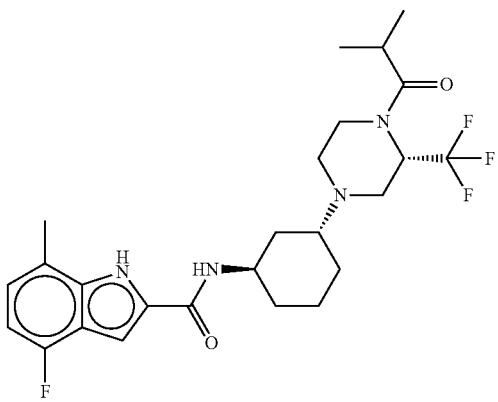 |
| 1173 | 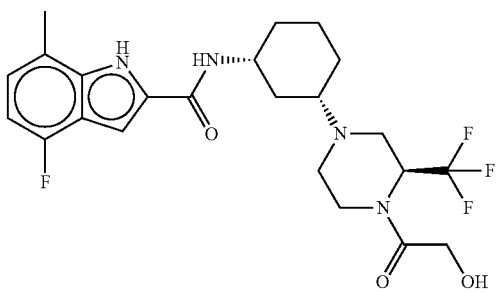 |
| 1174 | 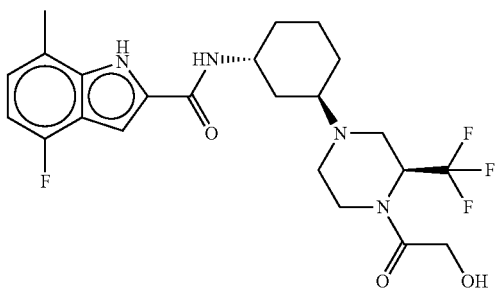 |

TABLE 1-continued
| Cpd. No. | Chemical Structure |
|---|---|
| 1175 | 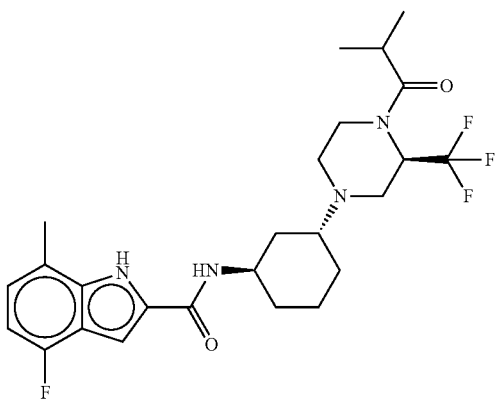 |
| 1176 | 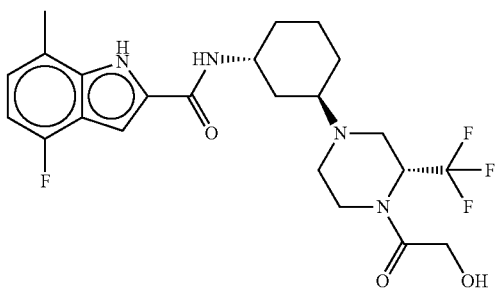 |
| 1177 | 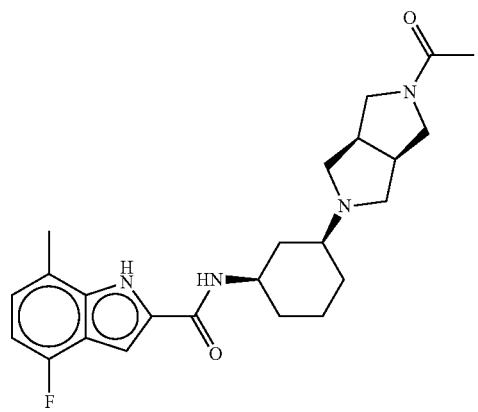 |
| 1178 | 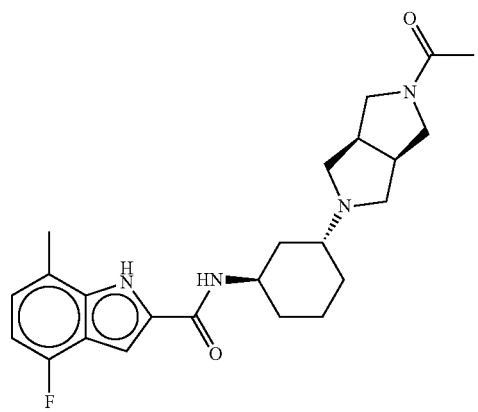 |

TABLE 1-continued
| Cpd. No. | Chemical Structure |
|---|---|
| 1179 | 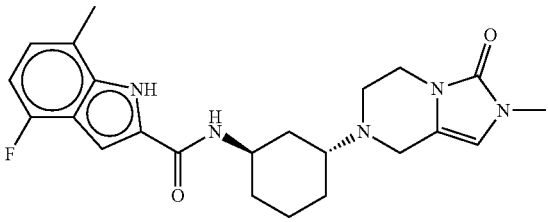 |
| 1180 | 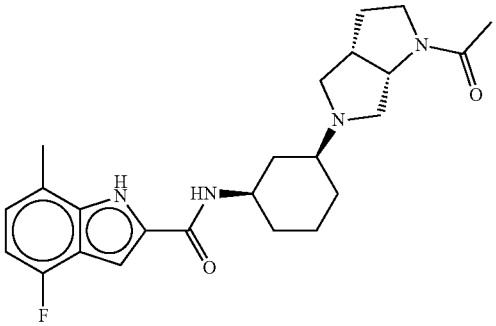 |
| 1181 | 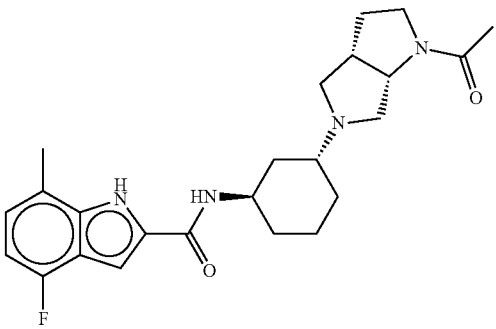 |
| 1182 | 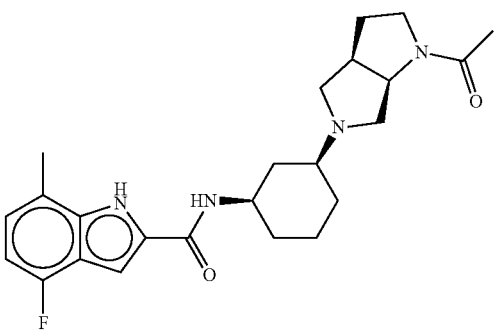 |
| 1183 | 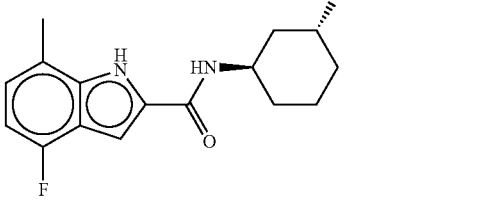 |

TABLE 1-continued

| Cpd. No. | Chemical Structure |
|---|---|
| 1184 | 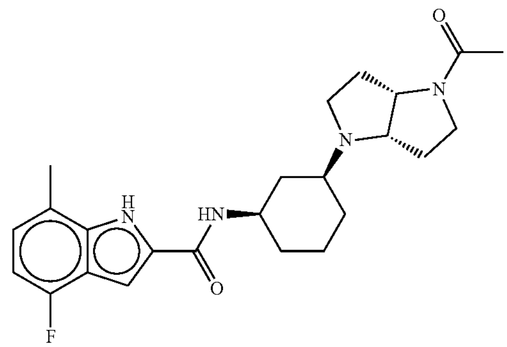 |
| 1185 | 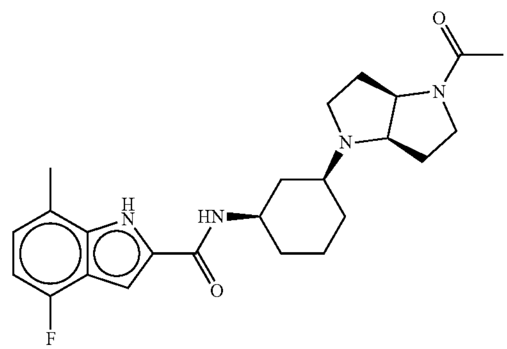 |
| 1186 | 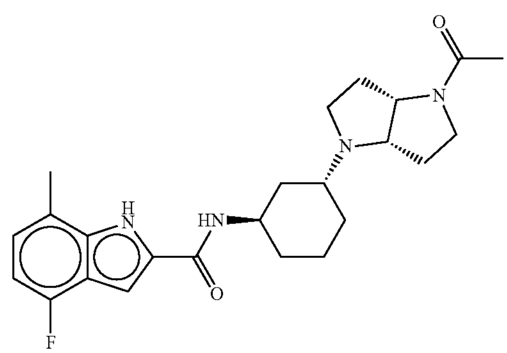 |
| 1187 | 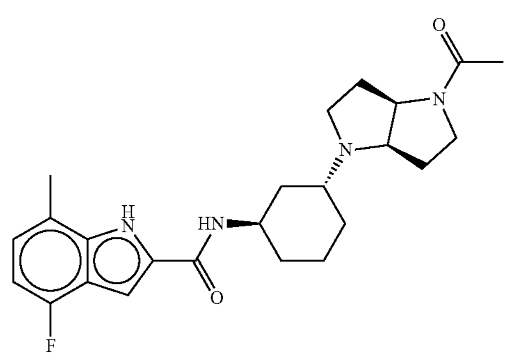 |

TABLE 1-continued
| Cpd. No. | Chemical Structure |
|---|---|
| 1188 | 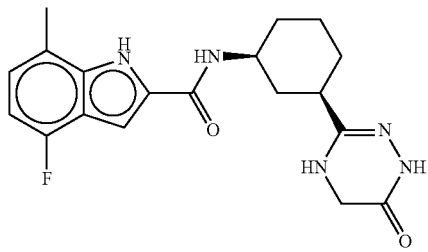 |
| 1189 | 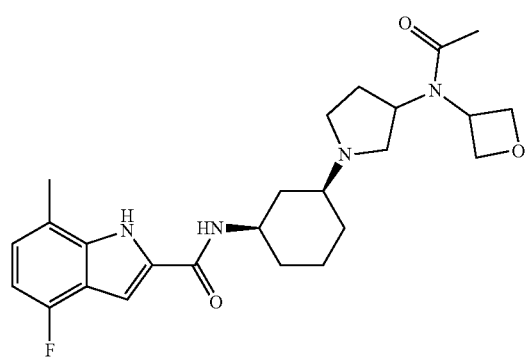 [SMILES: CC(=O)N(C1COC1)C1CCN([C@H]2CCC[C@@H](NC(=O)c3cc4c(F)ccc(C)c4[nH]3)C2)C1] |
| 1190 | 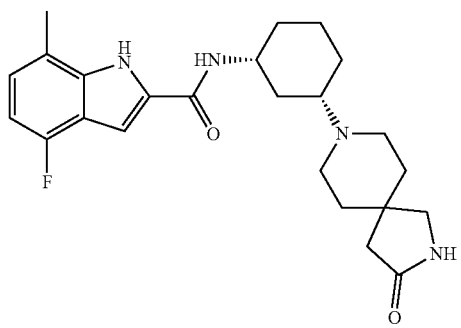 [SMILES: Cc1ccc(F)c2cc(C(=O)N[C@@H]3CCC[C@H](N4CCC5(CC4)CNC(=O)C5)C3)[nH]c12] |
| 1191 | 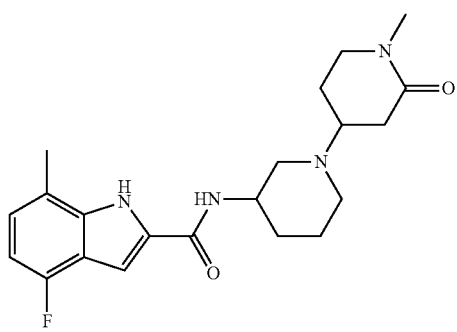 [SMILES: Cc1ccc(F)c2cc(C(=O)NC3CCCN(C4CCN(C)C(=O)C4)C3)[nH]c12] |

TABLE 1-continued
| Cpd. No. | Chemical Structure |
|---|---|
| 1192 | 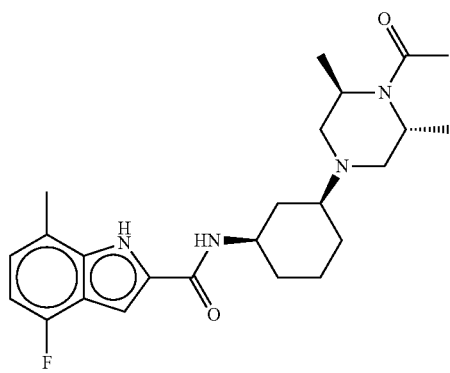 |
| 1193 | 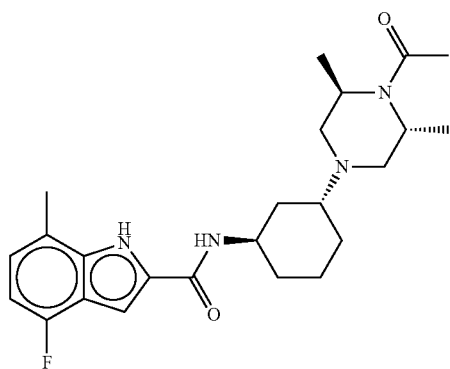 |
| 1194 | 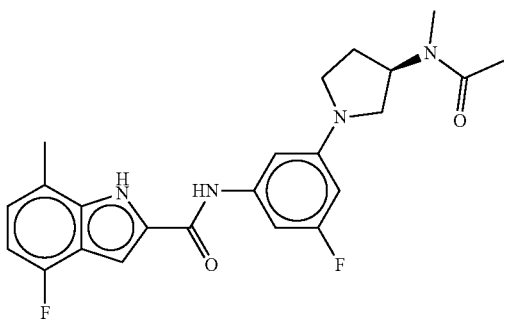 |
| 1195 | 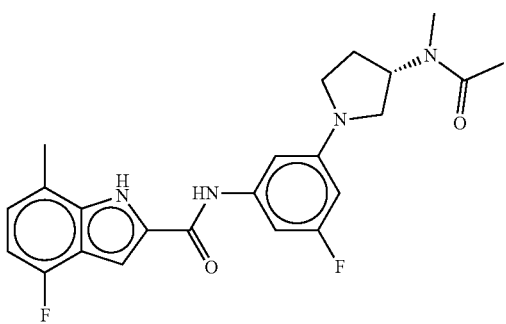 |

TABLE 1-continued

| Cpd. No. | Chemical Structure |
|---|---|
| 1196 | 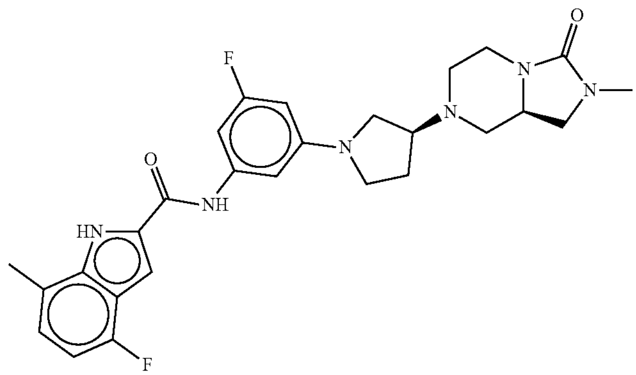 |
| 1197 | 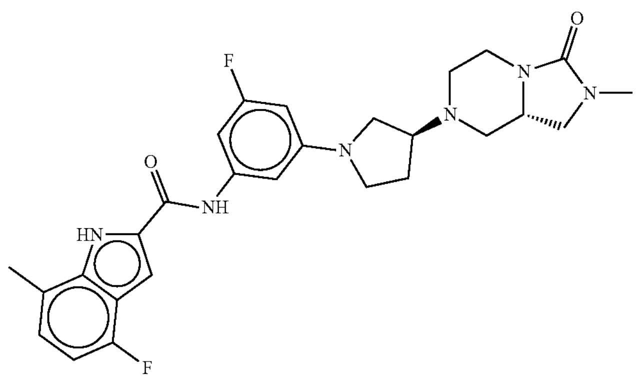 |
| 1198 | 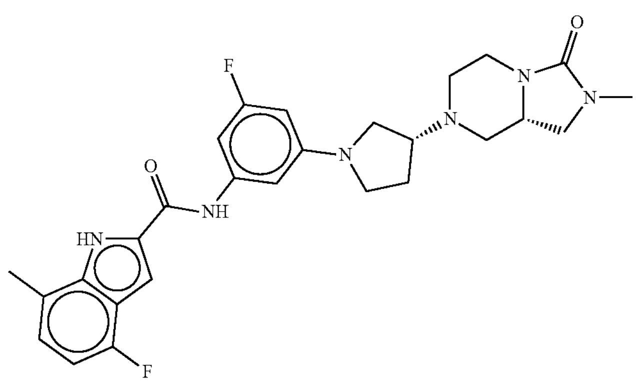 |
| 1199 | 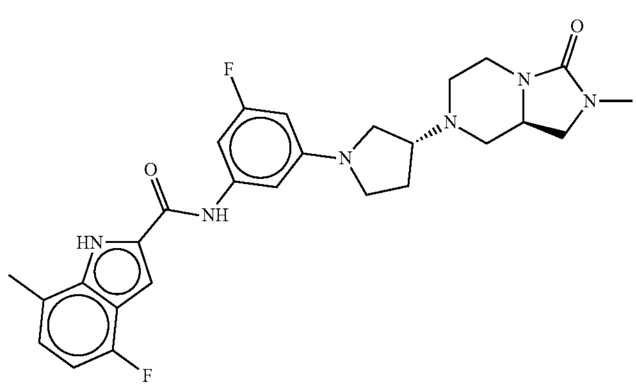 |

TABLE 1-continued
| Cpd. No. | Chemical Structure |
|---|---|
| 1200 | 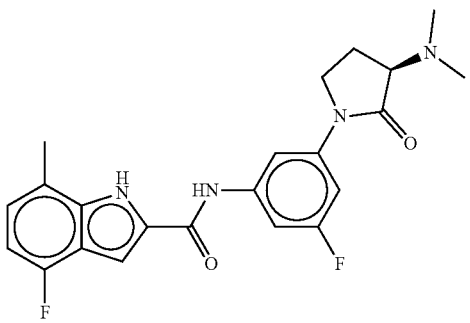 |
| 1201 | 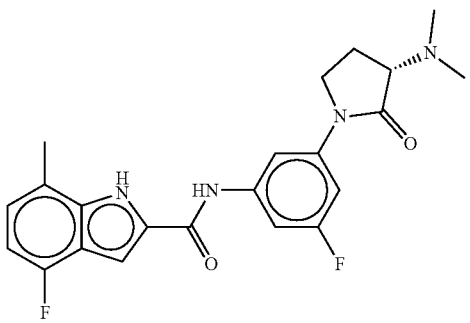 |
| 1202 | 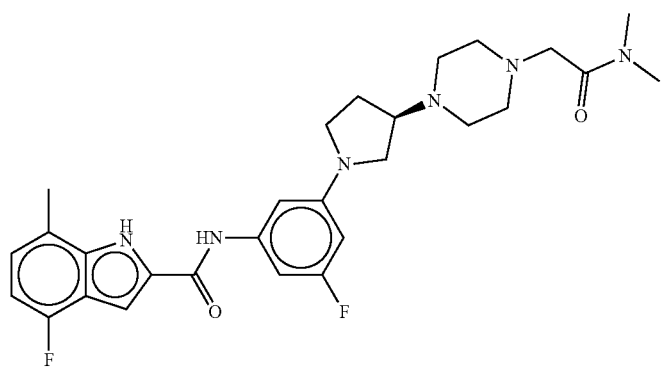 |
| 1203 | 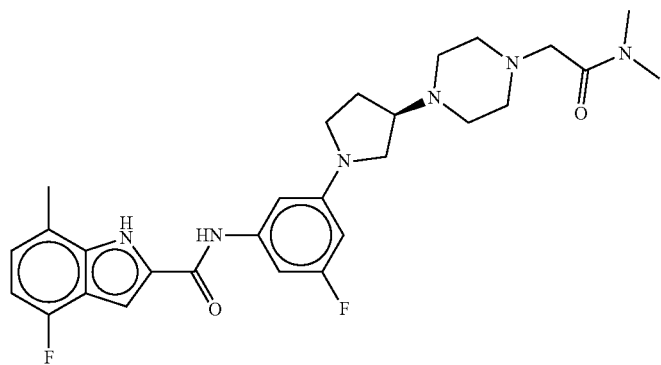 |

TABLE 1-continued

| Cpd. No. | Chemical Structure |
|---|---|
| 1204 | 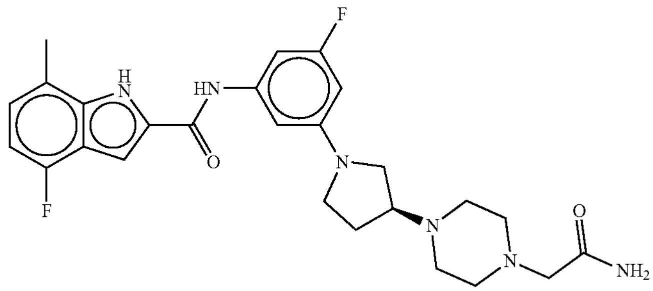 |
| 1205 | 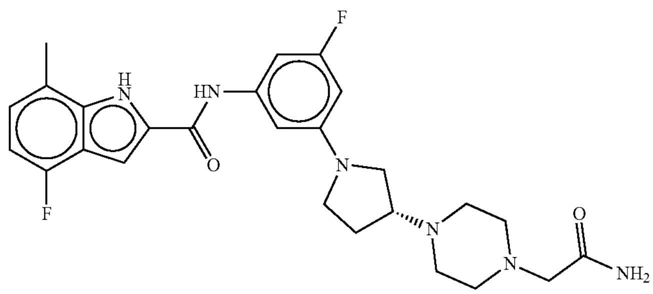 |
| 1206 | 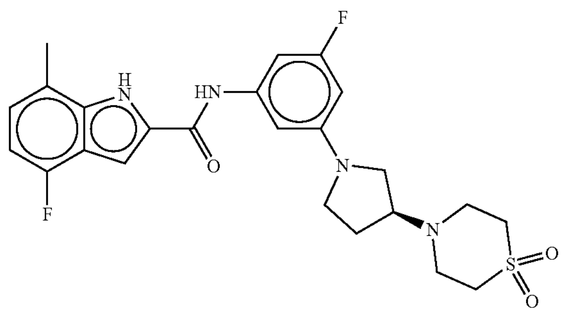 |
| 1207 | 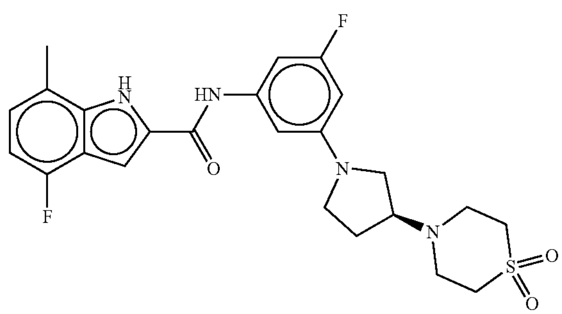 |
| 1208 | 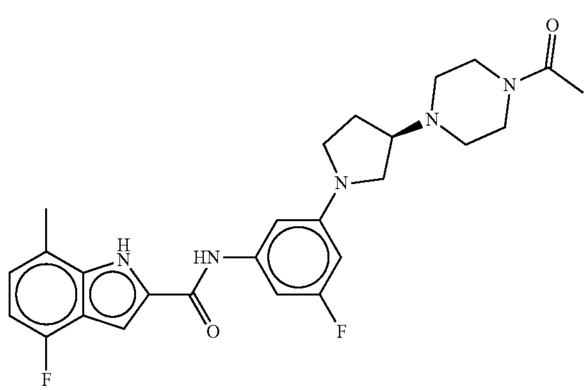 |

TABLE 1-continued
| Cpd. No. | Chemical Structure |
|---|---|
| 1209 | 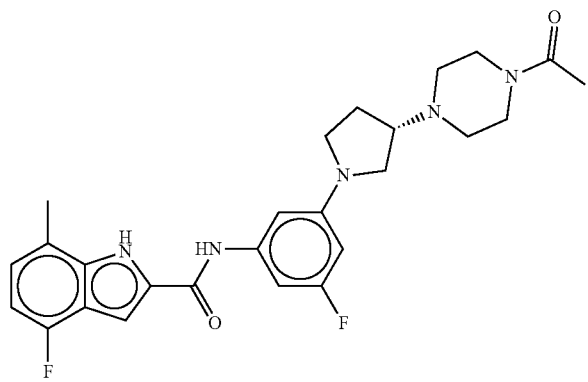 |
| 1210 | 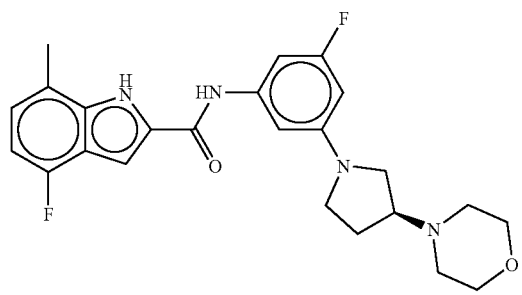 |
| 1211 | 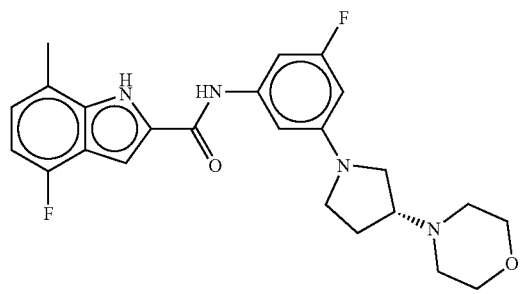 |
| 1212 | 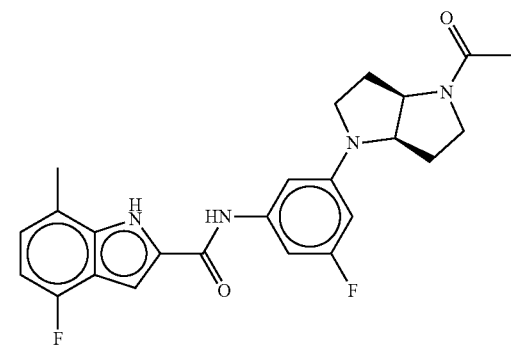 |

TABLE 1-continued
| Cpd. No. | Chemical Structure |
|---|---|
| 1213 | 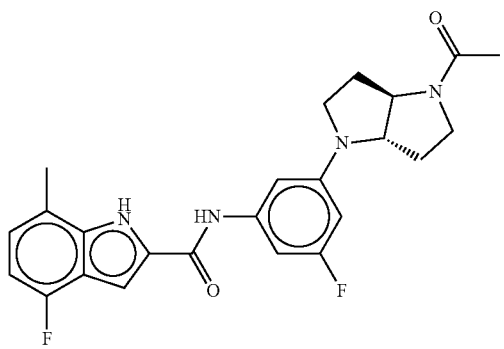 |
| 1214 | 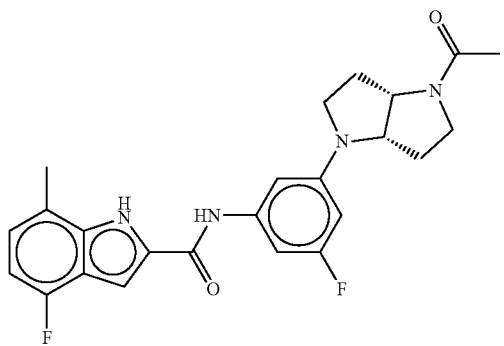 |
| 1215 | 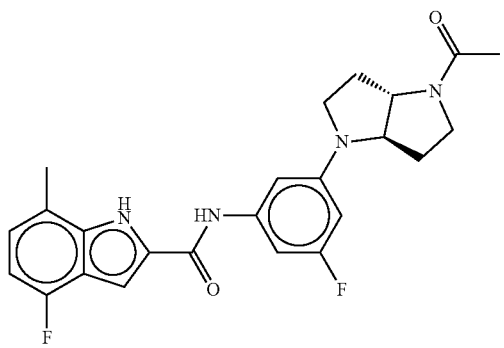 |
| 1216 | 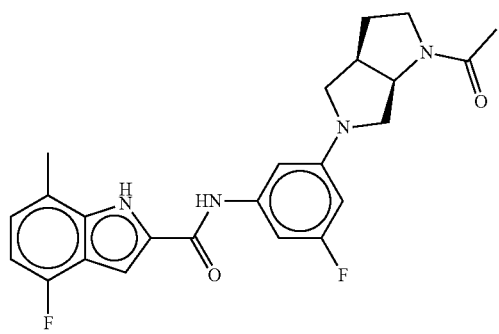 |

TABLE 1-continued
| Cpd. No. | Chemical Structure |
|---|---|
| 1217 | 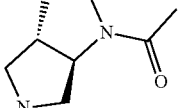 |
| 1218 | 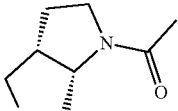 |
| 1219 | 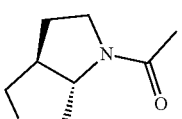 |
| 1220 | 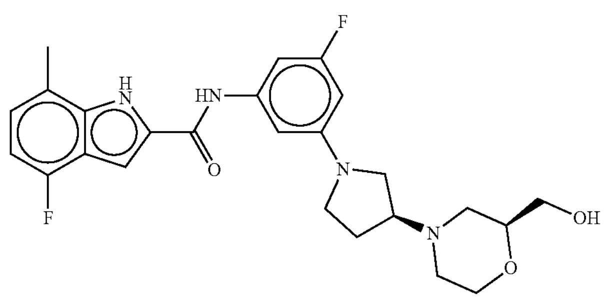 |
| 1221 | 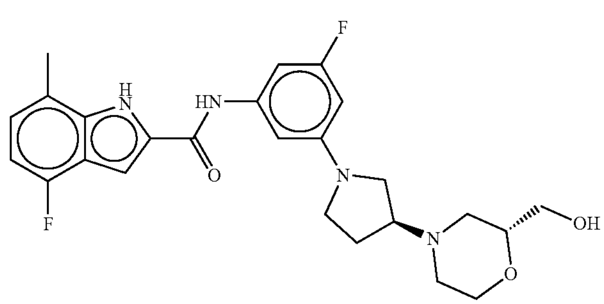 |

TABLE 1-continued

| Cpd. No. | Chemical Structure |
|---|---|
| 1222 | 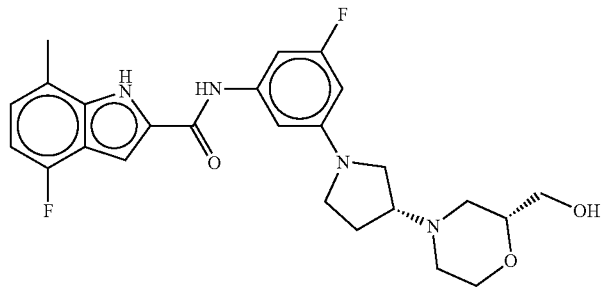 |
| 1223 | 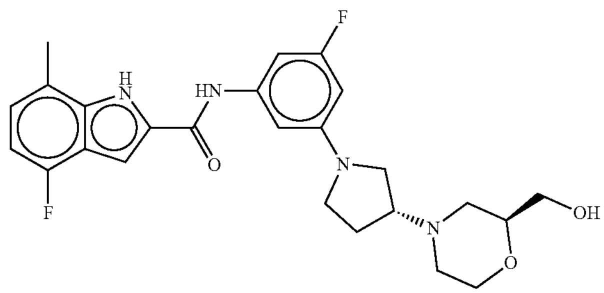 |
| 1224 | 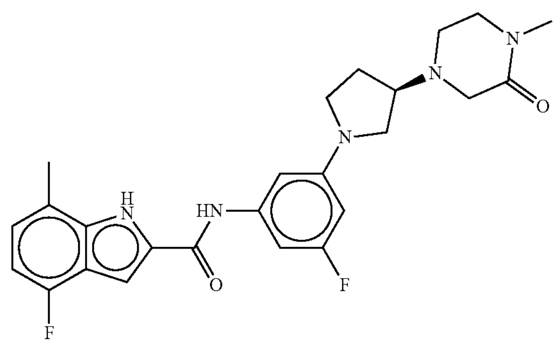 |
| 1225 | 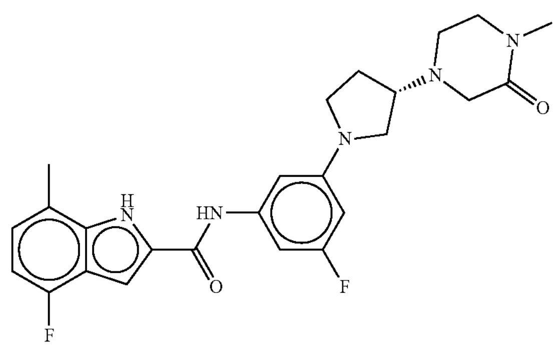 |
| 1226 | 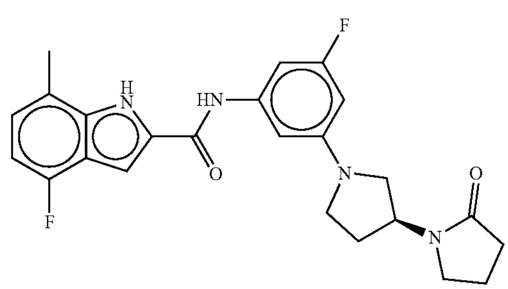 |

TABLE 1-continued

| Cpd. No. | Chemical Structure |
|---|---|
| 1227 | 7-methyl-4-fluoro-1H-indole-2-carboxamide linked via NH to a 3-fluorophenyl bearing a 3-(2-oxopyrrolidin-1-yl)pyrrolidin-1-yl substituent |

TABLE 1B

| Cpd. No. | Mass | Mass Ion Species | SETD2 (1434-1711) | SETD2 A549 | SMYD2 | SMYD3 |
|---|---|---|---|---|---|---|
| 1 | 427 | M + 1 | 0.007 | 0.03 | >200 | >200 |
| 2 | 531 | M + 23 | 0.005 | 0.03 | 134 | >200 |
| 3 | 413 | M + 1 | 0.004 | 0.03 | >200 | >200 |
| 4 | 525 | M + 1 | 0.006 | 0.03 | >200 | >200 |
| 5 | 489 | M + 23 | 0.008 | 0.04 | 182 | 189 |
| 6 | 519 | M + 23 | 0.006 | 0.04 | >200 | >200 |
| 7 | 413 | M + 1 | 0.01 | 0.04 | >200 | >200 |
| 8 | 416 | M + 1 | 0.009 | 0.04 | | |
| 9 | 482 | M + 1 | 0.008 | 0.04 | 154 | >200 |
| 10 | 425 | M + 1 | 0.01 | 0.04 | >200 | >200 |
| 11 | 441 | M + 1 | 0.006 | 0.04 | >200 | >200 |
| 12 | 443 | M + 1 | 0.01 | 0.05 | >200 | >200 |
| 13 | 439 | M + 1 | 0.01 | 0.05 | >200 | >200 |
| 14 | 439 | M + 1 | 0.007 | 0.05 | 172 | >200 |
| 15 | 401 | M + 1 | 0.02 | 0.05 | >200 | >200 |
| 16 | 471 | M + 1 | 0.01 | 0.05 | >200 | >200 |
| 17 | 490 | M + 23 | 0.009 | 0.05 | >200 | >200 |
| 18 | 439 | M + 1 | 0.008 | 0.06 | >200 | 33.9 |
| 19 | 453 | M + 1 | 0.01 | 0.06 | >200 | >200 |
| 20 | 399 | M + 1 | 0.009 | 0.06 | 59.3 | 57.4 |
| 21 | 434 | M + 23 | 0.01 | 0.06 | | |
| 22 | 457 | M + 1 | 0.01 | 0.06 | 192 | >200 |
| 23 | 437 | M + 1 | 0.01 | 0.06 | >200 | >200 |
| 24 | 416 | M + 1 | 0.02 | 0.06 | | |
| 25 | 442 | M + 1 | 0.01 | 0.07 | | |
| 26 | 424 | M + 1 | 0.01 | 0.07 | | |
| 27 | 407 | M + 1 | 0.02 | 0.07 | >200 | >200 |
| 28 | 461 | M + 1 | 0.01 | 0.07 | | |
| 29 | 477 | M + 1 | 0.02 | 0.07 | | |
| 30 | 489 | M + 23 | 0.008 | 0.07 | >200 | >200 |
| 31 | 429 | M + 1 | 0.01 | 0.08 | >200 | >200 |
| 32 | 409 | M + 1 | 0.02 | 0.08 | | |
| 34 | 395 | M + 1 | 0.02 | 0.08 | 190 | >200 |
| 35 | 454 | M + 1 | 0.006 | 0.08 | 131 | >200 |
| 36 | 409 | M + 1 | 0.03 | 0.09 | | |
| 37 | 406 | M + 1 | 0.02 | 0.09 | | |
| 38 | 431 | M + 23 | 0.01 | 0.09 | | |
| 39 | 525 | M + 1 | 0.004 | 0.09 | 65.6 | 59.9 |
| 40 | 475 | M + 1 | 0.04 | 0.1 | | |
| 41 | 457 | M + 1 | 0.03 | 0.1 | | |
| 42 | 423 | M + 1 | 0.02 | 0.1 | | |
| 43 | 492 | M + 23 | 0.007 | 0.1 | | |
| 44 | 447 | M + 23 | 0.04 | 0.1 | | |
| 45 | 394 | M + 1 | 0.03 | 0.1 | | |
| 46 | 415 | M + 1 | 0.03 | 0.1 | | |
| 47 | 431 | M + 1 | 0.01 | 0.1 | | |
| 48 | 402 | M + 1 | 0.02 | 0.1 | | |
| 49 | 458 | M + 1 | 0.03 | 0.1 | | |
| 50 | 398 | M + 1 | 0.06 | 0.1 | | |
| 51 | 406 | M + 1 | 0.02 | 0.1 | | |
| 52 | 435 | M + 23 | 0.07 | 0.1 | | |
| 53 | 399 | M + 1 | 0.005 | 0.1 | | |
| 54 | 422 | M + 1 | 0.03 | 0.1 | | |
| 55 | 424 | M + 1 | 0.05 | 0.1 | | |
| 56 | 398 | M + 1 | 0.03 | 0.1 | | |
| 57 | 393 | M + 1 | 0.03 | 0.1 | | |
| 58 | 403 | M + 23 | 0.04 | 0.1 | | |
| 59 | 381 | M + 1 | 0.01 | 0.1 | 68.7 | 12.4 |
| 60 | 337 | M + 1 | 0.03 | 0.1 | >200 | 61.4 |
| 61 | 397 | M + 1 | 0.01 | 0.1 | | |
| 62 | 456 | M + 1 | 0.009 | 0.1 | | |
| 63 | 399 | M + 1 | 0.02 | 0.1 | | |
| 64 | 347 | M + 1 | 0.06 | 0.1 | 43.5 | 17.4 |
| 65 | 367 | M + 1 | 0.02 | 0.1 | | |
| 66 | 354 | M + 1 | 0.03 | 0.2 | | |
| 68 | 394 | M + 1 | 0.006 | 0.2 | | |
| 69 | 412 | M + 1 | 0.003 | 0.2 | | |
| 70 | 470 | M + 1 | 0.009 | 0.2 | | |
| 71 | 423 | M + 1 | 0.04 | 0.2 | | |
| 72 | 411 | M + 1 | 0.03 | 0.2 | | |
| 73 | 380 | M + 1 | 0.04 | 0.2 | | |
| 74 | 423 | M + 1 | 0.03 | 0.2 | | |
| 75 | 439 | M + 1 | 0.06 | 0.2 | | |
| 76 | 437 | M + 1 | 0.03 | 0.2 | | |
| 77 | 485 | M + 23 | 0.06 | 0.2 | | |
| 78 | 423 | M + 1 | 0.04 | 0.2 | | |
| 79 | 435 | M + 23 | 0.07 | 0.2 | | |
| 80 | 413 | M + 1 | 0.003 | 0.2 | | |
| 81 | 397 | M + 1 | 0.03 | 0.2 | | |
| 82 | 338 | M + 1 | 0.04 | 0.2 | | |
| 83 | 465 | M + 1 | 0.02 | 0.2 | | |
| 84 | 459 | M + 1 | 0.04 | 0.2 | | |
| 85 | 392 | M + 1 | 0.04 | 0.2 | | |
| 86 | 407 | M + 1 | 0.005 | 0.2 | | |
| 87 | 382 | M + 1 | 0.1 | 0.2 | | |
| 88 | 395 | M + 1 | 0.05 | 0.2 | | |
| 89 | 453 | M + 1 | 0.03 | 0.2 | | |
| 90 | 406 | M + 1 | 0.03 | 0.2 | | |
| 91 | 401 | M + 1 | 0.01 | 0.2 | 137 | >200 |
| 92 | 413 | M + 1 | 0.03 | 0.2 | | |
| 93 | 443 | M + 23 | 0.06 | 0.2 | | |
| 94 | 381 | M + 1 | 0.02 | 0.2 | | |
| 95 | 423 | M + 1 | 0.02 | 0.2 | | |
| 96 | 424 | M + 1 | 0.04 | 0.2 | | |
| 97 | 445 | M + 23 | 0.04 | 0.2 | | |
| 98 | 407 | M + 1 | 0.009 | 0.2 | | |
| 99 | 409 | M + 1 | 0.03 | 0.2 | 87.7 | 11 |
| 100 | 407 | M + 1 | 0.03 | 0.2 | | |
| 101 | 353 | M + 1 | 0.05 | 0.2 | | |
| 102 | 381 | M + 1 | 0.02 | 0.2 | | |
| 103 | 412 | M + 1 | 0.03 | 0.2 | | |
| 104 | 467 | M + 1 | 0.03 | 0.2 | | |
| 105 | 411 | M + 1 | 0.008 | 0.2 | | |
| 106 | 428 | M + 1 | 0.003 | 0.2 | | |
| 107 | 383 | M + 1 | 0.04 | 0.2 | | |
| 108 | 336 | M + 1 | 0.06 | 0.2 | | |
| 109 | 451 | M + 1 | 0.01 | 0.2 | | |
| 110 | 475 | M + 1 | 0.1 | 0.2 | | |

TABLE 1B-continued

| Cpd. No. | Mass | Mass Ion Species | SETD2 (1434-1711) | SETD2 A549 | SMYD2 | SMYD3 |
|---|---|---|---|---|---|---|
| 111 | 409 | M + 1 | 0.008 | 0.2 | | |
| 112 | 451 | M + 1 | 0.03 | 0.2 | | |
| 113 | 395 | M + 1 | 0.02 | 0.2 | 36.6 | 39.1 |
| 114 | 424 | M + 1 | 0.06 | 0.2 | | |
| 115 | 384 | M + 1 | 0.05 | 0.2 | | |
| 116 | 346 | M + 1 | 0.04 | 0.2 | | |
| 117 | 409 | M + 1 | 0.02 | 0.2 | | |
| 118 | 352 | M + 1 | 0.05 | 0.2 | | |
| 119 | 377 | M + 1 | 0.03 | 0.2 | | |
| 120 | 415 | M + 1 | 0.006 | 0.3 | | |
| 121 | 433 | M + 23 | 0.05 | 0.3 | | |
| 122 | 411 | M + 1 | 0.01 | 0.3 | | |
| 123 | 394 | M + 1 | 0.05 | 0.3 | | |
| 124 | 393 | M + 1 | 0.007 | 0.3 | | |
| 125 | 388 | M + 1 | 0.08 | 0.3 | | |
| 126 | 368 | M + 1 | 0.05 | 0.3 | | |
| 127 | 487 | M + 23 | 0.04 | 0.3 | | |
| 128 | 367 | M + 1 | 0.01 | 0.3 | | |
| 129 | 368 | M + 1 | 0.06 | 0.3 | | |
| 130 | 413 | M + 1 | 0.04 | 0.3 | | |
| 131 | 353 | M + 1 | 0.1 | 0.3 | | |
| 132 | 410 | M + 1 | 0.05 | 0.3 | | |
| 133 | 398 | M + 1 | 0.1 | 0.3 | | |
| 134 | 320 | M + 1 | 0.06 | 0.3 | 45.3 | 76 |
| 135 | 379 | M + 1 | 0.02 | 0.3 | | |
| 136 | 474 | M + 23 | 0.4 | 0.3 | | |
| 137 | 346 | M + 1 | 0.05 | 0.3 | | |
| 138 | 478 | M + 1 | 0.01 | 0.3 | | |
| 139 | 432 | M + 23 | 0.05 | 0.3 | | |
| 140 | 441 | M + 1 | 0.01 | 0.3 | | |
| 141 | 432 | M + 1 | 0.04 | 0.3 | | |
| 142 | 471 | M + 1 | 0.04 | 0.3 | | |
| 143 | 394 | M + 1 | 0.06 | 0.3 | | |
| 144 | 381 | M + 1 | 0.02 | 0.3 | | |
| 145 | 381 | M + 1 | 0.03 | 0.3 | | |
| 146 | 423 | M + 1 | 0.2 | 0.3 | | |
| 147 | 367 | M + 1 | 0.03 | 0.3 | | |
| 148 | 433 | M + 23 | 0.02 | 0.3 | | |
| 149 | 447 | M + 23 | 0.07 | 0.3 | | |
| 150 | 431 | M + 23 | 0.02 | 0.3 | 42.8 | 9.71 |
| 151 | 349 | M + 1 | 0.08 | 0.3 | | |
| 152 | 450 | M + 1 | 0.01 | 0.3 | | |
| 153 | 457 | M + 1 | 0.05 | 0.3 | | |
| 154 | 397 | M + 1 | 0.03 | 0.3 | | |
| 155 | 437 | M + 1 | 0.05 | 0.3 | | |
| 156 | 425 | M + 1 | 0.03 | 0.3 | | |
| 157 | 444 | M + 1 | 0.05 | 0.3 | | |
| 159 | 455 | M + 1 | 0.08 | 0.3 | | |
| 160 | 380 | M + 1 | 0.09 | 0.3 | | |
| 161 | 418 | M + 1 | 0.03 | 0.3 | | |
| 162 | 336 | M + 1 | 0.09 | 0.3 | | |
| 163 | 421 | M + 1 | 0.03 | 0.3 | | |
| 164 | 448 | M + 1 | 0.1 | 0.3 | | |
| 165 | 393 | M + 1 | 0.01 | 0.3 | | |
| 166 | 406 | M + 1 | 0.07 | 0.3 | | |
| 167 | 411 | M + 1 | 0.05 | 0.3 | | |
| 168 | 366 | M + 1 | 0.02 | 0.3 | 103 | 20.6 |
| 169 | 387 | M + 1 | 0.2 | 0.3 | | |
| 170 | 442 | M + 23 | 0.05 | 0.3 | | |
| 171 | 349 | M + 1 | 0.1 | 0.3 | | |
| 172 | 407 | M + 1 | 0.02 | 0.3 | | |
| 173 | 440 | M + 1 | 0.07 | 0.3 | | |
| 174 | 409 | M + 1 | 0.05 | 0.3 | | |
| 175 | 414 | M + 1 | 0.07 | 0.3 | | |
| 176 | 431 | M + 1 | 0.1 | 0.3 | >200 | 19.9 |
| 177 | 352 | M + 1 | 0.1 | 0.4 | | |
| 178 | 393 | M + 1 | 0.01 | 0.4 | | |
| 179 | 393 | M + 1 | 0.01 | 0.4 | | |
| 180 | 421 | M + 1 | 0.03 | 0.4 | | |
| 181 | 430 | M + 23 | 0.03 | 0.4 | | |
| 182 | 407 | M + 1 | 0.02 | 0.4 | | |
| 183 | 413 | M + 1 | 0.09 | 0.4 | | |
| 184 | 393 | M + 1 | 0.01 | 0.4 | | |
| 185 | 413 | M + 1 | 0.1 | 0.4 | | |
| 186 | 435 | M + 23 | 0.03 | 0.4 | | |
| 187 | 409 | M + 1 | 0.02 | 0.4 | | |
| 188 | 513 | M + 1 | 0.02 | 0.4 | | |
| 189 | 407 | M + 1 | 0.006 | 0.4 | | |
| 190 | 429 | M + 1 | 0.008 | 0.4 | | |
| 191 | 389 | M + 23 | 0.03 | 0.4 | | |
| 192 | 367 | M + 1 | 0.03 | 0.4 | | |
| 193 | 473 | M + 23 | 0.1 | 0.4 | | |
| 194 | 354 | M + 1 | 0.1 | 0.4 | >200 | >200 |
| 195 | 410 | M + 1 | 0.04 | 0.4 | | |
| 196 | 336 | M + 1 | 0.1 | 0.4 | | |
| 197 | 349 | M + 1 | 0.1 | 0.4 | | |
| 198 | 382 | M + 1 | 0.07 | 0.4 | | |
| 199 | 407 | M + 1 | 0.05 | 0.4 | | |
| 200 | 381 | M + 1 | 0.05 | 0.4 | | |
| 201 | 409 | M + 1 | 0.09 | 0.4 | | |
| 202 | 409 | M + 1 | 0.02 | 0.4 | | |
| 203 | 411 | M + 1 | 0.01 | 0.4 | | |
| 204 | 397 | M + 1 | 0.08 | 0.4 | | |
| 205 | 409 | M + 1 | 0.03 | 0.4 | | |
| 206 | 493 | M + 23 | 0.09 | 0.4 | | |
| 207 | 437 | M + 1 | 0.1 | 0.4 | | |
| 208 | 438 | M + 1 | 0.06 | 0.4 | | |
| 209 | 368 | M + 1 | 0.2 | 0.4 | | |
| 210 | 411 | M + 1 | 0.03 | 0.4 | 122 | 7.94 |
| 211 | 360 | M + 1 | 0.1 | 0.4 | | |
| 212 | 421 | M + 1 | 0.02 | 0.4 | | |
| 213 | 434 | M + 1 | 0.007 | 0.5 | | |
| 214 | 445 | M + 23 | 0.1 | 0.5 | | |
| 215 | 385 | M + 1 | 0.07 | 0.5 | | |
| 216 | 368 | M + 1 | 0.1 | 0.5 | | |
| 217 | 380 | M + 1 | 0.01 | 0.5 | | |
| 218 | 366 | M + 1 | 0.07 | 0.5 | | |
| 219 | 379 | M + 1 | 0.06 | 0.5 | | |
| 220 | 393 | M + 1 | 0.04 | 0.5 | | |
| 221 | 335 | M + 1 | 0.1 | 0.5 | | |
| 222 | 409 | M + 1 | 0.02 | 0.5 | | |
| 223 | 411 | M + 1 | 0.09 | 0.5 | | |
| 224 | 325 | M + 1 | 0.2 | 0.5 | | |
| 225 | 409 | M + 1 | 0.03 | 0.5 | 90.7 | 8.66 |
| 226 | 423 | M + 1 | 0.06 | 0.5 | | |
| 227 | 455 | M + 1 | 0.03 | 0.5 | | |
| 228 | 425 | M + 1 | 0.08 | 0.5 | | |
| 229 | 435 | M + 1 | 0.1 | 0.5 | | |
| 230 | 452 | M + 1 | 0.04 | 0.5 | | |
| 231 | 405 | M + 1 | 0.1 | 0.5 | | |
| 232 | 407 | M + 1 | 0.06 | 0.5 | | |
| 233 | 389 | M + 1 | 0.05 | 0.5 | | |
| 234 | 367 | M + 1 | 0.07 | 0.5 | >200 | 120 |
| 235 | 385 | M + 1 | 0.1 | 0.5 | | |
| 236 | 393 | M + 1 | 0.2 | 0.6 | | |
| 237 | 350 | M + 1 | 0.1 | 0.6 | | |
| 238 | 320 | M + 1 | 0.2 | 0.6 | >200 | >200 |
| 239 | 349 | M + 1 | 0.2 | 0.6 | | |
| 240 | 433 | M + 23 | 0.02 | 0.6 | 131 | 14.2 |
| 241 | 407 | M + 1 | 0.01 | 0.6 | | |
| 242 | 463 | M + 1 | 0.1 | 0.6 | | |
| 243 | 395 | M + 1 | 0.05 | 0.6 | 104 | 3.14 |
| 244 | 395 | M + 1 | 0.08 | 0.6 | | |
| 245 | 393 | M + 1 | 0.01 | 0.6 | | |
| 246 | 443 | M + 1 | 0.009 | 0.6 | | |
| 247 | 406 | M + 1 | 0.05 | 0.6 | | |
| 248 | 409 | M + 1 | 0.1 | 0.6 | | |
| 249 | 337 | M + 1 | 0.2 | 0.6 | | |
| 250 | 380 | M + 1 | 0.1 | 0.6 | | |
| 251 | 406 | M + 1 | 0.01 | 0.6 | | |
| 252 | 335 | M + 1 | 0.2 | 0.6 | | |
| 253 | 439 | M + 1 | 0.05 | 0.6 | | |
| 254 | 447 | M + 23 | 0.06 | 0.6 | | |
| 255 | 419 | M + 1 | 0.03 | 0.6 | | |
| 256 | 354 | M + 1 | 0.2 | 0.6 | | |
| 257 | 407 | M + 1 | 0.2 | 0.6 | | |
| 258 | 514 | M + 1 | 0.04 | 0.6 | | |
| 259 | 471 | M + 1 | 0.1 | 0.6 | | |
| 260 | 453 | M + 1 | 0.2 | 0.7 | | |
| 261 | 336 | M + 1 | 0.08 | 0.7 | | |
| 262 | 396 | M + 1 | 0.2 | 0.7 | | |
| 263 | 424 | M + 23 | 0.7 | 0.7 | | |

TABLE 1B-continued

| Cpd. No. | Mass | Mass Ion Species | SETD2 (1434-1711) | SETD2 A549 | SMYD2 | SMYD3 |
|---|---|---|---|---|---|---|
| 264 | 380 | M + 1 | 0.02 | 0.7 | | |
| 265 | 384 | M + 1 | 0.2 | 0.7 | | |
| 266 | 402 | M + 1 | 0.06 | 0.7 | | |
| 267 | 455 | M + 1 | 0.01 | 0.7 | | |
| 268 | 465 | M + 1 | 0.06 | 0.7 | | |
| 269 | 368 | M + 1 | 0.1 | 0.7 | | |
| 270 | 381 | M + 1 | 0.05 | 0.8 | | |
| 271 | 399 | M + 1 | 0.2 | 0.8 | | |
| 272 | 385 | M + 1 | 0.1 | 0.8 | | |
| 273 | 434 | M + 1 | 0.2 | 0.8 | | |
| 274 | 427 | M + 1 | 0.04 | 0.8 | | |
| 276 | 393 | M + 1 | 0.09 | 0.9 | | |
| 277 | 397 | M + 1 | 0.2 | 0.9 | | |
| 278 | 385 | M + 1 | 0.07 | 0.9 | | |
| 279 | 381 | M + 1 | 0.04 | 0.9 | | |
| 280 | 409 | M + 1 | 0.1 | 0.9 | | |
| 281 | 336 | M + 1 | 0.2 | 0.9 | | |
| 282 | 380 | M + 1 | 0.04 | 1.0 | | |
| 283 | 338 | M + 1 | 0.04 | 1.0 | | |
| 284 | 366 | M + 1 | 0.2 | 1.0 | | |
| 285 | 346 | M + 1 | 0.04 | 1.0 | | |
| 286 | 385 | M + 1 | 0.1 | 1.0 | | |
| 287 | 380 | M + 1 | 0.2 | 1.0 | | |
| 288 | 368 | M + 1 | 0.3 | 1.0 | | |
| 289 | 382 | M + 1 | 0.4 | 1.1 | | |
| 290 | 385 | M + 1 | 0.4 | 1.1 | | |
| 291 | 380 | M + 1 | 0.3 | 1.1 | | |
| 292 | 429 | M + 23 | 0.7 | 1.1 | | |
| 293 | 354 | M + 1 | 0.4 | 1.1 | | |
| 294 | 406 | M + 1 | 0.03 | 1.1 | | |
| 295 | 397 | M + 1 | 0.3 | 1.1 | | |
| 296 | 337 | M + 1 | 0.1 | 1.1 | | |
| 297 | 352 | M + 1 | 0.1 | 1.1 | | |
| 298 | 445 | M + 23 | 0.3 | 1.1 | | |
| 299 | 385 | M + 1 | 0.2 | 1.1 | | |
| 300 | 326 | M + 1 | 0.2 | 1.2 | | |
| 301 | 435 | M + 23 | 0.1 | 1.2 | | |
| 302 | 380 | M + 1 | 0.03 | 1.2 | | |
| 303 | 409 | M + 1 | 0.06 | 1.2 | | |
| 304 | 358 | M + 23 | 0.3 | 1.2 | | |
| 305 | 431 | M + 1 | 0.5 | 1.2 | | |
| 306 | 394 | M + 1 | 0.4 | 1.2 | | |
| 307 | 354 | M + 1 | 0.2 | 1.2 | | |
| 308 | 409 | M + 1 | 0.1 | 1.3 | | |
| 309 | 400 | M + 1 | 0.2 | 1.3 | >200 | >200 |
| 310 | 367 | M + 1 | 0.05 | 1.3 | | |
| 311 | 445 | M + 1 | 0.03 | 1.3 | | |
| 312 | 429 | M + 1 | 0.8 | 1.3 | | |
| 313 | 412 | M + 1 | 0.03 | 1.3 | | |
| 314 | 403 | M + 23 | 0.04 | 1.3 | | |
| 315 | 349 | M + 23 | 0.6 | 1.4 | | |
| 316 | 347 | M + 1 | 0.1 | 1.4 | | |
| 317 | 446 | M + 1 | 0.1 | 1.4 | | |
| 318 | 381 | M + 1 | 0.2 | 1.4 | | |
| 319 | 352 | M + 1 | 0.1 | 1.4 | | |
| 320 | 381 | M + 1 | 0.2 | 1.4 | | |
| 321 | 367 | M + 1 | 0.2 | 1.5 | | |
| 322 | 335 | M + 1 | 0.5 | 1.5 | | |
| 323 | 356 | M + 1 | 0.07 | 1.5 | | |
| 324 | 380 | M + 1 | 0.05 | 1.5 | | |
| 325 | 381 | M + 1 | 0.07 | 1.5 | | |
| 326 | 375 | M + 1 | 0.2 | 1.6 | | |
| 327 | 352 | M + 1 | 0.5 | 1.6 | | |
| 328 | 391 | M + 1 | 0.04 | 1.6 | 129 | 91.9 |
| 329 | 340 | M + 1 | 0.6 | 1.6 | | |
| 330 | 367 | M + 1 | 0.07 | 1.6 | | |
| 331 | 398 | M + 1 | 0.6 | 1.6 | | |
| 332 | 338 | M + 1 | 0.2 | 1.6 | | |
| 333 | 402 | M + 1 | 0.3 | 1.6 | | |
| 334 | 439 | M + 1 | 0.7 | 1.6 | | |
| 335 | 395 | M + 1 | 0.08 | 1.6 | | |
| 336 | 394 | M + 1 | 0.4 | 1.6 | | |
| 337 | 335 | M + 1 | 0.4 | 1.6 | | |
| 338 | 407 | M + 1 | 0.1 | 1.7 | | |
| 339 | 428 | M + 1 | 0.04 | 1.7 | | |
| 340 | 368 | M + 1 | 0.2 | 1.7 | 165 | 16.7 |
| 341 | 313 | M + 1 | 0.2 | 1.7 | | |
| 342 | 381 | M + 1 | 0.1 | 1.8 | | |
| 343 | 394 | M + 1 | 0.08 | 1.8 | | |
| 344 | 368 | M + 1 | 0.2 | 1.8 | | |
| 345 | 420 | M + 1 | 0.06 | 1.8 | | |
| 346 | 375 | M + 1 | 0.1 | 1.8 | | |
| 347 | 436 | M + 1 | 0.003 | 1.9 | | |
| 348 | 379 | M + 1 | 0.07 | 1.9 | | |
| 349 | 393 | M + 1 | 0.2 | 2.0 | | |
| 350 | 418 | M + 1 | 0.08 | >2 | | |
| 351 | 395 | M + 1 | 0.09 | >2 | | |
| 352 | 380 | M + 1 | 0.1 | >2 | | |
| 353 | 454 | M + 1 | 0.1 | >2 | | |
| 354 | 385 | M + 1 | 0.3 | >2 | | |
| 355 | 407 | M + 1 | 0.5 | >2 | | |
| 356 | 432 | M + 1 | 0.6 | >2 | | |
| 357 | 349 | M + 1 | 0.7 | >2 | | |
| 358 | 487 | M + 1 | 0.9 | >2 | | |
| 359 | 401 | M + 1 | 0.9 | >2 | | |
| 360 | 416 | M + 1 | 1.2 | >2 | | |
| 361 | 353 | M + 1 | 1.3 | >2 | | |
| 362 | 374 | M + 1 | 1.4 | >2 | | |
| 363 | 403 | M + 1 | 1.5 | >2 | | |
| 364 | 338 | M + 1 | 2.0 | >2 | | |
| 365 | 407 | M + 1 | 2.6 | >2 | | |
| 366 | 401 | M + 1 | 3.0 | >2 | | |
| 367 | 387 | M + 1 | 4.2 | >2 | | |
| 368 | 355 | M + 1 | 6.1 | >2 | | |
| 369 | 353 | M + 1 | 6.3 | >2 | | |
| 370 | 401 | M + 1 | 6.8 | >2 | | |
| 371 | 356 | M + 1 | >10 | >2 | | |
| 372 | 401 | M + 1 | >10 | >2 | | |
| 373 | 401 | M + 1 | >10 | >2 | | |
| 374 | 360 | M + 1 | >10 | >2 | | |
| 375 | 463 | M + 1 | >10 | >2 | | |
| 376 | 387 | M + 1 | >10 | >2 | | |
| 377 | 361 | M + 1 | >10 | >2 | | |
| 378 | 375 | M + 1 | >10 | >2 | | |
| 379 | 353 | M + 1 | >10 | >2 | | |
| 380 | 353 | M + 1 | >10 | >2 | | |
| 381 | 360 | M + 1 | >10 | >2 | | |
| 382 | 387 | M + 1 | >10 | >2 | | |
| 383 | 401 | M + 1 | >10 | >2 | | |
| 384 | 347 | M + 1 | >10 | >2 | | |
| 385 | 415 | M + 1 | >10 | >2 | | |
| 386 | 361 | M + 1 | >10 | >2 | | |
| 387 | 401 | M + 1 | >10 | >2 | | |
| 388 | 374 | M + 1 | >10 | >2 | | |
| 389 | 433 | M + 44 | >10 | >2 | | |
| 390 | 366 | M + 1 | 0.5 | 2.0 | | |
| 391 | 407 | M + 1 | 0.2 | 2.0 | | |
| 392 | 421 | M + 1 | 0.06 | 2.0 | 76.6 | 79.7 |
| 393 | 336 | M + 1 | 0.7 | 2.0 | | |
| 394 | 349 | M + 1 | 0.2 | 2.1 | | |
| 395 | 365 | M + 43 | 0.1 | 2.2 | | |
| 396 | 392 | M + 1 | 0.3 | 2.3 | >200 | 24 |
| 397 | 350 | M + 1 | 0.5 | 2.4 | | |
| 398 | 423 | M + 1 | 0.07 | 2.4 | | |
| 399 | 347 | M + 1 | 1.8 | 2.4 | | |
| 400 | 377 | M + 1 | 0.3 | 2.4 | 73.8 | 1.37 |
| 401 | 418 | M + 1 | 0.03 | 2.4 | | |
| 402 | 496 | M + 1 | 0.3 | 2.5 | | |
| 403 | 324 | M + 1 | 2.5 | 2.7 | | |
| 404 | 398 | M + 1 | 0.3 | 2.8 | >200 | >200 |
| 405 | 498 | M + 1 | 0.4 | 2.8 | | |
| 406 | 397 | M + 1 | 0.3 | 2.8 | >200 | 7.92 |
| 407 | 381 | M + 1 | 0.3 | 2.8 | 148 | 98.1 |
| 408 | 370 | M + 1 | 0.4 | 2.9 | >200 | >200 |
| 409 | 432 | M + 1 | 0.1 | 3.0 | 59.5 | 9.81 |
| 410 | 368 | M + 1 | 0.7 | 3.0 | | |
| 411 | 407 | M + 1 | 0.8 | 3.0 | | |
| 412 | 478 | M + 1 | 0.1 | 3.1 | 108 | 58.4 |
| 413 | 410 | M + 1 | 0.03 | 3.1 | 66.9 | 6.75 |
| 414 | 528 | M + 1 | 0.08 | 3.2 | | |
| 415 | 435 | M + 1 | 0.1 | 3.2 | | |
| 416 | 419 | M + 1 | 0.04 | 3.3 | 21.2 | 16.5 |

TABLE 1B-continued

| Cpd. No. | Mass | Mass Ion Species | SETD2 (1434-1711) | SETD2 A549 | SMYD2 | SMYD3 |
|---|---|---|---|---|---|---|
| 417 | 457 | M + 1 | 0.9 | 3.4 | | |
| 418 | 312 | M + 1 | 0.1 | 3.4 | | |
| 419 | 340 | M + 1 | 0.8 | 3.4 | | |
| 420 | 421 | M + 1 | 2.4 | 3.6 | | |
| 421 | 381 | M + 1 | 0.4 | 3.6 | >200 | 105 |
| 422 | 388 | M + 23 | 1.5 | 3.7 | | |
| 423 | 536 | M + 1 | 0.6 | 3.8 | | |
| 424 | 377 | M + 1 | 0.7 | 3.8 | | |
| 425 | 338 | M + 1 | 0.3 | 3.9 | | |
| 426 | 412 | M + 1 | 0.4 | 3.9 | | |
| 427 | 348 | M + 1 | 0.4 | 4.0 | | |
| 428 | 335 | M + 1 | 1.0 | 4.1 | | |
| 429 | 496 | M + 1 | 0.1 | 4.3 | 87.1 | 9.66 |
| 430 | 500 | M + 1 | 0.6 | 4.4 | | |
| 431 | 447 | M + 1 | 2.1 | 4.4 | | |
| 432 | 363 | M + 1 | 0.7 | 4.5 | | |
| 433 | 447 | M + 1 | 0.03 | 4.6 | 81.4 | 22.5 |
| 434 | 435 | M + 1 | 4.3 | 4.6 | | |
| 435 | 446 | M + 1 | 0.7 | 4.7 | | |
| 436 | 421 | M + 1 | 0.3 | 4.7 | | |
| 437 | 302 | M + 1 | 0.6 | 4.8 | | |
| 438 | 352 | M + 1 | 0.3 | 4.9 | | |
| 439 | 406 | M + 1 | 0.2 | 5.0 | >200 | 20.9 |
| 440 | 523 | M + 1 | 0.8 | 5.0 | | |
| 441 | 482 | M + 23 | 4.4 | 5.1 | | |
| 442 | 364 | M + 1 | 2.1 | 5.1 | | |
| 443 | 443 | M + 1 | 0.6 | 5.1 | | |
| 444 | 350 | M + 1 | 0.4 | 5.2 | | |
| 445 | 386 | M + 1 | 1.4 | 5.2 | | |
| 446 | 379 | M + 1 | 6.3 | 5.4 | | |
| 447 | 482 | M + 1 | 2.8 | 5.5 | | |
| 448 | 427 | M + 1 | 0.9 | 5.5 | | |
| 449 | 442 | M + 1 | 0.2 | 5.5 | 136 | 9.32 |
| 450 | 339 | M + 1 | 2.3 | 5.6 | | |
| 451 | 432 | M + 1 | 0.4 | 5.6 | | |
| 452 | 392 | M + 1 | 0.06 | 5.7 | 160 | 52.5 |
| 453 | 413 | M + 1 | 0.7 | 5.8 | | |
| 454 | 348 | M + 1 | 2.8 | 5.9 | | |
| 455 | 432 | M + 1 | 0.4 | 5.9 | | |
| 456 | 364 | M + 1 | 1.4 | 6.1 | | |
| 457 | 340 | M + 1 | 0.5 | 6.1 | >200 | >200 |
| 458 | 338 | M + 1 | 2.2 | 6.2 | | |
| 459 | 291 | M + 1 | 1.5 | 6.2 | | |
| 460 | 457 | M + 1 | 4.5 | 6.2 | | |
| 461 | 529 | M + 1 | 0.5 | 6.3 | | |
| 462 | 338 | M + 1 | 0.7 | 6.3 | | |
| 463 | 320 | M + 1 | 1.2 | 6.4 | | |
| 464 | 435 | M + 1 | 8.4 | 6.6 | | |
| 465 | 414 | M + 1 | 0.4 | 6.6 | 136 | 72.3 |
| 466 | 303 | M + 1 | 1.9 | 7.0 | | |
| 467 | 378 | M + 1 | 0.4 | 7.3 | | |
| 468 | 411 | M + 1 | 0.9 | 7.5 | | |
| 469 | 363 | M + 1 | 1.4 | 7.9 | | |
| 470 | 460 | M + 1 | 0.6 | 8.0 | | |
| 471 | 308 | M + 1 | 5.4 | 8.5 | | |
| 472 | 370 | M + 1 | 0.9 | 8.5 | | |
| 473 | 401 | M + 1 | 0.2 | 8.8 | | |
| 474 | 322 | M + 1 | 4.2 | 8.9 | | |
| 475 | 320 | M + 1 | 2.1 | 8.9 | | |
| 476 | 456 | M + 1 | 0.8 | 9.1 | | |
| 477 | 432 | M + 1 | 2.1 | 9.3 | | |
| 478 | 350 | M + 1 | 4.1 | 9.4 | | |
| 479 | 251 | M + 1 | 4.2 | 9.5 | | |
| 480 | 294 | M + 1 | 7.0 | 9.5 | | |
| 481 | 378 | M + 1 | 1.9 | 9.7 | | |
| 482 | 334 | M + 1 | 2.2 | 10.2 | | |
| 483 | 378 | M + 1 | 4.1 | 10.3 | | |
| 484 | 292 | M + 1 | 7.6 | 10.6 | | |
| 485 | 449 | M + 1 | 10.0 | 10.8 | | |
| 486 | 336 | M + 1 | 1.8 | 10.8 | | |
| 487 | 400 | M + 1 | 1.6 | 11.0 | | |
| 488 | 363 | M + 1 | 2.5 | 11.8 | | |
| 489 | 379 | M + 1 | 7.9 | 11.8 | | |
| 490 | 350 | M + 1 | 6.5 | 12.1 | | |
| 491 | 355 | M + 1 | 12.1 | 12.2 | | |
| 492 | 335 | M + 1 | >50 | 12.5 | | |
| 493 | 321 | M + 1 | >50 | 13.1 | | |
| 494 | 435 | M + 1 | 6.0 | 13.2 | | |
| 495 | 362 | M + 1 | 1.8 | 13.3 | | |
| 496 | 460 | M + 1 | 0.4 | 13.4 | >200 | 79 |
| 497 | 338 | M + 1 | 5.5 | 13.8 | | |
| 498 | 324 | M + 1 | 9.4 | 13.8 | | |
| 499 | 391 | M + 1 | 9.1 | 13.9 | | |
| 500 | 334 | M + 1 | 3.0 | 14.5 | | |
| 501 | 350 | M + 1 | 0.4 | 14.6 | | |
| 502 | 351 | M + 1 | 0.5 | 14.7 | | |
| 503 | 327 | M + 1 | 9.7 | 14.8 | | |
| 504 | 271 | M + 1 | 3.8 | 14.9 | | |
| 505 | 259 | M + 1 | 11.2 | 14.9 | | |
| 506 | 336 | M + 1 | 4.9 | 15.1 | | |
| 507 | 374 | M + 1 | 1.1 | 15.1 | | |
| 508 | 356 | M + 1 | 10.4 | 15.2 | | |
| 509 | 403 | M + 1 | 22.4 | 15.4 | | |
| 510 | 432 | M + 1 | 0.6 | 15.5 | | |
| 511 | 364 | M + 1 | 11.6 | 15.8 | | |
| 512 | 354 | M + 23 | 13.2 | 16.1 | | |
| 513 | 334 | M + 1 | 4.0 | 17.4 | | |
| 514 | 451 | M + 1 | 24.9 | 18.3 | | |
| 515 | 437 | M + 1 | 25.1 | 18.5 | | |
| 516 | 446 | M + 1 | 0.4 | 18.5 | | |
| 517 | 403 | M + 1 | 3.7 | 18.5 | | |
| 518 | 321 | M + 1 | 50.0 | 18.9 | | |
| 519 | 374 | M + 1 | 50.0 | 19.3 | | |
| 520 | 334 | M + 1 | 12.3 | 19.8 | | |
| 521 | 334 | M + 1 | 6.9 | 19.9 | | |
| 522 | 257 | M + 1 | 10.6 | 20.6 | | |
| 523 | 428 | M + 1 | 8.8 | 20.8 | | |
| 524 | 351 | M + 1 | 1.5 | 20.9 | | |
| 525 | 415 | M + 1 | 12.6 | 20.9 | | |
| 526 | 301 | M + 1 | 1.9 | 22.6 | | |
| 527 | 362 | M + 1 | 14.7 | 24.2 | | |
| 528 | 334 | M + 1 | 10.0 | 24.6 | | |
| 529 | 474 | M + 1 | 8.6 | 24.9 | | |
| 530 | 450 | M + 1 | 0.007 | >25 | 51 | 7.13 |
| 531 | 393 | M + 1 | 0.2 | >25 | 83.3 | 9.57 |
| 532 | 351 | M + 1 | 0.2 | >25 | | |
| 533 | 303 | M + 1 | 0.4 | >25 | | |
| 534 | 339 | M + 18 | 0.4 | >25 | | |
| 535 | 418 | M + 1 | 0.6 | >25 | | |
| 536 | 366 | M + 1 | 0.8 | >25 | | |
| 537 | 376 | M + 1 | 0.9 | >25 | | |
| 538 | 319 | M + 1 | 1.0 | >25 | | |
| 539 | 443 | M + 1 | 1.6 | >25 | | |
| 540 | 395 | M + 1 | 1.7 | >25 | | |
| 541 | 401 | M + 1 | 2.0 | >25 | | |
| 542 | 396 | M + 1 | 2.4 | >25 | | |
| 543 | 357 | M + 1 | 2.6 | >25 | | |
| 544 | 382 | M + 1 | 2.9 | >25 | | |
| 545 | 353 | M + 1 | 3.1 | >25 | | |
| 546 | 348 | M + 1 | 3.9 | >25 | | |
| 547 | 402 | M + 1 | 4.0 | >25 | | |
| 548 | 356 | M + 1 | 5.1 | >25 | | |
| 549 | 433 | M + 1 | 5.8 | >25 | | |
| 550 | 417 | M + 1 | 6.5 | >25 | | |
| 551 | 362 | M + 1 | 6.7 | >25 | | |
| 552 | 369 | M + 1 | 7.7 | >25 | | |
| 553 | 407 | M + 1 | 8.3 | >25 | | |
| 554 | 363 | M + 1 | 8.7 | >25 | | |
| 555 | 441 | M + 1 | 9.2 | >25 | | |
| 556 | 355 | M + 1 | 9.9 | >25 | | |
| 557 | 358 | M + 1 | >10 | >25 | | |
| 558 | 356 | M + 1 | >10 | >25 | | |
| 559 | 357 | M + 1 | >10 | >25 | | |
| 560 | 397 | M + 1 | >10 | >25 | | |
| 561 | 356 | M + 1 | >10 | >25 | | |
| 562 | 356 | M + 1 | >10 | >25 | | |
| 563 | 348 | M + 1 | 10.1 | >25 | | |
| 564 | 360 | M + 1 | 10.9 | >25 | | |
| 565 | 384 | M + 1 | 11.6 | >25 | | |
| 566 | 421 | M + 1 | 12.9 | >25 | | |
| 567 | 406 | M + 1 | 13.6 | >25 | | |
| 568 | 336 | M + 1 | 13.9 | >25 | | |

TABLE 1B-continued

| Cpd. No. | Mass | Mass Ion Species | SETD2 (1434-1711) | SETD2 A549 | SMYD2 | SMYD3 |
|---|---|---|---|---|---|---|
| 569 | 356 | M + 1 | 14.0 | >25 | | |
| 570 | 305 | M + 1 | 15.0 | >25 | | |
| 571 | 421 | M + 1 | 15.9 | >25 | | |
| 572 | 420 | M + 1 | 16.6 | >25 | | |
| 573 | 432 | M + 1 | 16.9 | >25 | | |
| 574 | 336 | M + 1 | 17.3 | >25 | | |
| 575 | 350 | M + 1 | >18 | >25 | | |
| 576 | 336 | M + 1 | 18.6 | >25 | | |
| 577 | 431 | M + 1 | 21.8 | >25 | | |
| 578 | 291 | M + 1 | 22.5 | >25 | | |
| 579 | 448 | M + 1 | 23.0 | >25 | | |
| 580 | 345 | M + 1 | 24.5 | >25 | | |
| 581 | 393 | M + 1 | 28.2 | >25 | | |
| 582 | 393 | M + 1 | 31.2 | >25 | | |
| 583 | 431 | M + 1 | 32.4 | >25 | | |
| 584 | 432 | M + 1 | 33.7 | >25 | | |
| 585 | 341 | M + 1 | 34.0 | >25 | | |
| 586 | 351 | M + 1 | 36.4 | >25 | | |
| 587 | 411 | M + 1 | 37.4 | >25 | | |
| 588 | 357 | M + 1 | 40.4 | >25 | | |
| 589 | 399 | M + 1 | 43.6 | >25 | | |
| 590 | 357 | M + 1 | 50.0 | >25 | | |
| 591 | 321 | M + 1 | >50 | >25 | | |
| 592 | 343 | M + 1 | >50 | >25 | | |
| 593 | 329 | M + 1 | >50 | >25 | | |
| 594 | 315 | M + 1 | >50 | >25 | | |
| 595 | 308 | M + 1 | >50 | >25 | | |
| 596 | 315 | M + 1 | >50 | >25 | | |
| 597 | 315 | M + 1 | >50 | >25 | | |
| 598 | 321 | M + 1 | >50 | >25 | | |
| 599 | 321 | M + 1 | >50 | >25 | | |
| 600 | 329 | M + 1 | >50 | >25 | | |
| 601 | 393 | M + 1 | >50 | >25 | | |
| 602 | 339 | M + 1 | >50 | >25 | | |
| 603 | 323 | M + 1 | >50 | >25 | | |
| 604 | 308 | M + 1 | >50 | >25 | | |
| 605 | 391 | M + 1 | >50 | >25 | | |
| 606 | 350 | M + 1 | >50 | >25 | | |
| 607 | 322 | M + 1 | >50 | >25 | | |
| 608 | 321 | M + 1 | >50 | >25 | | |
| 609 | 320 | M + 1 | >50 | >25 | | |
| 612 | 368 | M + 1 | >50 | >25 | | |
| 613 | 320 | M + 1 | 51.5 | >25 | | |
| 614 | 357 | M + 1 | 62.7 | >25 | | |
| 615 | 363 | M + 1 | 71.1 | >25 | | |
| 616 | 295 | M + 1 | 105.0 | >25 | | |
| 617 | 362 | M + 1 | >200 | >25 | | |
| 618 | 386 | M + 1 | >200 | >25 | | |
| 619 | 331 | M + 1 | >200 | >25 | | |
| 620 | 334 | M + 1 | >200 | >25 | | |
| 622 | 398 | M + 1 | >200 | >25 | | |
| 623 | 292 | M + 1 | >200 | >25 | | |
| 624 | 364 | M + 1 | 10.9 | | | |
| 625 | 369 | M + 1 | 11.0 | | | |
| 626 | 336 | M + 1 | 12.5 | | | |
| 627 | 337 | M + 1 | 13.2 | | | |
| 628 | 330 | M + 1 | 13.3 | | | |
| 629 | 357 | M + 1 | 14.5 | | | |
| 630 | 329 | M + 1 | 14.6 | | | |
| 631 | 355 | M + 1 | 15.3 | | | |
| 632 | 252 | M + 1 | 15.6 | | | |
| 633 | 351 | M + 1 | 16.2 | | | |
| 634 | 371 | M + 1 | 16.3 | | | |
| 635 | 384 | M + 1 | 16.5 | | | |
| 636 | 349 | M + 1 | 16.8 | | | |
| 637 | 343 | M + 1 | 17.5 | | | |
| 638 | 308 | M + 1 | 18.1 | | | |
| 639 | 343 | M + 1 | 18.5 | | | |
| 640 | 369 | M + 1 | 18.5 | | | |
| 641 | 357 | M + 1 | 18.5 | | | |
| 642 | 351 | M + 1 | 18.6 | | | |
| 643 | 292 | M + 1 | 18.6 | | | |
| 644 | 357 | M + 1 | 19.5 | | | |
| 645 | 357 | M + 1 | 19.9 | | | |
| 646 | 379 | M + 1 | 20.3 | | | |
| 648 | 327 | M + 1 | 22.3 | | | |
| 649 | 343 | M + 1 | 22.3 | | | |
| 650 | 343 | M + 1 | >23 | | | |
| 652 | 345 | M + 1 | 24.8 | | | |
| 653 | 398 | M + 1 | >25 | | | |
| 654 | 269 | M + 1 | 25.1 | | | |
| 655 | 357 | M + 1 | 25.1 | | | |
| 656 | 369 | M + 1 | 25.2 | | | |
| 657 | 369 | M + 1 | 25.7 | | | |
| 658 | 338 | M + 1 | 26.8 | | | |
| 659 | 367 | M + 1 | 27.4 | | | |
| 660 | 306 | M + 1 | 27.9 | | | |
| 661 | 379 | M + 1 | 28.7 | | | |
| 662 | 287 | M + 1 | 29.7 | | | |
| 663 | 379 | M + 1 | 31.5 | | | |
| 664 | 343 | M + 1 | 31.7 | | | |
| 665 | 253 | M + 1 | 32.7 | | | |
| 666 | 337 | M + 1 | >33 | | | |
| 667 | 363 | M + 1 | 34.5 | | | |
| 668 | 299 | M + 1 | 34.5 | | | |
| 669 | 415 | M + 1 | 35.2 | | | |
| 670 | 300 | M + 1 | 35.4 | | | |
| 671 | 338 | M + 1 | 35.4 | | | |
| 672 | 355 | M + 1 | 35.9 | | | |
| 673 | 252 | M + 1 | 36.0 | | | |
| 674 | 348 | M + 1 | 37.0 | | | |
| 675 | 329 | M + 1 | 37.7 | | | |
| 676 | 338 | M + 1 | 38.1 | | | |
| 677 | 351 | M + 1 | 39.5 | | | |
| 678 | 287 | M + 1 | 39.7 | | | |
| 679 | 334 | M + 1 | 43.1 | | | |
| 680 | 307 | M + 1 | 44.8 | | | |
| 681 | 355 | M + 1 | 45.0 | | | |
| 682 | 351 | M + 1 | 45.4 | | | |
| 683 | 371 | M + 1 | 48.2 | | | |
| 684 | 291 | M + 1 | >50 | | | |
| 685 | 369 | M + 1 | 50.5 | | | |
| 686 | 331 | M + 23 | 51.3 | | | |
| 687 | 333 | M + 1 | 51.6 | | | |
| 688 | 300 | M + 1 | 52.1 | | | |
| 689 | 306 | M + 1 | 53.3 | | | |
| 690 | 337 | M + 1 | 55.8 | | | |
| 691 | 350 | M + 1 | 56.2 | | | |
| 692 | 309 | M + 1 | 56.9 | | | |
| 693 | 269 | M + 1 | 58.9 | | | |
| 694 | 319 | M + 1 | 62.1 | | | |
| 695 | 347 | M + 23 | 62.1 | | | |
| 697 | 363 | M + 1 | 62.8 | | | |
| 698 | 314 | M + 1 | 63.0 | | | |
| 699 | 320 | M + 1 | 66.7 | | | |
| 700 | 352 | M + 1 | 68.9 | | | |
| 701 | 323 | M + 1 | 69.2 | | | |
| 702 | 270 | M + 1 | 69.6 | | | |
| 703 | 295 | M + 1 | 70.7 | | | |
| 704 | 334 | M + 1 | 70.9 | | | |
| 705 | 295 | M + 1 | 71.6 | | | |
| 706 | 336 | M + 1 | 71.9 | | | |
| 707 | 355 | M + 1 | 72.0 | | | |
| 708 | 319 | M + 1 | 74.0 | | | |
| 709 | 364 | M + 1 | 78.4 | | | |
| 710 | 306 | M + 1 | 83.4 | | | |
| 711 | 371 | M + 1 | 85.9 | | | |
| 712 | 283 | M + 1 | 86.4 | | | |
| 713 | 293 | M + 1 | 91.2 | | | |
| 714 | 329 | M + 1 | 98.9 | | | |
| 715 | 258 | M + 1 | 98.9 | | | |
| 716 | 348 | M + 1 | >100 | | | |
| 717 | 374 | M + 1 | >100 | | | |
| 718 | 305 | M + 1 | 102.7 | | | |
| 719 | 270 | M + 1 | 107.4 | | | |
| 720 | 331 | M + 1 | 108.7 | | | |
| 721 | 284 | M + 1 | 113.5 | | | |
| 722 | 349 | M + 1 | 116.2 | | | |
| 723 | 281 | M + 1 | 116.3 | | | |
| 724 | 351 | M + 1 | 117.4 | | | |
| 725 | 337 | M + 1 | 122.6 | | | |
| 726 | 333 | M + 1 | 123.7 | | | |

TABLE 1B-continued

| Cpd. No. | Mass | Mass Ion Species | SETD2 (1434-1711) | SETD2 A549 | SMYD2 | SMYD3 |
|---|---|---|---|---|---|---|
| 727 | 363 | M + 1 | 125.1 | | | |
| 728 | 351 | M + 1 | 127.4 | | | |
| 729 | 255 | M + 1 | 128.8 | | | |
| 730 | 286 | M + 1 | >130 | | | |
| 731 | 259 | M + 1 | 136.6 | | | |
| 732 | 271 | M + 1 | 136.9 | | | |
| 733 | 256 | M + 1 | 146.8 | | | |
| 735 | 285 | M + 1 | 165.4 | | | |
| 736 | 286 | M + 1 | 167.9 | | | |
| 738 | 357 | M + 1 | 179.4 | | | |
| 746 | 288 | M + 1 | >200 | | | |
| 747 | 259 | M + 1 | >200 | | | |
| 748 | 291 | M + 1 | >200 | | | |
| 749 | 279 | M + 1 | >200 | | | |
| 750 | 348 | M + 1 | >200 | | | |
| 751 | 412 | M + 1 | >200 | | | |
| 752 | 348 | M + 1 | >200 | | | |
| 753 | 305 | M + 1 | >200 | | | |
| 754 | 347 | M + 23 | >200 | | | |
| 755 | 364 | M + 1 | >200 | | | |
| 756 | 286 | M + 1 | >200 | | | |
| 757 | 364 | M + 1 | >200 | | | |
| 758 | 412 | M + 1 | >200 | | | |
| 759 | 259 | M + 1 | >200 | | | |
| 761 | 286 | M + 1 | >200 | | | |
| 763 | 261 | M + 1 | >200 | | | |
| 764 | 371 | M + 1 | >200 | | | |
| 765 | 309 | M + 1 | >200 | | | |
| 766 | 332 | M + 1 | >200 | | | |
| 767 | 335 | M + 1 | >200 | | | |
| 768 | 270 | M + 1 | >200 | | | |
| 769 | 297 | M + 1 | >200 | | | |
| 771 | 286 | M + 1 | >200 | | | |
| 773 | 379 | M + 1 | >200 | | | |
| 774 | 417 | | >200 | | | |
| 775 | 337 | M + 1 | >200 | | | |
| 776 | 355 | M + 1 | >200 | | | |
| 777 | 367 | M + 1 | >200 | | | |
| 778 | 416 | | >200 | | | |
| 779 | 306 | M + 1 | >200 | | | |
| 780 | 325 | M + 1 | >200 | | | |
| 781 | 301 | M + 1 | >200 | | | |
| 782 | 285 | M + 1 | >200 | | | |
| 783 | 351 | M + 1 | >200 | | | |
| 784 | 269 | M + 1 | >200 | | | |
| 785 | 285 | M + 1 | >200 | | | |
| 786 | 272 | M + 1 | >200 | | | |
| 787 | 287 | M + 1 | >200 | | | |
| 788 | 347 | M + 1 | >200 | | | |
| 790 | 347 | M + 1 | >200 | | | |
| 791 | 368 | M + 1 | >200 | | | |
| 793 | 336 | M + 1 | >200 | | | |
| 794 | 258 | M + 1 | >200 | | | |
| 795 | 252 | M + 1 | >200 | | | |
| 796 | 291 | M + 1 | >200 | | | |
| 797 | 329 | M + 1 | >200 | | | |
| 798 | 329 | M + 1 | >200 | | | |
| 799 | 286 | M + 1 | >200 | | | |
| 800 | 272 | M + 1 | >200 | | | |
| 801 | 319 | M + 1 | >200 | | | |
| 802 | 348 | M + 1 | >200 | | | |
| 803 | 320 | M + 1 | >200 | | | |
| 804 | 303 | M + 1 | >200 | | | |
| 805 | 346 | M + 1 | >200 | | | |
| 808 | 338 | M + 1 | >200 | | | |
| 809 | 337 | M + 1 | >200 | | | |
| 810 | 281 | M + 1 | >200 | | | |
| 811 | 282 | M + 1 | >200 | | | |
| 812 | 282 | M + 1 | >200 | | | |
| 814 | 319 | M + 1 | >200 | | | |
| 815 | 336 | M + 1 | >200 | | | |
| 816 | 362 | M + 1 | >200 | | | |
| 817 | 396 | M + 1 | >200 | | | |
| 818 | 355 | M + 1 | >200 | | | |
| 819 | 348 | M + 1 | >200 | | | |
| 820 | 331 | M + 1 | >200 | | | |
| 821 | 374 | M + 1 | >200 | | | |
| 822 | 387 | M + 1 | 8.3 | | | |
| 823 | 387 | M + 1 | 0.4 | 0.4 | | |
| 824 | 431 | M + 1 | 0.01 | 0.04 | >200 | >200 |
| 825 | 431 | M + 1 | 1.2 | | | |
| 826 | 441 | M + 1 | 0.1 | 0.5 | | |
| 827 | 441 | M + 1 | 7.6 | | | |
| 828 | 472 | M + 1 | 0.02 | 0.04 | >200 | >200 |
| 829 | 472 | M + 1 | 1.5 | | | |
| 830 | 427 | M + 1 | 0.04 | | | |
| 831 | 427 | M + 1 | 2.3 | | | |
| 832 | 401 | M + 1 | 0.6 | | | |
| 833 | 401 | M + 1 | 0.04 | 0.4 | | |
| 834 | 401 | M + 1 | 5.0 | | | |
| 835 | 401 | M + 1 | 0.1 | | | |
| 836 | 401 | M + 1 | 4.0 | | | |
| 837 | 429 | M + 1 | 0.02 | 0.1 | | |
| 838 | 429 | M + 1 | | | | |
| 839 | 415 | M + 1 | 0.01 | 0.04 | | |
| 840 | 415 | M + 1 | 0.9 | >2 | | |
| 841 | 415 | M + 1 | 0.02 | 0.1 | >200 | >200 |
| 842 | 415 | M + 1 | 4.5 | >2 | | |
| 843 | 459 | M + 1 | 0.2 | 0.8 | | |
| 844 | 459 | M + 1 | 8.5 | >2 | | |
| 845 | 429 | M + 1 | 6.1 | >2 | | |
| 846 | 431 | M + 1 | 0.02 | 0.1 | | |
| 847 | 431 | M + 1 | 1.0 | >2 | | |
| 848 | 415 | M + 1 | 0.02 | 0.1 | | |
| 849 | 415 | M + 1 | 5.9 | >2 | | |
| 850 | 437 | M + 1 | 0.1 | 0.2 | | |
| 851 | 437 | M + 1 | 3.2 | >2 | | |
| 852 | 396 | M + 1 | 0.1 | 1.0 | | |
| 853 | 396 | M + 1 | 9.7 | | | |
| 854 | 444 | M + 1 | 0.02 | 0.5 | | |
| 855 | 444 | M + 1 | 4.7 | >2 | | |
| 856 | 383 | M + 1 | 0.2 | 0.3 | | |
| 857 | 383 | M + 1 | 7.4 | >2 | | |
| 858 | 430 | M + 1 | 0.4 | >2 | | |
| 859 | 444 | M + 1 | 0.5 | 1.9 | | |
| 860 | 396 | M + 1 | 0.1 | 1.6 | | |
| 861 | 396 | M + 1 | 1.9 | >2 | | |
| 862 | 443 | M + 1 | 0.4 | >2 | | |
| 863 | 413 | M + 1 | 0.01 | 0.02 | 197 | >200 |
| 864 | 413 | M + 1 | 0.2 | 1.2 | | |
| 865 | 415 | M + 1 | 0.03 | 0.1 | | |
| 866 | 415 | M + 1 | 0.9 | >2 | | |
| 867 | 415 | M + 1 | 0.4 | >2 | | |
| 868 | 397 | M + 1 | 0.1 | 0.2 | | |
| 869 | 397 | M + 1 | 6.6 | >2 | | |
| 870 | 417 | M + 1 | 0.01 | 0.04 | >200 | >200 |
| 871 | 417 | M + 1 | 0.7 | 1.3 | | |
| 872 | 445 | M + 1 | 0.1 | 1.2 | | |
| 873 | 445 | M + 1 | 1.1 | >2 | | |
| 874 | 427 | M + 1 | 0.4 | >2 | | |
| 875 | 431 | M + 1 | 0.7 | >2 | | |
| 876 | 431 | M + 1 | >10 | >2 | | |
| 877 | 401 | M + 1 | >10 | >2 | | |
| 878 | 437 | M + 1 | 0.02 | 0.1 | | |
| 879 | 437 | M + 1 | 0.6 | >2 | | |
| 880 | 445 | M + 1 | 0.02 | 0.1 | | |
| 881 | 445 | M + 1 | 3.5 | >2 | | |
| 882 | 427 | M + 1 | 0.1 | 0.7 | | |
| 883 | 427 | M + 1 | 4.9 | 2.0 | | |
| 884 | 401 | M + 1 | 0.1 | 0.2 | | |
| 885 | 401 | M + 1 | 7.6 | >2 | | |
| 886 | 415 | M + 1 | 8.9 | >2 | | |
| 887 | 401 | M + 1 | 0.1 | 0.3 | | |
| 888 | 413 | M + 1 | 0.04 | 0.2 | | |
| 889 | 413 | M + 1 | 2.5 | >2 | | |
| 890 | 428 | M + 1 | 0.1 | >2 | | |
| 891 | 444 | M + 1 | 0.9 | >2 | | |
| 892 | 444 | M + 1 | >10 | >2 | | |
| 893 | 387 | M + 1 | 0.1 | 0.9 | | |
| 894 | 427 | M + 1 | 0.03 | 1.4 | | |
| 895 | 429 | M + 1 | 0.05 | 1.5 | | |
| 896 | 427 | M + 1 | 0.1 | 1.8 | | |

TABLE 1B-continued

| Cpd. No. | Mass | Mass Ion Species | SETD2 (1434-1711) | SETD2 A549 | SMYD2 | SMYD3 |
|---|---|---|---|---|---|---|
| 897 | 399 | M + 1 | 0.01 | 0.1 | | |
| 898 | 399 | M + 1 | 4.3 | >2 | | |
| 899 | 451 | M + 1 | 0.01 | 0.04 | >200 | >200 |
| 900 | 451 | M + 1 | 0.8 | >2 | | |
| 901 | 451 | M + 1 | 1.9 | >2 | | |
| 902 | 352 | M + 1 | 4.2 | >2 | | |
| 903 | 352 | M + 1 | 0.04 | 0.3 | | |
| 904 | 352 | M + 1 | 8.1 | >2 | | |
| 905 | 352 | M + 1 | 2.9 | >2 | | |
| 906 | 415 | M + 1 | 0.01 | 0.01 | >200 | >200 |
| 907 | 415 | M + 1 | 0.9 | 1.7 | | |
| 908 | 458 | M + 1 | 0.004 | 0.6 | | |
| 909 | 458 | M + 1 | 4.7 | >2 | | |
| 910 | 427 | M + 1 | 0.03 | 0.1 | | |
| 911 | 427 | M + 1 | 1.0 | >2 | | |
| 912 | 352 | M + 1 | 3.2 | >2 | | |
| 913 | 352 | M + 1 | 1.0 | >2 | | |
| 914 | 352 | M + 1 | 0.01 | 0.3 | | |
| 915 | 352 | M + 1 | 2.4 | >2 | | |
| 916 | 387 | M + 1 | 1.0 | 1.3 | | |
| 917 | 387 | M + 1 | >10 | >2 | | |
| 918 | 443 | M + 1 | 0.02 | 0.1 | | |
| 919 | 443 | M + 1 | 0.9 | >2 | | |
| 920 | 413 | M + 1 | 0.02 | 0.1 | | |
| 921 | 413 | M + 1 | 0.4 | 1.0 | | |
| 922 | 413 | M + 1 | 0.01 | 0.01 | | |
| 923 | 413 | M + 1 | 0.3 | 0.7 | | |
| 924 | 429 | M + 1 | 0.1 | 0.6 | | |
| 925 | 429 | M + 1 | 8.8 | >2 | | |
| 926 | 427 | M + 1 | 0.02 | 0.1 | | |
| 927 | 427 | M + 1 | 1.7 | >2 | | |
| 928 | 427 | M + 1 | 0.03 | 0.9 | | |
| 929 | 427 | M + 1 | 1.7 | >2 | | |
| 930 | 415 | M + 1 | 0.004 | 0.01 | | |
| 931 | 415 | M + 1 | 1.1 | >2 | | |
| 932 | 387 | M + 1 | 0.03 | 0.2 | | |
| 933 | 387 | M + 1 | 0.7 | >2 | | |
| 934 | 431 | M + 1 | 0.01 | 0.1 | | |
| 935 | 431 | M + 1 | 1.9 | >2 | | |
| 936 | 413 | M + 1 | 0.1 | 0.5 | | |
| 937 | 413 | M + 1 | 6.8 | >2 | | |
| 938 | 427 | M + 1 | 0.03 | 0.5 | | |
| 939 | 427 | M + 1 | 0.5 | >2 | | |
| 940 | 428 | M + 1 | 0.02 | >2 | | |
| 941 | 428 | M + 1 | 1.3 | >2 | | |
| 942 | 451 | M + 1 | 0.005 | 0.02 | | |
| 943 | 451 | M + 1 | 0.01 | 0.1 | | |
| 944 | 401 | M + 1 | 0.03 | 0.1 | | |
| 945 | 401 | M + 1 | 0.1 | >2 | | |
| 946 | 457 | M + 1 | 0.02 | 0.1 | | |
| 947 | 457 | M + 1 | 5.5 | >2 | | |
| 948 | 430 | M + 1 | 0.01 | 0.1 | | |
| 949 | 452 | M + 23 | 0.7 | >2 | | |
| 950 | 413 | M + 1 | 0.4 | >2 | | |
| 951 | 413 | M + 1 | 7.0 | >2 | | |
| 952 | 427 | M + 1 | 0.04 | 0.4 | | |
| 953 | 427 | M + 1 | 3.0 | >2 | | |
| 954 | 400 | M + 1 | 10.0 | >2 | | |
| 955 | 400 | M + 1 | 0.2 | 0.8 | | |
| 956 | 359 | M + 1 | 0.1 | 0.7 | | |
| 957 | 359 | M + 1 | 1.5 | >2 | | |
| 958 | 429 | M + 1 | 0.04 | 0.2 | | |
| 959 | 429 | M + 1 | 2.3 | >2 | | |
| 960 | 401 | M + 1 | 0.02 | >2 | | |
| 961 | 427 | M + 1 | 0.03 | 0.4 | | |
| 962 | 427 | M + 1 | 0.8 | >2 | | |
| 963 | 429 | M + 1 | 0.02 | 0.6 | | |
| 964 | 429 | M + 1 | 0.5 | >2 | | |
| 965 | 509 | M + 1 | 0.02 | 0.2 | | |
| 966 | 509 | M + 1 | 0.6 | >2 | | |
| 967 | 415 | M + 1 | 0.02 | 0.1 | | |
| 968 | 415 | M + 1 | 1.9 | >2 | | |
| 969 | 443 | M + 1 | 0.004 | 0.1 | | |
| 970 | 443 | M + 1 | 5.0 | >2 | | |
| 971 | 441 | M + 1 | 0.01 | 0.1 | | |
| 972 | 441 | M + 1 | 4.9 | >2 | | |
| 973 | 443 | M + 1 | 0.04 | 0.2 | | |
| 974 | 443 | M + 1 | 2.6 | >2 | | |
| 975 | 357 | M + 1 | 0.1 | 0.4 | | |
| 976 | 357 | M + 1 | 6.6 | >2 | | |
| 977 | 413 | M + 1 | 0.02 | 0.2 | | |
| 978 | 413 | M + 1 | 2.3 | >2 | | |
| 979 | 415 | M + 1 | 0.06 | 0.5 | | |
| 980 | 415 | M + 1 | 0.9 | >2 | | |
| 981 | 451 | M + 1 | 0.03 | 0.6 | | |
| 982 | 451 | M + 1 | 1.0 | >2 | | |
| 983 | 431 | M + 1 | 0.02 | 0.1 | | |
| 984 | 431 | M + 1 | 5.3 | >2 | | |
| 985 | 403 | M + 1 | 6.6 | >2 | | |
| 986 | 403 | M + 1 | 0.06 | 0.2 | | |
| 987 | 403 | M + 1 | >10 | >2 | | |
| 988 | 403 | M + 1 | 4.1 | >2 | | |
| 989 | 465 | M + 1 | 0.1 | 0.8 | | |
| 990 | 465 | M + 1 | 3.2 | >2 | | |
| 991 | 396 | M + 1 | 0.06 | 0.3 | | |
| 992 | 396 | M + 1 | 1.9 | >2 | | |
| 993 | 464 | M + 1 | 0.04 | 0.2 | | |
| 994 | 464 | M + 1 | 1.8 | >2 | | |
| 995 | 431 | M + 1 | 0.008 | 0.03 | | |
| 996 | 431 | M + 1 | 0.8 | >2 | | |
| 997 | 445 | M + 1 | 0.01 | 0.08 | | |
| 998 | 445 | M + 1 | 1.5 | >2 | | |
| 999 | 487 | M + 1 | 0.01 | 0.06 | | |
| 1000 | 487 | M + 1 | 1.5 | >2 | | |
| 1002 | 401 | M + 1 | 1.2 | 1.8 | | |
| 1003 | 353 | M + 1 | 0.03 | 0.2 | | |
| 1006 | 416 | M + 1 | 1.0 | 1.8 | | |
| 1007 | 400 | M + 1 | 0.006 | 0.02 | | |
| 1011 | 357 | M + 1 | 0.3 | 0.9 | | |
| 1012 | 372 | M + 1 | 0.2 | 1.8 | | |
| 1013 | 369 | M + 1 | 0.7056 | >2 | | |
| 1014 | 400 | M + 1 | 0.2 | 0.7 | | |
| 1018 | 469 | M + 1 | 0.03 | 0.07 | | |
| 1021 | 415 | M + 1 | 0.05 | 0.09 | | |
| 1022 | 431 | M + 1 | 2.6 | >2 | | |
| 1024 | | | 0.05 | 0.06 | | |
| 1025 | 427 | M + 1 | 0.02 | 0.03 | | |
| 1031 | 465 | M + 1 | 0.2 | 1.4 | | |
| 1032 | 415 | M + 1 | 0.2 | 0.4 | | |
| 1037 | 486 | M + 1 | 0.03 | 0.3 | | |
| 1042 | 445 | M + 1 | 0.02 | 0.2 | | |
| 1043 | 445 | M + 1 | 0.008 | 0.04 | | |
| 1044 | 449 | M + 23 | 0.02 | 0.02 | | |
| 1045 | 451 | M + 23 | 0.008 | 0.03 | | |
| 1046 | 456 | M + 1 | 2.8 | >2 | | |
| 1048 | | | 0.02 | 0.07 | | |
| 1049 | 424 | M + 1 | 0.05 | 0.1 | | |
| 1050 | 414 | M + 1 | 1.0 | >2 | | |
| 1051 | 428 | M + 1 | 0.01 | 0.03 | | |
| 1052 | | | 0.02 | 0.05 | | |
| 1053 | 445 | M + 1 | 0.03 | 0.4 | | |
| 1054 | 465 | M + 1 | 0.01 | 0.09 | | |
| 1055 | 451 | M + 23 | 0.009 | 0.005 | | |
| 1056 | | | 0.09 | 0.3 | | |
| 1057 | 426 | M + 1 | 0.04 | 0.1 | | |
| 1058 | 413 | M + 1 | 0.04 | 0.6 | | |
| 1059 | 412 | M + 1 | 0.02 | 0.6 | | |
| 1061 | 481 | M + 1 | 0.02 | 0.3 | | |
| 1062 | 429 | M + 1 | 0.01 | 0.01 | | |
| 1063 | 445 | M + 1 | 2.9 | >2 | | |
| 1064 | 375 | M + 23 | 2.3 | >2 | | |
| 1065 | 357 | M + 1 | 9.1 | >2 | | |
| 1066 | 465 | M + 1 | 5.5 | >2 | | |
| 1067 | 451 | M + 23 | 0.9 | 1.2 | | |
| 1068 | 369 | M + 1 | 0.1 | 0.7 | | |
| 1070 | 469 | M + 1 | 0.01 | 0.01 | | |
| 1071 | 469 | M + 1 | 5.2 | >2 | | |
| 1072 | 469 | M + 1 | 2.3 | >2 | | |
| 1074 | 415 | M + 1 | 4.5 | >2 | | |
| 1076 | 431 | M + 1 | 1.4 | 1.7 | | |
| 1077 | 415 | M + 1 | >10 | >2 | | |
| 1078 | 427 | M + 1 | 0.01 | 0.03 | | |

TABLE 1B-continued

| Cpd. No. | Mass | Mass Ion Species | SETD2 (1434-1711) | SETD2 A549 | SMYD2 | SMYD3 |
|---|---|---|---|---|---|---|
| 1079 | 427 | M + 1 | 0.3 | 1.3 | | |
| 1080 | 427 | M + 1 | 0.5 | 1.7 | | |
| 1082 | 414 | M + 1 | 0.6 | >2 | | |
| 1083 | 414 | M + 1 | 0.02 | 0.05 | | |
| 1084 | 414 | M + 1 | 0.1 | 0.5 | | |
| 1085 | 429 | M + 1 | 0.03 | 0.1 | | |
| 1086 | 429 | M + 1 | 0.8 | >2 | | |
| 1087 | 373 | M + 1 | 0.01 | 0.5 | | |
| 1088 | 373 | M + 1 | 2.2 | >2 | | |
| 1090 | 401 | M + 1 | 0.5 | 1.1 | | |
| 1091 | 415 | M + 1 | 5.8 | >2 | | |
| 1092 | 415 | M + 1 | 0.8 | 0.8 | | |
| 1095 | 451 | M + 23 | 0.6 | >2 | | |
| 1096 | 451 | M + 23 | 2.4 | >2 | | |
| 1097 | 451 | M + 23 | 0.01 | 0.03 | | |
| 1098 | 431 | M + 1 | 0.03 | 0.3 | | |
| 1099 | 431 | M + 1 | 0.01 | 0.1 | | |
| 1100 | 427 | M + 1 | 0.9 | >2 | | |
| 1102 | 456 | M + 1 | 3.9 | >2 | | |
| 1103 | 456 | M + 1 | 0.1 | 0.1 | | |
| 1104 | 456 | M + 1 | 0.04 | 0.2 | | |
| 1106 | 413 | M + 1 | 3.0 | 2.0 | | |
| 1107 | 416 | M + 1 | 5.3 | >2 | | |
| 1108 | 416 | M + 1 | >10 | >2 | | |
| 1109 | 416 | M + 1 | >10 | >2 | | |
| 1110 | 410 | M + 1 | >10 | >0.7 | | |
| 1111 | | | 0.02 | 0.07 | | |
| 1112 | 497 | M + 1 | 0.02 | 0.02 | | |
| 1113 | 483 | M + 1 | 0.01 | 0.01 | | |
| 1114 | 440 | M + 1 | 0.04 | 1.6 | | |
| 1115 | 459 | M + 1 | 0.03 | 0.2 | | |
| 1116 | | | 0.02 | 0.05 | | |
| 1117 | 485 | M + 1 | 0.03 | 0.01 | | |
| 1120 | 445 | M + 1 | 5.9 | >2 | | |
| 1122 | 465 | M + 1 | 1.9 | >2 | | |
| 1123 | 429 | M + 1 | 0.5 | 1.4 | | |
| 1124 | 400 | M + 1 | 0.2 | 0.8 | | |
| 1126 | 428 | M + 1 | 0.02 | 0.08 | | |
| 1127 | 428 | M + 1 | 0.4 | 1.3 | | |
| 1128 | 428 | M + 1 | 0.3 | 1.6 | | |
| 1129 | 445 | M + 1 | 0.01 | 0.1 | | |
| 1130 | 445 | M + 1 | 4.0 | >2 | | |
| 1131 | | | 0.006 | 0.04 | | |
| 1132 | | | 2.3 | >2 | | |
| 1134 | | | 1.0 | >2 | | |
| 1135 | | | 0.02 | 0.07 | | |
| 1136 | | | 0.7 | >2 | | |
| 1137 | | | 2.0 | >2 | | |
| 1138 | | | 0.01 | 0.02 | | |
| 1139 | | | 0.5 | 1.7 | | |
| 1140 | | | 0.05 | 0.1 | | |
| 1141 | | | 0.4 | 1.3 | | |
| 1142 | | | 4.8 | >2 | | |
| 1143 | | | 1.9 | >2 | | |
| 1145 | | | 1.8 | >2 | | |
| 1146 | | | 0.04 | 0.2 | | |
| 1147 | | | 1.2 | >2 | | |
| 1148 | | | 0.9 | >2 | | |
| 1150 | 481 | M + 1 | 4.2 | >2 | | |
| 1151 | 481 | M + 1 | 5.8 | >2 | | |
| 1152 | 440 | M + 1 | 1.1 | >2 | | |
| 1153 | 299 | M + 1 | >200 | | | |
| 1154 | 313 | M + 1 | 6.0 | >25 | | |
| 1155 | 346 | M + 1 | 17.2 | | | |
| 1156 | 313 | M + 1 | 2.1 | 19.7 | | |
| 1157 | 371 | M + 1 | | | | |
| 1158 | 497 | M + 1 | 0.006 | 0.9 | | |
| 1159 | 370 | M + 1 | | >25 | | |
| 1160 | 445 | M + 1 | 4.3 | >2 | | |
| 1161 | 481 | M + 1 | 0.02 | 0.4 | | |
| 1162 | 429 | M + 1 | 0.07 | 0.2 | | |
| 1163 | 429 | M + 1 | 1.6 | >2 | | |
| 1164 | 483 | M + 1 | 2.1 | >2 | | |
| 1165 | 424 | M + 1 | 3.5 | >2 | | |
| 1166 | 412 | M + 1 | 1. | >2 | | |
| 1167 | 483 | M + 1 | 0.02 | 0.06 | | |
| 1168 | 483 | M + 1 | 1.3 | >2 | | |
| 1169 | 459 | M + 1 | 0.9 | >2 | | |
| 1170 | 486 | M + 1 | 1.8 | >2 | | |
| 1171 | 497 | M + 1 | 0.03 | 0.06 | | |
| 1172 | 497 | M + 1 | 3.1 | >2 | | |
| 1173 | 485 | M + 1 | 0.04 | 0.03 | | |
| 1174 | 485 | M + 1 | 4.8 | >2 | | |
| 1175 | 497 | M + 1 | 8.4 | >2 | | |
| 1176 | 485 | M + 1 | 2.9 | >2 | | |
| 1177 | 427 | M + 1 | 0.03 | 0.3 | | |
| 1178 | 427 | M + 1 | 3.9 | >2 | | |
| 1179 | 426 | M + 1 | 0.5 | 0.8 | | |
| 1180 | 427 | M + 1 | 0.01 | 0.01 | | |
| 1181 | 427 | M + 1 | 3.4 | >2 | | |
| 1182 | 427 | M + 1 | 0.02 | 0.05 | | |
| 1183 | 427 | M + 1 | 3.2 | >2 | | |
| 1184 | 427 | M + 1 | 0.01 | 0.005 | | |
| 1185 | 427 | M + 1 | 0.03 | 0.07 | | |
| 1186 | 427 | M + 1 | 3.7 | >2 | | |
| 1187 | 427 | M + 1 | 9.9 | >2 | | |
| 1188 | 372 | M + 1 | 0.2 | 1.8 | | |
| 1192 | | | 0.01 | 0.01 | | |
| 1193 | | | 0.6 | >2 | | |

The present disclosure encompasses the preparation and use of salts of the Compounds of the Disclosure, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like. The term "pharmaceutically acceptable salt" as used herein, refers to any salt, e.g., obtained by reaction with an acid or a base, of a Compound of the Disclosure that is physiologically tolerated in the target subject (e.g., a mammal, e.g., a human).

Acid addition salts can be formed by mixing a solution of the particular Compound of the Disclosure with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

II. Therapeutic Methods

The present disclosure is directed generally to a method for treating a disease, condition, or disorder in a subject suffering from, or at risk of suffering from, the disease, condition, or disorder, the method comprising administering to the subject an effective amount of a Compound of the Disclosure. In one embodiment, the disease, condition, or disorder is responsive to or mediated by the inhibition of SETD2 protein.

The present disclosure is also directed to a method of inhibiting SETD2 protein in subject in need thereof, the method comprising administering to the subject a therapeutically effective amount of a Compound of the Disclosure.

In one aspect, the present disclosure provides a method of treating a disease, disorder, or condition in a subject comprising administering a therapeutically effective amount of a Compound of the Disclosure.

In another aspect, the present disclosure provides a method of treating cancer in a subject comprising administering a therapeutically effective amount of a Compound of the Disclosure. While not being limited to a specific mechanism, in some embodiments, Compounds of the Disclosure treat cancer by inhibiting SETD2 protein. Examples of treatable cancers include, but are not limited to, the cancers listed in Table 2.

TABLE 2

| | |
|---|---|
| adrenal cancer | lymphoepithelioma |
| acinic cell carcinoma | lymphoma |
| acoustic neuroma | acute lymphocytic leukemia |
| acral lentigious melanoma | acute myelogeous leukemia |
| acrospiroma | chronic lymphocytic leukemia |

TABLE 2-continued

| | |
|---|---|
| acute eosinophilic leukemia | liver cancer |
| acute erythroid leukemia | small cell lung cancer |
| acute lymphoblastic leukemia | non-small cell lung cancer |
| acute megakaryoblastic leukemia | MALT lymphoma |
| acute monocytic leukemia | malignant fibrous histiocytoma |
| acute promyelocytic leukemia | malignant peripheral nerve sheath tumor |
| adenocarcinoma | malignant triton tumor |
| adenoid cystic carcinoma | mantle cell lymphoma |
| adenoma | marginal zone B-cell lymphoma |
| adenomatoid odontogenic tumor | mast cell leukemia |
| adenosquamous carcinoma | mediastinal germ cell tumor |
| adipose tissue neoplasm | medullary carcinoma of the breast |
| adrenocortical carcinoma | medullary thyroid cancer |
| adult T-cell leukemia/lymphoma | medulloblastoma |
| aggressive NK-cell leukemia | melanoma |
| AIDS-related lymphoma | meningioma |
| alveolar rhabdomyosarcoma | merkel cell cancer |
| alveolar soft part sarcoma | mesothelioma |
| ameloblastic fibroma | metastatic urothelial carcinoma |
| anaplastic large cell lymphoma | mixed Mullerian tumor |
| anaplastic thyroid cancer | mucinous tumor |
| angioimmunoblastic T-cell lymphoma | multiple myeloma |
| | muscle tissue neoplasm |
| angiomyolipoma | mycosis fungoides |
| angiosarcoma | myxoid liposarcoma |
| astrocytoma | myxoma |
| atypical teratoid rhabdoid tumor | myxosarcoma |
| B-cell chronic lymphocytic leukemia | nasopharyngeal carcinoma |
| | neurinoma |
| B-cell prolymphocytic leukemia | neuroblastoma |
| B-cell lymphoma | neurofibroma |
| basal cell carcinoma | neuroma |
| biliary tract cancer | nodular melanoma |
| bladder cancer | ocular cancer |
| blastoma | oligoastrocytoma |
| bone cancer | oligodendroglioma |
| Brenner tumor | oncocytoma |
| Brown tumor | optic nerve sheath meningioma |
| Burkitt's lymphoma | optic nerve tumor |
| breast cancer | oral cancer |
| brain cancer | osteosarcoma |
| carcinoma | ovarian cancer |
| carcinoma in situ | Pancoast tumor |
| carcinosarcoma | papillary thyroid cancer |
| cartilage tumor | paraganglioma |
| cementoma | pinealoblastoma |
| myeloid sarcoma | pineocytoma |
| chondroma | pituicytoma |
| chordoma | pituitary adenoma |
| choriocarcinoma | pituitary tumor |
| choroid plexus papilloma | plasmacytoma |
| clear-cell sarcoma of the kidney | polyembryoma |
| craniopharyngioma | precursor T-lymphoblastic lymphoma |
| cutaneous T-cell lymphoma | primary central nervous system lymphoma |
| cervical cancer | |
| colorectal cancer | primary effusion lymphoma |
| Degos disease | preimary peritoneal cancer |
| desmoplastic small round cell tumor | prostate cancer |
| | pancreatic cancer |
| diffuse large B-cell lymphoma | pharyngeal cancer |
| dysembryoplastic neuroepithelial tumor | pseudomyxoma periotonei |
| | renal cell carcinoma |
| dysgerminoma | renal medullary carcinoma |
| embryonal carcinoma | retinoblastoma |
| endocrine gland neoplasm | rhabdomyoma |
| endodermal sinus tumor | rhabdomyosarcoma |
| enteropathy-associated T-cell lymphoma | Richter's transformation |
| | rectal cancer |
| esophageal cancer | sarcoma |
| fetus in fetu | Schwannomatosis |
| fibroma | seminoma |
| fibrosarcoma | Sertoli cell tumor |
| follicular lymphoma | sex cord-gonadal stromal tumor |
| follicular thyroid cancer | signet ring cell carcinoma |
| ganglioneuroma | skin cancer |
| gastrointestinal cancer | small blue round cell tumors |
| germ cell tumor | small cell carcinoma |
| gestational choriocarcinoma | soft tissue sarcoma |
| giant cell fibroblastoma | somatostatinoma |
| giant cell tumor of the bone | soot wart |

TABLE 2-continued

| | |
|---|---|
| glial tumor | spinal tumor |
| glioblastoma multiforme | splenic marginal zone lymphoma |
| glioma | squamous cell carcinoma |
| gliomatosis cerebri | synovial sarcoma |
| glucagonoma | Sezary's disease |
| gonadoblastoma | small intestine cancer |
| granulosa cell tumor | squamous carcinoma |
| gynandroblastoma | stomach cancer |
| gallbladder cancer | T-cell lymphoma |
| gastric cancer | testicular cancer |
| hairy cell leukemia | thecoma |
| hemangioblastoma | thyroid cancer |
| head and neck cancer | transitional cell carcinoma |
| hemangiopericytoma | throat cancer |
| hematological malignancy | urachal cancer |
| hepatoblastoma | urogenital cancer |
| hepatosplenic T-cell lymphoma | urothelial carcinoma |
| Hodgkin's lymphoma | uveal melanoma |
| non-Hodgkin's lymphoma | uterine cancer |
| invasive lobular carcinoma | verrucous carcinoma |
| intestinal cancer | visual pathway glioma |
| kidney cancer | vulvar cancer |
| laryngeal cancer | vaginal cancer |
| lentigo maligna | Waldenstrom's macroglobulinemia |
| lethal midline carcinoma | Warthin's tumor |
| leukemia | Wilms' tumor. |
| leydig cell tumor | |
| liposarcoma | |
| lung cancer | |
| lymphangioma | |
| lymphangiosarcoma | |

In another embodiment, the cancer is pancreatic cancer or esophageal cancer.

In another embodiment, the cancer is selected from the group consisting of esophageal cancer, kidney cancer, stomach cancer, hepatocellular carcinoma, glioblastoma, central nervous system (CNS) cancer, soft tissue cancer, lung cancer, breast cancer, bladder/urinary tract cancer, head and neck cancer, prostate cancer, hematological cancer, pancreatic cancer, skin cancer, endometrial cancer, ovarian cancer, and colorectal cancer.

In another embodiment, the cancer or cancer cell is a hematological cancer. Exemplary hematological cancers include, but are not limited to, the cancers listed in Table 3.

TABLE 3

| | |
|---|---|
| acute lymphocytic leukemia (ALL) | acute eosinophilic leukemia |
| acute myeloid leukemia (AML) | acute erythroid leukemia |
| chronic lymphocytic leukemia (CLL) | acute lymphoblastic leukemia |
| small lymphocytic lymphoma (SLL) | acute megakaryoblastic leukemia |
| multiple myeloma (MM) | acute monocytic leukemia |
| Hodgkins lymphoma (HL) | acute promyelocytic leukemia |
| non-Hodgkin's lymphoma (NHL) | acute myelogeous leukemia |
| mantle cell lymphoma (MCL) | B-cell prolymphocytic leukemia |
| marginal zone B-cell lymphoma | B-cell lymphoma |
| splenic marginal zone lymphoma | MALT lymphoma |
| follicular lymphoma (FL) | precursor T-lymphoblastic lymphoma |
| Waldenstrom's macroglobulinemia (WM) | T-cell lymphoma |
| diffuse large B-cell lymphoma (DLBCL) | mast cell leukemia |
| | adult T cell leukemia/lymphoma |
| marginal zone lymphoma (MZL) | aggressive NK-cell leukemia |
| hairy cell leukemia (HCL) | angioimmunoblastic T-cell lymphoma |
| Burkitt's lymphoma (BL) | |
| Richter's transformation | |

In another embodiment, the cancer is multiple myeloma.

In another embodiment, the multiple myeloma is characterized as having chromosomal translocations involving the immunoglobulin heavy chain locus at 14q32. In another embodiment, the chromosomal translocation is a t(4;14) translocation, i.e., the multiple myeloma is t(4;14) multiple myeloma.

In another embodiment, the present disclosure provides a therapeutic method of modulating protein methylation, gene expression, cell proliferation, cell differentiation and/or apoptosis in vivo in the cancers mentioned above by administering a therapeutically effective amount of a Compound of the Disclosure to a subject in need of such therapy.

The present disclosure provides the following particular embodiments.

Embodiment I. A method of treating a subject in need thereof, the method comprising administering to the subject a therapeutically effective amount of a Compound of the Disclosure, wherein the subject has cancer.

Embodiment II. The method of Embodiment I, wherein the cancer is any one or more of the cancers of Table 2.

Embodiment III. The method of Embodiment I, wherein the cancer is a hematological cancer.

Embodiment IV. The method of Embodiment III, wherein the hematological cancer is any one or more of the cancers of Table 3, e.g., multiple myeloma.

Embodiment V. The method of Embodiment IV, wherein the hematological cancer is t(4;14) multiple myeloma.

Embodiment VI. The method of any one of Embodiments I-V further comprising administering a therapeutically effective amount of a second therapeutic agent useful in the treatment of cancer.

Embodiment VII. A pharmaceutical composition comprising a Compound of the Disclosure and a pharmaceutically acceptable carrier for use in treating cancer.

Embodiment VIII. The pharmaceutical composition of Embodiment VII, wherein the cancer is any one or more of the cancers of Table 2.

Embodiment IX. The pharmaceutical composition of Embodiment VII, wherein the cancer is a hematological cancer.

Embodiment X. The pharmaceutical composition of Embodiment IX, wherein the hematological cancer is any one or more of the cancers of Table 3, e.g., multiple myeloma.

Embodiment XI. The pharmaceutical composition of Embodiment X, wherein the hematological cancer is t(4;14) multiple myeloma.

Embodiment XII. A Compound of the Disclosure for use in treatment of cancer.

Embodiment XIII. The compound for use of Embodiment XII, wherein the cancer is any one or more of the cancers of Table 2.

Embodiment XIV. The compound for use of Embodiment XII, wherein the cancer is a hematological cancer.

Embodiment XV. The compound for use of Embodiment XIV, wherein the hematological cancer is any one or more of the cancers of Table 3, e.g., multiple myeloma.

Embodiment XVI. The compound for use of Embodiment XV, wherein the hematological cancer is t(4;14) multiple myeloma.

Embodiment XVII. Use of a Compound of the Disclosure for the manufacture of a medicament for treatment of cancer.

Embodiment XVIII. The use of Embodiment XVII, wherein the cancer is any one or more of the cancers of Table 2.

Embodiment XVIII. The use of Embodiment XVII, wherein the cancer is a hematological cancer.

Embodiment XIX. The use of Embodiment XVII, wherein the hematological cancer is any one or more of the cancers of Table 3, e.g., multiple myeloma.

Embodiment XX. The use of Embodiment XIX, wherein the hematological cancer is t(4;14) multiple myeloma.

Embodiment XXI The use of any one of Embodiments XVII-XX for comprising one or more additional therapeutic agents.

Embodiment XXII. A kit comprising a Compound of the Disclosure and instructions for administering the Compound of the Disclosure to a subject having cancer.

Embodiment XXIII. The kit of Embodiment XXII, wherein the cancer is any one or more of the cancers of Table 2.

Embodiment XXIV. The kit of Embodiment XXII, wherein the cancer is a hematological cancer.

Embodiment XXV. The kit of Embodiment XXIV, wherein the hematological cancer is any one or more of the cancers of Table 3, e.g., multiple myeloma.

Embodiment XXVI. The kit of Embodiment XXV, wherein the hematological cancer is t(4;14) multiple myeloma.

Embodiment XXVII. The kit of any one of Embodiments XXII-XXVI further comprising one or more additional therapeutic agents.

Compounds of the Disclosure can be administered to a subject in the form of a raw chemical without any other components present. Compounds of the Disclosure can also be administered to a mammal as part of a pharmaceutical composition containing the compound combined with a suitable pharmaceutically acceptable carrier. Such a carrier can be selected from pharmaceutically acceptable excipients and auxiliaries. The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, PA, 19th ed. 1995.

Pharmaceutical compositions within the scope of the present disclosure include all compositions where a Compound of the Disclosure is combined with one or more pharmaceutically acceptable carriers. In one embodiment, the Compound of the Disclosure is present in the composition in an amount that is effective to achieve its intended therapeutic purpose. While individual needs may vary, a determination of optimal ranges of effective amounts of each compound is within the skill of the art. Typically, a Compound of the Disclosure can be administered to a mammal, e.g., a human, orally at a dose of from about 0.0025 to about 1500 mg per kg body weight of the mammal, or an equivalent amount of a pharmaceutically acceptable salt or solvate thereof, per day to treat the particular disorder. A useful oral dose of a Compound of the Disclosure administered to a mammal is from about 0.0025 to about 50 mg per kg body weight of the mammal, or an equivalent amount of the pharmaceutically acceptable salt or solvate thereof. For intramuscular injection, the dose is typically about one-half of the oral dose.

A unit oral dose may comprise from about 0.01 mg to about 1 g of the Compound of the Disclosure, e.g., about 0.01 mg to about 500 mg, about 0.01 mg to about 250 mg, about 0.01 mg to about 100 mg, 0.01 mg to about 50 mg, e.g., about 0.1 mg to about 10 mg, of the compound. The unit dose can be administered one or more times daily, e.g., as one or more tablets or capsules, each containing from about 0.01 mg to about 1 g of the compound, or an equivalent amount of a pharmaceutically acceptable salt or solvate thereof.

A Compound of Disclosure or pharmaceutical composition comprising a Compound of the Disclosure can be administered to any subject, e.g., a cancer patient in need thereof, that may experience the beneficial effects of a Compound of the Disclosure. Foremost among such subject are mammals, e.g., humans and companion animals, although the disclosure is not intended to be so limited. In one embodiment, the subject is a human.

A pharmaceutical composition of the present disclosure can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a pharmaceutical composition of the present disclosure can be administered orally. In another embodiment, a pharmaceutical composition of the present disclosure can be administered orally and is formulated into tablets, dragees, capsules, or an oral liquid preparation. In one embodiment, the oral formulation comprises extruded multiparticulates comprising the Compound of the Disclosure.

Alternatively, a pharmaceutical composition of the present disclosure can be administered rectally, and is formulated in suppositories.

Alternatively, a pharmaceutical composition of the present disclosure can be administered by injection.

Alternatively, a pharmaceutical composition of the present disclosure can be administered transdermally.

Alternatively, a pharmaceutical composition of the present disclosure can be administered by inhalation or by intranasal or transmucosal administration.

Alternatively, a pharmaceutical composition of the present disclosure can be administered by the intravaginal route.

A pharmaceutical composition of the present disclosure can contain from about 0.01 to 99 percent by weight, e.g., from about 0.25 to 75 percent by weight, of a Compound of the Disclosure, e.g., about 1%, about 5%, about 10%, about 15%, about 20%, about 25%, about 30%, about 35%, about 40%, about 45%, about 50%, about 55%, about 60%, about 65%, about 70%, or about 75% by weight of a Compound of the Disclosure.

A pharmaceutical composition of the present disclosure is manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate can be used. Dye stuffs or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

III. Biomarkers

In another embodiment, present disclosure provides methods of treating a subject having cancer, e.g., multiple myeloma, comprising (a) determining whether a biomarker is present or absent in a biological sample taken from the subject; and (b) administering a therapeutically effective amount of a Compound of the Disclosure to the subject if the biomarker is present in the biological sample. See, e.g., Goossens et al., *Transl Cancer Res.* 4:256-269 (2015); Kamel and Al-Amodi, *Genomics Proteomics Bioinformatics* 15:220-235 (2017); and Konikova and Kusenda, *Neoplasma* 50:31-40 (2003).

The term "biomarker" as used herein refers to any biological compound, such as a gene, a protein, a fragment of a protein, a peptide, a polypeptide, a nucleic acid, etc., or chromosome abnormality, such as a chromosome translocation, that can be detected and/or quantified in a cancer patient in vivo or in a biological sample obtained from a cancer patient, e.g., in a cancer cell. A biomarker can be the entire intact molecule, or it can be a portion or fragment thereof. In one embodiment, the expression level of the biomarker is measured. The expression level of the biomarker can be measured, for example, by detecting the protein or RNA, e.g., mRNA, level of the biomarker. In some embodiments, portions or fragments of biomarkers can be detected or measured, for example, by an antibody or other specific binding agent. In some embodiments, a measurable aspect of the biomarker is associated with a given state of the patient, such as a particular stage of cancer. For biomarkers that are detected at the protein or RNA level, such measurable aspects may include, for example, the presence, absence, or concentration, i.e., expression level, of the biomarker in a cancer patient, or biological sample obtained from the cancer patient. For biomarkers that are detected at the nucleic acid level, such measurable aspects may include, for example, allelic versions of the biomarker or type, rate, and/or degree of mutation of the biomarker, also referred to herein as mutation status.

For biomarkers that are detected based on expression level of protein or RNA, expression level measured between different phenotypic statuses can be considered different, for example, if the mean or median expression level of the biomarker in the different groups is calculated to be statistically significant. Common tests for statistical significance include, among others, t-test, ANOVA, Kruskal-Wallis, Wilcoxon, Mann-Whitney, Significance Analysis of Microarrays, odds ratio, etc. Biomarkers, alone or in combination, provide measures of relative likelihood that a subject belongs to one phenotypic status or another. Therefore, they are useful, inter alia, as markers for disease and as indicators that particular therapeutic treatment regimens will likely result in beneficial patient outcomes.

Biomarkers include, but are not limited to, chromosomal translocations in a cancer, e.g., multiple myeloma, cell and WHSC1/NSD2/MMSET expression. In one embodiment, the measurable aspect of the biomarker is its expression status. In one embodiment, the measurable aspect of the biomarker is its mutation status.

In one embodiment, the biomarker is WHSC1/NSD2/MMSET expression which is differentially present in a subject of one phenotypic status, e.g., a subject having a hematological cancer, as compared with another phenotypic status, e.g., a normal undiseased subject or a patient having cancer without overexpression WHSC1/NSD2/MMSET. In one embodiment, the biomarker is overexpression of WHSC1/NSD2/MMSET.

Biomarker standards can be predetermined, determined concurrently, or determined after a biological sample is obtained from the subject. Biomarker standards for use with the methods described herein can, for example, include data from samples from subjects without cancer; data from samples from subjects with cancer, e.g., breast cancer, that is not metastatic; and data from samples from subjects with cancer, e.g., breast cancer, that metastatic. Comparisons can be made to establish predetermined threshold biomarker standards for different classes of subjects, e.g., diseased vs. non-diseased subjects. The standards can be run in the same assay or can be known standards from a previous assay.

A biomarker is differentially present between different phenotypic status groups if the mean or median expression or mutation levels of the biomarker is calculated to be different, i.e., higher or lower, between the groups. Thus, biomarkers provide an indication that a subject, e.g., a cancer patient, belongs to one phenotypic status or another.

In addition to individual biological compounds, e.g., WHSC1/NSD2/MMSET, the term "biomarker" as used herein is meant to include groups, sets, or arrays of multiple biological compounds. For example, the combination of WHSC1/NSD2/MMSET expression status and one or more chromosomal translocations may comprise a biomarker. The term "biomarker" may comprise one, two, three, four, five, six, seven, eight, nine, ten, fifteen, twenty, twenty five, thirty, or more, biological compounds.

The determination of the expression level or mutation status of a biomarker in a patient can be performed using any of the many methods known in the art. Any method known in the art for quantitating specific proteins and/or detecting WHSC1/NSD2/MMSET expression and/or chromosomal translocations, or the expression or mutation levels of any other biomarker in a patient or a biological sample may be used in the methods of the disclosure. Examples include, but are not limited to, PCR (polymerase chain reaction), or RT-PCR, flow cytometry, Northern blot, Western blot, ELISA (enzyme linked immunosorbent assay), RIA (radio-immunoassay), gene chip analysis of RNA expression, immunohistochemistry or immunofluorescence. See, e.g., Slagle et al. Cancer 83:1401 (1998); Hudlebusch et al., *Clin Cancer Res* 17:2919-2933 (2011). Certain embodiments of the disclosure include methods wherein biomarker RNA expression (transcription) is determined. Other embodiments of the disclosure include methods wherein protein expression in the biological sample is determined. See, e.g., Harlow et al., Antibodies: A Laboratory Manual, Cold Spring Harbor Laboratory, Cold Spring Harbor, NY, (1988); Ausubel et al., Current Protocols in Molecular Biology, John Wiley & Sons, New York 3rd Edition, (1995); Kamel and Al-Amodi, *Genomics Proteomics Bioinformatics* 15:220-235 (2017). For northern blot or RT-PCR analysis, RNA is isolated from the tumor tissue sample using RNAse free techniques. Such techniques are commonly known in the art.

In one embodiment of the disclosure, a biological sample is obtained from the patient and the biological sample is assayed for determination of a biomarker expression or mutation status.

In another embodiment of the disclosure, Northern blot analysis of biomarker transcription in a tumor cell sample is performed. Northern analysis is a standard method for detection and/or quantitation of mRNA levels in a sample. Initially, RNA is isolated from a sample to be assayed using Northern blot analysis. In the analysis, the RNA samples are first separated by size via electrophoresis in an agarose gel under denaturing conditions. The RNA is then transferred to a membrane, crosslinked and hybridized with a labeled probe. Typically, Northern hybridization involves polymerizing radiolabeled or nonisotopically labeled DNA, in vitro, or generation of oligonucleotides as hybridization probes. Typically, the membrane holding the RNA sample is pre-hybridized or blocked prior to probe hybridization to prevent the probe from coating the membrane and, thus, to reduce non-specific background signal. After hybridization, typically, unhybridized probe is removed by washing in several changes of buffer. Stringency of the wash and hybridization conditions can be designed, selected and implemented by any practitioner of ordinary skill in the art. Detection is accomplished using detectably labeled probes and a suitable detection method. Radiolabeled and non-radiolabled probes and their use are well known in the art. The presence and or relative levels of expression of the biomarker being assayed can be quantified using, for example, densitometry.

In another embodiment, biomarker expression and/or mutation status is determined using RT-PCR. RT-PCR allows detection of the progress of a PCR amplification of a target gene in real time. Design of the primers and probes required to detect expression and/or mutation status of a biomarker of the disclosure is within the skill of a practitioner of ordinary skill in the art. RT-PCR can be used to determine the level of RNA encoding a biomarker of the disclosure in a tumor tissue sample. In an embodiment of the disclosure, RNA from the biological sample is isolated, under RNAse free conditions, than converted to DNA by treatment with reverse transcriptase. Methods for reverse transcriptase conversion of RNA to DNA are well known in the art. A description of PCR is provided in the following references: Mullis et al., *Cold Spring Harbor Symp. Quant. Biol.* 51:263 (1986); EP 50,424; EP 84,796; EP 258,017; EP 237,362; EP 201,184; U.S. Pat. Nos. 4,683,202; 4,582,788; 4,683,194.

RT-PCR probes depend on the 5'-3' nuclease activity of the DNA polymerase used for PCR to hydrolyze an oligonucleotide that is hybridized to the target amplicon (biomarker gene). RT-PCR probes are oligonucleotides that have a fluorescent reporter dye attached to the 5' end and a quencher moiety coupled to the 3' end (or vice versa). These probes are designed to hybridize to an internal region of a PCR product. In the unhybridized state, the proximity of the fluor and the quench molecules prevents the detection of fluorescent signal from the probe. During PCR amplification, when the polymerase replicates a template on which an RT-PCR probe is bound, the 5'-3' nuclease activity of the polymerase cleaves the probe. This decouples the fluorescent and quenching dyes and FRET no longer occurs. Thus, fluorescence increases in each cycle, in a manner proportional to the amount of probe cleavage. Fluorescence signal emitted from the reaction can be measured or followed over time using equipment which is commercially available using routine and conventional techniques.

In another embodiment of the disclosure, expression of proteins encoded by biomarkers are detected by western blot analysis. A western blot (also known as an immunoblot) is a method for protein detection in a given sample of tissue homogenate or extract. It uses gel electrophoresis to separate denatured proteins by mass. The proteins are then transferred out of the gel and onto a membrane (e.g., nitrocellulose or polyvinylidene fluoride (PVDF)), where they are detected using a primary antibody that specifically bind to the protein. The bound antibody can then detected by a secondary antibody that is conjugated with a detectable label (e.g., biotin, horseradish peroxidase or alkaline phosphatase). Detection of the secondary label signal indicates the presence of the protein.

In another embodiment of the disclosure, the expression of a protein encoded by a biomarker is detected by enzyme-linked immunosorbent assay (ELISA). In one embodiment of the disclosure, "sandwich ELISA" comprises coating a plate with a capture antibody; adding sample wherein any antigen present binds to the capture antibody; adding a detecting antibody which also binds the antigen; adding an enzyme-linked secondary antibody which binds to detecting antibody; and adding substrate which is converted by an enzyme on the secondary antibody to a detectable form. Detection of the signal from the secondary antibody indicates presence of the biomarker antigen protein.

Multiple myeloma is a heterogeneous plasma cell disorder characterized by genetic abnormalities, including chromosomal translocations, deletions, duplications, and genetic mutations. Translocations involving the immunoglobulin heavy chain region at chromosome 14q32 are observed in approximately 40% of patients with multiple myeloma. Translocation of oncogenes into this region may lead to their increased expression, contributing to disease initiation, disease progression, and therapeutic resistance. For example, the t(4;14) translocation is associated with upregulation of the fibroblast growth factor receptor 3 (FGFR3) and the myeloma SET domain protein. Subjects with t(4;14) demonstrate an overall poor prognosis that is only partially mitigated using existing chemotherapeutic agents. An unmet medical need remains for subjects with this aberration. IgH translocations in patients with multiple myeloma are presented in Table 4. See, e.g., Kalff and Spencer, *Blood Cancer Journal* 2:e89 (2012).

TABLE 4

| Translocation | Prevalence, % | Upregulated oncogenes | Prognosis |
|---|---|---|---|
| t(4; 14) | 15 | MMSET, FGFR3 | Unfavorable |
| t(14; 16) | 5 | MAF | Unfavorable |
| t(14; 20) | 1-2 | MAF | Unfavorable |
| t(8; 14) | 2 | MAF | Unfavorable |
| t(11; 14) | 15-17 | Cyclin D1 | Favorable/neutral |
| t(6; 14) | 4 | Cyclin D3 | Favorable/neutral |

Abbreviations:
FGFR, fibroblast growth factor receptor;
IgH, immunoglobulin heavy chain;
MM, multiple myeloma;
MMSET, myeloma SET domain protein WHSC1/NSD2/MMSET is a histone methyl transferase located at the Chromosome 4p16 locus. In a subset of multiple myeloma, a chromosomal translocation takes place where this region is fused to chromosome 14q32. This translocation is commonly known as t(4;14). The result of t(4;14) in multiple myeloma is that the WHSC1/NSD2/MMSET gene is placed under the transcriptional control of the IgH promoter. This leads to a massive up-regulation of WHSC1/NSD2/MMSET (Chesi et al., *Blood* 92:3025-3034 (1998)). The increase in WHSC1/NSD2/MMSET leads to an increase in the di-methylation of histone H3 at lysine 36 (H3K36). (Kuo et al., *Mol. Cell* 44:609-620 (2011)). Like WHSC1/NSD2/MMSET, SETD2 also methylates H3K36 but adds three methyl groups instead of two. Based on the sensitivity of t(4;14) multiple myeloma cell lines to SETD2 inhibition, the oncogenic function resulting from increased H3K36me2 caused by WHSC1 over-expression likely also requires the ability of SETD2 to add an additional methyl group.

In one embodiment, the present disclosure provides a method of treating a subject having multiple myeloma, the method comprising: (a) determining whether a chromosomal translocation is present or absent in a biological sample taken from the subject; and (b) administering a therapeutically effective amount of a Compound of the Disclosure to the subject if a chromosomal translocation is present in the biological sample.

In another embodiment, the present disclosure provides a method of treating a subject having multiple myeloma, the method comprising administering a therapeutically effective amount of a Compound of the Disclosure to the subject having a chromosomal translocation.

In another embodiment, the present disclosure provides a method of identifying whether a subject having multiple myeloma as a candidate for treatment with a Compound of the Disclosure, the method comprising: (a) determining whether a chromosomal translocation is present or absent in a biological sample taken from the subject; and (b) identifying the subject as being a candidate for treatment if a chromosomal translocation is present; or (c) identifying the subject as not being a candidate for treatment if a chromosomal translocation is absent.

In another embodiment, the present disclosure provides a method of predicting treatment outcome in a subject having multiple myeloma, the method comprising determining whether a chromosomal translocation is present or absent in a biological sample taken from the subject, wherein (a) the presence of a chromosomal translocation in the biological sample indicates that administering a Compound of the Disclosure to the subject will likely cause a favorable therapeutic response; and (b) the absence of a chromosomal translocation in the biological sample indicates that administering a Compound of the Disclosure to the subject will likely cause an unfavorable therapeutic response.

In another embodiment, the present disclosure provides a method, comprising administering a therapeutically effective amount of a Compound of the Disclosure to a subject in need thereof, wherein: (a) the subject has multiple myeloma; and (b) the multiple myeloma is characterized as having a chromosomal translocation.

In any of the above embodiments, the chromosomal translocation is a t(4;14) translocation.

In one embodiment, the present disclosure provides a method of treating a subject having multiple myeloma, the method comprising: (a) determining whether an overexpression of WHSC1/NSD2/MMSET is present or absent in a biological sample taken from the subject; and (b) administering a therapeutically effective amount of a Compound of the Disclosure to the subject if an overexpression of WHSC1/NSD2/MMSET is present in the biological sample.

In one embodiment, the present disclosure provides a method of treating a subject having multiple myeloma, the method comprising administering a therapeutically effective amount of a Compound of the Disclosure to the subject if an overexpression of WHSC1/NSD2/MMSET is present in subject.

In another embodiment, the present disclosure provides a method of identifying whether a subject having multiple myeloma as a candidate for treatment with a Compound of the Disclosure, the method comprising: (a) determining whether an overexpression of WHSC1/NSD2/MMSET is present or absent in a biological sample taken from the subject; and (b) identifying the subject as being a candidate for treatment if an overexpression of WHSC1/NSD2/MMSET is present; or (c) identifying the subject as not being a candidate for treatment an overexpression of WHSC1/NSD2/MMSET is absent.

In another embodiment, the present disclosure provides a method of predicting treatment outcome in a subject having multiple myeloma, the method comprising determining whether an overexpression of WHSC1/NSD2/MMSET is present or absent in a biological sample taken from the subject, wherein: (a) the presence of an overexpression of WHSC1/NSD2/MMSET in the biological sample indicates that administering a Compound of the Disclosure to the subject will likely cause a favorable therapeutic response; and (b) the absence of an overexpression of WHSC1/NSD2/MMSET in the biological sample indicates that administering a Compound of the Disclosure to the subject will likely cause an unfavorable therapeutic response.

In another embodiment, the present disclosure provides a method, comprising administering a therapeutically effective amount of a Compound of the Disclosure to a subject in need thereof, wherein: (a) the subject has multiple myeloma; and (b) the multiple myeloma is characterized as having an overexpression of WHSC1/NSD2/MMSET.

IV. Definitions

The term "halo" as used herein by itself or as part of another group refers to —Cl, —F, —Br, or —I.

The term "nitro" as used herein by itself or as part of another group refers to —NO$_2$.

The term "cyano" as used herein by itself or as part of another group refers to —CN.

The term "hydroxy" as herein used by itself or as part of another group refers to —OH.

The term "alkyl" as used herein by itself or as part of another group refers to a straight- or branched-chain aliphatic hydrocarbon containing one to twelve carbon atoms, i.e., a $C_1$-$C_{12}$ alkyl, or the number of carbon atoms designated, e.g., a $C_1$ alkyl such as methyl, a $C_2$ alkyl such as ethyl, etc. In one embodiment, the alkyl is a $C_1$-$C_{10}$ alkyl. In another embodiment, the alkyl is a $C_1$-$C_6$ alkyl. In another embodiment, the alkyl is a $C_1$-$C_4$ alkyl. In another embodiment, the alkyl is a $C_1$-$C_3$ alkyl, i.e., methyl, ethyl, propyl, or isopropyl. Non-limiting exemplary $C_1$-$C_{12}$ alkyl groups include methyl, ethyl, propyl, isopropyl, butyl, sec-butyl, tert-butyl, iso-butyl, 3-pentyl, hexyl, heptyl, octyl, nonyl, and decyl.

The term "optionally substituted alkyl" as used herein by itself or as part of another group refers to an alkyl group that is either unsubstituted or substituted with one, two, or three substituents, wherein each substituent is independently nitro, haloalkoxy, aryloxy, aralkyloxy, alkylthio, sulfonamido, alkylcarbonyl, arylcarbonyl, alkylsulfonyl, arylsulfonyl, ureido, guanidino, carbamate, carboxy, alkoxycarbonyl, carboxy alkyl, —N($R^{56a}$)C(=O)$R^{56b}$, —N($R^{56c}$)S(=O)$_2$$R^{56d}$, —C(=O)$R^{57}$, —S(=O)$R^{56e}$, —S(=O)$_2$$R^{58}$, —N($R^{56a}$)C(=N—$R^{60}$)$R^{61}$, —N($R^{56a}$)C(=C—NO$_2$)$R^{64}$, —C(=N—$R^{60}$)$R^{61}$, or —C(=C—NO$_2$)$R^{64}$; wherein:

$R^{56a}$ is hydrogen or alkyl;

$R^{56b}$ is alkyl, haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{56c}$ is hydrogen or alkyl;

$R^{56d}$ is alkyl, haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{56e}$ is alkyl, haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{57}$ is haloalkyl, amino, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, optionally substituted heteroaryl, ($C_3$-$C_6$ cycloalkyl)oxy, or (4- to 8-membered heterocyclo)oxy;

$R^{58}$ is haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, or optionally substituted heteroaryl;

$R^{60}$ is selected from the group consisting of cyano, nitro, hydroxy, $C_1$-$C_6$ alkoxy, —C(=O)$R^{62}$, and —S(=O)$_2$$R^{62}$;

$R^{61}$ is selected from the group consisting of $C_1$-$C_6$ alkyl, $C_3$-$C_6$ cycloalkyl, and —N$R^{63a}$$R^{63b}$;

$R^{62}$ is selected from the group consisting of $C_1$-$C_6$ alkyl, $C_3$-$C_6$ cycloalkyl, and —N$R^{63a}$$R^{63b}$;

$R^{63a}$ is selected from the group consisting of hydrogen, $C_1$-$C_6$ alkyl, and $C_3$-$C_6$ cycloalkyl;

$R^{63b}$ is selected from the group consisting of hydrogen, $C_1$-$C_6$ alkyl, and $C_3$-$C_6$ cycloalkyl; or $R^{63a}$ and $R^{63b}$ taken together with the nitrogen atom to which they are attached form a 4- to 6-membered optionally substituted heterocyclo;

$R^{64}$ is selected from the group consisting of $C_1$-$C_6$ alkyl, $C_3$-$C_6$ cycloalkyl, and —N$R^{63c}$$R^{63d}$; and $R^{63c}$ is selected from the group consisting of hydrogen, $C_1$-$C_6$ alkyl, and $C_3$-$C_6$ cycloalkyl;

$R^{63d}$ is selected from the group consisting of hydrogen, $C_1$-$C_6$ alkyl, and $C_3$-$C_6$ cycloalkyl; or $R^{63c}$ and $R^{63d}$ taken together with the nitrogen atom to which they are attached form a 4- to 6-membered optionally substituted heterocyclo.

In one embodiment, the optionally substituted alkyl is either unsubstituted or substituted with one, two, or three substituents, wherein each substituent is independently nitro, haloalkoxy, aryloxy, aralkyloxy, alkylthio, sulfonamido, alkylcarbonyl, arylcarbonyl, alkylsulfonyl, arylsulfonyl, ureido, guanidino, carbamate, carboxy, alkoxycarbonyl, carboxyalkyl, —N($R^{56a}$)C(=O)$R^{56b}$, —N($R^{56c}$)S(=O)$_2$$R^{56d}$, —C(=O)$R^{57}$, —S(=O)$R^{56e}$, or —S(=O)$_2$$R^{58}$.

In another embodiment, the optionally substituted alkyl is substituted with two substituents. In another embodiment, the optionally substituted alkyl is substituted with one substituent. In another embodiment, the optionally substituted alkyl is an optionally substituted $C_1$-$C_6$ alkyl. In another embodiment, the optionally substituted alkyl is an optionally substituted $C_1$-$C_4$ alkyl. In one embodiment, the optionally substituted alkyl is an optionally substituted is a $C_1$ or $C_2$ alkyl. Non-limiting exemplary optionally substituted alkyl groups include —CH(CO$_2$Me)CH$_2$CO$_2$Me and —CH(CH$_3$)CH$_2$N(H)C(=O)O(CH$_3$)$_3$.

The term "alkenyl" as used herein by itself or as part of another group refers to an alkyl group containing one, two, or three carbon-to-carbon double bonds. In one embodiment, the alkenyl group is a C$_2$-C$_6$ alkenyl group. In another embodiment, the alkenyl group is a C$_2$-C$_4$ alkenyl group. In another embodiment, the alkenyl group has one carbon-to-carbon double bond. Non-limiting exemplary alkenyl groups include ethenyl, propenyl, isopropenyl, butenyl, sec-butenyl, pentenyl, and hexenyl.

The term "optionally substituted alkenyl" as used herein by itself or as part of another refers to an alkenyl group that is either unsubstituted or substituted with one, two or three substituents, wherein each substituent is independently halo, nitro, cyano, hydroxy, amino (e.g., alkylamino, dialkylamino), haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted cycloalkyl, alkenyl, alkynyl, optionally substituted aryl, optionally substituted heteroaryl, or optionally substituted heterocyclo. Non-limiting exemplary optionally substituted alkenyl groups include —CH=CHPh.

The term "alkynyl" as used herein by itself or as part of another group refers to an alkyl group containing one, two, or three carbon-to-carbon triple bonds. In one embodiment, the alkynyl has one carbon-to-carbon triple bond. In another embodiment, the alkynyl is a C$_1$-C$_6$ alkynyl. In another embodiment, the alkynyl is a C$_2$-C$_4$ alkynyl. In another embodiment, the alkynyl has one carbon-to-carbon triple bond. Non-limiting exemplary alkynyl groups include ethynyl, propynyl, butynyl, 2-butynyl, pentynyl, and hexynyl groups.

The term "optionally substituted alkynyl" as used herein by itself or as part of another group refers to an alkynyl group that is either unsubstituted or substituted with one, two or three substituents, wherein each substituent is independently halo, nitro, cyano, hydroxy, amino (e.g., alkylamino, dialkylamino), haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted cycloalkyl, alkenyl, alkynyl, optionally substituted aryl, optionally substituted heteroaryl, or optionally substituted heterocyclo. Non-limiting exemplary optionally substituted alkynyl groups include —CH≡CHPh.

The term "haloalkyl" as used herein by itself or as part of another group refers to an alkyl group substituted by one or more fluorine, chlorine, bromine, and/or iodine atoms. In one embodiment, the alkyl is substituted by one, two, or three fluorine and/or chlorine atoms. In another embodiment, the alkyl is substituted by one, two, or three fluorine atoms. In another embodiment, the alkyl is a C$_1$-C$_6$ alkyl. In another embodiment, the alkyl is a C$_1$-C$_4$ alkyl. In another embodiment, the alkyl group is a C$_1$ or C$_2$ alkyl. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

The terms "hydroxyalkyl" or "(hydroxy)alkyl" as used herein by themselves or as part of another group refer to an alkyl group substituted with one, two, or three hydroxy groups. In one embodiment, the alkyl is a C$_1$-C$_6$ alkyl. In another embodiment, the alkyl is a C$_1$-C$_4$ alkyl. In another embodiment, the hydroxyalkyl is a monohydroxyalkyl group, i.e., substituted with one hydroxy group. In another embodiment, the hydroxyalkyl group is a dihydroxyalkyl group, i.e., substituted with two hydroxy groups. Non-limiting exemplary (hydroxyl)alkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

The term "alkoxy" as used herein by itself or as part of another group refers to an alkyl group attached to a terminal oxygen atom. In one embodiment, the alkyl is a C$_1$-C$_6$ alkyl. In another embodiment, the alkyl is a C$_1$-C$_4$ alkyl group. Non-limiting exemplary alkoxy groups include methoxy, ethoxy, and tert-butoxy.

The term "haloalkoxy" as used herein by itself or as part of another group refers to a haloalkyl group attached to a terminal oxygen atom. In one embodiment, the haloalkyl is a C$_1$-C$_6$ alkyl. In another embodiment, the haloalkyl group is a C$_1$-C$_4$ haloalkyl group. Non-limiting exemplary haloalkoxy groups include fluoromethoxy, difluoromethoxy, trifluoromethoxy, and 2,2,2-trifluoroethoxy.

The term "alkylthio" as used herein by itself or as part of another group refers to an alkyl group attached to a terminal sulfur atom. In one embodiment, the alkyl group is a C$_1$-C$_4$ alkyl group. Non-limiting exemplary alkylthio groups include —SCH$_3$, and —SCH$_2$CH$_3$.

The terms "alkoxyalkyl" or "(alkoxy)alkyl" as used herein by themselves or as part of another group refers to an alkyl group substituted with one alkoxy group. In one embodiment, the alkoxy is a C$_1$-C$_6$ alkoxy. In another embodiment, the alkoxy is a C$_1$-C$_4$ alkoxy. In another embodiment, the alkyl is a C$_1$-C$_6$ alkyl. In another embodiment, the alkyl is a C$_1$-C$_4$ alkyl. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

The term "heteroalkyl" as used herein by itself or part of another group refers to a stable straight or branched chain hydrocarbon radical containing 1 to 10 carbon atoms and at least two heteroatoms, which can be the same or different, selected from O, N, or S, wherein the sulfur atom(s) can optionally be oxidized. The heteroatoms can be placed at any interior position of the heteroalkyl group or at a position at which the heteroalkyl group is attached to the remainder of the molecule. In one embodiment, the heteroalkyl contains two oxygen atoms. In another embodiment, the heteroalkyl contains one oxygen and one nitrogen atom. In another embodiment, the heteroalkyl contains two nitrogen atoms. Non-limiting exemplary heteroalkyl groups include —OCH$_2$CH$_2$NH$_2$, —NHCH$_2$CH$_2$OCH$_3$, and —OCH$_2$CH$_2$OCH$_3$.

The term "cycloalkyl" as used herein by itself or as part of another group refers to saturated and partially unsaturated, e.g., containing one or two double bonds, monocyclic, bicyclic, or tricyclic aliphatic hydrocarbons containing three to twelve carbon atoms, i.e., a C$_{3-12}$ cycloalkyl, or the number of carbons designated, e.g., a C$_3$ cycloalkyl such a cyclopropyl, a C$_4$ cycloalkyl such as cyclobutyl, etc. In one embodiment, the cycloalkyl is bicyclic, i.e., it has two rings. In another embodiment, the cycloalkyl is monocyclic, i.e., it has one ring. In another embodiment, the cycloalkyl is a C$_{3-8}$ cycloalkyl. In another embodiment, the cycloalkyl is a C$_{3-6}$ cycloalkyl, i.e., cyclopropyl, cyclobutyl, cyclopentyl, or cyclohexyl. In another embodiment, the cycloalkyl is a $C_5$ cycloalkyl, i.e., cyclopentyl. In another embodiment, the cycloalkyl is a $C_6$ cycloalkyl, i.e., cyclohexyl. Non-limiting exemplary $C_{3-12}$ cycloalkyl groups include cyclopropyl, cyclobutyl, cyclopentyl, cyclohexyl, cycloheptyl, cyclooctyl, norbornyl, decalin, adamantyl, cyclohexenyl, and spiro[3.3]heptane.

The term "optionally substituted cycloalkyl" as used herein by itself or as part of another group refers to a cycloalkyl group is either unsubstituted or substituted with one, two, or three substituents, wherein each substituent is independently halo, nitro, cyano, hydroxy, amino (e.g., —$NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —$N(R^{56a})C(=O)R^{56b}$, —$N(R^{56c})S(=O)_2R^{56d}$, —$C(=O)R^{57}$, —$S(=O)R^{56e}$, —$S(=O)_2R^{58}$, —$OR^{59}$, —$N(R^{56a})C(=N—R^{60})R^{61}$, —$N(R^{56a})C(=C—NO_2)R^{64}$, —$C(=N—R^{60})R^{61}$, or —$C(=C—NO_2)R^{64}$; wherein $R^{56a}$, $R^{56b}$, $R^{56c}$, $R^{56d}$, $R^{56e}$, $R^{57}$, $R^{58}$, $R^{60}$, $R^{61}$, and $R^{64}$ are as defined in connection with the term "optionally substituted alkyl" and $R^{59}$ is (hydroxy)alkyl or (amino)alkyl. Non-limiting exemplary optionally substituted cycloalkyl groups include 3-(4-acetylpiperazin-1-yl)cyclohexyl, 3-(3-(N-methylacetamido)pyrrolidin-1-yl)cyclohexyl, 3-morpholinocyclohexyl, and 3-(pyrimidin-5-yl)cyclohexyl. In one embodiment, the optionally substituted cycloalkyl is either unsubstituted or substituted with one, two, or three substituents, wherein each substituent is independently halo, nitro, cyano, hydroxy, amino (e.g., —$NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —$N(R^{56a})C(=O)R^{56b}$, —$N(R^{56c})S(=O)_2R^{56d}$, —$C(=O)R^{57}$, —$S(=O)R^{56e}$, —$S(=O)_2R^{58}$, and —$OR^{59}$.

The term "heterocyclo" as used herein by itself or as part of another group refers to saturated and partially unsaturated, e.g., containing one or two double bonds, monocyclic, bicyclic, or tricyclic groups containing three to fourteen ring members, i.e., a 3- to 14-membered heterocyclo, comprising one, two, three, or four heteroatoms. Each heteroatom is independently oxygen, sulfur, or nitrogen. Each sulfur atom is independently oxidized to give a sulfoxide, i.e., S(=O), or sulfone, i.e., $S(=O)_2$.

The term heterocyclo includes groups wherein one or more —$CH_2$— groups is replaced with one or more —$C(=O)$— groups, including cyclic ureido groups such as imidazolidinyl-2-one, cyclic amide groups such as pyrrolidin-2-one or piperidin-2-one, and cyclic carbamate groups such as oxazolidinyl-2-one.

The term heterocyclo also includes groups having fused optionally substituted aryl or optionally substituted heteroaryl groups such as indoline, indolin-2-one, 2,3-dihydro-1H-pyrrolo[2,3-c]pyridine, 2,3,4,5-tetrahydro-1H-benzo[d]azepine, or 1,3,4,5-tetrahydro-2H-benzo[d]azepin-2-one.

In one embodiment, the heterocyclo group is a 4- to 8-membered cyclic group containing one ring and one or two oxygen atoms, e.g., tetrahydrofuran or tetrahydropyran, or one or two nitrogen atoms, e.g., pyrrolidine, piperidine, or piperazine, or one oxygen and one nitrogen atom, e.g., morpholine, and, optionally, one —$CH_2$— group is replaced with one —$C(=O)$— group, e.g., pyrrolidin-2-one or piperazin-2-one. In another embodiment, the heterocyclo group is a 5- to 8-membered cyclic group containing one ring and one or two nitrogen atoms and, optionally, one —$CH_2$— group is replaced with one —$C(=O)$— group. In another embodiment, the heterocyclo group is a 5- or 6-membered cyclic group containing one ring and one or two nitrogen atoms and, optionally, one —$CH_2$— group is replaced with one —$C(=O)$— group. In another embodiment, the heterocyclo group is a 8- to 12-membered cyclic group containing two rings and one or two nitrogen atoms. The heterocyclo can be linked to the rest of the molecule through any available carbon or nitrogen atom. Non-limiting exemplary heterocyclo groups include:

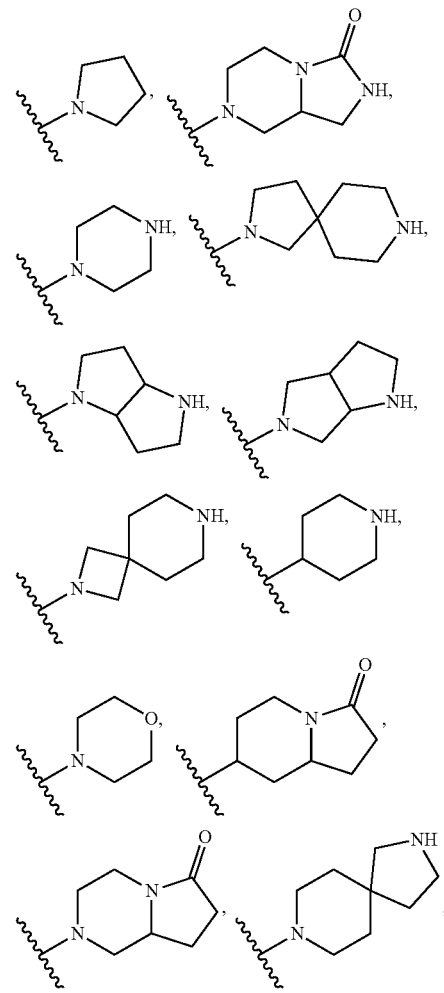

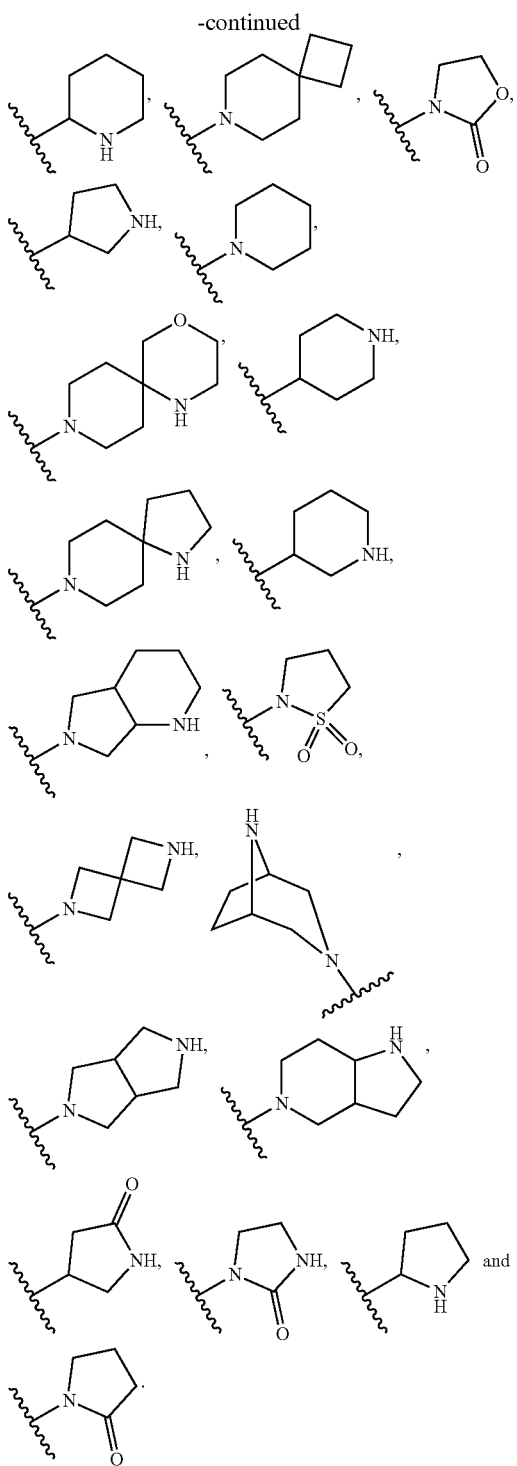

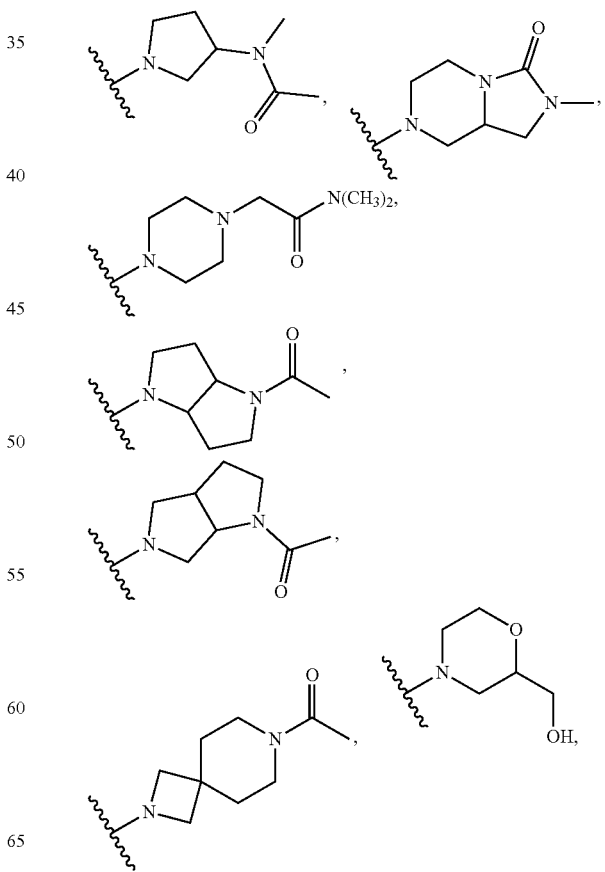

carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N($R^{56a}$)C(=O)$R^{56b}$, —N($R^{56c}$)S(=O)$_2R^{56d}$, —C(=O)$R^{57}$, —S(=O)$R^{56e}$, —S(=O)$_2R^{58}$, —O$R^{59}$, —N($R^{56a}$)C(=N—$R^{60}$)$R^{61}$, —N($R^{56a}$)C(=C—$NO_2$)$R^{64}$, —C(=N—$R^{60}$)$R^{61}$, or —C(=C—$NO_2$)$R^{64}$; wherein $R^{56a}$, $R^{56b}$, $R^{56c}$, $R^{56d}$, $R^{56e}$, $R^{57}$, $R^{58}$, $R^{59}$, $R^{60}$, $R^{61}$, and $R^{64}$ are as defined in connection with the term "optionally substituted cycloalkyl." Substitution may occur on any available carbon or nitrogen atom of the heterocyclo group. In one embodiment, the optionally substituted heterocyclo is either unsubstituted or substituted with one to four substituents, wherein each substituent is independently halo, nitro, cyano, hydroxy, amino, (e.g., —$NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N($R^{56a}$)C(=O)$R^{56b}$, —N($R^{56c}$)S(=O)$_2R^{56d}$, —C(=O)$R^{57}$, —S(=O)$R^{56e}$, —S(=O)$_2R^{58}$, or —O$R^{59}$.

Non-limiting exemplary optionally substituted heterocyclo groups include:

The term "optionally substituted heterocyclo" as used herein by itself or part of another group refers to a heterocyclo group that is either unsubstituted or substituted with one to four substituents, wherein each substituent is independently halo, nitro, cyano, hydroxy, amino, (e.g., —$NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino,

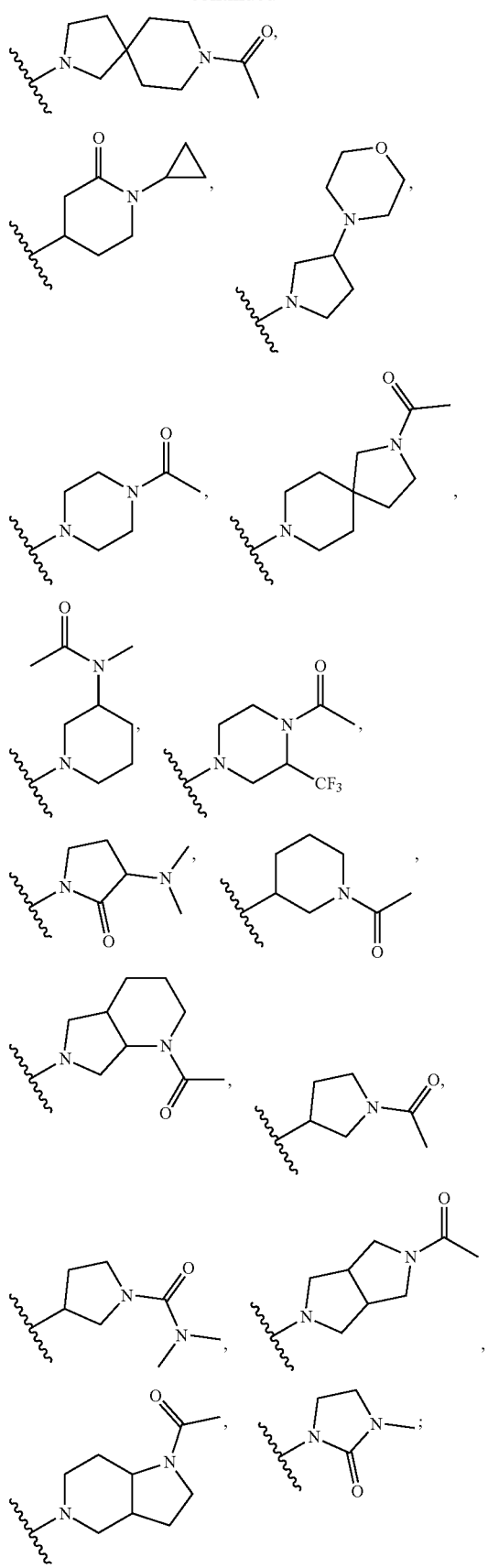

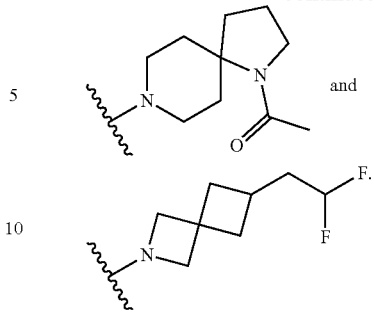

The term "aryl" as used herein by itself or as part of another group refers to an aromatic ring system having six to fourteen carbon atoms, i.e., $C_6$-$C_{14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl. In another embodiment, the aryl group is phenyl.

The term "optionally substituted aryl" as used herein by itself or as part of another group refers to aryl that is either unsubstituted or substituted with one to five substituents, wherein the substituents are each independently halo, nitro, cyano, hydroxy, amino, (e.g., —$NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —$N(R^{56a})C(=O)R^{56b}$, —$N(R^{56c})S(=O)_2R^{56d}$, —$C(=O)R^{57}$, —$S(=O)R^{56e}$, —$S(=O)_2R^{58}$, —$OR^{59}$, —$N(R^{56a})C(=N-R^{60})R^{61}$, —$N(R^{56a})C(=C-NO_2)R^{64}$, —$C(=N-R^{60})R^{61}$, or —$C(=C-NO_2)R^{64}$; wherein $R^{56a}$, $R^{56b}$, $R^{56c}$, $R^{56d}$, $R^{56e}$, $R^{57}$, $R^{58}$, $R^{59}$, $R^{60}$, $R^{61}$, and $R^{64}$ are as defined in connection with the term "optionally substituted cycloalkyl." In one embodiment, the optionally substituted aryl is either unsubstituted or substituted with one to five substituents, wherein the substituents are each independently halo, nitro, cyano, hydroxy, amino, (e.g., —$NH_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —$N(R^{56a})C(=O)R^{56b}$, —$N(R^{56c})S(=O)_2R^{56d}$, —$C(=O)R^{57}$, —$S(=O)R^{56e}$, —$S(=O)_2R^{58}$, or —$OR^{59}$.

In one embodiment, the optionally substituted aryl is an optionally substituted phenyl. In another embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary optionally substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, 3-chloro-4-fluorophenyl, and 2-phenylpropan-2-amine. The term optionally substituted aryl includes aryl groups having fused optionally substituted cycloalkyl groups and fused optionally substituted heterocyclo groups. Non-limiting examples include: 2,3-dihydro-1H-inden-1-yl, 1,2,3,4-tetrahydronaphthalen-1-yl, 1,3,4,5-tetrahydro-2H-benzo[c]azepin-2-yl, 1,2,3,4-tetrahydroisoquinolin-1-yl, and 2-oxo-2,3,4,5-tetrahydro-1H-benzo[d]azepin-1-yl.

The term "heteroaryl" as used herein by itself or as part of another group refers to monocyclic and bicyclic aromatic ring systems having five to 14 fourteen ring members, i.e., a 5- to 14-membered heteroaryl, comprising one, two, three, or four heteroatoms. Each heteroatom is independently oxygen, sulfur, or nitrogen. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term heteroaryl also includes N-oxides. A non-limiting exemplary N-oxide is pyridyl N-oxide.

The term "optionally substituted heteroaryl" as used herein by itself or as part of another group refers to a heteroaryl that is either unsubstituted or substituted with one to four substituents, wherein the substituents are independently halo, nitro, cyano, hydroxy, amino, (e.g., —NH$_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N(R$^{56a}$)C(=O)R$^{56b}$, —N(R$^{56c}$)S(=O)$_2$R$^{56d}$, —C(=O)R$^{57}$, —S(=O)R$^{56e}$, —S(=O)$_2$R$^{58}$, —OR$^{59}$, —N(R$^{56a}$)C(=N—R$^{60}$)R$^{61}$, —N(R$^{56a}$)C(=C—NO$_2$)R$^{64}$, —C(=N—R$^{60}$)R$^{61}$, or —C(=C—NO$_2$)R$^{64}$; wherein R$^{56a}$, R$^{56b}$, R$^{56c}$, R$^{56d}$, R$^{56e}$, R$^{57}$, R$^{58}$, R$^{59}$, R$^{60}$, R$^{61}$, and R$^{64}$ are as defined in connection with the term "optionally substituted cycloalkyl." In one embodiment, optionally substituted heteroaryl is either unsubstituted or substituted with one to four substituents, wherein the substituents are independently halo, nitro, cyano, hydroxy, amino, (e.g., —NH$_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N(R$^{56a}$)C(=O)R$^{56b}$, —N(R$^{56c}$)S(=O)$_2$R$^{56d}$, —C(=O)R$^{57}$, —S(=O)R$^{56e}$, —S(=O)$_2$R$^{58}$, or —OR$^{59}$.

In one embodiment, the optionally substituted heteroaryl has two substituents. In another embodiment, the optionally substituted heteroaryl has one substituent. Any available carbon or nitrogen atom can be substituted.

The term "aryloxy" as used herein by itself or as part of another group refers to an optionally substituted aryl attached to a terminal oxygen atom. A non-limiting exemplary aryloxy group is PhO—.

The term "heteroaryloxy" as used herein by itself or as part of another group refers to an optionally substituted heteroaryl attached to a terminal oxygen atom. A non-limiting exemplary aryloxy group is pyridyl-O—.

The term "aralkyloxy" as used herein by itself or as part of another group refers to an aralkyl attached to a terminal oxygen atom. A non-limiting exemplary aralkyloxy group is PhCH$_2$O—.

The term "(cycloalkyl)oxy" as used herein by itself or as part of another group refers to a cycloalkyl group attached to a terminal oxygen atom. A non-limiting exemplary cycloalkyloxy group is:

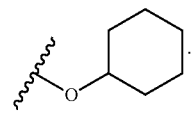

The term "(heterocyclo)oxy" as used herein by itself or as part of another group refers to a heterocyclo group attached to a terminal oxygen atom. A non-limiting exemplary (heterocyclo)oxy group is:

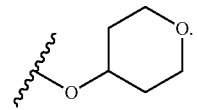 [SMILES: *OC1CCOCC1]

The term "(cyano)alkyl" as used herein by itself or as part of another group refers to an alkyl substituted with one, two, or three cyano groups. In one embodiment, the alkyl is substituted with one cyano group. In another embodiment, the alkyl is a $C_1$-$C_6$ alkyl In another embodiment, the alkyl is a $C_1$-$C_4$ alkyl. Non-limiting exemplary (cyano)alkyl groups include —$CH_2CH_2CN$ and —$CH_2CH_2CH_2CN$.

The term "(cycloalkyl)alkyl" as used herein by itself or as part of another group refers to an alkyl substituted with one optionally substituted cycloalkyl group. In one embodiment, the cycloalkyl group is an optionally substituted $C_3$-$C_6$ cycloalkyl. In another embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (cycloalkyl)alkyl groups include:

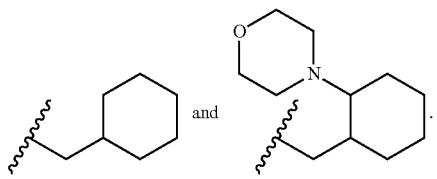 [SMILES: *CC1CCCCC1 ; *CC1CCCCC1N1CCOCC1]

The term "sulfonamido" as used herein by itself or as part of another group refers to a radical of the formula —$SO_2NR^{50a}R^{50b}$, wherein $R^{50a}$ and $R^{50b}$ are each independently hydrogen, alkyl, optionally substituted cycloalkyl, optionally substituted heterocyclo, optionally substituted aryl, or optionally substituted heteroaryl; or $R^{50a}$ and $R^{50b}$ taken together with the nitrogen to which they are attached form a 3- to 8-membered optionally substituted heterocyclo group. Non-limiting exemplary sulfonamido groups include —$SO_2NH_2$, —$SO_2N(H)CH_3$, and —$SO_2N(H)Ph$.

The term "alkylcarbonyl" as used herein by itself or as part of another group refers to a carbonyl group, i.e., —C(=O)—, substituted by an alkyl group. In one embodiment, the alkyl is a $C_1$-$C_4$ alkyl. A non-limiting exemplary alkylcarbonyl group is —$COCH_3$.

The term "arylcarbonyl" as used herein by itself or as part of another group refers to a carbonyl group, i.e., —C(=O)—, substituted by an optionally substituted aryl group. A non-limiting exemplary arylcarbonyl group is —COPh.

The term "alkylsulfonyl" as used herein by itself or as part of another group refers to a sulfonyl group, i.e., —$SO_2$—, substituted by an alkyl group. A non-limiting exemplary alkylsulfonyl group is —$SO_2CH_3$.

The term "arylsulfonyl" as used herein by itself or as part of another group refers to a sulfonyl group, i.e., —$SO_2$—, substituted by an optionally substituted aryl group. A non-limiting exemplary arylsulfonyl group is —$SO_2Ph$.

The term "mercaptoalkyl" as used herein by itself or as part of another group refers to an alkyl substituted by a —SH group.

The term "carboxy" as used by itself or as part of another group refers to a radical of the formula —C(=O)OH.

The term "ureido" as used herein by itself or as part of another group refers to a radical of the formula —$NR^{51a}$—C(=O)—$NR^{51b}R^{51c}$, wherein $R^{51a}$ is hydrogen or alkyl; and $R^{51b}$ and $R^{51c}$ are each independently hydrogen, alkyl, optionally substituted cycloalkyl, optionally substituted heterocyclo, optionally substituted aryl, or optionally substituted heteroaryl, or $R^{51b}$ and $R^{51c}$ taken together with the nitrogen to which they are attached form a 4- to 8-membered optionally substituted heterocyclo group. Non-limiting exemplary ureido groups include —NH—C(C=O)—$NH_2$ and —NH—C(C=O)—$NHCH_3$.

The term "guanidino" as used herein by itself or as part of another group refers to a radical of the formula —$NR^{52a}$—C(=$NR^{53}$)—$NR^{52b}R^{52c}$, wherein $R^{52a}$ is hydrogen or alkyl; $R^{52b}$ and $R^{53c}$ are each independently hydrogen, alkyl, optionally substituted cycloalkyl, optionally substituted heterocyclo, optionally substituted aryl, or optionally substituted heteroaryl; or $R^{52b}$ and $R^{52c}$ taken together with the nitrogen to which they are attached form a 4- to 8-membered optionally substituted heterocyclo group; and $R^{53}$ is hydrogen, alkyl, cyano, alkylsulfonyl, alkylcarbonyl, carboxamido, or sulfonamido. Non-limiting exemplary guanidino groups include —NH—C(C=NH)—$NH_2$, —NH—C(C=NCN)—$NH_2$, and —NH—C(C=NH)—$NHCH_3$.

The term "(heterocyclo)alkyl" as used herein by itself or as part of another group refers to an alkyl substituted with one, two, or three optionally substituted heterocyclo groups. In one embodiment, the alkyl is substituted with one optionally substituted 5- to 8-membered heterocyclo group. In another embodiment, alkyl is a $C_1$-$C_6$ alkyl. In another embodiment, alkyl is a $C_1$-$C_4$ alkyl. The heterocyclo group can be linked to the alkyl group through a carbon or nitrogen atom. Non-limiting exemplary (heterocyclo)alkyl groups include:

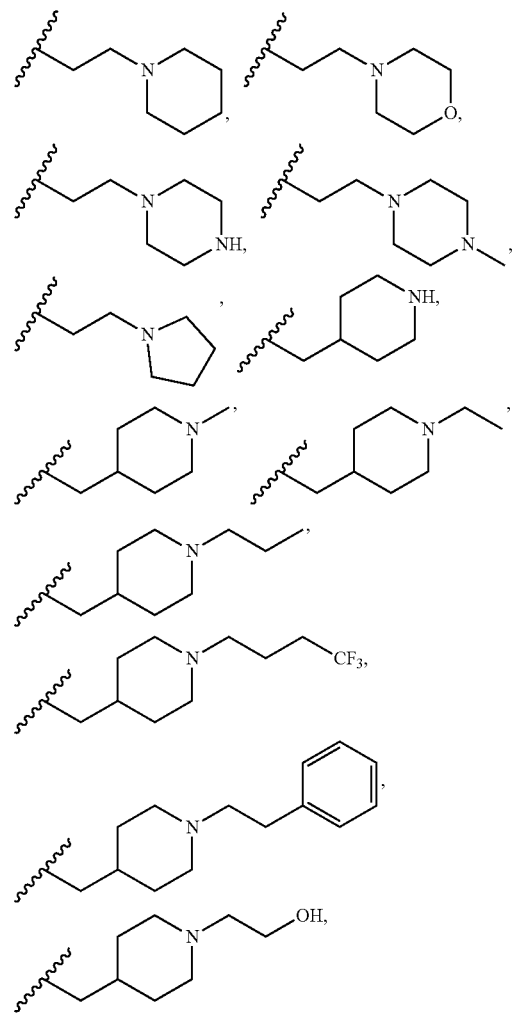

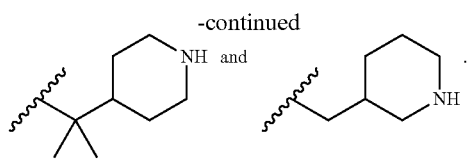

The term "carbamate" as used herein by itself or as part of another group refers to a radical of the formula —NR$^{54a}$—C(=O)—OR$^{54b}$, wherein R$^{54a}$ is hydrogen or alkyl, and R$^{54b}$ is hydrogen, alkyl, optionally substituted cycloalkyl, optionally substituted heterocyclo, optionally substituted aryl, or optionally substituted heteroaryl. A non-limiting exemplary carbamate group is —NH—(C=O)—OtBu.

The term "(heteroaryl)alkyl" as used herein by itself or as part of another group refers to an alkyl substituted with one or two optionally substituted heteroaryl groups. In one embodiment, the alkyl group is substituted with one optionally substituted 5- to 14-membered heteroaryl group. In another embodiment, the alkyl group is substituted with two optionally substituted 5- to 14-membered heteroaryl groups. In another embodiment, the alkyl group is substituted with one optionally substituted 5- to 9-membered heteroaryl group. In another embodiment, the alkyl group is substituted with two optionally substituted 5- to 9-membered heteroaryl groups. In another embodiment, the alkyl group is substituted with one optionally substituted 5- or 6-membered heteroaryl group. In another embodiment, the alkyl group is substituted with two optionally substituted 5- or 6-membered heteroaryl groups. In one embodiment, the alkyl group is a $C_1$-$C_6$ alkyl. In another embodiment, the alkyl group is a $C_1$-$C_4$ alkyl. In another embodiment, the alkyl group is a $C_1$ or $C_2$ alkyl. Non-limiting exemplary (heteroaryl)alkyl groups include:

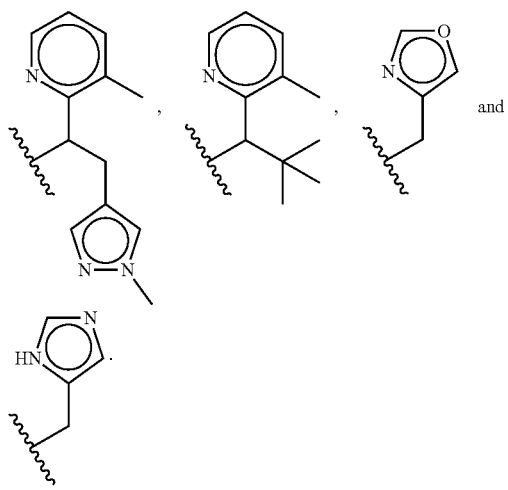

The term "(heteroaryl)(aryl)alkyl" as used herein by itself or as part of another group refers to an alkyl group substituted with one optionally substituted heteroaryl group and one optionally substituted aryl group. In one embodiment, the heteroaryl is an optionally substituted 5- to 9-membered heteroaryl group. In another embodiment, the heteroaryl is an optionally substituted 5- or 6-membered heteroaryl group. In one embodiment, the aryl is an optionally substituted phenyl group or optionally substituted naphthyl group. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (heteroaryl)(aryl)alkyl groups include:

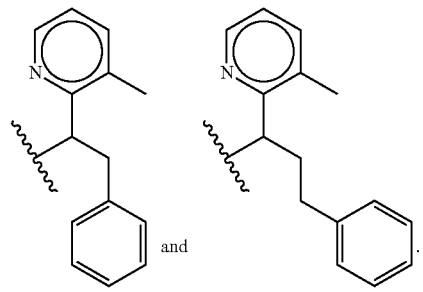

The term "(heteroaryl)(heterocyclo)alkyl" as used herein by itself or as part of another group refers to an alkyl group substituted with one optionally substituted heteroaryl group and one optionally substituted heterocyclo group. In one embodiment, the heteroaryl is an optionally substituted 5- to 9-membered heteroaryl group. In another embodiment, the heteroaryl is an optionally substituted 5- or 6-membered heteroaryl group. In one embodiment, the heterocyclo is an optionally substituted 5- to 8-membered heterocyclo. In another embodiment, the heterocyclo is an optionally substituted 5- or 6-membered heterocyclo. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. A non-limiting exemplary (heteroaryl)(heterocyclo)alkyl group is:

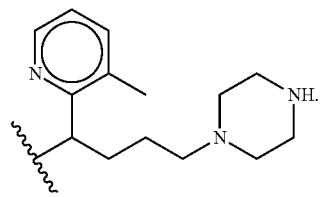

The term "(heteroaryl)(carboxamido)alkyl" as used herein by itself or as part of another group refers to an alkyl group substituted with one optionally substituted heteroaryl group and one carboxamido group. In one embodiment, the heteroaryl is an optionally substituted 5- to 9-membered heteroaryl group. In another embodiment, the heteroaryl is an optionally substituted 5- or 6-membered heteroaryl group. In one embodiment, the alkyl is a $C_1$-$C_6$ alkyl. In another embodiment, the alkyl is a $C_1$-$C_4$ alkyl. In another embodiment, the alkyl is a $C_1$-$C_3$ alkyl. Non-limiting exemplary (heteroaryl)(carboxamido)alkyl groups include:

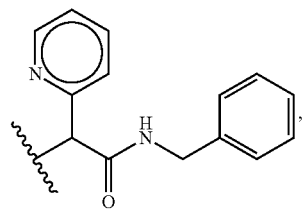

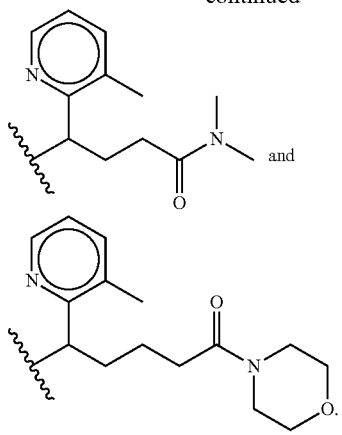 and

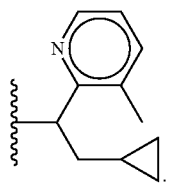

The term "carboxamido" as used herein by itself or as part of another group refers to a radical of formula —C(=O)NR$^{55a}$R$^{55b}$, wherein R$^{55a}$ and R$^{55b}$ are each independently hydrogen, optionally substituted alkyl, optionally substituted alkenyl, optionally substituted alkynyl, haloalkyl, (alkoxy)alkyl, (hydroxy)alkyl, (cyano)alkyl, optionally substituted cycloalkyl, optionally substituted heterocyclo, optionally substituted aryl, optionally substituted heteroaryl, (aryl)alkyl, (cycloalkyl)alkyl, (heterocyclo)alkyl, or (heteroaryl)alkyl; or R$^{55a}$ and R$^{55b}$ taken together with the nitrogen to which they are attached from a 4- to 8-membered optionally substituted heterocyclo group. Non-limiting exemplary carboxamido groups include: morpholine-4-carbonyl, N,N-dimethylaminocarbonyl, N-(1-methylpiperidin-4-yl)aminocarbonyl, 4-methylpiperazine-1-carbonyl, N-(3-aminocyclopentyl)aminocarbonyl, N-(pyridin-3-yl)aminocarbonyl, and N-(tetrahydrofuran-3-yl)aminocarbonyl.

The term "(heteroaryl)(cycloalkyl)alkyl" as used herein by itself or as part of another group refers to an alkyl group substituted with one optionally substituted heteroaryl group and one optionally substituted cycloalkyl group. In one embodiment, the heteroaryl is an optionally substituted 5- to 9-membered heteroaryl group. In another embodiment, the heteroaryl is an optionally substituted 5- or 6-membered heteroaryl group. In one embodiment, the cycloalkyl is an optionally substituted C$_3$-C$_6$ cycloalkyl. In one embodiment, the alkyl is a C$_1$-C$_6$ alkyl. In another embodiment, the alkyl is a C$_1$-C$_4$ alkyl. In another embodiment, the alkyl is a C$_1$-C$_3$ alkyl. A non-limiting exemplary (heteroaryl)(C$_3$-C$_6$ cycloalkyl) alkyl group is:

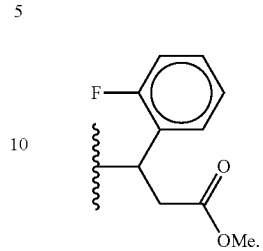

The term "(aryl)(alkoxycarbonyl)alkyl" as used herein by itself or as part of another group refers to an alkyl group substituted with one optionally substituted aryl group and one alkoxycarbonyl group. In one embodiment, the aryl is an optionally substituted phenyl group or optionally substituted naphthyl group. In another embodiment, the aryl is an optionally substituted phenyl group. In one embodiment, the alkyl is a C$_1$-C$_6$ alkyl. In another embodiment, the alkyl is a C$_1$-C$_4$ alkyl. In another embodiment, the alkyl is a C$_1$ or C$_2$ alkyl. A non-limiting exemplary (aryl)(alkoxycarbonyl)alkyl group is:

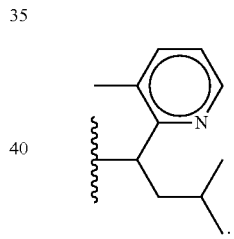

The term "alkoxycarbonyl" as used herein by itself or as part of another group refers to a carbonyl group, i.e., —C(=O)—, substituted by a C$_1$-C$_6$ alkoxy group. In one embodiment, the alkoxy group is a C$_1$-C$_4$ alkoxy. In another embodiment, the alkoxy group is a C$_1$-C$_3$ alkoxy. Non-limiting exemplary alkoxycarbonyl groups include —CO$_2$Me and —CO$_2$Et.

The term "(heteroaryl)(amino)alkyl" as used herein by itself or as part of another group refers to an alkyl group substituted with one optionally substituted heteroaryl group and one amino group. In one embodiment, the heteroaryl is an optionally substituted 5- to 9-membered heteroaryl group. In another embodiment, the heteroaryl is an optionally substituted 5- or 6-membered heteroaryl group. In one embodiment, the alkyl is a C$_1$-C$_6$ alkyl. In another embodiment, the alkyl is a C$_1$-C$_4$ alkyl. In another embodiment, the alkyl is a C$_1$ or C$_2$ alkyl. A non-limiting exemplary (heteroaryl)(amino)alkyl group is:

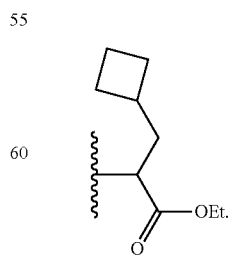

The term "(cycloalkyl)(alkoxycarbonyl)alkyl" as used herein by itself or as part of another group refers to an alkyl group substituted with one optionally substituted cycloalkyl group and one alkoxycarbonyl group. In one embodiment, the cycloalkyl is an optionally substituted C$_3$-C$_6$ cycloalkyl. In one embodiment, the alkyl is a C$_1$-C$_6$ alkyl. In another embodiment, the alkyl is a C$_1$-C$_4$ alkyl. In another embodiment, the alkyl is a C$_1$ or C$_2$ alkyl. A non-limiting exemplary (cycloalkyl)(alkoxycarbonyl)alkyl group is:

The term "(heteroaryl)(alkoxycarbonyl)alkyl" as used herein by itself or as part of another group refers to an alkyl group substituted with one optionally substituted heteroaryl group and one alkoxycarbonyl group. In one embodiment, the heteroaryl is an optionally substituted 5- to 9-membered heteroaryl group. In another embodiment, the heteroaryl is an optionally substituted 5- or 6-membered heteroaryl group. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (heteroaryl)(alkoxycarbonyl)alkyl groups include:

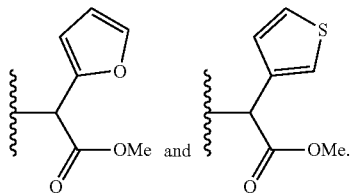 [SMILES: *C(C(=O)OC)c1ccco1 ; *C(C(=O)OC)c1ccsc1]

The term "(heterocyclo)(cycloalkyl)alkyl" as used herein by itself or as part of another group refers to an alkyl group substituted with one optionally substituted heterocyclo group and one optionally substituted cycloalkyl group. In one embodiment, the heterocyclo is an optionally substituted 5- to 8-membered heterocyclo. In another embodiment, the heterocyclo is an optionally substituted 5- or 6-membered heterocyclo. In one embodiment, the cycloalkyl is an optionally substituted $C_3$-$C_6$ cycloalkyl. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. A non-limiting exemplary (heterocyclo)(cycloalkyl) alkyl group is:

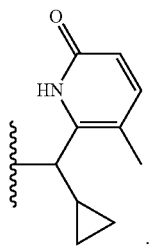 [SMILES: *C(c1[nH]c(=O)ccc1C)C1CC1]

The term "(aryl)(cycloalkyl)alkyl" as used herein by itself or as part of another group refers to an alkyl group substituted with one optionally substituted aryl group and one optionally substituted cycloalkyl group. In one embodiment, the aryl is an optionally substituted phenyl group or optionally substituted naphthyl group. In another embodiment, the aryl is an optionally substituted phenyl group. In one embodiment, the cycloalkyl is an optionally substituted $C_3$-$C_6$ cycloalkyl. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. A non-limiting exemplary (aryl)(cycloalkyl)alkyl group is:

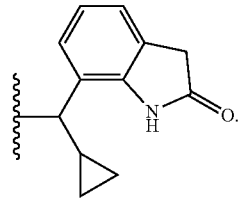 [SMILES: *C(c1cccc2c1NC(=O)C2)C1CC1]

The terms "aralkyl" or "(aryl)alkyl" as used herein by themselves or as part of another group refers to an alkyl substituted with one, two, or three optionally substituted aryl groups. In one embodiment, the alkyl is substituted with one optionally substituted aryl group. In another embodiment, the alkyl is substituted with two optionally substituted aryl groups. In one embodiment, the aryl is an optionally substituted phenyl or optionally substituted naphthyl. In another embodiment, the aryl is an optionally substituted phenyl. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (aryl)alkyl groups include benzyl, phenethyl, —CHPh$_2$, and —CH(4-F-Ph)$_2$.

The term "(aryl)(hydroxy)alkyl" as used herein by itself or as part of another group refers to an alkyl substituted with one optionally substituted aryl group and one hydroxyl group. In one embodiment, the aryl is an optionally substituted phenyl group or optionally substituted naphthyl group. In another embodiment, the aryl is an optionally substituted phenyl group. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (aryl)(hydroxy)alkyl groups include:

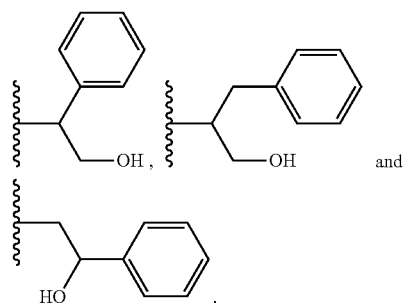

The term "(cycloalkyl)(hydroxy)alkyl" as used herein by itself or as part of another group refers to an alkyl group substituted with one optionally substituted cycloalkyl group and one hydroxyl group. In one embodiment, the cycloalkyl group is an optionally substituted $C_3$-$C_6$ cycloalkyl group. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. A non-limiting exemplary (cycloalkyl)(hydroxy)alkyl group is:

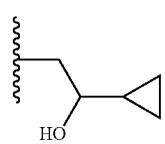

The term "(alkoxycarbonyl)alkyl" as used herein by itself or as part of another group refers to an alkyl substituted with one or two alkoxycarbonyl groups. In one embodiment, the alkyl is a $C_1$-$C_4$ alkyl. In another embodiment, the alkyl is a $C_1$ or $C_2$ alkyl. A non-limiting exemplary (alkoxycarbonyl)alkyl groups is:

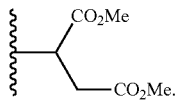

The term "(aryl)(haloalkyl)alkyl" as used herein by itself or as part of another group refers to an alkyl substituted with one optionally substituted aryl group and one haloalkyl group. In one embodiment, the aryl is an optionally substituted group or optionally substituted naphthyl. In another embodiment, the aryl is an optionally substituted phenyl. In one embodiment, the haloalkyl is a $C_1$-$C_4$ haloalkyl. In one embodiment, the alkyl is a $C_1$-$C_4$ alkyl. In another embodiment, the alkyl is a $C_1$ or $C_2$ alkyl. A non-limiting exemplary (aryl)(haloalkyl)alkyl groups is:

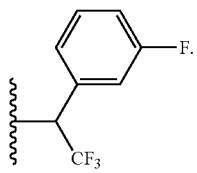 [SMILES: *C(c1cccc(F)c1)C(F)(F)F]

The term "(cycloalkyl)(haloalkyl)alkyl" as used herein by itself or as part of another group refers to an alkyl substituted with one optionally substituted cycloalkyl group and one haloalkyl group. In one embodiment, the cycloalkyl is an optionally substituted $C_3$-$C_6$ cycloalkyl. In one embodiment, the haloalkyl is a $C_1$-$C_4$ haloalkyl. In one embodiment, the alkyl is a $C_1$-$C_4$ alkyl. In another embodiment, the alkyl is a $C_1$ or $C_2$ alkyl. A non-limiting exemplary (cycloalkyl)(haloalkyl) alkyl groups is:

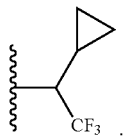

The term "(hydroxy)(haloalkyl)alkyl" as used herein by itself or as part of another group refers to an alkyl substituted with one hydroxy group and one haloalkyl group. In one embodiment, the haloalkyl is a $C_1$-$C_4$ haloalkyl. In one embodiment, the alkyl is a $C_1$-$C_4$ alkyl. In another embodiment, the alkyl is a $C_1$ or $C_2$ alkyl. A non-limiting exemplary (hydroxy)(haloalkyl)alkyl groups is:

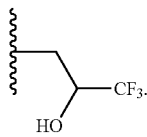

The term "(alkoxycarbonyl)(haloalkyl)alkyl" as used herein by itself or as part of another group refers to an alkyl substituted with one alkoxycarbonyl group and one haloalkyl group. In one embodiment, the haloalkyl is a $C_1$-$C_4$ haloalkyl. In one embodiment, the alkyl is a $C_1$-$C_4$ alkyl. In another embodiment, the alkyl is a $C_1$ or $C_2$ alkyl. A non-limiting exemplary (alkoxycarbonyl)(haloalkyl)alkyl groups is:

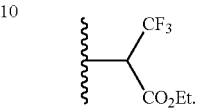

The term "(carboxamido)alkyl" as used herein by itself or as part of another group refers to an alkyl substituted with a carboxamido group. In one embodiment, the alkyl is a $C_1$-$C_4$ alkyl. In another embodiment, the alkyl is a $C_1$ or $C_2$ alkyl. Non-limiting exemplary (carboxamido)alkyl groups include —$CH_2C(=O)NH_2$, —$C(H)(CH_3)C(=O)NH_2$, —$CH_2C(=O)N(H)CH_3$, and —$CH_2C(=O)N(CH_3)_2$.

The term "(carboxy)alkyl" as used herein by itself or as part of another group refers to an alkyl substituted with —$C(=O)OH$. In one embodiment, the alkyl is a $C_1$-$C_4$ alkyl. In another embodiment, the alkyl is a $C_1$ or $C_2$ alkyl. A non-limiting exemplary (carboxy)alkyl group is —$CH_2CO_2H$.

The term "(amino)(hydroxy)alkyl" as used herein by itself or as part of another group refers to an alkyl substituted with one hydroxy group and one amino group. In one embodiment, the alkyl is a $C_1$-$C_4$ alkyl. A non-limiting exemplary "(amino)(hydroxy)alkyl group is:

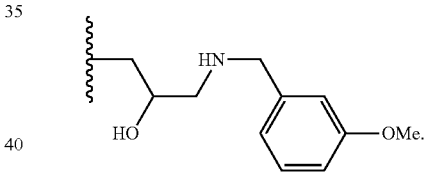

The term "(amino)(aryl)alkyl" as used herein by itself or as part of another group refers to an alkyl group substituted with one amino group and one optionally substituted aryl group. In one embodiment, the amino group is —$NH_2$, alkylamino, or dialkylamino. In one embodiment, the aryl group is an optionally substituted phenyl. In one embodiment, the alkyl is a $C_1$-$C_6$ alkyl. In another embodiment, the alkyl is a $C_1$-$C_4$ alkyl. Non-limiting exemplary (amino)(aryl)alkyl groups include:

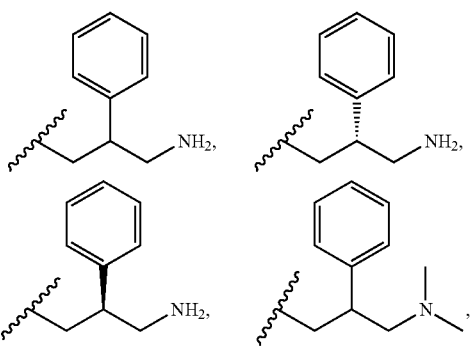

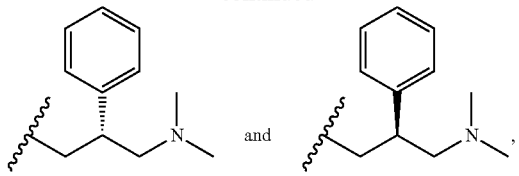
and

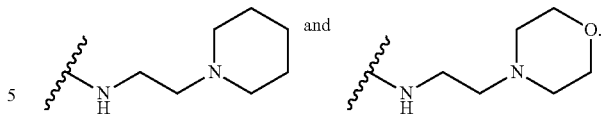

The term "amino" as used by itself or as part of another group refers to a radical of the formula —NR$^{55a}$R$^{55b}$, wherein R$^{55a}$ and R$^{55b}$ are independently hydrogen, optionally substituted alkyl, haloalkyl, (hydroxy)alkyl, (alkoxy)alkyl, (amino)alkyl, heteroalkyl, optionally substituted cycloalkyl, optionally substituted heterocyclo, optionally substituted aryl, optionally substituted heteroaryl, (aryl)alkyl, (cycloalkyl)alkyl, (heterocyclo)alkyl, or (heteroaryl)alkyl.

In one embodiment, the amino is —NH$_2$.

In another embodiment, the amino is an "alkylamino," i.e., an amino group wherein R$^{55a}$ is C$_{1-6}$ alkyl and R$^{55b}$ is hydrogen. In one embodiment, R$^{55a}$ is C$_1$-C$_4$ alkyl. Non-limiting exemplary alkylamino groups include —N(H)CH$_3$ and —N(H)CH$_2$CH$_3$.

In another embodiment, the amino is a "dialkylamino," i.e., an amino group wherein R$^{55a}$ and R$^{55b}$ are each independently C$_{1-6}$ alkyl. In one embodiment, R$^{55a}$ and R$^{55b}$ are each independently C$_1$-C$_4$ alkyl. Non-limiting exemplary dialkylamino groups include —N(CH$_3$)$_2$ and —N(CH$_3$)CH$_2$CH(CH$_3$)$_2$.

In another embodiment, the amino is a "hydroxyalkylamino," i.e., an amino group wherein R$^{55a}$ is (hydroxy)alkyl and R$^{55b}$ is hydrogen or C$_1$-C$_4$ alkyl.

In another embodiment, the amino is a "cycloalkylamino," i.e., an amino group wherein R$^{55a}$ is optionally substituted cycloalkyl and R$^{55b}$ is hydrogen or C$_1$-C$_4$ alkyl.

In another embodiment, the amino is a "aralkylamino," i.e., an amino group wherein R$^{55a}$ is aralkyl and R$^{55b}$ is hydrogen or C$_1$-C$_4$ alkyl. Non-limiting exemplary aralkylamino groups include —N(H)CH$_2$Ph, —N(H)CHPh$_2$, and —N(CH$_3$)CH$_2$Ph.

In another embodiment, the amino is a "(cycloalkyl)alkylamino," i.e., an amino group wherein R$^{55a}$ is (cycloalkyl)alkyl and R$^{55b}$ is hydrogen or C$_1$-C$_4$ alkyl. Non-limiting exemplary (cycloalkyl)alkylamino groups include:

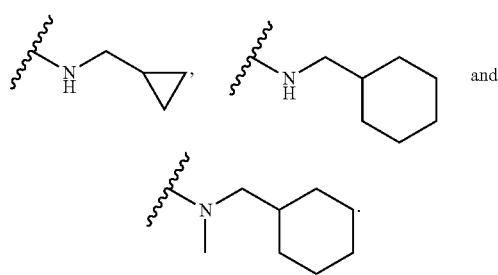

In another embodiment, the amino is a "(heterocyclo)alkylamino," i.e., an amino group wherein R$^{55a}$ is (heterocyclo)alkyl and R$^{55b}$ is hydrogen or C$_1$-C$_4$ alkyl. Non-limiting exemplary (heterocyclo)alkylamino groups include:

The term "(amino)alkyl" as used herein by itself or as part of another group refers to an alkyl substituted with one amino group. In one embodiment, the amino group is —NH$_2$. In one embodiment, the amino group is an alkylamino. In another embodiment, the amino group is a dialkylamino. In another embodiment, the alkyl is a C$_1$-C$_6$ alkyl. In another embodiment, the alkyl is a C$_1$-C$_4$ alkyl. Non-limiting exemplary (amino)alkyl groups include —CH$_2$NH$_2$, CH$_2$CH$_2$N(H)CH$_3$, —CH$_2$CH$_2$N(CH$_3$)$_2$, CH$_2$N(H)cyclopropyl, —CH$_2$N(H)cyclobutyl, and —CH$_2$N(H)cyclohexyl, and —CH$_2$CH$_2$CH$_2$N(H)CH$_2$Ph and —CH$_2$CH$_2$CH$_2$N(H)CH$_2$(4-CF$_3$-Ph).

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H (or deuterium (D)), $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, e.g., $^3$H, $^{11}$C, and $^{14}$C. In one embodiment, provided is a composition wherein substantially all of the atoms at a position within the Compound of the Disclosure are replaced by an atom having a different atomic mass or mass number. In another embodiment, provided is a composition wherein a portion of the atoms at a position within the Compound of the disclosure are replaced, i.e., the Compound of the Disclosure is enriched at a position with an atom having a different atomic mass or mass number." Isotopically-labelled Compounds of the Disclosure can be prepared by methods known in the art.

Compounds of the Disclosure may contain one or more asymmetric centers and may thus give rise to enantiomers, diastereomers, and other stereoisomeric forms. The present disclosure encompasses the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also encompassed by the present disclosure.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive. In one embodiment, Compounds of the Disclosure are racemic.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

In one embodiment, Compounds of the Disclosure having one or more chiral centers are enantiomerically enriched, e.g., the ee is about 5% or more. In another embodiment, the ee is about 10%. In another embodiment, the ee is about 20%. In another embodiment, the ee is about 30%. In another embodiment, the ee is about 40%. In another embodiment, the ee is about 50%. In another embodiment, the ee is about 60%. In another embodiment, the ee is about 70%. In another embodiment, the ee is about 80%. In another embodiment, the ee is about 85%. In another embodiment, the ee is about 90%. In another embodiment, the ee is about 91%. In another embodiment, the ee is about 92%. In another embodiment, the ee is about 93%. In another embodiment, the ee is about 94%. In another embodiment, the ee is about 95%. In another embodiment, the ee is about 96%. In another embodiment, the ee is about 97%. In another embodiment, the ee is about 98%. In another embodiment, the ee is about 99%.

The terms "a" and "an" refer to one or more.

The term "about," as used herein, includes the recited number±10%. Thus, "about 10" means 9 to 11.

The terms "treat," "treating," "treatment," and the like as used herein refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a Compound of the Disclosure to an individual in need of such treatment.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; modulate protein methylation in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

The term "disease" or "condition" or "disorder" denotes disturbances and/or anomalies that as a rule are regarded as being pathological conditions or functions, and that can manifest themselves in the form of particular signs, symptoms, and/or malfunctions. Compounds of the Disclosure inhibit SETD2 protein and can be used in treating diseases and conditions such as proliferative diseases, wherein inhibition of SETD2 protein provides a benefit. See, e.g., U.S. Provisional Appl. No. 62/545,353.

In some embodiments, the Compounds of the Disclosure can be used to treat a "SETD2 protein mediated disorder" A SETD2 protein mediated disorder is any pathological condition in which a SETD2 protein is known to play a role. In some embodiments, a SETD2 mediated disorder is a proliferative disease.

In some embodiments inhibiting SETD2 protein is the inhibition of the activity of one or more activities of SETD2 protein. In some embodiments, the activity of the SETD2 protein is the ability of the SETD2 protein to transfer a methyl group to a target protein, e.g., histone. It should be appreciated that the activity of SETD2 may be inhibited in vitro or in vivo. Exemplary levels of inhibition of the activity of SETD2 include at least 5% inhibition at least 10% inhibition, at least 20% inhibition, at least 30% inhibition, at least 40% inhibition, at least 50% inhibition, at least 60% inhibition, at least 70% inhibition, at least 80% inhibition, at least 90% inhibition, and up to about 100% inhibition.

The term "biological sample" as used herein refers any tissue or fluid from a subject that is suitable for detecting chromosomal translocations. Examples of useful biological samples include, but are not limited to, biopsied tissues and/or cells, e.g., solid tumor, lymph gland, inflamed tissue, tissue and/or cells involved in a condition or disease, blood, plasma, serous fluid, cerebrospinal fluid, saliva, urine, lymph, cerebral spinal fluid, and the like. Other suitable biological samples will be familiar to those of ordinary skill in the relevant arts. A biological sample can be analyzed for chromosomal translocations using any technique known in the art. Such techniques include, but are not limited to, polymerase chain reaction (PCR) methodology, reverse transcription-polymerase chain reaction (RT-PCR) methodology, or cytoplasmic light chain immunofluorescence combined with fluorescence in situ hybridization (cIg-FISH). A biological sample can be obtained using techniques that are well within the scope of ordinary knowledge of a clinical practioner. In one embodiment of the disclosure, the biological sample comprises blood cells.

General Synthesis of Compounds

Compounds of the Disclosure are prepared using methods known to those skilled in the art in view of this disclosure, or by the illustrative methods shown in the General Schemes below. In the General Schemes, $R^{1d}$, $R^{2b}$, $R^{2d}$, $R^{2e}$, $A^1$, $A^2$, $R^{11a}$, $R^{14a}$, $R^{14b}$, $R^{19}$, $R^{20}$, G, $Z^4$, and q are as defined in connection with Formulae II, III, IV, V, or VI, unless otherwise indicated. In any of the General Schemes, suitable protecting groups can be employed in the synthesis, for example, when Z is (amino)alkyl or any other group that may group that may require protection, or when $R^8$ is amino, (amino)alkyl, or any other group that may require protection. (See, Wuts, P. G. M.; Greene, T. W., "Greene's Protective Groups in Organic Synthesis", 4th Ed., J. Wiley & Sons, N Y, 2007) unless otherwise indicated.

In General Scheme 1, the aryl hydrazine of Formula (1) is reacted with ethyl 2-oxopropanoate to give a compound of Formula (2). In step 2, the compound of Formula (2) is converted to the indole of Formula (3) under acidic conditions. In step 3, the compound of Formula (3) is hydrolyzed to give the indole-2-carboxylic acid of Formula (4). In step 4, a compound of Formula (4) is reacted with $G^1NH_2$ under standard coupling conditions to give a compound of Formula II.

In General Scheme 2, a compound of Formula (5) is reacted with $R^{2b}$—H wherein $R^{2b}$ is a heterocyclo, e.g., $R^{2b}$—H is piperidine, or an amine, e.g., $R^{2b}$—H is dimethyl amine, to give a compound of Formula (6). The nitro group of the compound of Formula (6) is reduced to give a compound of Formula (7). In step 3, the compound of Formula (7) is reacted with a compound of Formula (4), see General Scheme 1, under standard coupling conditions to give a compound of Formula III, wherein $A^1$ and $A^2$ are CH and $R^{2b}$ is an optionally substituted heterocyclo or an amino group.

General Scheme 1

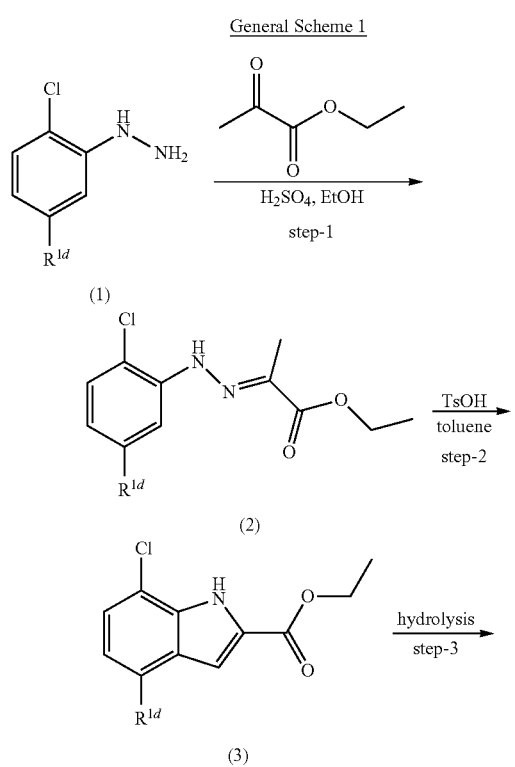

General Scheme 2

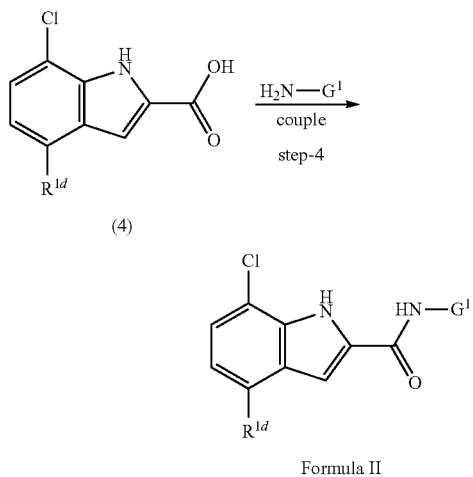

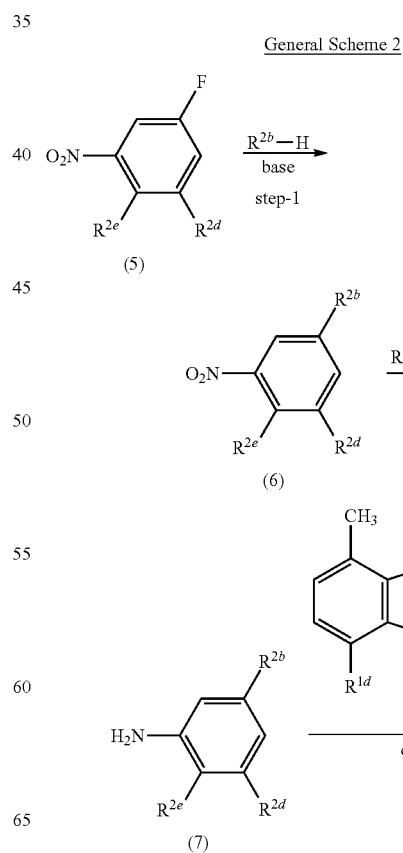

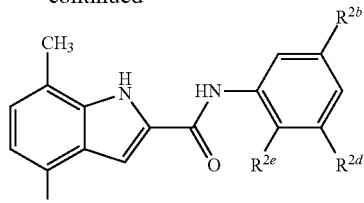

Formula III (wherein $A^1$ and $A^2$ are CH; and
$R^{2b}$ is optionally substituted heterocyclo or amino)

In General Scheme 3, a compound of Formula (8) is reacted with $R^{2b}$—H wherein $R^{2b}$ is a heterocyclo, e.g., $R^{2b}$—H is piperidine, or an amine, e.g., $R^{2b}$—H is dimethyl amine, to give a compound of Formula (9). In step 2, the compound of Formula (9) is reacted with a compound of Formula (10) to give a compound of Formula III, wherein $A^1$ and/or $A^2$ are N and $R^{2b}$ is an optionally substituted heterocyclo or an amino group.

General Scheme 3

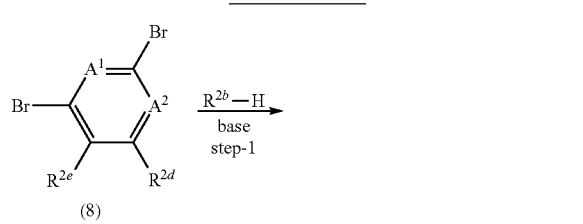

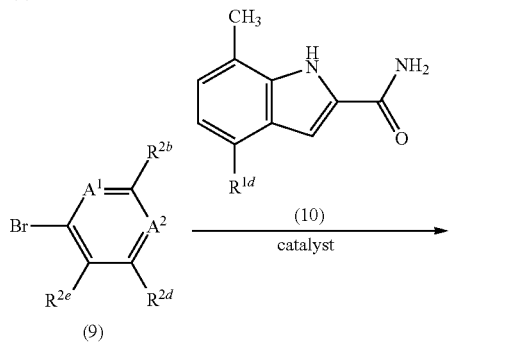

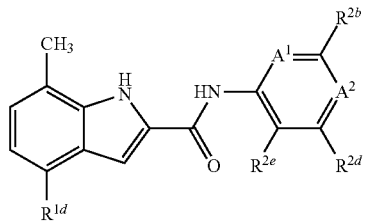

Formula III
(wherein $A^1$ and/or $A^2$ are N;
and $R^{2b}$ is optionally substituted
heterocyclo or amino)

In General Scheme 4, a compound of Formula (11) is reacted with $R^{11a}$—H, wherein $R^{11a}$ is a heterocyclo, e.g., $R^{11a}$—H is piperidine, to give a compound of Formula (12). In step 2, the Cbz group is removed to give a compound of Formula (13). The compound of Formula (13) is coupled with a compound of Formula (4) to give a compound of Formula IV, wherein $R^{11a}$ is optionally substituted heterocyclo and $Z^5$ is —$CH_2$—.

General Scheme 4

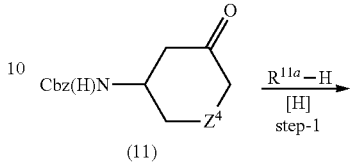

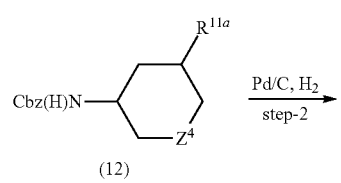

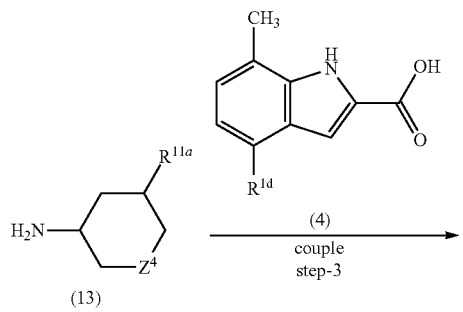

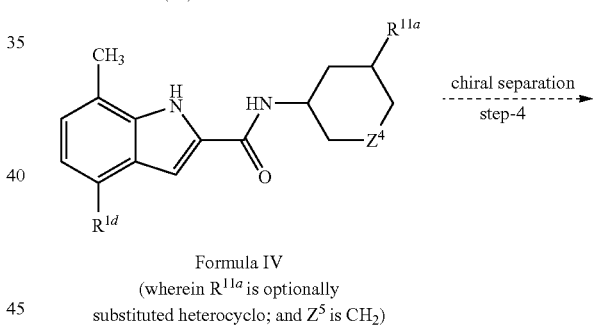

Formula IV
(wherein $R^{11a}$ is optionally
substituted heterocyclo; and $Z^5$ is $CH_2$)

Formula IV-A
Formula IV-B
Formula IV-C
Formula IV-D

In step 1 of General Scheme 5, a nitrile of Formula (14) is reacted with a Grignard reagent ($R^{14a}$—MgBr) and the resulting product is reduced to give a compound of Formula (15). The compound of Formula (15) is coupled with a compound of Formula (4) to give a compound of Formula V, wherein p is 0.

General Scheme 5

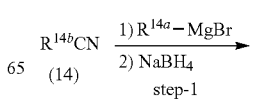

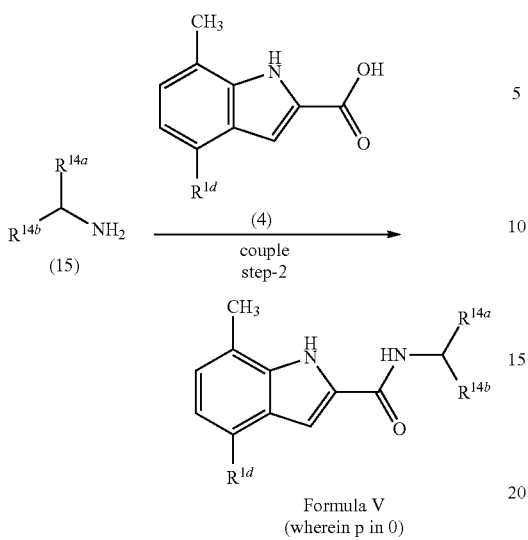

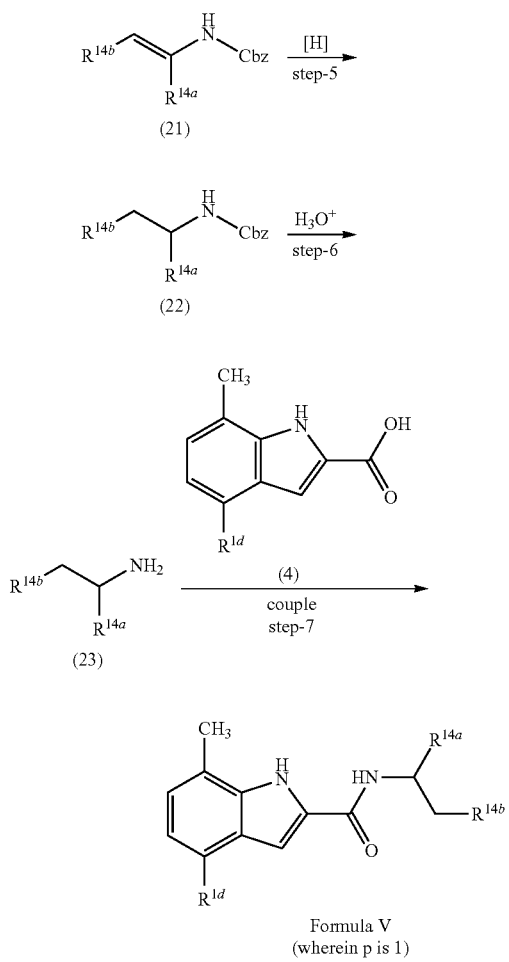

In General Scheme 6, an aldehyde of Formula (16) is reacted with an ester of Formula (17) to give a compound of Formula (18). In step 2, the compound of Formula (18) hydrolyzed to give a compound of Formula (19). In step 3, the compound of Formula (19) is converted to the isocyanate of Formula (20). The compound of Formula (20) is reacted with benzyl alcohol to give a compound of Formula (21). Hydrogenation of a compound of Formula (21) and removal of the Cbz groups gives an amine of Formula (23). Coupling a compound of Formula (23) with a compound of Formula (4) gives a compound of Formula V, wherein p is 1.

General Scheme 6

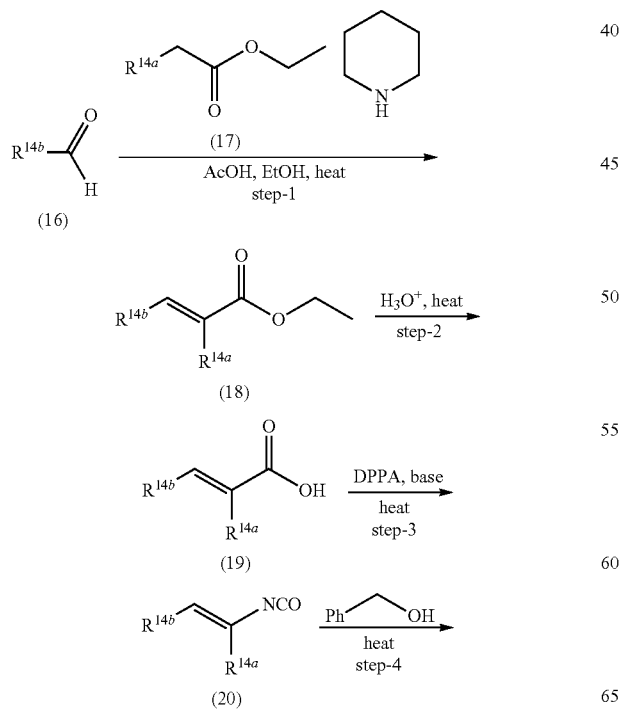

In General Scheme 7, the nitrile of Formula (24) is reduced to give an amine of Formula (25). The compound of Formula (25) is coupled with a compound of Formula (4) to give a compound of Formula VI.

General Scheme 7

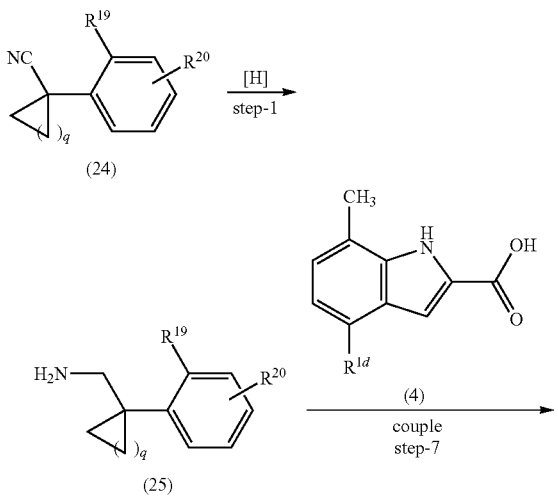

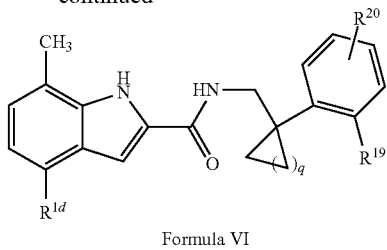

Formula VI

EXAMPLES

General Synthetic Methods

General methods and experimental procedures for preparing and characterizing Compounds of the Disclosure are set forth in the General Schemes above and the EXAMPLES below. Wherever needed, reactions were heated using conventional hotplate apparatus or heating mantle or microwave irradiation equipment. Reactions were conducted with or without stirring, under atmospheric or elevated pressure in either open or closed vessels. Reaction progress was monitored using conventional techniques such as TLC, HPLC, UPLC, or LCMS using instrumentation and methods described below. Reactions were quenched and crude compounds isolated using conventional methods as described in the specific examples provided. Solvent removal was carried out with or without heating, under atmospheric or reduced pressure, using either a rotary or centrifugal evaporator.

Compound purification was carried out as needed using a variety of traditional methods including, but not limited to, preparative chromatography under acidic, neutral, or basic conditions using either normal phase or reverse phase HPLC or flash columns or Prep-TLC plates. Compound purity and mass confirmations were conducted using standard HPLC and/or UPLC and/or MS spectrometers and/or LCMS and/or GC equipment (possibly including, but not limited to, the following instrumentation: Waters Alliance 2695 with 2996 PDA detector connected with ZQ detector and ESI source; Shimadzu LDMS-2020; Waters Acquity H Class with PDA detector connected with SQ detector and ESI source; Agilent 1100 Series with PDA detector; Waters Alliance 2695 with 2998 PDA detector; AB SCIEX API 2000 with ESI source; Agilent 7890 GC). Exemplified compounds were dissolved in either MeOH or MeCN to a concentration of approximately 1 mg/mL and analyzed by injection of 0.5-10 µL into an appropriate LCMS system using appropriate methods. MS data are presented in Table 1B. In all cases the mass detection method was ESI.

Compound structure confirmations were carried out using standard 300 or 400 MHz NMR spectrometers. Unless otherwise indicated, the LCMS methods used in EXAMPLES are as follows:

Method A
 Instrument: SHIMADZU LCMS-2010EV
Analysis Conditions:
LC Parameters:
 Column: Shim-pack XR-ODS 2.2 um 3.0*50 mm; Mobile Phase A: Water/0.05% TFA; Mobile Phase B: Acetonitrile/0.05% TFA; Gradient: 5% to 100% B in 2.0 minutes, 100% B for 0.7 minutes, 100% to 5% B in 0.05 minutes, then stop; Flow Rate: 1.2 mL/min; Column Temperature: 40° C.; Detector: PDA and ELSD; Sample Preparation: 1 mg/mL in methanol; Injection Volume: 1 µL; Report: Area Normalized Purity.
MS Parameters:
 Interface: ESI (Positive); Interface Voltage: 4.5 kv; Heat Block: 250° C.; Nebulizing Gas: 1.50 L/min; Scan Range: 90-900 (m/z); Detector voltage: 1.6 kv.
Method B
 Instrument: SHIMADZU LCMS-2020
Analysis Conditions:
LC Parameters:
 Column: Kinetex EVO C18 2.6 um 2.1*50 mm; Mobile Phase A: 6.5 mM Ammonium Bicarbonate in water adjusted to pH 10 with Ammonia solution; Mobile Phase B: Acetonitrile; Gradient: 5% to 100% B in 2.0 minutes, 100% B for 0.7 minutes, 100% to 5% B in 0.1 minutes, then stop; Flow Rate: 1.0 mL/min; Column Temperature: 35° C.; Detector: PDA and ELSD; Sample Preparation: 1 mg/mL in Methanol; Injection Volume: 1 µL; Report: Area Normalized Purity.
MS Parameters:
 Interface: ESI (Positive & Negative); Interface Voltage: Tuning File; Heat Block: 200° C.; Nebulizing Gas: 1.50 L/min; Scan Range: 90-900 (m/z); Detector voltage: 0.9 kv.
Method C
 Instrument: SHIMADZU LCMS-2020
Analysis Conditions:
LC Parameters:
 Column: CORTECS C18+2.7 um 2.1*50 mm; Mobile Phase A: Water/0.1% FA; Mobile Phase B: Acetonitrile/0.05% FA; Gradient: 5% to 100% B in 2.0 minutes, 100% B for 0.7 minutes, 100% to 5% B in 0.1 minutes, then stop; Flow Rate: 1.0 mL/min; Column Temperature: 40° C.; Detector: PDA and ELSD; Sample Preparation: 1 mg/mL in Acetonitrile; Injection Volume: 1 µL; Report: Area Normalized Purity.
MS Parameters:
 Interface: ESI (Positive & Negative); Interface Voltage: Tuning File; Heat Block: 200° C.; Nebulizing Gas: 1.50 L/min; Scan Range: 90-900 (m/z); Detector voltage: 1.2 kv.
Method D
 Instrument: SHIMADZU LCMS-2020
Analysis Conditions:
 LC Parameters:
 Column: Shim-pack XR-ODS 2.2 um 3.0*50 mm; Mobile Phase A: Water/0.05% TFA; Mobile Phase B: Acetonitrile/0.05% TFA; Gradient: 5% to 100% B in 2.0 minutes, 100% B for 0.7 minutes, 100% to 5% B in 0.05 minutes, then stop; Flow Rate: 1.2 mL/min; Column Temperature: 40° C.; Detector: PDA and ELSD; Sample Preparation: 1 mg/mL in Acetonitrile; Injection Volume: 1 µL; Report: Area Normalized Purity.
MS Parameters:
 Interface: ESI (Positive); Interface Voltage: Tuning File; Heat Block: 250° C.;
 Nebulizing Gas: 1.50 L/min; Scan Range: 90-900 (m/z); Detector voltage: 1.0 kv.
Method E
 Instrument: SHIMADZU LCMS-2020
Analysis Conditions:
LC Parameters:
 Column: Shim-pack XR-ODS 2.2 um 3.0*50 mm; Mobile Phase A: Water/0.05% TFA; Mobile Phase B: Acetonitrile/0.05% TFA; Gradient: 5% to 100% B in 2.0 minutes, 100% B for 0.7 minutes, 100% to 5% B in 0.05 minutes, then stop; Flow Rate: 1.2 mL/min; Column Temperature: 40° C.;

Detector: PDA and ELSD; Sample Preparation: 1 mg/mL in Acetonitrile; Injection Volume: 1 μL; Report: Area Normalized Purity.

MS Parameters:

Interface: ESI (Positive); Interface Voltage: Tuning File; Heat Block: 300° C.; Nebulizing Gas: 1.50 L/min; Scan Range: 90-900 (m/z); Detector voltage: 1.1 kv.

The following abbreviations may be used herein:

| Abbreviation | Meaning |
| --- | --- |
| ACN | acetonitrile |
| atm. | atmosphere |
| DCM | dichloromethane |
| DHP | dihydropyran |
| DIBAL | diisobutyl aluminum hydride |
| DIEA | diisopropyl ethylamine |
| DMF | dimethyl formamide |
| DMF-DMA | dimethyl formamide dimethyl acetal |
| DMSO | dimethyl sulfoxide |
| Dppf | 1,1'-bis(diphenylphosphino)ferrocene |
| EA | ethyl acetate |
| ESI | electrospray ionization |
| EtOH | Ethanol |
| FA | formic acid |
| GC | gas chromatography |
| H | hour |
| Hex | hexanes |
| HMDS | hexamethyl disilazide |
| HPLC | high performance liquid chromatography |
| IPA | Isopropanol |
| LCMS | liquid chromatography/mass spectrometry |
| MeOH | Methanol |
| Min | Minutes |
| NBS | N-bromo succinimide |
| NCS | N-chloro succinimide |
| NIS | N-iodo succinimide |
| NMR | nuclear magnetic resonance |
| nOe | nuclear Overhauser effect |
| Prep. | Preparative |
| PTSA | para-toluene sulfonic acid |
| Rf | retardation factor |
| rt | room temperature |
| RT | retention time |
| sat. | Saturated |
| SGC | silica gel chromatography |
| TBAF | tetrabutyl ammonium fluoride |
| TEA | Triethylamine |
| TFA | trifluoroacetic acid |
| THF | Tetrahydrofuran |
| TLC | thin layer chromatography |
| UPLC | ultra performance liquid chromatography |

Example 1

Synthesis of N-((1R,3S)-3-(4-acetylpiperazin-1-yl)cyclohexyl)-4-fluoro-7-methyl-1H-indole-2-carboxamide (Cpd. No. 15)

Step 1. Synthesis of ethyl (2E)-2-[2-(5-fluoro-2-methylphenyl)hydrazin-1-ylidene]propanoate

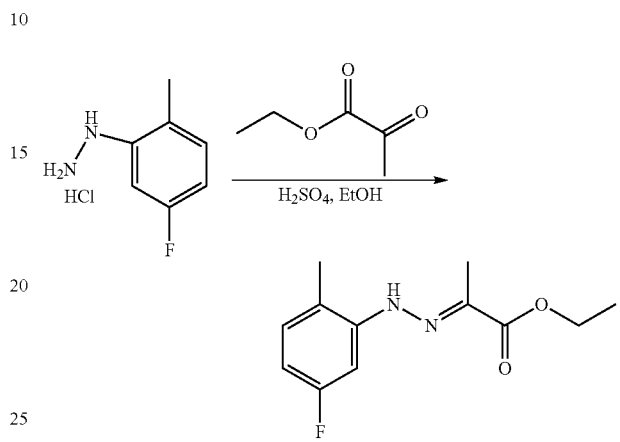

Into a 1000-mL round-bottom flask, was placed a solution of (5-fluoro-2-methylphenyl)hydrazine hydrochloride (100 g, 572.73 mmol, 1.00 equiv) in ethanol (400 mL), ethyl 2-oxopropanoate (66 g, 1.20 equiv), sulfuric acid (10 mL). The resulting solution was stirred for 2 h at 25° C. The reaction progress was monitored by LCMS. The resulting mixture was concentrated under vacuum. The solids were collected by filtration. This resulted in 120 g (yield=88%) of ethyl (2E)-2-[2-(5-fluoro-2-methylphenyl) hydrazin-1-ylidene]propanoate as a yellow solid. LCMS (Method A: ESI): RT=1.399 min, m/z=239.0 [M+H]$^+$. $^1$H NMR (400 MHz, DMSO-d$_6$) δ 11.96 (d, J=2.0 Hz, 1H), 7.15 (m, 2H), 6.62 (m, 1H), 4.25 (q, J=7.1 Hz, 2H), 2.12 (d, J=9.3 Hz, 6H), 1.29 (t, J=7.1 Hz, 3H) ppm.

Step 2. Synthesis of ethyl 4-fluoro-7-methyl-1H-indole-2-carboxylate

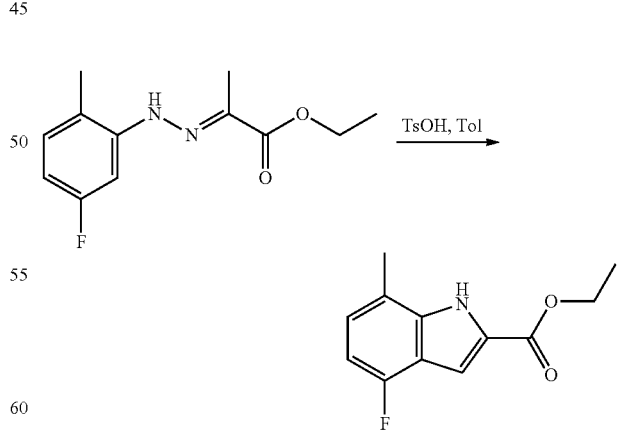

Into a 1000-mL round-bottom flask, was placed a solution of ethyl (2E)-2-[2-(5-fluoro-2-methylphenyl)hydrazin-1-ylidene]propanoate (40 g, 167.89 mmol, 1.00 equiv) in Toluene (400 mL), 4-methylbenzene-1-sulfonic acid (50 g, 290.36 mmol, 1.70 equiv). The resulting solution was stirred for 18 h at 100° C. The reaction progress was monitored by LCMS. The resulting solution was concentrated under vacuum, and the residue was dissolved by 100 ml of ethyl acetate. The resulting mixture was washed with 3×200 mL of saturated aqueous NaHCO₃. The residue was applied onto a silica gel column with ethyl acetate/petroleum ether (1:5). The resulting mixture was concentrated under vacuum. The solid was purified by recrystalization from ethanol. This resulted in 9.0 g (yield=24%) of ethyl 4-fluoro-7-methyl-1H-indole-2-carboxylate as a yellow solid. LCMS (Method A, ESI): RT=1.354 min: m/z=222.0 [M+H]⁺. ¹H NMR (400 MHz, DMSO-d₆) δ 12.07 (s, 1H), 7.17 (d, J=2.1 Hz, 1H), 7.00 (m, 1H), 6.77 (m, 7.8 Hz, 1H), 4.36 (q, J=7.1 Hz, 2H), 2.49 (d, J=1.0 Hz, 3H), 1.35 (t, J=7.1 Hz, 3H) ppm.

Step 3. Synthesis of
4-fluoro-7-methyl-1H-indole-2-carboxylic acid

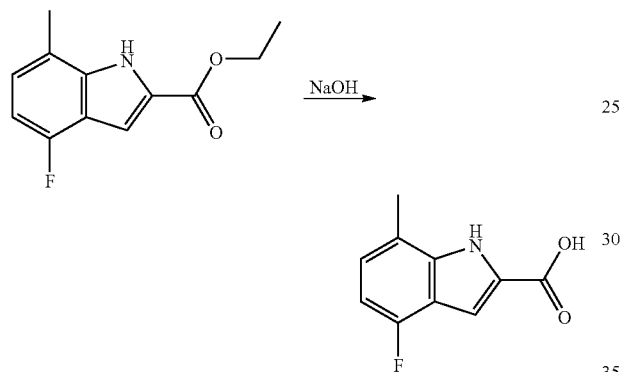

Into a 500-mL round-bottom flask, was placed a solution of ethyl 4-fluoro-7-methyl-1H-indole-2-carboxylate (9.1 g, 41.13 mmol, 1.00 equiv) in tetrahydrofuran (150 mL), sodium hydroxide (8 g, 200.00 mmol, 5.00 equiv), water (50 mL), methanol (2 mL). The resulting solution was stirred for 6 h at 25° C. The resulting mixture was concentrated under vacuum. The residue was diluted with water 50 ml, then adjusted to pH 5 with hydrogen chloride (3.0 mol/L). The resulting solution was extracted with 3×50 mL of ethyl acetate. The solid was collected by filtration. This resulted in 8.0 (yield=81%) g of 4-fluoro-7-methyl-1H-indole-2-carboxylic acid as a brown solid. LCMS (Method C, ESI): RT=0.989 min, m/z=192.0 [M−H]⁺. ¹H NMR (300 MHz, DMSO-d₆) δ 13.10 (s, 1H), 11.94 (s, 1H), 7.09 (d, J=2.1 Hz, 1H), 6.96 (m, 1H), 6.73 (m, 1H), 2.46 (d, J=1.1 Hz, 3H) ppm.

Step 4. Synthesis of tert-butyl N-[3-(4-acetylpiperazin-1-yl)cyclohexyl]carbamate

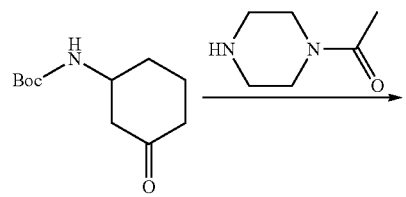

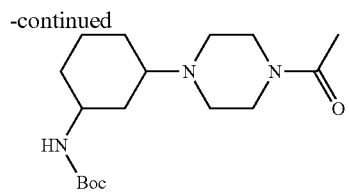

Into a 100-mL round-bottom flask, was placed tert-butyl N-(3-oxocyclohexyl)carbamate (800 mg, 3.75 mmol, 1.00 equiv), 1-(piperazin-1-yl)ethan-1-one (800 mg, 6.24 mmol, 1.66 equiv), methanol (10 mL), Pd/C (0.2 g), and to the above mixture, hydrogen was introduced. The resulting solution was stirred for 2 h at 25° C. The reaction progress was monitored by LCMS. The solids were filtered out. The resulting mixture was concentrated under vacuum. The crude product (900 mg) was purified by Flash-Prep-HPLC with the following conditions: Column, C18 silica gel; mobile phase; Detector, UV 254/220 nm. This resulted in 700 mg (yield=57%) of tert butyl N-[3-(4-acetylpiperazin-1-yl)cyclohexyl]carbamate as colorless oil. LCMS (Method A, ESI): RT=1.361 min, m/z=325.9 [M+H]⁺.

Step 5. Synthesis of 1-[4-(3-aminocyclohexyl)piperazin-1-yl]ethan-1-one

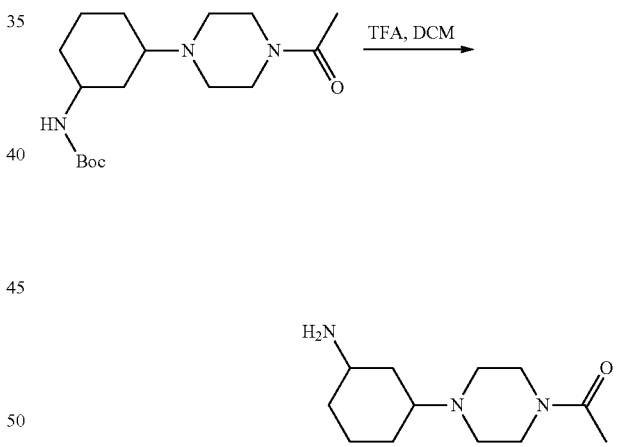

Into a 100-mL round-bottom flask, was placed tert-butyl N-[3-(4-acetylpiperazin-1-yl)cyclohexyl]carbamate (700 mg, 2.15 mmol, 1.00 equiv), dichloromethane (3 mL), trifluoroacetic acid (2 mL) was added by dropwise. The resulting solution was stirred for 2 h at 25° C. The reaction progress was monitored by LCMS. The resulting mixture was concentrated under vacuum. This resulted in 700 mg of 1-[4-(3-aminocyclohexyl)piperazin-1-yl]ethan-1-one as a brown oil. LCMS (Method A, ES): RT=0.647 min. m/z=225.95 [M+H]⁺.

Step 6. Synthesis of N-[(1R,3S)-3-(4-acetylpiperazin-1-yl)cyclohexyl]-4-fluoro-7-methyl-1H-indole-2-carboxamide (as the TFA Salt)

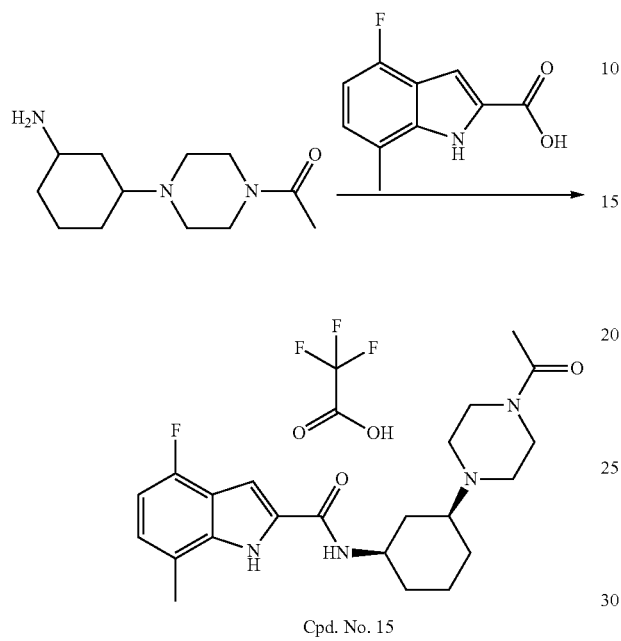

Cpd. No. 15

Into a 100-mL round-bottom flask, was placed 4-fluoro-7-methyl-1H-indole-2-carboxylic acid (100 mg, 0.52 mmol, 1.00 equiv), 1-[4-(3-aminocyclohexyl)piperazin-1-yl]ethan-1-one (110 mg, 0.49 mmol, 0.94 equiv), N,N-dimethylformamide (4 mL), DIEA (200 mg, 1.55 mmol, 2.99 equiv), HATU (260 mg, 0.68 mmol, 1.32 equiv) was added batchwise. The resulting solution was stirred for 2 h at 25° C. The reaction progress was monitored by LCMS, and the reaction solution was quenched by 10 ml of water. The resulting solution was extracted with 3×15 ml of ethyl acetate and the organic layers combined and concentrated under vacuum. The residue was applied onto a silica gel column with ethyl acetate/petroleum ether (1:1). The crude product was purified by Chiral-Prep-HPLC with the following conditions: Column, (R,R)-WHELK-014.6*50 mm, 3.5 μm:1-78220-30056749; mobile phase, Hexane (0.1% DEA):EtOH=85:15; Detector, UV 254 nm/220 nm. The product thus obtained was further purified by Prep-HPLC with the following conditions: Column, XBridge Prep Phenyl OBD Column, 5 μm, 19*150 mm; mobile phase, Water with 10 mmol TFA and MeCN (20.0% MeCN up to 30.0% in 10 min, up to 95.0% in 1 min, hold 95.0% in 1 min, down to 20.0% in 2 min); Detector, UV 254/220 nm. This resulted in 30.5 mg (yield=11%) of N-[(1R,3S)-3-(4-acetylpiperazin-1-yl)cyclohexyl]-4-fluoro-7-methyl-1H-indole-2-carboxamide trifluoroacetic acid salt as a white solid. LCMS (Method B, ES): RT=1.138 min, m/z=401.0 [M-TFA]$^+$. $^1$H NMR (300 MHz, Methanol-d4) δ 7.18 (s, 1H), 6.94-6.92 (m, 1H), 6.64-6.62 (m, 1H), 4.03-3.88 (m, 1H), 3.57-3.55 (m, 4H), 2.65 (t, J=16.4 Hz, 5H), 2.48 (t, J=1.0 Hz, 3H), 2.23 (d, J=12.0 Hz, 1H), 2.09 (s, 3H), 1.93 (d, J=12.2 Hz, 3H), 1.53-1.18 (m, 4H) ppm.

Example 2

Synthesis of 4-fluoro-7-methyl-N-(2-(4-methylpiperazin-1-yl)pyridin-4-yl)-1H-indole-2-carboxamide (Cpd. No. 340)

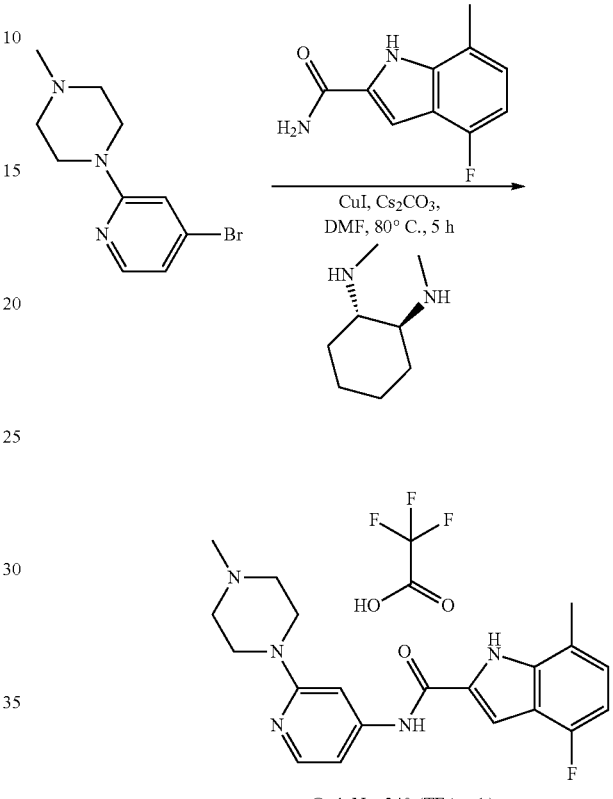

Cpd. No. 340 (TFA salt)

Into a 100-mL round-bottom flask purged and maintained with an inert atmosphere of nitrogen, was placed a solution of 4-fluoro-7-methyl-1H-indole-2-carboxamide (632 mg, 3.29 mmol, 1.20 equiv) in N,N-dimethylformamide (15 ml), 1-(4-bromopyridin-2-yl)-4-methylpiperazine (700 mg, 2.73 mmol, 1.00 equiv), (1R,2S)-1-N,2-N-dimethylcyclohexane-1,2-diamine (785 mg, 5.52 mmol, 2.00 equiv), CuI (522 mg, 2.74 mmol, 1.00 equiv), Cs$_2$CO$_3$ (2.7 g, 8.29 mmol, 3.00 equiv). The resulting solution was stirred for 15 h at 80° C. The reaction progress was monitored by LCMS. The crude product (100 mg) was purified by Prep-HPLC with the following conditions: Column, XSelect CSH Prep C18 OBD Column, 5 μm, 19*150 mm; mobile phase, Water (0.05% TFA) and ACN (15.0% ACN up to 40.0% in 9 min); Detector, UV 254/220 nm. This resulted in 58.8 mg (4%) of 4-fluoro-7-methyl-N-[2-(4-methylpiperazin-1-yl)pyridin-4-yl]-1H-indole-2-carboxamide as the trifluoroacetic acid salt as a white solid. LCMS (Method B, ESI): RT=2.543 min, m/z=368.0 [M+H]$^+$. $^1$H NMR (400 MHz, Methanol-d4) δ 8.14 (dd, J=2.4 Hz, 4.5 Hz, 1H), 7.88 (s, 1H), 7.51 (d, J=1.5 Hz, 1H), 7.38 (d, J=5.1 Hz, 1H), 7.08 (dd, J=3.9 Hz, 5.7 Hz, 1H), 6.72 (dd, J=6.0 Hz, 7.8 Hz, 1H), 3.93 (br, 4H), 3.51 (s, 4H), 3.02 (s, 3H), 2.54 (s, 3H) ppm.

Example 3

Synthesis of 4-fluoro-7-methyl-N-((1-(2-(4-methylpiperazin-1-yl)phenyl)cyclopropyl)methyl)-1H-indole-2-carboxamide (Cpd. No. 392)

Step 1. Synthesis of 1-[2-(4-methylpiperazin-1-yl)phenyl]cyclopropane-1-carbonitrile

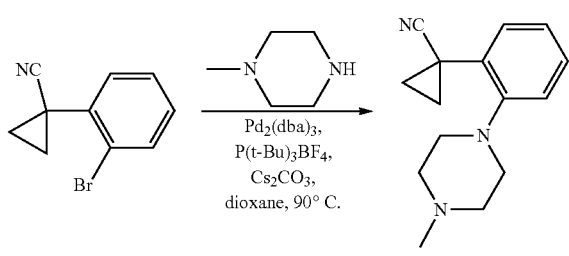

Into a 30-mL microwave tube purged and maintained with an inert atmosphere of nitrogen, was placed 1-(2-bromophenyl)cyclopropane-1-carbonitrile (2.0 g, 9.01 mmol, 1.00 equiv), 1-methylpiperazine (4.5 g, 44.93 mmol, 4.99 equiv), Pd$_2$(dba)$_3$ (800 mg, 0.87 mmol, 0.10 equiv), P(t-Bu)$_3$BF$_4$ (0.52 g 1.79 mmol, 2.00 equiv), Cs$_2$CO$_3$ (8.8 g, 27.01 mmol, 3.00 equiv), dioxane (8 mL). The resulting solution was stirred for 3 h at 90° C. in an oil bath. The reaction progress was monitored by LCMS. The resulting solution was extracted with (30 mL×3) of dichloromethane and the organic layers combined and dried over anhydrous sodium sulfate and concentrated under vacuum. The residue was applied onto a silica gel column with dichloromethane/methanol (10:1). The collected fractions were combined and concentrated under vacuum. This resulted in 0.2 g (yield=9%) of 1-[2-(4-methylpiperazin-1-yl)phenyl]cyclopropane-1-carbonitrile as brown oil. LCMS (Method A, ESI): RT=1.05 min, m/z=323.0 [M+1]$^+$.

Step 2. Synthesis of (1-(2-(4-methylpiperazin-1-yl)phenyl)cyclopropyl) methanamine

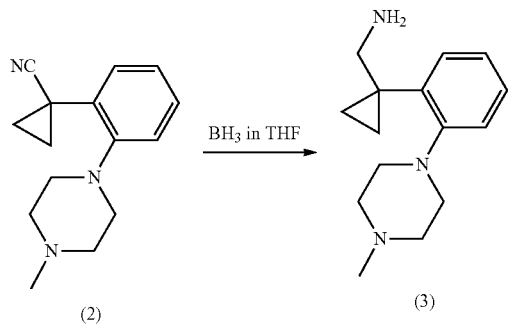 [SMILES: CN1CCN(c2ccccc2C2(C#N)CC2)CC1 ; CN1CCN(c2ccccc2C2(CN)CC2)CC1]

Into a 25-mL round-bottom flask, was placed 1-[2-(4-methylpiperazin-1-yl)phenyl]cyclopropane-1-carbonitrile (200 mg, 0.83 mmol, 1.00 equiv), tetrahydrofuran (4.1 mL), BH$_3$/THF (4.1 mL). The resulting solution was stirred for 3 h at 25° C. in nitrogen atmosphere. The reaction progress was monitored by LCMS. The pH value of the solution was adjusted to 8 with sodium bicarbonate (20% aq). The resulting solution was extracted with (3×15 mL) of dichloromethane and the organic layers combined, concentrated under vacuum and 120 mg (yield=60%) of (1-(2-(4-methylpiperazin-1-yl)phenyl)cyclopropyl) methanamine was obtained. LCMS (Method A, ESI): RT=0.92 min. m/z=246.0 [M+1]$^+$.

Step 3. Synthesis of 4-fluoro-7-methyl-N-([1-[2-(4-methylpiperazin-1-yl)phenyl]cyclopropyl]methyl)-1H-indole-2-carboxamide

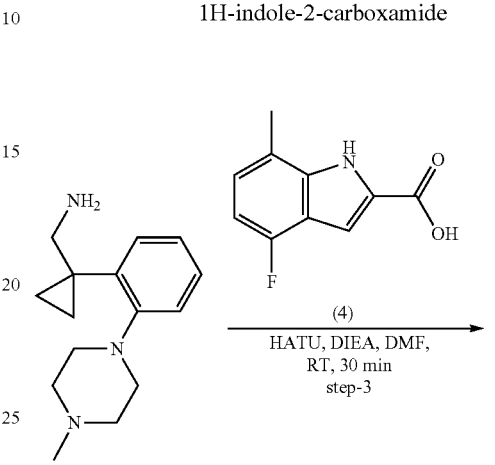

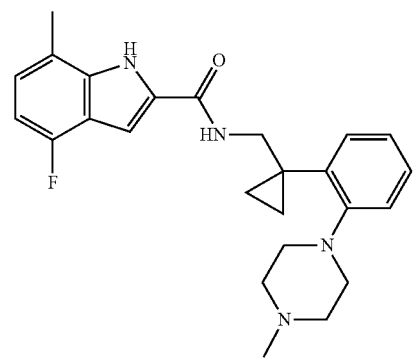

Cpd. No. 392

Into a 25-mL round-bottom flask, was placed 4-fluoro-7-methyl-1H-indole-2-carboxylic acid (50 mg, 0.26 mmol, 1.00 equiv), 1-[2-(4-methylpiperazin-1-yl)phenyl]cyclopropylmethanamine (82.5 mg, 0.34 mmol, 1.30 equiv), N,N-dimethylformamide (1 mL), DIEA (166 mg, 1.28 mmol, 4.96 equiv), HATU (98 mg, 0.26 mmol, 1.00 equiv) was added batchwise. The resulting solution was stirred for 30 min at 25° C. The crude product (80 mg) was purified by Prep-HPLC with the following conditions: Column, Kinetex EVO C18 Column, 21.2*150, 5 μm; mobile phase, Water (10 mmol/L NH$_4$HCO$_3$) and ACN (50.0% ACN up to 70.0% in 7 min); Detector, UV 254/220 nm. This resulted in 23 mg (yield=21%) of 4-fluoro-7-methyl-N-([1-[2-(4-methylpiperazin-1-yl)phenyl]cyclopropyl]methyl)-1H-indole-2-carboxamide as an off-white solid. LCMS (Method B, ESI): RT=1.95 min, m/z=421.1 [M+1]$^+$. $^1$H NMR (400 MHz, Methanol-d4) δ 7.33 (dd, J=7.6, 1.5 Hz, 1H), 7.29-7.19 (m, 2H), 7.10-7.02 (m, 2H), 6.98-6.91 (m, 1H), 6.65 (dd, J=10.4, 7.8 Hz, 1H), 3.82 (s, 2H), 3.09 (s, 4H), 2.72 (s, 4H), 2.46 (d, J=1.0 Hz, 3H), 2.41 (s, 3H), 1.08-0.97 (m, 2H), 0.95-0.80 (m, 2H) ppm.

Example 4

Synthesis of N-(cyclopropyl(isoquinolin-1-yl)methyl)-4-fluoro-7-methyl-1H-indole-2-carboxamide (Cpd. No. 507)

Step 1. Synthesis of cyclopropyl(isoquinolin-1-yl)methanamine

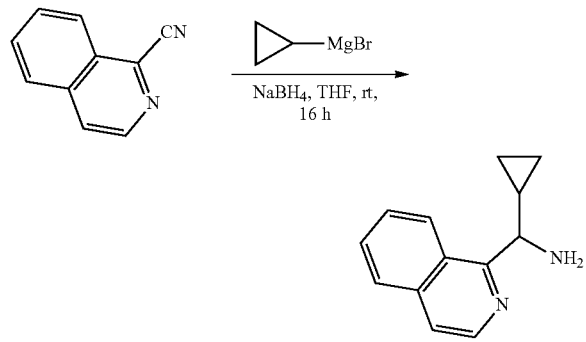

Into a 250-mL 3-necked round-bottom flask, was placed isoquinoline-1-carbonitrile (500 mg, 3.24 mmol, 1.00 equiv) in tetrahydrofuran (10 mL), and the solution was cooled to 0° C. bromo(cyclopropyl)magnesium (1 mol/L) (33 ml, 1.00 equiv) was added by dropwise, after stirring for 30 min at this temperature, methanol (10 ml) was added and NaBH₄ (350 mg, 9.25 mmol, 2.85 equiv) was added by batchwise at 0° C. The resulting solution was stirred for 4 h at 25° C. The reaction progress was monitored by LCMS. The reaction solution was quenched by 10 ml of ice/water. The resulting solution was extracted with 3×30 mL of ethyl acetate and the organic layers combined and dried over anhydrous sodium sulfate and concentrated under vacuum. The residue was applied onto a silica gel column with dichloromethane/methanol (10/1), This resulted in 300 mg (yield=60%) of cyclopropyl(isoquinolin-1-yl)methanamine as an off-white solid. LCMS (Method A, ESI): RT=0.865 min, m/z=199.00 [M+H]⁺.

Step 2. Synthesis of N-(cyclopropyl(isoquinolin-1-yl)methyl)-4-fluoro-7-methyl-1H-indole-2-carboxamide

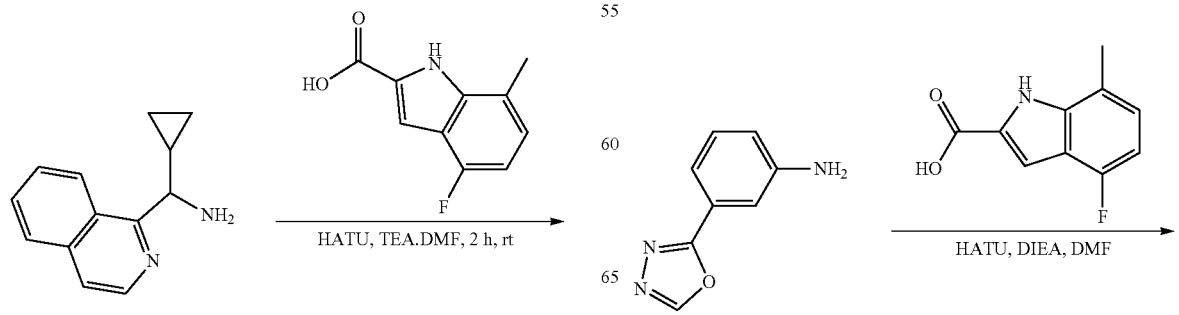

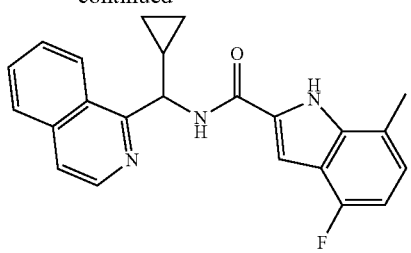

Cpd. No. 507

Into a 100-mL round-bottom flask, was placed cyclopropyl(isoquinolin-1-yl)methanamine (300 mg, 1.51 mmol, 1.00 equiv), TEA (450 mg, 4.45 mmol, 2.94 equiv), N,N-dimethylformamide (30 mL), 4-fluoro-7-methyl-1H-indole-2-carboxylic acid (300 mg, 1.55 mmol, 1.03 equiv), HATU (550 mg, 1.45 mmol, 0.96 equiv). The resulting solution was stirred for 2 h at 25° C. The reaction progress was monitored by LCMS. The resulting solution was quenched with 10 mL of ice/water. The resulting solution was extracted with 3×50 mL of ethyl acetate and the organic layers combined and dried over anhydrous sodium sulfate and concentrated under vacuum. The crude product (100 mg) was purified by Prep-HPLC with the following conditions: Column, Kinetex EVO C18 Column, 21.2*150.5 µm; mobile phase, Water (10 mmol/L NH₄HCO₃) and ACN (50.0% ACN up to 75.0% in 7 min); Detector, UV 254/220 nm. This resulted in 60.2 mg (yield=11%) of N-[cyclopropyl(isoquinolin-1-yl)methyl]-4-fluoro-7-methyl-1H-indole-2-carboxamide as a white solid. LCMS (Method D, ESI): RT=1.55 min, m/z=374.00 [M+H]⁺. ¹H NMR (300 MHz, Methanol-d4) δ 8.47 (t, J=6.5 Hz, 2H), 8.00-7.90 (m, 1H), 7.83-7.65 (m, 3H), 7.24 (s, 1H), 7.00-6.89 (m, 1H), 6.67-6.61 (m, 1H), 5.65 (d, J=8.6 Hz, 1H), 2.48 (s, 3H), 1.72-1.55 (m, 1H), 0.65-0.42 (m, 4H) ppm.

Example 5

Synthesis of N-(3-(1,3,4-oxadiazol-2-yl)phenyl)-4-fluoro-7-methyl-1H-indole-2-carboxamide (Cpd. No. 60)

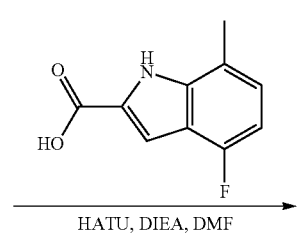

-continued

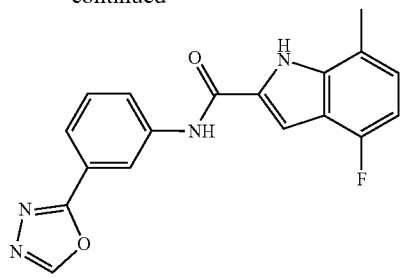

Cpd. No. 60

Into a 15-mL vial, was placed 3-(1,3,4-oxadiazol-2-yl) aniline (120 mg, 0.74 mmol, 1.00 equiv), 4-fluoro-7-methyl-1H-indole-2-carboxylic acid (168 mg, 0.87 mmol, 1.17 equiv), N,N-dimethylformamide (3 mL), DIEA (288 mg, 2.23 mmol, 2.99 equiv), HATU (336 mg, 0.88 mmol, 1.19 equiv) was added batchwise. The resulting solution was stirred for 2 h at 25° C. The reaction progress was monitored by LCMS. The reaction was quenched by 10 ml of ice/water. The resulting solution was extracted with 3×12 mL of ethyl acetate and the organic layers combined. The organic phase was concentrated under vacuum. The residue was applied onto a silica gel column with ethyl acetate/petroleum ether (1:4). The crude product was purified by Prep-HPLC with the following conditions: Column, XBridge Prep Phenyl OBD Column, 5 μm, 19*150 mm; mobile phase, Water with 10 mmol NH$_4$HCO$_3$ and MeCN (20.0% MeCN up to 30.0% in 10 min, up to 95.0% in 1 min, hold 95.0% in 1 min, down to 20.0% in 2 min); Detector, UV 254/220 nm. This resulted in 51.1 mg (yield=20%) of 4-fluoro-7-methyl-N-[3-(1,3,4-oxadiazol-2-yl)phenyl]-1H-indole-2-carboxamide as an off-white solid. LCMS (Method E, ESI): RT=0.924 min, m/z=337.1 [M+H]$^+$. $^1$H-NMR (300 MHz, DMSO-d$_6$): δ 11.98 (s, 1H); 10.55 (s, 1H); 9.38 (s, 1H); 8.59 (s, 1H); 8.14-8.11 (d, J=12.0 Hz, 1H); 7.78-7.76 (m, 1H); 7.01-6.97 (m, 1H); 6.81-6.75 (m, 1H); 2.51 (s, 3H) ppm.

Example 6

Synthesis of N-((5-((1H-imidazol-1-yl)methyl)-3-methylpyridin-2-yl)(cyclopropyl) methyl)-4-fluoro-7-methyl-1H-indole-2-carboxamide (Cpd. No. 161)

Step 1. Synthesis of (5-bromo-3-methylpyridin-2-yl)(cyclopropyl)methanamine

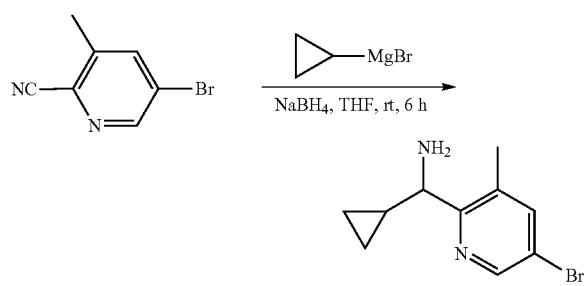

Into a 100-mL 3-necked round-bottom flask purged and maintained with an inert atmosphere of nitrogen, was placed a solution of 5-bromo-3-methylpyridine-2-carbonitrile (1 g, 5.10 mmol, 1.00 equiv), in tetrahydrofuran (10 mL), bromo(cyclopropyl)magnesium (1 mol/L) (5.1 mL, 5.10 mmol, 1.00 equiv) was added by dropwise at 0° C. The resulting solution was stirred for 30 min at this temperature, methanol (10 ml) was added and NaBH$_4$ (0.58 g, 15.30 mmol, 3.00 equiv) was added batchwise at 0° C. The resulting solution was stirred for 12 h at 25° C. The reaction progress was monitored by LCMS. The reaction solution was quenched by 10 ml of ice/water. The resulting solution was extracted with 3×30 mL of ethyl acetate and the organic layers combined and dried over anhydrous sodium sulfate and concentrated under vacuum. The residue was applied onto a silica gel column with dichloromethane/methanol (10/1). This resulted in 600 mg (yield=60%) of (5-bromo-3-methylpyridin-2-yl)(cyclopropyl)methanamine as orange oil. LCMS (Method A, ESI): RT=1.109 min, m/z=241.0 [M+H]$^+$.

Step 2. Synthesis of tert-butyl N-[(5-bromo-3-methylpyridin-2-yl)(cyclopropyl)methyl]carbamate

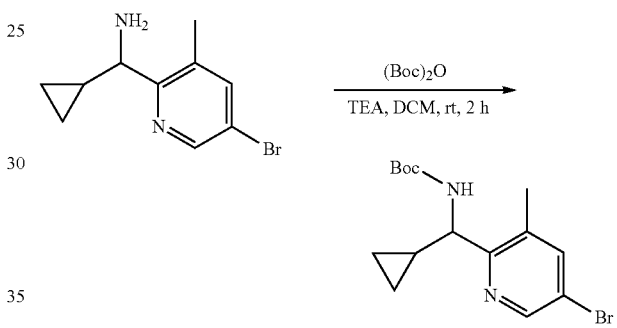

Into a 250-mL round-bottom flask, was placed (5-bromo-3-methylpyridin-2-yl)(cyclopropyl)methanamine (5 g, 20.74 mmol, 1.00 equiv), TEA (10.37 g, 103.7 mmol, 5.00 equiv), in dichloromethane (150 mL), di-tert-butyl dicarbonate (8.8 g, 40.32 mmol, 2.00 equiv) was added dropwise in dichloromethane 10 mL at 0° C. The resulting solution was stirred for 12 h at 25° C. The reaction progress was monitored by LCMS. The resulting mixture was washed with 3×100 mL of water. The mixture was dried over anhydrous sodium sulfate and concentrated under vacuum. The residue was applied onto a silica gel column with ethyl acetate/petroleum ether (1:3). This resulted in 6.00 g (yield=85%) of tert-butyl N-[(5-bromo-3-methylpyridin-2-yl)(cyclopropyl)methyl] carbamate as a yellow solid. LCMS (Method C, ESI): RT=1.356 min, m/z=341.0 [M+H]$^+$.

Step 3. Synthesis of 6-([[(tert-butoxy)carbonyl]amino](cyclopropyl) methyl)-5-methylpyridine-3-carboxylate

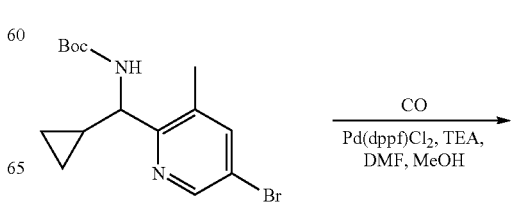

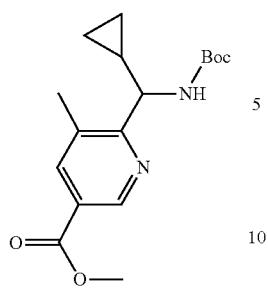

Into a 100-mL round-bottom flask purged and maintained with an inert atmosphere of nitrogen, was placed tert-butyl N-[(5-bromo-3-methylpyridin-2-yl)(cyclopropyl)methyl]carbamate (5.0 g, 14.65 mmol, 1.00 equiv), Pd(dppf)Cl$_2$ (1.8 g, 2.46 mmol, 0.17 equiv), TEA (5.0 g, 49.41 mmol, 3.37 equiv) in methanol 30 mL. Carbon monoxide was introduced to the above mixture. The resulting solution was stirred for 16 h at 80° C. in an oil bath. The reaction progress was monitored by LCMS. The resulting mixture was concentrated under vacuum. The residue was applied onto a silica gel column with ethyl acetate/petroleum ether (1:2). This resulted in 4.3 g (yield=80%) of methyl 6-([[(tert-butoxy)carbonyl]amino](cyclopropyl)methyl)-5-methylpyridine-3-carboxylate as yellow oil. LCMS (Method A, ESI): RT=1.263 min, m/z=321.0 [M+H]$^+$. $^1$H NMR (300 MHz, Methanol-d$_4$) δ 8.95 (s, 1H), 8.15 (s, 1H), 3.95 (s, 3H), 3.36-3.30 (m, 1H), 2.50 (s, 3H), 2.46-2.38 (m, 1H), 1.52 (s, 9H), 0.53-0.48 (m, 4H)

Step 4. Synthesis of tert-butyl N-[(5-carbamoyl-3-methylpyridin-2-yl)(cyclopropyl)methyl]carbamate

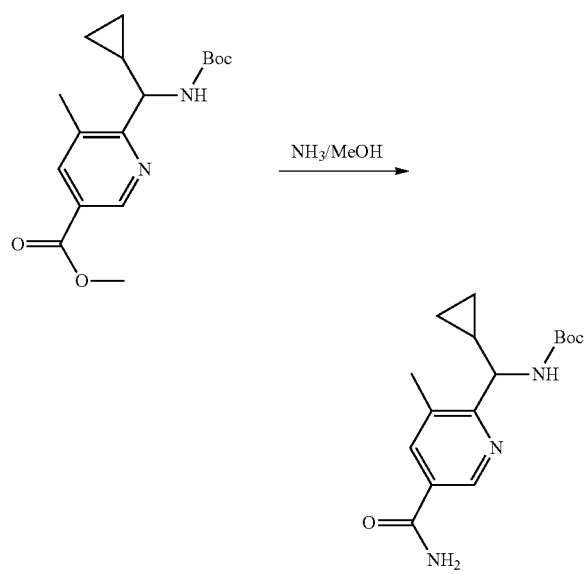

Into a 100-mL round-bottom flask, was placed methyl 6-([[(tert-butoxy)carbonyl]amino](cyclopropyl)methyl)-5-methylpyridine-3-carboxylate (600 mg, 1.87 mmol, 1.00 equiv), NH3/MeOH (10 mL). The resulting solution was stirred for 16 h at 80° C. in an oil bath. The reaction progress was monitored by LCMS. The resulting mixture was concentrated under vacuum. This resulted in 450 mg (yield=79%) of tert-butyl N-[(5-carbamoyl-3-methylpyridin-2-yl)(cyclopropyl)methyl]carbamate as yellow oil. LCMS (Method A, ESI): RT=0.978 min, m/z=306.0 [M+H]$^+$.

Step 5. Synthesis of tert-butyl N-[[5-(aminomethyl)-3-methylpyridin-2-yl](cyclopropyl)methyl]carbamate Into a 100-mL round-bottom flask purged and maintained with an inert atmosphere of nitrogen, was placed tert-butyl N-[(5-carbamoyl-3-methylpyridin-2-yl)(cyclopropyl)methyl]carbamate (400 mg, 1.31 mmol, 1.00 equiv), tetrahydrofuran (2 mL), NaBH$_4$ (250 mg, 6.61 mmol, 5.05 equiv) was added batchwise at 0° C., the resulting solution was stirred for 1 h, BF$_3$-Et$_2$O (1.5 mL) was added dropwise at 0° C. The resulting solution was stirred for 3 h at 25° C. The reaction progress was monitored by LCMS. The reaction solution was quenched by 5 ml of methanol, the resulting mixture was concentrated and the residue was dissolved by 20 ml of dichloromethane, the solution was washed by water (3×10 ml), the organic phase was dried over anhydrous sodium sulfate, and concentrated. This resulted in 300 mg (yield=79%) of tert-butyl N-[[5-(aminomethyl)-3-methylpyridin-2-yl](cyclopropyl)methyl]carbamate as yellow oil, used directly for the next step. LCMS (Method A, ESI): RT=0.837 min, m/z=292.0 [M+H]$^+$.

Step 6. Synthesis of tert-butyl N-[cyclopropyl[5-(1H-imidazol-1-ylmethyl)-3-methylpyridin-2-yl]methyl]carbamate

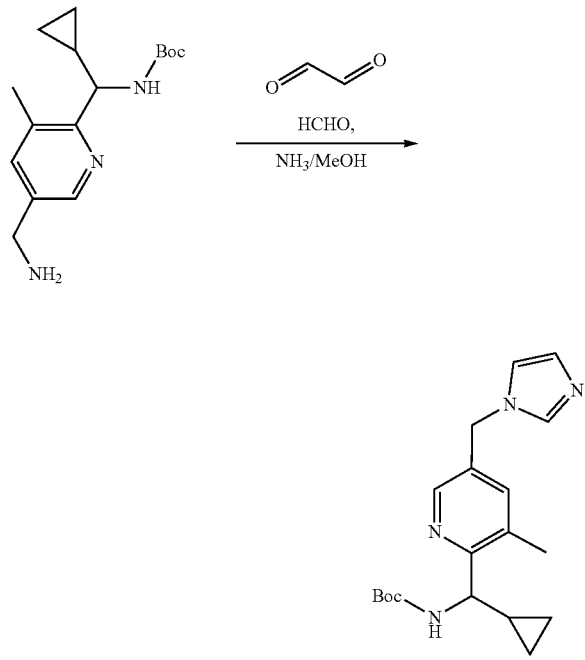

Into a 100-mL round-bottom flask, was placed tert-butyl N-[[5-(aminomethyl)-3-methylpyridin-2-yl](cyclopropyl)methyl]carbamate (300 mg, 1.03 mmol, 1.00 equiv), HCHO (40% in water) (2 mL), NH3/MeOH (7 mol/L) (3 mL), oxaldehyde (2 mL). The resulting solution was stirred for 4 h at 60° C. in an oil bath. The reaction progress was monitored by LCMS, and the resulting solution was concentrated under vacuum. The residue was applied onto a silica gel column with dichloromethane/methanol (10:1). This resulted in 300 mg (yield=85%) of tert-butyl N-[cyclopropyl[5-(1H-imidazol-1-ylmethyl)-3-methylpyridin-2-yl]methyl]carbamate as yellow oil. LCMS (Method A, ESI): RT=1.291 min, m/z=343.0 [M+H]⁺.

Step 7. Synthesis of (5-((1H-imidazol-1-yl)methyl)-3-methylpyridin-2-yl)(cyclopropyl)methanamine hydrochloride

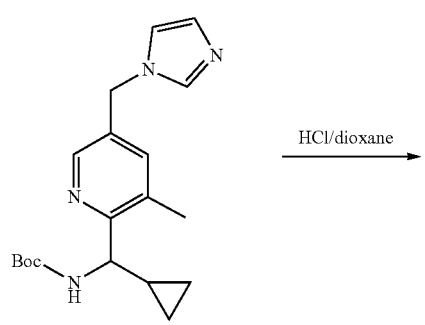

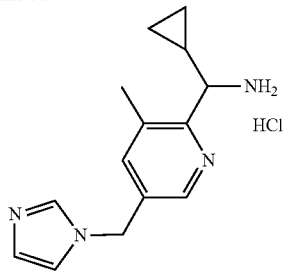

Into a 25-mL round-bottom flask, was placed tert-butyl (5-((1H-imidazol-1-yl)methyl)-3-methylpyridin-2-yl)(cyclopropyl)methylcarbamate (300.00 mg, 0.87 mmol, 1.00 equiv), HCl (g)/dioxane (2 mol/L) (4.00 mL), and the resulting solution was stirred for 30 min at 25° C. The reaction progress was monitored by LCMS. The resulting mixture was concentrated under vacuum. This resulted in 260.00 mg (crude) of (5-((1H-imidazol-1-yl)methyl)-3-methylpyridin-2-yl)(cyclopropyl)methanamine hydrochloride as an off-white solid. LCMS (Method A, ESI): RT=0.861 min, m/z=243.0 [M+H]⁺.

Step 8. Synthesis of N-((5-((1H-imidazol-1-yl)methyl)-3-methylpyridin-2-yl)(cyclopropyl)methyl)-4-fluoro-7-methyl-1H-indole-2-carboxamide

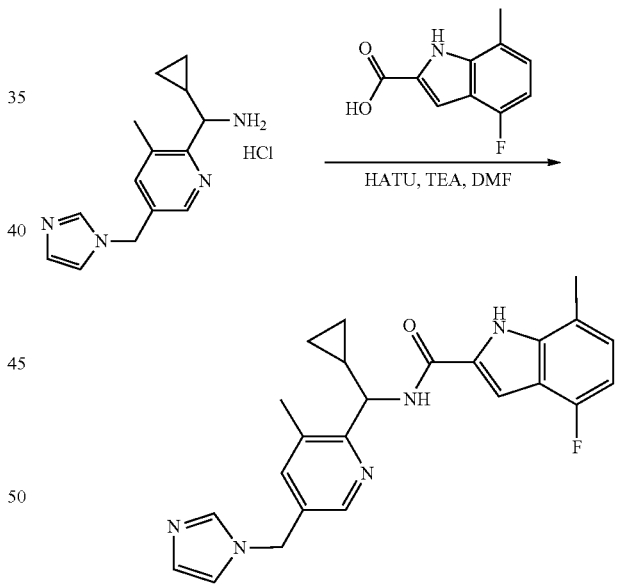

Cpd. No. 161

Into a 100-mL round-bottom flask, was placed cyclopropyl[5-(1H-imidazol-1-ylmethyl)-3-methylpyridin-2-yl]methanamine (260 mg, 0.95 mmol, 1.00 equiv), TEA (375 mg, 3.71 mmol, 2.99 equiv), N,N-dimethylformamide (2 mL), 4-fluoro-7-methyl-1H-indole-2-carboxylic acid (263 mg, 1.36 mmol, 1.10 equiv), HATU (565 mg, 1.49 mmol, 1.20 equiv) was added batchwise. The resulting solution was stirred for 2 h at 25° C. The reaction progress was monitored by LCMS, and the reaction solution was quenched by 5 ml of water, and the solids were collected by filtration. The crude product was purified by Prep-HPLC with the following conditions: Column, X-bridge Shield RP 18, 5 μm, 19*150 mm; mobile phase, water with 10 mmol NH$_4$HCO$_3$ and CH$_3$CN (10.0% CH$_3$CN up to 28.0% in 2 min, up to 46.0% in 10 min, up to 100.0% in 1 min, down to 10.0% in 1 min); Detector, UV 254/220 nm. This resulted in 11.5 mg (yield=2%) of N-((5-(((1H-imidazol-1-yl)methyl)-3-methylpyridin-2-yl)(cyclopropyl)methyl)-4-fluoro-7-methyl-1H-indole-2-carboxamide as a white solid. LCMS (Method B, ESI): RT=1.27 min, m/z=418.0 [M+H]$^+$. $^1$H NMR (400 MHz, Methanol-d$_4$) δ 8.37 (s, 1H), 7.81 (s, 1H), 7.52 (s, 1H), 7.22 (s, 1H), 7.17 (s, 1H), 7.04 (s, 1H), 7.01-6.92 (m, 1H), 6.66 (t, J=10.3 Hz, 1H), 5.27 (s, 2H), 4.93 (d, J=8.9 Hz, 1H), 2.50 (s, 6H), 1.51-1.45 (m, 1H), 0.72-0.62 (m, 1H), 0.60-0.47 (m, 1H), 0.47 (t, J=5.3 Hz, 2H) ppm.

Example 7

Synthesis of N-(1-((1r,4r)-4-(dimethylamino)cyclohexyl)-1H-indazol-4-yl)-4-fluoro-7-methyl-1H-indole-2-carboxamide (Cpd. No. 213)

Step 1. Synthesis of tert-butyl N-[(1r,4r)-4-(4-nitro-1H-indazol-1-yl)cyclohexyl]carbamate

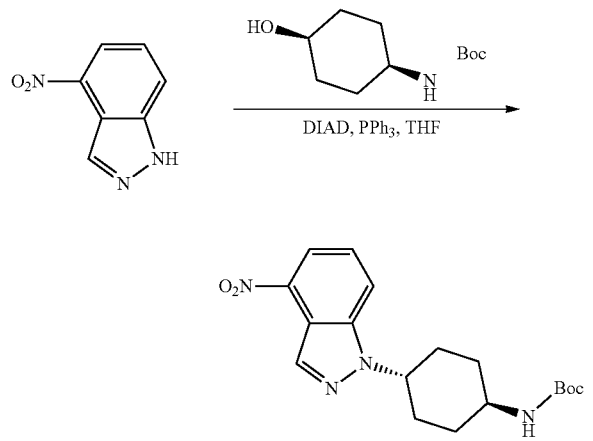

Into a 25-mL 2-necked round-bottom flask purged and maintained with an inert atmosphere of nitrogen, was placed a solution of 4-nitro-1H-indazole (500 mg, 3.06 mmol, 1.00 equiv) in tetrahydrofuran (12 mL), tert-butyl N-[(1s,4s)-4-hydroxycyclohexyl]carbamate (700 mg, 3.25 mmol, 1.20 equiv), PPh3 (700 mg, 2.67 mmol, 1.20 equiv). This was followed by the addition of DIAD (700 mg, 3.46 mmol, 1.20 equiv) dropwise with stirring at 0° C. in 10 min. The resulting solution was stirred for 12 h at 25° C. The reaction progress was monitored by LCMS. The resulting mixture was concentrated under vacuum. The residue was applied onto a silica gel column with ethyl acetate/petroleum ether (1:6). This resulted in 260 mg (yield=24%) of tert-butyl N-[(1r,4r)-4-(4-nitro-1H-indazol-1-yl)cyclohexyl]carbamate as a light yellow solid. LCMS (Method A, ESI): m/z=361.2 [M+H]$^+$. $^1$H NMR (400 MHz, DMSO-d$_6$) δ 8.91 (s, 1H), 8.21-8.19 (dd, J=8.1, 4.8 Hz, 2H), 7.51-7.47 (t, J=8.1 Hz, 1H), 6.88-6.86 (d, J=7.7 Hz, 1H), 4.68-4.62 (m, 1H), 3.46-3.34 (m, 1H), 2.12-2.07 (m, 4H), 2.03-1.96 (m, 2H), 1.52-1.44 (m, 2H), 1.40 (s, 9H) ppm.

Step 2. Synthesis of tert-butyl N-[(1r,4r)-4-(4-amino-1H-indazol-1-yl)cyclohexyl]carbamate

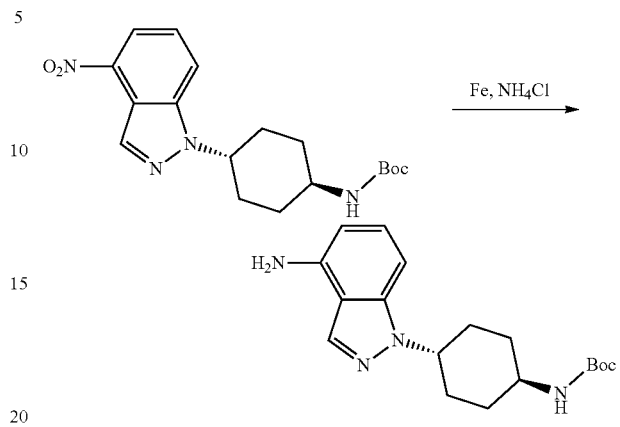

Into a 40-mL vial, was placed a solution of tert-butyl N-[(1r,4r)-4-(4-nitro-1H-indazol-1-yl)cyclohexyl]carbamate (100 mg, 0.28 mmol, 1.00 equiv) in ethanol (20 mL), Fe powder (100 mg, 5.00 equiv) in water (3 mL), NH$_4$Cl (100 mg, 1.87 mmol, 5.00 equiv). The resulting solution was stirred for 2 h at 80° C. The reaction progress was monitored by LCMS. The solids were removed by filtration. The filtrate was concentrated under vacuum. The residue was applied onto a silica gel column with dichloromethane/methanol (10/1). This resulted in 80 mg (yield=87%) of tert-butyl N-[(1r,4r)-4-(4-amino-1H-indazol-1-yl)cyclohexyl]carbamate as a light yellow solid. LCMS (Method A, ESI): RT=0.753 min, m/z=331.2 [M+H]$^+$. $^1$H NMR (400 MHz, DMSO-d$_6$) δ 8.05 (s, 1H), 7.01-6.97 (dd, J=8.3, 7.4 Hz, 1H), 6.85-6.83 (d, J=7.8 Hz, 1H), 6.73-6.71 (d, J=8.3 Hz, 1H), 6.14-6.12 (d, J=7.4 Hz, 1H), 5.71 (s, 2H), 4.36-4.33 (m, 1H), 3.38-3.35 (m, 1H), 1.99-1.89 (m, 6H), 1.48-1.41 (m, 2H), 1.40 (s, 9H) ppm.

Step 3. Synthesis of tert-butyl N-[(1r,4r)-4-[4-(4-fluoro-7-methyl-1H-indole-2-amido)-1H-indazol-1-yl]cyclohexyl]carbamate

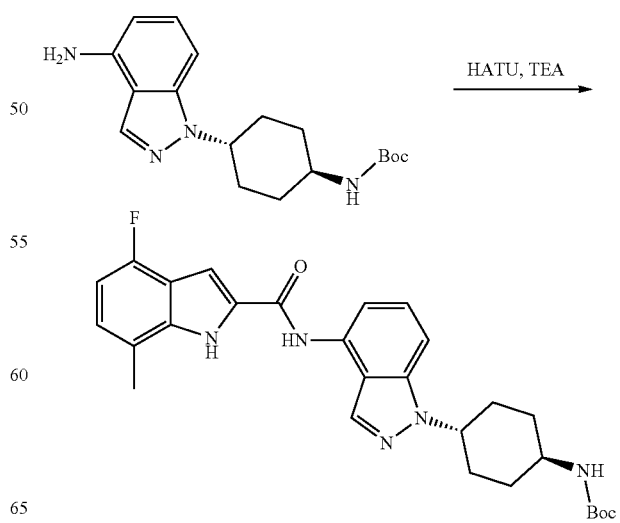

Into a 40-mL round-bottom flask, was placed a solution of tert-butyl N-[(1r,4r)-4-(4-amino-1H-indazol-1-yl)cyclohexyl]carbamate (200 mg, 0.61 mmol, 1.00 equiv) in N,N-dimethylformamide (10 mL), 4-fluoro-7-methyl-1H-indole-2-carboxylic acid (160 mg, 0.83 mmol, 1.20 equiv), TEA (260 mg, 2.57 mmol, 3.00 equiv), HATU (423 mg, 1.11 mmol, 1.30 equiv) was added batchwise. The resulting solution was stirred for 2 h at 25° C. The reaction progress was monitored by LCMS. The resulting mixture was quenched by 30 mL of water. The resulting solution was extracted with 3×10 mL of ethyl acetate and the organic layers combined. The filtrate was concentrated under vacuum. The residue was applied onto a silica gel column with ethyl acetate/petroleum ether (1:1). This resulted in 190 mg (yield=62%) of tert-butyl N-[(1r,4r)-4-[4-(4-fluoro-7-methyl-1H-indole-2-amido)-1H-indazol-1-yl]cyclohexyl]carbamate as light yellow oil. LCMS (Method D, ESI): RT=1.253 min, m/z=506.2 [M+H]+. 1H NMR (400 MHz, DMSO-d6) δ 11.95 (s, 1H), 10.39 (s, 1H), 8.26 (s, 1H), 7.60-7.59 (d, J=2.1 Hz, 1H), 7.56-7.50 (dd, J=18.3, 7.9 Hz, 2H), 7.40-7.36 (dd, J=8.4, 7.5 Hz, 1H), 7.01-6.97 (dd, J=7.8, 5.2, 1.0 Hz, 1H), 6.89-6.87 (d, J=7.7 Hz, 1H), 6.80-6.75 (dd, J=10.4, 7.8 Hz, 1H), 4.60-4.57 (m, 1H), 3.17 (s, 1H), 2.52 (s, 3H), 2.05-1.93 (m, 6H), 1.56-1.46 (m, 5.9 Hz, 2H), 1.41 (s, 9H) ppm.

Step 4. Synthesis of 4-fluoro-7-methyl-N-[1-[(1r,4r)-4-aminocyclohexyl]-1H-indazol-4-yl]-1H-indole-2-carboxamide

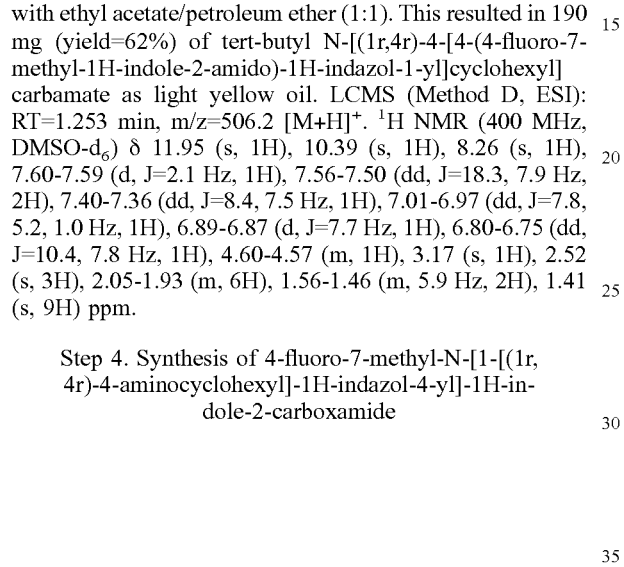

Into a 8-mL vial, was placed tert-butyl N-[(1r,4r)-4-[4-(4-fluoro-7-methyl-1H-indole-2-amido)-1H-indazol-1-yl]cyclohexyl]carbamate (200 mg, 0.40 mmol, 1.00 equiv), hydrogen chloride/1,4-dioxane (2 mol/L) (10 mL). The resulting solution was stirred for 2 h at 25° C. The reaction progress was monitored by LCMS. The resulting mixture was concentrated under vacuum. This resulted in 150 mg (yield=94%) of 4-fluoro-7-methyl-N-[1-[(1r,4r)-4-aminocyclohexyl]-1H-indazol-4-yl]-1H-indole-2-carboxamide as light yellow oil. LCMS (Method A, ESI): RT=1.423 min. m/z=406.2 [M+H]+. 1H NMR (400 MHz, DMSO-d6) δ 12.22 (s, 1H), 10.64 (s, 1H), 8.33 (s, 1H), 7.59-7.53 (m, 3H), 7.41-7.36 (dd, J=8.3, 7.6 Hz, 1H), 7.00-6.97 (dd, J=7.7, 5.2 Hz, 1H), 6.79-6.75 (dd, J=10.4, 7.8 Hz, 1H), 4.67-4.58 (d, J=8.0 Hz, 1H), 3.63-3.60 (m, 1H), 2.54 (s, 3H), 2.17-2.10 (m, 6H), 2.08-1.99 (m, 2H), 1.72-1.59 (m, 2H) ppm.

Step 5. Synthesis of N-(1-((1r,4r)-4-(dimethylamino)cyclohexyl)-1H-indazol-4-yl)-4-fluoro-7-methyl-1H-indole-2-carboxamide

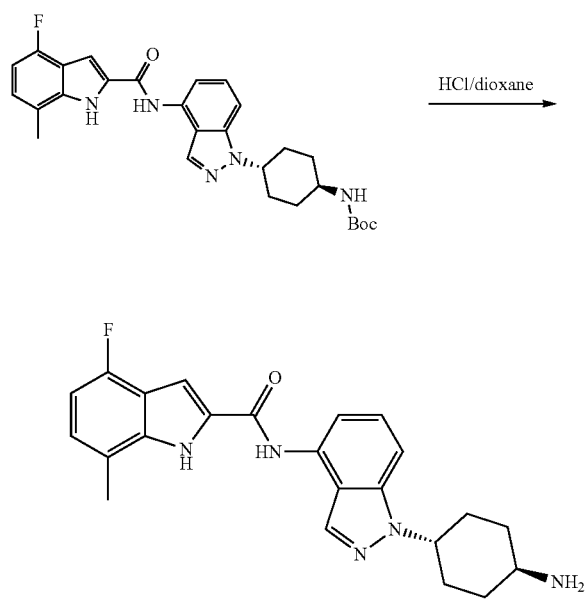

Cpd. No. 213

Into a 40-mL round-bottom flask, was placed a solution of 4-fluoro-7-methyl-N-[1-[(1r,4r)-4-aminocyclohexyl]-1H-indazol-4-yl]-1H-indole-2-carboxamide (350 mg, 0.86 mmol, 1.00 equiv) in methanol (10 mL). This was followed by the addition of CH2O (40% in water) (3 mL). To this was added NaBH3CN (160 mg, 2.5 mmol 3.00 equiv) batchwise. The resulting solution was stirred for 2 h at 25° C. The reaction progress was monitored by LCMS. The resulting mixture was quenched with 30 mL of water. The resulting solution was extracted with 3×10 mL of ethyl acetate and the organic layers combined. The resulting mixture was concentrated under vacuum. The crude product (180 mg) was purified by Prep-HPLC with the following conditions: Column, XSelect CSH Prep C18 OBD Column, 5 μm, 19*150 mm; mobile phase, Water (0.05% TFA) and ACN (22.0% ACN up to 45.0% in 7 min); Detector, UV 220/254 nm. This resulted in 36.2 mg (yield=9.6%) of 4-fluoro-7-methyl-N-[1-[(1r,4r)-4-(dimethylamino) cyclohexyl]-1H-indazol-4-yl]-1H-indole-2-carboxamide trifluoroacetic acid salt as a white solid. LCMS (Method D, ESI): RT=1.510 min, m/z=434.2 [M+H]+. 1H NMR (300 MHz, Methanol-d4) δ 8.22 (s, 1H), 7.47-7.43 (m, 4H), 7.02-6.97 (m, 1H), 6.74-6.64 (m, 1H), 4.72-4.62 (m, 1H), 3.43-3.41 (m, 1H), 2.93 (s, 6H), 2.53 (s, 3H), 2.32-2.15 (m, 6H), 1.98-1.80 (m, 2H) ppm.

Example 8

Synthesis of 4-fluoro-N-(7-fluoroisoquinolin-5-yl)-7-methyl-1H-indole-2-carboxamide (Cpd. No. 82)

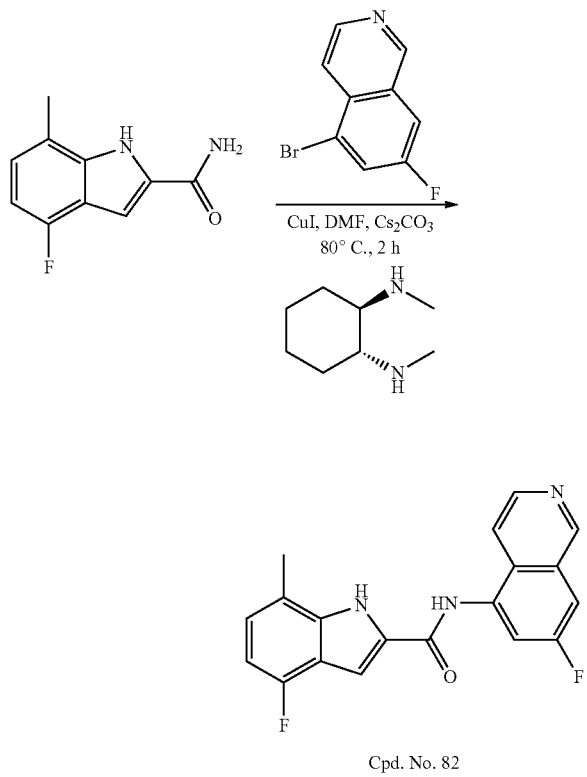

Cpd. No. 82

Into a 40-mL vial purged and maintained with an inert atmosphere of nitrogen, was placed a solution of 4-fluoro-7-methyl-1H-indole-2-carboxamide (100 mg, 0.52 mmol, 1.00 equiv) in N,N-dimethylformamide (10 mL), 7-fluoroisoquinolin-5-amine (100 mg, 0.62 mmol, 1.20 equiv), CuI (110 mg, 0.58 mmol, 1.00 equiv), $Cs_2CO_3$ (537 mg, 1.65 mmol, 3.00 equiv), (1S,2S)-1-N,2-N-dimethylcyclohexane-1,2-diamine (100 mg, 0.70 mmol, 1.40 equiv). The resulting solution was stirred for 2 h at 80° C. The reaction progress was monitored by LCMS. The resulting solution was quenched by 20 ml of water/ice. The resulting solution was extracted with 3×10 mL of ethyl acetate and the organic layers combined. The resulting mixture was washed with 3×10 mL of $H_2O$. The crude product (300 mg) was purified by Prep-HPLC with the following conditions: Column, XBridge Prep OBD C18 Column, 30*150 mm 5 μm; mobile phase, Water (10 mmol/L $NH_4HCO_3$) and ACN (39% ACN up to 61% in 7 min); Detector, UV 254/220 nm. This resulted in 31.8 mg (yield=18%) of 4-fluoro-N-(7-fluoroisoquinolin-5-yl)-7-methyl-1H-indole-2-carboxamide as a white solid. LCMS (Method B, ESI): m/z=337.9 [M+H]$^+$.
$^1$H NMR (300 MHz, DMSO-$d_6$) δ 12.03 (s, 1H), 10.69 (s, 1H), 9.37 (s, 1H), 8.58 (d, J=6.0 Hz, 1H), 8.03 (t, J=4.5 Hz, 6.0 Hz, 2H), 7.91 (d, J=9.0 Hz, 1H), 7.68 (s, 1H), 7.01 (t, J=6.9 Hz, 5.7 Hz, 1H), 6.85-6.75 (m, 1H), 3.30 (s, 3H) ppm.

Example 9

Synthesis of 4-fluoro-7-methyl-N-(2-(1-methyl-1H-pyrazol-4-yl)-1-(3-methylpyridin-2-yl)ethyl)-1H-indole-2-carboxamide (Cpd. No. 85)

Step 1. Synthesis of 1-methyl-1H-pyrazole-4-carbaldehyde

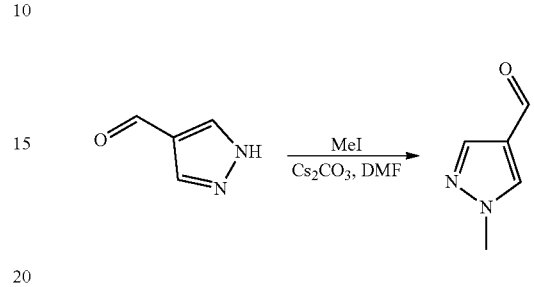

Into a 8-mL vial, was placed a solution of 1H-pyrazole-4-carbaldehyde (50 mg, 0.52 mmol, 1.00 equiv) in N,N-dimethylformamide (1 mL), $CH_3I$ (96 mg, 0.68 mmol, 1.30 equiv), $Cs_2CO_3$ (510 mg, 1.57 mmol, 3.00 equiv). The resulting solution was stirred for 1 h at 60° C. The reaction progress was monitored by LCMS. The reaction was quenched by 10 ml of water. The resulting solution was extracted with 3×12 mL of ethyl acetate and the organic layers combined. The organic phase was concentrated under vacuum. The residue was applied onto a silica gel column with ethyl acetate/petroleum ether (1:4). This resulted in 40 mg (yield=80%) of 1-methyl-1H-pyrazole-4-carbaldehyde as white solid. LCMS (Method A, ESI): RT=0.699 min, m/z=111.1[M+H]$^+$.

Step 2. Synthesis of E)-ethyl 3-(1-methyl-1H-pyrazol-4-yl)-2-(3-methylpyridin-2-yl)acrylate

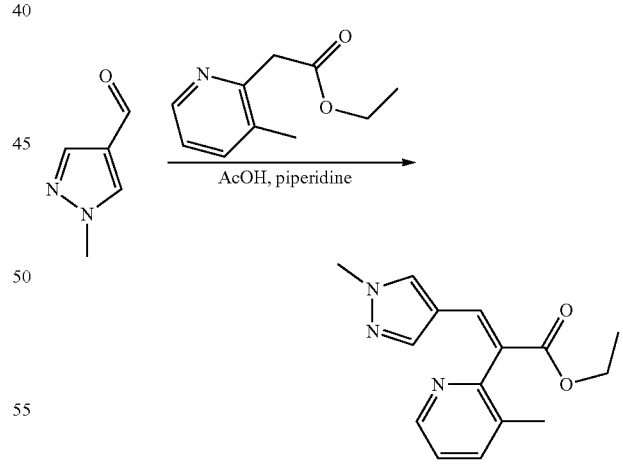

Into a 40-mL vial purged and maintained with an inert atmosphere of nitrogen, was placed a solution of 1-methyl-1H-pyrazole-4-carbaldehyde (465 mg, 4.22 mmol, 1.50 equiv) in ethanol (20 mL), ethyl 2-(3-methylpyridin-2-yl)acetate (500 mg, 2.79 mmol, 1.00 equiv), acetic acid (840 mg, 13.99 mmol, 5.00 equiv), piperidine (1.2 g, 14.09 mmol, 5.00 equiv). The resulting solution was stirred for 48 h at 80° C. The reaction progress was monitored by LCMS. The resulting solution was concentrated under vacuum and the residue was dissolved by 20 ml of dichloromethane, and the resulting mixture was washed by 3×15 ml of water, the organic phase was dried over anhydrous sodium sulfate, and concentrated. The residue was applied onto a silica gel column with dichloromethane/methanol (10:1). This resulted in 620.00 mg (yield=75%) of (E)-ethyl 3-(1-methyl-1H-pyrazol-4-yl)-2-(3-methylpyridin-2-yl)acrylate as a white solid. LCMS (Method A, ESI): RT=0.842 min, m/z=272.1 [M+H]$^+$. $^1$H NMR (300 MHz, DMSO-d$_6$) δ 8.48 (t, J=3.0 Hz, 1H), 7.75 (s, 2H), 7.37 (t, J=6.0 Hz, 1H), 7.30 (s, 1H), 6.44 (s, 1H), 4.14 (q, J=6.0 Hz, 15 Hz, 2H), 3.72 (s, 3H), 2.06 (s, 3H), 1.17 (t, J=6.0 Hz, 3H) ppm.

Step 3. Synthesis of E)-3-(1-methyl-1H-pyrazol-4-yl)-2-(3-methylpyridin-2-yl)acrylic acid

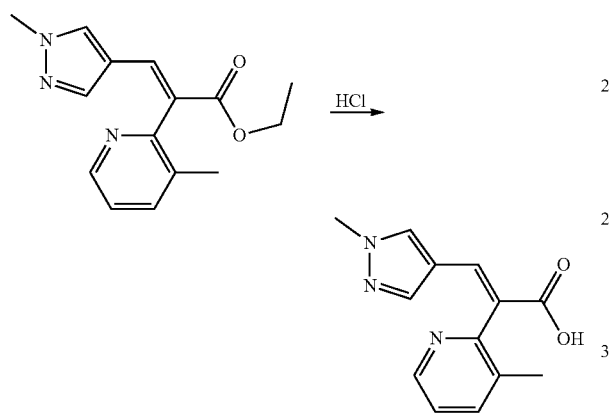

Into a 40-mL vial, was placed a solution of ethyl (2E)-3-(1-methyl-1H-pyrazol-4-yl)-2-(3-methylpyridin-2-yl)prop-2-enoate (620 mg, 2.29 mmol, 1.00 equiv) in hydrogen chloride (6 mol/L) (20 mL). The resulting solution was stirred for 15 h at 800° C. The reaction progress was monitored by LCMS. The resulting solution was concentrated under vacuum, This resulted in 500.00 mg (yield=80%) of (E)-3-(1-methyl-1H-pyrazol-4-yl)-2-(3-methylpyridin-2-yl)acrylic acid as a white solid, which was used for next step without further purification. LCMS (Method A, ESI): RT=0.745 min, m/z=244.0[M+H]$^+$.

Step 4. Synthesis of (E)-2-(1-isocyanato-2-(1-methyl-1H-pyrazol-4-yl)vinyl)-3-methylpyridine

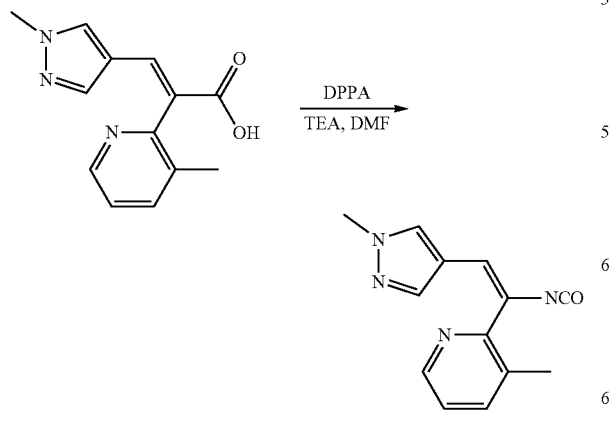

Into a 40-mL vial purged and maintained with an inert atmosphere of nitrogen, was placed a solution of (2E)-3-(1-methyl-1H-pyrazol-4-yl)-2-(3-methylpyridin-2-yl)prop-2-enoic acid (500 mg, 2.06 mmol, 1.00 equiv) in N,N-dimethylformamide (20 mL), DPPA (850 mg, 3.09 mmol, 1.50 equiv), TEA (1.05 g, 10.38 mmol, 5.00 equiv). The resulting solution was stirred for 2 h at 80° C. The reaction progress was monitored by LCMS. The resulting solution was quenched by 30 ml of water, and the resulting mixture was extracted by 3×35 ml of dichloromethane, the organic phase was dried over anhydrous sodium sulfate, concentrated. The residue was applied onto a silica gel column with dichloromethane/methanol (20:1). This resulted in 170.00 mg (yield=34%) of (E)-2-(1-isocyanato-2-(1-methyl-1H-pyrazol-4-yl)vinyl)-3-methylpyridine as solid. LCMS (ESI): RT=0.736 min, m/z=241.0 [M+H]$^+$.

Step 5. Synthesis of (E)-benzyl 2-(1-methyl-1H-pyrazol-4-yl)-1-(3-methylpyridin-2-yl)vinylcarbamate

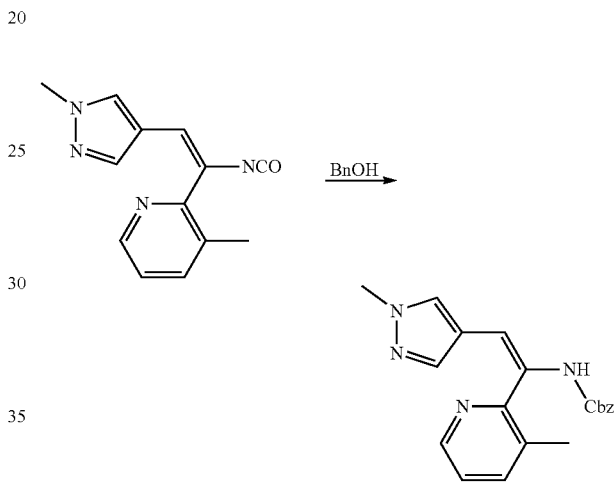

Into a 20-mL vial, was placed a solution of 2-[(E)-1-isocyanato-2-(1-methyl-1H-pyrazol-4-yl)ethenyl]-3-methylpyridine (170 mg, 0.71 mmol, 1.00 equiv) in benzyl alcohol (2 mL). The resulting solution was stirred for 15 h at 100° C. The reaction progress was monitored by LCMS. The resulting solution was quenched by 30 ml of water, and the resulting mixture was extracted by 3×20 ml of dichloromethane, the organic phase was dried over anhydrous sodium sulfate, and concentrated. The residue was applied onto a silica gel column with dichloromethane/methanol (15:1). This resulted in 80.00 mg (yield=46%) of (E)-benzyl 2-(1-methyl-1H-pyrazol-4-yl)-1-(3-methylpyridin-2-yl)vinylcarbamate as white solid. LCMS (Method, ESI): RT=0.859 min, m/z=349.0[M+H]$^+$.

Step 6. Synthesis of 2-(1-methyl-1H-pyrazol-4-yl)-1-(3-methylpyridin-2-yl)ethanamine

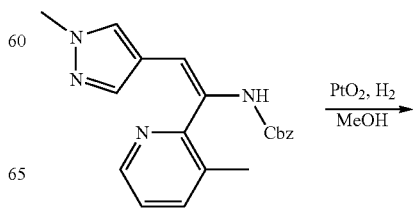

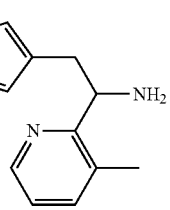

Into a 50-mL round-bottom flask, was placed a solution of benzyl N-[(E)-2-(1-methyl-1H-pyrazol-4-yl)-1-(3-methylpyridin-2-yl)ethenyl]carbamate (80 mg, 0.23 mmol, 1.00 equiv) in MeOH (5 mL), PtO₂ (20 mg). To the above mixture, hydrogen was introduced. The resulting solution was stirred for 20 min at 25° C. The reaction progress was monitored by LCMS. The solids were removed by filtration, the resulting mixture was concentrated under vacuum, and 70 mg (yield=85%) of 2-(1-methyl-1H-pyrazol-4-yl)-1-(3-methylpyridin-2-yl)ethanamine was obtained. LCMS (Method A, ESI): RT=0.326 min, m/z=216.0 [M+H]⁺.

Step 7. Synthesis of 4-fluoro-7-methyl-N-(2-(1-methyl-1H-pyrazol-4-yl)-1-(3-methylpyridin-2-yl)ethyl)-1H-indole-2-carboxamide Into a 100-mL round-bottom flask, was placed a solution of 2-(1-methyl-1H-pyrazol-4-yl)-1-(3-methylpyridin-2-yl) ethan-1-amine (80 mg, 0.37 mmol, 1.00 equiv) in N,N-dimethylformamide (3 mL), 4-fluoro-7-methyl-1H-indole-2-carboxylic acid (80 mg, 0.41 mmol, 1.10 equiv), TEA (113 mg, 1.12 mmol, 3.00 equiv), HATU (183 mg, 0.48 mmol, 1.30 equiv) was added batchwise. The resulting solution was stirred for 1 h at 25° C. The crude product (100 mg) was purified by Prep-HPLC with the following conditions: Column, XSelect CSH Prep C18 OBD Column, 5 μm, 19*150 mm; mobile phase, Water (0.05% TFA) and ACN (16.0% ACN up to 42.0% in 7 min); Detector, UV 220/254 nm. This resulted in 37.5 mg (yield=20%) of 4-fluoro-7-methyl-N-[2-(1-methyl-1H-pyrazol-4-yl)-1-(3-methylpyridin-2-yl) ethyl]-1H-indole-2-carboxamide as the trifluoroacetic acid salt as a white solid. LCMS (Method A, ESI): m/z=391.9 [M+H]⁺. ¹H NMR (400 MHz, Methanol-d₄) δ 8.56 (s, 1H), 8.16 (s, 1H), 7.68 (s, 1H), 7.41 (d, J=2.7 Hz, 1H), 7.32 (d, J=1.1 Hz, 1H), 7.20 (d, J=4.7 Hz, 1H), 6.99-6.96 (m, 1H), 6.73-6.63 (m, 1H), 5.56 (t, J=7.6 Hz, 1H), 4.86 (s, 3H), 3.36 (s, 1H), 3.27-3.17 (m, 1H), 2.53-2.45 (m, 6H) ppm.

Example 10

Synthesis of 4-fluoro-N-(3-fluoro-5-(3-(N-methylacetamido)pyrrolidin-1-yl)phenyl)-7-methyl-1H-indole-2-carboxamide (Cpd. No. 1)

Step 1. Synthesis of tert-butyl N-[1-(3-fluoro-5-nitrophenyl)pyrrolidin-3-yl]-N-methylcarbamate

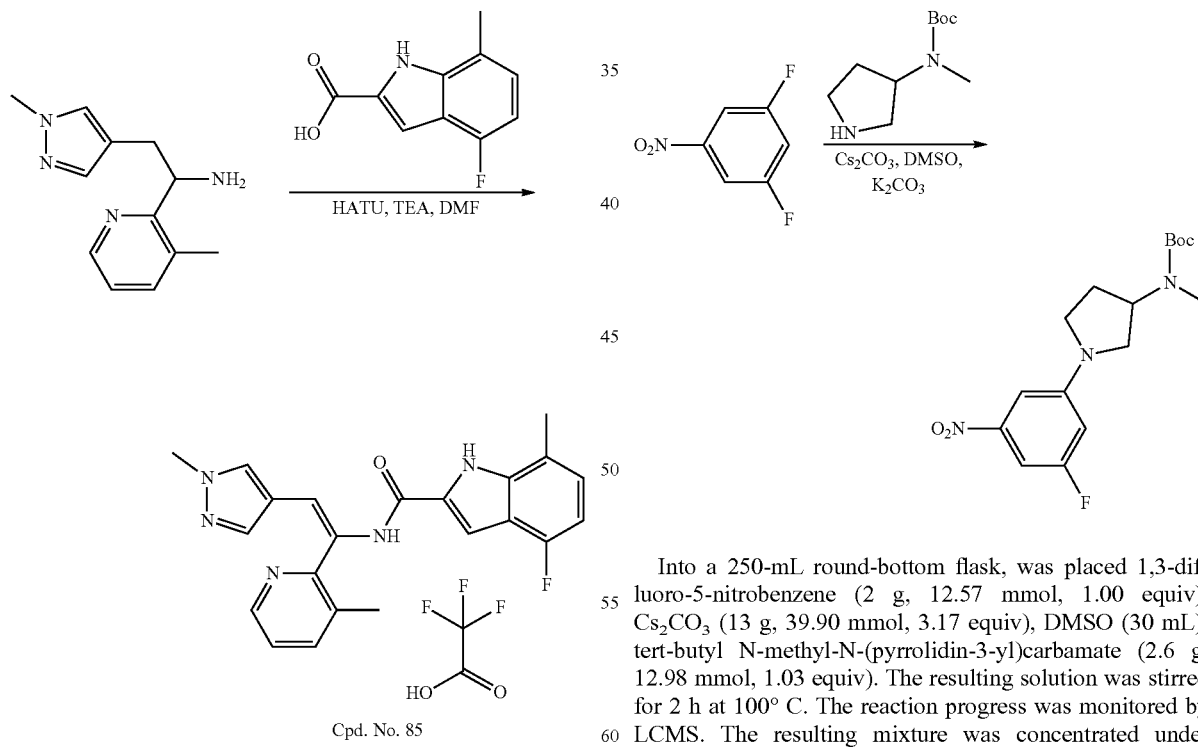

Into a 250-mL round-bottom flask, was placed 1,3-difluoro-5-nitrobenzene (2 g, 12.57 mmol, 1.00 equiv), Cs₂CO₃ (13 g, 39.90 mmol, 3.17 equiv), DMSO (30 mL), tert-butyl N-methyl-N-(pyrrolidin-3-yl)carbamate (2.6 g, 12.98 mmol, 1.03 equiv). The resulting solution was stirred for 2 h at 100° C. The reaction progress was monitored by LCMS. The resulting mixture was concentrated under vacuum. The residue was applied onto a silica gel column with ethyl acetate/petroleum ether (1:1). The collected fractions were combined and concentrated under vacuum. This resulted in 680 mg (yield=16%) of tert-butyl N-[1-(3-fluoro-5-nitrophenyl)pyrrolidin-3-yl]-N-methylcarbamate as a light yellow solid. LCMS (Method A, ESI): RT=2.876 min, m/z=340.00 [M+H]⁺.

Step 2. Synthesis of 1-(3-fluoro-5-nitrophenyl)-N-methylpyrrolidin-3-amine

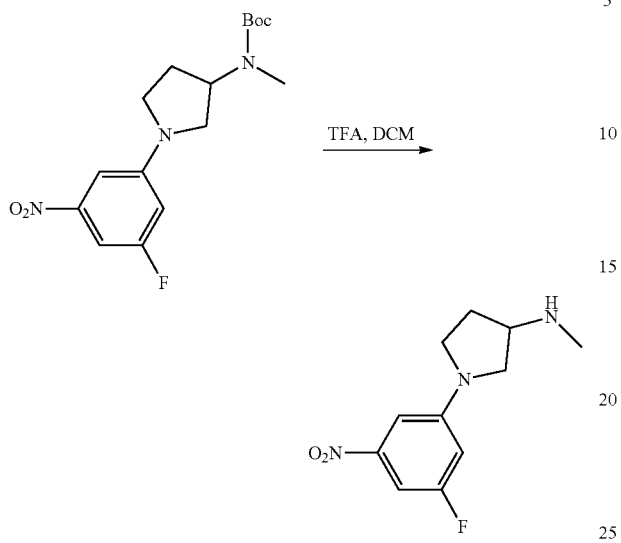

Into a 40-mL vial, was placed tert-butyl N-[1-(3-fluoro-5-nitrophenyl)pyrrolidin-3-yl]-N-methylcarbamate (650 mg, 1.92 mmol, 1.00 equiv) in dichloromethane (7 mL), trifluoroacetic acid (3 mL). The resulting solution was stirred for 1 h at 25° C. and the reaction progress was monitored by LCMS. The resulting mixture was concentrated under vacuum. This resulted in 350 mg (yield=76%) of 1-(3-fluoro-5-nitrophenyl)-N-methylpyrrolidin-3-amine as a light yellow solid. LCMS (Method A, ES): RT=0.900 min, m/z=240.00 [M+H]$^+$.

Step 3. Synthesis of N-[1-(3-fluoro-5-nitrophenyl)pyrrolidin-3-yl]-N-methylacetamide

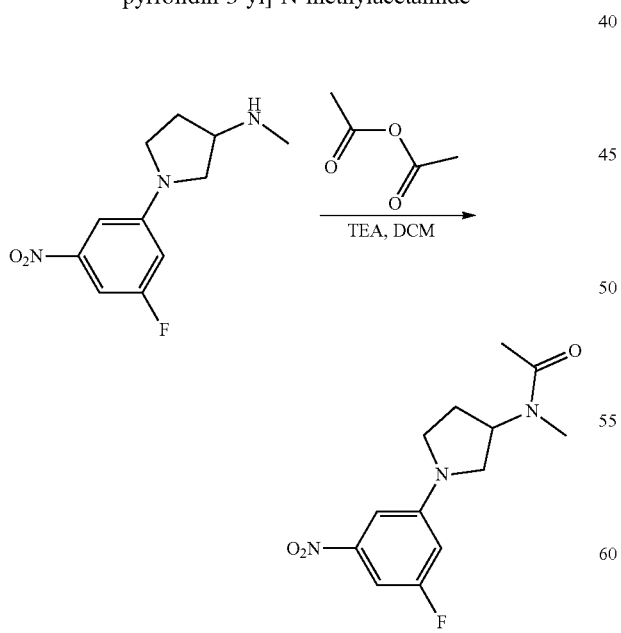

Into a 40-mL vial was placed 1-(3-fluoro-5-nitrophenyl)-N-methylpyrrolidin-3-amine (1 g, 4.18 mmol, 1.00 equiv), TEA (2 g, 19.76 mmol, 4.73 equiv) in dichloromethane (10 mL), and acetyl acetate (750 mg, 7.35 mmol, 1.76 equiv) was added by dropwise at 0° C. The resulting solution was stirred for 2 h at 25° C. The reaction progress was monitored by LCMS. The resulting mixture was concentrated under vacuum. The residue was applied onto a silica gel column with ethyl acetate/petroleum ether (1:1). The collected fractions were combined and concentrated under vacuum. This resulted in 900 mg (yield=77%) of N-[1-(3-fluoro-5-nitrophenyl)pyrrolidin-3-yl]-N-methylacetamide as a light yellow solid. LCMS (Method A, ES): RT=1.188 min, m/z=282.00 [M+H]$^+$.

Step 4. Synthesis of N-[1-(3-amino-5-fluorophenyl)pyrrolidin-3-yl]-N-methylacetamide

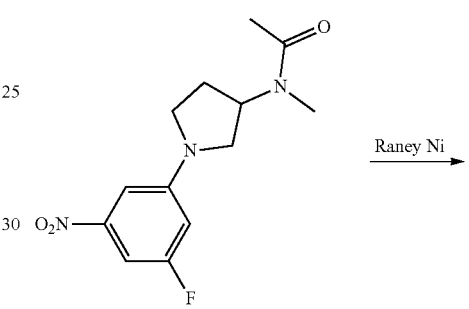

Into a 100-mL round-bottom flask was placed N-[1-(3-fluoro-5-nitrophenyl)pyrrolidin-3-yl]-N-methylacetamide (300 mg, 1.07 mmol, 1.00 equiv), Raney Ni (100 mg) in methanol (10 mL). To the above mixture hydrogen was introduced. The resulting solution was stirred for 1 h at 25° C. The reaction progress was monitored by LCMS. The solids were filtered out. The resulting mixture was concentrated under vacuum. This resulted in 220 mg (yield=82%) of N-[1-(3-amino-5-fluorophenyl)pyrrolidin-3-yl]-N-methylacetamide as an off-white solid. LCMS (Method A, ESI): RT=0.834 min, m/z=252.00 [M+H]$^+$.

Step 5. Synthesis of 4-fluoro-N-(3-fluoro-5-(3-(N-methylacetamido)pyrrolidin-1-yl)phenyl)-7-methyl-1H-indole-2-carboxamide

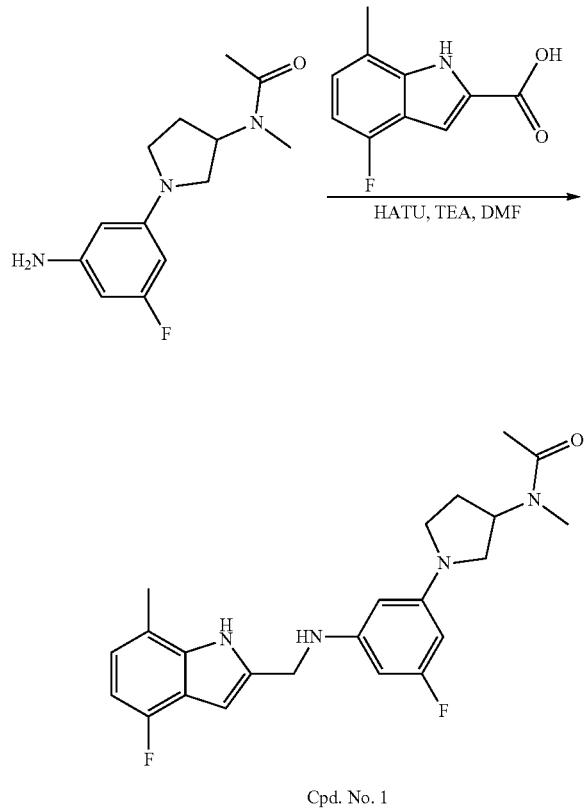

Cpd. No. 1

Into a 40-mL vial was placed N-[1-(3-amino-5-fluorophenyl)pyrrolidin-3-yl]-N-methylacetamide (330 mg, 1.31 mmol, 1.00 equiv), TEA (700 mg, 6.92 mmol, 5.27 equiv) in N,N-dimethylformamide (10 mL), 4-fluoro-7-methyl-1H-indole-2-carboxylic acid (250 mg, 1.29 mmol, 0.99 equiv) and HATU (649 mg, 1.71 mmol, 1.30 equiv) was added batchwise. The resulting solution was stirred for 2 h at 25° C. The resulting mixture was concentrated under vacuum. The reaction progress was monitored by LCMS, and the reaction solution was quenched by 20 ml of water. The resulting solution was extracted with 3×20 ml of ethyl acetate and the organic layers combined and concentrated under vacuum. The residue was applied onto a silica gel column with ethyl acetate/petroleum ether (1:1). The crude product (200 mg) was purified by Prep-HPLC with the following conditions: Column, XBridge Shield RP18 OBD Column, 5 µm, 19*150 mm; mobile phase, Water (10 mmol/L NH$_4$HCO$_3$) and ACN (40.0% ACN up to 68.0% in 7 min); Detector, UV 220/254 nm. This resulted in 47.4 mg (yield=8%) of 4-fluoro-N-(3-fluoro-5-(3-(N-methylacetamido)pyrrolidin-1-yl)phenyl)-7-methyl-1H-indole-2-carboxamide as a light yellow solid. LCMS (Method B, ES): RT=3.206 min, m/z=427 [M+H]$^+$. $^1$H NMR (400 MHz, DMSO-d$_6$) δ11.92 (s, 1H), 10.19 (s, 1H), 7.51 (s, 1H), 7.19-7.08 (m, 1H), 7.03-6.93 (m, 1H), 6.87 (d, J=2.1 Hz, 1H), 6.86-6.73 (m, 1H), 6.17-6.13 (m, 1H), 5.23-4.63 (m, 1H), 3.54-3.33 (m, 2H), 3.26-3.16 (m, 2H), 2.90 (s, 2H), 2.76 (s, 1H), 2.61-2.51 (s, 3H), 2.24-2.00 (m, 5H) ppm.

Example 11

In-Cell Western (ICW) Assay of SETD2 Inhibitors (A549 Assay)

Representative Compounds of the Disclosure were tested in the A549 assay according the following protocol. A549 assay results are provided in Table 1B.

Protocol:

1. Reagents and Consumables:

| Reagent Number | Reagent Name | Reagent Source | Catalog Number |
|---|---|---|---|
| 1 | A549 | ATCC | CCL-185 |
| 2 | F12K | Hyclone | SH30526.01 |
| 3 | FBS | Gbico | 10099-141 |
| 4 | Penicillin-Streptomycin | Gbico | 15140-122 |
| 5 | Poly-D-Lysine Black/Clear Microtest (TM) Tissue-Culture Treated Polystyrene, 384-well plate | Corning | 356663 |
| 6 | Methanol | Concord Technology | R266 |
| 7 | PBS powder | Solarbio | P1010 |
| 8 | Odyssey Blocking Buffer | LI-COR | 927-40000 |
| 9 | Tri-Methyl-Histone H3 (Lys36) (D5A7) XP ® Rabbit mAb | CST | 4909S |
| 10 | Tween-20 | Sigma | P2287 |
| 12 | IRDye 800CW Goat anti-Rabbit IgG (H + L)(LI-COR, 926-32211, 0.5 mg) | LI-COR | 926-32211 |
| 13 | DRAQ5 (CST, 4084L, 200 ul) | CST | 4084L |
| 14 | 384-Well Clear plate | Labcyte | P-05525 |

2. Tools and Equipment:

| Tool Number | Tool Name | Brand | Model |
|---|---|---|---|
| 1 | Cell Counter | Invitrogen | Countess ® Automated Cell Counter |
| 2 | CO$_2$ incubator | Thermo Scientific | 371 |
| 3 | Biological Safety Cabinet (Class II) | Thermo Scientific | 1389 |
| 4 | Centrifuge | Eppendorf | 5810R |
| 5 | ELx405 plate washer | BioTek | ELx405 Select CW |
| 6 | Echo 550 | Echo | Echo 550 |
| 7 | Plate Shaker | Eppendorf | MixMate |
| 8 | ODYSSEY CLx | LI-COR | ODYSSEY CLx |
| 9 | Multiflo | Biotek | MultiFlo FX |
| 10 | Liquid handle system | Tecan | Freedom EVO200 |

3. Screening Method

Prepare plates with compounds. Seed A549 cells to the plates with compounds, 4,000 cells/well, 50 µl/well. Put the plates at room temperature on a non-vibrating surface for 20 minutes before placing in the incubator. Incubate the plate at 37° C. incubator with CO$_2$ for 3 days. Remove plate from incubator and bring to room temperature. Blot media out of the plate and add 50 µL of ice cold 100% methanol. Incubate 30 minutes at room temperature. Remove methanol by aspiration. Wash 3× with PBST. Add 50 µL of Blocking Buffer+0.1% Tween 20. Incubate 1 hour. Remove Blocking Buffer, wash 3× with PBST. Add 20 µL of H3K36me3 (1:1000 dilution). (Cell Signaling Technologies mAb #4909). Incubate overnight at 4° C. Wash plate 5× with PBS-T. Add 20 µL of DRAQ5 (1:1000) and IRDye 800CW Goat anti-Rabbit IgG (1:500). Incubate for 1 hour in the dark. Wash plate 5× with PBS-T. Wash plate 3× with water. Dry by blotting on paper towel, then centrifuge plate upside down on a thin layer of paper towels for 1 minute at 1000 rpm to remove excess reagent. Leave plate uncovered for ~10 minutes out of direct light before reading. Read on Licor instrument.

4. Licor Instrument Settings:

Preset: Plate; Resolution: 84 µm; Quality: low; Focus offset: 4.0; 700 channel intensity: 2; and 800 channel intensity: 3.

Example 12

SETD2 (1434-1711) Assay

Representative Compounds of the Disclosure were tested in the SETD2 (1434-1711) assay using the following protocol. SETD2 (1434-1711) assay results are provided in Table 1B.

1. Reagents

| Reagent Number | Reagent Name | Reagent Source | Catalog Number |
|---|---|---|---|
| 1 | 0.5 M Bicine pH 8.0 | Alfa Aesar | J63924 |
| 2 | Tween 20, 100% | Sigma | P2287 |
| 3 | β-mercaptoethanol (β-Me) | Sigma | M3148 |
| 4 | Bovine Serum Gelatin (BSG), 2% | Sigma | G1393 |
| 5 | Peptide #6 (H3 26-40, 15-mer) | Biopeptide | N/A |
| 6 | Tritium isotope, $^3$H SAM 1 mCi, (12.5 µM) | ARC | ART0288 |
| 7 | S-5'-adenosyl -L methionine chloride (SAM) | ARC | ARCD0767 |
| 8 | SETD2(1434-1711) (RCP-83-1, 198 µM) | Supplied by Epizyme | N/A |

2. List of Tools/Equipment

| Tool Number | Tool Name | Tool Source |
|---|---|---|
| 1 | Multi-channel pipettes | Rainin & Thermo Scientific Matrix |
| 2 | Multi-drop | Thermo Scientific |
| 3 | TopCount | Perkin Elmer |
| 4 | Platemate | Thermo |
| 5 | ELx406 plate washer | BioTek |

3. Reagent Formulations

| Prepared Reagent Number | Prepared Reagent Name/Description | Prepared Reagent Volume | Component Name | Component Quantity | Final Component Conc |
|---|---|---|---|---|---|
| 3 | Fresh made SAM (from powder) | 10 mL | dH$_2$0 SAM | 10 mL 4.35 mg | 1 mM |
| 4 | COLD SAM aliquots | 10 mL | dH$_2$0 200 mM SAM | 10 mL 869.8 mg | 200 mM |
| 4 | Tween-20 | 100 mL | Tween 20 dH$_2$0 | 10 mL 90 mL | 10% |

4. Procedure Description

| Step Number | Step Description |
|---|---|
| 1 | Add 40 µL per well of Enzyme mix using Multi-drop to wells of prepared Compound Stock plate. |
| 2 | Incubate the enzyme in the Compound Stock plate for 30 minutes. |
| 3 | Add 10 µL per well of Substrate mix to Compound Stock plate using Multi-drop. |
| 4 | Cover plate and incubate 2.5 hours at room temperature. |

-continued

| Step Number | Step Description |
|---|---|
| 5 | Stop reaction with addition of 10 µL per well of Stop mix; added using Multi-drop. |
| 6 | Transfer 50 µL of volume per well to Flashplate from Compound Stock plate using a Thermo Platemate. |
| 7 | Cover Flashplate and incubate for 2 hr minimum at room temperature or overnight at 4 degrees C. |
| 8 | Wash Flashplate with dH2O + 0.1% Tween using the BioTek plate washer, program 'Flashplate Wash 1X.LHC'. Plate is washed 1X, with final aspiration (Appendix 6). Seal Flashplate with TopSeal. |
| 9 | Read plate in TopCount. |

Example 13

14 Day KMS-34 Long Term Proliferation (LTP) Assay

Figure 2:
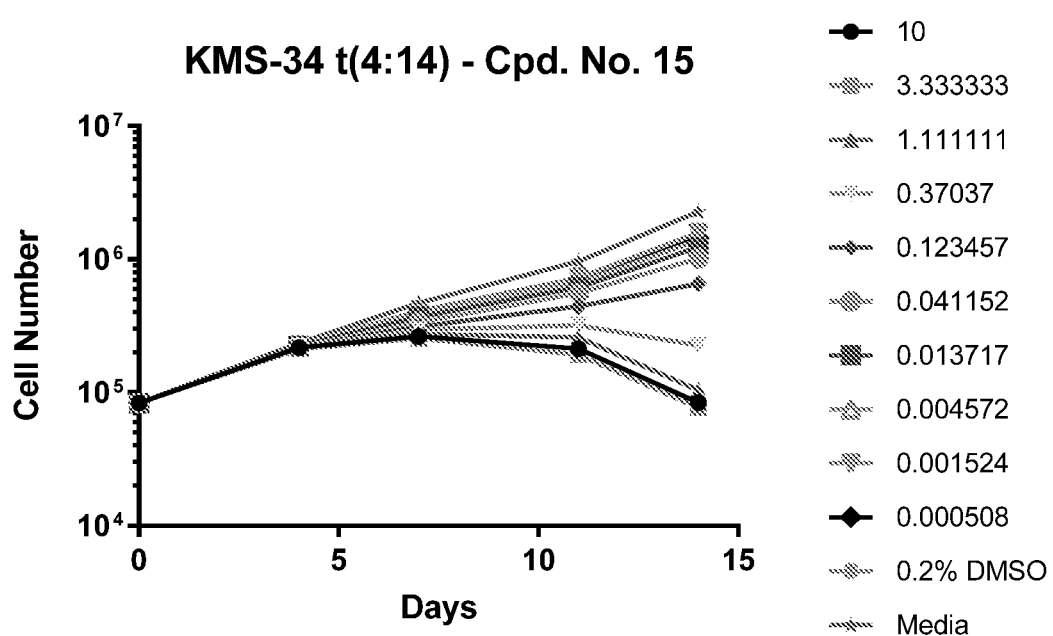
FIG. 2 is a line graph showing that KMS-34, a t(4;14) multiple myeloma cell line has a cytotoxic response to Cpd. No. 15 with an proliferation $IC_{50}$ of 80 nM in a 14-day assay. The Y-axis is the cell number at each time point on a log scale. Each line represents the indicated dose of Cpd. No. 15.
Figure 3:
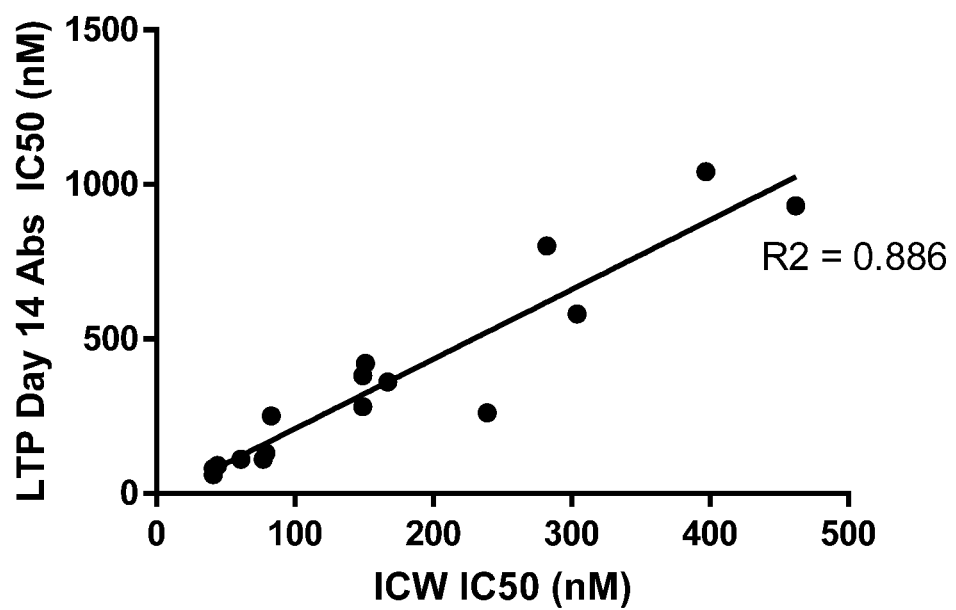
FIG. 3 is a line graph comparing the H3K36me3 inhibition potency and the anti-proliferative potency of representative Compounds of the Disclosure. Each point represents a Compound of the Disclosure run in an A549 H3K36me3 assay and a KMS-34 proliferation assay.

Representative Compounds of the Disclosure were tested in the 14 day KMS-34 LTP assay using the following protocol. Assay results for 14 day KMS-34 LTP assay are provided in Table 5 and FIG. 2. FIG. 3 compares the KMS-34 LTP activity with the A549 H3K36me3 activity, see Example 11, of Cpd. Nos. 7, 11, 15, 22, 31, 32, 34, 64, 65, 66, 76, 115, 134, 151, 194, and 221.

1. Reagents, Consumables, and Equipment:

| Materials | Source | Cat. No. | Lot. No |
|---|---|---|---|
| KMS-34 | | | |
| RPMI 1640 | Invitrogen | 11875-119 | 1694256 |
| FBS | BI | 04-002-1A | 1609758 |
| 96-well plate, flat | Corning | 3599 | |
| Poly-D-Lysine 96-well Microplates, black/clear | BD BIOCOAT | 356640 | |
| Calcein-AM | Invitrogen | C3099 | 1887153 |

2. Screening Method

Day 0:

In a flat bottom 96-well plate, add 100 µl of cells per well at 1.25×10$^5$ cells/ml density (Note: Only internal wells. PBS placed in all outer wells to avoid evaporation of the internal wells.) Add 50 µl of compounds to each well. Final volume in each well is 150 µl. Incubate plates for 96 hrs.

Day 1, 2, 3: wait

Day 4:

Pipette cells up and down to mix in each well. Aspirate 20 µl of cell suspension in the V-bottom plate and add to a poly-D-lysine coated 96-well plate. Add 30 µl HBSS and 50 µl of HBSS containing 2 µm Calcein-AM. The final concentration is 1 µm. Let cells sit at RT for 10 mins followed by a quick spin to get cells settled on the bottom of the wells. Incubate the plate for additional 40 mins in the incubator (to load Calcein AM and to give cells more time to attach). Take out the plate and read by Acumen. Calculate the cell numbers taken into account the dilution factors. Split the master plate by taking the total viable cell count calculated. Pipette cells up and down to mix in each well. Aspirate 1.1* of calculated cell suspension from each well and add to a V-bottom plate. Spin the plate at 1100 rpm for 5 minutes. Following the spin remove the media, careful not to disturb the cell pellet. Resuspend pellet in 110 μl fresh media. Pipette cells up and down to mix in each well. Aspirate 100 μl of cell suspension from each well and add to a new 96-well flat bottom plate. Add 50 μl of compound solution. Incubate plates for 72 hrs.

Day 7:

Pipette cells up and down to mix in each well. Aspirate 20 μl of cell suspension in the V-bottom plate and add to a poly-D-lysine coated 96-well plate. Add 30 μl HBSS and 50 μl of HBSS containing 2 μm Calcein-AM. The final concentration is 1 μm. Let cells sit at RT for 10 mins followed by a quick spin to get cells settled on the bottom of the wells. Incubate the plate for additional 40 mins in the incubator (to load Calcein AM and to give cells more time to attach). Take out the plate and read by Acumen. Calculate the cell numbers taken into account the dilution factors. Split the master plate by taking the total viable cell count calculated. Pipette cells up and down to mix in each well. Aspirate 1.1* of calculated cell suspension from each well and add to a V-bottom plate. Spin the plate at 1100 rpm for 5 minutes. Following the spin remove the media, careful not to disturb the cell pellet. Resuspend pellet in 110 uL fresh media. Pipette cells up and down to mix in each well. Aspirate 100 μl of cell suspension from each well and add to a new 96-well flat bottom plate. Add 50 μl of compound solution. Incubate plates for 96 hrs.

Day 11:

Pipette cells up and down to mix in each well. Aspirate 20 μl of cell suspension in the V-bottom plate and add to a poly-D-lysine coated 96-well plate. Add 30 μl HBSS and 50 μl of HBSS containing 2 μm Calcein-AM. The final concentration is 1 μm. Let cells sit at RT for 10 mins followed by a quick spin to get cells settled on the bottom of the wells. Incubate the plate for additional 40 mins in the incubator (to load Calcein AM and to give cells more time to attach). Take out the plate and read by Acumen. Calculate the cell numbers taken into account the dilution factors. Split the master plate by taking the total viable cell count calculated. To reduce the variation that may be caused by pippeting: Pipette cells up and down to mix in each well. Aspirate all the cell suspension from B1-2, C1-2, D1-2 and add to a V-bottom plate. Aspirate 1.1* of calculated cell suspension from the other wells and add to a V-bottom plate. Spin the plate at 1100 rpm for 5 minutes. Following the spin remove the media, careful not to disturb the cell pellet. Resuspend pellet in B1-2, C1-2, D1-2 in 100 uL fresh media. Pipette cells up and down to mix in each well. Resuspend pellet in the other wells in 110 μl fresh media. Pipette cells up and down to mix in each well. Aspirate 100 μl of cell suspension from each well and add to a new 96-well flat bottom plate.

Day 14: Pipette cells up and down to mix in each well. Aspirate 20 μl of cell suspension in the V-bottom plate and add to a poly-D-lysine coated 96-well plate. Add 30 μl HBSS and 50 μl of HBSS containing 2 μm Calcein-AM. The final concentration is 1 μm. Let cells sit at RT for 10 mins followed by a quick spin to get cells settled on the bottom of the wells. Incubate the plate for additional 40 mins in the incubator (to load Calcein AM and to give cells more time to attach. Take out the plate and read by Acumen. Calculate the cell numbers taken into account the dilution factors.

To calculate growth for days 4, 7, 11, and 14:

1. Calculate the split factor for day 4 to 7, day 7 to 11, and day 11-14 The split factor is the viable cells/mL on Day X (either 4, 7, or 11) divided by the density the cells are being split back to.
2. For growth of cells from day 4 to 7, multiply the day 7 viable cells/mL density by the split factor from day 4.
3. For growth of cells from day 7 to 11, multiply the day 11 viable cells/mL density by the days 4, and 7 split factors.
4. For growth of cells from Day 11 to 14, multiply the Day 14 viable cells/mL density by the days 4, 7, and 11 split factors.
5. Plot growth on semi-log chart (viable cells/mL on Y axis, in log, and days on X axis).

Compound Preparation:

Compounds were dissolved in DMSO at 10 mM and were stored at −20° C. Compounds were diluted with DMSO in 3-fold serial dilution. From 5 mM to 0.25 μm. Transfer 1.2 μl of compounds from compound plate and add to a 96-well plate with 200 μl of media in each well. Mix well by pipetting up and down. Transfer 50 μl of compound-containing media to the cell plate.

TABLE 5

| Cpd. No. | LTP Day 14 Abs IC$_{50}$ (nM) |
|---|---|
| 7 | 60 |
| 11 | 90 |
| 15 | 80 |
| 22 | 110 |
| 31 | 130 |
| 32 | 110 |
| 34 | 250 |
| 64 | 380 |
| 65 | 280 |
| 66 | 420 |
| 76 | 360 |
| 115 | 260 |
| 134 | 800 |
| 151 | 580 |
| 194 | 1,040 |
| 221 | 930 |
| 359 | 7800 |
| 372 | 10,000 |
| 373 | 10,000 |
| 509 | 2600 |

Example 14

14 Day LTP Assay in Multiple Myeloma Cells

Cpd. No. 15 was tested in several multiple myeloma cell lines in the LTP assay described in EXAMPLE 13. The results are presented in Table 6 and FIG. 1.

TABLE 6

| Cell Line | Translocation | 14 day LTP IC$_{50}$ (μM) |
|---|---|---|
| NCI-H929 | t(4: 14) | 0.24 |
| LP-1 | t(4: 14) | 0.07 |
| OPM-2 | t(4: 14) | 0.09 |
| KMS-11 | t(4: 14) | 0.14 |
| KMS-28-BM | t(4: 14) | >10 |
| KMS-34 | t(4: 14) | 0.08 |
| KMS-12-BM | t(11: 14) | 1.9 |
| MM.1R | t(4: 16) | 1.2 |
| MM.1S | t(4: 16) | 3 |
| U266B1 | t(11: 14) | 6.1 |
| HuNS1 | None | 0.6 |
| RPMI | t(14: 16) | 3.3 |

Example 15

Evaluation of the Anti-Tumor Activity of Cpd. No. 15 as a Single Agent in Human Myeloma KMS-11 Tumor-bearing NOD SCID Mice Animals Species & Strain: NOD SCID mice; Age: 6 to 8 weeks; Total Number: 75 mice including spare, study used 50 mice; Sex: Female; Body Weight: 18 to 22 g Groups and Treatments Groups and treatments were started when the mean tumor volume reached about 118 mm$^3$. Based on the tumor volume and body weight, mice were assigned to respective groups such that the average starting tumor size and body weight was the same for each treatment group. The study groups and number of animals per group are shown in Table 7.

TABLE 7

Group and Treatments for efficacy study

| Group # | Drug | Animals/group | Dose (mg/kg) | Vol (ml/kg) | Route | Regimen | Duration |
|---|---|---|---|---|---|---|---|
| 1 | Vehicle control | 10 | — | 10 | p.o. | BID | 28 days |
| 2 | Cpd. No. 15 | 10 | 31.25 | 10 | p.o. | BID | 28 days |
| 3 | Cpd. No. 15 | 10 | 62.5 | 10 | p.o. | BID | 28 days |
| 4 | Cpd. No. 15 | 10 | 125 | 10 | p.o. | BID | 18 days |
|   |   |   |   |   |   | BID(3D– 4D+) | 7 days |
| 5 | Cpd. No. 15 | 10 | 175 | 10 | p.o. | BID | 11 days |
|   |   |   |   |   |   | BID(3D– 4D+) | 14 days |

Method for Cell Culture

The KMS-11 tumor cell line was maintained in vitro as monolayer culture in RPMI-1640+10% FBS at 37° C. in an atmosphere of 5% $CO_2$ in air. The tumor cells were routinely subcultured before confluence, not to exceed 4-5 passages. The cells growing in an exponential growth phase were harvested and counted for tumor inoculation.

Method for Tumor Inoculation

Each mouse was inoculated subcutaneously on the right flank with KMS-11 tumor cells ($1\times10^7$) and matrigel mixture (1:1 ratio) in 0.1 ml of RPMI-1640 for tumor development. The treatment was started when the mean tumor size reached 118 mm$^3$. Mice were then assigned to groups such that the mean tumor volume was the same for each treatment group and time point. The treatments were administered to the tumor-bearing mice accordingly to the study design showed in Table 7.

Tumor Measurements

The measurement of tumor size was conducted twice weekly with a caliper and the tumor volume (mm3) is estimated using the formula: TV=a×b×b/2, where "a" and "b" are long and short diameters of a tumor, respectively. The TVs are used for calculation of the tumor growth inhibition and tumor growth delay. For the tumor growth inhibition (TGI), the value using the formula:

% ΔT/ΔC=(TreatedTVfinal−TreatedTVinitial)/(VehicleTVfina−VehicleTVinitial)*100     a.

% TGI=[1−(TreatedTVfinal−TreatedVTinitial)/(VehicleTVfinal−VehicleTVinitial)]*100     b.

The "TVfinal" and "TVinitial" are the mean tumor volumes on the final day and initial day of dosing.

After take down 5 mice of G2~G5 post the final dosing, the remaining mice were maintained for monitoring tumor outgrowth twice weekly.

Termination Criterion

Animals that were observed to be in a continuing deteriorating condition or their tumor size exceeding 3,000 mm3 (individual tumor or group average>3,000 mm$^3$) were euthanized prior to death, or before reaching a comatose state. Animals showing obvious signs of severe distress and/or pain were humanely sacrificed by carbon dioxide followed by cervical dislocation to ensure death.

Samples Collection

Tumor samples and plasma were collect at the indicated day.

Data Acquisition and Statistical Analysis

Data Acquisition: Protocol-required measurements and observations were recorded manually on appropriate forms, or directly on a computerized database.

Statistical Analysis: All statistical tests were conducted, and the level of significance was set at 5% or P<0.05. The group means, standard deviation were calculated for all measurement parameters as study designed. Two-way RM ANOVA followed by Tukeys post hoc comparisons of the means.

Tumor Volumes

Figure 4:
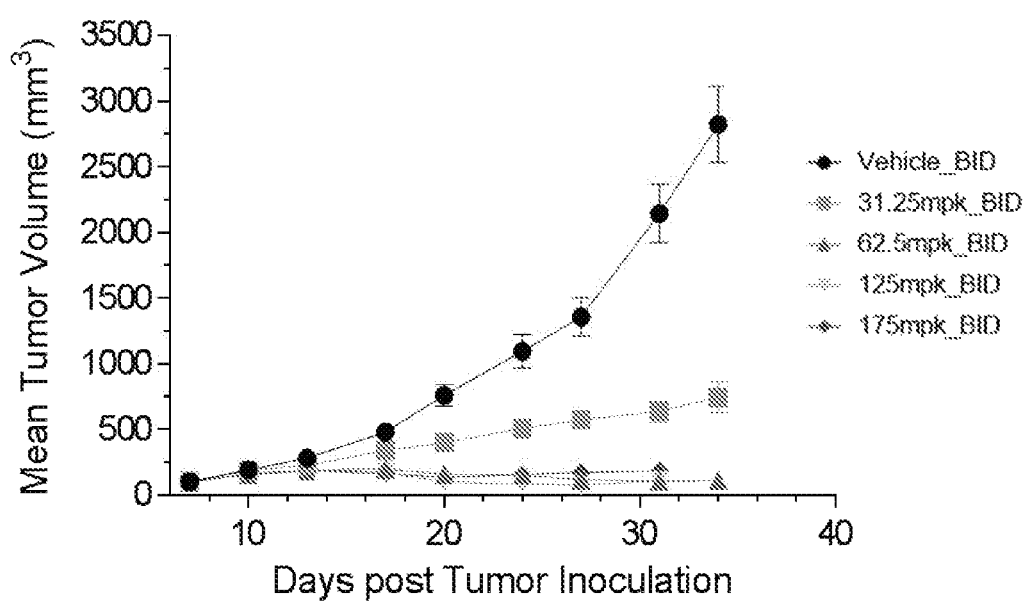
FIG. 4 is a line graph showing the antitumor activity of Cpd. No. 15 in the KMS11 xenograft model.

The therapeutic effects of compound as a single agent in the KMS-11 subcutaneous xenograft model were evaluated. The tumor sizes in different groups at different time points during the treatment period are shown Tables 8 and 9, and FIG. 4,

TABLE 8

The Mean Value of Tumor Sizes in the Different Treatment Groups [Tumor volume (mm3, Mean ± SEM)]

| Group | PG-D1<br>D 7 | PG-D4<br>D 10 | PG-D7<br>D 13 | PG-D11<br>D 17 | PG-D14<br>D 20 | PG-D18<br>D 24 | PG-D21<br>D 27 | PG-D25<br>D 31 |
|---|---|---|---|---|---|---|---|---|
| G1 | 118 ± 5 | 229 ± 23 | 338 ± 29 | 573 ± 50 | 908 ± 112 | 1320 ± 178 | 1624 ± 199 | 2558 ± 301 |
| G2 | 119 ± 6 | 225 ± 21 | 271 ± 19 | 408 ± 46 | 478 ± 54 | 609 ± 71 | 686 ± 80 | 763 ± 97 |

TABLE 8-continued

The Mean Value of Tumor Sizes in the Different Treatment Groups [Tumor volume (mm3, Mean ± SEM)]

| Group | PG-D1 D 7 | PG-D4 D 10 | PG-D7 D 13 | PG-D11 D 17 | PG-D14 D 20 | PG-D18 D 24 | PG-D21 D 27 | PG-D25 D 31 |
|---|---|---|---|---|---|---|---|---|
| G3 | 117 ± 6 | 178 ± 11 | 216 ± 11 | 231 ± 16 | 184 ± 17 | 176 ± 22 | 129 ± 25 | 115 ± 30 |
| G4 | 117 ± 6 | 191 ± 11 | 219 ± 9 | 196 ± 11 | 119 ± 10 | 99 ± 16 | 85 ± 20 | 131 ± 39 |
| G5 | 119 ± 6 | 192 ± 13 | 221 ± 17 | 199 ± 24 | 167 ± 27 | 189 ± 32 | 214 ± 45 | 225 ± 45 |

TABLE 9

The Mean Value of Tumor Sizes in the Different Treatment Groups Post the Final Dosing Group [Tumor volume (mm3, Mean ± SEM)]

| Group | PG-D28 D 34 | | PG-D32 D 38 | | PG-D35 D 41 | | PG-D39 D 45 | |
|---|---|---|---|---|---|---|---|---|
| G1 | 3362 ± 387 | n = 10 | | | | | | |
| G2 | 882 ± 131 | n = 10 | 1123 ± 149 | n = 5 | 1499 ± 196 | n = 4 | 1747 ± 243 | n = 3 |
| G3 | 117 ± 36 | n = 10 | 65 ± 23 | n = 5 | 150 ± 60 | n = 5 | 309 ± 108 | n = 5 |
| G4 | 99 ± 20 | n = 4 | 239 ± 68 | n = 4 | 421 ± 108 | n = 4 | 757 ± 215 | n = 4 |
| G5 | 269 ± 146 | n = 4 | 589 ± 378 | n = 3 | 732 ± 422 | n = 3 | 1183 ± 686 | n = 3 |

Inhibition Rate for Tumor Growth

The inhibition rate for tumor growth of each group is shown in Table 10.

TABLE 10

Antitumor Activity in KMS-11 Subcutaneous Xenograft Model

| Treatment | Tumor Size (mm3) at PG-Day 25 | ΔT/ΔC (%)b | TGI (%)c | P Valued |
|---|---|---|---|---|
| G1, Vehicle control, p.o., BID × 28 days | 2558 ± 301 | — | — | — |
| G2, , 31.25 mg/kg, p.o., BID × 28 days | 763 ± 97 | 26 | 74 | **** |
| G3, 3, 62.5 mg/kg, p.o., BID × 28 days | 115 ± 30 | 0 | 100 | **** |
| G4, 125 mg/kg, p.o., BID × 18 days, BID(3D-4D+) × 7 days | 131 ± 39 | 1 | 99 | **** |
| G5, 175 mg/kg, p.o., BID × 18 days, BID(3D-4D+) × 14 days | 225 ± 45 | 4 | 96 | **** |

Note:
aMean ± SEM;
bΔT/ΔC = (TV treated final-TV treated initial)/(TV Vehicle final- TV Vehicle initial) *100%;
cTGI = [1-(TV treated final-TV treated initial)/(TV Vehicle final- TV Vehicle initial)] *100%;
dvs. Vehicle control, via Tukeys multiple comparisons test; P < 0.01, *P < 0.001, ****P < 0.0001, ns: no significant.

Figure 5:
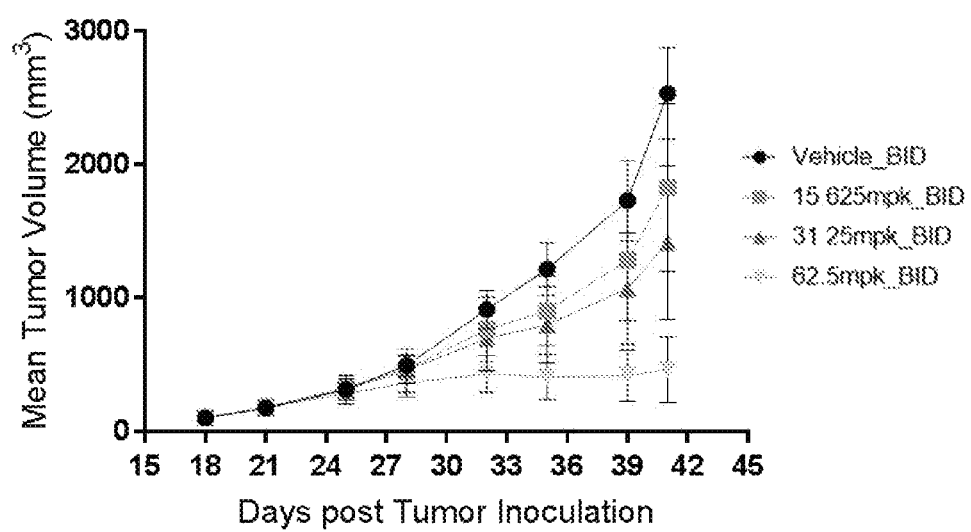
FIG. 5 is a line graph showing the antitumor activity of Cpd. No. 15 in the MM.1S xenograft model

Cpd. No. 15 was also tested in MM.1S a non-t(4;14) multiple myeloma xenograft model using similar methods and BID dosing. The results are provided in FIG. 5.

Having now fully described this invention, it will be understood by those of ordinary skill in the art that the same can be performed within a wide and equivalent range of conditions, formulations, and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound of Formula IV:

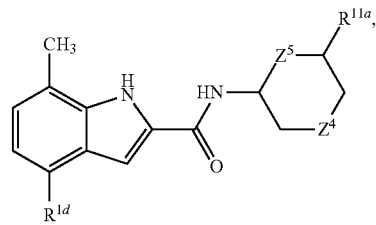

IV wherein:

$R^{1d}$ is fluoro;

$Z^4$ is selected from the group consisting of —O—, —C($R^{28a}$)($R^{28b}$)—, and —N($R^{23}$)—; or $Z^4$ is absent;

$Z^5$ is selected from the group consisting of —CH$_2$— and —CH$_2$CH$_2$—;

$R^{11a}$ is selected from the group consisting of optionally substituted alkyl, optionally substituted heterocyclo, optionally substituted heteroaryl, and —N($R^{12b}$)C(=O)$R^{13c}$;

$R^{12b}$ is selected from the group consisting of hydrogen, alkyl, cycloalkyl, and heterocyclo, ($C_1$-$C_4$ alkoxy)$C_1$-$C_4$ alkyl, and (hydroxy)$C_1$-$C_4$ alkyl;

$R^{13c}$ is selected from the group consisting of alkyl, haloalkyl, alkoxy, (alkoxy)alkyl, (hydroxy)alkyl, (cyano)alkyl, optionally substituted aryl, optionally substituted heteroaryl, optionally substituted cycloalkyl, optionally substituted heterocycle, amino, (amino)alkyl, ($C_3$-$C_6$ cycloalkyl)oxy, and (4- to 8-membered heterocyclo)oxy;

$R^{23}$ is selected from the group consisting of hydrogen and $C_1$-$C_4$ alkyl; and $R^{28a}$ and $R^{28b}$ are independently selected from the group consisting of hydrogen, alkyl, and halo;

or a pharmaceutically acceptable salt or solvate thereof.

2. The compound of claim 1 of Formula IV-A:

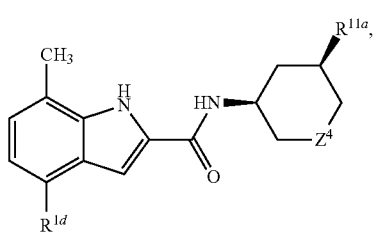

or a pharmaceutically acceptable salt or solvate thereof.

3. The compound of claim 2, wherein:

$R^{11a}$ is selected from the group consisting of:
(A) unsubstituted 4- to 14-membered heterocyclo;
(B) substituted 4- to 14-membered heterocyclo having one, two or three substituents independently selected from the group consisting of:
(i) —N($R^{12a}$)C(=O)$R^{13a}$; (ii) —C(=O)$R^{13b}$; (iii) $C_1$-$C_4$ alkyl; (iv) ($C_1$-$C_4$ alkoxy)$C_1$-$C_4$ alkyl; (v) (hydroxy)$C_1$-$C_4$ alkyl; (vi) $C_1$-$C_4$ haloalkyl; (vii) amino; (vii) hydroxy; (viii) —N($R^{12a}$)S(=O)$_2R^{24}$; (ix) —S(=O)$_2R^{24}$; (x) unsubstituted $C_3$-$C_6$ cycloalkyl; (xi) substituted $C_3$-$C_6$ cycloalkyl having one or two substituents independently selected from the group consisting of halo, hydroxy, $C_1$-$C_4$ alkyl, amino, and (amino)$C_1$-$C_4$ alkyl; (xii) unsubstituted 4- to 14-membered heterocyclo; and substituted 4- to 14-membered heterocyclo having one or two substituents independently selected from the group consisting of amino, hydroxy, and $C_1$-$C_4$ alkyl; (xiii) —C(=N—$R^{60}$)$R^{61}$; and (xiv) —C(=C—$NO_2$)$R^{64}$;
(C) unsubstituted 5- to 10-membered heteroaryl;
(D) substituted 5- or 6-membered heteroaryl having one, two, three, or four substituents independently selected from the group consisting of halo and $C_1$-$C_4$ alkyl;
(E) $C_1$-$C_6$ alkyl; and
(F) —N($R^{12b}$)C(=O)$R^{13c}$;

$R^{12a}$ and $R^{12b}$ are each independently selected from the group consisting of hydrogen, $C_1$-$C_4$ alkyl, ($C_1$-$C_4$ alkoxy)$C_1$-$C_4$ alkyl, and (hydroxy)$C_1$-$C_4$ alkyl;

$R^{13a}$, $R^{13b}$, and $R^{13c}$ are each independently selected from the group consisting of (A) $C_1$-$C_6$ alkyl; (B) $C_1$-$C_6$ haloalkyl; (C) unsubstituted $C_3$-$C_6$ cycloalkyl; (D) $C_1$-$C_6$ alkoxy; (E) ($C_1$-$C_4$ alkoxy)$C_1$-$C_4$ alkyl; (F) (hydroxy)$C_1$-$C_4$ alkyl; (G) (cyano)alkyl; (H) unsubstituted $C_6$-$C_{10}$ aryl; (I) substituted $C_6$-$C_{10}$ aryl, having one, two, three, or four substituents independently selected from the group consisting of halo, amino, hydroxy, and $C_1$-$C_4$ alkyl; (J) unsubstituted 5- or 6-membered heteroaryl; (K) substituted 5- or 6-membered heteroaryl having one, two, three, or four substituents independently selected from the group consisting of halo, amino, hydroxy, and $C_1$-$C_4$ alkyl; (L) unsubstituted 4- to 14-membered heterocyclo; (M) substituted 4- to 14-membered heterocyclo having one or two substituents independently selected from the group consisting of amino, hydroxy, and $C_1$-$C_4$ alkyl; (N) amino; (0) (amino)alkyl; (P) ($C_3$-$C_6$ cycloalkyl)oxy; and (Q) (4- to 8-membered heterocyclo)oxy;

$R^{24}$ is selected from the group consisting of $C_1$-$C_4$ alkyl and (hydroxy)$C_1$-$C_4$ alkyl;

$R^{60}$ is selected from the group consisting of cyano, nitro, hydroxy, $C_1$-$C_6$ alkoxy, —C(=O)$R^{62}$ and —S(=O)$_2R^{62}$;

$R^{61}$ is selected from the group consisting of $C_1$-$C_6$ alkyl, $C_3$-$C_6$ cycloalkyl, and —N$R^{63a}R^{63b}$;

$R^{62}$ is selected from the group consisting of $C_1$-$C_6$ alkyl, $C_3$-$C_6$ cycloalkyl, and —N$R^{63a}R^{63b}$;

$R^{63a}$ is selected from the group consisting of hydrogen, $C_1$-$C_6$ alkyl, and $C_3$-$C_6$ cycloalkyl;

$R^{63b}$ is selected from the group consisting of hydrogen, $C_1$-$C_6$ alkyl, and $C_3$-$C_6$ cycloalkyl; or $R^{63a}$ and $R^{63b}$ taken together with the nitrogen atom to which they are attached form a 4- to 6-membered optionally substituted heterocyclo;

$R^{64}$ is selected from the group consisting of $C_1$-$C_6$ alkyl, $C_3$-$C_6$ cycloalkyl, and —N$R^{63c}R^{63d}$;

$R^{63c}$ is selected from the group consisting of hydrogen, $C_1$-$C_6$ alkyl, and $C_3$-$C_6$ cycloalkyl; and $R^{63d}$ is selected from the group consisting of hydrogen, $C_1$-$C_6$ alkyl, and $C_3$-$C_6$ cycloalkyl; or $R^{63c}$ and $R^{63d}$ taken together with the nitrogen atom to which they are attached form a 4- to 6-membered optionally substituted heterocyclo, or a pharmaceutically acceptable salt or solvate thereof.

4. The compound of claim 3, wherein $R^{11a}$ is a substituted 4- to 14-membered heterocyclo selected from the group consisting of:

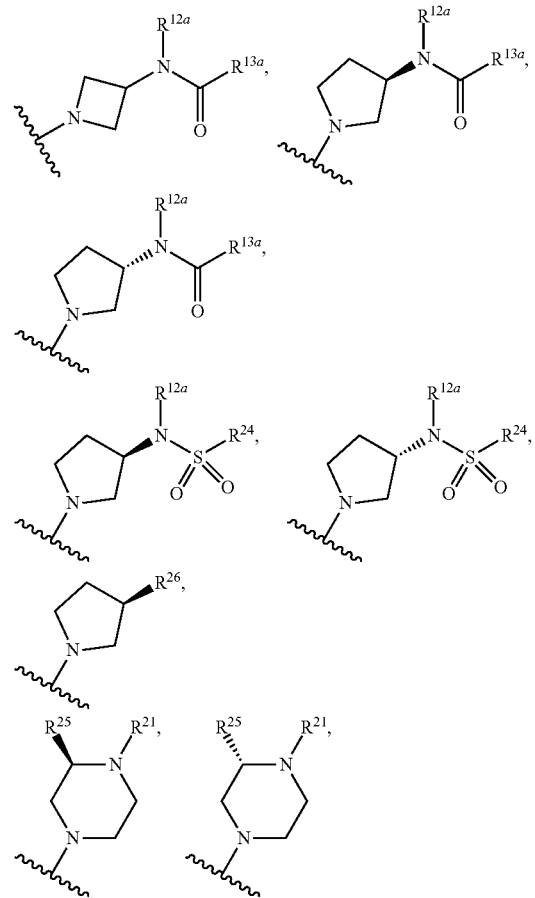

-continued

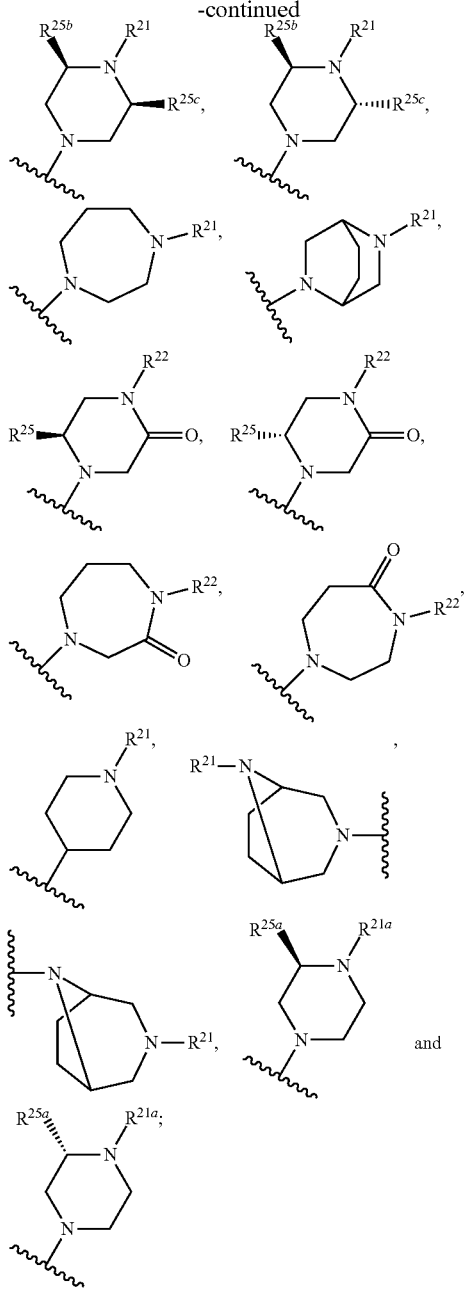

R$^{12a}$ is selected from the group consisting of hydrogen, C$_1$-C$_3$ alkyl, (C$_1$-C$_4$ alkoxy)C$_1$-C$_4$ alkyl, and (hydroxy)C$_1$-C$_4$ alkyl;

R$^{13a}$ is selected from the group consisting of C$_1$-C$_4$ alkyl; amino; unsubstituted C$_3$-C$_6$ cycloalkyl; substituted C$_3$-C$_6$ cycloalkyl having one or two substituents independently selected from the group consisting of halo, hydroxy, C$_1$-C$_4$ alkyl, amino, and (amino)C$_1$-C$_4$ alkyl; (C$_1$-C$_4$ alkoxy)C$_1$-C$_4$ alkyl; (hydroxy)C$_1$-C$_4$ alkyl; unsubstituted 4- to 14-membered heterocyclo; and substituted 4- to 14-membered heterocyclo having one or two substituents independently selected from the group consisting of amino, hydroxy, and C$_1$-C$_4$ alkyl;

R$^{13b}$ is selected from the group consisting of C$_1$-C$_4$ alkyl; amino; C$_1$-C$_4$ haloalkyl; C$_1$-C$_4$ alkoxy; (hydroxy)C$_1$-C$_4$ alkyl; (C$_1$-C$_4$ alkoxy)C$_1$-C$_4$ alkyl; (amino)alkyl; unsubstituted C$_3$-C$_6$ cycloalkyl; substituted C$_3$-C$_6$ cycloalkyl having one or two substituents independently selected from the group consisting of halo, hydroxy, C$_1$-C$_4$ alkyl, amino, and (amino)C$_1$-C$_4$ alkyl; unsubstituted 4-to 14-membered heterocyclo; and substituted 4- to 14-membered heterocyclo having one or two substituents independently selected from the group consisting of amino, hydroxy, and C$_1$-C$_4$ alkyl; (C$_3$-C$_6$ cycloalkyl)oxy; and (4- to 8-membered heterocyclo)oxy;

R$^{21}$ is selected from the group consisting of hydrogen, —C(═O)R$^{13b}$, C$_1$-C$_4$ alkyl, C$_1$-C$_4$ haloalkyl, unsubstituted 4- to 14-membered heterocyclo, and —S(═O)$_2$R$^{24}$;

R$^{22}$ is selected from the group consisting of C$_1$-C$_4$ alkyl; unsubstituted C$_3$-C$_6$ cycloalkyl; substituted C$_3$-C$_6$ cycloalkyl having one or two substituents independently selected from the group consisting of halo, hydroxy, C$_1$-C$_4$ alkyl, amino, and (amino)C$_1$-C$_4$ alkyl; unsubstituted 4- to 14-membered heterocyclo; and substituted 4- to 14-membered heterocyclo having one or two substituents independently selected from the group consisting of amino, hydroxy, and C$_1$-C$_4$ alkyl;

R$^{24}$ is selected from the group consisting of C$_1$-C$_4$ alkyl and (hydroxy)C$_1$-C$_4$ alkyl;

R$^{25}$ is selected from the group consisting of hydrogen, C$_1$-C$_4$ alkyl, and C$_1$-C$_4$ haloalkyl;

R$^{25b}$ and R$^{25c}$ are independently selected from the group consisting of C$_1$-C$_4$ alkyl and C$_1$-C$_4$ haloalkyl;

R$^{26}$ is selected from the group consisting of unsubstituted 4- to 14-membered heterocyclo; and substituted 4- to 14-membered heterocyclo having one or two substituents independently selected from the group consisting of amino, hydroxy, and C$_1$-C$_4$ alkyl; and R$^{21a}$ and R$^{25a}$ taken together with the atoms to which they are attached form an optionally substituted 4- to 8-membered heterocyclo, or a pharmaceutically acceptable salt or solvate thereof.

5. The compound of claim 3, wherein R$^{11a}$ is a substituted 4- to 14-membered heterocyclo selected from the group consisting of:

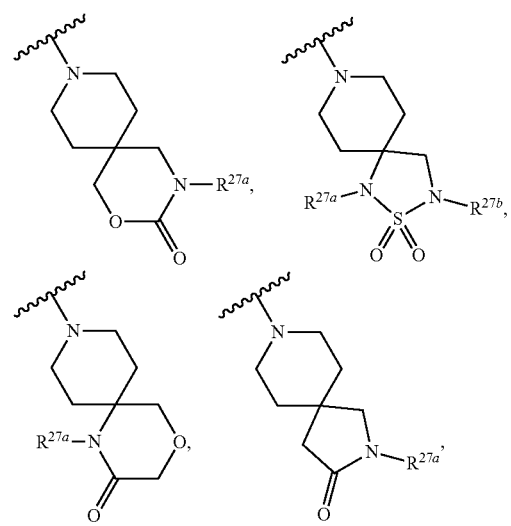

631
-continued
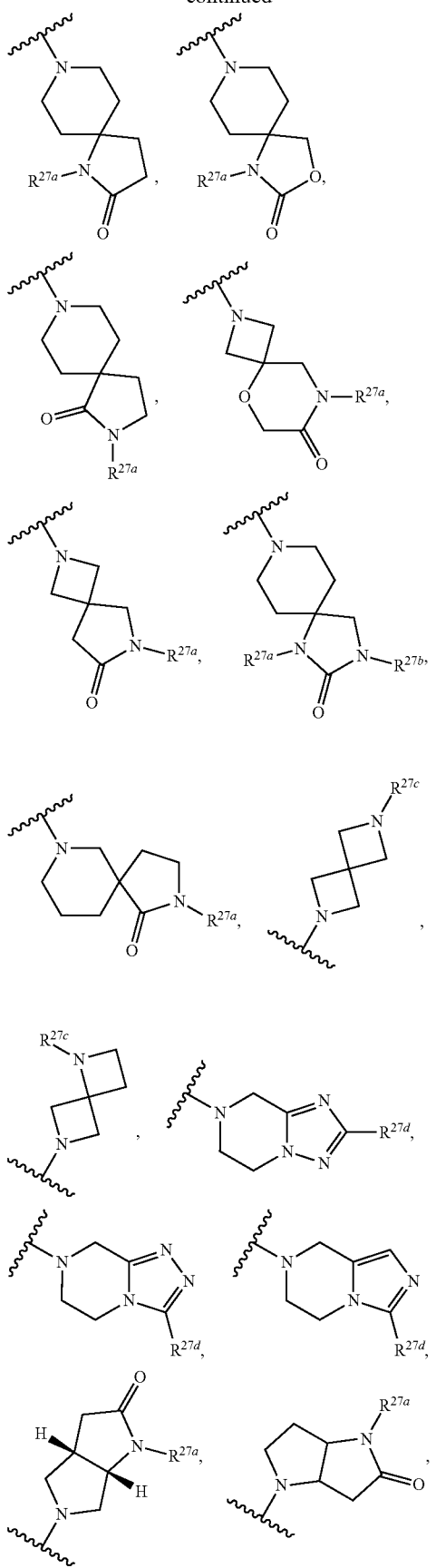
632
-continued
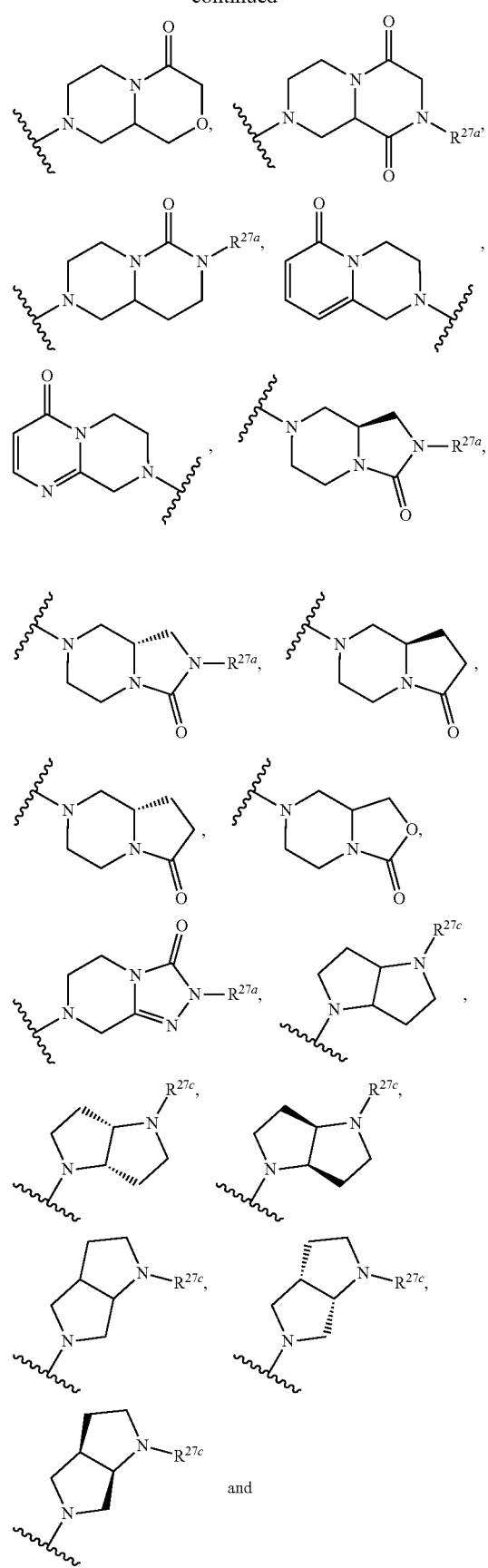

-continued

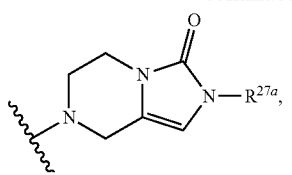

R$^{27a}$ and R$^{27b}$ are each independently selected from the group consisting of hydrogen, C$_1$-C$_4$ alkyl, C$_1$-C$_4$ haloalkyl, (C$_1$-C$_4$ alkoxy)C$_1$-C$_4$ alkyl, and (hydroxy) C$_1$-C$_4$ alkyl;

R$^{27c}$ is selected from the group consisting of hydrogen; —C(=O)R$^{13b}$; C$_1$-C$_4$ alkyl; C$_1$-C$_4$ haloalkyl; unsubstituted 4- to 14-membered heterocyclo; and substituted 4- to 14-membered heterocyclo having one or two substituents independently selected from the group consisting of amino, hydroxy, and C$_1$-C$_4$ alkyl; and —S(=O)$_2$R$^{24}$;

R$^{27d}$ is selected from the group consisting of hydrogen; C$_1$-C$_4$ alkyl; and C$_1$-C$_4$ haloalkyl;

R$^{13b}$ is selected from the group consisting of C$_1$-C$_4$ alkyl; aminoC$_1$-C$_4$ haloalkyl; C$_1$-C$_4$ alkoxy; (hydroxy)C$_1$-C$_4$ alkyl; (C$_1$-C$_4$ alkoxy)C$_1$-C$_4$ alkyl; (amino)alkyl; unsubstituted C$_3$-C$_6$ cycloalkyl; substituted C$_3$-C$_6$ cycloalkyl having one or two substituents independently selected from the group consisting of halo, hydroxy, C$_1$-C$_4$ alkyl, amino, and (amino)C$_1$-C$_4$ alkyl; unsubstituted 4-to 14-membered heterocyclo; substituted 4- to 14-membered heterocyclo having one or two substituents independently selected from the group consisting of amino, hydroxy, and C$_1$-C$_4$ alkyl; (C$_3$-C$_6$ cycloalkyl) oxy; and (4- to 8-membered heterocyclo)oxy; and R$^{24}$ is selected from the group consisting of C$_1$-C$_4$ alkyl and (hydroxy)C$_1$-C$_4$ alkyl, or a pharmaceutically acceptable salt or solvate thereof.

6. The compound of claim 5, wherein R$^{11a}$ is a substituted 4- to 14-membered heterocyclo selected from the group consisting of:

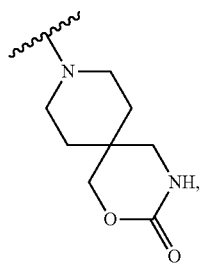

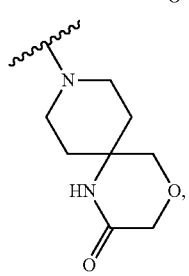

-continued

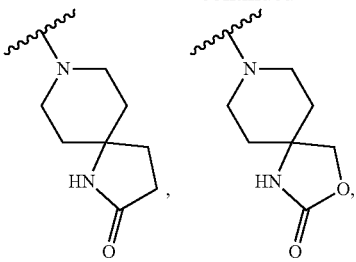

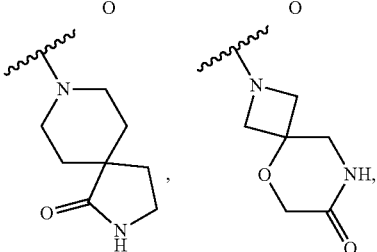

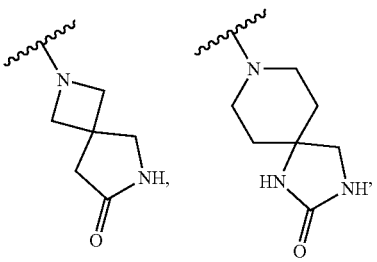

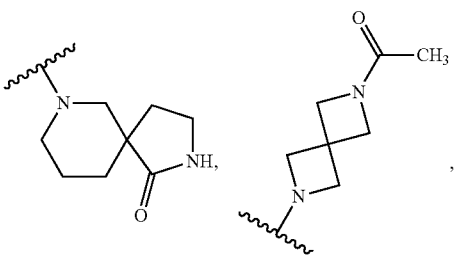

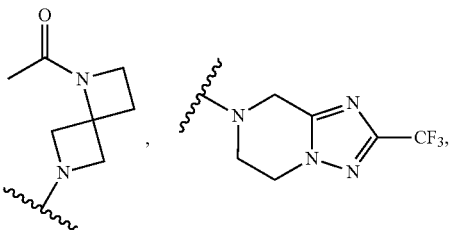

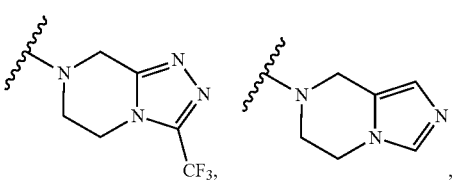

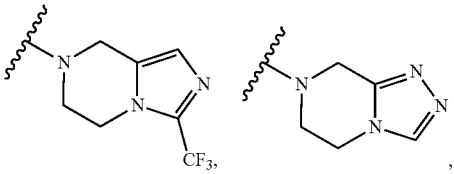

635
-continued
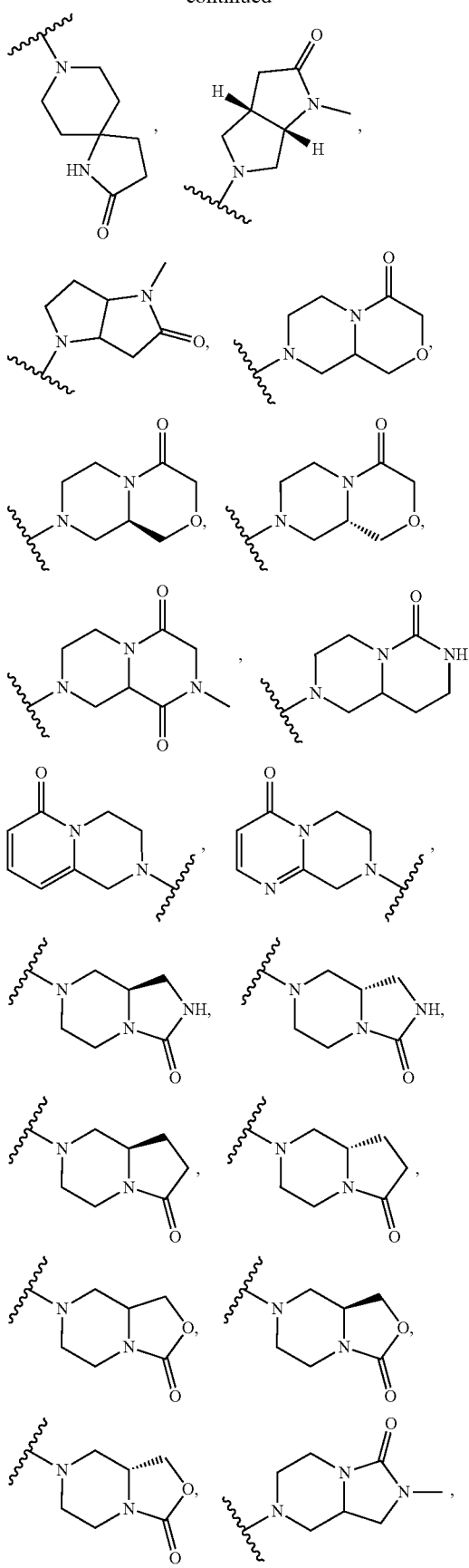
636
-continued
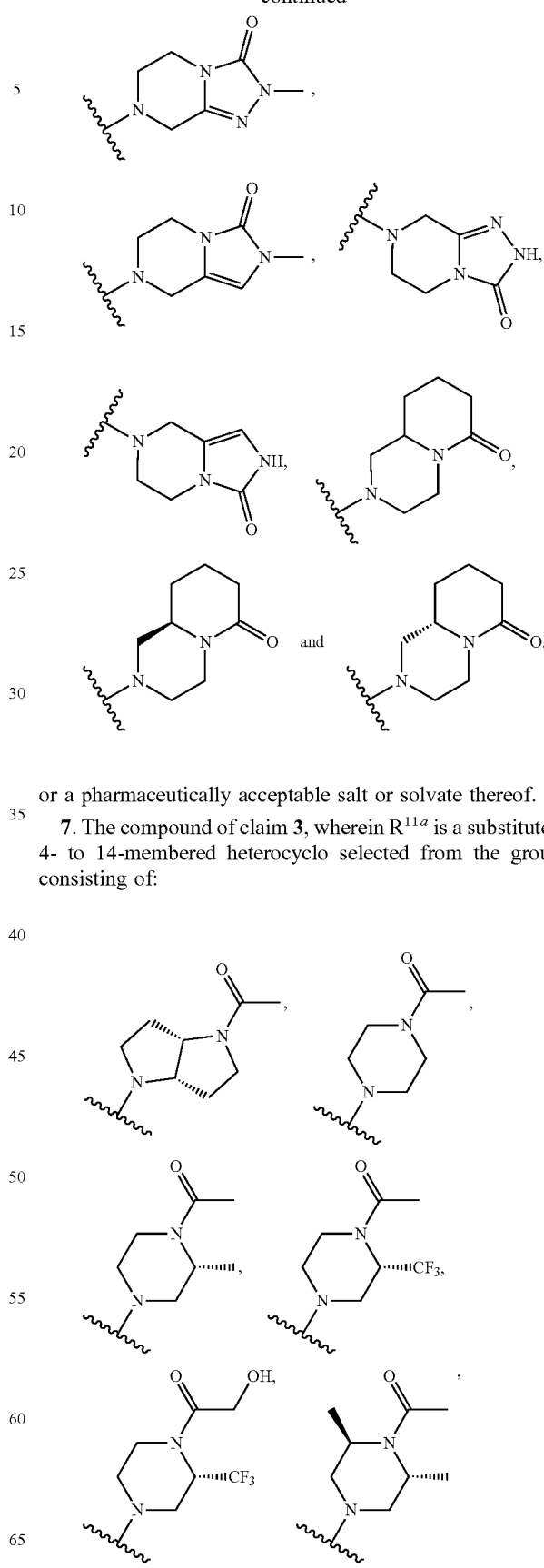
or a pharmaceutically acceptable salt or solvate thereof.
7. The compound of claim 3, wherein $R^{11a}$ is a substituted 4- to 14-membered heterocyclo selected from the group consisting of:

637

-continued

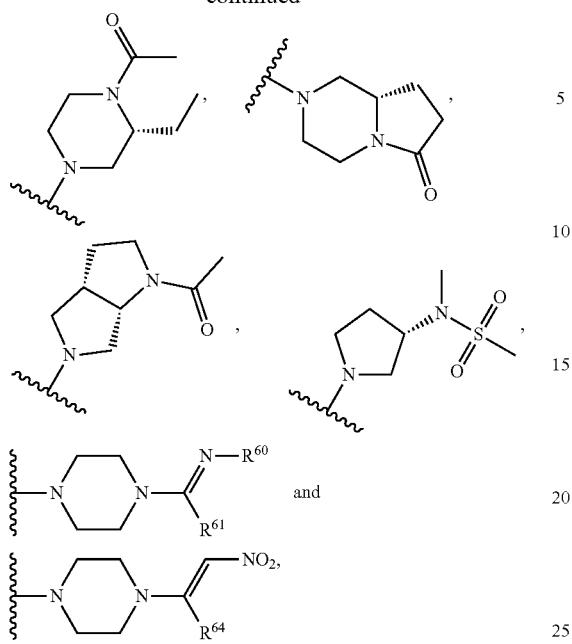

or a pharmaceutically acceptable salt or solvate thereof.

8. The compound of claim 2, wherein $Z^4$ is —CH$_2$—, or a pharmaceutically acceptable salt or solvate thereof.

9. The compound of claim 2, wherein $R^{11a}$ is a substituted 4- to 14-membered heterocyclo is selected from the group consisting of

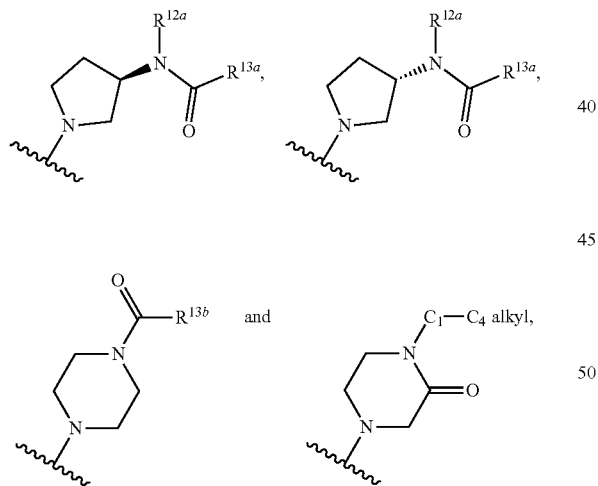

or a pharmaceutically acceptable salt or solvate thereof.

10. The compound of claim 9, wherein: $R^{12a}$ is selected from the group consisting of hydrogen and C$_1$-C$_3$ alkyl; $R^{13a}$ is C$_1$-C$_4$ alkyl; and $R^{13b}$ is C$_1$-C$_4$ alkyl, or a pharmaceutically acceptable salt or solvate thereof.

11. The compound of claim 10, wherein: $R^{12a}$ is selected from the group consisting of hydrogen and methyl; $R^{13a}$ is methyl; and $R^{13b}$ is methyl, or a pharmaceutically acceptable salt or solvate thereof.

638

12. A compound selected from the group consisting of:

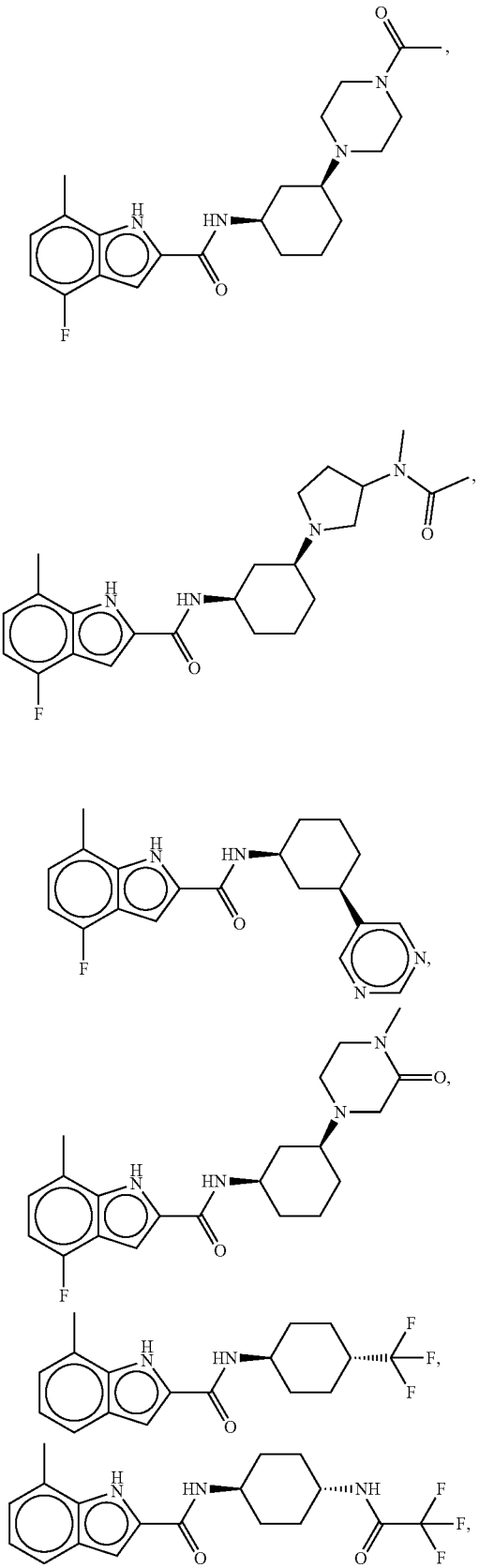

639
-continued
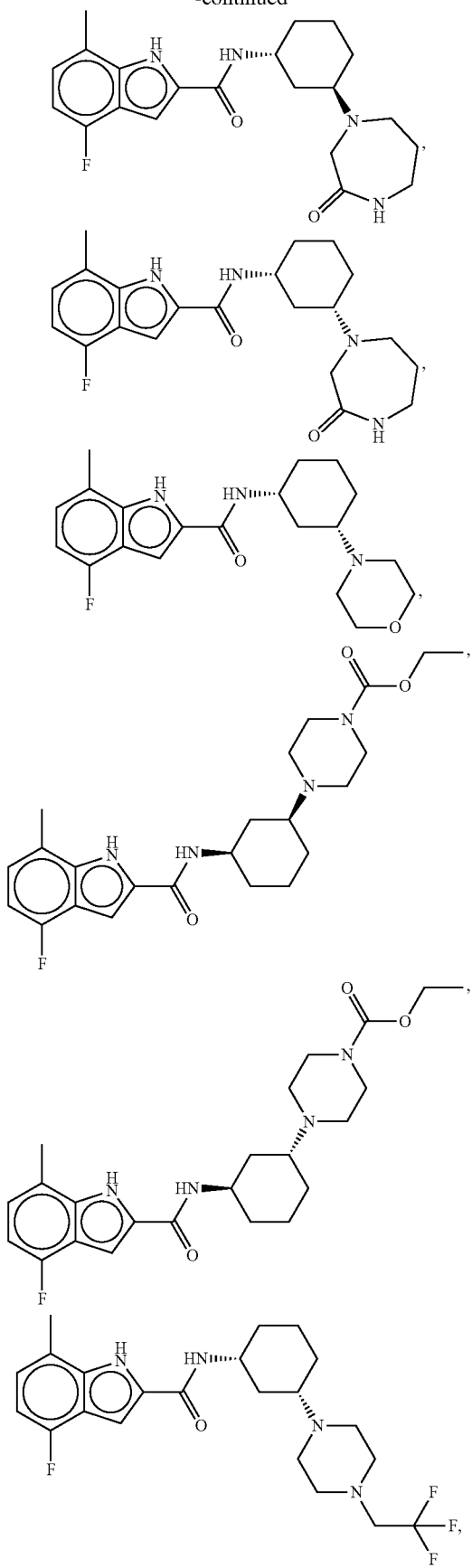
640
-continued
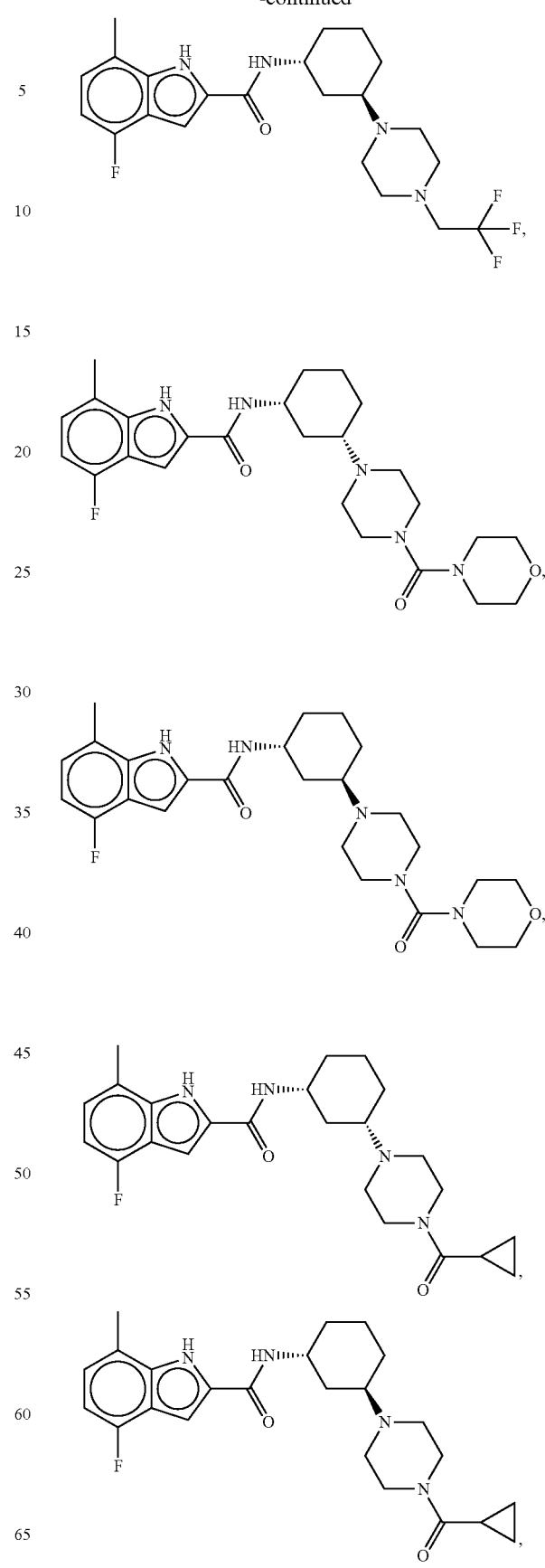

641
-continued
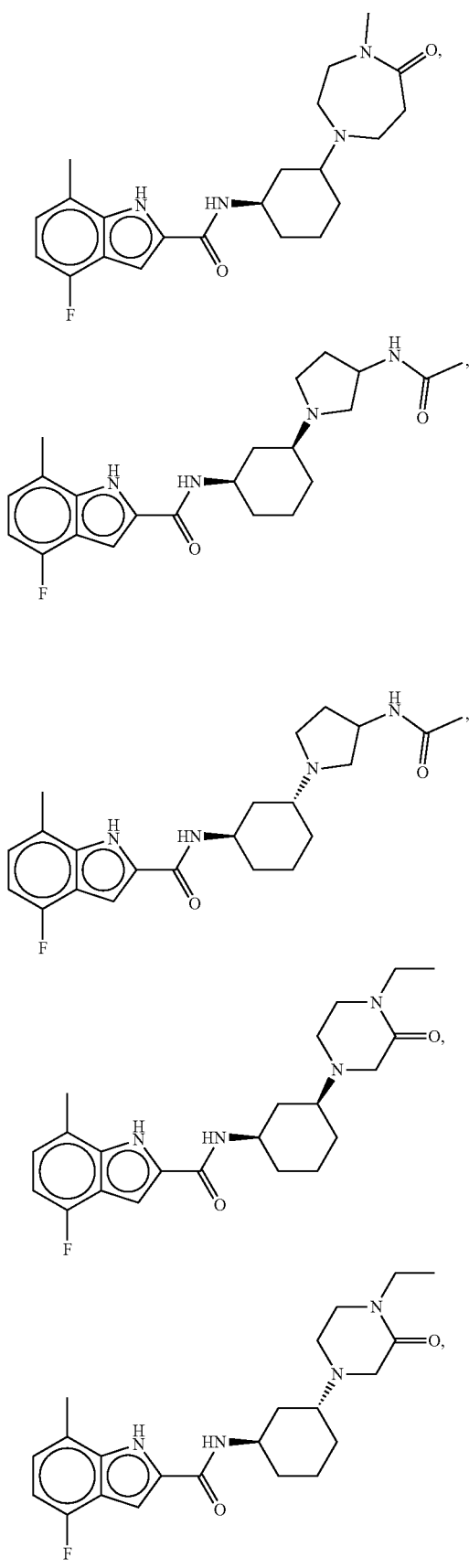
642
-continued
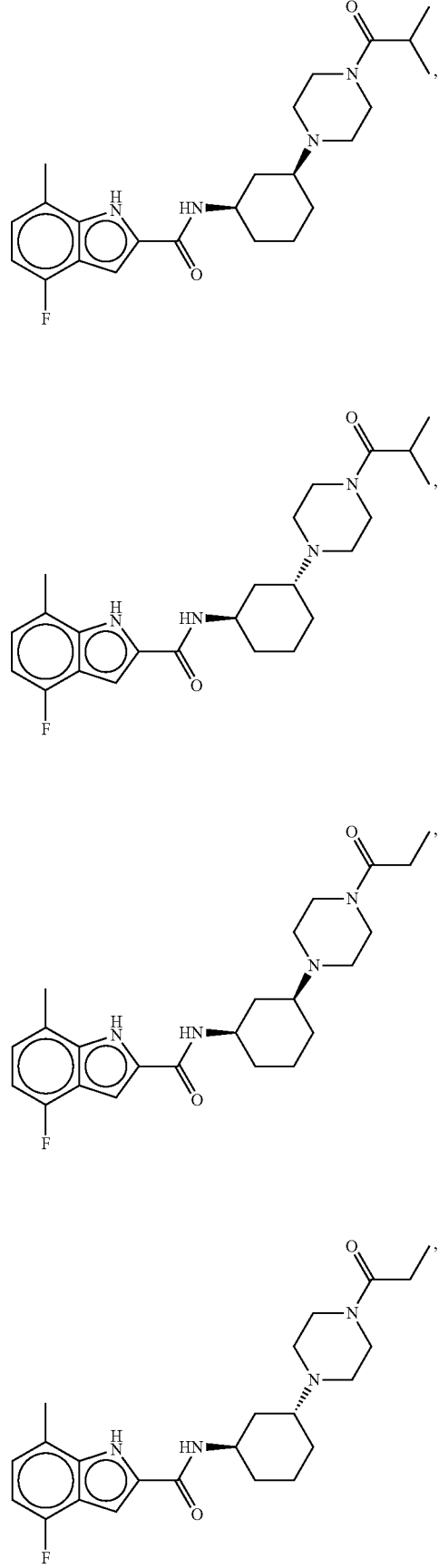

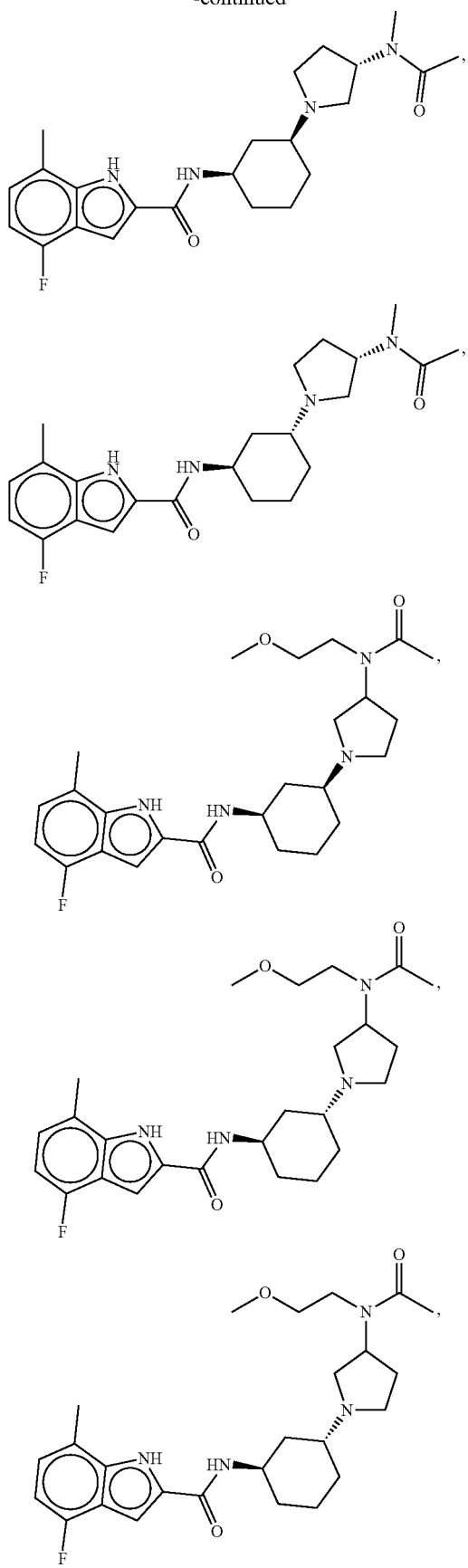
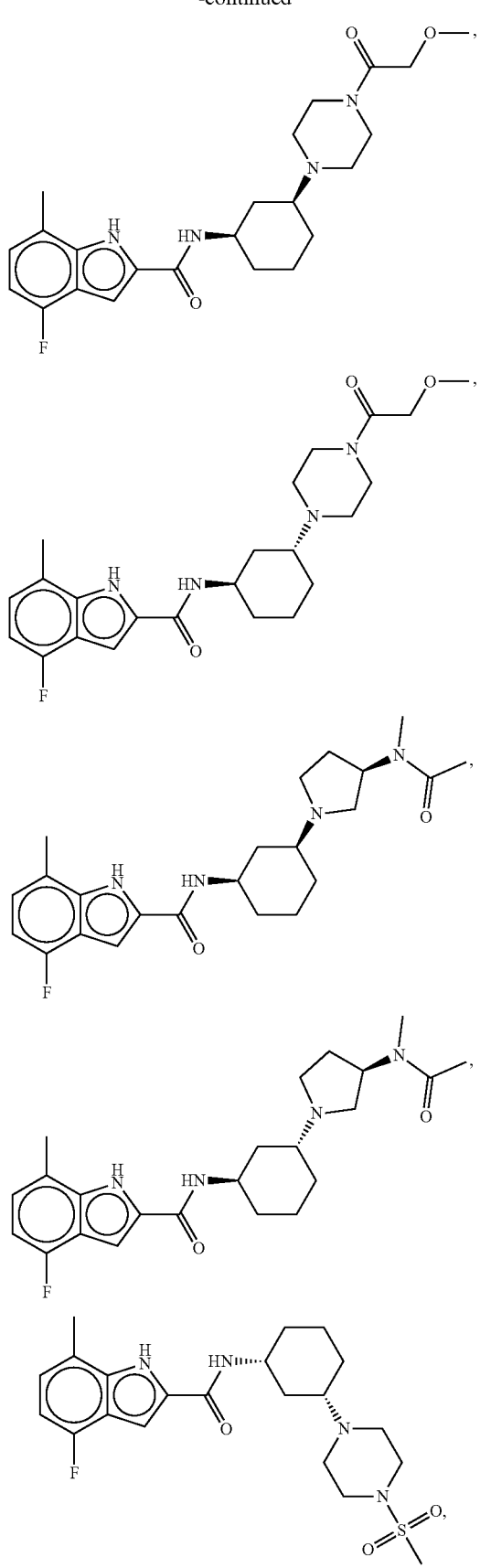

645
-continued
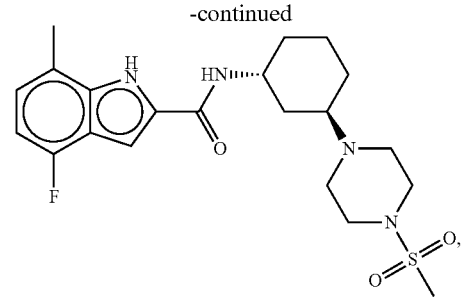
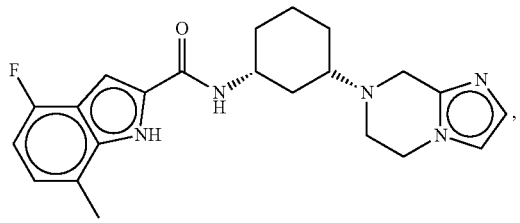
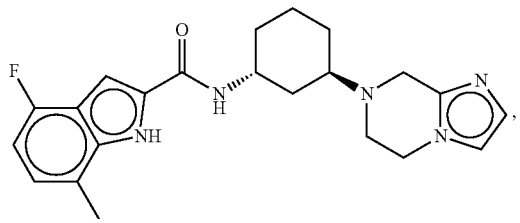
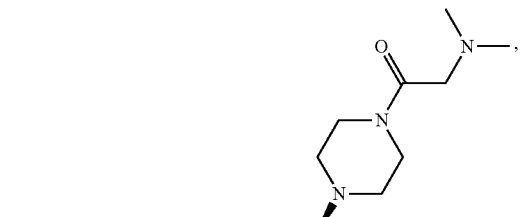
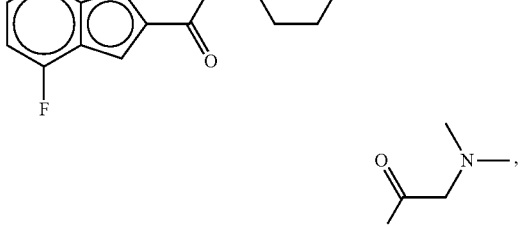
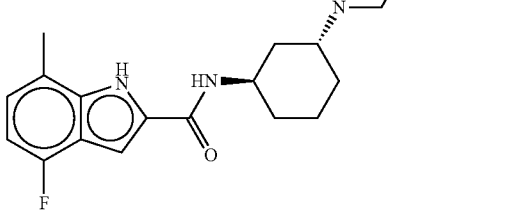
646
-continued
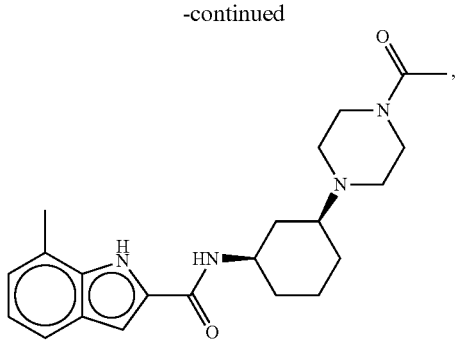
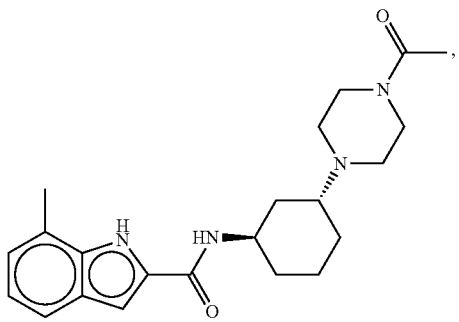
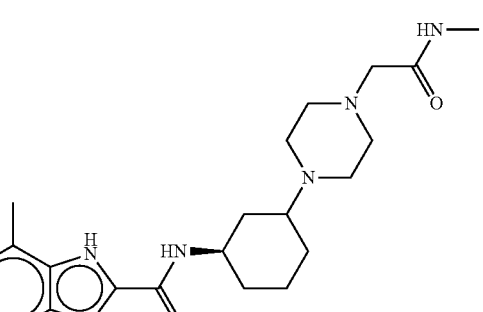
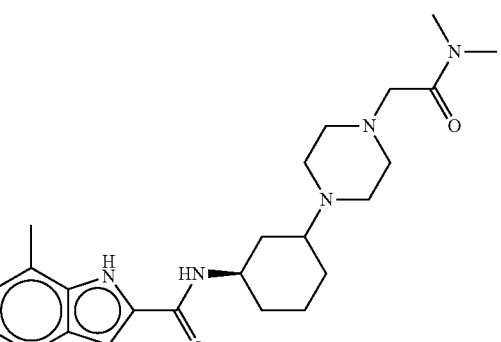
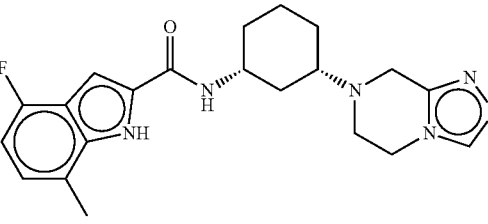

647
-continued
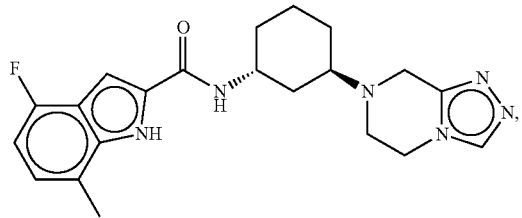
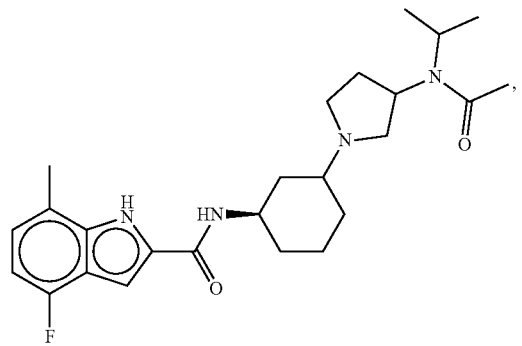
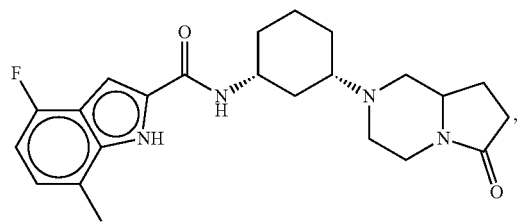
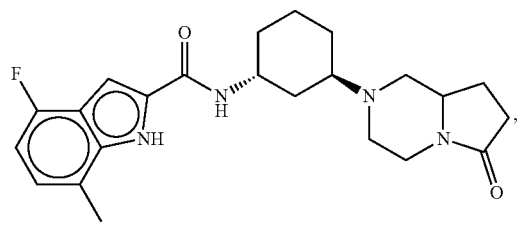
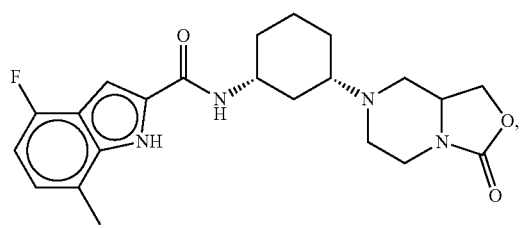
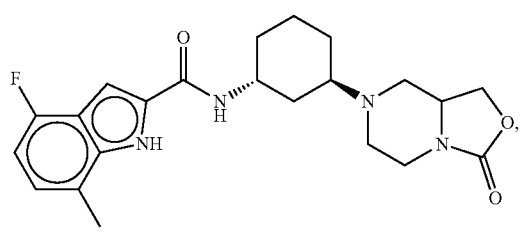
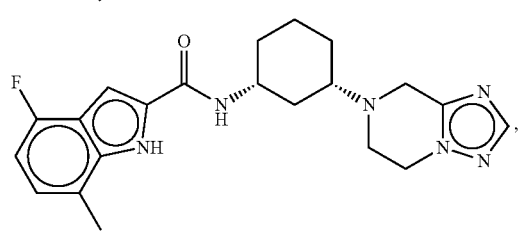
648
-continued
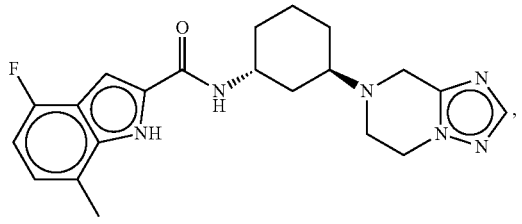
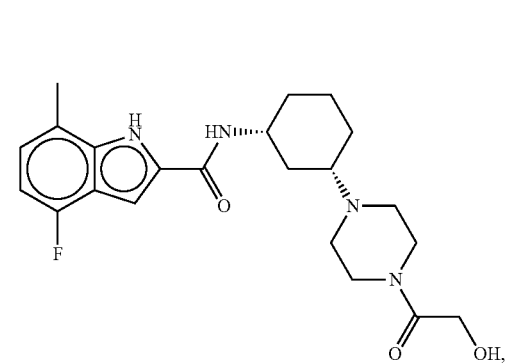
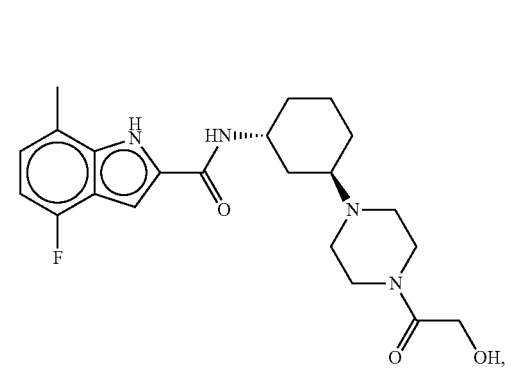
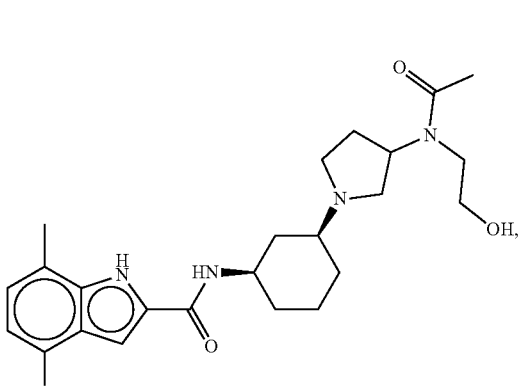
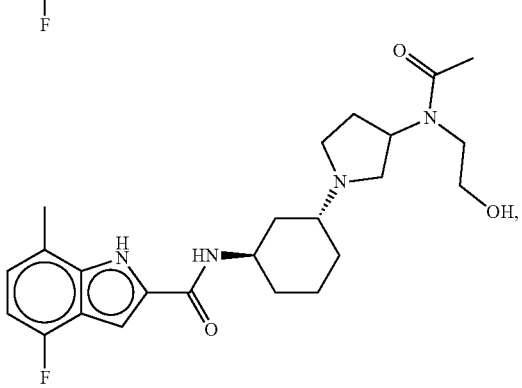

649
-continued
650
-continued
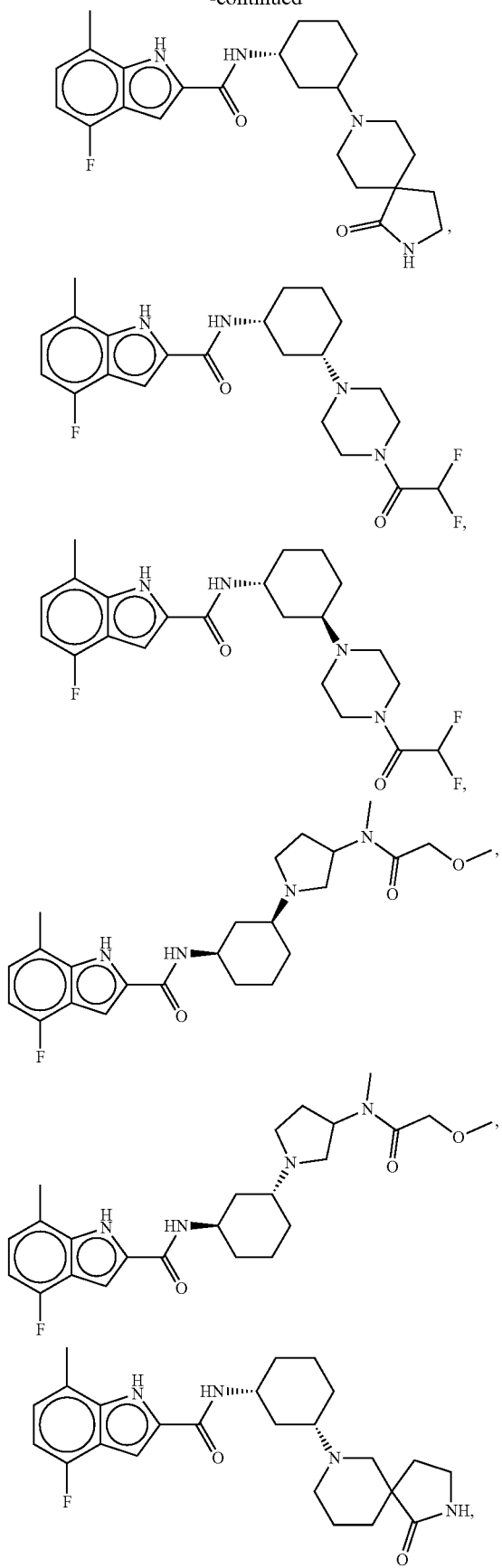
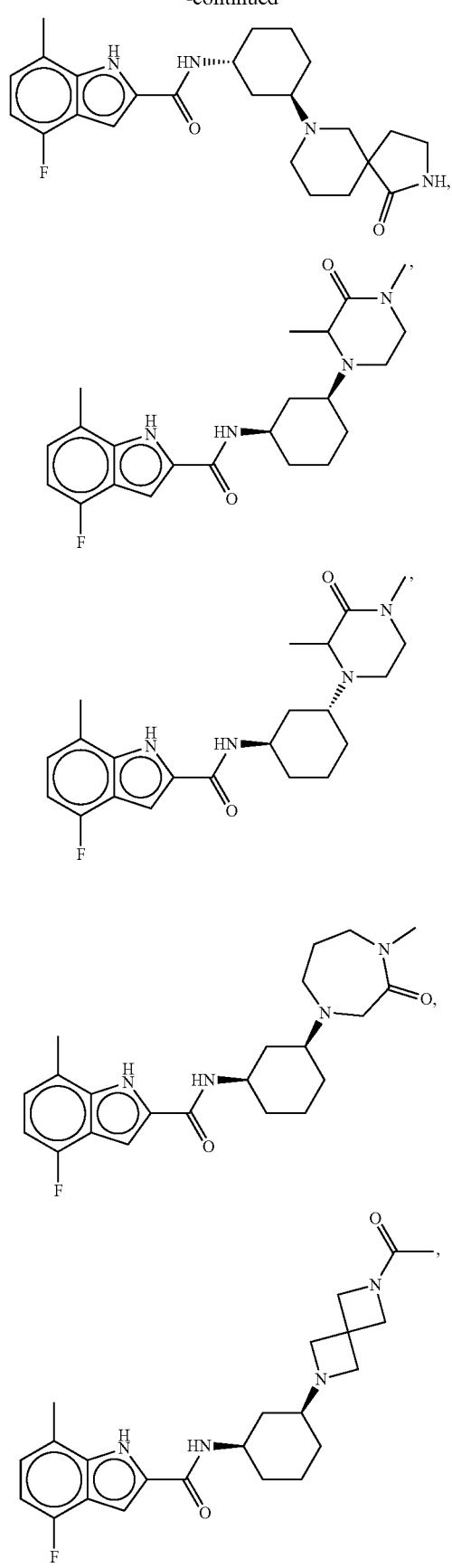

651
-continued
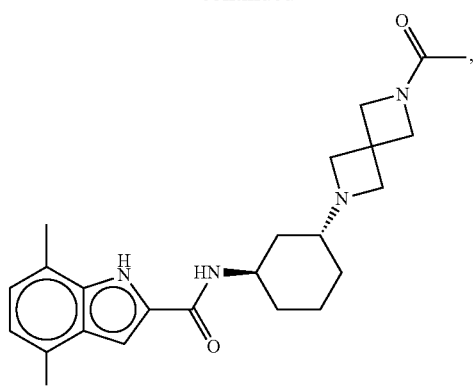
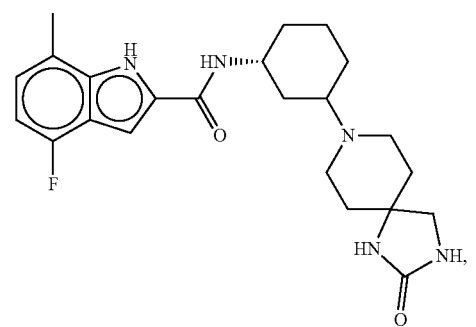
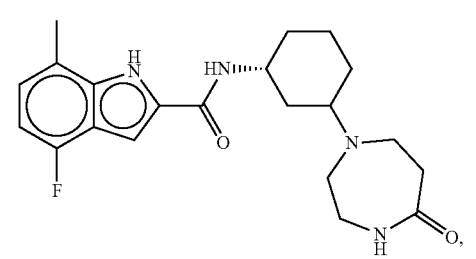
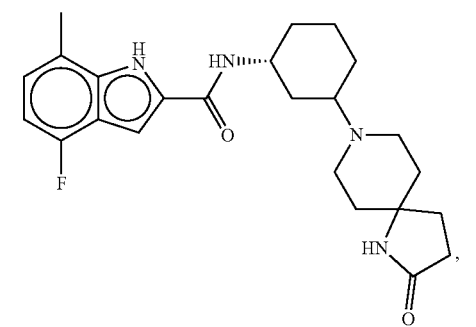
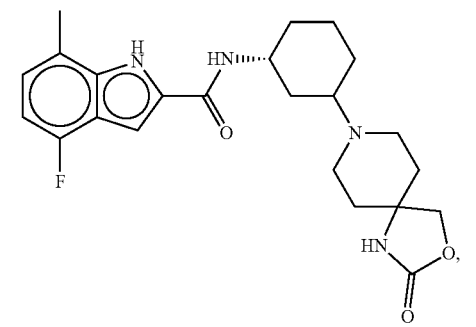
652
-continued
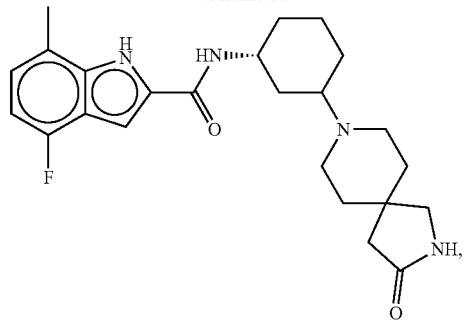
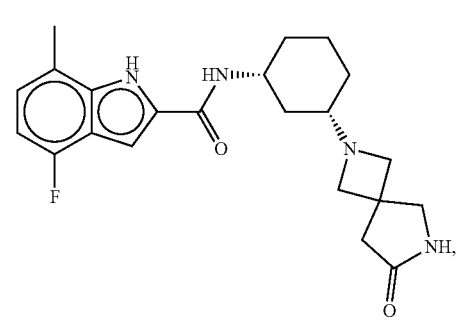
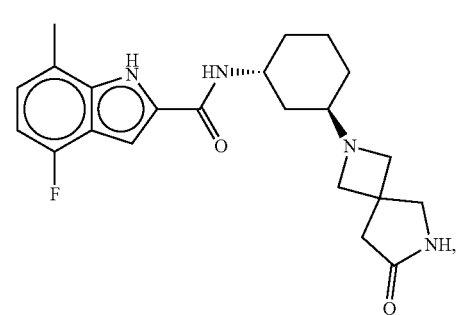
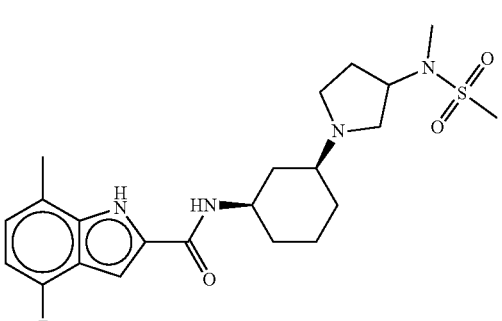
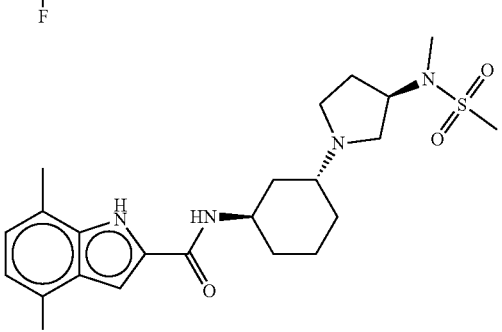

653
-continued

654
-continued

-continued
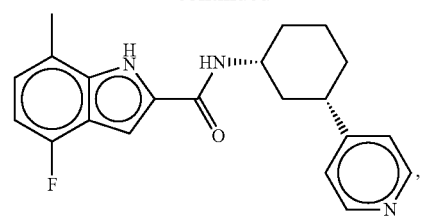
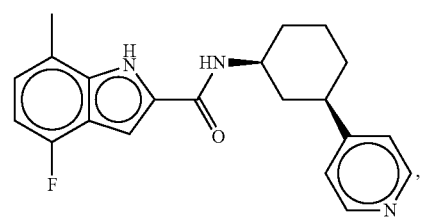
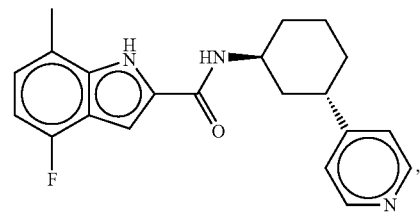
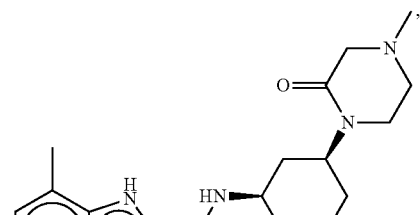
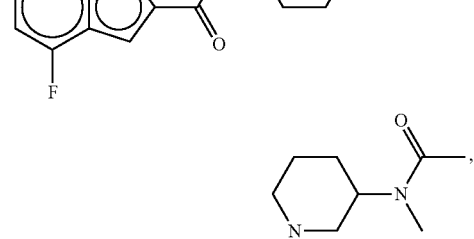
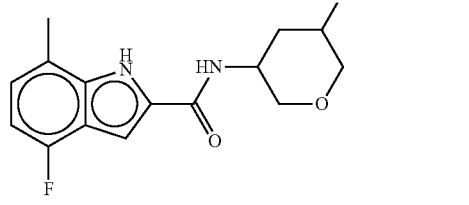
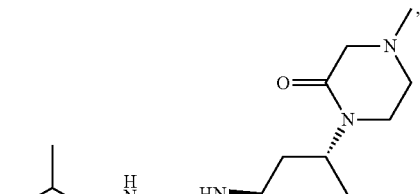
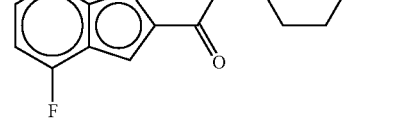
-continued
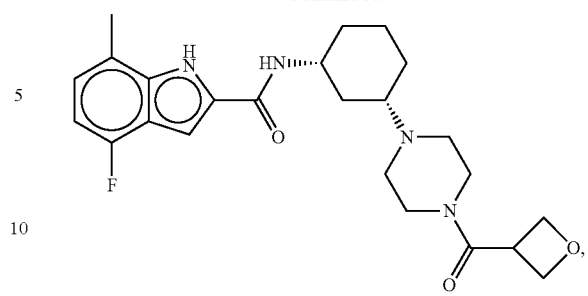
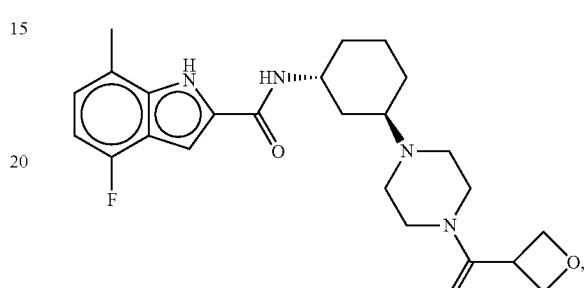
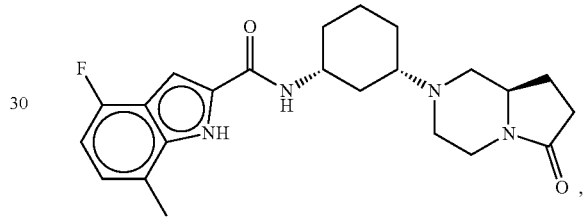
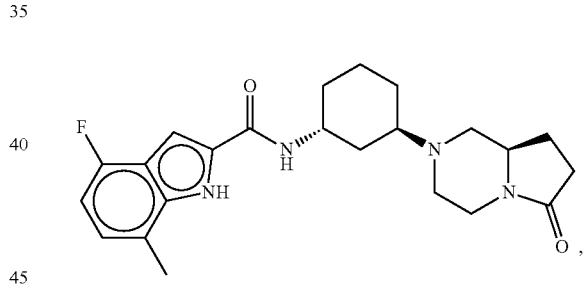
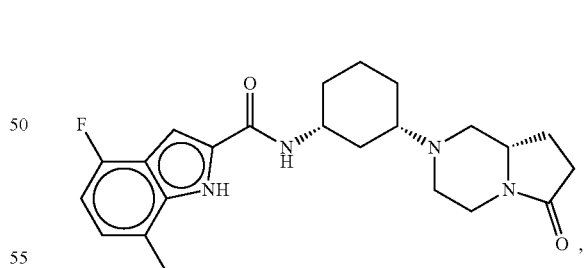
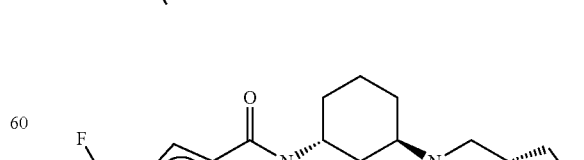
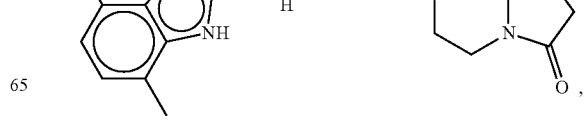

657
-continued
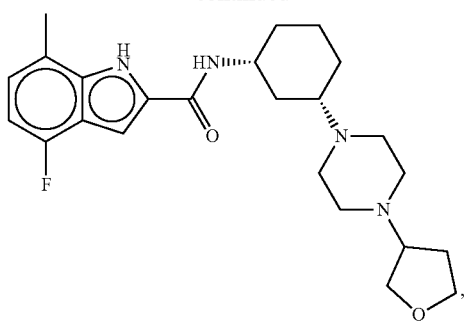
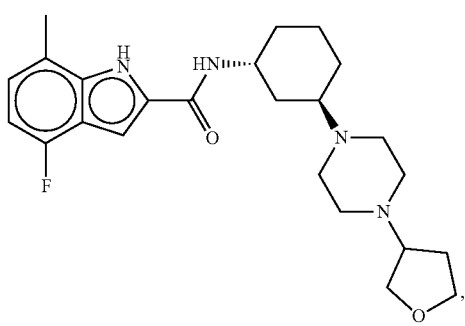
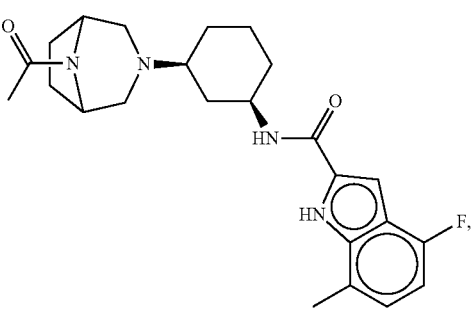
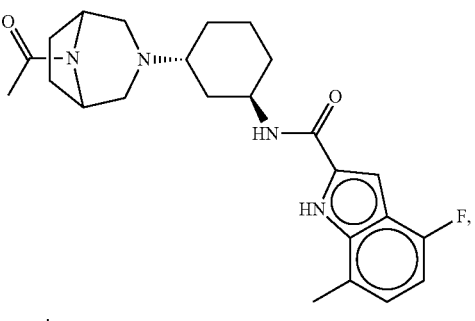
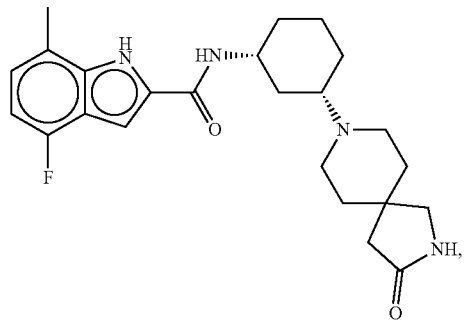
658
-continued
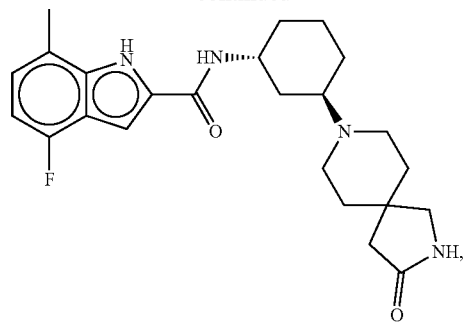
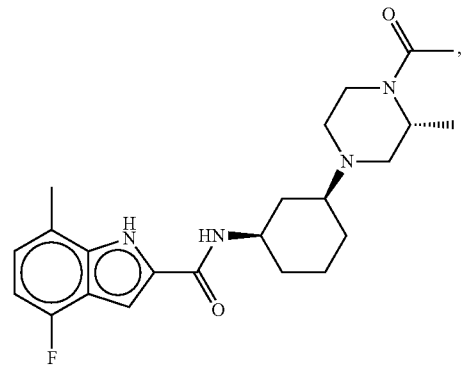
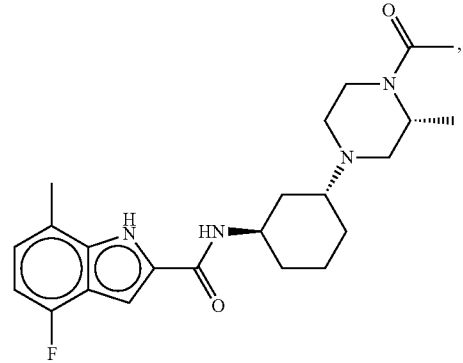
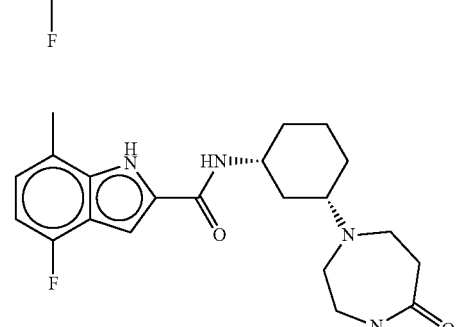
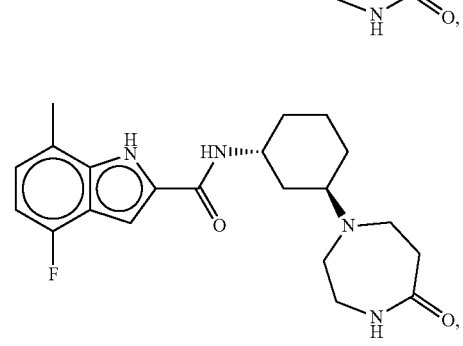

659
-continued
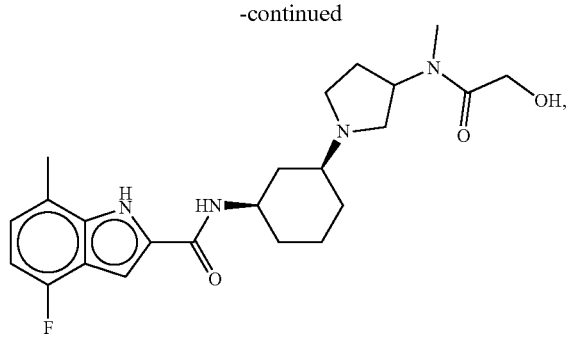
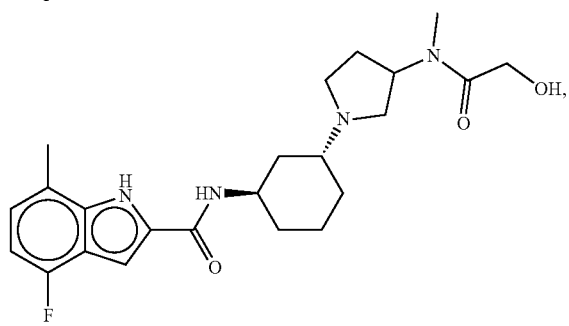
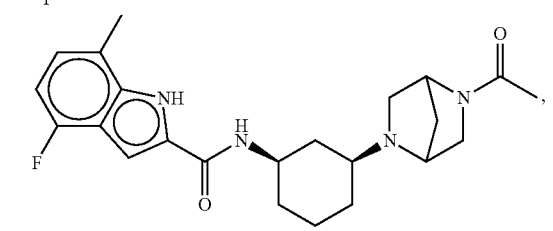
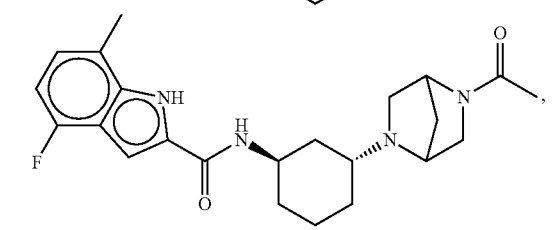
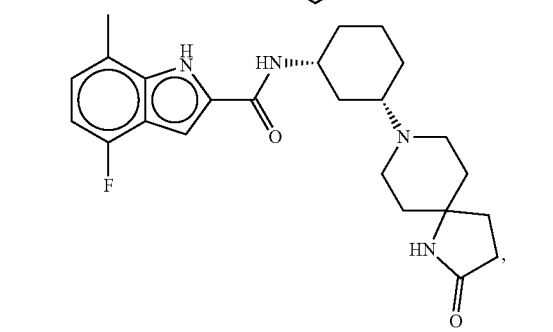
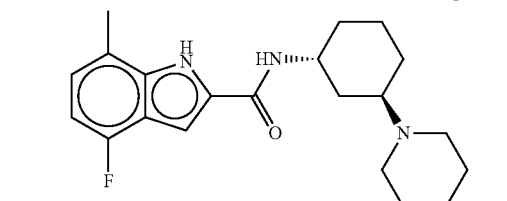
660
-continued
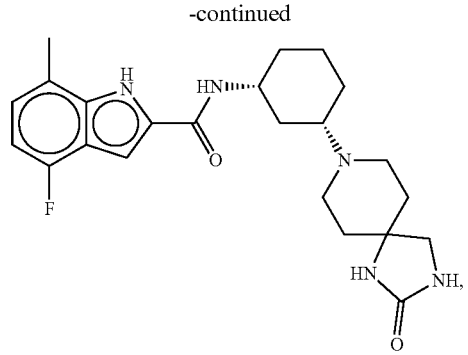
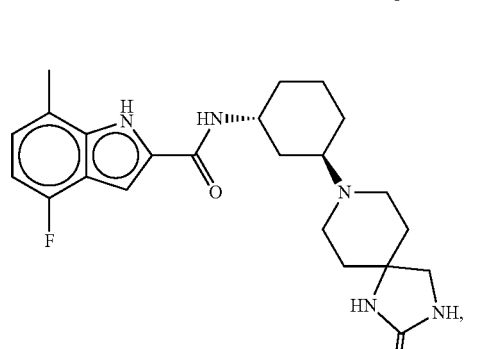
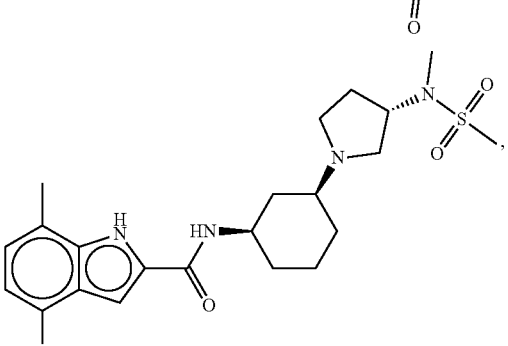
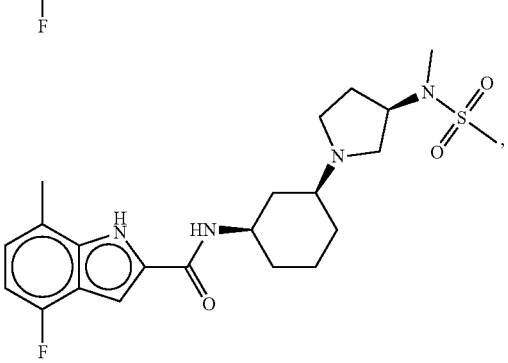
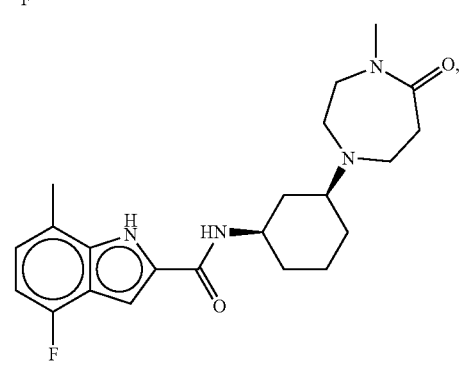

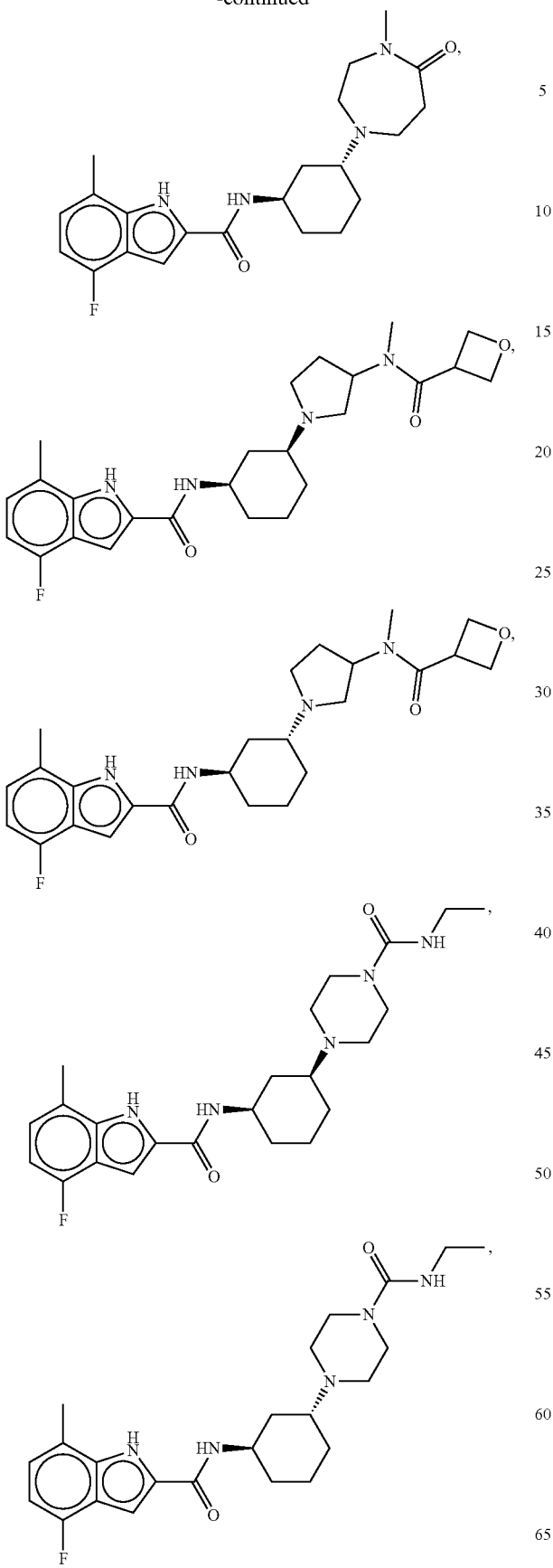
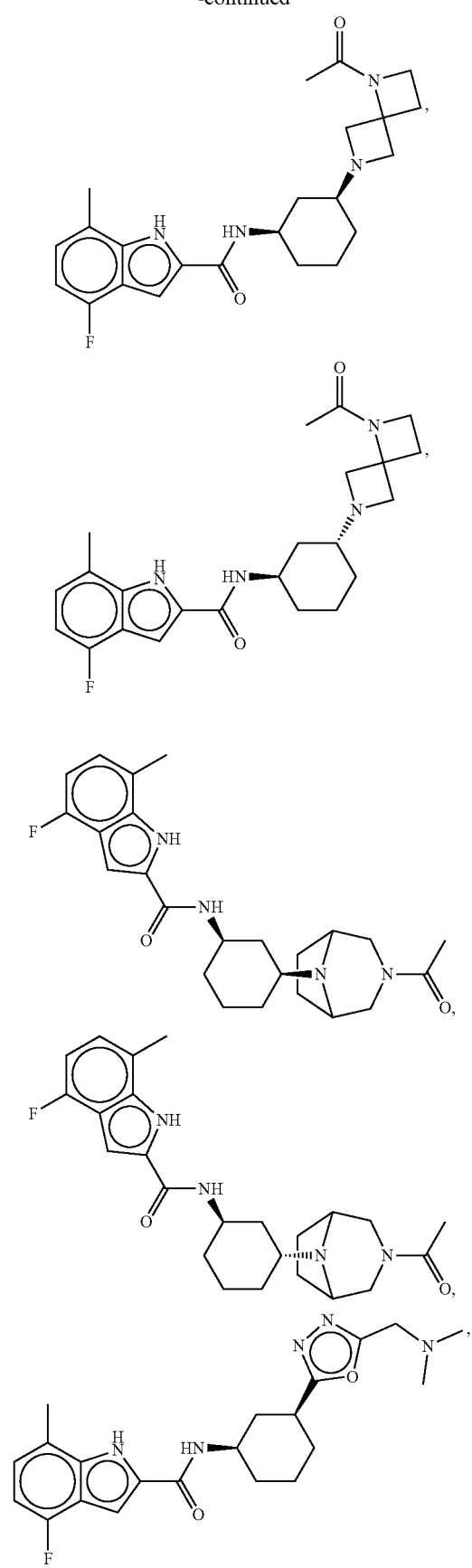

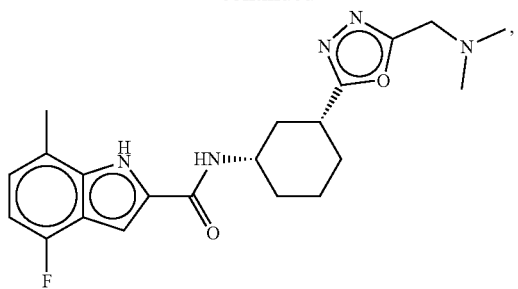
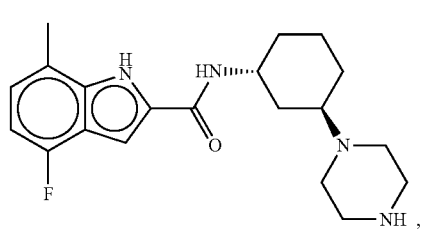
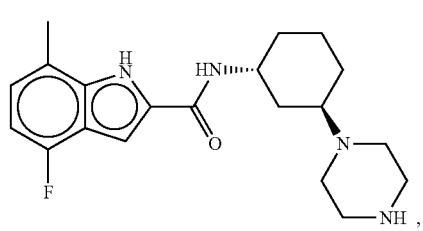
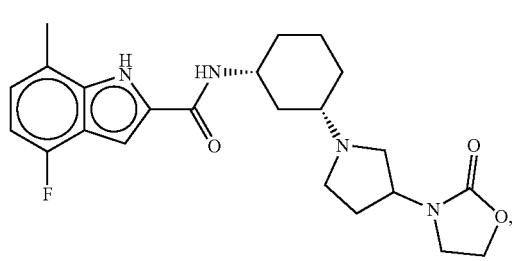
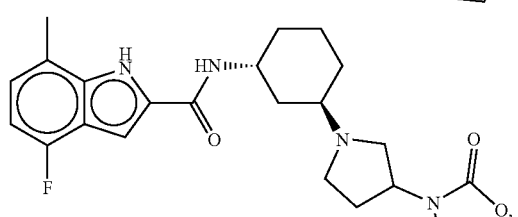
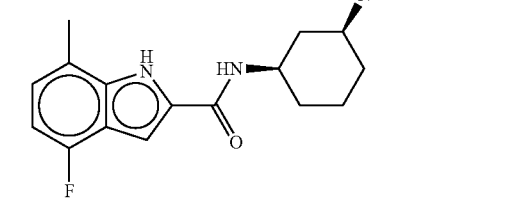
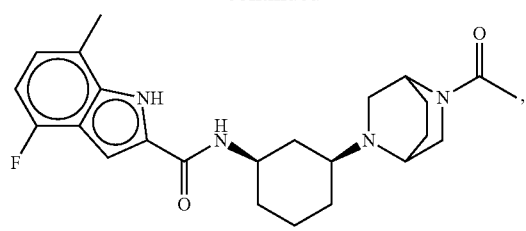
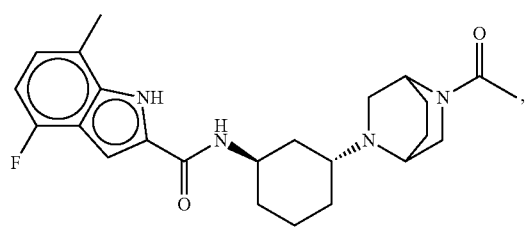
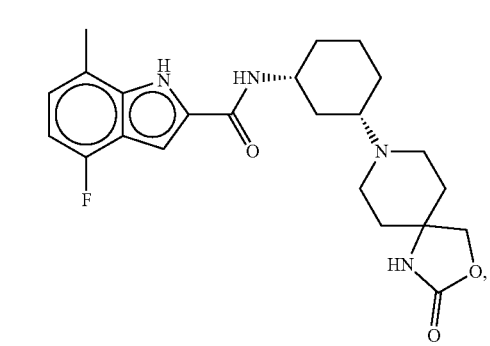
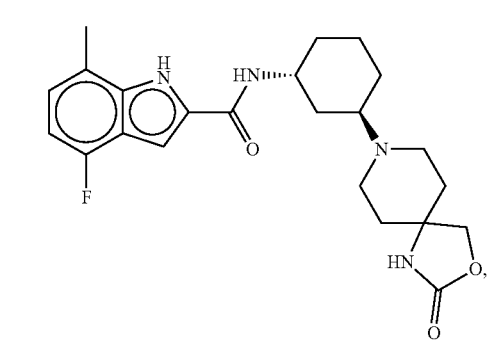
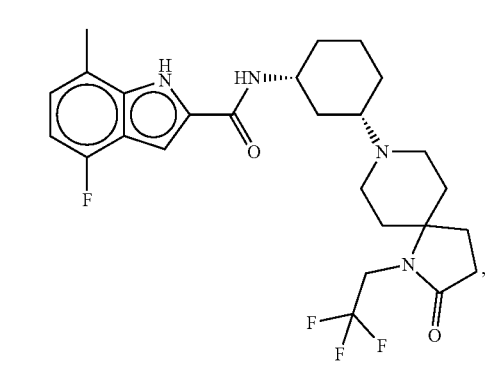

665
-continued
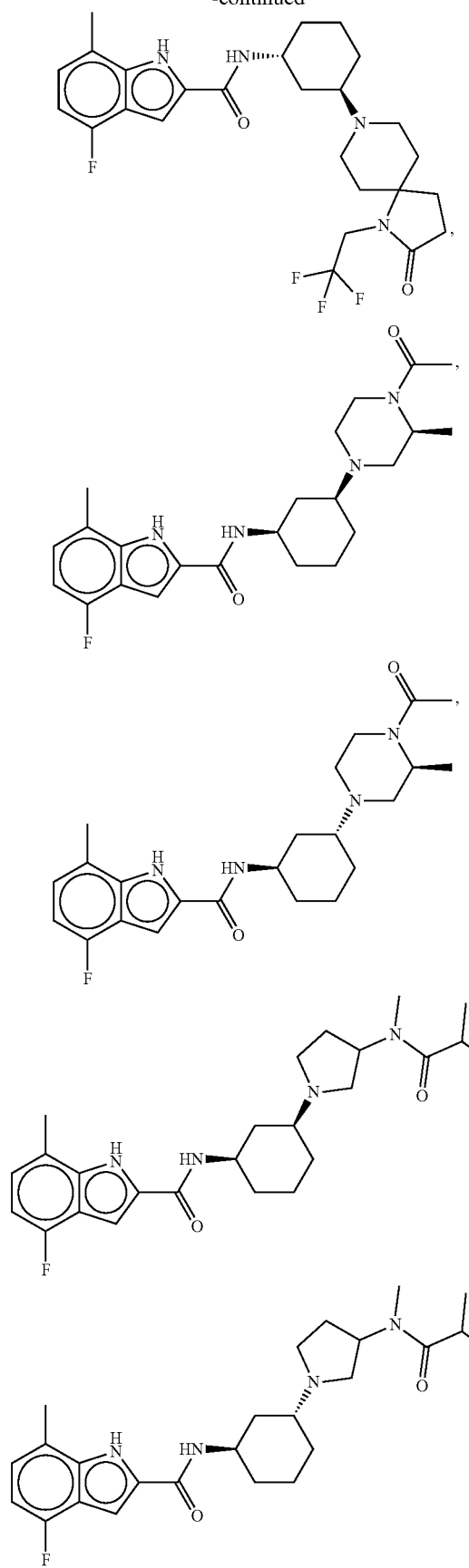
666
-continued
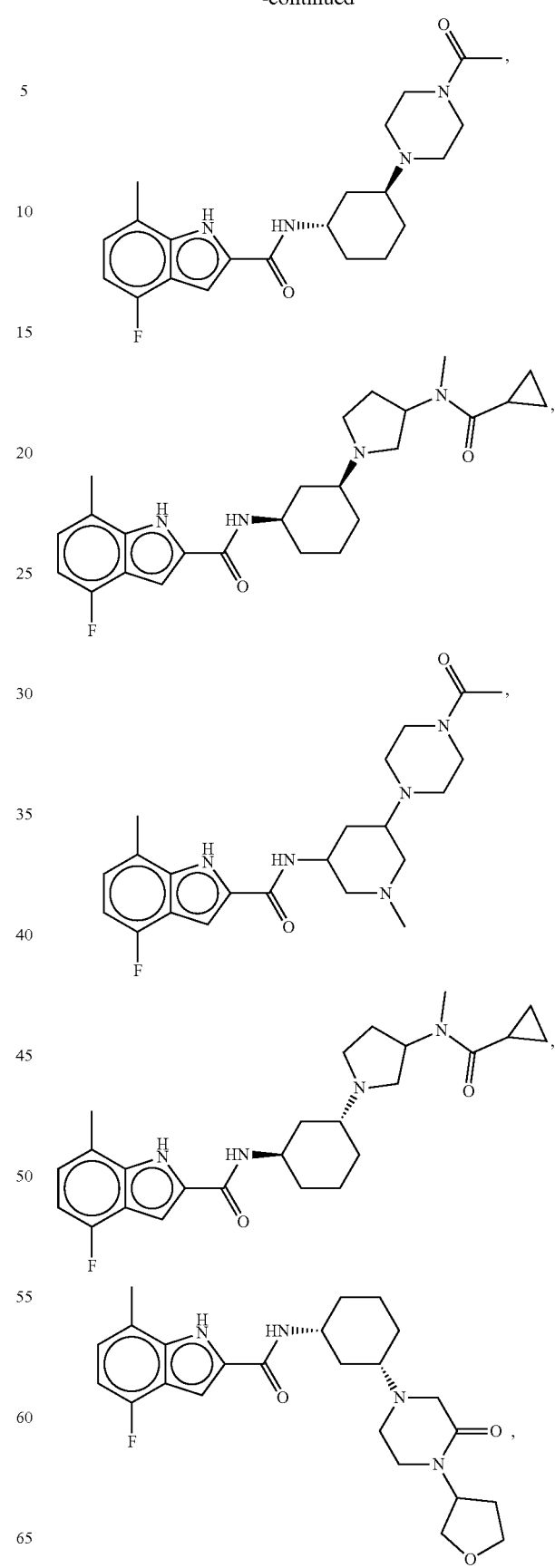

667
-continued
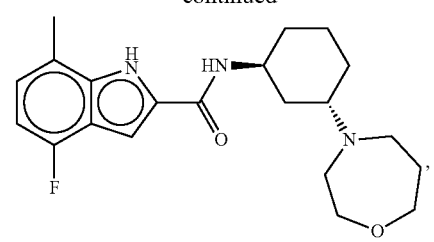
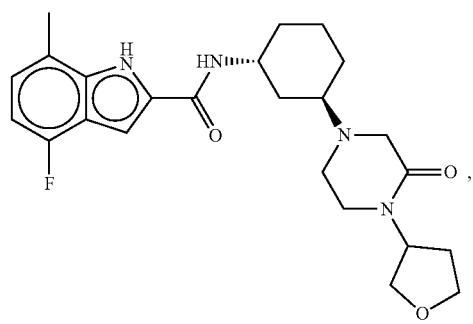
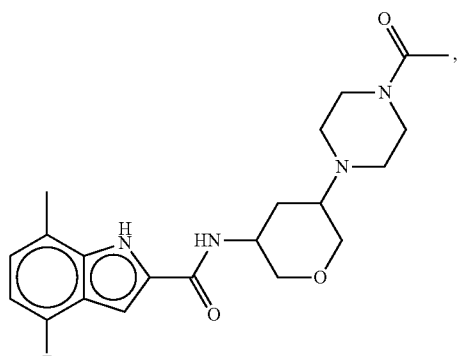
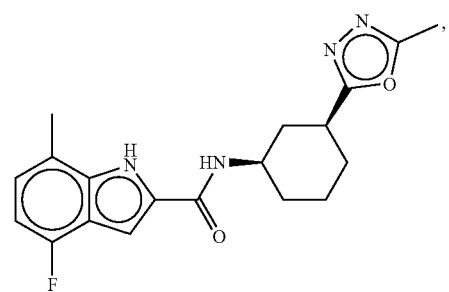
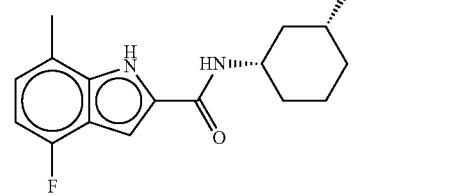
668
-continued
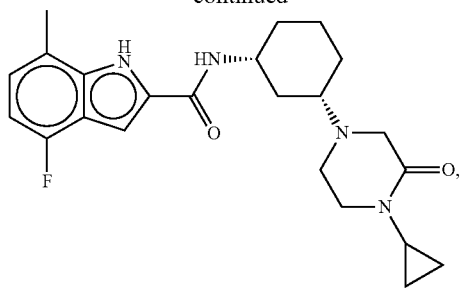
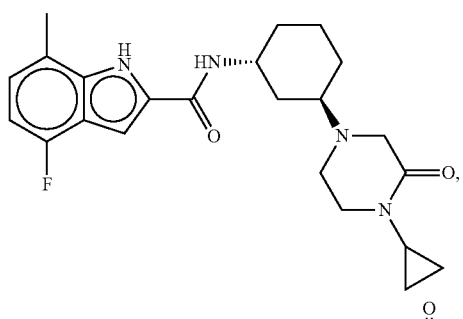
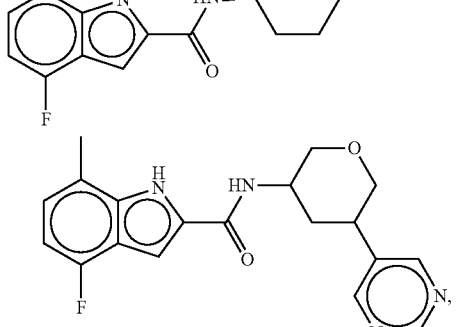
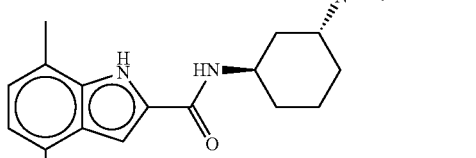
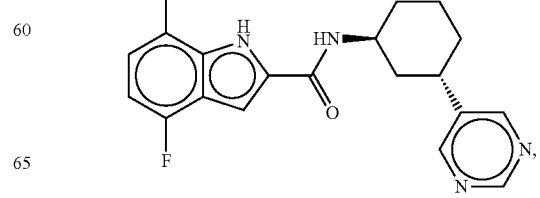

669
-continued
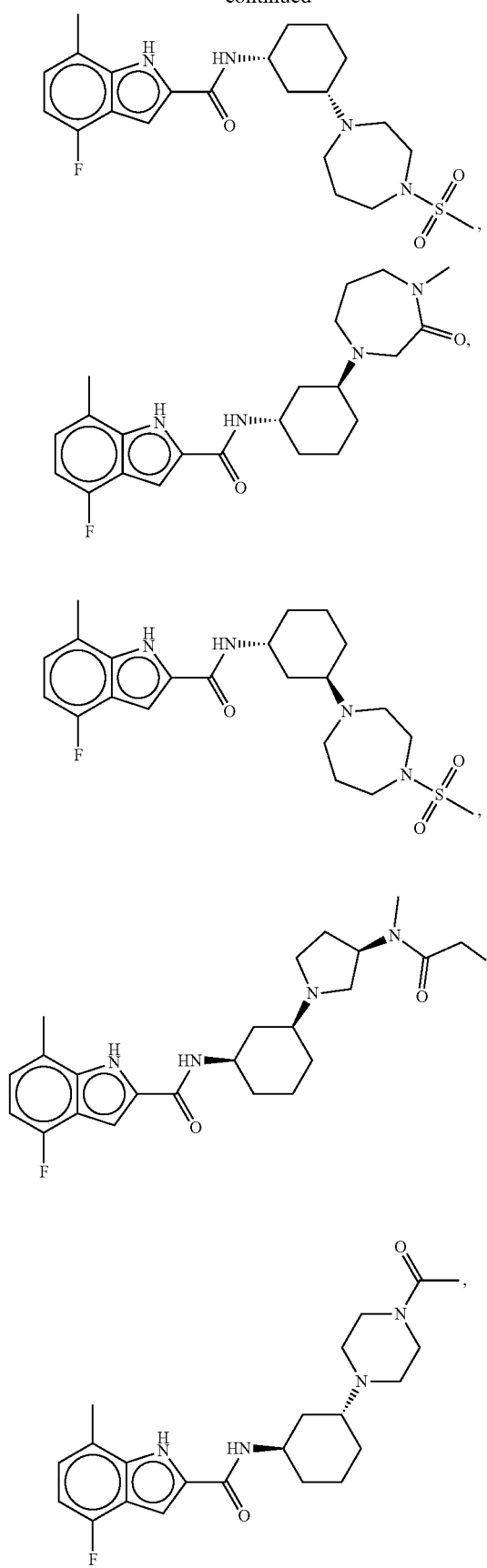
670
-continued
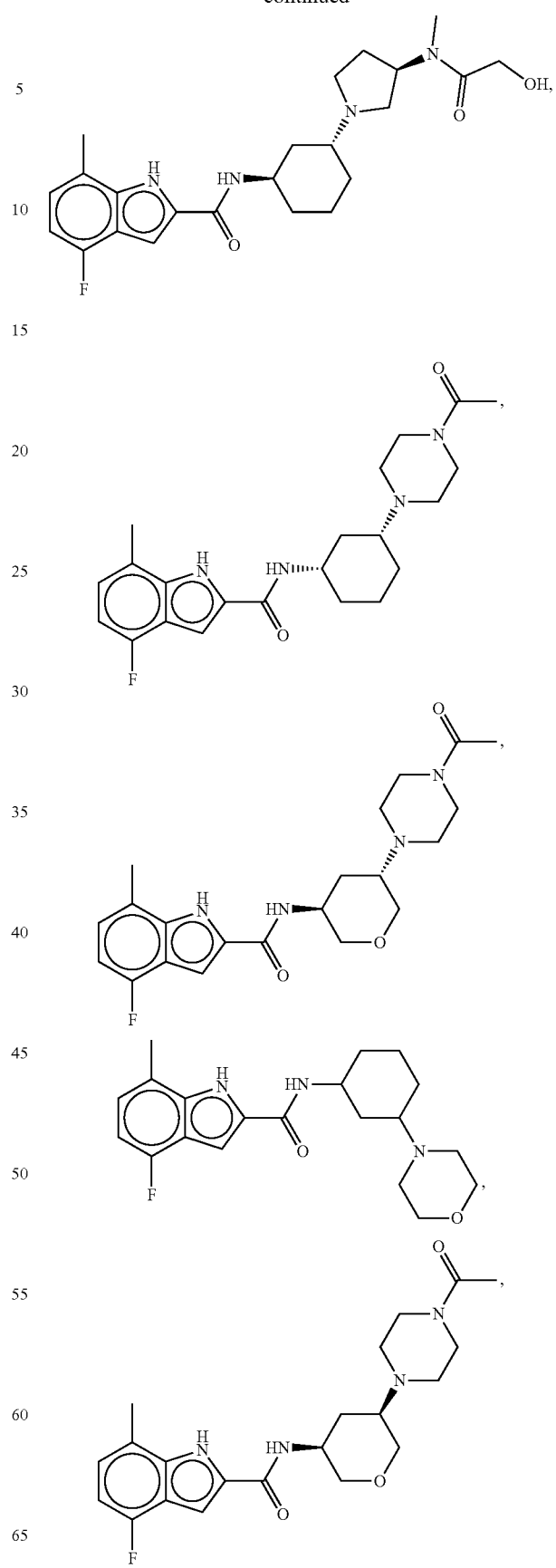

-continued
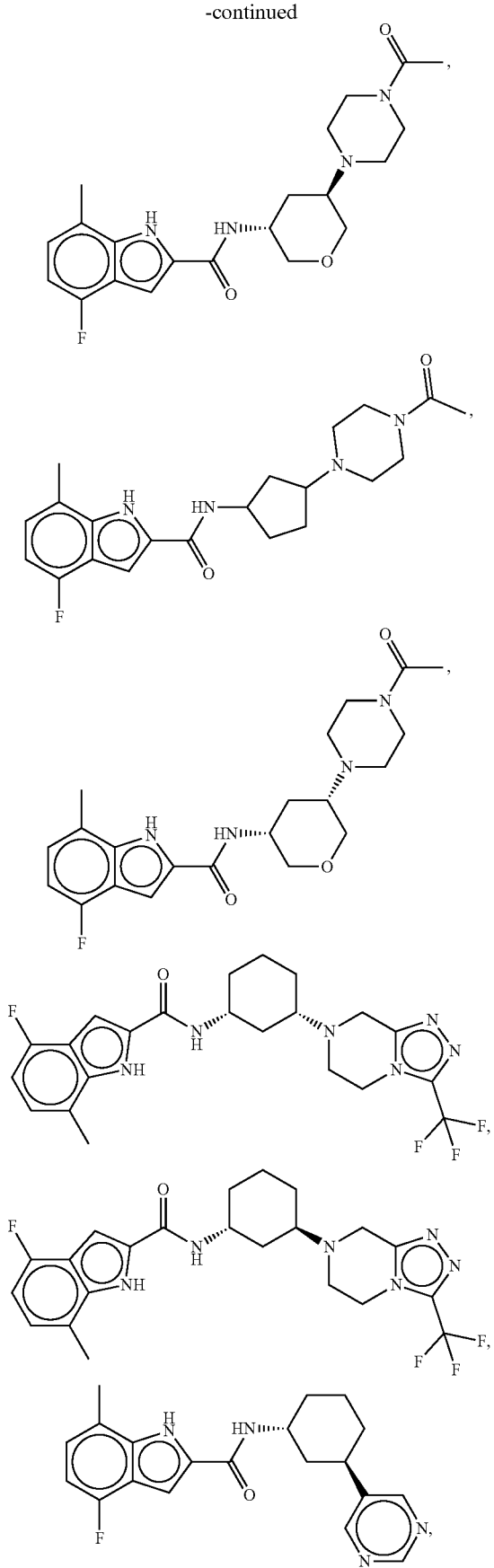
-continued
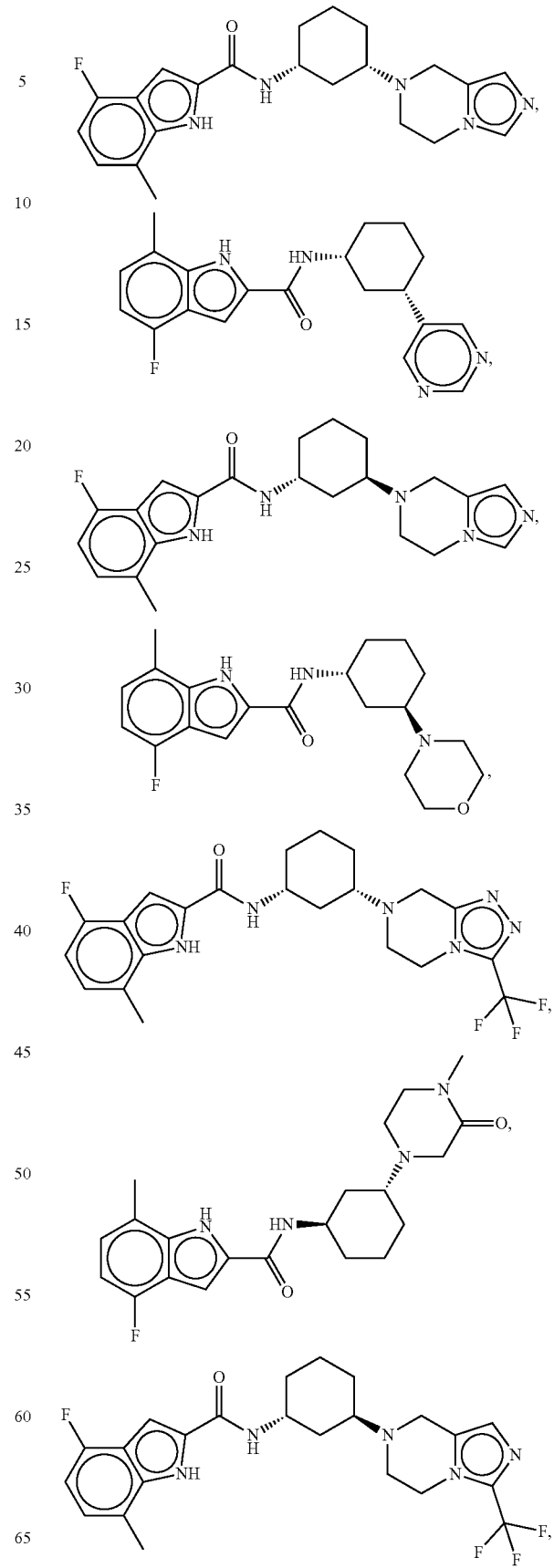

673
-continued
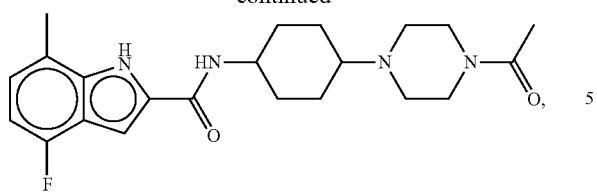
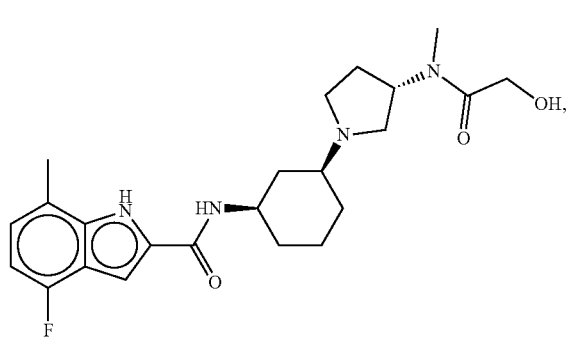
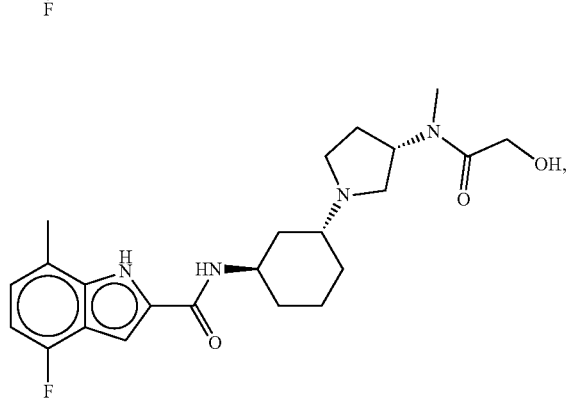
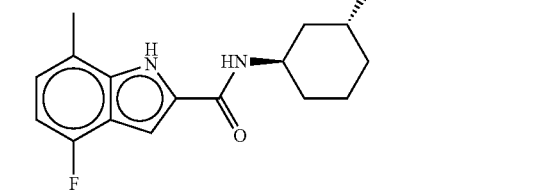
674
-continued
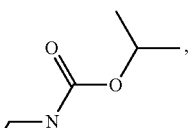
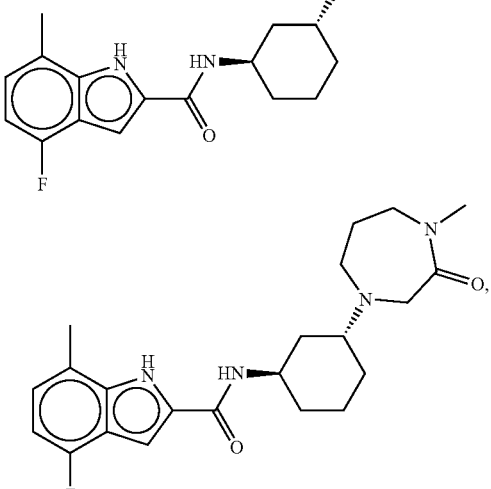
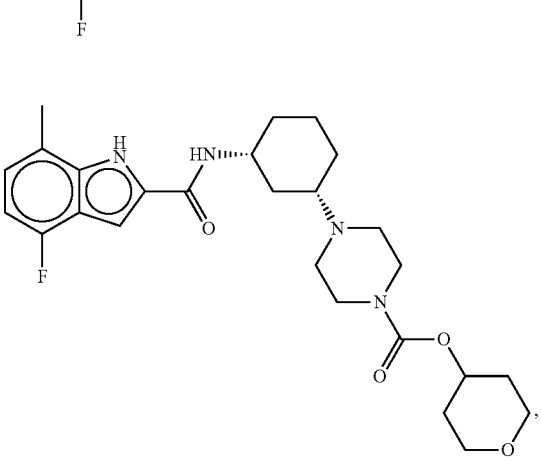
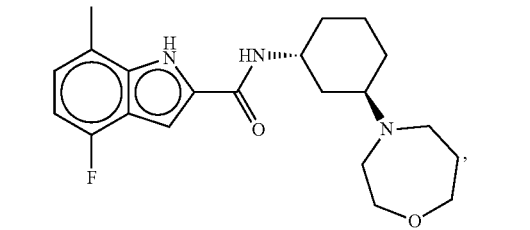
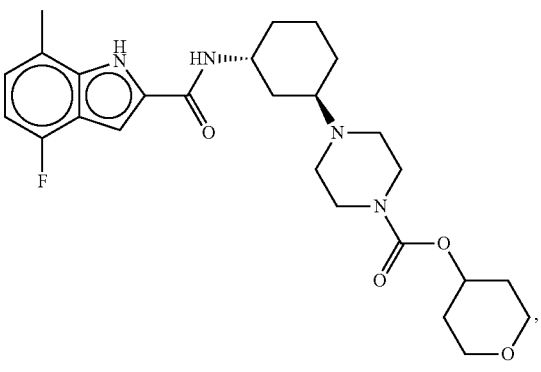

-continued
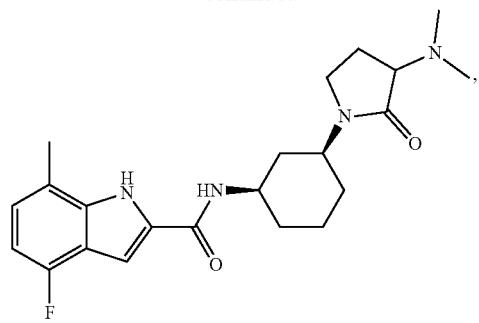
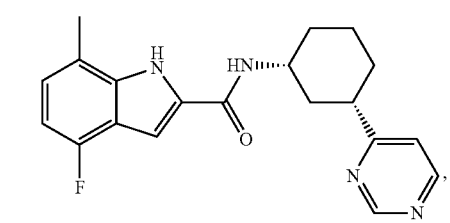
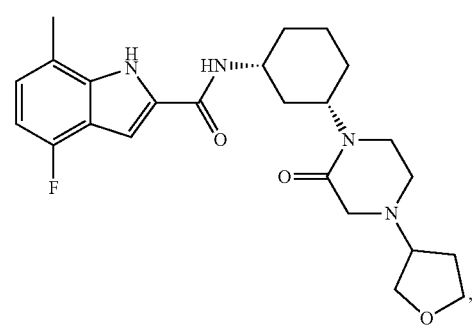
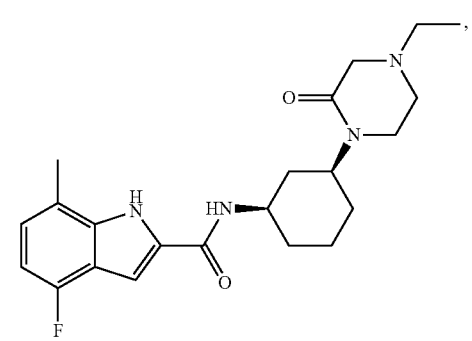
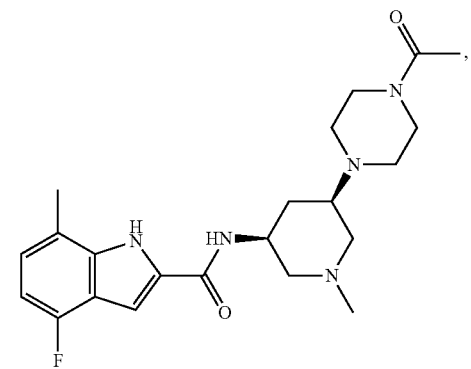
-continued
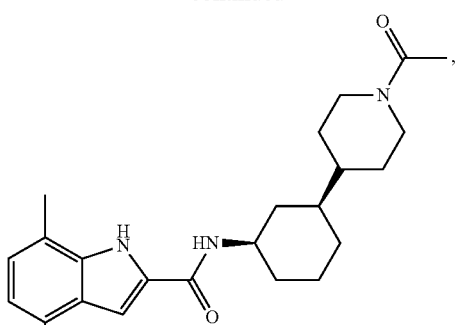
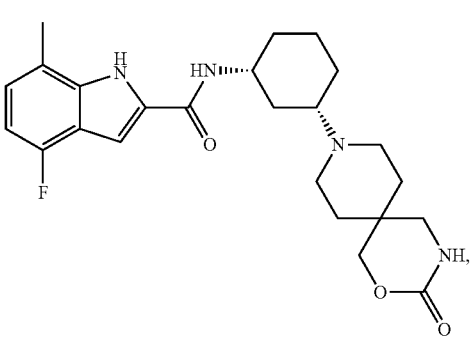
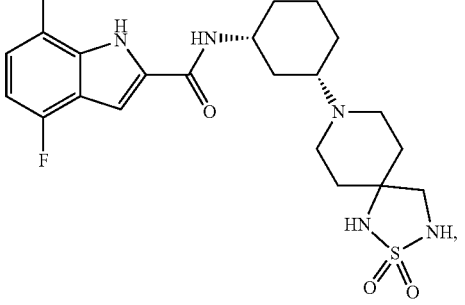
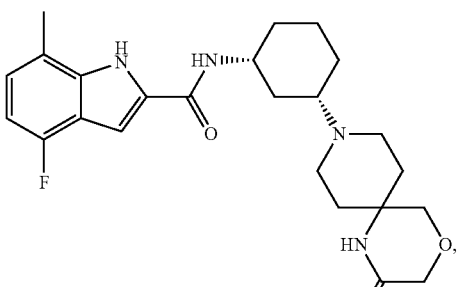
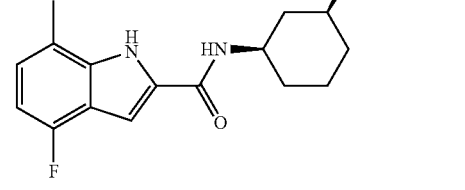

677
-continued
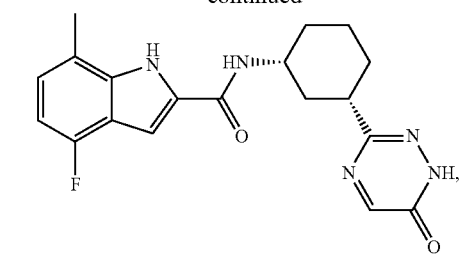
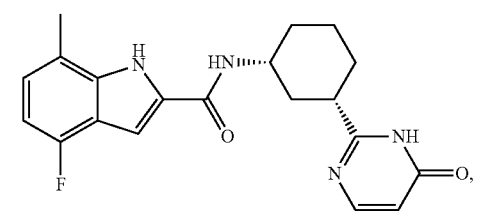
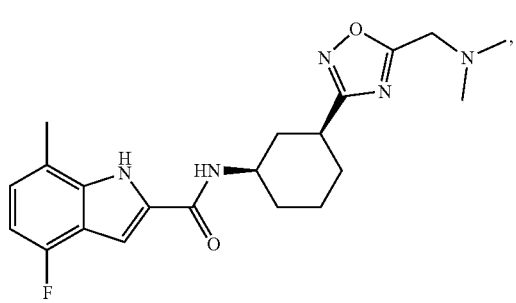
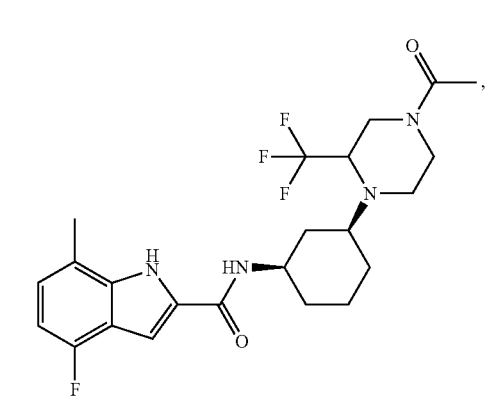
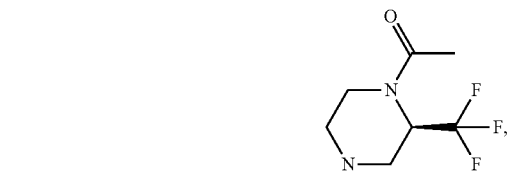
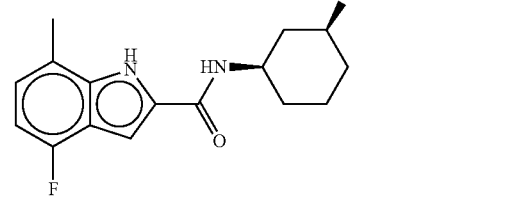
678
-continued
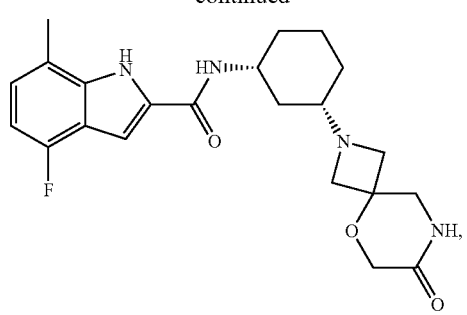
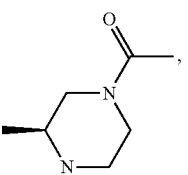
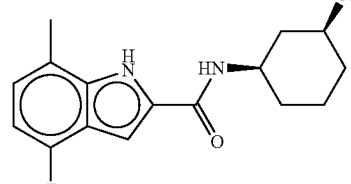
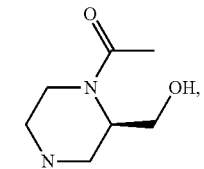
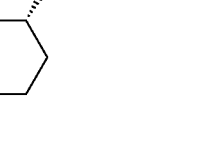
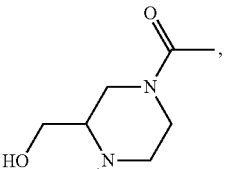

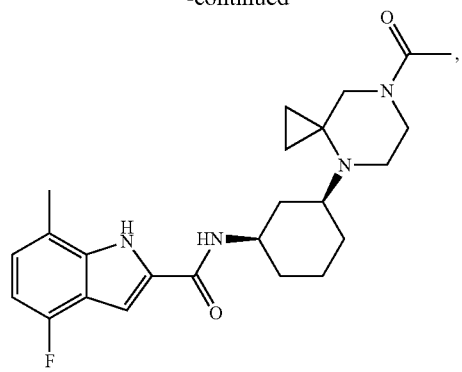
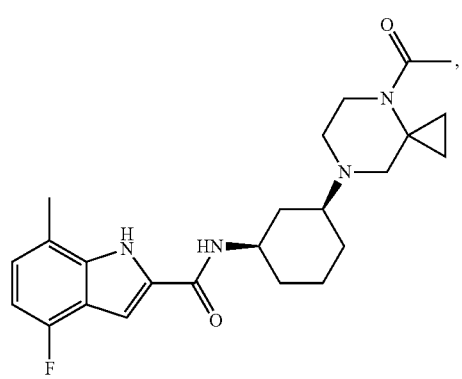
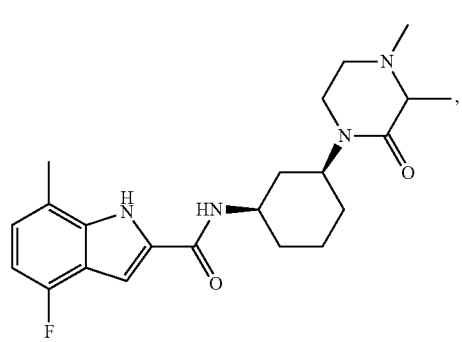
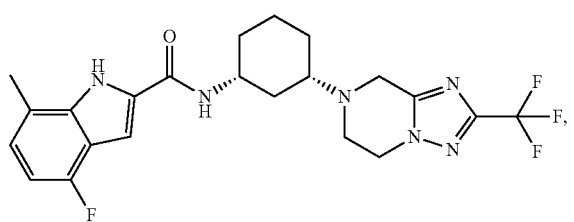
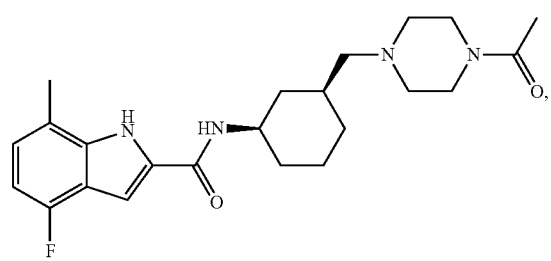
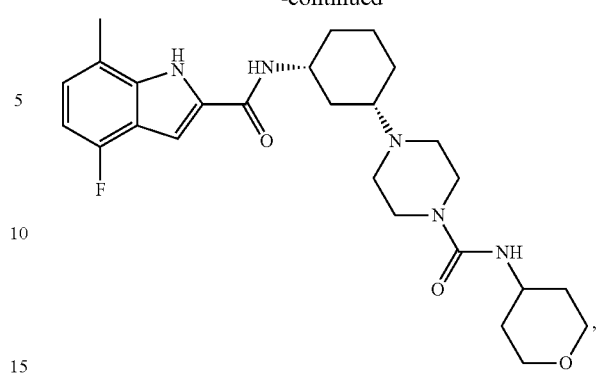
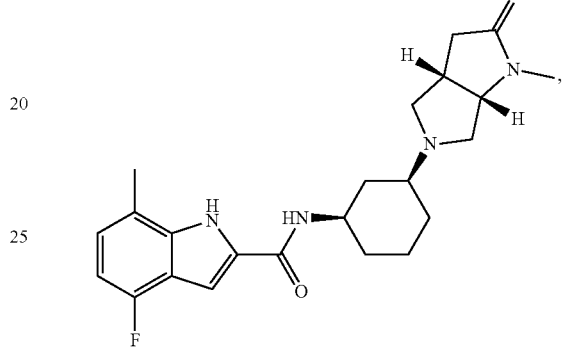
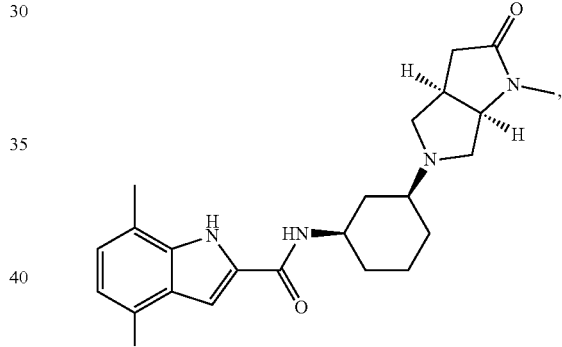
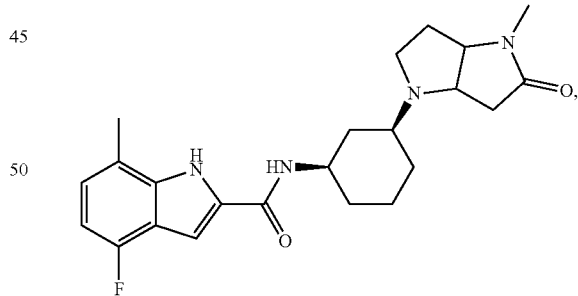
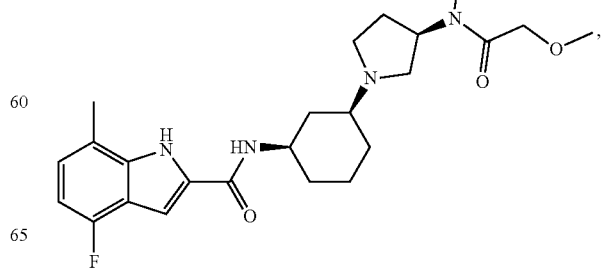

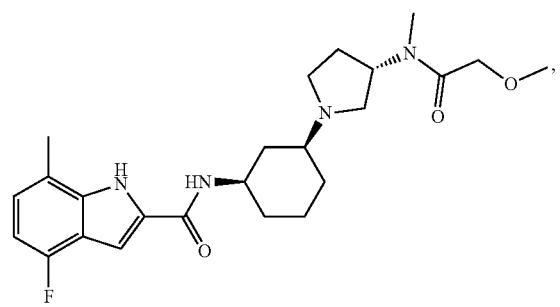
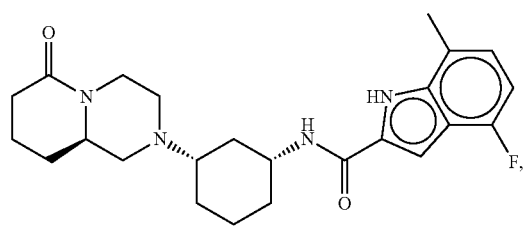
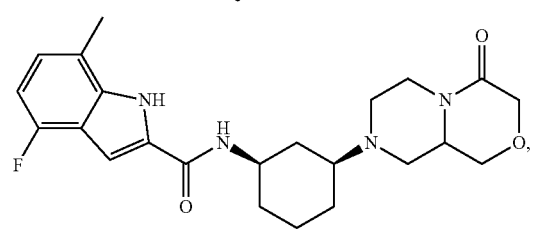
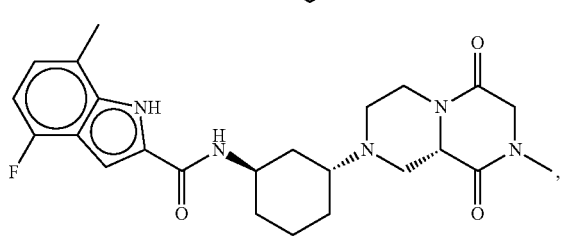
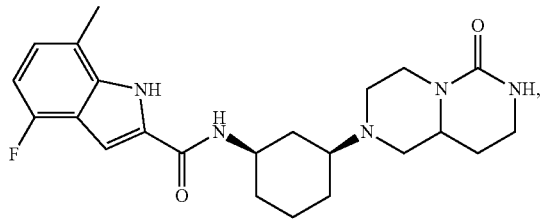
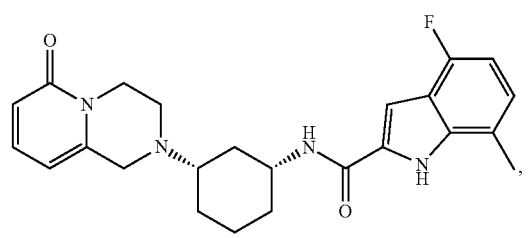
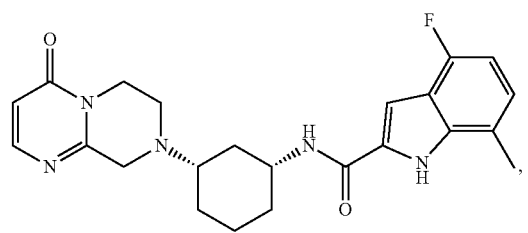
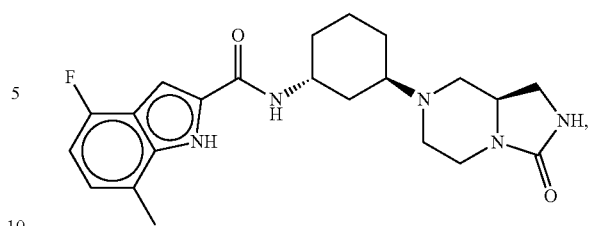
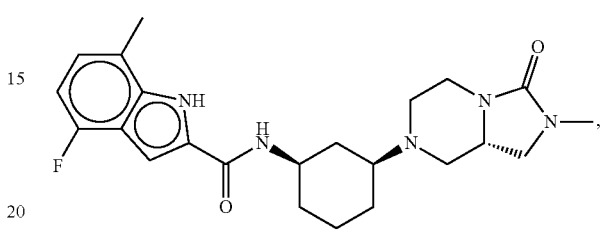
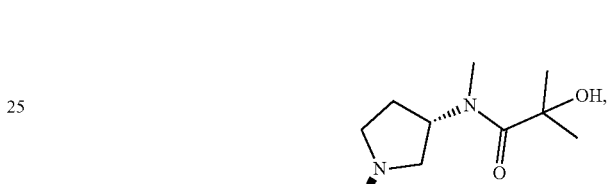
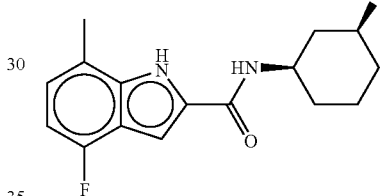
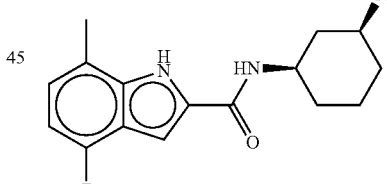
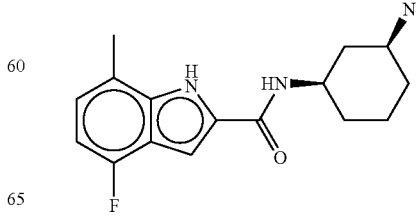

683
-continued
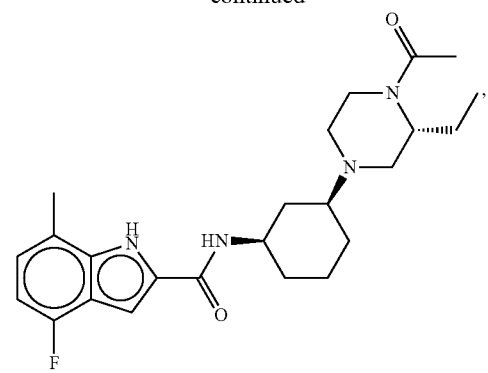
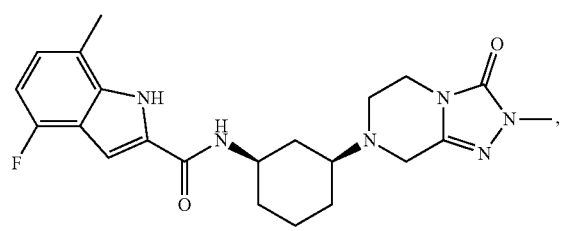
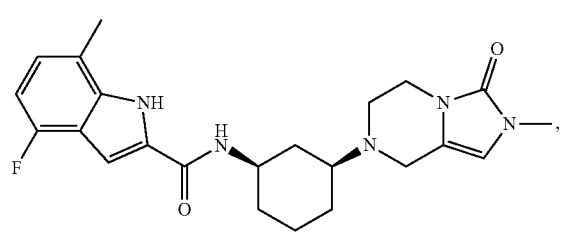
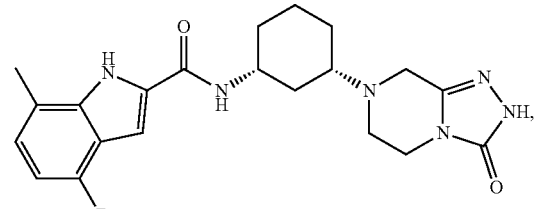
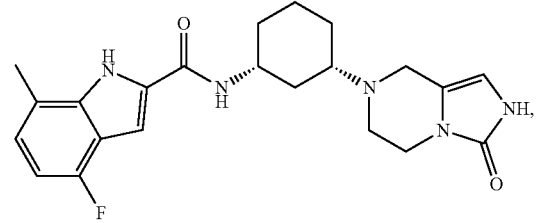
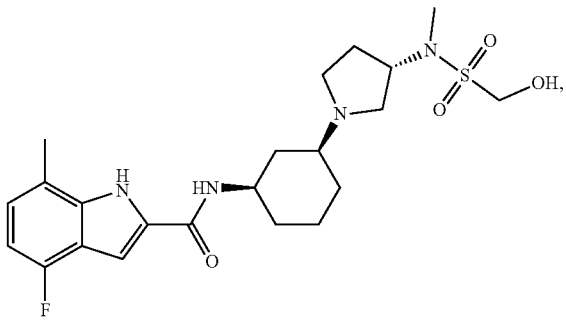
684
-continued
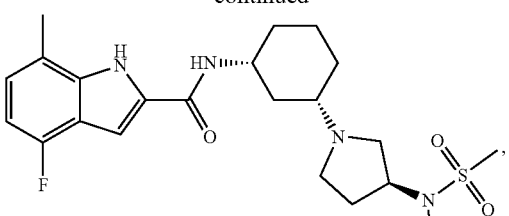
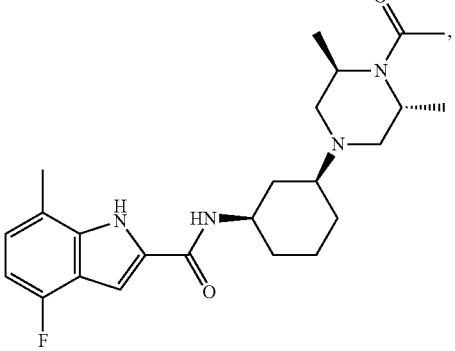
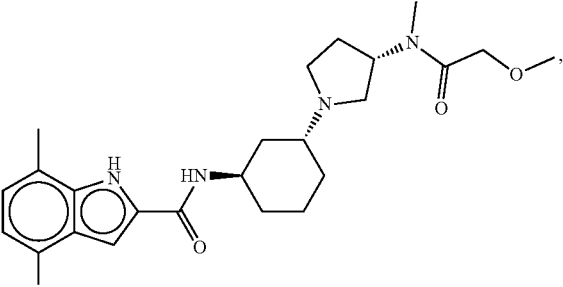
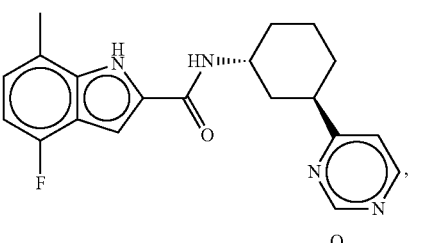
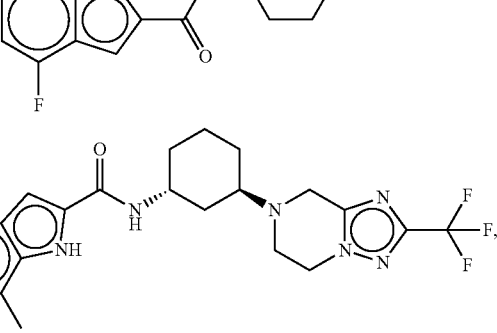

685
-continued
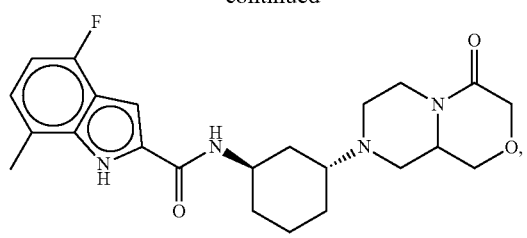
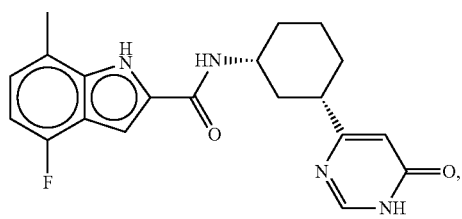
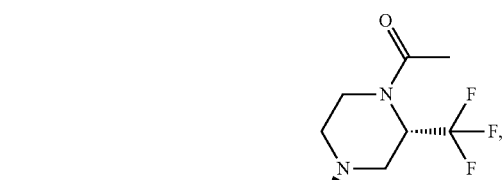
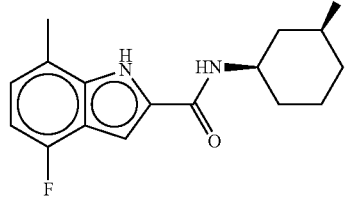
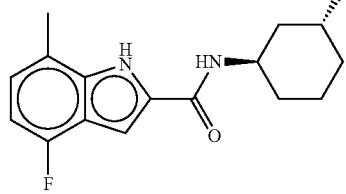
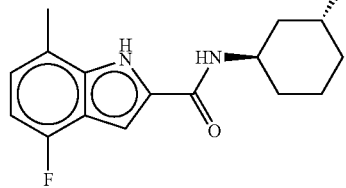
686
-continued
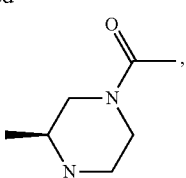
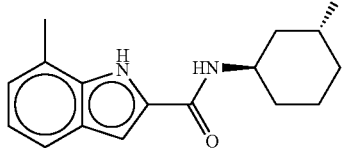
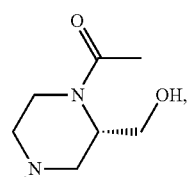
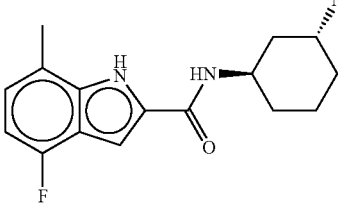
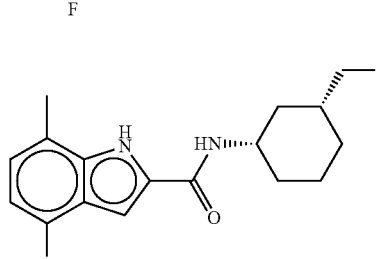
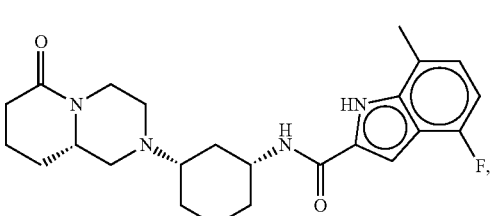
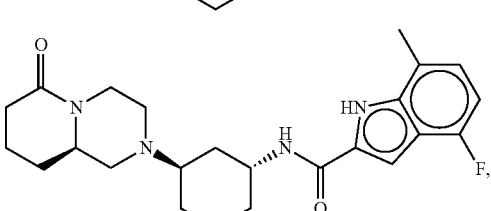
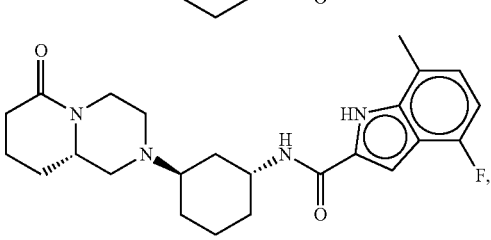

687
-continued
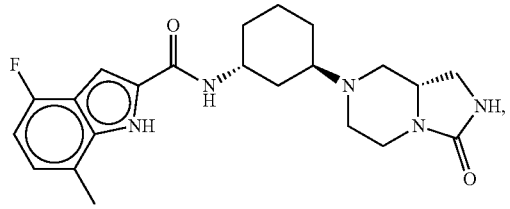
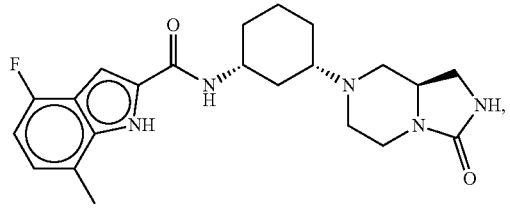
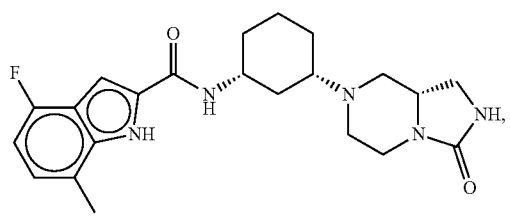
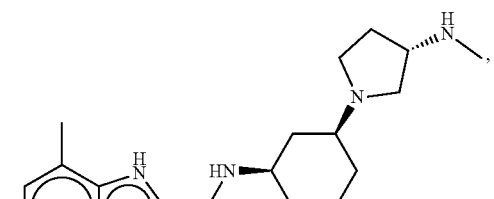
688
-continued
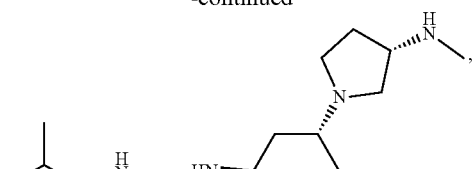
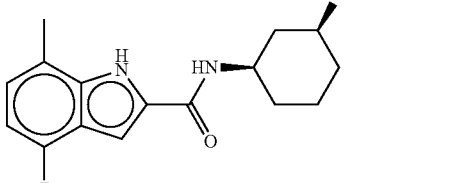
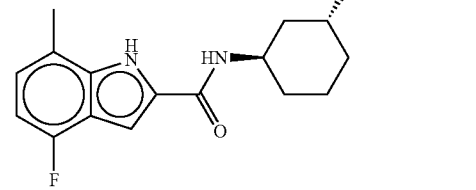
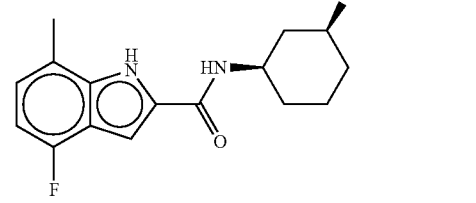
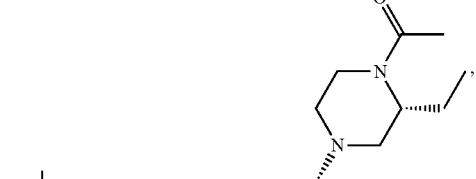

689
-continued
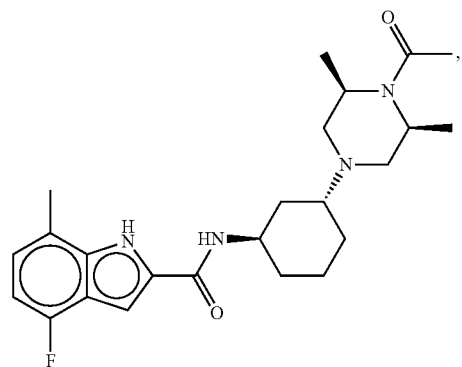
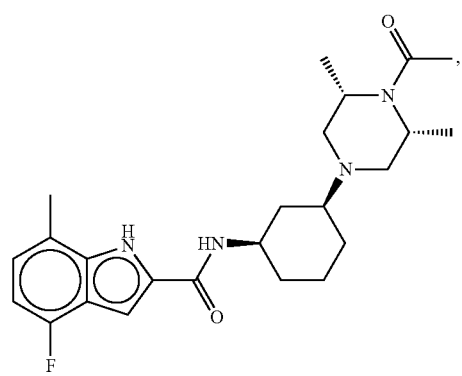
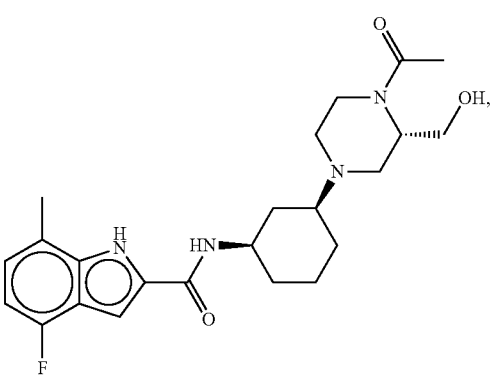
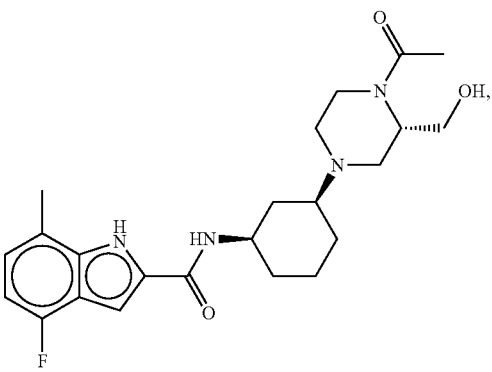
690
-continued
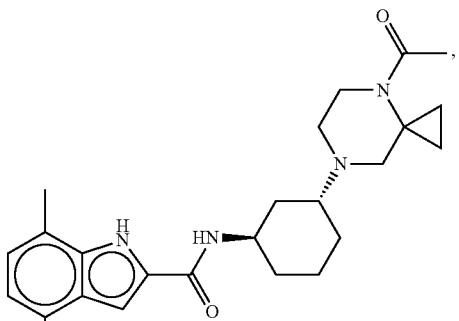
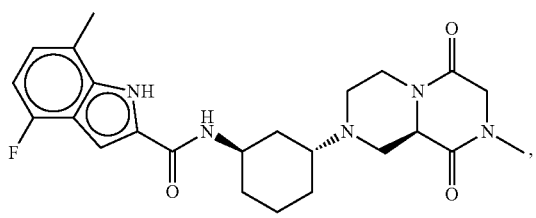
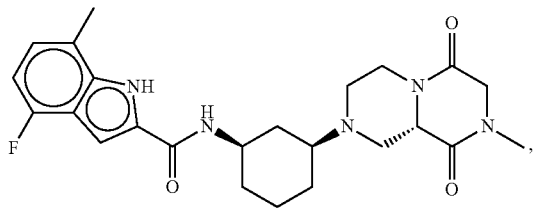
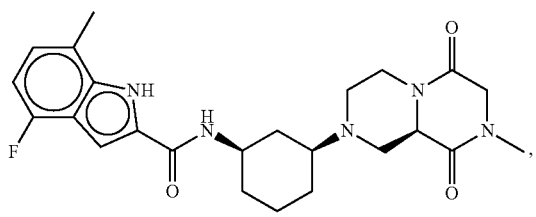
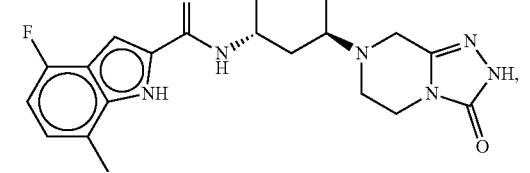
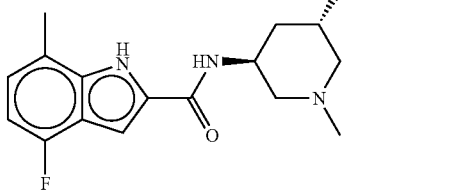

691
-continued
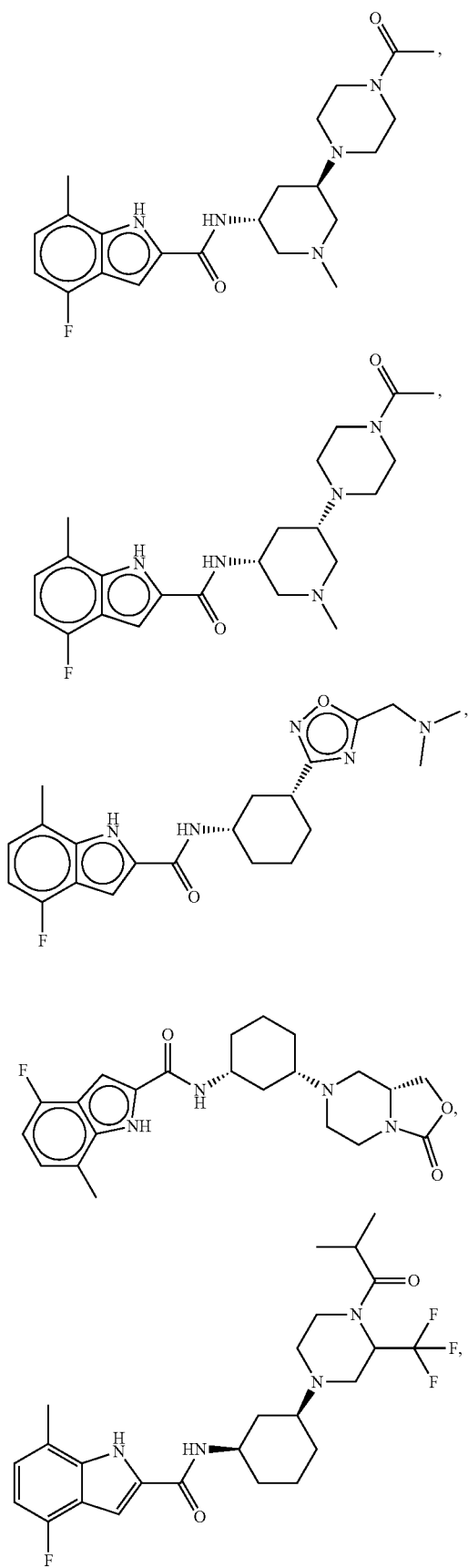
692
-continued
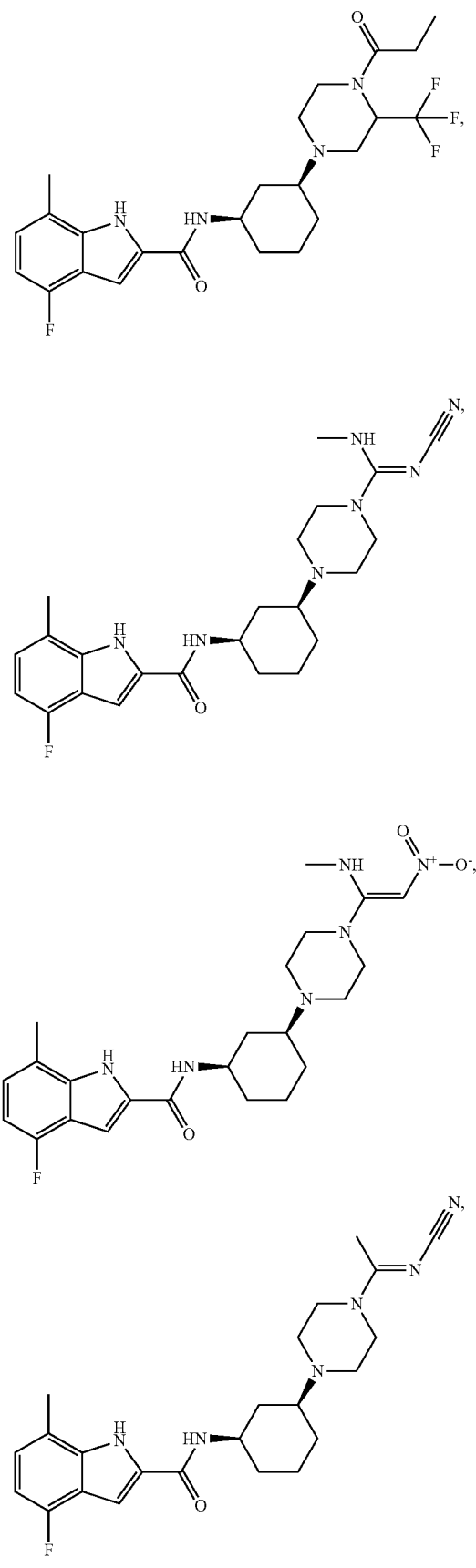

693
-continued
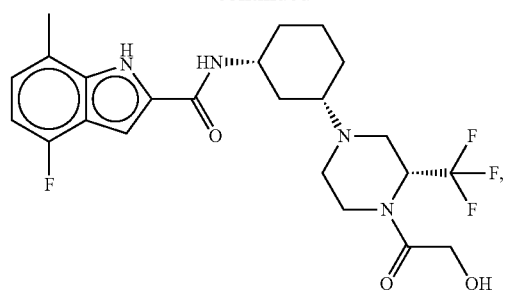
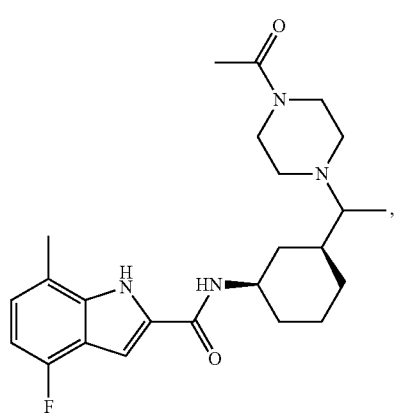
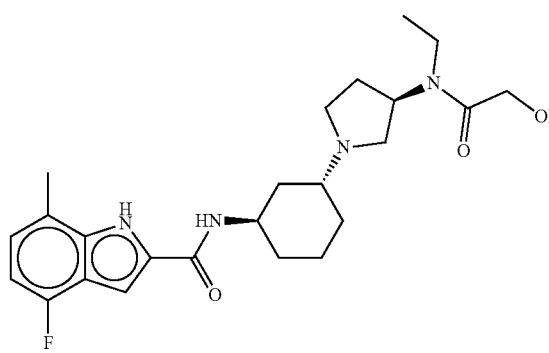
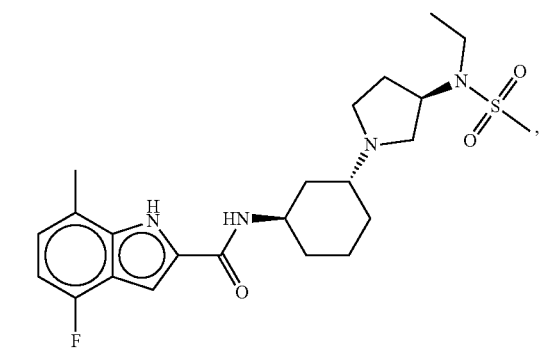
694
-continued
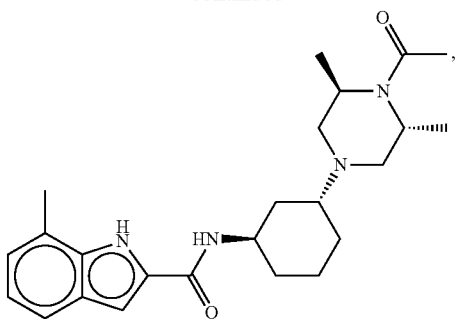
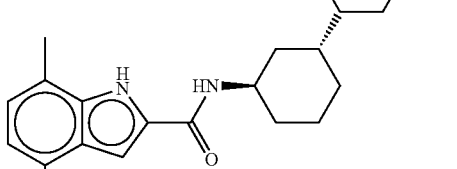
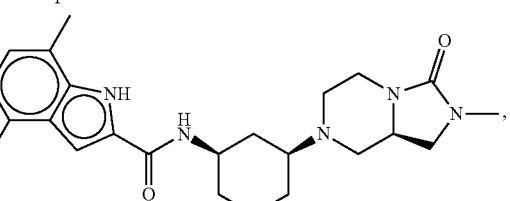
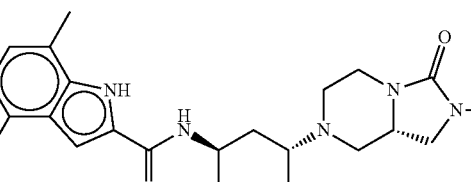
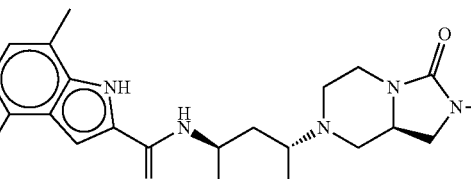
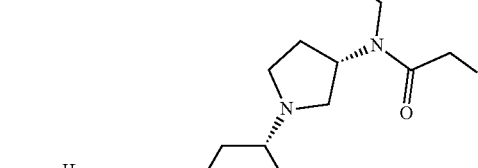

695
-continued
696
-continued
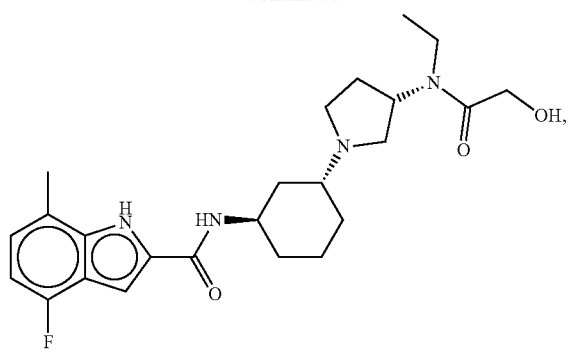
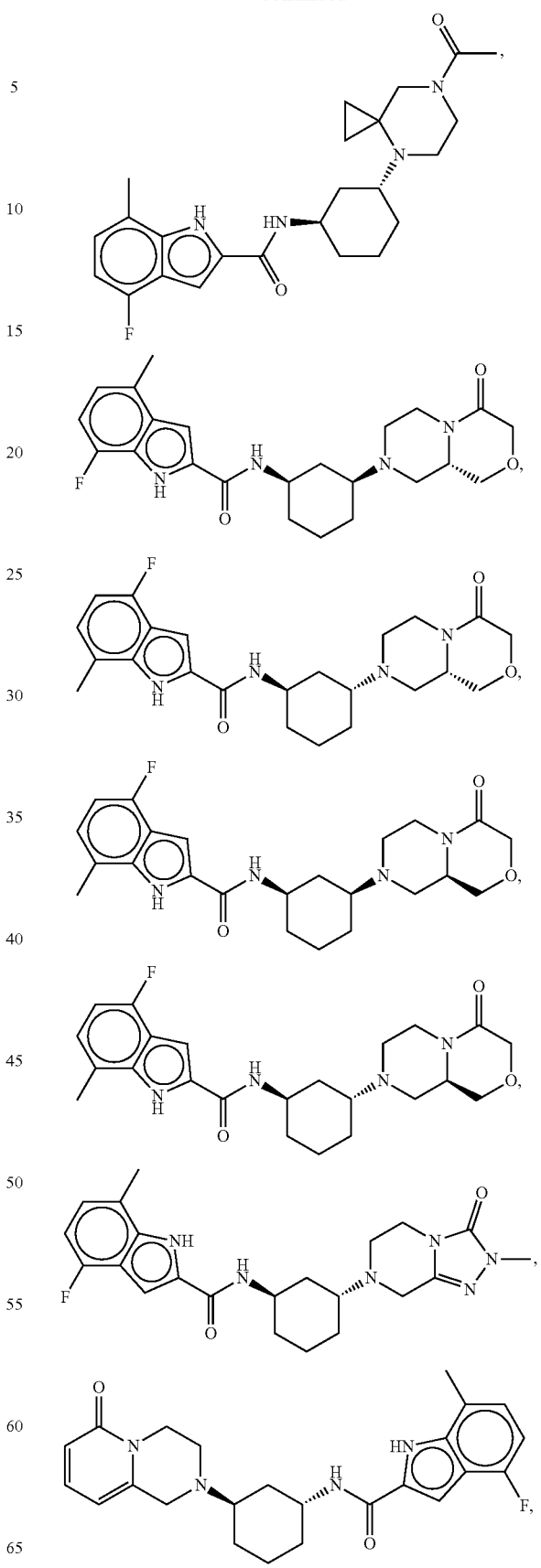

697
-continued
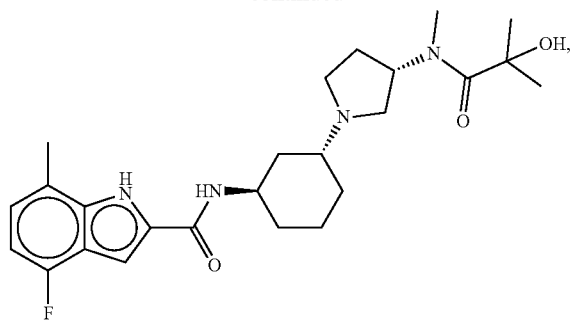
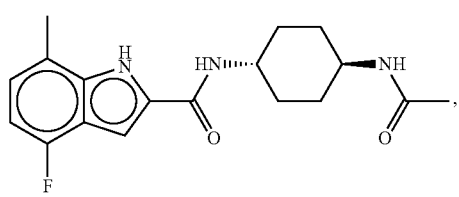
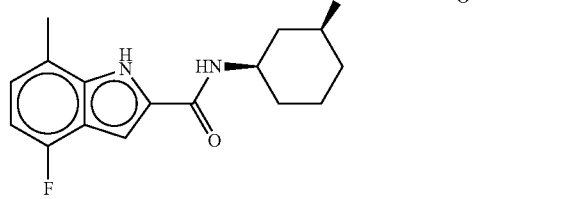
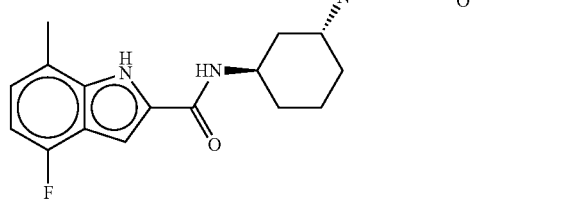
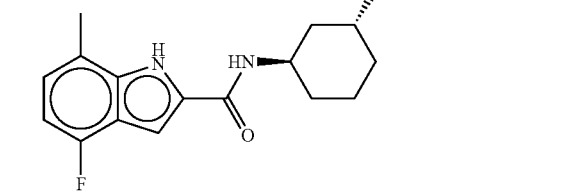
698
-continued
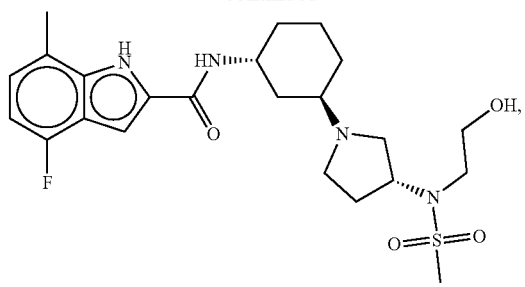
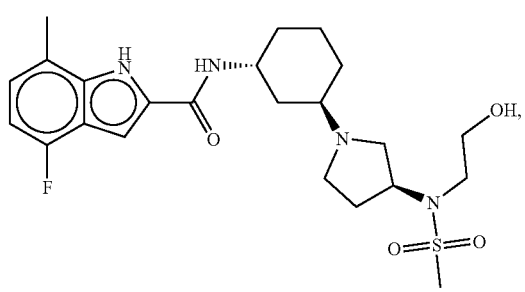
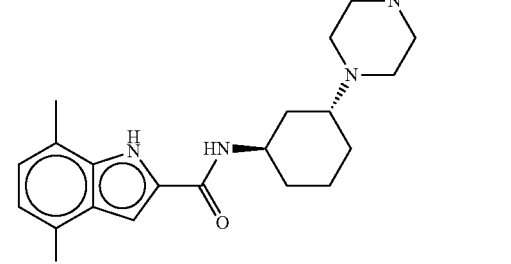
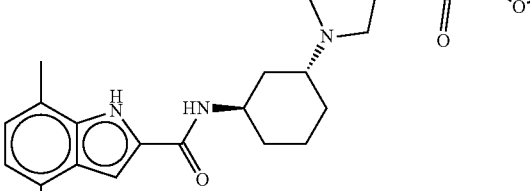
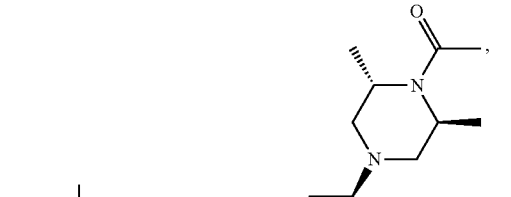
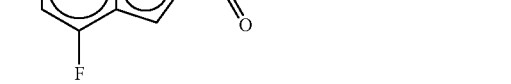

699
-continued
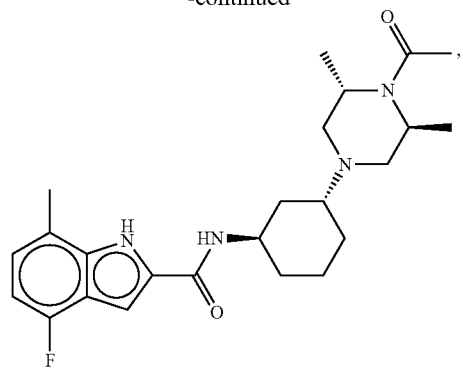
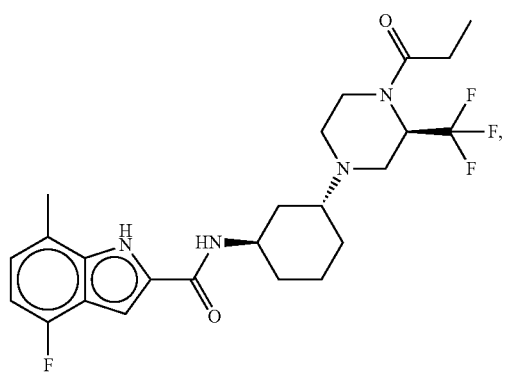
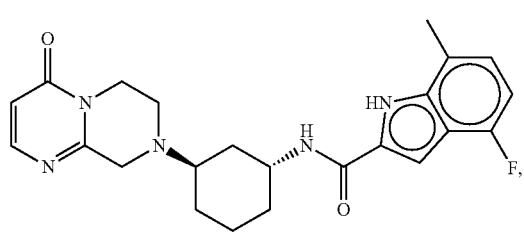
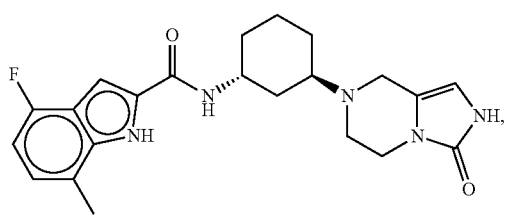
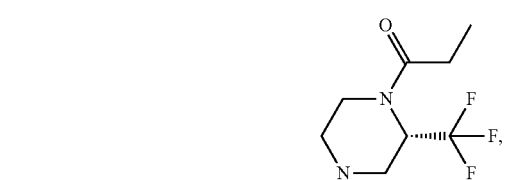
700
-continued
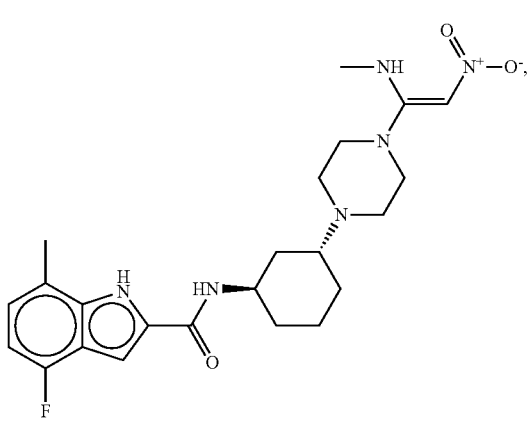
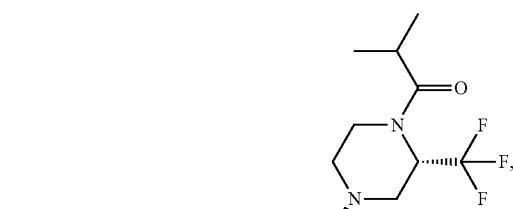

701
-continued
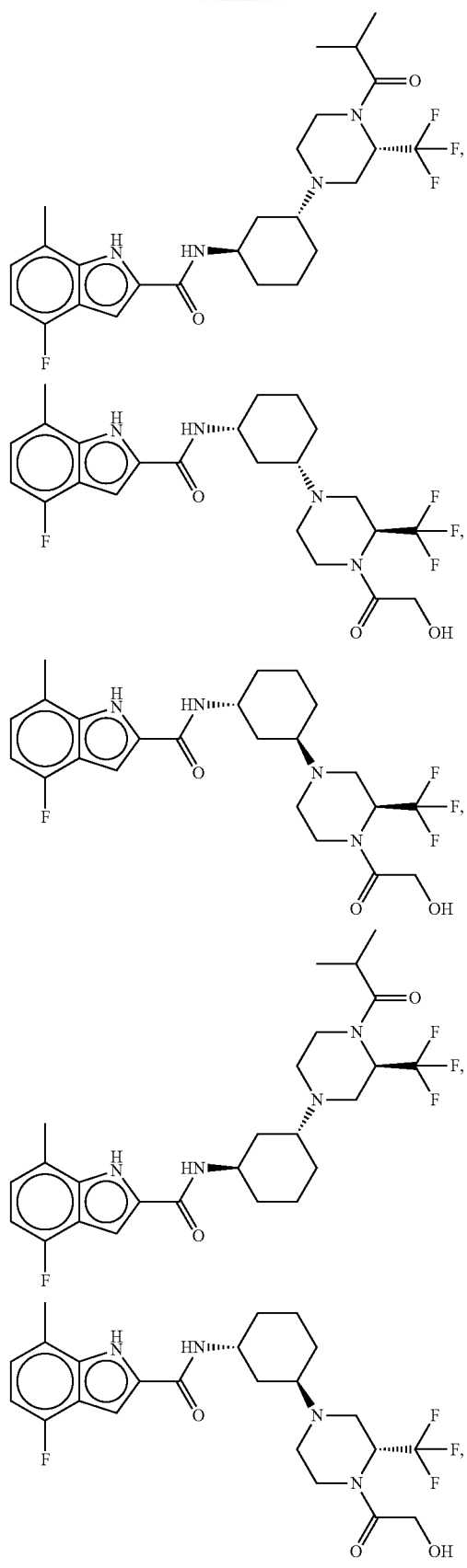
702
-continued
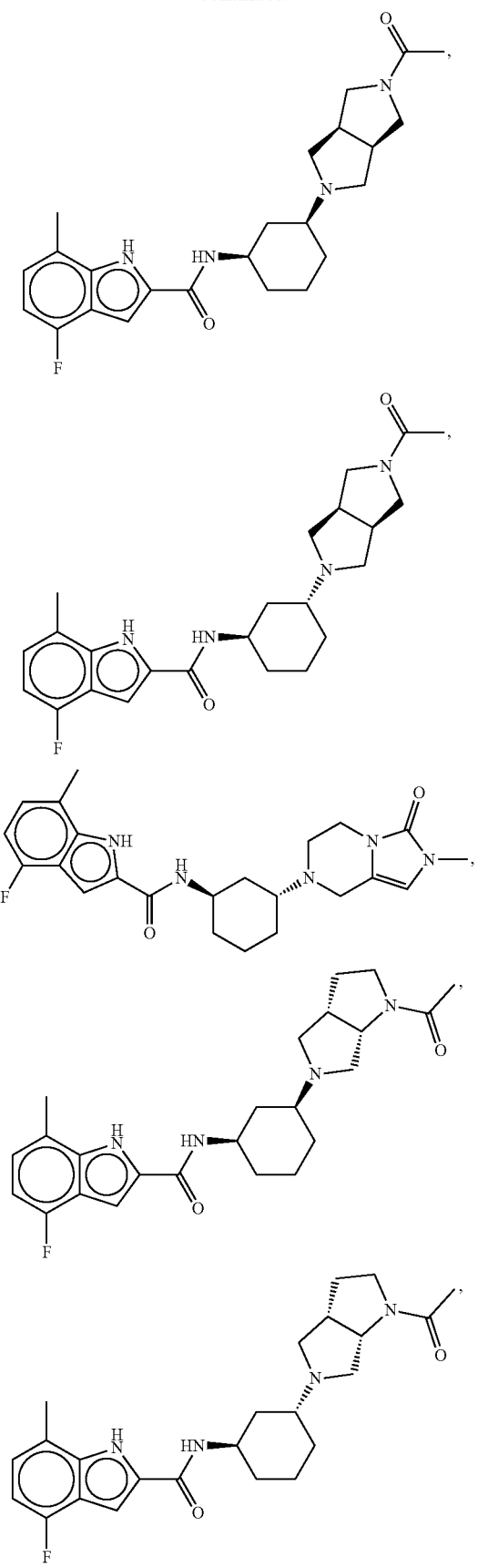

703
-continued
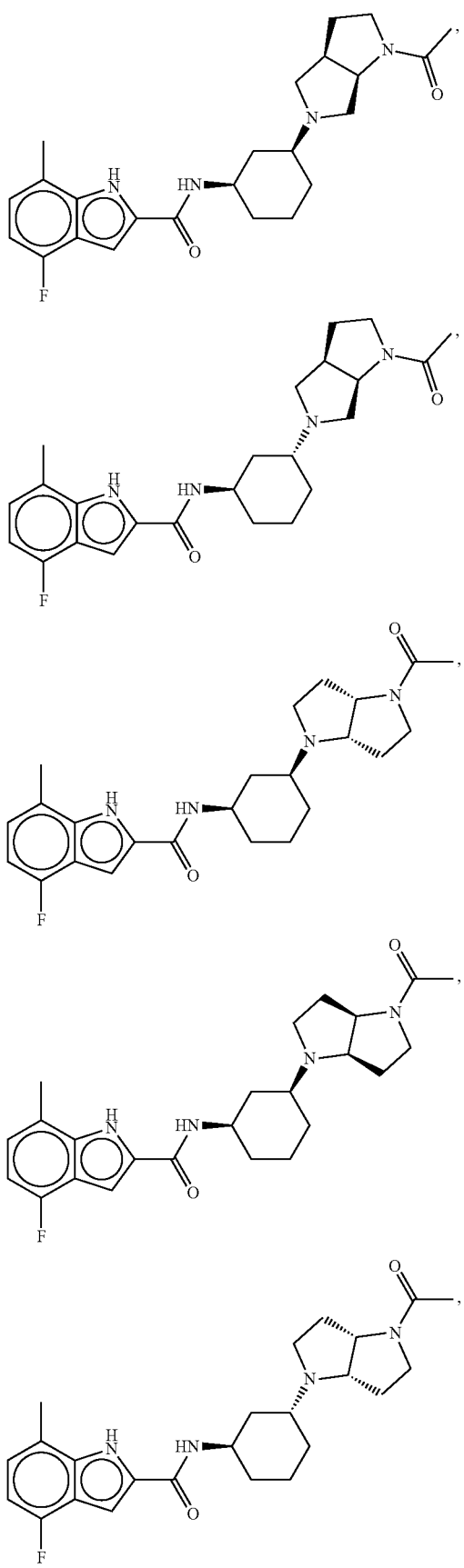
704
-continued
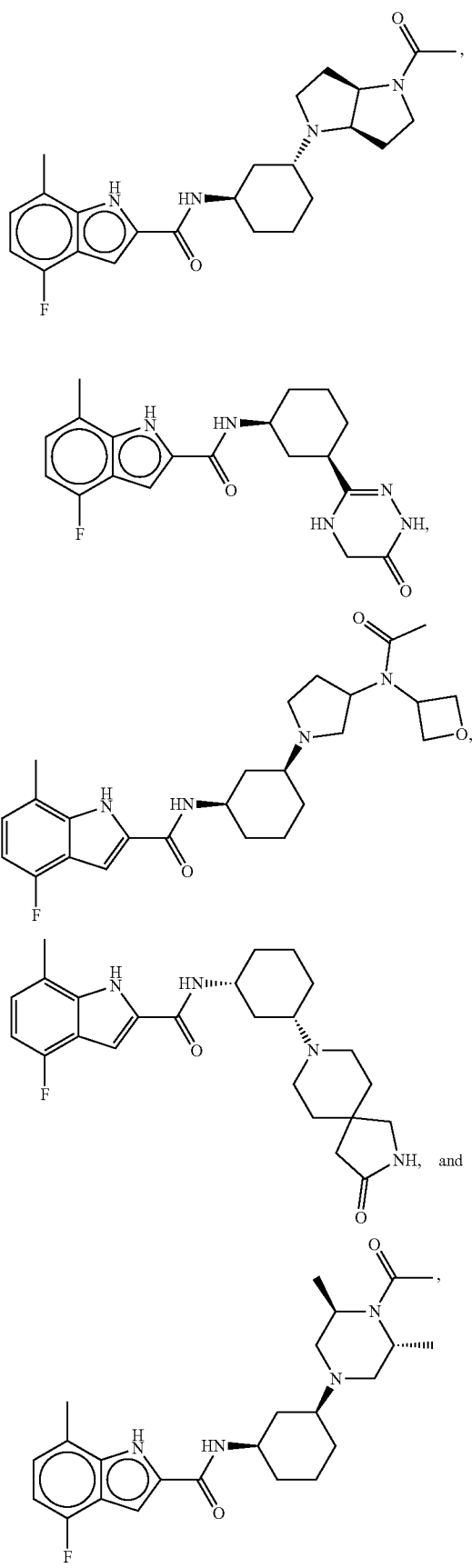

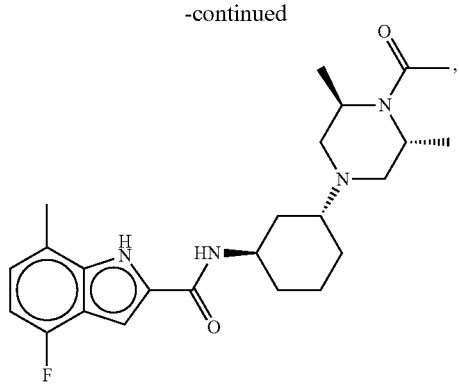

or a pharmaceutically acceptable salt or solvate thereof.

13. A pharmaceutical composition comprising the compound of claim 1, or a pharmaceutically acceptable salt or solvate thereof, and a pharmaceutically acceptable carrier.

14. A method of treating a subject in need thereof, the method comprising administering to the subject the compound of claim 1, or a pharmaceutically acceptable salt or solvate thereof, wherein the subject has multiple myeloma.

15. A kit comprising the compound of claim 1, or a pharmaceutically acceptable salt or solvate thereof, and instructions for administering the compound, or a pharmaceutically acceptable salt or solvate thereof, to a subject having multiple myeloma, diffuse large B-cell lymphoma, or renal cell carcinoma.

16. A method, comprising administering a compound of claim 1, or a pharmaceutically acceptable salt or solvate thereof, to a subject in need thereof, wherein: (a) the subject has multiple myeloma; and (b) the multiple myeloma is characterized as having a chromosomal translocation.

17. The compound of claim 12 that is:

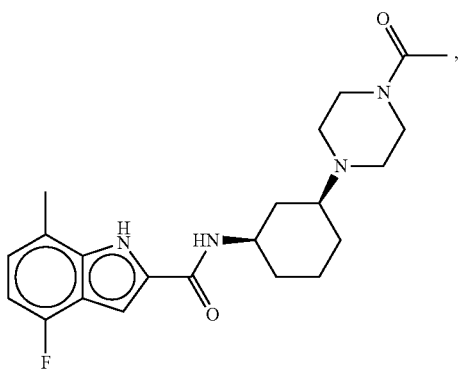

or a pharmaceutically acceptable salt or solvate thereof.

18. The compound of claim 12 that is:

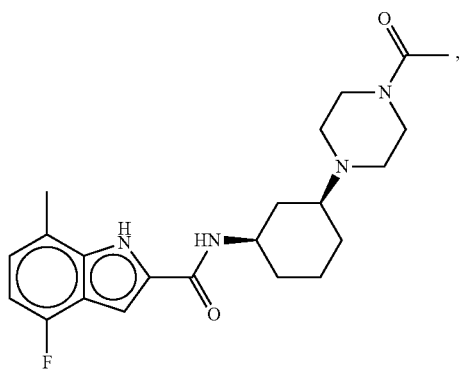

or a pharmaceutically acceptable salt thereof.

19. The compound of claim 12 that is:

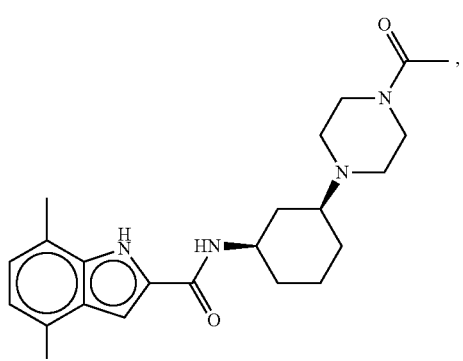

or a pharmaceutically acceptable solvate thereof.

20. The compound of claim 12 that is:

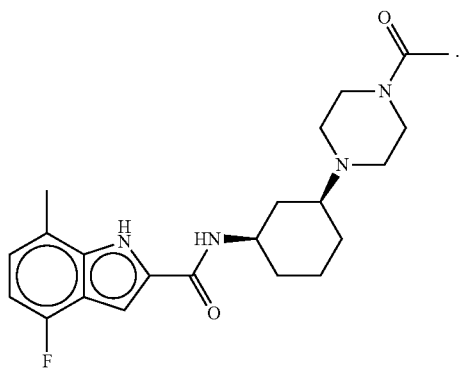

21. The compound of claim 12 that is:

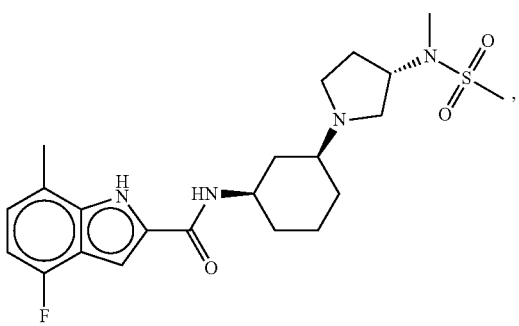

or a pharmaceutically acceptable salt or solvate thereof.

22. The compound of claim 12 that is:

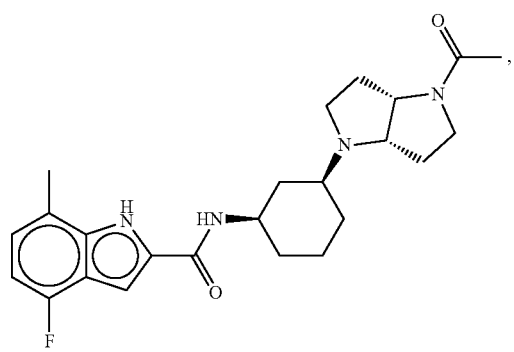

or a pharmaceutically acceptable salt or solvate thereof.

23. The compound of claim 2, wherein:
$Z^4$ is —CH$_2$—;
$R^{11a}$ is selected from the group consisting of:

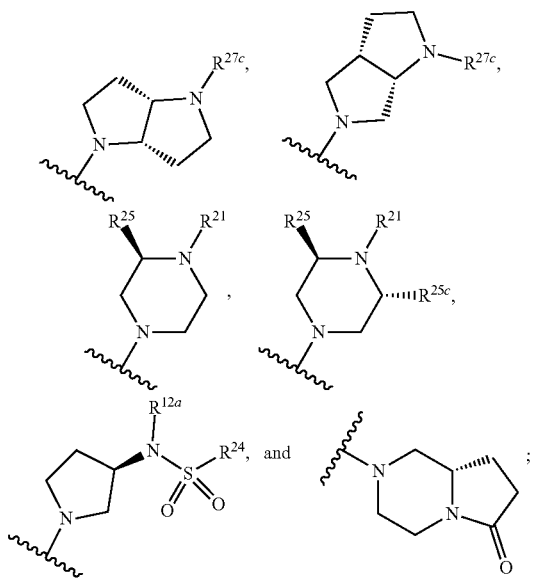

$R^{12a}$ is selected from the group consisting of hydrogen and C$_1$-C$_3$ alkyl;
$R^{21}$ is —C(=O)R$^{13b}$;
$R^{27c}$ is —C(=O)R$^{13b}$;

$R^{13b}$ is selected from the group consisting of C$_1$-C$_4$ alkyl and (hydroxy)C$_1$-C$_4$ alkyl;
$R^{24}$ is C$_1$-C$_4$ alkyl;
$R^{25}$ is selected from the group consisting of hydrogen, C$_1$-C$_4$ alkyl, and C$_1$-C$_4$ haloalkyl; and
$R^{25b}$ and $R^{25c}$ are independently selected from the group consisting of C$_1$-C$_4$ alkyl and C$_1$-C$_4$ haloalkyl, or a pharmaceutically acceptable salt or solvate thereof.

24. A compound of Formula IV:

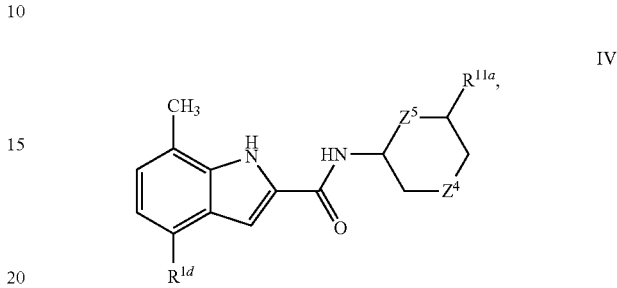

wherein:
$R^{1d}$ is selected from the group consisting of hydrogen, halogen, alkyl, alkenyl, (hydroxy)alkyl, and alkoxy;
$Z^4$ is selected from the group consisting of —O— and —CH$_2$—; or $Z^4$ is absent;
$Z^5$ is selected from the group consisting of —CH$_2$— and —CH$_2$CH$_2$—;
$R^{11a}$ is selected from the group consisting of optionally substituted alkyl, optionally substituted heterocyclo, optionally substituted heteroaryl, and —N(R$^{12b}$)C(=O)R$^{13c}$;
$R^{12b}$ is selected from the group consisting of hydrogen and alkyl; and
$R^{13c}$ is selected from the group consisting of alkyl, haloalkyl, alkoxy, (alkoxy)alkyl, (hydroxy)alkyl, (cyano)alkyl, optionally substituted aryl, optionally substituted heteroaryl, optionally substituted cycloalkyl, and optionally substituted heterocycle,
or a pharmaceutically acceptable salt or solvate thereof.

25. The compound of claim 24 of Formula IV-A:

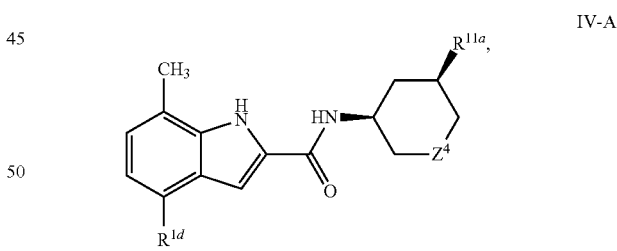

or a pharmaceutically acceptable salt or solvate thereof.

26. The compound of claim 25, wherein:
$R^{11a}$ is selected from the group consisting of:
(A) unsubstituted 4- to 14-membered heterocyclo;
(B) substituted 4- to 14-membered heterocyclo having one, two or three substituents independently selected from the group consisting of:
(i) —N(R$^{12a}$)C(=O)R$^{13a}$; (ii) —C(=O)R$^{13b}$; and (iii) C$_1$-C$_4$ alkyl;
(C) unsubstituted 5- to 10-membered heteroaryl;
(D) substituted 5- or 6-membered heteroaryl having one, two, three, or four substituents independently selected from the group consisting of halo and C$_1$-C$_4$ alkyl;

(E) $C_1$-$C_6$ alkyl; and
(F) —N($R^{12b}$)C(=O)$R^{13c}$;
$R^{12a}$ and $R^{12b}$ are each independently selected from the group consisting of hydrogen and $C_1$-$C_4$ alkyl;
$R^{13a}$, $R^{13b}$, and $R^{13c}$ are each independently selected from the group consisting of (A) $C_1$-$C_6$ alkyl; (B) $C_1$-$C_6$ haloalkyl; (C) unsubstituted $C_3$-$C_6$ cycloalkyl; (D) $C_1$-$C_6$ alkoxy; (E) ($C_1$-$C_4$ alkoxy)$C_1$-$C_4$ alkyl; (F) (hydroxy)$C_1$-$C_4$ alkyl; (G) (cyano)alkyl; (H) unsubstituted $C_6$-$C_{10}$ aryl; (I) substituted $C_6$-$C_{10}$ aryl, having one, two, three, or four substituents independently selected from the group consisting of halo, amino, hydroxy, and $C_1$-$C_4$ alkyl; (J) unsubstituted 5- or 6-membered heteroaryl; (K) substituted 5- or 6-membered heteroaryl having one, two, three, or four substituents independently selected from the group consisting of halo, amino, hydroxy, and $C_1$-$C_4$ alkyl; (L) unsubstituted 4- to 14-membered heterocyclo; and (M) substituted 4- to 14-membered heterocyclo having one or two substituents independently selected from the group consisting of amino, hydroxy, and $C_1$-$C_4$ alkyl, or a pharmaceutically acceptable salt or solvate thereof.

27. The compound of claim 25, wherein $Z^4$ is —CH$_2$—, or a pharmaceutically acceptable salt or solvate thereof.

28. The compound of claim 25, wherein $R^{11a}$ is a substituted 4- to 14-membered heterocyclo is selected from the group consisting of

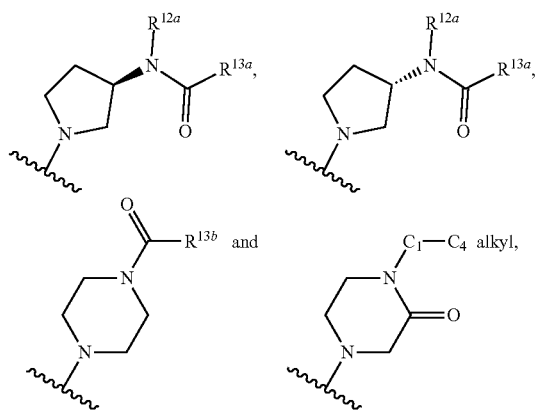

or a pharmaceutically acceptable salt or solvate thereof.

29. The compound of claim 28, wherein: $R^{12a}$ is selected from the group consisting of hydrogen and $C_1$-$C_3$ alkyl; $R^{13a}$ is $C_1$-$C_4$ alkyl; and $R^{13b}$ is $C_1$-$C_4$ alkyl, or a pharmaceutically acceptable salt or solvate thereof.

30. The compound of claim 29, wherein: $R^{12a}$ is selected from the group consisting of hydrogen and methyl; $R^{13a}$ is methyl; and $R^{13b}$ is methyl, or a pharmaceutically acceptable salt or solvate thereof.

31. The compound of claim 25, wherein $R^{1d}$ is fluoro, or a pharmaceutically acceptable salt or solvate thereof.

32. A method of treating a subject in need thereof, the method comprising administering to the subject the compound of claim 1, or a pharmaceutically acceptable salt or solvate thereof, wherein the subject has diffuse large B-cell lymphoma.

33. A method of treating a subject in need thereof, the method comprising administering to the subject the compound of claim 1, or a pharmaceutically acceptable salt or solvate thereof, wherein the subject has renal cell carcinoma.

34. The method of claim 16, wherein the chromosomal translocation is a t(4;14) translocation.

35. A method, comprising administering the compound of claim 1, or a pharmaceutically acceptable salt or solvate thereof, to a subject in need thereof, wherein:
(a) the subject has multiple myeloma; and
(b) the multiple myeloma is characterized as having an overexpression of WHSC1/NSD2/MMSET.

36. A pharmaceutical composition comprising the compound of claim 24, or a pharmaceutically acceptable salt or solvate thereof, and a pharmaceutically acceptable carrier.

37. A method of treating a subject in need thereof, the method comprising administering to the subject the compound of claim 24, or a pharmaceutically acceptable salt or solvate thereof, wherein the subject has multiple myeloma.

38. A method of treating a subject in need thereof, the method comprising administering to the subject the compound of claim 24, or a pharmaceutically acceptable salt or solvate thereof, wherein the subject has diffuse large B-cell lymphoma.

39. A method of treating a subject in need thereof, the method comprising administering to the subject the compound of claim 24, or a pharmaceutically acceptable salt or solvate thereof, wherein the subject has renal cell carcinoma.

40. A method, comprising administering the compound of claim 24, or a pharmaceutically acceptable salt or solvate thereof, to a subject in need thereof, wherein: (a) the subject has multiple myeloma; and (b) the multiple myeloma is characterized as having a chromosomal translocation.

41. The method of claim 40, wherein the chromosomal translocation is a t(4;14) translocation.

42. A method, comprising administering the compound of claim 24, or a pharmaceutically acceptable salt or solvate thereof, to a subject in need thereof, wherein:
(a) the subject has multiple myeloma; and
(b) the multiple myeloma is characterized as having an overexpression of WHSC1/NSD2/MMSET.

43. A pharmaceutical composition comprising the compound of claim 17, or a pharmaceutically acceptable salt or solvate thereof, and a pharmaceutically acceptable carrier.

44. A method of treating a subject in need thereof, the method comprising administering to the subject the compound of claim 17, or a pharmaceutically acceptable salt or solvate thereof, wherein the subject has multiple myeloma.

45. A method of treating a subject in need thereof, the method comprising administering to the subject the compound of claim 17, or a pharmaceutically acceptable salt or solvate thereof, wherein the subject has diffuse large B-cell lymphoma.

46. A method of treating a subject in need thereof, the method comprising administering to the subject the compound of claim 17, or a pharmaceutically acceptable salt or solvate thereof, wherein the subject has renal cell carcinoma.

47. A method, comprising administering the compound of claim 17, or a pharmaceutically acceptable salt or solvate thereof, to a subject in need thereof, wherein: (a) the subject has multiple myeloma; and (b) the multiple myeloma is characterized as having a chromosomal translocation.

48. The method of claim 47, wherein the chromosomal translocation is a t(4;14) translocation.

49. A method, comprising administering the compound of claim 17, or a pharmaceutically acceptable salt or solvate thereof, to a subject in need thereof, wherein:
(a) the subject has multiple myeloma; and
(b) the multiple myeloma is characterized as having an overexpression of WHSC1/NSD2/MMSET.

50. A pharmaceutical composition comprising the compound of claim 18, or a pharmaceutically acceptable salt thereof, and a pharmaceutically acceptable carrier.

51. A method of treating a subject in need thereof, the method comprising administering to the subject the compound of claim 18, or a pharmaceutically acceptable salt thereof, wherein the subject has multiple myeloma.

52. A method of treating a subject in need thereof, the method comprising administering to the subject the compound of claim 18, or a pharmaceutically acceptable salt thereof, wherein the subject has diffuse large B-cell lymphoma.

53. A method of treating a subject in need thereof, the method comprising administering to the subject the compound of claim 18, or a pharmaceutically acceptable salt thereof, wherein the subject has renal cell carcinoma.

54. A method, comprising administering the compound of claim 18, or a pharmaceutically acceptable salt thereof, to a subject in need thereof, wherein: (a) the subject has multiple myeloma; and (b) the multiple myeloma is characterized as having a chromosomal translocation.

55. The method of claim 54, wherein the chromosomal translocation is a t(4;14) translocation.

56. A method, comprising administering the compound of claim 18, or a pharmaceutically acceptable salt thereof, to a subject in need thereof, wherein:
(a) the subject has multiple myeloma; and
(b) the multiple myeloma is characterized as having an overexpression of WHSC1/NSD2/MMSET.

57. A pharmaceutical composition comprising the compound of claim 19, or a pharmaceutically acceptable solvate thereof, and a pharmaceutically acceptable carrier.

58. A method of treating a subject in need thereof, the method comprising administering to the subject the compound of claim 19, or a pharmaceutically acceptable solvate thereof, wherein the subject has multiple myeloma.

59. A method of treating a subject in need thereof, the method comprising administering to the subject the compound of claim 19, or a pharmaceutically acceptable solvate thereof, wherein the subject has diffuse large B-cell lymphoma.

60. A method of treating a subject in need thereof, the method comprising administering to the subject the compound of claim 19, or a pharmaceutically acceptable solvate thereof, wherein the subject has renal cell carcinoma.

61. A method, comprising administering the compound of claim 19, or a pharmaceutically acceptable solvate thereof, to a subject in need thereof, wherein: (a) the subject has multiple myeloma; and (b) the multiple myeloma is characterized as having a chromosomal translocation.

62. The method of claim 61, wherein the chromosomal translocation is a t(4;14) translocation.

63. A method, comprising administering the compound of claim 19, or a pharmaceutically acceptable solvate thereof, to a subject in need thereof, wherein:
(a) the subject has multiple myeloma; and
(b) the multiple myeloma is characterized as having an overexpression of WHSC1/NSD2/MMSET.

64. A pharmaceutical composition comprising the compound of claim 20 and a pharmaceutically acceptable carrier.

65. A method of treating a subject in need thereof, the method comprising administering to the subject the compound of claim 20 wherein the subject has multiple myeloma.

66. A method of treating a subject in need thereof, the method comprising administering to the subject the compound of claim 20 wherein the subject has diffuse large B-cell lymphoma.

67. A method of treating a subject in need thereof, the method comprising administering to the subject the compound of claim 20, wherein the subject has renal cell carcinoma.

68. A method, comprising administering the compound of claim 20 to a subject in need thereof, wherein: (a) the subject has multiple myeloma; and (b) the multiple myeloma is characterized as having a chromosomal translocation.

69. The method of claim 68, wherein the chromosomal translocation is a t(4;14) translocation.

70. A method, comprising administering the compound of claim 20 to a subject in need thereof, wherein:
(a) the subject has multiple myeloma; and
(b) the multiple myeloma is characterized as having an overexpression of WHSC1/NSD2/MMSET.

\* \* \* \* \*

UNITED STATES PATENT AND TRADEMARK OFFICE
CERTIFICATE OF CORRECTION

| | |
|---|---|
| PATENT NO. | : 12,116,358 B2 |
| APPLICATION NO. | : 17/268151 |
| DATED | : October 15, 2024 |
| INVENTOR(S) | : Lampe et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 814 days.

Signed and Sealed this
Twenty-fourth Day of June, 2025

Coke Morgan Stewart
*Acting Director of the United States Patent and Trademark Office*